US012441995B2

(12) United States Patent
Zhang et al.

(10) Patent No.: US 12,441,995 B2
(45) Date of Patent: Oct. 14, 2025

(54) FUNCTIONAL GENOMICS USING CRISPR-Cas SYSTEMS, COMPOSITIONS, METHODS, SCREENS AND APPLICATIONS THEREOF

(71) Applicants: The Broad Institute, Inc., Cambridge, MA (US); Massachusetts Institute of Technology, Cambridge, MA (US)

(72) Inventors: Feng Zhang, Cambridge, MA (US); Ophir Shalem, Cambridge, MA (US); Neville Espi Sanjana, Cambridge, MA (US); John Doench, Cambridge, MA (US); David Root, Cambridge, MA (US); Ella Nicole Biewener Hartenian, Cambridge, MA (US)

(73) Assignees: THE BROAD INSTITUTE, INC., Cambridge, MA (US); MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 1299 days.

(21) Appl. No.: 17/027,151

(22) Filed: Sep. 21, 2020

(65) Prior Publication Data

US 2021/0108196 A1 Apr. 15, 2021

Related U.S. Application Data

(63) Continuation of application No. 14/973,062, filed on Dec. 17, 2015, now Pat. No. 10,781,444, which is a continuation-in-part of application No. PCT/US2014/041806, filed on Jun. 10, 2014.

(60) Provisional application No. 61/836,123, filed on Jun. 17, 2013, provisional application No. 61/960,777, filed on Sep. 25, 2013, provisional application No. 61/995,636, filed on Apr. 15, 2014.

(51) Int. Cl.

| | |
|---|---|
| ***C12N 15/10*** | (2006.01) |
| ***C12N 9/22*** | (2006.01) |
| ***C12N 15/63*** | (2006.01) |
| ***C12N 15/90*** | (2006.01) |

(52) U.S. Cl.

CPC .......... *C12N 15/1093* (2013.01); *C12N 9/22* (2013.01); *C12N 15/102* (2013.01); *C12N 15/1082* (2013.01); *C12N 15/63* (2013.01); *C12N 15/907* (2013.01); *C12N 2310/20* (2017.05)

(58) Field of Classification Search

None

See application file for complete search history.

(56) References Cited

U.S. PATENT DOCUMENTS

| | | | |
|---|---|---|---|
| 5,622,856 | A | 4/1997 | Natsoulis |
| 6,251,677 | B1 | 6/2001 | Wilson et al. |
| 7,601,492 | B2 | 10/2009 | Fu et al. |
| 7,691,995 | B2 | 4/2010 | Zamore et al. |
| 8,697,359 | B1 | 4/2014 | Zhang |
| 8,771,945 | B1 | 7/2014 | Zhang |
| 8,865,406 | B2 | 10/2014 | Zhang et al. |
| 8,871,445 | B2 | 10/2014 | Cong et al. |
| 8,889,418 | B2 | 11/2014 | Zhang et al. |
| 8,895,308 | B1 | 11/2014 | Zhang et al. |
| 8,932,814 | B2 | 1/2015 | Cong et al. |
| 8,945,839 | B2 | 2/2015 | Zhang |
| 8,993,233 | B2 | 3/2015 | Zhang et al. |
| 9,512,446 | B1 | 12/2016 | Joung et al. |
| 9,549,901 | B2 | 1/2017 | Shi et al. |
| 9,597,357 | B2 | 3/2017 | Gregory et al. |
| 9,623,071 | B2 | 4/2017 | Guo et al. |
| 9,637,739 | B2 | 5/2017 | Siksnys et al. |
| 9,701,964 | B2 | 7/2017 | Clube et al. |
| 9,738,908 | B2 | 8/2017 | Wu |
| 9,834,791 | B2 | 12/2017 | Zhang et al. |
| 9,873,894 | B2 | 1/2018 | Conway et al. |
| 9,926,546 | B2 | 3/2018 | Joung et al. |
| 10,301,651 | B2 | 5/2019 | Doudna et al. |
| 10,494,621 | B2 | 12/2019 | Zhang et al. |
| 10,583,203 | B2 | 3/2020 | De Fougerolles et al. |
| 10,660,943 | B2 | 5/2020 | Bikard et al. |
| 10,669,557 | B2 | 6/2020 | Guschin et al. |
| 10,781,444 | B2 | 9/2020 | Zhang et al. |
| 10,930,367 | B2 | 2/2021 | Zhang et al. |
| 10,941,395 | B2 | 3/2021 | Yin |
| 11,116,729 | B2 | 9/2021 | Dahlman |
| 11,124,796 | B2 | 9/2021 | Sharp |
| 11,559,588 | B2 | 1/2023 | Lundberg |

(Continued)

FOREIGN PATENT DOCUMENTS

| | | | |
|---|---|---|---|
| BR | 112015013784 | | 7/2017 |
| CA | 2619833 | A1 | 3/2007 |

(Continued)

OTHER PUBLICATIONS

Bethea et al., "Beta2-Microglobulin: Its Significance and Clinical Usefulness," Annals of Clinical and Laboratory Science, vol. 20, No. 3 (pages), 1998.

(Continued)

*Primary Examiner* — Nancy J Leith

(74) *Attorney, Agent, or Firm* — FOLEY & LARDNER LLP

(57) ABSTRACT

The present invention generally relates to libraries, compositions, methods, applications, kits and screens used in functional genomics that focus on gene function in a cell and that may use vector systems and other aspects related to Clustered Regularly Interspaced Short Palindromic Repeats (CRISPR)-Cas systems and components thereof. Provided are vectors and vector systems, some of which encode one or more components of a CRISPR complex, as well as methods for the design and use of such vectors. Also provided are methods of directing CRISPR complex formation in eukaryotic cells and methods for utilizing the CRISPR-Cas system.

17 Claims, 105 Drawing Sheets
(65 of 105 Drawing Sheet(s) Filed in Color)
Specification includes a Sequence Listing.

(56) References Cited

U.S. PATENT DOCUMENTS

| | | | |
|---|---|---|---|
| 11,578,312 | B2 | 2/2023 | Zhang et al. |
| 2003/0186238 | A1 | 10/2003 | Allawi et al. |
| 2004/0111221 | A1 | 6/2004 | Beattie et al. |
| 2005/0196851 | A1 | 9/2005 | Uckun |
| 2005/0220796 | A1 | 10/2005 | Dynan et al. |
| 2006/0178297 | A1 | 8/2006 | Troy et al. |
| 2006/0234247 | A1 | 10/2006 | Puttaraju et al. |
| 2007/0016012 | A1 | 1/2007 | Hartlep et al. |
| 2007/0244031 | A1 | 10/2007 | Lu et al. |
| 2008/0293655 | A1 | 11/2008 | Aygun et al. |
| 2009/0215169 | A1 | 8/2009 | Wandless et al. |
| 2010/0055798 | A1 | 3/2010 | Battersby |
| 2010/0076057 | A1 | 3/2010 | Sontheimer et al. |
| 2010/0081707 | A1 | 4/2010 | Ali et al. |
| 2010/0093617 | A1 | 4/2010 | Barrangou et al. |
| 2010/0233084 | A1 | 9/2010 | Narasimhaswamy et al. |
| 2011/0016540 | A1 | 1/2011 | Weinstein et al. |
| 2011/0059502 | A1 | 3/2011 | Chalasani |
| 2011/0189776 | A1 | 8/2011 | Terns et al. |
| 2011/0223638 | A1 | 9/2011 | Wiedenheft et al. |
| 2011/0239315 | A1 | 9/2011 | Bonas et al. |
| 2012/0029891 | A1 | 2/2012 | Behlke et al. |
| 2013/0096182 | A1 | 4/2013 | Chatterjee et al. |
| 2013/0130248 | A1 | 5/2013 | Haurwitz et al. |
| 2013/0315831 | A1 | 11/2013 | Shi et al. |
| 2014/0068797 | A1 | 3/2014 | Doudna et al. |
| 2014/0294771 | A1 | 10/2014 | Schaffer et al. |
| 2014/0295557 | A1 | 10/2014 | Joung et al. |
| 2014/0315985 | A1 | 10/2014 | May et al. |
| 2014/0342456 | A1 | 11/2014 | Mali et al. |
| 2014/0356956 | A1 | 12/2014 | Church et al. |
| 2014/0357530 | A1 | 12/2014 | Zhang et al. |
| 2015/0045546 | A1 | 2/2015 | Siksnys et al. |
| 2015/0071899 | A1 | 3/2015 | Liu et al. |
| 2015/0071903 | A1 | 3/2015 | Liu et al. |
| 2015/0071906 | A1 | 3/2015 | Liu et al. |
| 2015/0232881 | A1 | 8/2015 | Glucksmann et al. |
| 2015/0247150 | A1 | 9/2015 | Zhang et al. |
| 2015/0291965 | A1 | 10/2015 | Zhang et al. |
| 2015/0322457 | A1 | 11/2015 | Kim et al. |
| 2015/0353905 | A1 | 12/2015 | Weiss et al. |
| 2016/0017366 | A1 | 1/2016 | Chen et al. |
| 2016/0024510 | A1 | 1/2016 | Bikard et al. |
| 2016/0024524 | A1 | 1/2016 | Joung et al. |
| 2016/0130609 | A1 | 5/2016 | Doudna et al. |
| 2016/0237456 | A1 | 8/2016 | Church et al. |
| 2016/0251648 | A1 | 9/2016 | Wang et al. |
| 2016/0281072 | A1 | 9/2016 | Zhang |
| 2016/0298135 | A1 | 10/2016 | Chen et al. |
| 2016/0298137 | A1 | 10/2016 | Chen et al. |
| 2016/0312199 | A1 | 10/2016 | Joung et al. |
| 2016/0324938 | A1 | 11/2016 | Bikard et al. |
| 2016/0340662 | A1 | 11/2016 | Zhang et al. |
| 2017/0175144 | A1 | 6/2017 | Zhang et al. |
| 2017/0191082 | A1 | 7/2017 | Chen et al. |
| 2017/0327806 | A1 | 11/2017 | Joung et al. |
| 2018/0127783 | A1 | 5/2018 | Zhang et al. |
| 2018/0230495 | A1 | 8/2018 | Doudna et al. |
| 2019/0010471 | A1 | 1/2019 | Zhang et al. |
| 2020/0282026 | A1 | 9/2020 | Bikard et al. |
| 2020/0282027 | A1 | 9/2020 | Bikard et al. |
| 2021/0060140 | A1 | 3/2021 | Bikard et al. |
| 2021/0060141 | A1 | 3/2021 | Bikard et al. |
| 2022/0273566 | A1 | 9/2022 | Dahlman |

FOREIGN PATENT DOCUMENTS

| | | | |
|---|---|---|---|
| CN | 101228176 | | 7/2008 |
| CN | 103343120 | | 10/2013 |
| CN | 103388006 | | 11/2013 |
| CN | 103668472 | | 3/2014 |
| CN | 104520429 | A | 4/2015 |
| CN | 104854241 | A | 8/2015 |
| CN | 107532161 | A | 1/2018 |
| EP | 2 591 770 | A2 | 5/2013 |
| EP | 2 784 162 | | 1/2014 |
| EP | 2 764 103 | | 8/2014 |
| EP | 2 771 468 | | 9/2014 |
| EP | 2 828 386 | A1 | 1/2015 |
| FR | 2872170 | A1 | 12/2005 |
| IN | 49/2015 | | 12/2015 |
| JP | 2004-519245 | A | 7/2004 |
| JP | 2004-537285 | A | 12/2004 |
| JP | 2005-509409 | A | 4/2005 |
| JP | 2006-513694 | A | 4/2006 |
| JP | 2006-518996 | A | 8/2006 |
| JP | 2007-501626 | A | 2/2007 |
| JP | 2009-502170 | A | 1/2009 |
| JP | 2009-536827 | A | 10/2009 |
| JP | 2010-507680 | A | 3/2010 |
| JP | 2010-522547 | A | 7/2010 |
| JP | 2012-506254 | A | 3/2012 |
| JP | 2012-508235 | | 4/2012 |
| JP | 2012-510812 | A | 5/2012 |
| JP | 2012-511332 | A | 5/2012 |
| JP | 2012-523234 | A | 10/2012 |
| JP | 2012-529287 | A | 11/2012 |
| JP | 2013-500045 | A | 1/2013 |
| JP | 2013-513389 | A | 4/2013 |
| JP | 2013-518602 | A | 5/2013 |
| JP | 2013-544077 | A | 12/2013 |
| JP | 2014-526279 | A | 10/2014 |
| JP | 2015-523856 | A | 8/2015 |
| JP | 2016-500003 | A | 1/2016 |
| JP | 2016-500262 | A | 1/2016 |
| JP | 2016-501531 | | 1/2016 |
| JP | 2016-501532 | A | 1/2016 |
| JP | 2016-025710 | A | 2/2016 |
| JP | 2016-502840 | A | 2/2016 |
| JP | 2016-504026 | A | 2/2016 |
| JP | 2016-505256 | A | 2/2016 |
| JP | 2016-093196 | | 5/2016 |
| JP | 2016-516169 | A | 6/2016 |
| JP | 2016-517954 | A | 6/2016 |
| JP | 2016-131404 | A | 7/2016 |
| JP | 2016-520317 | A | 7/2016 |
| JP | 2016-521554 | A | 7/2016 |
| JP | 2016-521975 | A | 7/2016 |
| JP | 2016-521995 | | 7/2016 |
| JP | 2016-523082 | A | 8/2016 |
| JP | 2016-524472 | | 8/2016 |
| JP | 2016-182140 | A | 10/2016 |
| JP | 2017-501151 | A | 1/2017 |
| JP | 2017-501699 | | 1/2017 |
| JP | 6395765 | | 9/2018 |
| RU | 2009136452 | A | 4/2011 |
| WO | WO-02/074968 | A1 | 9/2002 |
| WO | WO-02/080851 | A2 | 10/2002 |
| WO | WO-03/014318 | A2 | 2/2003 |
| WO | WO-03/104414 | A2 | 12/2003 |
| WO | WO-2004/029219 | A2 | 4/2004 |
| WO | WO-2004/046321 | A2 | 6/2004 |
| WO | WO-2004/062618 | A2 | 7/2004 |
| WO | WO-2005/014791 | | 2/2005 |
| WO | WO-2005/049642 | A2 | 6/2005 |
| WO | WO-2007/014275 | A2 | 2/2007 |
| WO | WO-2007/134161 | A2 | 11/2007 |
| WO | WO-2008/093152 | A1 | 8/2008 |
| WO | WO-2008/108989 | | 9/2008 |
| WO | WO-2008/116860 | A2 | 10/2008 |
| WO | WO-2008/147438 | A2 | 12/2008 |
| WO | WO-2010/011961 | A2 | 1/2010 |
| WO | WO-2010/048228 | A2 | 4/2010 |
| WO | WO-2010/054108 | | 5/2010 |
| WO | WO-2010/065123 | A1 | 6/2010 |
| WO | WO-2010/068816 | A1 | 6/2010 |
| WO | WO-2010/075424 | A2 | 7/2010 |
| WO | WO-2010/079430 | A1 | 7/2010 |
| WO | WO-2010/118077 | A1 | 10/2010 |
| WO | WO-2010/143917 | | 12/2010 |
| WO | WO-2011/011767 | A1 | 1/2011 |
| WO | WO-2011/016840 | A2 | 2/2011 |
| WO | WO-2011/036510 | A1 | 3/2011 |
| WO | WO-2011/064736 | A1 | 6/2011 |

(56) References Cited

FOREIGN PATENT DOCUMENTS

WO WO-2011/072246 A2 6/2011
WO WO-2011/076873 A1 6/2011
WO WO-2011/100058 8/2011
WO WO-2011/146121 A1 11/2011
WO WO-2012/012738 A1 1/2012
WO WO-2012/031205 3/2012
WO WO-2012/051343 A1 4/2012
WO WO-2012/149470 A1 11/2012
WO WO-2012/164565 A1 12/2012
WO WO-2013/044008 A2 3/2013
WO WO-2013/052681 4/2013
WO WO-2013/5052681 A1 4/2013
WO WO-2013/071440 A1 5/2013
WO WO-2013/078400 A1 5/2013
WO WO-2013/082519 A2 6/2013
WO WO-2013/098244 7/2013
WO WO-2013/130824 A1 9/2013
WO WO-2013/141680 A1 9/2013
WO WO-2013/142578 A1 9/2013
WO WO-2013/155572 10/2013
WO WO-2013/176772 A1 11/2013
WO WO-2014/165349 A1 3/2014
WO WO-2014/065596 A1 5/2014
WO WO-2014/089290 A1 6/2014
WO WO-2014/093479 6/2014
WO WO-2014/093595 6/2014
WO WO-2014/093622 A2 6/2014
WO WO-2014/093635 A1 6/2014
WO WO-2014/093655 6/2014
WO WO-2014/093661 6/2014
WO WO-2014/093694 A1 6/2014
WO WO-2014/093701 A1 6/2014
WO WO-2014/093709 6/2014
WO WO-2014/093712 A1 6/2014
WO WO-2014/093718 6/2014
WO WO-2014/099744 6/2014
WO WO-2014/099750 A2 6/2014
WO WO-2015/031775 8/2014
WO WO-2014/144761 A2 9/2014
WO WO-2014/165825 A2 10/2014
WO WO-2014/186585 A2 11/2014
WO WO-2014/191518 A1 12/2014
WO WO-2014/197568 A2 12/2014
WO WO-2014/197748 A2 12/2014
WO WO-2014/204724 A1 12/2014
WO WO-2014/204725 12/2014
WO WO-2014/204726 A1 12/2014
WO WO-2014/204727 A1 12/2014
WO WO-2014/204728 12/2014
WO WO-2014/204729 A1 12/2014
WO WO-2015/006747 A2 1/2015
WO WO-2015/035136 A2 3/2015
WO WO-2015/048577 4/2015
WO WO-2015/048690 4/2015
WO WO-2015/065964 A1 5/2015
WO WO-2015/070083 A1 5/2015
WO WO-2015/071474 A2 5/2015
WO WO-2015/089351 A1 6/2015
WO WO-2015/089364 6/2015
WO WO-2015/089419 A2 6/2015
WO WO-2015/089427 A1 6/2015
WO WO-2015/113063 A1 7/2015
WO WO-2016/022866 A1 2/2016
WO WO-2016/073955 A2 5/2016
WO WO-2016/141224 A1 9/2016

OTHER PUBLICATIONS

Declaration of Feng Zhang dated Jan. 30, 2014 (40 pages).

Adhin et al., "Complete nucleotide sequence of the group I RNA bacteriophage fr," Biochimica et Biophysica Acta, Elsevier, vol. 1050, 1990 pp. 104-109.

Anders et al., "Structural basis of PAM-dependent target DNA recognition by the Cas9 endonuclease," Nature, vol. 513, Sep. 25, 2014 pp. 569-573.

Anguela et al., "Robust ZFN-mediated geno1ne editing in adult hemophilic mice", Blood, vol. 122, No. 19, Nov. 7, 2013, (pp. 3283-3287).

Bikard et al., "Exploiting CRISPR-Cas nucleases to produce sequence-specific antimicrobials", Nature Biotechnology, vol. 32, No. 11, Nov. 2014 (pp. 1146-1151).

Chapdelaine et al., "Meganucleases can restore the reading frame of a mutated dystrophin", Gene Therapy, vol. 17, 2010 (pp. 846-858).

Database UniPro Accession No. J7RUA5, 2012, [online] downloaded from https://www.uniprot.org/uniprol/J7RUA5 on Mar. 23, 2021 (10 pages).

He et al., "Pollen fertility restoration by nuclear gene Fr in CMS common bean: an Fr linkage map and the mode of Fr action," Theor. Appl. Genet. vol. 90, 1995, pp. 1056-1062.

Hemphill et al., "Optical Control of CRISPR/Cas9 Gene Editing," Journal of the American Chemical Society, vol. 137, May 6, 2015 (9 pages).

Huang and Honkanen, "Molecular Cloning, Expression, and Characterization of a Novel Human Serine/Threonine Protein Phosphatase, PP7, That Is Homologous to '*Drosophila*' Retinal Degeneration C Gene Product (rdgC)*," The Journal of Biological Chemistry, vol. 273, No. 3, Iss. 16, 1998, pp. 1462-1468.

Koonin et al., "Diversity, classification and evolution of CRISPR-Cas systems", Current Opinion in Microbiology vol. 37, 2017 (pp. 67-78).

Sorek et al., "CRISPR-Mediated Adaptive Immune Systems in Bacteria and Archea", Annual Review of Biochemistry, vol. 82, 2013, (pp. 237-266).

"Crispr Genome Engineering Resources" XP055167591, Oct. 5, 2013, https://web.archive.org/web/2013100500 [retrieved on Feb. 5, 2015].

"Fixes, extra genomes, and improvements to the CRISPR Design Tool" Google Groups, XP055167583, Oct. 21, 2013, URL:https://groups.google.com/forum/#!topic/crispr/g9Q8U1tNSis [retrieved on Feb. 5, 2015].

"The CRISPR Revolution," Catalyst Magazine, College of Chemistry, University of California, Berkeley, http://catalyst.berkeley.edu/slideshow/the-crispr-revolution/[Dec. 19, 2014 12:40:53] (Jul. 9, 2014).

A. Amsterdam et al., "Identification of 315 genes essential for early zebrafish development," proc Natl Acad Sci., vol. 101, Aug. 31, 2004, pp. 12792-12797, 6 pages.

A. Fire et al., "Potent and specific genetic interference by double-stranded RNA in Caenorhabditis elegans," Nature, vol. 391, Feb. 19, 1998, pp. 806-811, 6 pages.

A. Subramanian et al., "Gene set enrichment analysis: a knowledge-based approach for interpreting genome-wide expression profiles," Proc Natl Acad Sci., vol. 102, Oct. 25, 2005, pp. 15545-15550, 6 pages.

A.C. Spradling et al., "The Berkeley *Drosophila* Genome Project Gene Disruption Project: Single P-Element Insertions Mutating 25% of Vital *Drosophila* Genes," Genetics, vol. 153, Sep. 1999, pp. 135-177, 43 pages.

A.H. Tong et al., "Global mapping of the yeast genetic interaction network," Science, vol. 303, Feb. 6, 2004, pp. 808-813, 6 pages.

A.L. Lin and D.H Gutmann, "Advances in the treatment of neurofibromatosis-associated tumours," Nature, vol. 10, Nov. 2013, pp. 616-624, 9 pages.

A.P. Blanchard and L. Hood, "Sequence to array: probing the genome's secrets," Nat Biotechnol, vol. 14, Dec. 14, 1996, p. 1649.

Abudayyeh, et al., "C2c2 is a single-component programmable RNA-guided RNA-targeting CRISPR effector," Science, vol. 10, Jun. 2, 2016, pp. 1-16, 18 pages.

Addgene Materials, "CRISPR/cas Plasmids and Resources", downloaded from https://www.addgene.org/crispr/, May 6, 2015, 3 pages.

Addgene Materials, "Engineering with Addgene's Help", Addgene Newsletter, Mar. 2013, downloaded from https://archive.constantcontact.com/fs126/1103481513180/archive/1112756362265.html, Oct. 14, 2014, 4 pages.

Addgene Reagent distribution list for Zhang Lab with Plasmid Name, date unknown (prior to May 10, 2015), 2 pages.

(56) References Cited

OTHER PUBLICATIONS

Addgene, "gRNA_Cloning Vector", retrieved on Jan. 30, 2019, <https://www/addgenen.org/41824/> 2 pages.
Al-Attar, et al., "Clustered regularly interspaced short palindromic repeats (CRISPRs): the hallmark of an ingenious antiviral defense mechanism in prokaryotes" Biol Chem., vol. 392, No. 4, Apr. 2011, pp. 277-289, 13 pages.
Alberts, et al., "Intracellular Compartments and Protein Sorting," Garland Science, 4 ed., 2002, pp. 671-676, 8 pages.
Allen, et al., "Liposomal drug delivery systems: From concept to clinical applications" Advanced Drug Delivery Reviews, vol. 65, 2013, pp. 36-48, 13 pages.
Andreas, et al., "Enhanced efficiency through nuclear localization signal fusion on phage C31-integrase: activity comparison with Cre and FLPe recombinase in mammalian cells", Nucleic Acids Research, Apr. 15, 2002, vol. 30, No. 11, pp. 2299-2306, 8 pages.
*Arbitron, Inc.* v. *Kiefl*, No. 09-CV-04013 PAC, 2010 WL 3239414, at *1 (S.D.N.Y. Aug. 13, 2010), 7 pages.
Asuri, P., et al., "Directed Evolution of Adeno-Associated Virus for Enhanced Gene Delivery and Gene Targeting in Human Pluripotent Stem Cells," Molecular Therapy, vol. 30, 2012, No. pp. 329-338, 10 pages.
Au, et al., "Characterization of a baculovirus nuclear localization signal domain in the late express factor 3 protein", Virology, vol. 385, 2009, pp. 209-217.
Ausubel, et al. "Compendium of Methods from Current Protocols in Molecular Biology", Short Protocols in Molecular Biology, 4 ed., 1999, 9-0, 9-4, 5 pages.
Autofluorescence MIT Flow Cytometry Core Facility (2018), 6 pages.
B. Langmead et al., "Ultrafast and memory-efficient alignment of short DNA sequences to the human genome," Genome biology, vol. 10, Mar. 4, 2009, 10 pages.
B.Langmead and S.L. Salzberg, "Fast gapped-read alignment with Bowtie 2," Nat Meth, vol. 9, 2012, pp. 357-359, 3 pages.
B.Scappini et al., "Changes associated with the development of resistance to imatinib (STI571) in two leukemia cell lines expressing p210 Bcr/Abl protein," Cancer, vol. 100, Apr. 1, 2004, pp. 1459-1471, 13 pages.
B.Sonnichsen et al., "Full-genome RNAi profiling of early embryogenesis in Caenorhabditis elegans," Nature, vol. 434, Mar. 24, 2005, pp. 462-469, 8 pages.
Bae, T. and Schneewind, O. "Allelic replacement in *Staphylococcus aureus* with inducible counter-selection," Plasmid, vol. 55, 2006, pp. 58-63, 6 pages.
Baena-Lopez, L., et al., "Accelerated homologous recombination and subsequent genome modification in *Drosophila*," Development, vol. 140, 2013, pp. 4818-4835, including Supplementary Material, 8 pages.
Baiker, et al. "The Immediate-Early 63 Protein of Varicella-Zoster Virus: Analysis of Functional Domains Required for Replication In Vitro and for T-Cell and Skin Tropism in the SCIDhu Model In Vivo", Journal of Virology, 2004, vol. 78 pp. 1181-1194, 14 pages.
Baker, M., "Gene editing at CRISPR Speed," Nature Biotechnology, vol. 32, 2014, pp. 309-312, 4 pages.
Balboa, et al., "Conditionally Stabilized dCas9 Activator for Controlling Gene Expression in Human Cell Reprogramming and Differentiation. (plus Supplemental Information)", Stem Cell Reports, vol. 5, Sep. 8, 2015, pp. 448-459, 12 pages.
Banaszewska, A., et al., "Proprotein Convertase Subtilisin/Kexin Type 9: A New Target Molecule For Gene Therapy," Cellular & Molecular Biology Letters, vol. 17, 2012, pp. 228-239, 12 pages.
Barrangou and Van Der Oost (Eds.), "CRISPR-Cas Systems," Springer Heidelberg, 2013, pp. i-299.
Barrangou, R. et al., "CRISPR provides acquired resistance against viruses in prokaryotes," Science, vol. 315, Mar. 23, 2007, pp. 1709-1712, 6 pages.
Barrangou, R., "RNA-mediated programmable DNA cleavage," Nature Biotechnology, vol. 30, 2012, pp. 836-388, 13 pages.
Bassett, et al. "Highly Efficient Targeted Mutagenesis of *Drosophila* with the CRISPR/Cas9 System" Cell Reports, vol. 4, Jul. 11, 2013, p. 220.
Bassett, et al., "A Genome-Wide CRISPR Library for High-Throughput Genetic Screening in *Drosophila* Cells," Journal of Genetics and Genomics, vol. 42, Apr. 18, 2015, pp. 301-309, 9 pages.
Bauer, et al, "An Erythroid Enhancer of BCL11A Subject to Genetic Variation Determines Fetal Hemoglobin Level," Science, vol. 342, Oct. 11, 2013, pp. 253-257, 4 pages.
Beerli, et al. "Positive and negative regulation of endogenous genes by designed transcription factors" PNAS, vol. 97, Feb. 15, 2000, pp. 1495-1500.
Beerli, et al., "Toward controlling gene expression at will: Specific regulation of the erbB-2/HER-2 promoter by using polydactyl zinc finger proteins constructed from modular building blocks", Proc. Natl. Acad. Sci., vol. 95, Oct. 7, 1998, pp. 14628-14633.
Beerli, R., et al., "Engineering polydactyl zinc-finger transcription factors," Nature Biotechnology, vol. 20, Feb. 2002, pp. 135-141.
Bennett, et al., "Stable transgene expression in rod photoreceptors after recombinant adeno-associated virus-mediated gene transfer to monkey retina", Proc. Natl. Acad. Sci., vol. 96, Aug. 1999, pp. 9920-9925.
Bergemann, et al., Excision of specific DNA-sequences from integrated retroviral vectors via site-specific recombination:, Nucleic Acids Res., vol. 23, Oct. 2, 1995, pp. 4451-4456.
Berns, K., et al., "A Large-Scale RNAi Screen in Human Cells Identifies New Components of the p53 Pathway," Nature, vol. 428, Mar. 25, 2004, pp. 431-437.
Bhaya, D., et al., "CRISPR-Cas Systems in Bacteria and Archaea: Versatile Small RNAs for Adaptive Defense and Regulation," Annual Review of Genetics, vol. 45, 2011, pp. 273-297.
Bikard, et al. "CRISPR Interference Can Prevent Natural Transformation And Virulence Acquisition During In Vivo Bacterial Infection," Cell Host & Microbe, vol. 12, 2012, pp. 177-186.
Bikard, et al., Supplementary Information for: "CRISPR Interference Can Prevent Natural Transformation And Virulence Acquisition During In Vivo Bacterial Infection," Cell Host & Microbe, vol. 12, 2012, pp. 177-186.
Birch, et al., "Plant Transformation: Problems and Strategies for Practical Application", Annu. Rev. Plant Physiol. Plant Mol. Biol., vol. 48, 1997, pp. 297-326.
Bloom, et al., "Inactivation of hepatitis B virus replication in cultured cells and in vivo with engineered transcription activator-like effector nucleases", Molecular Therapy, vol. 21, Oct. 2013, pp. 1889-1897.
Bobis-Wozowicz, S., et al., "Targeted genome editing in pluripotent stem cells using zinc-finger nucleases," Methods, vol. 53, 2012, pp. 339-346.
Boch, et al., "Breaking the Code of DNA Binding Specificity of TAL-Type III Effectors". Science, vol. 326, 2009, pp. 1509-1512.
Boch, et al., "Xanthomonas AvrBs3 Family-Type III Effectors: Discovery And Function", Annu. Rev. Phytopathol, vol. 48, 2010, pp. 419-436.
Boden, et al., "Efficient Gene Transfer of HIV-1-Specific Short Hairpin RNA into Human Lymphocytic Cells Using Recombinant Adeno-associated Virus Vectors", Molecular Therapy, vol. 9, 2004, pp. 396-402.
Bogdanove, et al., "TAL Effectors: Customizable Proteins for DNA Targeting", Science, vol. 333, 2011, pp. 1843-1846.
Bohm et al., "The computer program LUDI: A new method for the de novo design of enzyme inhibitors", Journal of Computer-Aided Molecular Design, vol. 6, 1992, pp. 61-78.
Botta, S. et al, "Transcriptional Repression with Zinc-Finger and Tale Protein Scaffold", Molecular Therapy, 2013, Supplement 1, p. S208, Abstract No. 539.
Bouard, et al., "Themed Section: Vector Design and Drug Delivery Review, Viral vectors: from virology to transgene expression", British Journal of Pharmacology, vol. 157, 2009, pp. 153-165.
Boutros, et al., "Genome-wide RNAi analysis of growth and viability in *Drosophila* cells," Science, American Association for the Advancement of Science, vol. 303, Feb. 6, 2004, pp. 832-835.

(56) References Cited

OTHER PUBLICATIONS

Branden, C., and Tooze, J., "Prediction, Engineering, and Design of Protein Structures: Introduction to Protein Structure," Garland Publishing, Inc., Chapter 16, 1991, p. 247.
Briner, et al., "Guide RNA Functional Modules Direct Cas9 Activity and Orthogonality", Molecular Cell, vol. 56, 2014, pp. 333-339.
Brouns, S., "A Swiss Army Knife of Immunity," Science, vol. 337, 2012, pp. 808-809.
Brouns, S., et al., "Small CRISPR RNAs Guide Antiviral Defense in Prokaryotes," Science, vol. 321, Aug. 15, 2008, pp. 960-964.
Brummelkamp TR et al., "A system for stable expression of short interfering RNAs in mammalian cells," Science, vol. 296, Apr. 19, 2002, pp. 550-553.
C. Cayrol et al., "The THAP-zinc finger protein THAP1 regulates endothelial cell proliferation through modulation of pRB/E2F cell-cycle target genes," Blood, vol. 109, 2007, pp. 584-594.
C. Trapnell et al., "Differential gene and transcript expression analysis of RNA-seq experiments with TopHat and Cufflinks," Nature protocols, vol. 7, 2012, p. 562.
C. Trapnell et al., "TopHat: discovering splice junctions with RNA-Seq.," Bioinformatics, vol. 25, 2009, pp. 1105-1111.
C.J, Echeverri et al., "Minimizing the risk of reporting false positives in large-scale RNAi screens," Nature methods, vol. 3, Oct. 2006, p. 777.
C.M. Johannessen et al., "COT drives resistance to RAF inhibition through MAP kinase pathway reactivation," Nature, vol. 468, Dec. 16, 2010, p. 968.
C.M. Johnston et al., "Large-scale population study of human cell lines indicate that dosage compensation is virtually complete," PLoS Genet., vol. 4, Jan. 2008, pp. 88-98, 11 pages.
Campeau, et al., "A Versatile Viral System for Expression and Depletion of Proteins in Mammalian Cells", PLoS One, vol. 4, 2009, pp. 1-17.
Canver, et al., "BCL11A enhancer dissection by Cas9-mediated in situ saturating mutagenesis," Nature, vol. 527, 2015, pp. 192-197, including Supplementary Material.
Carr, et al., "Genome engineering", Nature Biotechnology, vol. 27, 2009, pp. 1151-1162.
Carroll, D., "A CRISPR Approach to Gene Targeting," Molecular Therapy, vol. 20, 2012, pp. 1658-1660.
Carroll., "Genome Engineering With Zing-Finger Nucleases", Genetics, vol. 188, 2011, pp. 773-782.
Carroll., "Progress and prospects: Zinc-finger nucleases as gene therapy agents", Gene Therapy, vol. 15, 2008, pp. 1463-1468.
Carte, J., et al., "Cas6 is an endoribonuclease that generates guide RNAs for invader defense in prokaryotes," Genes Dev., vol. 22, 2008, pp. 3489-3496.
Cermak, T., et al., "Efficient design and assembly of custom TALEN and other TAL Effector-Based Constructs For DNA Targeting", Nucleic Acids Research, vol. 39, 2011, pp. 1-11.
Chadderton, N., et al., "Improved Retinal Function in a Mouse Model of Dominant Retinitis Pigmentosa Following AAV-delivered Gene Therapy", Molecular Therapy, vol. 17, Apr. 2009, pp. 593-599.
Chan, et al. "Characterization of the Kinetochore Binding Domain of CENP-E Reveals Interactions with the Kinetochore Proteins CENP-F and hBuBR1", The Journal of Cell Biology, vol. 143, 1998, pp. 49-63.
Chan, Wai-Ting, et al., "Toxin-Antitoxin Genes of the Gram-Positive Pathogen *Streptococcus pneumoniae*: So Few and Yet So Many", Microbiology and Molecular Biology Reviews, vol. 76, 2012, pp. 773-791.
Chang, N., et al. "Genome editing with RNA-guided Cas9 nuclease in Zebrafish embryos", Cell Research, vol. 23, 2013, pp. 465-472.
Chen, B., et al., "Dynamic Imaging of Genomic Loci in Living Human Cells by an Optimized CRISPR/Cas System," Cell, vol. 155, 2013, pp. 1479-1491.
Chen, Fuqiang, et al., "High-frequency genome editing using ssDNA oligonucleotides with zinc-finger nucleases". Nature Methods, 2011, vol. 8, pp. 753-755, including Supplemental Online Methods.
Chen, Jieliang, et al., "An Efficient Antiviral Strategy for Targeting Hepatitis B Virus Genome Using Transcription Activator-Like Effector Nucleases", Molecular Therapy, vol. 22, 2014, pp. 303-311.
Chen, S., et al., "Genome-wide CRISPR Screen in a Mouse Model of Tumor Growth and Metastasis", Cell, vol. 160, 2015, pp. 1-15, http://dx.doi.org/10.1016/j.cell.2015.02.038.
Chevalier et al., "Homing endonuclease: structural and functional insight into the catalysts of intron/intein mobility," Oxford University Press., vol. 29, 2001, pp. 3757-3774.
Chinnasamy, D., et al., "Multicistronic lentiviral vectors containing the FMCV 2A Cleavage factor demonstrate robust expression of encoded genes at limiting MOI," Virology Journal, vol. 3, 2006, pp. 1-16.
Chiu, et al., "Engineered GFP as a vital reporter in plants", Current Biology, vol. 6, 1996, pp. 325-330.
Cho, A., et al., "Generation of Transgenic Mice," Current Protocols in Cell Biology, Chapter Unit 19.11, 2009, pp. 1-29.
Cho, Minseon, et al., "Quantitative selection and parallel characterization of aptamers," PNAS, vol. 110, Nov. 12, 2013, pp. 18460-18465.
Cho, Seung Woo, et al. "Analysis off-target effects of CRISPR/Cas-derived RNA-guided endonucleases and nickases" Genome Research, vol. 24, 2014, pp. 132-141.
Cho, Seung Woo, et al., "Targeted genome engineering in human cells with the Cas9 RNA-guided endonuclease," Nature Biotechnology, vol. 31 pp. 230-232, including Supplementary Information, 14 pages, 2013.
Chou, JY, and Mansfield, BC., "Recombinant AAV-directed gene therapy for type I glycogen storage diseases," Expert Opinion on Biological Therapy, vol. 11, Aug. 2011, pp. 1011-1024.
Choulika, et al., "Transfer of Single Gene-Containing Long Terminal Repeats into the Genome of Mammalian Cells by a Retroviral Vector Carrying the cre Gene and the loxP site", Journal of Virology, vol. 70, 1996, pp. 1792-1798.
Christian, et al., "Supporting Information-Targeting DNA Double-Strand Breaks With TAL Effector Nucleases", Genetics, 2010, pp. 1-8, DOI:10.1534/110.120717:1SI-8SI.
Christian, et al., "Targeting DNA Double-Strand Breaks With TAL Effector Nucleases", Genetics, vol. 186, 2010, pp. 757-761.
Chylinski, et al., "Classification and evolution of type II CRISPR-Cas systems", Nucleic Acids Research, vol. 42, 2014, pp. 6091-6105, doi:10.1093Inarlgku241.
Chylinski, K., et al., "The tracrRNA and Cas9 Families of Type II CRISPR-Cas Immunity Systems," RNA Biology, vol. 10, 2013, pp. 726-737.
Clark, K., et al., "A Tale of Two Nucleases: Gene Targeting for the Masses?" Zebrafish, vol. 8, No. 3, 2011, pp. 147-149.
Cockrell, "Berkeley's Wikipedian-in-residence is a first," NewsCenter, Feb. 25, 2014, downloaded from https://newscenter.berkeley.edu/2014/02/25/berkeleys-wikipedian-in-residence-is-a-first/, May 8, 2015, 3 pages.
Community Corner, "CRISPR technology for gene therapy," Nature Medicine, vol. 20, May 2014, pp. 476-477.
Cong, et al., Oct. 5, 2012 Manuscript including Supplementary Materials, "CRISPR-Assisted Mammalian Genome Engineering," published as "Multiplex Genome Engineering Using CRISPR-Cas Systems," Science, vol. 339, 2013, pp. 819-823.
Cong, L., et al., "Comprehensive interrogation of natural TALE DNA-binding modules and transcriptional repressor domains," Nature Communications, vol. 3, Jul. 24, 2012, pp. 968-973.
Cong, L., et al., "In Vivo Genome Engineering With AAV Vector Carrying CRISPR-Cas9 System," Molecular Therapy, vol. 22, May 2014, Supplement 1, p. S214.
Cong, L., et al., "Multiplex Genome Engineering Using CRISPR-Cas Systems," Science, vol. 339, 2013, pp. 819-823.
Cong, L., et al., Supplementary Material for: "Multiplex Genome Engineering Using CRISPR-Cas Systems," Science, vol. 339, 2013, pp. 819-823.
Connor, S., "Scientific split—the human genome breakthrough dividing former colleagues," The Independent, http://www.independent.co.uk/news/science/scientific-split--the-human-genome-breakthrough-dividing-former-colleagues-9300456.html, dated Apr. 25, 2014, 5 pages.

(56) References Cited

OTHER PUBLICATIONS

Costantino, et al., "Enhanced levels of alpha Red-mediated recombinants in mismatch repair mutants", PNAS, vol. 100, 2003, pp. 15748-15753.
Cotropia, et al., "Copying in Patent Law," N.C.L. Rev., Stanford Public Law Working Paper No. 1270160, 2009, pp. 1-46.
Cummings et al., "Fourteen and counting: unraveling trinucleotide repeat diseases", Human Molecular Genetics, vol. 9, 2000, pp. 909-916.
D.J.Burgess et al., "Topoisomerase levels determine chemotherapy response in vitro and in vivo," Proceedings of the National Academy of Sciences, vol. 105, Jul. 1, 2008, pp. 9053-9058.
Daboussi, F., et al., "Chromosomal context and epigenetic mechanisms control the efficacy of genome editing by rare-cutting designer endonucleases," Nucleic Acids Research, vol. 40, 2012, pp. 6367-6379.
Dahlman, J., et al., "In vivo endothelial siRNA delivery using polymeric nanoparticles with low molecular weight," Nature Nanotechnology, vol. 9, 2014, pp. 648-655.
Dai, et al. "Genes:Structures and Regulation: The Transcription Factors GATA4 and dHAND Physically Interact to Synergistically Activate Cardiac Gene Expression through a p300-dependent Mechanism", J. Biol. Chem., vol. 277, 2002 pp. 24390-24398.
Daley, J., and Wilson, T., "Rejoining of DNA Double-Strand Breaks as a Function of Overhang Length," Molecular and Cellular Biology, vol. 25, 2005, pp. 896-906.
Damian, M., and Porteus, M., "A Crisper Look at Genome Editing: RNA-guided Genome Modification," Molecular Therapy, vol. 21, Apr. 2013, pp. 720-722.
Database GenBank, "*Staphylococcus aureus* subsp.aureus ORFX gene and pseudo SCCmec-SCC-SCCCRISPR element, strain M06/0171," Accession No. HE980450, http://www.ncbi.nlm.nih.gov/nuccore/HE980450, dated Aug. 18, 2016, 22 pages.
Database GenBank: "CRISPR-associated protein, Csn1 family, *Staphylococcus pseudintermedius* ED99," Accession No. ADX75954, http://www.uniprot.org/uniprot/G1UFN3.txt?version=3, dated Nov. 21, 2011, 1 page.
Database UniProt: "CRISPR-associated endonuclease Cas9: *Staphylococcus aureus*," UniProtKB, J7RUA5 (CAS9_STAAU), XP002738511M, https://www.uniprot.org/uniprot/J7RUA5#, dated Oct. 31, 2012, 7 pages.
Database UniProtKB/TrEMBL [online], Accession No. QOP897, "The genome sequence of the food-borne pathogen Campylobacter jejuni reveals hypervariable sequences," Subname: Full=Putative CRISPR-associated protein, Oct. 3, 2012 uploaded, [retrieved on Nov. 22, 2017], URL, http://www.uniprot.org/uniprot/Q0P897.txt?version=28.
Database UniProtKB/TrEMBL, Accession No. D0W2Z9, http://www.uniprot.org/uniprot/D0W2Z9.txt?version=4, dated Oct. 3, 2012, 1 page.
Database UniProtKB/TrEMBL, Accession No. G1UFN3, http://www.uniprot.org/uniprot/G1UFN3.txt?version=3, dated Oct. 3, 2012, 1 page.
Database UniProtKB/TrEMBL, Accession No. J3TRJ9, http://www.uniprot.org/uniprot/J3TRJ9.txt?version=2, dated Oct. 31, 2012, 1 page.
Database UniProtKB/TrEMBL, Accession No. Q6NK13, http://www.uniprot.org/uniprot/Q6NKI3.txt?version=43, dated Jun. 13, 2012, 1 page.
Database UniProtKB/TrEMBL, Accession No. Q73QW6, http://www.uniprot.org/uniprot/Q73QW6.txt?version=4, dated Nov. 28, 2012, 2 pages.
Database WPI, Week 201437 Thomson Scientific, London, GB; AN 2014-J79552, XP-002737563, 2 pages.
Datsenko, et al. "Molecular memory of prior infections activates the CRISPR/Cas adaptive bacterial immunity system", Nature Communications, vol. 3, 2012, pp. 1-7.
Dean., "Recent Advances in Drug Design Methods: Where Will They Lead?", BioEssays, vol. 16, Sep. 1994, pp. 683-687.
Declaration of Feng Zhang for U.S. Appl. No. 14/054,414 dated Jan. 30, 2014 (10 pages).
Declaration of Technical Expert Paul Simons dated Dec. 22, 2015, 76 pages.
Deltcheva, E., et al., "CRISPR RNA maturation by trans-encoded small RNA and host Factor RNase III," Nature, vol. 471, 2011, pp. 602-609.
Deltcheva, et al., "Supplementary Information: CRISPR RNA Maturation By Trans-Encoded Small RNA and Host Factor RNase III" Nature, pp. 1-35, 2011.
Deveau, H. et al., "Phage response to CRISPR-encoded resistance in *Streptococcus thermophilus*," Journal of Bacteriology, vol. 190, Feb. 2008, pp. 1390-1400.
Deveau, H., et al., "CRISPR/Cas system and its role in phage-bacteria interactions," Annu. Rev. Microbiol., vol. 64, 2010, pp. 475-493.
Dicarlo, et al., "Genome engineering in *Saccharomyces cerevisiae* using CRISPTR-Cas systems", Nucleic Acids Research, vol. 41, 2013 pp. 4336-4343.
Dingwall, et al. "A Polypeptide Domain That Specifies Migration Of Nucleoplasmin into The Nucleus", Cell, vol. 30, 1982, pp. 449-458, (Abstract only).
Dingwall, et al., "The Nucleoplasmin Nuclear Location Sequence Is Larger and More Complex than That of SV-40 Large T Antigen", The Journal of Cell Biology, vol. 107, 1988, pp. 841-849.
Do, et al., "Identification of multiple nuclear localization signals in murine Elf3, an ETS transcription factor" FEBS Letters, vol. 580, 2006, pp. 1865-1871.
Doench, et al., "Rational design of highly active sgRNAs for CRISPR-Cas9-mediated gene inactivation," Nature Biotechnology, vol. 32, 2014, pp. 1262-1267, including Supplementary Material, 17 pages.
Dominguez, et al., "Beyond editing: repurposing CRISPR-Cas 9 for precision genome regulation and interrogation" Nat Rev Mol Cell Biol., vol. 17, 2016, 17 pp. 5-15.
Dong, et al., "The crystal structure of Cpf1 in complex with CRISPR RNA," Nature, vol. 532, 2016, pp. 523-525.
Drittanti, et al. "High throughput production, screening and analysis of adeno-associated viral vectors", Gene Therapy, vol. 7, 2000, pp. 924-929.
Dworetzky, S., et al., "The Effects of Variations in the Number and Sequence of Targeting Signals on Nuclear Uptake," The Journal of Cell Biology, vol. 107, 1988, pp. 1279-1287.
E.S. Lander, "Initial impact of the sequencing of the human genome," Nature, vol. 470, Feb. 10, 2011, p. 187-197.
Ebina, H., et al., "Harnessing the CRISPR/Cas9 system to disrupt latent HIV-1 provirus," Scientific Reports, vol. 3, 2013, pp. 1-7, art. 2510.
Edgar, R. and Qimron, U., "The *Escherichia coli* CRISPR system protects from λ lysogenization, lysogens, and prophage induction," Journal of Bacteriology, vol. 192, Dec. 2010, pp. 6291-6294.
Ellis, B., et al., "Zinc-finger nuclease-mediated gene correction using single AAV vector transduction and enhanced by Food and Drug Administration-Approved Drugs," Gene Therapy, vol. 20, 2013, pp. 35-42.
Ellis, et al., "Macromolecular Crowding: Obvious But Underappreciated", Trends in Biochemical Sciences, vol. 26, 2001, pp. 597-604.
Ellis, Hilary, et al., "High efficiency mutagenesis, repair, and engineering of chromosomal DNA using single-stranded oligonucleotids" PNAS, vol. 98, 2001, pp. 6742-6746.
Enyeart, et al., "Biotechnological applications of mobile group II introns and their reverse transcriptases: gene targeting, RNA-seq, and non-coding RNA analysis", Mobile DNA, vol. 5, 2014, pp. 1-19 http://www.mobilednajournal.com/contents5/1/2.
Espinoza, et al., "Characterization of the structure, function, and mechanism of B2 RNA, an ncRNA repressor of RNA polymerase II transcription", RNA, vol. 13, 2007, pp. 583-596.
Esvelt et. al., "Orthogonal Cas9 proteins for RNA-guided gene regulation and editing", Nature Methods, vol. 10, No. 11, Nov. 2013 (available online Sep. 29, 2013), pp. 1116-1123.
Excerpt from Dr. Feng Zhang's Jan. 30, 2014 Declaration (Exhibit C1), 11 pages.

(56) References Cited

OTHER PUBLICATIONS

Federal Circuit decision in *Dow Chemical Co.* v. *Nova Chemicals Corp.*, Appeal Nos. 2014-1431, 2014-1462 (Fed. Cir. Aug. 28, 2015) (*Dow* v. *Nova*), 25 pages.
Feldgarden et al., "*Staphylococcus aureus* M0408 acrHk-supercont1. 1, whole genome shotgun sequence", NCBI Reference Sequence: NK_KB821326.1, Direct Submission, Dec. 10, 2012, pp. 1-4.
Fieck, et al., "Modifications of the *E.coli* Lac repressor for expression in eukaryotic cells: effects of nuclear signal sequences on protein activity and nuclear accumulation", Nucleic Acids Research, vol. 20, 1992, pp. 1785-1791.
Fischer, S. et al., "An archaeal immune system can detect multiple Protospacer Adjacent Motifs (PAMs) to target invader DNA," J. Biol. Chem., vol. 287, Sep. 28, 2012, pp. 33351-33363.
Fischer-Fantuzzi, L., and Vesco, C., "Cell-dependent efficiency of reiterated nuclear signals in a mutant simian virus 40 oncoprotein targeted to the nucleus," Molecular and Cellular Biology, vol. 8, 1988, pp. 5495-5503.
Flannery, J. G., "Ribozyme-Mediated Gene Therapy for Autosomal Dominant Retinal Degeneration", Retinal Degenerative Diseases and Experimental Therapy, 1999, pp. 277-291.
Fleming, J., et al., "Adeno-Associated Virus and Lentivirus Vectors Mediate Efficient and Sustained Transduction of Cultured Mouse and Human Dorsal Root Ganglia Sensory Neurons," Human Gene Therapy, vol. 12, Jan. 1, 2001, pp. 77-86.
Foecking, et al. "Powerful and versatile enhance-promoter unit for mammalian expression vectors", Gene, vol. 45, 1986, pp. 101-105.
Fonfara et al., "Phylogeny of Cas9 determines functional exchangeability of dual-RNA and Cas9 among orthologous type II CRISPR-Cas systems", Nucleic Acids Research, 2014, vol. 42, No. 4, pp. 2577-2590.
Freitas, et al., "Mechanisms and Signals for the Nuclear Import of Proteins", Current Genomics, vol. 10, 2009, pp. 550-557.
Fu, et al., "High-frequency off-target mutagenesis induced by CRISPR-Cas nucleases in human cells", Nature Biotechnology, vol. 31, 2013, pp. 822-826.
Fu, et al., "Targeted genome editing in human cells using CRISPR/Cas nucleases and truncated guide RNAs", The Use of CRISPR/Cas9 ZFNs and Talens in Generating Site-Specific Genome Alterations; Elsivier Inc., 2014, pp. 21-45.
G. Giaever et al., "Functional profiling of the *Saccharomyces cerevisiae* genome," Nature, vol. 418, Jul. 25, 2002, pp. 387-391.
G. Guo et al., "Mismatch repair genes identified using genetic screens in Blm-deficient embryonic stem cells," Nature, vol. 429, Jun. 24, 2004, p. 891.
Gabriel, R., et al., "An unbiased genome-wide analysis of zinc-finger nuclease specificity," Nature Biotechnology, vol. 29, 2011, pp. 816-823.
Gaj, T., et al., "Targeted Gene knockout by direct delivery of zinc-finger nuclease proteins," Nature Methods, vol. 9, 2012, pp. 805-807, including supplemental pages.
Gaj, T., et al., "ZFN, TALEN, and CRISPR/Cas-Based Methods for Genome Engineering," Trends in Biotechnology, vol. 31, 2013, pp. 397-405.
Gama Sosa, M., et al., "Animal transgenesis: an overview," Brain Structure and Function, vol. 214,0 2010, pp. 91-109.
Gao, et al. "Engineered Cpf1 variants with altered PAM specificities", Nature Biotechnology, vol. 35, Jun. 8, 2017, pp. 1-4 (789-792), doi: 10.1038/nbt.3900, advanced online publication including Supplementary Information.
Gao, et al., "A Sustained, Cytoplasmic Transgene Expression System delivered by Cationic Liposomes", Biochemical and Biophysical Research Communications, vol. 200, May 16, 1994, pp. 1201-1206.
Garcia-Bustos, et al., "Nuclear protein localization", Biochimica et Biophysica Acta, vol. 1071, 1991, pp. 83-101.
Gardlik, R., et al., "Vectors and delivery systems in gene therapy," Medical Science Monitor, vol. 11, No. 4, pp. RA110-RA121, dated Apr. 1, 2005, 12 pages.
Garg, et al. "Engineering synthetic TAL effectors with orthogonal target sites", Nucleic Acids Research, 2012, vol. 40, pp. 7584-7595, doi:10.1093/nar/gks404.
Garneau, et al., "The CRISPR-Cas bacterial immune systems cleaves bacteriophage and plasmid DNA", Nature, vol. 468, 2010, pp. 67-71.
Garriga-Canut, M., et al., "Synthetic zinc finger repressors reduce mutant huntingtin expression in the brain of R6/2 mice," Proceedings of the National Academy of Sciences, vol. 109, Oct. 10, 2012, pp. E3136-E3145.
Gasiunas, G, et al., "Cas9-crRNA ribonucleoprotein complex mediates specific DNA cleavage for adaptive immunity in bacteria," Proceedings of the National Academy of Sciences, vol. 109, 2012, p. E2579-2586.
Geibler, et al., "Transcriptional Activators of Human Genes with Programmable DNA-Specificity", PLone, vol. 6, 2011, pp. 1-7 Doi: 10.1371/hournal.pone.0019509.
Geisinger, et al., "In vivo blunt-end cloning through CRISPR /CAS9-facilitated non-homologous end-joining", Nucleic Acid Research Advance Access, vol. 44, 2016, pp. 1-15.
GenBank: "CRISPR-associated protein Cas9/Csn1 [*Staphylococcus aureus* subsp. aureus]", GenBank: CCK74173.1, Year: 2012, http://www.ncbi.nlm.nih.gov/protein/403411236?sat=16&satkey=13804560, dated Dec. 14, 2016, 2 pages.
Gibson, D.G. et al., "Enzymatic assembly of DNA molecules up to several hundred kilobases," Nat methods, vol. 6, 2009, pp. 343-345.
Gilbert, L., et al., "CRISPR-Mediated Modular RNA-Guided Regulation of Transcription in Eukaryotes," Cell, vol. 154, 2013, pp. 442-451.
Goldfarb, et al. "Synthetic peptides as nuclear localization signals", Nature, vol. 322, 1986, pp. 641-644.
Gomaa, et al. "Programmable removal of bacterial strains by use of genome-targeting CRISPR-Cas systems", MBio., vol. 5, 2014, pp. 1-9.
Goncalves, M., et al., "Concerted nicking of donor and chromosomal acceptor DNA promotes homology-directed gene targeting in Human Cells," Nucleic Acids Research, vol. 40, 2012, pp. 3443-3455.
Gratz, et al., "Genome Engineering of *Drosophila* with the CRISPR RNA-Guided Cas9 Nuclease", Genetics, vol. 194, 2013, pp. 1029-1035.
Greenspan, et al., "Two Nuclear Location Signals in the Influenza Virus NS1 Nonstructural Protein", Journal of Virology, vol. 62, 1988, pp. 3020-3026.
Greenwald, D L, et al., "Engineered Zinc Finger Nuclease-Mediated Homologous Recombination of the Human Rhodopsin Gene", Investigative Ophthalmology & Visual Science, vol. 51, Dec. 2010, pp. 6374-6380.
Grens, "Enzyme Improves CRISPR A smaller Cas9 protein enables in vivo genome engineering via viral vectors", The Scientist, Apr. 1, 2015.
Grieger, J., and Samulski, R., "Packaging Capacity of Adeno-Associated Virus Serotypes: Impact of Larger Genomes on Infectivity and Postentry Steps," Journal of Virology, vol. 79, 2005, pp. 9933-9944.
Grissa, I., et al., "CRISPRFinder: a web tool to identify clustered regularly interspaced short palindromic repeats," Nucleic Acids Research, vol. 35, 2007, pp. W52-W57.
Grosse, et al. "Meganuclease-medicated Inhibition of HSV1 Infection in Cultured Cells", Molecular Therapy, vol. 19, No. 4, Apr. 1, 2011, pp. 694-702.
Guan, et al., "Heritable endogenous gene regulation in plants with designed polydactyl zinc finger transcription factors", PNAS, vol. 99, 2002, pp. 13296-13301.
Gudbergsdottir, S. et al., "Dynamic properties of the Sulfolobus CRISPR/Cas and CRISPR/Cmr systems when challenged with vector-borne viral and plasmid genes and protospacers," Mol. Microbiology, vol. 79, 2011, pp. 35-49.
Gustafsson, et al. "Codon Bias and heterologous protein expression", Trends in Biotechnology, Jul. 2004, vol. 22, pp. 346-353.
H. Davies et al., "Mutations of the BRAF gene in human cancer," Nature, vol. 417, Jun. 27, 2002, p. 949-954.

(56) References Cited

OTHER PUBLICATIONS

H.W Cheung et al., "Systematic investigation of genetic vulnerabilities across cancer cell lines reveals lineage-specific dependencies in ovarian cancer," Proceedings of the National Academy of Sciences, vol. 108, Jul. 26, 2011, p. 12372-12377.
Habib, N., Assignment to Broad Institute, dated Jun. 9, 2014, 4 pages.
Haft, D., et al., "A Guild of 45 CRISPR-Associated (Cas) Protein Families and Multiple CRISPR/Cas Subtypes Exist in Prokaryotic Genomes," PLoS Computational Biology, vol. 1, 2005, pp. 0474-0483.
Haft, D.H., "Hmm Summary Page: TIGR04330", 2012, XP-002757584, http://jcvi.org/cgi-bin/tigrfams/HmmReportPage.cgi?acc=TIGR04330, 1 page.
Hale, et al. "Essential Features and Rational Design Of CRISPR RNAs that Function With The Cas RAMP Module Complex To Cleave RNAs", Molecular Cell, vol. 45, 2012, pp. 292-302.
Hale, et al. "RNA-Guided RNA Cleavage by a CRISPR RNA-Cas Protein Complex", Cell, vol. 139, 2009, pp. 945-956.
Hale, et al., "Prokaryotic silencing (psi) RNAs in Pyrococcus furiosus", RNA, vol. 14, 2008, pp. 2572-2579.
Hall, B., et al., "Overview: Generation of Gene Knockout Mice," Current Protocols in Cell Biology, unit 19.12, suppl. 44, Sep. 2009, pp. 1-17.
Handel, E., et al., "Versatile and Efficient Genome Editing in Human Cells by Combining Zinc-Finger Nucleases With Adeno-Associated Viral-Vectors," Human Gene Therapy, vol. 23, 2012, pp. 321-329.
Harrison, et al., "A CRISPR view of development", Genes & Development, vol. 28, 2014, pp. 1859-1872.
Hatoum-Aslan, A., et al., "Mature clustered, regularly interspaced, short palindromic repeats RNA (crRNA) length is measured by a ruler mechanism anchored at the precursor processing site," Proc. Natl. Acad. Sci., vol. 108, Dec. 27, 2011, pp. 21218-21222.
Haurwitz, R.E., et al., "Sequence- and structure-specific RNA processing by a CRISPR endonuclease," Science, vol. 329, 2010, pp. 1355-1358.
Havarstein, L.S., et al., "An unmodified heptadecapeptide pheromone induces competence for genetic transformation in *Streptococcus pneumoniae*," Proc. Natl. Acad. Sci., vol. 92, Nov. 1995, pp. 11140-11144.
Heintze, et al. "A CRISPR CASe for high-throughput silencing", Frontiers in Genetics, vol. 4, 2013, pp. 1-6 DOI:10.3389/gfene.2013.00193.
Hemann et al., "An epi-allelic series of p53 hypomorphs created by stable RNAi produces distinct tumor phenotypes in vivo," Nat Genetics, vol. 33, Mar. 2003, pp. 396-400.
Hibbitt, O., et al., "RNAi-mediated knockdown of HMG CoA reductase enhances gene expression from physiologically regulated low-density lipoprotein receptor therapeutic vectors in vivo," Gene Therapy, vol. 19, 2012, pp. 463-467.
Hicks, et al. "Protein Import Into the Nucleus: An Integrated View", Annu. Rev. Cell Dev. Biology, vol. 11, 1995, pp. 155-188.
Ho, et al., "Targeting non-coding RNAs with the CRISPR/Cas9 system in human cell lines," Nucleic Acids Research, vol. 43, 2015, pp. 1-11.
Hockemeyer, et al., "Highly efficient gene targeting of expressed and silent genes in human ESCs and iPSCs using zinc finger nucleases", Nat Biotechnology, vol. 27, 2009, pp. 851-857, doi:10.1038/nbt.1562.
Holkers, M., et al., "Adenoviral vector DNA for accurate genome editing with engineered nucleases," Nature Methods, vol. 11, 2014, pp. 1051-1057, (Only Abstract Available).
Holmes, "CRISPR Genome Engineering Resources" XP055167586, Oct. 2, 2013, https://groups.google/forum/#!top1c/crispr/5BpJj_Y3yIG [retrieved on Feb. 5, 2015].
Holmes, "Understanding Scores" XP055167918, Oct. 23, 2013, https://groups.google.com/forum/#!profo_nt50txrP9Yb6e_LXccolb9hNf7gKeMLt6rgaVQ4fOsQ/crispr/fkhX7Fu3r-I/rziHxKT76pYJ [retrieved on Feb. 6, 2015].
Horinouchi, S. and Weisblum, B., "Nucleotide sequence and functional map of pC194, a plasmid that specifies inducible chloramphenicol resistance," J. Bacteriology, vol. 150, May 1982, pp. 815-825.
Horton, R.M., "In Vitro recombination and Mutagenesis of DNA: SOEing Together Tailor-Made Genes," Methods Mol. Biology, vol. 15, 1993, pp. 251-261.
Horvath, P. and Barrangou, R. "CRISPR/Cas, the immune system of bacteria and archaea," Science, vol. 327, Jan. 8, 2010, pp. 167-170.
Horvath, P., and Barrangou, R., "RNA-guided genome editing a la carte," Cell Research, vol. 23, 2013, pp. 733-734.
Hosaka, T. et al., "The novel mutation K87E in ribosomal protein S12 enhances protein synthesis activity during the late growth phase in *Escherichia coli*." Mol. Gen. Genomics, vol. 271, 2004, pp. 317-324.
Hoskins, J. et al., "Genome of the bacterium *Streptococcus pneumoniae* strain R6," Journal of Bacteriology, vol. 183, Oct. 2001, pp. 5709-5717.
Hou, Z., et al., "Efficient genome engineering in human pluripotent stem cells using Cas9 from Neisseria meningitides," Proceedings of the National Academy of Sciences, vol. 110, 2013, pp. 15644-15649.
Houdebine, L., "The methods to generate transgenic animals and to control transgene expression," Journal of Biotechnology, vol. 98, 2002, pp. 145-160.
Hsu et al., "Supplementary Information—DNA targeting specificity of RNA-guided Cas9 nucleases," Nature Biotechnology, 2013, doi:10.1038/nbt.2647.
Hsu, et al., "DNA targeting specificity of RNA-guided Cas9 nucleases," Nature Biotechnology, vol. 31, 2013, pp. 827-834.
Hsu, P., et al., "Development and Applications of CRISPR-Cas9 for Genome Engineering," Cell, vol. 157, 2014, pp. 1262-1278.
*Huang* v. *California Institute of Technology*, 2004 WL 2296330 (C.D. Cal. Feb. 18, 2004), 20 pages.
Hung, S., et al., "AAV-Mediated CRISPR/Cas Gene Editing of Retinal Cells in Vivo," Investigative Ophthalmology & Visual Science, vol. 57, 2016, pp. 3470-3476.
Husmann, L.K., et al., "Expression of the Arp protein, a member of the M protein family, is not sufficient to inhibit phagocytosis of *Streptococcus pyogenes*," Infection and immunity, vol. 63, Jan. 1995, pp. 345-348.
Hwang W., et al., "Efficient In Vivo Genome Editing Using RNA-Guided Nucleases," Nature Biotechnology, vol. 31, No. 3, Mar. 2013, pp. 227-229 (12 pages).
Hwang, W.Y., et al., "Efficient Genome Editing in Zebrafish Using a CRISPR-Cas System", Nature Biotechnology, vol. 31, No. 3, Jan. 29, 2013, pp. 227-229.
Imagawa, et al., "Two nuclear localization signals are required for nuclear translocation of nuclear factor 1-A", FEBS Letters, vol. 484, 2000, pp. 118-124.
Incontro, S., et al., "Efficient, Complete Deletion of Synaptic Proteins using CRISPR," Neuron, vol. 83, 2014, pp. 1051-1057, 13 pages.
Ishino Y. et al., "Nucleotide sequence of the iap gene, responsible for alkaline phosphatase isozyme conversion in *Escherichia coli*, and identification of the gene product," J. Bacteriology, vol. 169, Dec. 1987, pp. 5429-5433, 5 pages.
Iwamoto et al., "A General Chemical Method to Regulate Protein Stability in the Mammalian Central Nervous System", Chemistry and Biology, Current Biology, vol. 17, Sep. 24, 2010, pp. 981-988, 8 pages.
J. Merkin et al., "Evolutionary dynamics of gene and isoform regulation in Mammalian tissues," Science, vol. 338, Dec. 21, 2012, p. 1593-1599, 7 pages. Includes Supplementary Information, 34 pages.
J.E. Carette et al., "Haploid genetic screens in human cells identify host factors used by pathogens," Science, vol. 326, Nov. 27, 2009, p. 1231-1235, 5 pages.
J.F. Rual et al., "Toward Improving Caenorhabditis elegans Phenome Mapping with an ORFeome-Based RNAi Library," Genome Research, vol. 14, 2004, pp. 2162-2168, 7 pages.
J.M. Engreitz et al., "The Xist IncRNA exploits three-dimensional genome architecture to spread across the X chromosome," Science, vol. 341, Aug. 16, 2013, pp. 1-8, 8 pages.

(56) References Cited

OTHER PUBLICATIONS

Jackson, A., et al., "Widespread siRNA "off-target" transcript silencing mediated by seed region sequence complementarity," RNA vol. 12, 2006, pp. 1179-1187, 10 pages.
Jansen R. et al., "Identification of genes that are associated with DNA repeats in prokaryotes," Molecular Microbiology, vol. 43, 2002, pp. 1565-1575, 11 pages.
Janssen, et al., "Mouse Models of K-ras-Initiated Carcinogenesis", Biochimicia et Biophysica Acta, vol. 1756 2005, pp. 145-154, 10 pages.
Jao, et al., "Efficient multiplex biallelic zebrafish genome editing using a CRISPR nuclease system", Proceeding of the National Academy of Sciences, PNAS 2013, pp. 1-6, includes supplementary information, pp. 1-10. www.pnas.org/cgi/doi/10.1073/pnas.1308335110.
Jiang, W., et al., "RNA-guided editing of bacterial genomes using CRISPR-Cas systems," Nature Biotechnology, vol. 31, Mar. 2013, pp. 233-239, 30 pages, including supplementary information.
Jinek, M., et al., "A Programmable Dual-RNA-Guided DNA Endonuclease In Adaptive Bacterial Immunity," Science, vol. 337, Aug. 17, 2012 pp. 816-821, including supplementary information, 45 pages.
Jinek, M., et al., "RNA-programmed genome editing in human cells", eLIFE, vol. 2, No. e00471, 2013, 9 pages.
Jinek, M., et al., Figures and figure supplements for: "RNA-programmed genome editing in human cells," eLIFE, vol. 2, 2013, 5 pages.
JL. Mummery-Widmer et al., "Genome-wide analysis of Notch signalling in *Drosophila* by transgenic RNAi," Nature, vol. 458, Apr. 23, 2009, pp. 987-992, 6 pages. Includes Supplementary information, 2 pages.
Joseph, T., and Osman, R., "Thermodynamic basis of selectivity in guide-target-mismatched RNA interference," Proteins, vol. 80, 2012, pp. 1283-1298, 26 pages.
Joshi, et al., "Evolution of I-Scel homing endonucleases with increased DNA recognition site specificity", Journal of Molecular Biology, 2011, vol. 405, pp. 185-200, 16 pages. Includes supplementary information, 14 pages.
Joung, et al., "TALENS: a widely applicable technology for targeted genome editing", Nat Ref. Mol. Cell Biology, vol. 14, 2013, pp. 49-55, 7 pages. doi:10.1038/nrm3586.
K. Yoshimoto et al., "Complex DNA repair pathways as possible therapeutic targets to overcome temozolomide resistance in glioblastoma," Front Oncology, vol. 2, Dec. 2012, pp. 1-8, 8 pages.
K.T Flaherty et al., "Inhibition of mutated, activated BRAF in metastatic melanoma," The New England Journal of Medicine, vol. 363, Aug. 26, 2010, pp. 1-22, 22 pages.
Kalderon, et al., "A Short Amino Acid Sequence Able to Specify Nuclear Location", Cell, vol. 39, 1984, pp. 499-509, 11 pages.
Kanasty, R., et al., "Delivery materials for siRNA therapeutics," Nature Materials, vol. 12, 2013, pp. 967-977, 11 pages.
Karvelis, et al., "crRNA and tracrRNA guide Cas9-mediated DNA interference in *Streptococcus thermophiles*" RNA Biology, vol. 10, 2013, pp. 841-851, 11 pages.
Karvelis, et al., "Supplemental Material to: crRNA and tracrRNA guide Cas9-mediated DNA interference in *Streptococcus thermophiles*", Landes Bioscience, vol. 10, 2013, pp. 1-8, 9 pages. http://dx.doi.org/10.4161/rna.24203.
Kiani, et al., "CAS9 gRNA engineering for genome editing, activation and repression", Nature Methods, Advanced Online Publication, 2015, pp. 1-6. DOI:10.1038/NMETH.3580.
Kim et al., "High Cleavage Efficiency of a 2A Peptide Derived from Porcine Teschovirus-1 in Human Cell Lines, Zebrafish and Mice," PLoS One, vol. 6, Apr. 2011, pp. 1-8, 8 pages.
Kim, E., et al., "Precision genome engineering with programmable DNA-nicking enzymes," Genome Research, vol. 22, 2012, pp. 1327-1333, 8 pages.
Kim, et al., "Crystal structure of Cas1 from Archaeoglobus fulgidus and characterization of its nucleolytic activity", Biochemical and Biophysical Research Communications, 2013, vol. 441, 2013, pp. 720-725, 6 pages.
Kim, S., et al., "CRISPER RNAs trigger innate immune responses in human cells," Genome Research, 2018, pp. 1-7, 8 pages.
Kinnevey, P., et al., "Emergence of Sequence Type 779 Methicillin-Resistant *Staphylococcus aureus* Harboring a Novel Pseudo Staphylococcal Cassette Chromosome mec (SCCmec)-SCC-SCC CRISPR Composite Element in Irish Hospitals," Antimicrobial Agents and Chemotherapy, vol. 57, 2013, pp. 524-531, 8 pages. Includes Supplementary information, 9 pages.
Kleinstiver et al., "High-fidelity CRISP-Cas9 nucleases with no detectable genome-wide off-target effects", Nature, vol. 529, Jan. 28, 2016, pp. 490-495, 6 pages. Includes Supplementary information, 12 pages.
Kleinstiver, et al. "Engineered CRISPR-Cas9 nucleases with altered PAM specificities," Nature, vol. 523, vol. 523, 2015, pp. 1-27, 27 pages.
Koike-Yusa, H., et al., "Genome-wide recessive genetic screening in mammalian cells with a lentiviral CRISPR-guide RNA library," Nat Biotechnology, vol. 32, Mar. 2014, pp. 267-273, 7 pages. Including Supplemental information, 3 pages. doi:10.1038/nbt.2800.
Kondo, et al., "Highly Improved Gene Targeting by Germline-Specific Cas9 Expression in *Drosphila*", Genetics, vol. 195, 2013, pp. 715-721, 7 pages. Including Supplemental information 14 pages.
Konermann, et al., "Genome-scale transcriptional activation by an engineered CRISPR-Cas9 complex", Nature, vol. 517, 2015, pp. 583-588, 6 pages. Including Supplemental information, 12 pages.
Koo et al., "Measuring and Reducing Off-Target Activities of Programmable Nucleases Including CRISPR-Cas9", Molecules and Cells, vol. 38, 2015, pp. 475-481, 7 pages.
Koornneef, A., et al., "Apoliprotein B Knockdown By AAV-Delivered shRNA Lowers Plasma Cholesterol In Mice," Molecular Therapy, vol. 19, 2011, pp. 731-740, 10 pages.
Kosugi, et al. "Six Classes of Nuclear Localization Signals Specific to Different Binding Grooves of Importin a .. " The Journal of Biological Chemistry, 2009, vol. 284 pp. 478-485, 8 pages. Including Supplemental information, 21 pages.
Kowalski, Thomas J., PowerPoint Presentation, Presented and Discussed during Sep. 9, 2015 Interview (Exhibit B), 51 pages.
Krauer, et al. "Identification of the nuclear localization signals within the Epstein-Barr virus EBNA-6 protein", Journal of General Virology, vol. 85, 2005, pp. 165-172, 8 pages.
Kuhlman, et al. "A place for everything—Chromosomal intergration of large constructs", Bioengineered Bugs, vol. 1, 2010, pp. 296-299, 4 pages.
Kuhlman, et al., "Site-specific chromosomal integration of large synthetic constructs", Nucleic Acids Research, 2010, vol. 38, pp. 1-10, 10 pages. doi:10.1093/nar/gkp1193.
Kumar, M., et al., "Systematic Determination of the Packaging Limit of Lentiviral Vectors," Human Gene Therapy, vol. 12, Oct. 10, 2001, pp. 1893-1905, 21 pages.
Kuwayama, H., "Enhancement of Homologous Recombination Efficiency by Homologous Oligonucleotides," Cell 2012, pp. 233-244, 12 pages. IntechOpen, DOI: 10.5772/47779.
Laganiere et. al., "An Engineered Zinc Finger Protein Activator of the Endogenous Glial Cell Line-Derived Neurotrophic Factor Gene Provides Functional Neuroprotection in a Rat Model of Parkinson's Disease", The Journal of Neuroscience, vol. 30, Dec. 8, 2010, pp. 16469-16474, 6 pages.
Lambowitz, et al., "Group II Introns: Mobile Ribozymes that Invade DNA", Cold Spring Harb Perspect Biology, 2011, pp. 1-20, 20 pages. 3:a003616.
Lanford, et al., "Induction of Nuclear Transport with a Synthetic Peptide Homologous to the SV40 T Antigen Transport Signal", Cell, vol. 46, Aug. 15, 1986, pp. 575-582, 8 pages.
Lange, et al. "Classical Nuclear Localization Signals: Definition, Function, and Interaction with Importin$2026" J. Biology, vol. 282, 2007, pp. 5101-5105, including Supplemental information, 5 pages.

(56) References Cited

OTHER PUBLICATIONS

Larson, et al., "CRISPR interference (CRISPRi) for sequence-specific control of gene expression", Nature Protocols, vol. 8, 2013, pp. 2180-2196, 17 pages.
Lebherz, C., et al., "Gene therapy with novel adeno-associated virus vectors substantially diminished atherosclerosis in a murine model of familial hypercholesterolemia," The Journal of Gene Medicine, vol. 6, 2004, pp. 663-672, 10 pages.
Lee, C., et al., "Correction of the F508 Mutation in the Cystic Fibrosis Transmembrane Conductance Regulator Gene by Zinc-Finger Nuclease Homology-Directed Repair," Bioresearch Open Access, vol. 1, No. 3, pp. 99-108, dated 2012, 12 pages.
Leenay, et al., "Identifying and Visualizing Functional PAM Diversity across CRISPR-Cas Systems", Molecular Cell, vol. 62, 2016, pp. 137-147, 11 pages.
Lemay, et al., "Folding of the Adenine Riboswitch", Chemistry & Biology, vol. 13, 2006, pp. 857-868, 12 pages.
Levitt, J., et al., "Intrinsic fluorescence and redox changes associated with apoptosis of primary human epithelial cells," Journal of Biomedical Optics, vol. 11, No. 6, pp. 064012-1 to 064012-10, dated Nov./Dec. 2006, 10 pages.
Lewin, et al., "Nuclear localization sequences target proteins to the nucleus" Cells, vol. 5, 2006, 224.
Lewis, et al., "The c-myc and PyMT oncogenes induce different tumor types in a somatic mouse model for pancreatic cancer" Genes & Development, 2003, vol. 17 pp. 3127-3138, 14 pages.
Li et al., "Coevolution of CRISPR-Cas system with bacteria and phages", Hereditas, vol. 33, 2011, pp. 213-218, 6 pages.
Li, et al., "In vivo genome editing restores hemostasis in a mouse model of hemophilia" Nature, 2011, vol. 475, pp. 217-221, 5 pages. doi: 10.1038/nature10177.
Li, et al., "Multiplex and homologous recombination-mediated genome editing in *Arabidopsis* and Nicotaina benthamiana using guide RNA and Cas9" Nature Biotechnology, 2013, vol. 31 pp. 688-691, 4 pages.
Li, P., et al., "Biallelic knockout of alpha-1,3 galactosyltransferase gene in porcine liver-derived cells using zing finger nucleases," Journal of Surgical Research, vol. 181, 2013, pp. E39-E45, 7 pages.
Li, Ting, et al. "Modularly assembled designer TAL effector nucleases for targeted gene knockout and gene replacement in eukaryotes" Nucleic Acids Research, vol. 39, 2011, pp. 6315-6325, 11 pages.
Liu, et al. "Epstein-Barr Virus DNase Contains Two Nuclear Localization Signals Which Are Different in Sensitivity to the Hydrophobic Regions" Virology, vol. 247, pp. 62-73, 10 pages, 1998.
Lombardo, A., et al., "Gene editing in human stem cells using zinc finger nucleases and integrase-defective lentiviral vector delivery," Nature Biotechnology, vol. 25, 2007, pp. 1298-1306, 9 pages.
Los, et al., "Halotag Technology: Cell Imaging and Protein Analysis" Cell Notes, vol. 14, 2006, pp. 10-14, 5 pages.
Luo, B., et al., "Highly parallel identification of essential genes in cancer cells," Proceeding of the National Academy of Sciences, vol. 105, 2006, pp. 20380-20385, 6 pages.
Luo, Ming, et al., "Multiple Nuclear Localization Sequences Allow Modulation of 5-Lipoxygenase Nuclear Import" Traffic, 2004, vol. 5, pp. 847-854, 8 pages.
Lyssenko, et al., "Cognate putative nuclear localization signal effects strong nuclear localization of a GFP reporter and facilitates gene expression studies in Caenorhabditis elegans" BioTechniques, 2007, vol. 43 pp. 596-600, 5 pages.
M. Booker et al., "False negative rates in *Drosophila* cell-based RNAi screens: a case study," BMC Genomics, vol. 12, 2011, pp. 1-11, 11 pages.
M. Costanzo et al., "The genetic landscape of a cell," Science, vol. 327, Jan. 22, 2010, pp. 425-431, 8 pages.
Ma, M., et al., "A Guide RNA Sequence Design Platform for the CRISPR/Cas9 System for Model Organism Genomes," Hindawi, vol. 2013, 2013, art. 270805, pp. 1-5, 5 pages.
Maczuga, P., et al., "Embedding siRNA sequences targeting Apolipoprotein B100 in shRNA and miRNA scaffolds results in differential processing and in vivo efficacy," Molecular Therapy, vol. 21, 2013, pp. 217-227, 11 pages.
Madisen et al., "A robust and high-throughput Cre reporting and characterization system for the whole mouse brain," Nat. Neuroscience, vol. 13, Jan. 2010, pp. 133-140, 8 pages.
Maeder, et al., "CRISPR RNA-guided activation of endogenous human genes" Nature Methods, vol. 10, 2013, pp. 977-979, 3 pages. doi.10.1038/nmeth.2556.
Maeder, M., and Gersbach, C., "Genome-editing Technologies for Gene and Cell Therapy," Molecular Therapy, vol. 24, 2016, pp. 430-446, 17 pages.
Maeder, M., et al., "Robust, synergistic regulation of human gene expression using TALE activators," Nature Methods, vol. 10, 2013, pp. 243-245, 3 pages. Including Supplemental information, 6 pages.
Mahfouz, et al., "Targeted transcriptional repression using a chimeric TALE-SRDX repressor protein" Plant Mol Biology, vol. 78, 2012, pp. 311-321, 11 pages.
Mahfouz, M., et al., "De novo-engineered transcription activator-like effector (TALE) hybrid nuclease with novel DNA binding specificity creates double-strand breaks," Proceedings of the National Academy of Science, vol. 108, 2011, pp. 2623-2628, 6 pages.
Makarova, et al., "An updated evolutionary classification of CRISPR-Cas systems" Nature Reviews-Microbiology, vol. 13 2015, pp. 722-736, 15 pages.
Makarova, K., et al., "Evolution and classification of the CRISPR-CAS Systems," Nature Reviews Microbiology, vol. 9, 2011, pp. 467-477, 11 pages. Including Supplemental information, 23 pages.
Makarova, K., et al., "Unification of Cas protein families and a simple scenario for the origin and evolution of CRISPR-Cas systems," Biology Direct, vol. 6, No. 38, 2011, pp. 1-27, 27 pages.
Mali, et al. "RNA-Guided Human Genome Engineering Via Cas9" Science, vol. 339, pp. 823-826, dated Feb. 15, 2013, 41 pages (Includes Supplemental Information).
Mali, et al., Supplementary Information for "Use of adjacent sgRNA: Cas9 complexes for transcriptional activation and genome engineering," Nature Biotechnology, pp. 1-36, 36 pages. doi:10.1037/nbt.2675, 2013.
Mali, P., et al., "CAS9 transcriptional activators for target specificity screening and paired nickases for cooperative genome engineering," Nature Biotechnology, vol. 31, No. 9, pp. 833-838, dated Aug. 1, 2013, 44 pages (Includes Supplemental Information).
Mali, P., et al., Supplementary Information for: "RNA-Guided Human Genome Engineering via Cas9," Science, vol. 339, pp. 823-826, 2013, 8 pages.
Malina, A., et al., "Repurposing CRISPR/Cas9 for in situ functional assays," Genes & Development, vol. 27, 2013, pp. 2602-2614, 13 pages.
Manjunath, N., et al., "Newer Gene Editing Technologies toward HIV Gene Therapy," Viruses, vol. 5, pp. 2748-2766, 2013, 19 pages.
*Manning* v. *Paradis*, 296 F.3d 1098 (Fed. Cir. 2012), 9 pages.
Marraffini, L., "CRISPR-Cas Immunity against Phages: Its Effects on the Evolution and Survival of Bacterial Pathogens," PLOS, Dec. 12, 2013, pp. 1-6, 6 pages.
Marraffini, L., Assignment to Rockefeller University, dated Dec. 12, 2013, 3 pages.
Marraffini, L., et al., "Self vs. non-self discrimination during CRISPR RNA-directed immunity," Nature, vol. 463, 2010, pp. 568-571, 13 pages.
Marraffini, L.A., et al., "Sortases and the art of anchoring proteins to the envelopes of gram-positive bacteria," Microbiol. Mol. Biology Review vol. 70, Mar. 2006, pp. 192-221, 3 pages.
Martin, M., "Cutadapt removes adapter sequences from high-throughput sequencing reads," EMBnet.journal, vol. 17, 2011, pp. 10-12, 3 pages.
Mastroianni, et al., "Group II Intron-Based Gene Targeting Reactions in Eukaryotes" Plos One, vol. 3, 2008, pp. 1-15, 15 pages. Doi:10.1371/journal.pone.0003121.
*Maxwell* v. *The Stanley Works*, 2006 WL 1967012, *5 (M.D. Tenn. Jul. 11, 2006), 7 pages.
Meshorer, et al., "Chromatin in pluripotent embryonic stem cells and differentiation" Nature Reviews Molecular Cell Biology, vol. 7, 2006, pp. 540-546, 7 pages.

(56) References Cited

OTHER PUBLICATIONS

Miller, et al., "A Tale nuclease architecture for efficient genome editing" Nature Biotechnology, vol. 29, 2011, pp. 143-150, 8 pages.
Mincer, J., and Simon, S., "Simulations of nuclear pore transport yield mechanistic insights and quantitative predictions," Proceedings of the National Academy of Science, vol. 108, pp. E351-E358, 8 pages, 2011.
Minton, "How can biochemical reactions within cells differ from those in test tubes?" Journal Of Cell Science, 2006, vol. 119, pp. 2863-2869, 7 pages.
Moffat J et al., "A lentiviral RNAi library for human and mouse genes applied to an arrayed viral high-content screen," Cell, vol. 124, Mar. 24, 2006, pp. 1283-1298, 16 pages.
Mojica F. J. M et al., "Biological significance of a family of regularly spaced repeats in the genomes of Archaea, Bacteria and mitochondria," Molecular Microbiology, vol. 36, 2000, pp. 244-246, 3 pages.
Mojica, F. J., et al., "Short motif sequences determine the targets of the prokaryotic CRISPR defence system," Microbiology, vol. 155, 2009, pp. 733-740, 8 pages.
Mojica, F. J., et al., Supplementary Material for: "Short motif sequences determine the targets of the prokaryotic CRISPR defence system," Microbiology, vol. 155, 2009, 37 pages.
Morbitzer, et al., "Assembly of custom TALE-type DNA binding domains by modular cloning," Nucleic Acids Research, vol. 39, pp. 5790-5799, 10 pages, 2011.
Morbitzer, et al., "Regulation of selected genome loci using de novo-engineered transcription activator-like effector (TALE)-type transcription factors" PNAS, vol. 108, 2010, pp. 21617-21622, 6 pages.
Morgan, et al., "Inducible Expression and Cytogenetic Effects of the EcoRI Restriction Endonuclease in Chinese Hamster Ovary Cells" Molecular and Cellular Biology, vol. 8, 1988, pp. 4204-4211, 8 pages.
Morin, et al., "Nuclear Localization of the Adenovirus DNA-Binding Protein: Requirement for Two Signals and Complementation during Viral Infection" Molecular and Cellular Biology, vol. 9, 1989, pp. 4372-4380, 9 pages.
Morris et al., "Distributed automated docking of flexible ligands to proteins: Parallel applications of AutoDock 2.4*", Journal of Computer-Aided Molecular Design, 1996, vol. 10, pp. 293-304.
Moscou, et al., "A Simple Cipher Governs DNA Recognition by TAL Effectors" Science, vol. 326, 2009, p. 1501.
Motamedi, M.R., et al., "Double-strand-break repair recombination in *Escherichia coli*: physical evidence for a DNA replication mechanism in vivo," Genes Dev., vol. 13, 1999, pp. 2889-2903.
Mukhopadyay, R., "On the Same Wavelength," ASBMB Today, http://www.asbmb.org/asbmbtoday/201408/Features/Doudna/, dated Aug. 2014, 6 pages.
Mussolino, et al., "TALE nucleases: tailored genome engineering made easy" Current Opinion in Biotechnology, vol. 23, 2012, pp. 644-650, 7 pages.
Musunuru, "Abstract 18593: Use of a CRISPR/Cas System for Cardiovascular Disease Modeling and Therapeutic Applications", Circulation, vol. 128, 2013, 4 pages (Meeting info: American Heart Association, 2013 Scientific Sessions and Resuscitation Science Symposium, Dallas, TX, US, Nov. 16-20, 2013).
Muther, N., et al., "Viral Hybrid Vectors for Somatic Integration—Are They the Better Solution?" Viruses, vol. 1, 2009, pp. 1295-1324, 30 pages.
Nagarajan, et al., "A Hierarchy of Nuclear Localization Signals Governs the Import of the Regulatory Factor X Complex Subunits and MHC Class II Expression" The Journal of Immunology, vol. 173, 2004, pp. 410-419, 11 pages.
Nakai, et al., "PSORT: a program for detecting sorting signals in proteins and predicting their subcellular localization" Trends in Biochem Sciences, vol. 24, 1999, pp. 34-35, 2 pages.
Nakamura, et al., "Codon usage tabulated from international DNA sequence databases: status for the year 2000" Nucleic Acids Research, vol. 28, 2000, p. 292.
Nishimasu, et al., "Crystal Structure of Cas9 in Complex with Guide RNA and Target DNA", Cell, Feb. 27, 2014, vol. 156, pp. 935-949.
Nishimasu, H., et al., "Crystal Structure of *Staphylococcus aureus* Cas9," Cell, vol. 162, Aug. 27, 2015, pp. 1113-1126, 15 pages.
Noguchi, et al., "PDX-1 Protein Containing Its Own Antennapedia-Like Protein Transduction Domain Can Transduce Pancreatic Duct and Islet Cells" Diabetes, 2003, vol. 52 pp. 1732-1737, 6 pages.
Nomura, S., et al., "Low-density lipoprotein receptor gene therapy using helper-dependent adenovirus produces long-term protection against atherosclerosis in a mouse model of familial hypercholesterolemia," Gene Therapy, vol. 11, 2004, pp. 1540-1548, 10 pages.
Notice of Opposition filed Aug. 11, 2017 by Schlich against EP Patent No. 2840140, 58 pages.
Notice of Opposition filed Aug. 14, 2017 by Grund against EP Patent No. 2840140, 64 pages.
Notice of Opposition filed Aug. 16, 2017 by Mathys & Squire LLP against EP Patent No. 2840140, 36 pages.
Notice of Opposition filed by Aug. 16, 2017 by Vossius against EP Patent No. 2840140, 67 pages.
O'Hare, et al., "Transformation of mouse fibroblasts to methotrexate resistance by a recombinant plasmid expressing a prokaryotic dihydrofolate reductase" Proc. Natl. Acad. Sci., vol. 78 2011, 1527-1531, 5 pages.
Opposition Against Appl. Ser. No. EP13818570.7 submitted by Schlich dated Oct. 26, 2015, 8 pages.
Opposition Against EP Appl. Ser. No. 2771468-B1 dated Oct. 26, 2015, 40 pages.
Ozawa, K., "Gene therapy using AAV," Virus, vol. 57, pp. 47-55, dated, 2007, 13 pages (with English Abstract; No English Translation).
Paddison et al., "A resource for large-scale RNA-interference-based screens in mammals," Nature, vol. 428, Mar. 25, 2004, pp. 427-431, 5 pages.
Pandika, et al., www.ozy.com/rising-stars-and-provocateurs/jennifer-doudna-crispr-code-killer/4690; Jan. 7, 2014.
Panyam, J., and Labhasetwar, V., "Biodegradable nanoparticles for drug and gene delivery to cells and tissue," Advanced Drug Delivery Reviews, vol. 55, 2003, pp. 329-347, 19 pages.
Park, et al., "Regulation of Ribosomal S6 Kinase 2 by Mammalian Target of Rapamycin", The Journal of Biological Chemistry, vol. 277, 2002, pp. 31423-31429, 7 pages.
Pattanayak, et al., "High-throughput profiling of off-target DNA cleavage reveals RNA-programmed Cas9 nuclease specificity," Nature Biotechnology, vol. 31, 2013, pp. 839-843, 5 pages. Including Supplementary Materials, 2 pages.
Patterson, et al., "Codon optimization of bacterial luciferase (lux) for expression in mammalian cells" J. Ind. Microbio. Biotechnology, vol. 32, 2005, 115-123, 9 pages.
Perez-Pinera, et al., "Advances in Targeted Genome Editing" Curr Opin Chem Biology, vol. 16, 2012, pp. 268-277, 10 pages. doi:10.1016/j.cbpa.2012.06.007, 17 pages.
Perez-Pinera, et al., "RNA-guided gene activation by CRISPR-Cas9-based transcription factors" Nature Methods, 2013, vol. 10, pp. 1-12.
Phillips, A., "The challenge of gene therapy and DNA delivery," The Journal of Pharmacy and Pharmacology, vol. 53, 2011, pp. 1169-1174, 6 pages.
Planey, et al. "Mechanisms of Signal Transduction: Inhibition of Glucocorticoid-induced Apoptosis in 697 Pre-B Lymphocytes by the Mineralocorticoid Receptor N-terminal Domain", Journal of Biological Chemistry, vol. 277, 2002, pp. 42188-42196, 9 pages.
Platt, R., et al., "CRISPR-Cas9 Knockin Mice for Genome Editing and Cancer Modeling," Cell, vol. 159, 2014, pp. 440-455, 16 pages.
Podbielski, A., et al., "R. Novel series of plasmid vectors for gene inactivation and expression analysis in group A streptococci (GAS)," Gene, vol. 177, 1996, pp. 137-147, 11 pages.
Porteus, et al., "Gene targeting using zinc finger nucleases" Nature Biotechnology, Aug. 2005, vol. 23 pp. 967-973, 7 pages.
Porteus, M., and Balitmore, D., "Chimeric Nucleases Stimulate Gene Targeting in Human Cells," Science, vol. 300, 2003, p. 763, 2 pages.

(56) References Cited

OTHER PUBLICATIONS

Posfai, et al., "Markerless gene replacement in *Escherichia coli* stimulated by a double-strand break in the chromosome" Nucleic Acids Research, vol. 27, 1999, pp. 4409-4415, 7 pages.
Pougach, et al., "Transcription, Processing and Function of CRISPR Cassettes in *Escherichia coli*" Mol. Microbiology, vol. 77, 2010, pp. 1367-1379, 14 pages.
Pougach, K.S., et al., "CRISPR Adaptive Immunity Systems of Prokaryotes," Molecular Biology, vol. 46, Apr. 2012, pp. 195-203, 1 page (English Abstract).
Pride, D., et al., "Analysis of Streptococcal CRISPRs from Human Saliva Reveals Substantial Sequence Diversity Within and Between Subjects Over Time," Genome Research, vol. 21, 2011, pp. 126-136, 11 pages.
Primo, et al., "Lentiviral vectors for cutaneous RNA managing" Experimental Dermatology, vol. 21, 2012. 162-170, 9 pages.
Qi, et al., "Repurposing CRISPR as an RNA-Guided Platform for Sequence-Specific Control of Gene Expression" Cell, vol. 152, 2013, pp. 1173-1183, 11 pages.
Qi, J., et al., "microRNAs regulate human embryonic stem cell division," Cell Cycle, vol. 8, 2009, pp. 3729-3741, 13 pages.
R. Rad et al., "PiggyBac transposon mutagenesis: a tool for cancer gene discovery in mice," Science, vol. 330, Nov. 19, 2010, p. 1104-1107, 4 pages.
R.D Kolodner and G.T. Marsischky, "Eukaryotic DNA mismatch repair," Current Opinion in Genetics and Development, vol. 9, 1999, p. 89-96, 8 pages.
R.Renella et al., "Codanin-1 mutations in congenital dyserthropoietic anemia type 1 affect HP1α localization in erythroblasts," Blood, vol. 117, Jun. 2011, pp. 6928-6938, 11 pages.
Radecke, S., et al., "Zinc-finger Nuclease-induced Gene Repair With Oligodeoxynucleotides: Wanted and Unwanted Target Locus Modifications," Molecular Therapy, vol. 18, Apr. 2010, pp. 743-753, 11 pages.
Radulovich, et al., "Modified gateway system for double shRNA expression and Cre/lox based gene expression" BMC Biotechnology, 2011, vol. 11, pp. 1-9, 10 pages.
Ran et al., "Double Nicking by RNA-guided CRISPR Cas9 for enhanced genome editing specificity", Cell, Sep. 12, 2013, vol. 154, pp. 1380-1389.
Ran, F., et al, "In vivo genome editing using *Staphylococcus aureus* Cas9," Nature, vol. 520, 2015, pp. 186-191,6 pages. Includes Supplemental information, 12 pages.
Ran, F., et al., "Genome engineering using the CRISPR-Cas9 system," Nature Protocols, vol. 8, 2013, pp. 2281-2308, 28 pages.
Rand, et al. "Argonaute2 Cleaves the Anti-Guide Strand of siRNA during RISC Activation" Cell, vol. 123, 2005, pp. 621-629, 9 pages.
Raymond, et al. "High-Efficiency FLP and PC31 Site-Specific Recombination in Mammalian Cells" PLoS One, vol. 2, Jan. 2007, pp. 1-4. Doi. 10.1371/journal.pone.0000162.
Rebar, et al., "Induction of angiogenesis in a mouse model using engineered transcription factors" Nature Medicine, vol. 8, 2002, pp. 1427-1432, 6 pages.
Redeclaration—37 C.F.R. 41.203(c); filed Mar. 17, 2016 in Patent Interference No. 106,048 (DK), 14 pages.
Reiss, et al., "RecA protein stimulates homologous recombination in plants" Proc. Natl. Acad. Sci. vol. 93, 1996, pp. 3094-3098, 5 pages.
Response to Third Party Observations in EP No. 13824232.6 filed Oct. 2, 2014, with Redlined and Clean Amended Claims, 14 pages.
Rho, M., et al., "Diverse CRISPRs Evolving in Human Microbiomes," PLOS Genetics, vol. 8, Jun. 2012 e1002441, 12 pages.
Rhun, A., and Charpentier, E., "Small RNAs in streptococci," RNA Biology, vol. 9, 2012, pp. 414-426, 13 pages.
Roberts, et al. "Nuclear location signal-mediated protein transport" Biochimica et Biophysica Act, vol. 1008, 1989, pp. 263-280, 18 pages.
Roberts, et al., "The Effect of Protein Content on Nuclear Location Signal Function" Cell, vol. 50, 1989, pp. 465-475, 11 pages.
Rockefeller University and Broad Institute of MIT and Harvard announce update to CRISPR-Cas9 portfolio filed by Broad, Press Release dated Jan. 15, 2018, retrieved from: https://www.broadinstitute.org/news/rockefeller-university-and-broad-institute-mit-and-harvard-announce-update-crispr-cas9, 3 pages.
Rodrigues, et al., "Red Fluorescent Protein (DsRed) as a Reporter in *Saccharomyces cerevisiae*" Journal of Bacteriology, vol. 183, 2001, pp. 3791-3794, 4 pages.
Rodriguez et al., "AAV-CRISPR: A New Therapeutic Approach To Nucleotide Repeat Diseases", Molecular Therapy, vol. 22, 2014, Supplement 1, Abstract 247, p. S94.
Rolling, "Recombinant AAV-mediated gene transfer to the retina: gene therapy perspectives", Gene Therapy, vol. 11, 2004, pp. S26-S32, 5 pages.
*Rubin* v. *The General Hospital Corp.*, 2011-1439 (Fed. Cir. Mar. 28, 2013), 8 pages.
S. Huang et al., "MED12 Controls the Response to Multiple Cancer Drugs through Regulation of TGF-ß; Receptor Signaling," Cell, vol. 151, 2012, pp. 937-950, 14 pages.
S. Konermann et al., "Optical control of mammalian endogenous transcription and epigenetic states," Nature, vol. 500, Aug. 22, 2013, pp. 472-476, 5 pages. Includes Supplemental Information, 13 pages.
S.H. Chen et al., "A Knockout Mouse Approach Reveals that TCTP Functions as an Essential Factor for Cell Proliferation and Survival in a Tissue- or Cell Type-specific Manner," Molecular Biology of the Cell, vol. 18, Jul. 2007, pp. 2525-2532, 8 pages.
S.R. Whittaker et al., "A Genome-Scale RNA Interference Screen Implicates NF1 Loss in Resistance to RAF Inhibition," Cancer Discovery, vol. 3, 2013, pp. 350-362, 14 pages.
S.S. Liu et al., "Identification and characterization of a novel gene, clorf109, encoding a CK2 substrate that is involved in cancer cell proliferation," Journal of Biomedical Science, vol. 19, 2012, 12 pages.
S.Xue and M. Barna, "Specialized ribosomes: a new frontier in gene regulation and organismal biology," Nat Rev Mol Cell Biology, vol. 13, Jun. 2012. pp. 355-369, 15 pages.
Sadowski, M., and Jones, D., "The sequence-structure relationship and protein function prediction," Current Opinion in Structural Biology, vol. 19, 2009, pp. 357-362, 6 pages.
Sambrook, et al., "Molecular Cloning, A Laboratory Manual on the Web", Cold Spring Harbor Laboratory Press, Chapter 16, 2001, downloaded from http://www.molecularcloning.com/members/chapter.jsp?chapter=127 on Feb. 19, 2002, 13 pages.
Sander, et al., "CRISPR-Cas systems for editing, regulating and targeting genomes," Nature Biotechnology, vol. 32, 2014, pp. 347-355, 9 pages.
Sanders, "Cheap and easy technique to snip DNA could revolutionize gene therapy", UC Berkeley Press Release, Jan. 7, 2013, available at http://newscenter.berkeley.edu/2013/01/07/cheap-and-easy-technique-to-snip-dna-could-revolutionize-gene-therapy/.
Sanders, et al., "Use of a macromolecular crowding agent to dissect interactions and define functions in transcriptional activation by a DNA-tracking protein: Bacteriophage T4 gene 45 protein and late transcription" PNAS, vol. 9 2014, pp. 7703-7707, 5 pages.
Sanjana, et al., "Improved vectors and genome-wide libraries for CRISPR screening," HHS Public Access Author Manuscript, vol. 11, 2014, pp. 2145-2148, 4 pages.
Sanjana, N., et al., "A Transcription Activator-Like Effector (TALE) Toolbox for Genome Engineering," Nature Protocols, vol. 7, 2012, pp. 171-192, 39 pages.
Sapranauskas, R., et al., "The *Streptococcus thermophilus* CRISPR-Cas system provides immunity in *Escherichia coli*," Nucleic Acids Research, vol. 3, 2011, pp. 9275-9282, 8 pages.
Sarra, G., et al., "Gene replacement therapy in the retinal degeneration slow (rds) mouse: the effect on retinal degeneration following partial transduction of the retina", Human Molecular Genetics, vol. 10, 2001, pp. 2353-2361, 9 pages.
Sato, et al. "Generation of Adeno-Associated Virus Vector Enabling Functional Expressionof Oxytocin Receptor and Fluorescence Marker Genes Using the Human eIF4G Internal Ribosome Entry Site Elemet" Biosci. Biotechno. Biochem, vol. 73, 2009, pp. 2145-2148, 4 pages.

(56) References Cited

OTHER PUBLICATIONS

Sauer, "Functional Expression of the cre-lox Site-Specific Recombination System in the Yeast *Saccharomyces cerevisiae*" Mol. Cell. Biology, vol. 7, 1987, pp. 2087-2096, 10 pages.
Sauer, et al. "Site-specific DNA recombination in mammalian cells by the Cre recombinase of bacteriophage P1" Proc. Natl. Acad. Sci. vol. 85, 1988, pp. 5166-5170, 5 pages.
Schiffer, et al. "Targeted DNA Mutagenesis for the Cure of Chronic Viral Infections" Journal of Virology, vol. 86, No. 17, Jun. 20, 2012, pp. 8920-8936.
Schiffer, et al., "Predictors of Hepatitis B Cure Using Gene Therapy to Deliver DNA Cleavage Enzymes: A Mathematical Modeling Approach" PLOS Computational Biology, vol. 9, 2013, pp. 1-16. www.ploscompbiol.org.
Scholze, et al., "TAL effector-DNA specificity", Virulence, vol. 1, No. 5, Sep. 1, 2010, pp. 428-432, 5 pages. DOI:10.4161/viru.1.5.12863.
Schramm et al., "Recruitment of RNA polymerase III to its target promoters" Genes & Development, vol. 16, 2002, 2593-2620, pp. 28 pages.
Schunder et al., "First indication for a functional CRISPR/Cas system in Francisella tularensis", International Journal of Medical Microbiology, vol. 303, 2013, pp. 51-60, 10 pages.
Sebastiani, et al., "BCL11A enhancer haplotypes and fetal hemoglobin in sickle cell anemia," Blood Cells, vol. 54, 2015, pp. 2240230, 7 pages.
Sebo, et al., "A simplified and efficient germline-specific CRISPR/Cas9 system for *Drosophila* genomic engineering" Fly, 2014, vol. 8, pp. 52-57, 8 pages.
Seffernick, J., et al., "Melamine Deaminase and Atrazine Chlorohydrolase: 98 Percent Identical but Functionally Different," Journal of Bacteriology, vol. 183, No. 8, Apr. 2001, pp. 2405-2410, 6 pages.
Semenova, E. et al., "Interference by clustered regularly interspaced short palindromic repeat (CRISPR) RNA is governed by a seed sequence," Proc. Natl. Acad. Sci., vol. 108, Jun. 21, 2011, pp. 10089-10103, 7 pages.
Senis, E., et al., "CRISPR/Cas9-mediated genome engineering: An adeno-associated viral (AAV) vector toolbox," Biotechnology Journal, vol. 9, 2014, pp. 1402-1412, 12 pages.
Senturk et al., "A rapid and tunable method to temporally control cas9 expression enables the identification of essential genes and the interrogation of functional gene interactions in vitro and in vivo," vol. 9, 2015, pp. 1-27, XP002756303, doi:10.1101/023366, Retrieved from the Internet: URL:http://biorxiv.org/content/early/2015/07/28/023366 [retrieved on Apr. 11, 2016).
Shalem, et al., "High-throughput functional genomics using CRISP-Cas9," Nature Reviews Genetics, vol. 16, No. 5, pp. 299-311, May 2015.
Shalem, O., et al., "Genome-Scale CRISPR-Cas9 Knockout Screening in Human Cells," Science, vol. 343, 2014, pp. 84-87, 5 pages.
Sharan, et al., "Recombineering: A Homologous Recombination-Based Method of Genetic Engineering" Nat. Protoc., 2009, vol. 4 pp. 206-223, 18 pages. doi:10.1038/nprot.2008.227.
Shen, B., et al., "Generation of gene-modified mice via Cas9/RNA-mediated gene targeting," Cell Research, vol. 23, 2013, pp. 720-723.
Shen, et al., "Efficient genome modification by CRISPR-Cas9 mickase with minimal off-target effects" 2014, Nature Methods, vol. 11, pp. 399-404, 6 pages.
Shengdar Tsai et al., "Dimeric CRISPR RNS-guided Fokl nucleases for highly specific genome editing", Nature Biotechnology, vol. 32, Jun. 2014, pp. 569-576, 18 pages.
Shieh, et al., "Nuclear Targeting of the Maize R. Protein Requires Two Nuclear Localization Sequences" Plant Physiol, 1993, vol. 101 pp. 353-361, 9 pages.
Siegl, et al., "I-SceI endonuclease: a new tool for DNA repair studies and genetic manipulations in streptomycetes" Appl Microbiol Bitotechnol, vol. 87, 2010, pp. 1525-1532, 8 pages.
Sims, D., et al., "High-throughput RNA interference screening using pooled shRNA libraries and next generation sequencing," Genome Biology, vol. 12, 2011, pp. 1-13.
Singer, et al., "Applications of Lentiviral Vectors for shRNA Delivery and Transgenesis" Curr Gene Ther., vol. 8, 2008 pp. 483-488, 6 pages.
Slaymaker et al., "Rationally engineered Cas9 nucleases with improved specificity", Science, American Association for the Advancement of Science, US, vol. 351, Jan. 1, 2016, pp. 84-88.
Sontheimer, "Project 7: Establishing RNA-Directed DNA Targeting in Eukaryotic Cells" Physical Sciences-Onc., Nov. 16, 2011-Dec. 31, 2012, 2 pages. htt://groups.molbiosci.northwestern.edu/sontheimer/Sontheimer_cv.php) Molecular Biosciences, 2 pages.
Spencer, J.M., et al., "Development of a Nuclease Screen to Improve Cas9 Targeting Specificity", Molecular Therapy, May 2015, vol. 23, Suppl. 1, S136(340).
Stewart SA et al., "Lentivirus-delivered stable gene silencing by RNAi in primary cells," RNA, vol. 9, 2003, pp. 493-501, 9 pages.
Stolfi, et al., "Tissue-specific genome editing in Ciona embryos by CRISPR/Cas9," Development, vol. 141, 2014, pp. 4115-4120, 6 pages. doi:10.1242/dev.114488.
Stoller, J. and Aboussouan, L., "Alpha1-antitrypsin deficiency," The Lancet, Seminar, vol. 365, 2005, pp. 2225-2236, 12 pages.
Stratikopoulos, E., et al., "The hormonal action of IGF1 in postnatal mouse growth," Proceedings of the National Academy of Sciences, vol. 105, Dec. 9, 2008, pp. 19378-19383, 6 pages.
Straub, C., et al., "CRISPR/Cas9-Mediated Gene Knock-Down in Post-Mitotic Neurons," PLOS One, vol. 9, art. E105584, Aug. 20, 2014, pp. 1-5, 6 pages.
Sung, et al., "An rpsL Cassette, Janus, for Gene Replacement through Negative Selectionin *Streptococcus pneumoniae*" Applied and Environmental Microbiology, vol. 67, 2001, pp. 5190-5196, 7 pages.
Sung, M., et al., "The importance of valency in enhancing the import and cell routing potential of protein transduction domain-containing molecules," Biochimica et Biophysica Aeta, vol. 1758, pp. 355-363, dated 2006, 9 pages.
Sung, Young Hoon, et al., "Mouse genetics: Catalogue and scissors" BMB Reports, 2012, vol. 45 pp. 686-692, 7 pages.
Suzuki, K., et al., "In vivo genome editing via CRISPR/Cas9 mediated homology-independent targeted integration," Nature, vol. 540, art. 7631, 2015, pp. 1-44.
Swarthout, J., et al., "Zinc Finger Nucleases: A new era for transgenic animals," Annals of Neurosciences, vol. 18, 2011, pp. 25-28, 4 pages.
Swiech et al., "CRISPR-Mediated Genome Editing in the Mammalian Brain", Molecular Therapy, 747, vol. 22, 2014, p. S289.
Swiech, L., et al., "In vivo interrogation of gene function in the mammalian brain using CRISPR-Cas9," Nature Biotechnology, vol. 33, 2014, pp. 102-106, 5 pages. Including Supplemental information, 4 pages.
Symington et al., "Double-Strand Break End Resection and Repair Pathway Choice", Annual Review of Genetics, vol. 45, 2011, pp. 247-271, 25 pages.
T. Horii et al., "Generation of an ICF Syndrome Model by Efficient Genome Editing of Human Induced Pluripotent Stem Cells Using the CRISPR System," International Journal of Molecular Sciences, vol. 14, 2013, p. 19774-19781, 9 pages.
T.J. Cradick et al., "CRISPR/Cas9 systems targeting ß-globin and CCR5 genes have substantial off-target activity," Nucleic Acids Research, vol. 41, 2013, 9584-9592, 9 pages.
T.Yan et al., "DNA mismatch repair (MMR) mediates 6-thioguanine genetoxicity by introducing single-strand breaks to signal a G2-M arrest in MMR-proficient RKO cells," Clinical Cancer Research, vol. 9, Jun. 2003, p. 2327-2334, 9 pages.
Takara Bio USA, Inc., "Lenti-X™ Tet-On © 3G CRISPR/Cas9 System User Manual", 2016, pp. 1-35.
Tang, T., et al., "A mouse knockout library for secreted and transmembrane proteins," Nature Biotechnology, vol. 28, No. 7, Jul. 2010, pp. 749-755, pp. 7 pages. Including Supplemental information, 2 pages.

(56) References Cited

OTHER PUBLICATIONS

Terns, M., and Terns, R., "CRISPR-based adaptive immune systems," Current Opinion in Microbiology, vol. 14, 2011, pp. 321-327, 8 pages.
*The Broad Inst.* v. *The Regents of University of UCA*-Decision on Motions for Patent Interference No. 106,048 filed Feb. 15, 2017, 51 pages.
Third Party Observation for Application No. EP20130824232 dated Sep. 22, 2014, 19 pages.
Third Party Observation in Application No. PCT/US2013/074819 dated Apr. 10, 2015, 10 pages.
Third Party Observation Under Article 115 EPC in Application No. 13818570.7 dated Oct. 1, 2014.
Third Party Observations Concerning App. No. GB1420270.9, dated Jun. 30, 2015, 71 pages.
Third Party Observations Concerning Appl. No. EP2800811, dated Jul. 24, 2015, 108 pages.
Third Party Observations Concerning Appl. No. EP2800811, dated Sep. 4, 2015.
Third Party Observations Concerning Appl. No. GB1420270.9 dated Jun. 30, 2015.
Third Party Observations Concerning Appl. No. GB1420270.9, dated Jul. 13, 2015.
Third Party Observations in Accordance with Article 115 EPC, Appl. No. EP13824232.6, Pub. No. EP2764103A, Mar. 25, 2015.
Third Party Observations submitted by Broad Institute Inc. Concerning Appl. Ser. No. EP13793997.1 dated Jul. 24, 2015, 108 pages.
Third Party Observations submitted by Broad Institute Inc. Concerning Appl. Ser. No. EP13793997.1 dated Sep. 4, 2015, 25 pages.
Third Party Observations submitted by Regents of the University of California et al. Concerning App. No. GB1420270.9 dated Jul. 13, 2015, 18 pages.
Third Party-Observations, Appl. No. 1382432.6, Pub. No. EP2764103, dated Feb. 16, 2015, 12 pages.
Third-Party Observation for Application No. EP20130824232 dated Sep. 8, 2014, 47 pages.
Tinland, et al., "The T-DNA-linked VirD2 protein contains two distinct functional nuclear localization signals" Proc. Natl. Acad. Sci, vol. 89, 1992, pp. 7442-7446, 5 pages.
Tiscornia, et al. "Development of Lentiviral Vectors Expressing siRNA" Gene Transfer-Delivery and Expression of DNA and RNA—A Laboratory Manual, 2007, Chapter 3 pp. 23-34, 12 pages.
Tolia, et al., "Slicer and the Argonautes" Nature Chemical Biology, vol. 3, 2007, pp. 36-43, 8 pages.
Trafton, A., "CRISPR-carrying nanoparticles edit the genome," MIT News, dated Nov. 13, 2017, 3 pages.
Trevino, et al., "Genome Editing Using Cas9 Nickases" Methods in Enxymology, vol. 546 pp. 161-174, 14 pages, 2014.
Tulpan, D., et al., "Free energy estimation of short DNA duplex hybridizations," BMC Bioinformatics, vol. 11, 2012, pp. 105-127, 23 pages.
Type V CRISPR-associated protein Cpfi [*Acidaminococcus* sp. Bv3L6], 2017, NCBI Reference Sequence: WP_02173622.1, Non-redundant Protein Sequence, 2 pages.
*Ultra-Precision Mfg. Ltd.* v. *Ford Motor Co.*, 2004 WL 3507671, *7, *11-12 (E.D. Mich. Mar. 30, 2004).
Urnov, et al., "Highly efficient endogenous human gene correction using designed zinc-finger nucleases" Nature, vol. 435, 2005, pp. 646-651, 6 pages.
Urnov, F., et al., "Genome editing with engineered zinc finger nucleases," Nature Reviews, Genetics, vol. 11, pp. 637-646, dated Sep. 2010, 11 pages.
Urrutia, et al., "KRAB-containing zing finger repressor proteins" Genome Biology, vol. 4, Sep. 23, 2003, pp. 231-231.8, 8 pages.
V.N. Ngo et al., "A loss-of-function RNA interference screen for molecular targets in cancer," Nature, vol. 441, May 4, 2006, pp. 106-110, 5 pages.
Van Den Ackerveken, et al., "Recognition of the Bacterial Avirulence Protein AvrBs3 Occurs inside the Host Plant Cell" Cell, vol. 87, Dec. 27, 1996, pp. 1307-1316, 10 pages.
Van Der Oost, "New tool for genome surgery", Science, vol. 339, Feb. 15, 2013, pp. 768-770, 3 pages.
Van Der Oost, J., et al., "CRISPR-based adaptive and heritable immunity in prokaryotes," Trends. Biochem. Sci., vol. 34, 2009, pp. 401-407, 7 pages.
Van Nierop, G., et al., "Stimulation of homology-directed gene targeting at an endogenous human locus by a nicking endonuclease," Nucleic Acids Research, vol. 37, 2009, pp. 5725-5736, 12 pages.
Venken et al., "P[acman]: A BAC Transgenic Platform for Targeted Insertion of Large DNA Fragments in D. melanogaster", Science, vol. 314, Dec. 15, 2006, pp. 1747-1751, 5 pages.
Vestergaard et al., "CRISPR adaptive immune systems of Archaea", RNA Biology, vol. 11,2014, pp. 156-167, 12 pages.
Villion, et al., "The double-edged sword of CRISPR-Cas systems" Cell Research, 2013, vol. 23 pp. 15-17, 3 pages.
W.G. Kaelin., "Use and Abuse of RNAi to Study Mammalian Gene Function," Science, vol. 337, Jul. 27, 2012, p. 421-422, 2 pages.
Wang, et al. "Genetic Screens in Human Cells Using the CRISPR-Cas9 System", Science, 2014, 343:80-84.
Wang, H., et al., "One-Step Generation Of Mice Carrying Mutations In Multiple Genes By CRISPR/Cas-Mediated Genome Engineering," Cell, vol. 153, 2013, pp. 910-918, 9 pages.
Wang, H.H. et al., "Genome-scale promoter engineering by coselection MAGE," Nat methods, vol. 9, Jun. 2012, pp. 591-593, 3 pages.
Wayengera, M., "Identity of zinc finger nucleases with specificity to herpes simplex virus type II genomic DNA; novel HSV-2 vaccine/therapy precursors", Theoretical Biology and Medical Modelling, vol. 8, No. 1, Jun. 24, 2011, p. 23.
Wayengera, M., "Zinc finger arrays binding human papillomavirus types 16 and 18 genomic DNA: precursors of gene-therapeutics for in-situ reversal of associated cervical neoplasia", Theoretical Biology and Medical Modeling, vol. 9, No. 1, Jul. 28, 2012, p. 30.
Weber et al., "TALENS Targeting HBV: Designer Endonuclease Therapies for Viral Infections", Molecular Therapy, vol. 21, Oct. 2013, pp. 1819-1821, 3 pages.
Welch, et al., "Designing Genes For Successful Protein Expression" Methods in Enzymology, 2011, vol. 498, pp. 43-66, 24 pages. DOI: 10.1016/B978-0-12-385120-8.00003-6.
Wiedenheft, B. et al., "RNA-guided complex from a bacterial immune system enhances target recognition through seed sequence interactions," Proc. Natl. Acad. Sci., vol. 108, Jun. 21, 2011, 10092-10097, 7 pages.
Wiedenheft, B. et al., "RNA-guided genetic silencing systems in bacteria and archaea", Nature, vol. 482, Feb. 16, 2012, pp. 331-338.
Wienert, B., et al., "In vitro transcribed guide RNAs trigger an innate immune response via the RIG-I pathway," BioRxiv Preprint, 2018, 1-28, 28 pages.
Witkowski, A., et al., "Conversion of a Beta-Ketoacyl Synthase to a Malonyl Decarboxylase by Replacement of the Active-Site Cysteine with Glutamine," Biochemistry, vol. 38, 1999, pp. 11643-11650, 8 pages.
Wittmann et al., "Engineered riboswitches: Expanding researchers' toolbox with synthetic RNA regulators", FEBS Letters, vol. 586, 2012, pp. 2076-2083, 8 pages.
Wolff, et al., "Nuclear security breached" Nature Biotechnology, Dec. 2001, vol. 19, 1118-1120, 3 pages.
Wu, X., et al., "Genome-wide binding of the CRISPR endonuclease Cas9 in mammalian cells," Nature Biotechnology, 2014, 1-7, 7 pages. Including Supplemental information, 2 pages.
Wu, Y., et al., "Correction of a Genetic Disease in Mouse via Use of CRISPR-Cas9," Cell Stem Cell, vol. 13, 2013, pp. 659-662, 4 pages.
Wu, Z., et al., "Effect of Genome Size on AAV Vector Packaging," The American Society of Gene & Cell Therapy, vol. 18, 2010, pp. 80-86, 7 pages.
X.Liu et al., "STAGA recruits Mediator to the MYC oncoprotein to stimulate transcription and cell proliferation," Molecular and cellular biology, vol. 28, Jan. 2008, p. 108-121, 14 pages.

(56) References Cited

OTHER PUBLICATIONS

Xiao, et al., "Chromosomal deletions and inversions mediated by TALENs and CRIPPR/Cas in zebrafish" Nucleic Acids Research, vol. 41, 2013, pp. 1-11, Including Supplemental information, 31 pages. doi:10.1093/nar/gkt464.
Xiao, et al., "Production of High-Titer Recombinant Adeno-Associated Virus Vectors in the Absence of Helper Adenovirus" Journal of Virology, Mar. 1998, vol. 72, No. 3, pp. 2224-2232, 9 pages.
Xiao, W., et al., "Gene Therapy Vectors Based on Adeno-Associated Virus Type 1", Journal of Virology, May 1999, vol. 73, No. 5, p. 3994-4003.
Xie, et al. "RNA-Guided Genome Editing in Plants Using a CRISPR-Cas System" Molecular Plant, vol. 6, Nov. 2013, 1975-1983, 9 pages.
Xu, Zhi-Li et al., "Regulated gene expression from adenovirus vectors: a systematic comparison of various inducible systems," Gene, vol. 309, 2003, pp. 145-151, 7 pages.
Yaghmai, et al., "Optimized Regulation of Gene Expression Using Artificial Transcription Factors", Molecular Therapy, Jun. 2002, vol. 5, No. 6, pp. 685-694.
Yamano, et al., "Crystal Structure of Cpf1 in Complex with Guide RNA and Target DNA" Cell, vol. 165, May 5, 2016, pp. 949-962, 14 pages.
Yanfang Fu et al., "Improving CRISPR-Cas nuclease specificity using truncated guide RNAs" (with Supplement Table), Nature Biotechnology, vol. 32, Mar. 2014, pp. 1-18.
Yang et al., "HIV-1 TAT-mediated protein transduction and subcellular localization using novel expression vectors," FEBS Letters, vol. 532, 2012, pp. 36-44, 9 pages.
Yang, H., et al., "One-Step Generation of Mice Carrying Reporter and Conditional Alleles by CRISPR/Cas-Mediated Genome Engineering," Cell, vol. 154, 2013, pp. 1370-1379, 10 pages. Including Supplemental information, 4 pages.
Yi, et al., "Current Advances in Retroviral Gene Therapy" Current Gene Therapy, vol. 11, 2011, pp. 218-228, 11 pages.
Yin, H., et al., "Structure-guided chemical modification of guide RNA enables potent non-viral in vivo genome editing," Nature Biotechnology, vol. 35, Dec. 2017, pp. 1-22.
Yu, et al., "An efficient recombination system for chromosome engineering in *Escherichia coli*" PNAS, 2000, vol. 97, pp. 5978-5983, 6 pages.
Yu, W., et al., "Nrl knockdown by AAV-delivered CRISPR/Cas9 prevents retinal degeneration in mice," Nature Communications, vol. 8, 2017, art. 14716, 15 pages.
Yu, Zhongshen, et al., "Highly Efficient Genome Modifications Mediated by CRISPR/Cas9 in *Drosophila*" Genetics, 2013, vol. 195 pp. 289-291, 3 pages.
Yusuke Miyazaki et al., Destabilizing Domains Derived from the Human Estrogen Receptor:, Journal of the American Chemical Society, vol. 134, Mar. 7, 2012, pp. 3942-3945, 4 pages.
Zahner, D. and Hakenbeck, R. "The *Streptococcus pneumoniae* beta-galactosidase is a surface protein," J. Bacteriology, vol. 182, Oct. 2000, pp. 5919-5921, 3 pages.
Zeng Y et al., "Both natural and designed micro RNAs can inhibit the expression of cognate mRNAs when expressed in human cells," Mol Cell., vol. 9, Jun. 2002, pp. 1327-1333, 7 pages.
Zetsche et al. "A split-Cas9 architecture for inducible genome editing and transcription modulation" Nature biotechnology, 2015, vol. 33, 139-142, 4 pages.
Zetsche et al., "Cpf1 is a single RNA-guided endonuclease of a class 2 CRISPR-Cas system", Cell, vol. 163, Oct. 22, 2015, pp. 759-771, 13 pages.
Zhang, "Processing-Independent CRISPR RNAs Limit Natural Transformation in Neisseria meningitidis", Molecular Cell, vol. 50, May 23, 2013 pp. 488-503.
Zhang, et al. "Optogenetic interrogation of neural circuits: technology for probing mammalian brain structures" Nat Protoc., 2010, 5(3):439-456, doi:10.1038/nprot.2009.226.
Zhang, et al., "Optimized CRISPR Design", MIT, XP055167487, Oct. 23, 2013, URL:http//crispr.mit.edu/about[retrieved on Feb. 5, 2015].
Zhang, et al., "Efficient construction of sequence-specific TAL effectors for modulating mammalian transcription" nature biotechnology, vol. 29, 2011, 149-154, 6 pages.
Zhang, F., PowerPoint Presentation: "Development and Applications of CRISPR-Cas9 for Genome Editing," Broad Institute/MIT, dated Sep. 9, 2015, 50 pages.
Zhang, L., et al., "Efficient Expression of CFTR Function with Adeno-Associated Virus Vectors that Carry Shortened CFTR Genes," Proceedings of the National Academy of Science USA, vol. 95, 1998, pp. 10158-10163, 6 pages.
Zhang, X. D., et al., "CSSMD: assessing collective activity for addressing off-target effects in genome-scale RNA interference screens," Bioinformatics, vol. 27, pp. 2775-2781, 2011, 7 pages.
Zhou, et al., "High-throughput screening of a CRISPR/Cas9 library for functional genomics in human cells," Nature, vol. 509, pp. 487-491, 5 pages, 2014.
Zhu, et al. "Crystal structure of Cmr2 suggests a nucleotide cyclase-related enzyme in type III CRISPR-Cas sytems" FEBS Letters, 2012, 939-945, 6 pages. Doi:10.1016/j.febslet2012.02.036.
Zolkiewska, et al., "ADAM Proteases:Ligand Processing and Modulation of the Notch Pathway" Cell Mol Life Sci, 2008, vol. 65 pp. 2056-2068, 13 pages.
Zuris, et al., "Cationic lipid-mediated delivery proteins enables efficient protein-based genome editing in vitro and in vivo", Nature Biotechnology, vol. 33, No. 1, Jan. 2015, pp. 73-80.
Zuris, et al., "Efficient Delivery of Genome-Editing Proteins In Vitro and In Vivo" Nature Biotechnology, vol. 33, No. 1, Jan. 2015, pp. 1-26.
Zuris, et al., Supplementary Information—"Cationic lipid-mediated delivery proteins enables efficient protein-based genome editing in vitro and in vivo" Nature Biotechnology, vol. 33, No. 1, Jan. 2015, pp. 1-49. doi: 10.1038/nbt.3081.
Brief of Amici Curiae Scientists in Support of Appellants and Reversal; Case: 22-1594; Document: 18; Nos. 22-1594, 22-1653; Filed: Oct. 7, 2022 (24 pages).
Corrected Opening Brief for Cross-Appellants; Appeal Nos. 2022-1594, 2022-1653; Document: 31; Filed: Feb. 15, 2023 (111 pages).
Love et al., "Lipid-like materials for low-dose, in vivo gene silencing," Proceedings of the National Academy of Sciences, Feb. 2, 2010, vol. 107, No. 5 (pp. 1864-1869).
Motion of Regeneron Pharmaceuticals, Inc. For Leave to File a Brief as Amicus Curiae in Support of Appellants and Reversal; Case: 22-1594; Document: 22-1; Nos. 22-1594 and 22-1653; Filed: Oct. 7, 2022 (29 pages).
Opening Brief for Appellants The Regents of the University of California, University of Vienna, Emmanuelle Charpentier; Nos. 2022-1594 & 2022-1653; Case: 22-1594 Document: 17-1 Filed, Sep. 30, 2022 (81 pages).
Patent Interference No. 106,115; Decision on Motions 37 C.F.R. Section 41.125(a); Filed: Sep. 10, 2020 (113 pages).
Patent Interference No. 106, 115; Decision on Priority 37 C.F.R. Section 41.125(a), Filed: Feb. 28, 2022 (84 pages).
Patent Interference No. 106, 126; Decision on Motions 37 C.F.R. Section 125(a); Filed: Sep. 28, 2022 (54 pages).
Patent Interference No. 106, 133; Decision on Motions 37 C.F.R. Section 41.125(a) Filed: Dec. 14, 2022 (40 pages).
Semple et al., "Rational design of cationic lipids for siRNA delivery," Nature Biotechnology, Feb. 2010, vol. 28, No. 2 (pp. 172-178).
Jinek et al., "RNA-programmed genome editing in human cells", eLife, vol. 2, 2013, DOI: 10.7554/eLife.00471 (9 pages).
Stoddard, "Homing endonuclease structure and function," Quarterly Reviews of Biophysics, Cambridge University Press, 2005 (pp. 1-47).
Voytas, Daniel F., "Plant genome engineering with sequence-specific nucleases," Annual Review of Plant Biology May 1, 2013, vol. 64 (pp. 327-350).
Wiles et al., "CRISPR-Cas9-medicated genome editing and guide RNA Design," Mammalian Genome, May 20, 2015, vol. 26, No. 9 (10 pages).

(56) References Cited

OTHER PUBLICATIONS

Workman et al., "A natural single-guide RNA repurposes Cas9 to autoregulate CRISPR-Cas expression," Cell Press, vol. 184, Feb. 4, 2021 (pp. 675-688).
Declaration of Interference—PTAB, *The Broad Institute, Inc., Massachusetts Institute of Technology, and President and Fellows of Harvard College* v. *Toolgen, Inc.*, filed Dec. 14, 2020, in Patent Interference No. 106,126 (DK), 19 pages.
Bauer et al., "Fine-Mapping and Genome Editing Reveal an Essential Erythroid Enhancer at the HbF-Associated BCL11A Locus," Blood, Nov. 15, 2013, vol. 122, No. 21 (3 pages).
Bryant et al., "Gene Therapy for Retinal Disease," Review of Ophthalmology, Apr. 5, 2012 (5 pages).
Chen et al., "Cut Site Selection by the Two Nuclease Domains of the Cas9 RNA-guided Endonuclease," The Journal of Biological Chemistry, May 9, 2014, vol. 289, No. 19 (p. 13284-13294).
Heidenreich et al., Applications of CRISPR-Cas systems in neuroscience, Nature, Jan. 2016, vol. 17, No. 1 (pp. 35-44).
Koller et al., "Inactivating the beta2-microglobulin locus in mouse embryonic stem cells by homologous recombination," Proceedings of the National Academy of Sciences, USA, Nov. 1989, vol. 86 (pp. 8932-8935).
Li et al., "Genetic correction using engineered nucleases for gene therapy applications," The Japanese Society of Developmental Biologists; Development, Growth & Differentiation, 2014, vol. 56 (pp. 63-77).
Louwen et al., "The Role of CRISPR-Cas Systems in Virulence of Pathogenic Bacteria," Microbiology and Molecular Biology Reviews, Mar. 2014, vol. 78, No. 1 (pp. 74-88).
Magana et al., "Perspectives on gene Therapy in Myotonic Dystrophy Type 1," Journal of Neuroscience research, 2011, vol. 89 (pp. 275-285).
Reik et al., "Targeted Gene Modification in Hematopoietic Stem Cells: A Potential Treatment for Thalassemia and Sickle Cell Anemia," Blood, American Society of Hematology, Nov. 1, 2013, vol. 122, No. 21 (p. 434).
Singleton, "Exome sequencing: a transformative technology," The Lancet/neurology, Oct. 2011, vol. 10 (pp. 942-946).
Xu et al., "Identification of BCL 11 A Structure Function Domains for Fetal Hemoglobin Silencing," Blood, Nov. 15, 2013, vol. 122, No. 21 (4 pages).
Zoghbi et al., "Spinocerebellar ataxia type 1," Seminars in Cell Biology, Feb. 1995, vol. 6, No. 1 (pp. 29-35).
Decision on Motions—PTAB, *The Regents of the University of California* v. *The Broad Institute, Inc.*, filed Sep. 10, 2020, in Patent Interference No. 106,115 (DK), 113 pages.
Hirano et al., "Structure and Engineering of Francisella novicida Cas9," Cell, vol. 164, Feb. 25, 2016, pp. 950-961.
Ran, F.A., "CRISPR-Cas: Development and Applications for Mammalian Genome Editing", Ph.D. Dissertation, Harvard University, Apr. 2014.
Redeclaration—PTAB, *The Regents of the University of California* v. *The Broad Institute, Inc.*, filed Aug. 26, 2019, in Patent Interference No. 106,115 (DK), 20 pages.
Redeclaration—PTAB, *The Regents of the University of California* v. *The Broad Institute, Inc.*, filed Sep. 10, 2020, in Patent Interference No. 106,115 (DK), 3 pages.
Yamada et al., "Crystal Structure of the Minimal Cas9 from Campylobacter jejuni Reveals the Molecular Diversity in the CRISPR-Cas9 Systems," Molecular Cell, vol. 65, Mar. 16, 2017, pp. 1109-1121.
David et al., "Non-viral nanosystems for systemic siRNA delivery," Pharmacological Research, 2010, vol. 62 (pp. 100-114).
Gjetting et al., "In vitro and in vivo effects of polyethylene glycol (PEG)-modified lipid in DOTAP/cholesterol-mediated gene transfection," International Journal of Nanomedicine, 2010, vol. 5 (pp. 371-383).
Hwang et al., "Efficient genome editing in zebrafish using a CRISPR-Cas system," Nature Biotechnology, Jan. 1, 2013, vol. 31, No. 3, Supplementary Materials (pp. 1-21).
Gentarget Inc., "CRISPR gRNA lentivector cloning kits," GenTarget Inc., Jan. 1, 2013 (pp. 1-2).
Kocak D. D., "Synthetic Transcription Factors and their Effects on Endogenous DNA Methylation in Human Cells," Thesis Degree of Master of Science, Jan. 1, 2013, Department of Biomedical Engineering Duke University (35 pages).
Bhattacharya et al., "A simple genotyping method to detect small CRISPR-Cas9 induced indels by agarose gel electrophoresis," Scientific Reports, Mar. 14, 2019, vol. 9, No. 4437 (7 pages).
Cameron et al., "Mapping the genomic landscape of CRISPR-Cas9 cleavage," Nature Methods, Jun. 2017, vol. 14, No. 6 (pp. 600-606).
Finn et al., "A Single Administration of CRISPR/Cas9 Lipid Nanoparticles Achieves Robust and Persistent In Vivo Genome Editing," Cell Reports, Cell Press, 2018, vol. 22 (pp. 2227-2235).
Guilinger et al., "Fusion of catalytically inactive Cas9 to FokI nuclease improves the specificity of genome modification," Nature Biotechnology, vol. 32, No. 6, Jun. 2014 (pp. 577-582).
Raveux et al., "Optimization of the production of knock-in alleles by CRISPR/Cas9 microinjection into the mouse zygote," Scientific Reports, Feb. 17, 2017, vol. 7, No. 42661 (11 pages).
Shapiro et al., "Increasing CRISPR Efficiency and Measuring Its Specificity in HSPCs Using a Clinically Relevant System," Molecular Therapy: Methods & Clinical Development, Jun. 12, 2020, vol. 17 (pp. 1097-1107).
Slaymaker et al., "Rationally engineered Cas9 nucleases with improved specificity", Science, vol. 351, No. 6268, Jan. 1, 2016, pp. 84-88.
Taylor, G., "Introduction to phasing," Acta Crystallographica Section D Biological Crystallography, 2010, D66 (pp. 325-338).
Cutrona et al., "Effects in live cells of a c-myc anti-gene PNA linked to a nuclear localization signal," Nature Biotechnology, Mar. 2000, vol. 18 (pp. 300-303).
U.S. Appl. No. 14/054,414, filed Oct. 15, 2013, Leith, Nancy J.
U.S. Appl. No. 14/104,837, filed Dec. 12, 2013, Poliakova-Georgan, Ekaterina.
U.S. Appl. No. 14/104,900, filed Dec. 12, 2013, Leith, Nancy J.
U.S. Appl. No. 14/104,977, filed Dec. 12, 2013, Holland, Paul J.
U.S. Appl. No. 14/104,990, filed Dec. 12, 2013, Leith, Nancy J.
U.S. Appl. No. 14/105,017, filed Dec. 12, 2013, Leith, Nancy J.
U.S. Appl. No. 14/105,031, filed Dec. 12, 2013, Leith, Nancy J.
U.S. Appl. No. 14/105,035, filed Dec. 12, 2013, Leith, Nancy J.
U.S. Appl. No. 14/183,429, filed Feb. 18, 2014, Leith, Nancy J.
U.S. Appl. No. 14/183,471, filed Feb. 18, 2014, Leith, Nancy J.
U.S. Appl. No. 14/183,486, filed Feb. 18, 2014, Leith, Nancy J.
U.S. Appl. No. 14/183,512, filed Feb. 18, 2014, Poliakova-Georgan, Ekaterina.
U.S. Appl. No. 14/222,930, filed Mar. 24, 2014, Leith, Nancy J.
U.S. Appl. No. 14/226,274, filed Mar. 26, 2014, Leith, Nancy J.
U.S. Appl. No. 14/256,912, filed Apr. 18, 2014, Leith, Nancy J.
U.S. Appl. No. 14/258,458, filed Apr. 22, 2014, Leith, Nancy J.
U.S. Appl. No. 14/259,420, filed Apr. 23, 2014, Leith, Nancy J.
U.S. Appl. No. 14/290,575, filed May 29, 2014, Whisenant, Ethan C.
U.S. Appl. No. 14/293,498, filed Jun. 2, 2014, Holland, Paul J.
U.S. Appl. No. 14/293,674, filed Jun. 2, 2014, Holland, Paul J.
U.S. Appl. No. 14/324,960, filed Jul. 7, 2014, Brown, Mindy G.
U.S. Appl. No. 14/463,253, filed Aug. 19, 2014, Zhang, Kaijiang.
U.S. Appl. No. 14/481,339, filed Sep. 9, 2014, Marvich, Maria.
U.S. Appl. No. 14/497,627, filed Sep. 26, 2014, Leith, Nancy J.
U.S. Appl. No. 14/523,799, filed Oct. 24, 2014, Leith, Nancy J.
U.S. Appl. No. 14/681,382, filed Apr. 8, 2015, Leith, Nancy J.
U.S. Appl. No. 14/703,511, filed May 4, 2015, Leith, Nancy J.
U.S. Appl. No. 14/704,551, filed May 5, 2015, Leonard, Arthur S.
U.S. Appl. No. 14/738,398, filed Jun. 12, 2015, Ramirez, Delia M.
U.S. Appl. No. 14/738,483, filed Jun. 12, 2015, Woitach, Joseph T.
U.S. Appl. No. 14/970,967, filed Dec. 16, 2015, Leith, Nancy J.
U.S. Appl. No. 14/971,169, filed Dec. 16, 2015, Aron, Kimberly A.
U.S. Appl. No. 14/971,356, filed Dec. 16, 2015, Noble, Marcia Stephens.
U.S. Appl. No. 14/972,523, filed Dec. 17, 2015, Montanari, David A.
U.S. Appl. No. 14/972,927, filed Dec. 17, 2015, Leonard, Arthur S.
U.S. Appl. No. 14/973,062, filed Dec. 17, 2015, Leith, Nancy J.

(56) References Cited

OTHER PUBLICATIONS

U.S. Appl. No. 14/990,444, filed Jan. 7, 2016, Leith, Nancy J.
U.S. Appl. No. 14/991,083, filed Jan. 8, 2016, Leith, Nancy J.
U.S. Appl. No. 15/160,710, filed Mar. 20, 2016, Leith, Nancy J.
U.S. Appl. No. 15/217,489, filed Jul. 22, 2016, Brown, Mindy G.
U.S. Appl. No. 15/229,702, filed Aug. 5, 2016, Leith, Nancy J.
U.S. Appl. No. 15/230,025, filed Aug. 5, 2016, Leith, Nancy J.
U.S. Appl. No. 15/230,161, filed Aug. 5, 2016, Leith, Nancy J.
U.S. Appl. No. 15/330,876, filed Nov. 7, 2016, Holland, Paul J.
U.S. Appl. No. 15/349,603, filed Nov. 11, 2016, Marvich, Maria.
U.S. Appl. No. 15/430,260, filed Jun. 10, 2017, Leith, Nancy J.
U.S. Appl. No. 15/834,736, filed Dec. 7, 2017.
U.S. Appl. No. 15/838,064, filed Dec. 11, 2017, Leith, Nancy J.
U.S. Appl. No. 15/887,377, filed Feb. 2, 2018, Leith, Nancy J.
U.S. Appl. No. 15/967,464, filed Apr. 30, 2018, Leith, Nancy J.
U.S. Appl. No. 15/967,495, filed Apr. 30, 2018, Leith, Nancy J.
U.S. Appl. No. 15/967,510, filed Apr. 30, 2018, Leith, Nancy J.
U.S. Appl. No. 16/012,692, filed Jun. 19, 2018, Leith, Nancy J.
U.S. Appl. No. 16/177,403, filed Oct. 31, 2018, Leith, Nancy J.
U.S. Appl. No. 16/178,551, filed Nov. 1, 2018, Leith, Nancy J.
U.S. Appl. No. 16/445,150, filed Jun. 18, 2019, Leith, Nancy J.
U.S. Appl. No. 16/445,156, filed Jun. 18, 2019, Leith, Nancy J.
U.S. Appl. No. 16/525,531, filed Jul. 29, 2019, Zhang, Kaijiang.
U.S. Appl. No. 16/532,442, filed Aug. 5, 2019.
U.S. Appl. No. 16/535,043, filed Aug. 7, 2019.
U.S. Appl. No. 16/800,988, filed Feb. 25, 2020.
U.S. Appl. No. 16/844,548, filed Apr. 9, 2020.
U.S. Appl. No. 16/906,580, filed Jun. 19, 2020.
U.S. Appl. No. 16/938,110, filed Jul. 24, 2020.
U.S. Appl. No. 17/034,754, filed Sep. 28, 2020.
U.S. Appl. No. 17/182,817, filed Feb. 23, 2021.
U.S. Appl. No. 17/201,347, filed Mar. 15, 2021.
U.S. Appl. No. 17/245,952, filed Apr. 30, 2021.
U.S. Appl. No. 17/321,872, filed May 17, 2021.
U.S. Appl. No. 17/503,928, filed Oct. 18, 2021.
Bachman et al., "Dnmt3a and Dnmt3b Are Transcriptional Repressors That Exhibit Unique Localization Properties to Heterochromatin," the Journal of Biological Chemistry, Aug. 24, 2001, vol. 276, No. 34, (pp. 32282-32287).
Johnson et al., "Achromatopsia caused by novel mutations in both CNGA3 and CNGB3," Journal of Medical Genetics, Online mutation report, Feb. 2004, vol. 41, No. 2 (5 pages).
Mao et al., "Long-Term Rescue of Retinal Structure and Function by Rhodopsin RNA Replacement with a Single Adeno-Associated Viral Vector in P23H RHO Transgenic Mice," Human Gene Therapy, Apr. 2012, vol. 23 (pp. 356-366).
Kugler et al., "Human synapsin 1 gene promoter confers highly neuron-specific long-term transgene expression from an adenoviral vector in the adult rat brain depending on the transduced area," Gene Therapy, 2003, vol. 10 (pp. 337-347).
Riley et al., "Improving the Performance of Cascade Correlation Neural Networks on Multimodal Functions," Proceedings of the World Congress on Engineering 2010 vol III WCE 2010, Jun. 30-Jul. 2, 2010, London, U.K. (7 pages).
Satterwhite et al., "The BCL11 gene family: involvement of "BCL11A" in lymphoid malignancies," Blood, Neoplasia, vol. 98, No. 12, Dec. 1, 2001 (pp. 3413-3420).
Bothmer et al., "Characterization of the interplay between DNA repair and CRISPR/Cas9-induced DNA lesions at an endogenous locus," Nature Communications, 2017, vol. 8 (pp. 1-12).
Huesken et al., "Design of a genome-wide siRNA library using an artificial neural network," Nature Biotechnology, 2006, vol. 23, No. 8 (pp. 995-1001).
Keskin et al., "A new, structurally nonredundant, diverse data set of protein-protein interfaces and its implications," Protein Science, 2004, vol. 13 (pp. 1043-1055).
Pakula et al., "Genetic Analysis of Protein Stability and Function," Annual Review of Genetics, Dec. 1989, vol. 23 (pp. 289-310).

FIG. 2E

PAM

Target locus 5'-..AGCTGGAGGAGGAAGGGCCTGAGTCCGAGCAGAAGAAGAAGGGCTCCCAC..-3'

3'-..TCGACCTCCTCCTTCCCGGACTCAGGCTCGTCTTCTTCTTCCCGAGGGTG..-5' crRNA 5'- GAGUCCGAGCAGAAGAAGAAGUUUUAGAGC..-3'

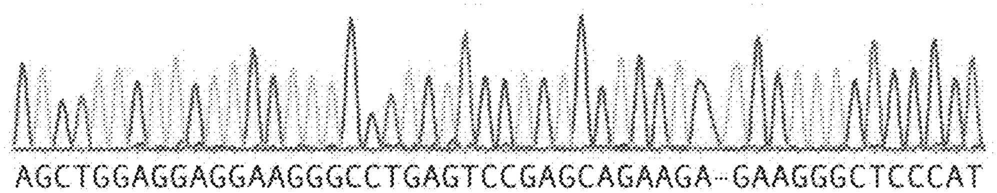

indel AGCTGGAGGAGGAAGGGCCTGAGTCCGAGCAGAAGA-GAAGGGCTCCCAT

FIG. 2F human *EMX1* protospacer target (mutation in 5 of 43 sequenced clones = 11.6%)

WT 5'-..CTGGAGGAGGAAGGGCCTGAGTCCGAGCAGAAG AAGAAGGGCTCCCATCACAT..-3'

Δ1 CTGGAGGAGGAAGGGCCTGAGTCCGAGCAGAAG--AGAAGGGCTCCCATCACAT

+1 CTGGAGGAGGAAGGGCCTGAGTCCGAGCAGAAGAAAGAAGGGCTCCCATCACAT

Δ3 CTGGAGGAGGAAGGGCCTGAGTCCGAGCAGAAG----AAGGGCTCCCATCACAT m1, Δ6 CTGGAGGAGGAAGGGCCTGAGCCCGAGCAGAAG-------GGCTCCCATCACAT

| Cas9 | target species | gene | protospacer ID | protospacer sequence (5' to 3') | PAM | strand | cell line tested | % indel (pre-crRNA + tracrRNA) | % indel (chimeric RNA) |
|---|---|---|---|---|---|---|---|---|---|
| *S. pyogenes* SF370 type II CRISPR | *Homo sapiens* | *EMX1* | 1 | GGAAGGGCCTGAGTCCGAGCAGAAGAAGAA | GGG | + | 293FT | 20 ± 1.8 | 6.7 ± 0.62 |
| | | *EMX1* | 2 | CATTGGAGGTGACATCGATGTCCTCCCCAT | TGG | – | 293FT | 2.1 ± 0.31 | N.D. |
| | | *EMX1* | 3 | GGACATCGATGTCACCTCCAATGACTAGGG | TGG | + | 293FT | 14 ± 1.1 | N.D. |
| | | *EMX1* | 4 | CATCGATGTCCTCCCCATTGGCCTGCTTCG | TGG | – | 293FT | 11 ± 1.7 | N.D. |
| | | *EMX1* | 5 | TTCGTGGCAATGCGCCACCGGTTGATGTGA | TGG | – | 293FT | 4.3 ± 0.46 | 2.1 ± 0.51 |
| | | *EMX1* | 6 | TCGTGGCAATGCGCCACCGGTTGATGTGAT | GGG | – | 293FT | 4.0 ± 0.66 | 0.41 ± 0.25 |
| | | *EMX1* | 7 | TCCAGCTTCTGCCGTTTGTACTTTGTCCTC | CGG | – | 293FT | 1.5 ± 0.12 | N.D. |
| | | *EMX1* | 8 | GGAGGGAGGGGCACAGATGAGAAACTCAGG | AGG | – | 293FT | 7.8 ± 0.83 | 2.3 ± 1.2 |
| | *Homo sapiens* | *PVALB* | 9 | AGGGGCCGAGATTGGGTGTTCAGGGCAGAG | AGG | + | 293FT | 21 ± 2.6 | 6.5 ± 0.32 |
| | | *PVALB* | 10 | ATGCAGGAGGGTGGCGAGAGGGGCCGAGAT | TGG | + | 293FT | N.D. | N.D. |
| | | *PVALB* | 11 | GGTGGCGAGAGGGGCCGAGATTGGGTGTTC | AGG | + | 293FT | N.D. | N.D. |
| | *Mus musculus* | *Th* | 12 | CAAGCACTGAGTGCCATTAGCTAAATGCAT | AGG | – | Neuro2A | 27 ± 4.3 | 4.1 ± 2.2 |
| | | *Th* | 13 | AATGCATAGGGTACCACCCACAGGTGCCAG | GGG | – | Neuro2A | 4.8 ± 1.2 | N.D. |
| | | *Th* | 14 | ACACACATGGGAAAGCCTCTGGGCCAGGAA | AGG | + | Neuro2A | 11.3 ± 1.3 | N.D. |
| *S. thermophilus* LMD-9 CRISPR1 | *Homo sapiens* | *EMX1* | 15 | GGAGGAGGTAGTATACAGAAACACAGAGAA | GTAGAAT | – | 293FT | 14 ± 0.88 | N.T. |
| | | *EMX1* | 16 | AGAATGTAGAGGAGTCACAGAAACTCAGCA | CTAGAAA | – | 293FT | 7.8 ± 0.77 | N.T. |

FIG. 5

$$\% \text{ indel} = \left(1 - \sqrt{1 - (a + b)/(a + b + c)}\right) * 100$$

FIG. 9A
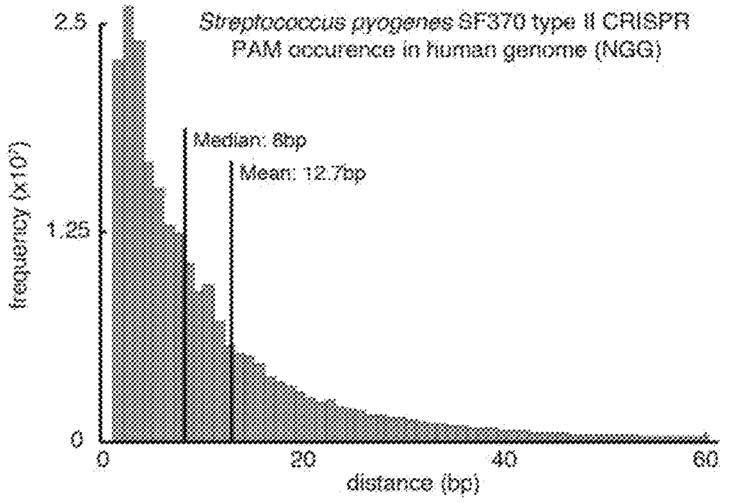
FIG. 9B
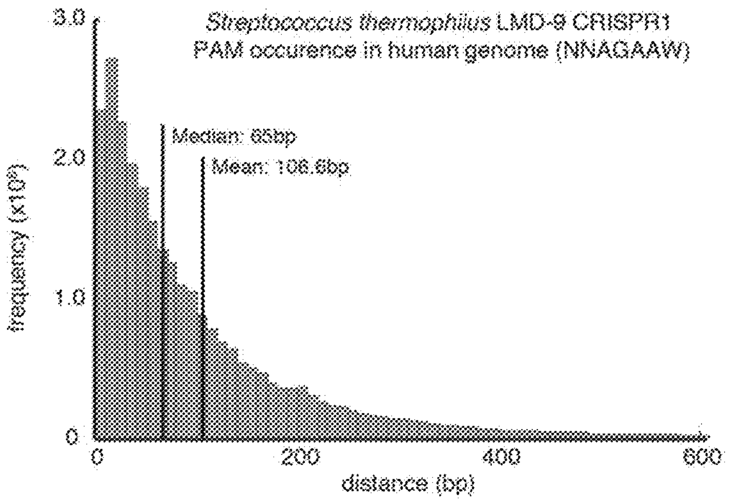
FIG. 9C
| | NGG | | NNAGAAW | |
|---|---|---|---|---|
| Chr | median | mean | median | mean |
| 1 | 7 | 12.8 | 67 | 115.8 |
| 2 | 8 | 12.7 | 64 | 100.8 |
| 3 | 8 | 13.0 | 63 | 98.5 |
| 4 | 9 | 14.0 | 61 | 94.5 |
| 5 | 8 | 13.1 | 63 | 97.9 |
| 6 | 8 | 13.1 | 63 | 98.5 |
| 7 | 8 | 12.4 | 64 | 102.9 |
| 8 | 8 | 12.8 | 64 | 100.9 |
| 9 | 7 | 13.9 | 65 | 120.5 |
| 10 | 7 | 12.1 | 66 | 107.0 |
| 11 | 7 | 12.0 | 65 | 105.8 |
| 12 | 8 | 12.4 | 65 | 103.5 |
| 13 | 8 | 13.6 | 62 | 94.6 |
| 14 | 8 | 12.0 | 65 | 101.5 |
| 15 | 7 | 11.5 | 68 | 107.7 |
| 16 | 7 | 11.7 | 74 | 136.8 |
| 17 | 6 | 10.3 | 76 | 127.9 |
| 18 | 8 | 13.4 | 63 | 101.8 |
| 19 | 6 | 9.4 | 82 | 145.4 |
| 20 | 7 | 11.1 | 72 | 121.8 |
| 21 | 7 | 13.4 | 64 | 111.4 |
| 22 | 6 | 9.2 | 85 | 140.3 |
| X | 8 | 13.2 | 63 | 99.0 |
| Y | 8 | 29.2 | 62 | 223.7 |

| Primer name | Assay | Genomic Target | Primer sequence |
|---|---|---|---|
| Sp-EMX1-F | SURVEYOR assay, sequencing | *EMX1* | AAAACCACCCTTCTCTCTGGC |
| Sp-EMX1-R | SURVEYOR assay, sequencing | *EMX1* | GGAGATTGGAGACACGGAGAG |
| Sp-PVALB-F | SURVEYOR assay, sequencing | *PVALB* | CTGGAAAGCCAATGCCTGAC |
| Sp-PVALB-R | SURVEYOR assay, sequencing | *PVALB* | GGCAGCAAACTCCTTGTCCT |
| Sp-Th-F | SURVEYOR assay, sequencing | *Th* | GTGCTTTGCAGAGGCCTACC |
| Sp-Th-R | SURVEYOR assay, sequencing | *Th* | CCTGGAGCGCATGCAGTAGT |
| St-EMX1-F | SURVEYOR assay, sequencing | *EMX1* | ACCTTCTGTGTTTCCACCATTC |
| St-EMX1-R | SURVEYOR assay, sequencing | *EMX1* | TTGGGGAGTGCACAGACTTC |
| Sp-EMX1-RFLP-F | RFLP, sequencing | *EMX1* | GGCTCCCTGGGTTCAAAGTA |
| Sp-EMX1-RFLP-R | RFLP, sequencing | *EMX1* | AGAGGGGTCTGGATGTCGTAA |
| Pb_EMX1_sp1 | Northern Blot Probe | Not applicable | TAGCTCTAAAACTTCTTCTTCTGCTCGGAC |
| Pb_tracrRNA | Northern Blot Probe | Not applicable | CTAGCCTTATTTTAACTTGCTATGCTGTTT |

FIG. 15

NGS indel data on EGFP cells

```
EGFP gRNA 1                     EGFP gRNA 2          EGFP gRNA 3
ATGGTGAGCAAGGGCGAGGAGCTGTTCACCGGGGTGGTGCCCATCCTGGTCGAGCTGGACGGCGACGTAAACGGCCACAAGTTCAGCGTGTCCGGCGAGG
||||||||||||||||||||||||||||||||||||||||||||||||||||||||||||||||||||||||||||||||||||||||||||||||||||
TACCACTCGTTCCCGCTCCTCGACAAGTGGCCCCACCACGGGTAGGACCAGCTCGACCTGCCGCTGCATTTGCCGGTGTTCAAGTCGCACAGGCCGCTCC

GCGAGGGCGATGCCACCTACGGCAAGCTGACCCTGAAGTTCATCTGCACCACCGGCAAGCTGCCCGTGCCCTGGCCCACCCTCGTGACCACCCTGACCTA
||||||||||||||||||||||||||||||||||||||||||||||||||||||||||||||||||||||||||||||||||||||||||||||||||||
CGCTCCCGCTACGGTGGATGCCGTTCGACTGGGACTTCAAGTAGACGTGGTGGCCGTTCGACGGGCACGGGACCGGGTGGGAGCACTGGTGGGACTGGAT

EGFP gRNA 4
CGGCGTGCAGTGCTTCAGCCGCTACCCCGACCACATGAAGCAGCACGACTTCTTCAAGTCCGCCATGCCCGAAGGCTACGTCCAGGAGCGCACCATCTTC
||||||||||||||||||||||||||||||||||||||||||||||||||||||||||||||||||||||||||||||||||||||||||||||||||||
GCCGCACGTCACGAAGTCGGCGATGGGGCTGGTGTACTTCGTCGTGCTGAAGAAGTTCAGGCGGTACGGGCTTCCGATGCAGGTCCTCGCGTGGTAGAAG

EGFP gRNA 4 (cont.)   EGFP gRNA 5   EGFP gRNA 6
TTCAAGGACGACGGCAACTACAAGACCCGCGCCGAGGTGAAGTTCGAGGGCGACACCCTGGTGAACCGCATCGAGCTGAAGGGCATCGACTTCAAGGAGG
||||||||||||||||||||||||||||||||||||||||||||||||||||||||||||||||||||||||||||||||||||||||||||||||||||
AAGTTCCTGCTGCCGTTGATGTTCTGGGCGCGGCTCCACTTCAAGCTCCCGCTGTGGGACCACTTGGCGTAGCTCGACTTCCCGTAGCTGAAGTTCCTCC

ACGGCAACATCCTGGGGCACAAGCTGGAGTACAACTACAACAGCCACAACGTCTATATCATGGCCGACAAGCAGAAGAACGGCATCAAGGTGAACTTCAA
||||||||||||||||||||||||||||||||||||||||||||||||||||||||||||||||||||||||||||||||||||||||||||||||||||
TGCCGTTGTAGGACCCCGTGTTCGACCTCATGTTGATGTTGTCGGTGTTGCAGATATAGTACCGGCTGTTCGTCTTCTTGCCGTAGTTCCACTTGAAGTT

GATCCGCCACAACATCGAGGACGGCAGCGTGCAGCTCGCCGACCACTACCAGCAGAACACCCCCATCGGCGACGGCCCCGTGCTGCTGCCCGACAACCAC
||||||||||||||||||||||||||||||||||||||||||||||||||||||||||||||||||||||||||||||||||||||||||||||||||||
CTAGGCGGTGTTGTAGCTCCTGCCGTCGCACGTCGAGCGGCTGGTGATGGTCGTCTTGTGGGGGTAGCCGCTGCCGGGGCACGACGACGGGCTGTTGGTG

TACCTGAGCACCCAGTCCGCCCTGAGCAAAGACCCCAACGAGAAGCGCGATCACATGGTCCTGCTGGAGTTCGTGACCGCCGCCGGGATCACTCTCGGCA
||||||||||||||||||||||||||||||||||||||||||||||||||||||||||||||||||||||||||||||||||||||||||||||||||||
ATGGACTCGTGGGTCAGGCGGGACTCGTTTCTGGGGTTGCTCTTCGCGCTAGTGTACCAGGACGACCTCAAGCACTGGCGGCGGCCCTAGTGAGAGCCGT

TGGACGAGCTGTACAAGTAA
||||||||||||||||||||
ACCTGCTCGACATGTTCATT
```

FIG. 29

| A375 | | HUES62 | |
|---|---|---|---|
| gene_name | mean depletion | gene_name | mean depletion |
| RPS19 | -2.882652431 | RPS19 | -3.183585341 |
| TCOF1 | -2.808435977 | SUMO1 | -2.958691468 |
| NIP7 | -2.577017439 | IGFN1 | -2.816486619 |
| CARS2 | -2.524564219 | AGAP5 | -2.781890338 |
| RPL7 | -2.510763424 | VOPP1 | -2.764536999 |
| ARL17A | -2.452404991 | JAKMIP1 | -2.722075866 |
| RPS18 | -2.360007937 | HIST2H2AC | -2.609990396 |
| RPS11 | -2.331818955 | SPHAR | -2.582311984 |
| RPL32 | -2.27812036 | LCE3E | -2.525929706 |
| DENR | -2.257042611 | PDRG1 | -2.499694407 |
| RPL6 | -2.23869209 | RRP1B | -2.361922343 |
| ADSL | -2.237218508 | PFDN4 | -2.321026472 |
| DNM2 | -2.213359485 | OVGP1 | -2.294064989 |
| ACTL6A | -2.197447807 | CCDC58 | -2.290819552 |
| PPAN | -2.178384698 | HIST1H2BJ | -2.288803994 |
| NT5C1B-RDH | -2.175777594 | CCDC73 | -2.279966592 |
| ENO1 | -2.17247027 | ZSCAN18 | -2.277760787 |
| DOLK | -2.140854234 | DENR | -2.253261386 |
| ASH2L | -2.137162022 | CHKA | -2.231856136 |
| SNRPF | -2.129389793 | FAM185A | -2.226396662 |
| RPL26 | -2.125670091 | OCM | -2.225306785 |
| GABPA | -2.106954316 | KBTBD11 | -2.2083224 |
| VOPP1 | -2.088272162 | RPL32 | -2.198484015 |
| RSL1D1 | -2.077068149 | RBMXL2 | -2.193406936 |
| RRAGA | -2.075755103 | LRRC37A3 | -2.188978264 |
| URB1 | -2.061968502 | SNRPG | -2.180311606 |
| MRP63 | -2.058260881 | POLR2J | -2.179863073 |
| NAA30 | -2.056104946 | EID1 | -2.177256367 |
| KPNB1 | -2.045863711 | HMGN4 | -2.152073487 |
| RPL39 | -2.042789125 | FJX1 | -2.144074596 |
| EIF2B5 | -2.018537107 | MRPS18C | -2.143839164 |
| XRN1 | -2.007802712 | UTP18 | -2.13822949 |
| LSM2 | -2.006908746 | GCSH | -2.123373465 |
| MASP2 | -1.996597431 | HIST1H2AG | -2.10248405 |
| DEFB131 | -1.981628571 | MT1E | -2.102441783 |
| LSM7 | -1.977614338 | RPL30 | -2.087694615 |
| NHP2L1 | -1.977025309 | TMEM52 | -2.078628045 |
| RPS15A | -1.964623412 | XPA | -2.075701399 |
| EEF1A1 | -1.940570892 | ARHGEF19 | -2.074475526 |
| RBX1 | -1.931878232 | RAMP2 | -2.071163793 |
| PTPMT1 | -1.931127795 | MTA3 | -2.060680607 |
| CCDC146 | -1.930330138 | POLRMT | -2.058734986 |
| COBRA1 | -1.924683023 | ZNF524 | -2.051959832 |
| VPS25 | -1.919175993 | RSL24D1 | -2.047403722 |
| RPL8 | -1.915827854 | EXOSC1 | -2.036942474 |
| POLR2I | -1.914363716 | BATF | -2.035568177 |
| NHP2 | -1.908840701 | KRTAP11-1 | -2.033591989 |
| OR5M3 | -1.903054531 | FCF1 | -2.03040005 |
| SDAD1 | -1.898279431 | NEUROG1 | -2.024122047 |
| DNAJA3 | -1.895932148 | NSRP1 | -2.016177389 |
| IMP4 | -1.886050088 | XYLT1 | -2.013363239 |
| MOAP1 | -1.882851477 | CNIH4 | -2.010919939 |
| NUTF2 | -1.873263167 | RPS7 | -2.005077402 |
| PTPN23 | -1.869411288 | PLAC9 | -1.99787552 |
| RPL14 | -1.854061225 | DCPS | -1.993526745 |
| RP11-110H1. | -1.838203216 | HMGN1 | -1.985137369 |
| TPT1 | -1.834186561 | HIST1H2BM | -1.966034904 |
| COPS3 | -1.830313031 | RPS11 | -1.958203408 |
| HARS | -1.808567224 | TP53TG5 | -1.952603327 |
| ATP6V0C | -1.806752366 | KRT82 | -1.951720459 |
| CCNH | -1.802427683 | MRP63 | -1.950917553 |
| RPL7A | -1.801850968 | OR51V1 | -1.950395101 |
| COL25A1 | -1.789186395 | RPL7A | -1.945684794 |
| EEF2 | -1.773430832 | MTMR1 | -1.942316422 |
| EEFSEC | -1.773082367 | TMEM144 | -1.940658066 |
| LGALS8 | -1.772564445 | ACSM1 | -1.938959493 |
| SFPQ | -1.771314781 | RRN3 | -1.933600629 |
| EIF2S3 | -1.769731164 | IPO4 | -1.932523341 |
| COPB1 | -1.762259717 | HNRNPU | -1.929921878 |
| RBMX2 | -1.758857017 | GTF3C1 | -1.924067851 |
| POLR3H | -1.753585716 | RPL6 | -1.923613883 |
| RPL10 | -1.75174146 | CCDC90B | -1.916359703 |
| TMLHE | -1.750717975 | C15orf42 | -1.912360544 |
| TUBG1 | -1.749877928 | CITED4 | -1.912125059 |
| ANKRD30A | -1.74932094 | CXCR3 | -1.910371663 |
| KCNJ16 | -1.74542423 | ICOS | -1.907257673 |
| ZNF207 | -1.743830295 | AKR1A1 | -1.904032674 |
| PTRH2 | -1.735681069 | WDR83OS | -1.902920977 |
| CAPZB | -1.733659665 | RMI1 | -1.900641673 |

FIG. 45A

| | | | |
|---|---|---|---|
| HNRNPU | -1.732106008 | RFC5 | -1.894008779 |
| YEATS2 | -1.72409334 | OR5AR1 | -1.888994891 |
| RPL37 | -1.72397052 | FAM96B | -1.88827946 |
| RPF1 | -1.722952482 | PCDHB1 | -1.887315952 |
| SUMO2 | -1.722198581 | RPL8 | -1.862649576 |
| ACACA | -1.719950822 | TTLL4 | -1.862595159 |
| CAPZA1 | -1.719035764 | ELOVL2 | -1.858705763 |
| FARSB | -1.707506458 | JAG2 | -1.853386152 |
| CTDP1 | -1.705884315 | RBMX2 | -1.842871507 |
| SS18L2 | -1.70390379 | POLR3K | -1.8372641 |
| CENPI | -1.703824885 | ZBTB39 | -1.834577541 |
| PRPF38B | -1.703372866 | PKD1 | -1.834139042 |
| SF3B1 | -1.702731503 | MFSD2A | -1.833483748 |
| MAPK1 | -1.69651763 | RAE1 | -1.833119559 |
| MOCS3 | -1.68666595 | RIMBP3B | -1.832150575 |
| POP7 | -1.685420318 | PKN3 | -1.831875987 |
| UTP18 | -1.684192052 | YY1 | -1.830589818 |
| ME3 | -1.683035372 | CWC25 | -1.829810575 |
| PSMC2 | -1.681322654 | ARSE | -1.823179326 |
| TBC1D2B | -1.680850452 | NBR1 | -1.823032991 |
| MRPL17 | -1.678664073 | PRNP | -1.815793705 |
| PIGW | -1.676457135 | NUDC | -1.81045846 |
| RPL30 | -1.674678234 | KDM4E | -1.810122958 |
| GFM1 | -1.672030725 | RBX1 | -1.800761527 |
| APPL1 | -1.667691292 | TSPYL2 | -1.800195078 |
| PRAMEF18 | -1.661579353 | RALGDS | -1.798929091 |
| THOC2 | -1.659978325 | C14orf80 | -1.796756631 |
| DCPS | -1.65488046 | APBA3 | -1.791344673 |
| RPS21 | -1.649662797 | ENO1 | -1.79011033 |
| POLR2L | -1.647400059 | SMG1 | -1.784878697 |
| DPPA3 | -1.643632209 | C9orf169 | -1.778113126 |
| PRAMEF11 | -1.640377216 | ZNRD1 | -1.774181477 |
| TBCC | -1.637735404 | KCNJ16 | -1.769711082 |
| MRPS12 | -1.637593143 | POLR2I | -1.769423783 |
| EFTUD2 | -1.63609533 | UBA52 | -1.768260354 |
| BEX1 | -1.634269725 | NOC4L | -1.764945455 |
| NOL6 | -1.63270992 | HORMAD2 | -1.764870613 |
| HNRNPK | -1.631201515 | OR9Q2 | -1.760481348 |
| SNRNP70 | -1.630423532 | HPN | -1.75865726 |
| RPL4 | -1.628309405 | KRT24 | -1.758465732 |
| H3F3B | -1.621875698 | FOXH1 | -1.757242912 |
| MATR3 | -1.620666917 | GDF9 | -1.756109302 |
| RPL38 | -1.618433284 | CEP290 | -1.753803294 |
| PGD | -1.617906932 | ADRA2C | -1.753773058 |
| DAP3 | -1.616024661 | TULP1 | -1.749849627 |
| TSR1 | -1.612896573 | LTBR | -1.749021049 |
| SMC1A | -1.607195432 | ZCCHC12 | -1.746744432 |
| RPL9 | -1.60619161 | RPAIN | -1.73474472 |
| RPS12 | -1.603986362 | B3GALT4 | -1.733297288 |
| SNRNP200 | -1.597597784 | ATP1A2 | -1.728486738 |
| ZNRD1 | -1.595667827 | PCDHB16 | -1.728250573 |
| TFAM | -1.592538964 | CDAN1 | -1.724068055 |
| TLN1 | -1.592240013 | PIP5K1C | -1.723834562 |
| CHST7 | -1.591104236 | MPP4 | -1.722234521 |
| RFK | -1.589972652 | SPOCD1 | -1.721697697 |
| VARS | -1.589849258 | H3F3B | -1.721342781 |
| WT1 | -1.588292311 | RPS21 | -1.717399432 |
| PDAP1 | -1.588174658 | BEX1 | -1.716075951 |
| WARS2 | -1.586972934 | DDX41 | -1.716023943 |
| OCM | -1.586564929 | ATP12A | -1.714599078 |
| TEX14 | -1.582436009 | PLEKHA6 | -1.71359395 |
| OR7C2 | -1.580970812 | SIGLEC5 | -1.711535603 |
| SNAP23 | -1.579522004 | GPR115 | -1.711244409 |
| FURIN | -1.579107358 | PGBD4 | -1.709127717 |
| C19orf25 | -1.576034681 | ABCC3 | -1.709096583 |
| GNB2L1 | -1.57535027 | C1QTNF4 | -1.704914364 |
| PCF11 | -1.573868556 | SUZ12 | -1.702460494 |
| C6orf226 | -1.573804931 | IRS1 | -1.701590078 |
| DHX15 | -1.570412486 | POLR1A | -1.7013335 |
| NUP88 | -1.567264532 | TMEM183A | -1.700220613 |
| EIF2S1 | -1.563321294 | OR52B4 | -1.699496045 |
| PET117 | -1.562889941 | SLC13A2 | -1.699062296 |
| PPP2CA | -1.562824258 | TUBGCP3 | -1.695027009 |
| CMPK1 | -1.557510591 | GGT7 | -1.690668273 |
| RAE1 | -1.553916339 | OR1D2 | -1.689507147 |
| CIRH1A | -1.55196902 | TUBG2 | -1.686771713 |
| DDX42 | -1.548957925 | FOXB1 | -1.686159699 |
| POLR3A | -1.54531119 | COX4I2 | -1.685145656 |
| RPS5 | -1.544242565 | CFHR5 | -1.684484434 |
| RUVBL2 | -1.54307586 | COX7B2 | -1.683824823 |
| KHDRBS1 | -1.540530485 | ZMYND8 | -1.679931871 |
| UBQLN3 | -1.539875621 | ANKLE2 | -1.67977325 |
| SART3 | -1.538803977 | ZBTB32 | -1.677758798 |
| CTU2 | -1.532672693 | MEX3A | -1.67283445 |
| EXOSC9 | -1.53240283 | IRF2BPL | -1.66817721 |

FIG. 45B

| | | | |
|---|---|---|---|
| EIF3D | -1.531272229 | XPO1 | -1.665911185 |
| FOSL1 | -1.525912762 | SERPINB3 | -1.665420952 |
| SKIV2L2 | -1.524792166 | SPC24 | -1.664003074 |
| NSL1 | -1.523902984 | ZNF835 | -1.663591136 |
| PKD2L2 | -1.522030203 | HSP90AB1 | -1.65845304 |
| COX17 | -1.521428227 | C1orf52 | -1.657906239 |
| RAB3GAP1 | -1.518439462 | EXOSC8 | -1.657418649 |
| SBDS | -1.518313565 | PPP1R7 | -1.654337881 |
| HSD17B10 | -1.516651173 | ANAPC7 | -1.654087519 |
| RPL34 | -1.514777041 | PDP2 | -1.652883515 |
| MRPL41 | -1.514148656 | LRRC6 | -1.649462528 |
| KIF23 | -1.511701917 | PCDHGC5 | -1.641146446 |
| BRIP1 | -1.510169164 | ECH1 | -1.637984733 |
| PSMA3 | -1.50978052 | BIRC6 | -1.635174985 |
| MYO18A | -1.506084393 | CHMP4C | -1.631396522 |
| OR5K3 | -1.501361245 | URB1 | -1.628023834 |
| PCNA | -1.500086419 | PPP4C | -1.626848674 |
| COX4I1 | -1.495514571 | LRRC3 | -1.624158807 |
| CCDC23 | -1.491525997 | FAM207A | -1.623564041 |
| SLC26A7 | -1.491379231 | TSSK1B | -1.623386054 |
| GJA3 | -1.490625294 | SNRNP35 | -1.622193825 |
| PMF1 | -1.489084741 | ENTPD7 | -1.621420381 |
| ZNF259 | -1.488562555 | ZNF559 | -1.619457887 |
| ARHGAP11A | -1.487361831 | PLEKHA3 | -1.619359014 |
| INTS8 | -1.485702565 | PSMB11 | -1.619357614 |
| COX5B | -1.483628484 | C12orf57 | -1.6192204 |
| BCL2L2-PABF | -1.479334824 | BCL9L | -1.616431663 |
| ATP6AP2 | -1.476781098 | COL6A2 | -1.616189888 |
| FNTB | -1.473951658 | PHLDA2 | -1.616178629 |
| MTA3 | -1.473861711 | ERAS | -1.613501381 |
| TDRD10 | -1.473540335 | GAS8 | -1.611441409 |
| TSG101 | -1.472472944 | ANAPC1 | -1.609927961 |
| HSP90B1 | -1.472220581 | PHIP | -1.606091841 |
| KIF2A | -1.471850262 | TMEM234 | -1.605376698 |
| MED14 | -1.469852205 | RPL13A | -1.603258551 |
| ANKRD49 | -1.469829543 | USP44 | -1.601487248 |
| PSMB4 | -1.468797099 | HNRNPA0 | -1.601341264 |
| COX5A | -1.467673157 | COX6B1 | -1.598937125 |
| PCBP1 | -1.465993867 | KRTCAP2 | -1.597973049 |
| FCF1 | -1.465773243 | CASKIN1 | -1.597967074 |
| TINF2 | -1.465625197 | IFNB1 | -1.588890032 |
| LAMTOR3 | -1.461323319 | MED21 | -1.588539266 |
| RPL11 | -1.459385197 | SDSL | -1.588435672 |
| MDM2 | -1.457827281 | RPS6 | -1.587775088 |
| CTNNBL1 | -1.45731148 | DDX42 | -1.587535926 |
| RPL15 | -1.457245851 | LIN7C | -1.587142859 |
| SOX10 | -1.457045107 | UBXN4 | -1.587070505 |
| TUBGCP3 | -1.455922895 | DSN1 | -1.582628585 |
| KDSR | -1.45079145 | NTAN1 | -1.581097107 |
| HSPA8 | -1.44920478 | CDC26 | -1.580081851 |
| MAD2L1 | -1.448620304 | PIGM | -1.578178236 |
| ZFHX3 | -1.447869343 | CHD6 | -1.577282235 |
| DYNLL1 | -1.446908968 | CHORDC1 | -1.574916503 |
| C17orf81 | -1.444492658 | UVRAG | -1.573957952 |
| NGDN | -1.444452376 | ZNF580 | -1.572557983 |
| CENPC1 | -1.444330973 | OR4D10 | -1.570303265 |
| POLR3K | -1.444320245 | COG6 | -1.569988804 |
| KRI1 | -1.443946118 | FBXO41 | -1.567074156 |
| DNAJB1 | -1.443734639 | C1orf150 | -1.566762543 |
| SLC35C2 | -1.442854155 | MMP23B | -1.56595931 |
| SAE1 | -1.437585047 | FFAR3 | -1.562720247 |
| NR1I3 | -1.437194199 | PIGW | -1.562033012 |
| NKAP | -1.436957722 | ZRSR2 | -1.560314358 |
| TBCA | -1.436566244 | ARMC7 | -1.56023241 |
| CABIN1 | -1.434611745 | EIF6 | -1.558951618 |
| HJURP | -1.433849464 | ANKRD49 | -1.55887604 |
| TRMT112 | -1.433490187 | PIK3CA | -1.558845668 |
| ZNF529 | -1.432525336 | DEFB131 | -1.55797361 |
| RPS27A | -1.432347982 | CLDN4 | -1.550420395 |
| ARMC7 | -1.429603057 | C5orf62 | -1.548815903 |
| AGAP6 | -1.429039924 | C7 | -1.548712647 |
| POLR1B | -1.428651863 | COPB1 | -1.548302258 |
| FAM96B | -1.427271021 | STX18 | -1.547594206 |
| PMVK | -1.42708923 | MASP2 | -1.545823489 |
| CSNK2B | -1.426586006 | RP11-528L24.3 | -1.545098873 |
| KPNA4 | -1.426305655 | PEX16 | -1.544210673 |
| RPL13 | -1.425968515 | TMCC3 | -1.542308989 |
| RPL35A | -1.425528555 | FTSJD1 | -1.54122008 |
| CUL1 | -1.425420937 | PDF | -1.540774209 |
| SUPT6H | -1.424775226 | TSR1 | -1.537975442 |
| RPS3 | -1.424672812 | WWC2 | -1.535385295 |
| RRP1 | -1.424495031 | EIF4E1B | -1.535041313 |
| SF1 | -1.422731301 | PCDHB7 | -1.534750337 |
| IL9 | -1.422056509 | ASNS | -1.533747699 |
| BUB1 | -1.421531126 | GNG7 | -1.533427432 |

FIG. 45C

| | | | |
|---|---|---|---|
| YY1 | -1.419062109 | RBM48 | -1.531893314 |
| SMARCA5 | -1.416042074 | HIST2H2BE | -1.530781789 |
| PSMD12 | -1.415969492 | CGB1 | -1.530628903 |
| RANBP1 | -1.415302054 | S100A11 | -1.529786068 |
| PSMB1 | -1.415056441 | EIF5 | -1.52717872 |
| WDR74 | -1.414139191 | DGCR8 | -1.52706625 |
| RPL13A | -1.413479285 | ZNF226 | -1.526829346 |
| BUD31 | -1.413072743 | PI4K2A | -1.52350573 |
| CDC45 | -1.412488904 | LRRK1 | -1.520636889 |
| PPA1 | -1.410634008 | SGTA | -1.519321666 |
| RPS14 | -1.410592726 | TOMM22 | -1.518878323 |
| NOC4L | -1.409986802 | POTED | -1.517539425 |
| CCDC59 | -1.409761529 | PSME3 | -1.514880312 |
| EXOSC8 | -1.409548516 | ZBTB8OS | -1.514406895 |
| POLR2E | -1.408878942 | LCN8 | -1.513494042 |
| DGCR8 | -1.406358064 | CDC42BPB | -1.512815457 |
| TOR1AIP1 | -1.406117404 | PA2G4 | -1.511632954 |
| EXOSC5 | -1.405249481 | PLEKHH1 | -1.510365559 |
| CSTF3 | -1.403919466 | POP7 | -1.50968476 |
| USP1 | -1.403615672 | TFAM | -1.509576181 |
| ANAPC7 | -1.401430164 | ATP6V0C | -1.508572478 |
| MDN1 | -1.401349647 | C6orf226 | -1.507967003 |
| GAPDH | -1.400273726 | MEIS1 | -1.506671145 |
| ST13 | -1.398019204 | PRDM14 | -1.505804106 |
| CCDC73 | -1.394548173 | QRFP | -1.504909604 |
| TERF2 | -1.394231255 | BRAT1 | -1.504170191 |
| NOL12 | -1.391253457 | WDR76 | -1.502637608 |
| DBR1 | -1.390682155 | VWDE | -1.499084118 |
| RBBP5 | -1.390436818 | KLHL34 | -1.497309165 |
| CASC5 | -1.390361403 | ALLC | -1.497016423 |
| ARL2 | -1.390023083 | CAPZA1 | -1.496931761 |
| ISCA2 | -1.38933325 | CTU1 | -1.496320563 |
| MTHFD1 | -1.386699362 | C1orf106 | -1.494150836 |
| RFC5 | -1.383251013 | C8orf87 | -1.491902933 |
| PRKRIR | -1.382824438 | KRT13 | -1.49155935 |
| UBC | -1.382750556 | CLUL1 | -1.491275178 |
| CHTF8 | -1.38225867 | PSMB3 | -1.490755153 |
| MORF4L1 | -1.381829505 | OR4D9 | -1.489301628 |
| CAD | -1.379757313 | ZNF286B | -1.488105536 |
| HDAC3 | -1.37833297 | KIF7 | -1.486770611 |
| DDX56 | -1.377476726 | LIPA | -1.486482578 |
| PPP1R8 | -1.375613344 | DDN | -1.485213685 |
| PSMB3 | -1.374687561 | RSL1D1 | -1.48495182 |
| VCP | -1.374559966 | SNAPC4 | -1.481726315 |
| RAB18 | -1.373544935 | TWF1 | -1.478742287 |
| KRT18 | -1.372653828 | SKIDA1 | -1.477895018 |
| EIF3H | -1.372395627 | DSCAM | -1.477613686 |
| MRPS21 | -1.371688338 | CEND1 | -1.476763069 |
| SPATA5 | -1.371546126 | USP43 | -1.47642241 |
| SF3B5 | -1.369704708 | PHPT1 | -1.475208586 |
| DHX36 | -1.368521429 | IGSF23 | -1.473471073 |
| CTDSPL | -1.368281653 | CTSZ | -1.473223599 |
| C15orf63 | -1.368169783 | HYI | -1.471848137 |
| MND1 | -1.367148567 | UCN | -1.471798831 |
| CHEK1 | -1.365498493 | JUNB | -1.471440183 |
| PSMB2 | -1.364829623 | GRB2 | -1.471324217 |
| HSCB | -1.36414551 | TAF1C | -1.469335239 |
| PFN1 | -1.363847136 | PFDN6 | -1.4692714 |
| GTPBP4 | -1.363346727 | EID2B | -1.468609431 |
| TRAPPC4 | -1.363085076 | GSTZ1 | -1.468284552 |
| TSEN54 | -1.362994692 | PPYR1 | -1.467815553 |
| RAPGEF6 | -1.362698559 | WBP1L | -1.467487002 |
| CDCA8 | -1.361945902 | ATR | -1.46714143 |
| ATP2A2 | -1.359896755 | CAPZB | -1.466475244 |
| PSMA6 | -1.359123109 | EBF2 | -1.465721319 |
| COX6B1 | -1.358954106 | RFC4 | -1.465537537 |
| CDK11A | -1.358922606 | SBDS | -1.465522817 |
| SNRPD3 | -1.358794551 | GCNT4 | -1.465420968 |
| ZBTB8OS | -1.357703857 | USF2 | -1.464916149 |
| MRTO4 | -1.356742848 | ANKRD39 | -1.462602755 |
| AP3B1 | -1.355796412 | ZNF207 | -1.461823849 |
| INTS6 | -1.35449457 | SLC43A1 | -1.461538671 |
| EIF6 | -1.35358833 | NOL3 | -1.46141808 |
| RPLP0 | -1.353376057 | MARCH11 | -1.461169146 |
| CDAN1 | -1.35102352 | SMPD2 | -1.460881076 |
| ZFAND1 | -1.350180008 | C11orf86 | -1.460075591 |
| RSL24D1 | -1.349719816 | MTRNR2L5 | -1.459134583 |
| SRSF10 | -1.349670653 | ZRANB2 | -1.458627153 |
| CINP | -1.349546146 | OR5K3 | -1.458559144 |
| PES1 | -1.348241514 | HOXA5 | -1.458453821 |
| EIF1AD | -1.347681684 | ARL17A | -1.457715258 |
| SKP1 | -1.347077683 | PPP2CA | -1.455987502 |
| CLEC10A | -1.346590066 | TBL3 | -1.455849732 |
| POLR2D | -1.344792099 | RNF20 | -1.455503496 |
| EIF1 | -1.344559124 | TBCA | -1.455477108 |

FIG. 45D

| | | | |
|---|---|---|---|
| WDR83 | -1.344216107 | RP11-865B13.1 | -1.455277909 |
| SOD1 | -1.340312573 | PCBP1 | -1.454318626 |
| SRSF3 | -1.340212883 | KDSR | -1.453151002 |
| TAF3 | -1.340156516 | BCAS2 | -1.451342376 |
| SNRPC | -1.338898127 | XIAP | -1.450998896 |
| HMGCS1 | -1.338505207 | TPM1 | -1.449883189 |
| HSPD1 | -1.33600512 | GPAM | -1.449815505 |
| PPA2 | -1.335089026 | GARS | -1.449537798 |
| PFDN6 | -1.334945087 | ALPK3 | -1.448868238 |
| NDUFB10 | -1.332788339 | TFPT | -1.447926352 |
| IRS2 | -1.332719121 | RNF112 | -1.447803365 |
| MED21 | -1.330290534 | TCTEX1D2 | -1.446558259 |
| CRCP | -1.329915908 | SLC27A5 | -1.446399836 |
| SCO2 | -1.329754225 | VPS13C | -1.445038424 |
| LYRM4 | -1.328951694 | IBSP | -1.443552161 |
| NDUFB9 | -1.32771624 | NBPF3 | -1.443366804 |
| WDR55 | -1.327002318 | KRTAP4-6 | -1.4424052 |
| PSMD6 | -1.325359209 | OR9I1 | -1.44221679 |
| C10orf55 | -1.324464755 | CMTM3 | -1.437804933 |
| SNAPC2 | -1.323520448 | AGR2 | -1.436764518 |
| TRAIP | -1.322210841 | HSD17B10 | -1.436364916 |
| FBL | -1.319362758 | MSI2 | -1.436233319 |
| SRSF11 | -1.319216433 | DCAF12 | -1.435991517 |
| DIMT1 | -1.317151465 | DNAJC11 | -1.435812507 |
| MKI67IP | -1.315985385 | NIP7 | -1.434745113 |
| NOP16 | -1.312616718 | MKL1 | -1.434161817 |
| CWC25 | -1.31108751 | PATE2 | -1.434142561 |
| FSCN1 | -1.310209463 | RTEL1 | -1.432960631 |
| UBE2M | -1.309779639 | F10 | -1.432954392 |
| SRP54 | -1.30952802 | KCND2 | -1.432764699 |
| RPA3 | -1.309065263 | PRR23C | -1.432736286 |
| C11orf75 | -1.308307405 | EXOSC7 | -1.431428179 |
| AMD1 | -1.307680016 | RIF1 | -1.429355634 |
| PTK2 | -1.307634623 | KRT28 | -1.426931464 |
| PRRG4 | -1.304157843 | GPR124 | -1.426512806 |
| SFXN4 | -1.303922126 | DLL3 | -1.422088402 |
| DHX8 | -1.302999971 | C10orf131 | -1.421588642 |
| SMC2 | -1.302938995 | ATF5 | -1.420593385 |
| ACY1 | -1.302662808 | KRTAP19-4 | -1.420517301 |
| GPN3 | -1.298923505 | PRODH | -1.41981364 |
| SOCS3 | -1.298536471 | C21orf59 | -1.419547323 |
| NTN4 | -1.296514333 | LCE3D | -1.418646134 |
| UTP14A | -1.296499694 | CRH | -1.418237482 |
| CHORDC1 | -1.295389856 | BCL2L1 | -1.418154714 |
| RBM48 | -1.294610249 | TOX4 | -1.416333246 |
| MRPS27 | -1.291129159 | FAM98B | -1.416148755 |
| DDX41 | -1.290973169 | MYC | -1.415587444 |
| MARS2 | -1.2900804 | PSIP1 | -1.414341502 |
| PSME3 | -1.289452298 | NRF1 | -1.414197906 |
| CENPE | -1.288374691 | EEF1A1 | -1.414055367 |
| VPS54 | -1.288113709 | OR4F5 | -1.41217241 |
| C1orf21 | -1.287670003 | MPLKIP | -1.412154342 |
| AURKA | -1.287485326 | LRRN1 | -1.412104794 |
| NCL | -1.286720673 | CASC4 | -1.411972135 |
| RNGTT | -1.286293458 | NUTF2 | -1.410112582 |
| RPS20 | -1.285376604 | TC2N | -1.409869276 |
| PRIM1 | -1.285117926 | C19orf60 | -1.409097495 |
| CERS1 | -1.28449224 | DESI1 | -1.408796498 |
| SRRM1 | -1.283215691 | AHSA2 | -1.408275819 |
| RPS9 | -1.281865487 | BCHE | -1.408238246 |
| POLR3B | -1.280777839 | CHIC1 | -1.408053615 |
| MPLKIP | -1.280705404 | CUBN | -1.406323811 |
| UFD1L | -1.278303239 | C1orf159 | -1.40503451 |
| ATP6AP1 | -1.277872404 | OSBPL7 | -1.404804585 |
| ZMYND8 | -1.273803762 | FGF11 | -1.403468367 |
| CCDC7 | -1.273509948 | FAM70B | -1.403401331 |
| ABHD11 | -1.273190504 | EIF2C2 | -1.402259615 |
| CCNA2 | -1.272760173 | C9orf152 | -1.401137235 |
| GABPB1 | -1.269810752 | KRTAP4-2 | -1.400786406 |
| HIVEP3 | -1.269565848 | NTSDC1 | -1.400673886 |
| BRD2 | -1.267679421 | RPS27A | -1.399937957 |
| DCTN4 | -1.26703886 | C19orf52 | -1.399507166 |
| BUB3 | -1.26667183 | NAA30 | -1.399482582 |
| CDS2 | -1.266463258 | SLN | -1.39886606 |
| UGGT2 | -1.26644049 | CEACAM19 | -1.398622812 |
| AC021066.1 | -1.262823058 | ZDHHC22 | -1.398296295 |
| ROMO1 | -1.262617798 | CDCA5 | -1.398148249 |
| DPY30 | -1.262071007 | KIF5A | -1.39306444 |
| ALG2 | -1.262064248 | USP12 | -1.393017011 |
| C21orf91 | -1.260758473 | C17orf85 | -1.392817653 |
| RPAIN | -1.259313103 | RNF186 | -1.392626488 |
| PSMG3 | -1.257309475 | GLS2 | -1.391718029 |
| METTL14 | -1.256067935 | ADM2 | -1.391549928 |
| NLE1 | -1.255704259 | GLRA1 | -1.39120265 |
| PLDN | -1.254998982 | RFC3 | -1.391106035 |

FIG. 45E

| | | | |
|---|---|---|---|
| EIF2S2 | -1.253613636 | HIST1H1B | -1.390959146 |
| SNAPC4 | -1.252507915 | EIF2S2 | -1.389038266 |
| PSMC3 | -1.252237063 | LSM2 | -1.388382414 |
| FCGR1A | -1.250801945 | UBASH3A | -1.388123983 |
| C10orf111 | -1.250410155 | GINS1 | -1.386895008 |
| ELMOD3 | -1.249168045 | PCDH18 | -1.386154855 |
| PFDN4 | -1.248643001 | CLN6 | -1.385735235 |
| EIF3A | -1.247652565 | NSUN5 | -1.384773039 |
| GPN1 | -1.246678919 | C5orf55 | -1.384724887 |
| MRPL53 | -1.246345719 | MYLPF | -1.384722044 |
| VMP1 | -1.245973445 | SGCA | -1.384606557 |
| C5orf62 | -1.245529521 | CIRH1A | -1.383945728 |
| ENTHD1 | -1.245322091 | ACTR6 | -1.38346989 |
| C7orf23 | -1.245093698 | FNBP4 | -1.383464816 |
| ANAPC4 | -1.243819302 | SAFB | -1.382666602 |
| C20orf111 | -1.242250028 | ZXDC | -1.381995699 |
| FAM118B | -1.240759583 | HAUS1 | -1.381551871 |
| ZNF662 | -1.24014827 | POM121 | -1.381439568 |
| ASXL3 | -1.24012825 | C3orf71 | -1.381187345 |
| COPB2 | -1.240117622 | NAALAD2 | -1.380921778 |
| REV3L | -1.239474867 | LGALS3BP | -1.379993411 |
| EMC7 | -1.237474252 | SMURF2 | -1.378588024 |
| PGP | -1.237066107 | FGF17 | -1.378469131 |
| ACTR6 | -1.237008101 | DLG5 | -1.378430761 |
| CNPY2 | -1.236908843 | SAE1 | -1.377958941 |
| CCDC58 | -1.236367735 | EVX1 | -1.377129469 |
| DDX43 | -1.236336025 | VPS13D | -1.376473958 |
| NUP93 | -1.235748149 | CST5 | -1.376150445 |
| MCM3AP | -1.235507764 | UTP14A | -1.374721263 |
| POLE2 | -1.235250832 | DUOX1 | -1.373580298 |
| PHTF2 | -1.234956081 | MOCS3 | -1.373232039 |
| SERAC1 | -1.234566406 | CRYGC | -1.371555233 |
| SOD2 | -1.234331381 | MED1 | -1.370418999 |
| SERPINH1 | -1.23380727 | HIGD2A | -1.370369165 |
| RFC3 | -1.233260688 | C1D | -1.370106538 |
| PLK1 | -1.233203838 | OR51F1 | -1.369826586 |
| CD36 | -1.232948853 | WDR38 | -1.369345635 |
| POLR1A | -1.232242665 | VTN | -1.368899379 |
| RABGGTB | -1.230581642 | MRPL24 | -1.368804619 |
| GEMIN5 | -1.230490006 | KDELR2 | -1.368235204 |
| COG1 | -1.229778648 | COX6B2 | -1.367659662 |
| RPL24 | -1.228478564 | C15orf26 | -1.367240793 |
| YBEY | -1.227685906 | CCDC74A | -1.366619756 |
| SLC25A26 | -1.223487939 | CALML6 | -1.366577799 |
| PKM | -1.223253054 | TXLNG | -1.365995186 |
| AP2M1 | -1.222511508 | PRPF38B | -1.365813346 |
| DDX1 | -1.222329678 | FAM171B | -1.364097696 |
| NOD1 | -1.222163777 | OR2V1 | -1.361959507 |
| ZW10 | -1.220811588 | KIAA0586 | -1.361875388 |
| NAA50 | -1.219337957 | CCNA2 | -1.3611912 |
| CEP152 | -1.217191245 | GPR158 | -1.360513184 |
| ATAD1 | -1.21710062 | SLCO1B7 | -1.360342489 |
| CDK9 | -1.216810421 | RANBP1 | -1.359068915 |
| TRMT6 | -1.214842285 | PIGS | -1.359026633 |
| EIF4E | -1.214767047 | ARL4D | -1.358847203 |
| YPEL1 | -1.214622995 | TSSK6 | -1.358756483 |
| HEATR1 | -1.212823082 | PARM1 | -1.358529964 |
| TXNRD3NB | -1.212362854 | COMMD3 | -1.358148481 |
| TRIAP1 | -1.211850501 | TMEM97 | -1.357995121 |
| TOR1B | -1.211612357 | CTU2 | -1.35618708 |
| OR5AR1 | -1.211248944 | SPAG17 | -1.355854461 |
| VPS36 | -1.210217087 | RRH | -1.355793945 |
| PIK3C3 | -1.209547893 | DUSP27 | -1.355709242 |
| MAX | -1.208188717 | CDC45 | -1.355669646 |
| INO80E | -1.208066348 | GLIPR2 | -1.355630221 |
| STX18 | -1.207721724 | PPP1R36 | -1.354665552 |
| SNRPG | -1.205566222 | PCDHB3 | -1.35424942 |
| CXorf36 | -1.204906269 | DVL2 | -1.353664249 |
| ARPC4 | -1.203668806 | SMEK2 | -1.353253501 |
| MIOS | -1.203407099 | CATSPERB | -1.352848215 |
| FMO5 | -1.203239408 | YME1L1 | -1.352625477 |
| RPA1 | -1.202357297 | BSX | -1.351907715 |
| RBMX | -1.202132754 | OR7C1 | -1.351017588 |
| VAC14 | -1.200270595 | CTTNBP2NL | -1.350201785 |
| COASY | -1.199434983 | PSMC2 | -1.34990278 |
| TPR | -1.199227411 | CEP250 | -1.349774107 |
| IGBP1 | -1.194961933 | CD70 | -1.349522814 |
| DIS3 | -1.193716642 | NKAIN1 | -1.349086317 |
| CRKL | -1.193291148 | TRIM61 | -1.34874964 |
| IL36G | -1.192801712 | BRI3 | -1.348477965 |
| CUL2 | -1.192688233 | BTF3L4 | -1.346826486 |
| POLRMT | -1.192245098 | SART3 | -1.345977605 |
| GCSH | -1.191032683 | LSS | -1.345250492 |
| PDRG1 | -1.190777209 | NDUFA7 | -1.344087552 |
| NRF1 | -1.190661017 | FOXC2 | -1.343846067 |

FIG. 45F

| | | | |
|---|---|---|---|
| EIF5 | -1.190554147 | PPP2R3C | -1.342320823 |
| LIPT1 | -1.189385756 | EIF3H | -1.341234842 |
| DTYMK | -1.189362568 | GRPEL1 | -1.340914975 |
| C11orf10 | -1.187078268 | TTC30A | -1.340200386 |
| RPS8 | -1.185370569 | ZFYVE20 | -1.339636254 |
| AP2B1 | -1.183349851 | TRIAP1 | -1.339070801 |
| ELAC2 | -1.183255107 | CFHR4 | -1.339041868 |
| USP24 | -1.18298842 | RILPL1 | -1.338786857 |
| TRAPPC11 | -1.182986448 | NEK7 | -1.338619307 |
| LAS1L | -1.182768104 | YIPF3 | -1.338477848 |
| ORC6 | -1.182407257 | H1FNT | -1.338271675 |
| ATP6V0D1 | -1.181753715 | RPL37A | -1.338252799 |
| PSMB6 | -1.180012028 | GPR125 | -1.33796122 |
| CENPW | -1.178819363 | CYP39A1 | -1.335737633 |
| RAN | -1.178639669 | HIST1H2AB | -1.335236803 |
| ARGLU1 | -1.177706953 | CCDC28B | -1.333231002 |
| ZWINT | -1.177622511 | HIST1H2AA | -1.331941737 |
| CD2 | -1.17577558 | CEACAM5 | -1.331889985 |
| RPAP3 | -1.174222309 | TCHHL1 | -1.331605136 |
| PPP1R37 | -1.169861545 | DOK1 | -1.331588865 |
| BCAS2 | -1.169813503 | RPL10 | -1.330485089 |
| NR2C2AP | -1.169190743 | DUSP12 | -1.330474476 |
| GINS3 | -1.168900802 | PSMA6 | -1.329932606 |
| CTU1 | -1.168672797 | FOXF2 | -1.329367582 |
| PFDN2 | -1.168490662 | TPT1 | -1.32921217 |
| CCT6B | -1.166890337 | FAM75A1 | -1.327873728 |
| DCLRE1B | -1.165112882 | MYPN | -1.326591013 |
| THAP1 | -1.164708443 | C12orf76 | -1.325023563 |
| EPHB6 | -1.164094347 | DHH | -1.324505465 |
| C12orf50 | -1.163923228 | ACTL6A | -1.324089056 |
| SRM | -1.162425297 | PITPNA | -1.323550188 |
| CCT6A | -1.161600828 | SNRPF | -1.322855177 |
| CNIH4 | -1.161143723 | CCR7 | -1.322225566 |
| VCL | -1.160033322 | PADI4 | -1.322023506 |
| TIPRL | -1.159975204 | RBPMS | -1.321787351 |
| EXOSC1 | -1.159391695 | SLC38A5 | -1.321627333 |
| GINS2 | -1.159330215 | ASH2L | -1.321380735 |
| POLR2G | -1.159291555 | C11orf87 | -1.320546465 |
| SMU1 | -1.158961843 | USP3 | -1.319967007 |
| TAF1C | -1.158389693 | ZNF259 | -1.319516798 |
| ATP10B | -1.155904663 | ZBTB34 | -1.319356965 |
| EIF5A | -1.155231855 | PDE6C | -1.318981816 |
| PSMD14 | -1.15495698 | C15orf63 | -1.318881749 |
| TARS | -1.154929744 | SUSD3 | -1.318679868 |
| SIAE | -1.154924856 | TUBG1 | -1.318445333 |
| CIAO1 | -1.152202616 | CPSF4L | -1.317067473 |
| VPS4A | -1.151884009 | RBM28 | -1.316596094 |
| RBBP6 | -1.151745314 | EEF2 | -1.315436524 |
| DHX9 | -1.151186658 | OR7D4 | -1.31497022 |
| POLD3 | -1.150523831 | SRCAP | -1.313693399 |
| UQCC | -1.150131829 | RPL36 | -1.313347615 |
| RRP9 | -1.148982525 | OR6B1 | -1.311657279 |
| MRC1 | -1.148911799 | UBQLN4 | -1.310950948 |
| MAP3K2 | -1.148652316 | 39880 | -1.310145651 |
| RQCD1 | -1.148569283 | SH3TC1 | -1.309541761 |
| SF3A2 | -1.148353051 | TTC36 | -1.308622776 |
| TMED3 | -1.147828583 | C11orf35 | -1.307697103 |
| PRPF4 | -1.147629016 | DNAJC17 | -1.307558425 |
| CTDSP2 | -1.14696236 | WDR91 | -1.307428734 |
| KHSRP | -1.14691668 | RGS9 | -1.307422463 |
| RPL36 | -1.146558928 | C12orf75 | -1.307402341 |
| EXOSC10 | -1.146338594 | C6orf89 | -1.307252925 |
| MRPS18C | -1.146127592 | AGTR2 | -1.306679621 |
| NFS1 | -1.142463597 | ATP2B3 | -1.306345401 |
| SGSM3 | -1.140855098 | SNRNP200 | -1.306334581 |
| MRPL36 | -1.14048396 | FKBPL | -1.306307148 |
| RPL19 | -1.140146421 | KCNJ15 | -1.306238033 |
| C1orf228 | -1.139447078 | PRKCH | -1.306146129 |
| CCT8 | -1.137811964 | EID2 | -1.305751897 |
| ACO2 | -1.137710016 | UBL4B | -1.304917945 |
| MFAP1 | -1.13741397 | KDM1A | -1.304656676 |
| FERMT2 | -1.136351485 | BHLHA9 | -1.304141607 |
| S100G | -1.136310018 | MEF2BNB | -1.303573291 |
| FXN | -1.135711566 | PPFIA4 | -1.303480594 |
| NME5 | -1.13560789 | SLC4A1 | -1.303428597 |
| KLF1 | -1.135604126 | CNPY2 | -1.302819574 |
| EIF3B | -1.135426481 | GPR85 | -1.302577615 |
| SLC35D1 | -1.135048079 | C17orf81 | -1.301560659 |
| TSEN34 | -1.133407996 | TIMM22 | -1.300694924 |
| FAM185A | -1.133299596 | LMOD3 | -1.299696123 |
| YARS2 | -1.132928814 | TDO2 | -1.298072075 |
| VN1R2 | -1.132829488 | SRSF7 | -1.297876366 |
| SETDB1 | -1.132566535 | H2BFM | -1.297338338 |
| ARIH1 | -1.131807267 | PPP2R5D | -1.29660803 |
| VPS13D | -1.129654371 | RNF168 | -1.295142446 |

FIG. 45G

| | | | |
|---|---|---|---|
| ANAPC1 | -1.127929837 | WDR88 | -1.295032877 |
| C16orf72 | -1.126826866 | DSC3 | -1.295010072 |
| WWTR1 | -1.126787364 | GJA9 | -1.293636712 |
| CEBPZ | -1.126574933 | TCFL5 | -1.293523283 |
| TCEB2 | -1.124750634 | C3orf25 | -1.293387208 |
| NDUFA2 | -1.124713541 | CCL13 | -1.29259661 |
| STX5 | -1.124386769 | BEGAIN | -1.292257661 |
| RPL5 | -1.123550445 | DUSP21 | -1.291745466 |
| U2AF1L4 | -1.12303907 | TBX5 | -1.291047766 |
| FARSA | -1.122975506 | GTPBP4 | -1.290879142 |
| MAT2A | -1.12249972 | FBXW4 | -1.290656771 |
| CCDC101 | -1.12247241 | TRAF3IP3 | -1.289221532 |
| NBR1 | -1.122159404 | LAIR2 | -1.289006794 |
| S100PBP | -1.120559064 | CCDC17 | -1.288946689 |
| PSMD2 | -1.120410134 | NSUN6 | -1.288379213 |
| CIT | -1.12012829 | HSD17B7 | -1.287990136 |
| TUBGCP4 | -1.119913794 | SIGLEC15 | -1.286365988 |
| POLG2 | -1.119353373 | YPEL1 | -1.285892981 |
| MASTL | -1.119162982 | C12orf71 | -1.284890782 |
| PSMC5 | -1.116680643 | RPS18 | -1.284861476 |
| TRA2B | -1.116641119 | PAQR3 | -1.284117989 |
| FUS | -1.115787787 | PRPF6 | -1.283508664 |
| LMLN | -1.115653475 | HSPA8 | -1.283421376 |
| XRCC4 | -1.115385414 | PLS1 | -1.283356689 |
| XPO1 | -1.115279503 | FXYD7 | -1.283150611 |
| KRTCAP2 | -1.113876033 | OR10A7 | -1.283133705 |
| C19orf69 | -1.113102098 | IDI1 | -1.282895812 |
| RRP1B | -1.11248171 | PRRC2A | -1.28242491 |
| SLC25A3 | -1.111489522 | NDNL2 | -1.281118975 |
| TCP1 | -1.111045616 | SYNGR2 | -1.280972586 |
| TNFSF12-TNF | -1.110535589 | ADO | -1.280890515 |
| PHF5A | -1.110430938 | C7orf50 | -1.280705584 |
| ACTR2 | -1.110401685 | NKD2 | -1.280529982 |
| PRMT5 | -1.110228976 | RBFOX3 | -1.280326165 |
| NUDCD3 | -1.110181528 | AIDA | -1.280056233 |
| SPTLC1 | -1.109882016 | RPS5 | -1.279801141 |
| SLC6A20 | -1.10960873 | MMS22L | -1.279507467 |
| NSA2 | -1.108398885 | THUMPD2 | -1.278957779 |
| EIF1AX | -1.107846414 | RBM39 | -1.278334778 |
| CFHR4 | -1.107841871 | CLCF1 | -1.278317998 |
| ATG5 | -1.106912764 | BLOC1S3 | -1.278020097 |
| SRCAP | -1.106872561 | C14orf102 | -1.277830268 |
| HAUS1 | -1.10619977 | SHC2 | -1.277777602 |
| N6AMT1 | -1.105902466 | PIEZO1 | -1.277394418 |
| ATR | -1.105837161 | FBXO22 | -1.277239442 |
| AHSA2 | -1.105334266 | SCTR | -1.276928082 |
| EIF3E | -1.104727511 | POLR1B | -1.274172151 |
| SPHAR | -1.104417387 | IMPDH1 | -1.271891241 |
| UBLCP1 | -1.104115654 | TRAF3IP1 | -1.271830307 |
| MRPL13 | -1.103021585 | RBM12B | -1.271554476 |
| RPLP2 | -1.102899636 | BUD31 | -1.271033674 |
| SLC39A7 | -1.102517103 | FANCM | -1.270720506 |
| TRIM59 | -1.101629427 | TGFBI | -1.270325791 |
| UQCRFS1 | -1.101448558 | FAHD2B | -1.270249913 |
| DR1 | -1.101431414 | DNAJC4 | -1.270196078 |
| CKAP2 | -1.100557384 | EIF1 | -1.269589844 |
| TAF5 | -1.100398036 | SLC11A1 | -1.268889719 |
| SRSF1 | -1.100306853 | CHD4 | -1.268686586 |
| FBXW11 | -1.100215742 | RPS9 | -1.268593949 |
| VPS28 | -1.099537324 | SPATA6 | -1.268105502 |
| PGM5 | -1.099134342 | PI4K2B | -1.267829829 |
| F11 | -1.099064319 | TCF3 | -1.267404331 |
| NUPL1 | -1.09900294 | MMGT1 | -1.266883109 |
| PMPCB | -1.098865487 | LILRA3 | -1.266264471 |
| UFM1 | -1.098637778 | OR5C1 | -1.265249631 |
| PHB2 | -1.098532471 | RBBP4 | -1.264947428 |
| HMGCR | -1.09752676 | ISM1 | -1.264866462 |
| SMG1 | -1.097265312 | KPNB1 | -1.264830663 |
| ZNF687 | -1.09657735 | SSTR1 | -1.26426376 |
| DCTN5 | -1.096499524 | TGM7 | -1.264152913 |
| PPP2R1A | -1.096393988 | C9orf16 | -1.261885101 |
| KIAA0586 | -1.095557469 | PAPPA | -1.261561488 |
| CCT4 | -1.094423341 | PNPLA6 | -1.261024012 |
| EMC6 | -1.092820255 | CLDN25 | -1.260772739 |
| RPP21 | -1.092777508 | CCDC135 | -1.260731285 |
| IPO11 | -1.092724416 | ELAC2 | -1.260434805 |
| NFYB | -1.091286106 | RPL37 | -1.260333546 |
| EIF4ENIF1 | -1.089089412 | MUSK | -1.259842432 |
| C9orf114 | -1.08779364 | NANOGNB | -1.259692167 |
| LSM11 | -1.086214526 | SLC6A12 | -1.259572819 |
| VRK1 | -1.085903324 | ATP5I | -1.257875017 |
| TBC1D8B | -1.085879458 | OR5I1 | -1.257011177 |
| MNAT1 | -1.085864628 | TMEM108 | -1.256942661 |
| NDNL2 | -1.085694726 | GUSB | -1.256846011 |
| BBX | -1.084538793 | KIAA0907 | -1.256773131 |

FIG. 45H

| | | | |
|---|---|---|---|
| SEC61B | -1.084477868 | CALML3 | -1.256468225 |
| OR5H14 | -1.083994931 | CXorf69 | -1.256375774 |
| ACTL6B | -1.083909903 | SLC6A7 | -1.255921349 |
| RCL1 | -1.08390836 | RSPH6A | -1.25582562 |
| CSF3R | -1.083676018 | UBR5 | -1.254988844 |
| NOP14 | -1.083433165 | FLT3LG | -1.254392482 |
| RPL18 | -1.082684121 | TOR1B | -1.252985237 |
| MMS22L | -1.081960406 | PCF11 | -1.252952564 |
| UBA52 | -1.081345178 | TAZ | -1.252841935 |
| SMG7 | -1.08026779 | GPR6 | -1.252350231 |
| C10orf2 | -1.079750514 | METTL24 | -1.252115773 |
| INTS4 | -1.078930568 | IRF2BP1 | -1.250916795 |
| FAM193B | -1.078919565 | PTPRCAP | -1.250840383 |
| PRMT1 | -1.078538807 | HOXC12 | -1.250203552 |
| DNM1L | -1.078189135 | NCL | -1.249314414 |
| POTEG | -1.077913378 | HS3ST4 | -1.249259524 |
| RPE | -1.077516895 | PPAN | -1.249103141 |
| ALG11 | -1.076921234 | PAF1 | -1.249100724 |
| NCOA6 | -1.076214389 | IL17F | -1.249081312 |
| HNRNPC | -1.075667291 | RAB1B | -1.24893481 |
| DEF8 | -1.07564974 | C14orf182 | -1.248906915 |
| POLR2F | -1.075425174 | ABCA2 | -1.247666282 |
| EXOC7 | -1.075263175 | SGSH | -1.246684444 |
| TLCD1 | -1.075185546 | ARID5B | -1.246500494 |
| PPP2R3C | -1.074589668 | GABPA | -1.245979186 |
| CCDC80 | -1.073109498 | FAM110C | -1.245498786 |
| HYOU1 | -1.072267629 | HDAC3 | -1.245107157 |
| PXDN | -1.072229736 | SLFNL1 | -1.244651245 |
| PRPF19 | -1.071373607 | NUF2 | -1.244465095 |
| TXN2 | -1.071195412 | MCM10 | -1.243457887 |
| NUBP2 | -1.070243769 | SKP1 | -1.24308702 |
| MPDU1 | -1.069829362 | OR11G2 | -1.243033762 |
| LIMS1 | -1.068624485 | FCGR1A | -1.242907399 |
| TDGF1 | -1.068623975 | SLC52A3 | -1.241971506 |
| ABCB7 | -1.068075668 | ARL11 | -1.24181862 |
| RAB5A | -1.06710304 | ENDOG | -1.241603576 |
| GTF2A2 | -1.066927423 | ZMIZ1 | -1.240752857 |
| PRPF6 | -1.066762079 | CCDC64B | -1.240671479 |
| ECD | -1.066306395 | CXCR6 | -1.240561222 |
| LSG1 | -1.066166811 | PKD2L1 | -1.23962038 |
| RCC1 | -1.065960233 | ADAM23 | -1.239416475 |
| ATP5I | -1.065074601 | LCA5L | -1.239150196 |
| SERPINE2 | -1.061809596 | POLR3H | -1.238997098 |
| EIF5B | -1.061589138 | RPIA | -1.238667289 |
| PMM2 | -1.061509898 | EGR1 | -1.238577588 |
| HCFC1 | -1.060512155 | UBA3 | -1.237905617 |
| PPP1R10 | -1.059547758 | CHERP | -1.237857017 |
| BAI3 | -1.059330662 | RNF24 | -1.237140122 |
| SNRNP48 | -1.059000499 | PDCL3 | -1.237007234 |
| PABPN1 | -1.058415348 | UFD1L | -1.236799288 |
| GFM2 | -1.057955433 | RAN | -1.236747906 |
| EPS15L1 | -1.057193106 | ADORA1 | -1.236481798 |
| RPS4X | -1.057139324 | CELA1 | -1.236286873 |
| BARD1 | -1.05653207 | C7orf23 | -1.236025047 |
| GS1-211B7.1 | -1.055638252 | RBBP5 | -1.235719984 |
| RANBP3L | -1.055603566 | HOXD9 | -1.235074569 |
| C19orf43 | -1.055590894 | NPFF | -1.234690934 |
| PSMA4 | -1.054967252 | CUL1 | -1.234042029 |
| CDC16 | -1.054451543 | C2orf84 | -1.233967522 |
| SFSWAP | -1.054306701 | TRIM4 | -1.233856391 |
| RER1 | -1.053547878 | ZKSCAN2 | -1.233848704 |
| BOD1L1 | -1.053227865 | CEBPZ | -1.233787188 |
| FPGT | -1.052739242 | TRAF4 | -1.233764083 |
| G6PD | -1.052583161 | PRPF38A | -1.233432633 |
| MBD6 | -1.051540404 | RP4-725G10.1 | -1.233421201 |
| TIRAP | -1.051294407 | MCL1 | -1.2331853 |
| FLI1 | -1.050933914 | C11orf52 | -1.230877202 |
| KIF11 | -1.050846083 | SHROOM1 | -1.230429373 |
| GINS1 | -1.050225728 | KDM5A | -1.230174275 |
| ATP5B | -1.049973223 | AKR1C2 | -1.228724497 |
| GNL2 | -1.049765519 | PLEKHG4 | -1.228060686 |
| MRPL12 | -1.049447717 | POLR3B | -1.227057585 |
| CHMP3 | -1.049124508 | PIGY | -1.227016347 |
| PWP2 | -1.049006238 | PYGO2 | -1.226863313 |
| PPP4C | -1.048409595 | TWSG1 | -1.226773792 |
| ZNF513 | -1.047739956 | C1orf158 | -1.226411543 |
| AKIRIN2 | -1.046196936 | ABHD15 | -1.226344221 |
| C15orf42 | -1.046178886 | PLLP | -1.225999885 |
| ZFC3H1 | -1.045841485 | PDCD7 | -1.225947903 |
| CHKA | -1.045756653 | HIGD1A | -1.225303705 |
| MAPK10 | -1.045274203 | VN1R2 | -1.224415174 |
| LAMA2 | -1.044167976 | OR1L3 | -1.223408953 |
| UTP3 | -1.042571135 | C3orf33 | -1.223260954 |
| MED11 | -1.04114091 | ANO1 | -1.223137022 |
| RPRD1B | -1.040728493 | RBMX | -1.222987895 |

FIG. 45I

| | | | |
|---|---|---|---|
| AWAT1 | -1.040684879 | DZIP1 | -1.222901383 |
| RBM39 | -1.04067574 | DOCK5 | -1.222322295 |
| MCMBP | -1.040424041 | KCTD10 | -1.221109248 |
| ZNHIT6 | -1.039714905 | UBL7 | -1.220450127 |
| CENPH | -1.039411904 | KCTD3 | -1.219907579 |
| HAUS5 | -1.039171405 | PMF1 | -1.219794741 |
| KIAA1731 | -1.039098244 | PYGL | -1.21943985 |
| RABGEF1 | -1.038855914 | TRIP13 | -1.219009527 |
| ENOPH1 | -1.038800689 | ALKBH3 | -1.218969454 |
| FANCM | -1.038460637 | GSTA1 | -1.218703181 |
| FPGS | -1.038400291 | JMJD8 | -1.218210725 |
| EFCAB4A | -1.038199677 | PNMA1 | -1.217902567 |
| DNAJC17 | -1.038010644 | PAX4 | -1.217814145 |
| ASB11 | -1.036929888 | PTAR1 | -1.217028717 |
| ORC3 | -1.03682261 | PMM1 | -1.216559665 |
| MTOR | -1.035784209 | GINS2 | -1.216551298 |
| HAUS3 | -1.03550743 | ALDH3B2 | -1.216469875 |
| CHMP2A | -1.034698839 | TULP3 | -1.216324414 |
| SPICE1 | -1.03438403 | ARL3 | -1.216315431 |
| COPS6 | -1.034307376 | GCGR | -1.215878806 |
| ZNHIT2 | -1.033205846 | HAUS5 | -1.215854539 |
| SNRNP25 | -1.03234706 | RPS15A | -1.21583725 |
| RPS13 | -1.032046119 | PDAP1 | -1.215830382 |
| M6PR | -1.031904362 | ATP5B | -1.215816343 |
| GUF1 | -1.031816394 | RABEP2 | -1.214264623 |
| C3orf67 | -1.030683122 | P2RX1 | -1.213876172 |
| PPP1R12A | -1.02965238 | RDBP | -1.213758401 |
| RPL28 | -1.029185679 | FKBP1A | -1.213560915 |
| C21orf59 | -1.028385996 | HIST1H2AD | -1.213480645 |
| RAB6C | -1.02779821 | RAD18 | -1.213377205 |
| WARS | -1.027713458 | GTF3C2 | -1.213167613 |
| TDO2 | -1.027643685 | SLC43A3 | -1.213037935 |
| CNKSR2 | -1.027506652 | NAA40 | -1.212609012 |
| TUBB | -1.027459775 | SNRNP70 | -1.212520924 |
| CISD2 | -1.026484231 | DEFB1 | -1.212123838 |
| SKA1 | -1.026374844 | AP3M1 | -1.211835974 |
| IL32 | -1.025804163 | ACAN | -1.211816439 |
| PARP14 | -1.023925458 | C2orf66 | -1.210920926 |
| BRAT1 | -1.023290534 | GRPR | -1.210663229 |
| OR2A5 | -1.023199598 | AURKA | -1.210453093 |
| ATP6V0B | -1.023178105 | KTI12 | -1.210192529 |
| HINFP | -1.022734346 | MAPK1 | -1.209830295 |
| KCTD15 | -1.021975211 | OR2V2 | -1.209764782 |
| NDUFB2 | -1.021247536 | C16orf48 | -1.209577881 |
| PBRM1 | -1.021207796 | ARL2 | -1.209176992 |
| ANXA10 | -1.020889365 | PRR14 | -1.208238549 |
| NOP10 | -1.020826147 | ZC3H15 | -1.20763772 |
| TMEM106B | -1.020700587 | RBBP9 | -1.207494145 |
| NOP58 | -1.019570934 | JRKL | -1.207250525 |
| TMX2 | -1.018594261 | TLE4 | -1.206517106 |
| PSMD8 | -1.01767613 | DUS3L | -1.206353618 |
| EIF2B1 | -1.017493236 | ZBTB5 | -1.205970284 |
| PTPDC1 | -1.014494149 | MRPS17 | -1.205828906 |
| MMD2 | -1.014114046 | MYPOP | -1.205188753 |
| HEATR7B2 | -1.013780521 | ADRB3 | -1.205153273 |
| STXBP3 | -1.013247945 | POU6F1 | -1.205067176 |
| TOMM22 | -1.012558371 | ASPDH | -1.204316403 |
| CEP192 | -1.012469221 | U2AF1 | -1.203610591 |
| HAUS7 | -1.011401537 | GMEB2 | -1.203026471 |
| OVGP1 | -1.01054944 | MGST1 | -1.202845243 |
| SCD | -1.009733678 | ALG2 | -1.202776548 |
| MRPS16 | -1.009396417 | SMURF1 | -1.202329155 |
| RFT1 | -1.009339903 | TTC16 | -1.20179783 |
| SEPHS2 | -1.008627614 | RHOD | -1.201014791 |
| LRMP | -1.008251055 | MFAP1 | -1.200742731 |
| TSPAN33 | -1.007460428 | SFSWAP | -1.200478122 |
| MED26 | -1.00731284 | MAX | -1.200087952 |
| NCAPG | -1.006836369 | NHP2L1 | -1.199623442 |
| PPCDC | -1.006405797 | PRDX1 | -1.199068532 |
| CSTL1 | -1.005623976 | SAYSD1 | -1.1987253 |
| RRP8 | -1.005554672 | MGEA5 | -1.198453769 |
| HNRPDL | -1.005407422 | OR8H1 | -1.198218642 |
| TOR1AIP2 | -1.004804503 | ABR | -1.19759339 |
| SMC5 | -1.00450648 | MCM3AP | -1.197466411 |
| LRRC55 | -1.004111456 | FBXL17 | -1.196987742 |
| C19orf52 | -1.004058784 | RPS2 | -1.19681493 |
| PARN | -1.00373213 | RP4-811H24.6 | -1.196547503 |
| ARPC3 | -1.002802732 | RPL27A | -1.196479726 |
| DDB1 | -1.001257599 | ZBTB17 | -1.196076621 |
| WDR33 | -1.000650574 | HELZ | -1.196045885 |
| LCE1A | -1.000021373 | IL10RA | -1.195419237 |
| U2AF1 | -1.00001316 | SRRM2 | -1.195138055 |
| HSDL2 | -0.99953368 | RPP21 | -1.194847512 |
| CCNYL1 | -0.999129699 | ARID5A | -1.194303294 |
| ZNHIT1 | -0.999059485 | TRMT6 | -1.193704371 |

FIG. 45J

| | | | |
|---|---|---|---|
| ORC5 | -0.999022729 | GLYR1 | -1.193375028 |
| TAF7 | -0.998960964 | TSR2 | -1.193336722 |
| HORMAD2 | -0.998922287 | RELL1 | -1.192137068 |
| BFSP1 | -0.997408668 | ISG20 | -1.19202823 |
| STT3A | -0.996413479 | BRWD3 | -1.191959771 |
| NDOR1 | -0.996169109 | HSPD1 | -1.191481897 |
| RRP15 | -0.995951965 | WDR55 | -1.19100909 |
| HM13 | -0.99565163 | CGNL1 | -1.190965918 |
| MCM6 | -0.99521859 | TMEM99 | -1.190704403 |
| CCDC99 | -0.992692391 | LSM11 | -1.190349618 |
| CHPF2 | -0.992254578 | GATA2 | -1.190148311 |
| GLRA1 | -0.992025418 | KRT34 | -1.189748177 |
| TTC37 | -0.991617863 | RGS9BP | -1.188853876 |
| FAM98B | -0.991481224 | KCTD11 | -1.188848339 |
| NAA38 | -0.991438467 | FARSA | -1.188748461 |
| DHDDS | -0.988691739 | PES1 | -1.188565898 |
| GTPBP2 | -0.988589701 | KRTAP19-8 | -1.188438649 |
| CLEC2L | -0.987481869 | PGP | -1.188016303 |
| ATMIN | -0.98739107 | SSH1 | -1.18739853 |
| MTRNR2L3 | -0.986897737 | KRT75 | -1.187200015 |
| PEA15 | -0.985880842 | HIST3H2A | -1.186323206 |
| NDC80 | -0.98584922 | PPM1D | -1.186030197 |
| POLR2A | -0.985787997 | COX7A2 | -1.18513762 |
| DDX39B | -0.985042674 | RADIL | -1.185009391 |
| RNF224 | -0.984658566 | ABHD12B | -1.184327384 |
| METTL23 | -0.984552151 | SLC7A6 | -1.183846881 |
| C11orf58 | -0.983361828 | ZFHX3 | -1.183840398 |
| GABPB2 | -0.982871152 | ELP3 | -1.183438845 |
| MCF2L | -0.982605638 | KIF20A | -1.182917249 |
| ERAL1 | -0.981807872 | C16orf54 | -1.181264225 |
| HUWE1 | -0.981603706 | PACSIN3 | -1.181015708 |
| HECTD3 | -0.981147627 | DYNLL1 | -1.180939788 |
| SCAP | -0.981101285 | USP40 | -1.180477424 |
| IMP3 | -0.98032947 | SORCS2 | -1.179876485 |
| IFRD1 | -0.980315771 | KRT6B | -1.179807981 |
| CSNK1D | -0.980279306 | ACTA2 | -1.179634896 |
| CHCHD1 | -0.979858879 | GNMT | -1.178859953 |
| ZNF596 | -0.979802333 | SCUBE1 | -1.178794037 |
| GKAP1 | -0.978385757 | DPM2 | -1.178333695 |
| DDX21 | -0.978364079 | ASB14 | -1.178204751 |
| MYC | -0.976957246 | C17orf28 | -1.177601279 |
| LRR1 | -0.976572281 | C19orf69 | -1.177499613 |
| GART | -0.975986622 | ADIPOR1 | -1.17704494 |
| RTTN | -0.975004871 | DEFB4A | -1.177042772 |
| SLC7A1 | -0.974823835 | RPA3 | -1.17610571 |
| PDCD7 | -0.974538454 | C22orf15 | -1.175284917 |
| MRPS35 | -0.974029897 | SALL4 | -1.17474053 |
| KRT71 | -0.973981095 | USP1 | -1.174349639 |
| PSIP1 | -0.973643021 | TRIM68 | -1.173558611 |
| ZMYND11 | -0.973034439 | RFXAP | -1.172835458 |
| TFB2M | -0.972935954 | ZNF513 | -1.172789767 |
| RPL29 | -0.971958171 | C12orf39 | -1.172351943 |
| OSGEP | -0.971890991 | DDX23 | -1.17190298 |
| AGPS | -0.971461161 | COQ3 | -1.17111272 |
| WDR18 | -0.970454648 | SUPT6H | -1.17109365 |
| SUGP1 | -0.970082497 | CHCHD6 | -1.170420985 |
| KDM4B | -0.969836749 | CTNNBL1 | -1.169866122 |
| CCDC86 | -0.969745821 | TMEM14C | -1.169789864 |
| GTF2H5 | -0.969218429 | DIABLO | -1.169779046 |
| CAPN9 | -0.968995126 | SLC2A12 | -1.169624174 |
| DCTN6 | -0.968546036 | ACTL6B | -1.169372636 |
| RNASEH2C | -0.968090028 | SHD | -1.168908091 |
| HIST2H3D | -0.967550433 | VPS26B | -1.16833126 |
| RPL27 | -0.967489478 | GGTLC1 | -1.168228071 |
| ZNF407 | -0.96713655 | EVL | -1.168155498 |
| GINS4 | -0.966658728 | RNF133 | -1.16814253 |
| ACSM4 | -0.966503553 | FAM63B | -1.167835578 |
| SLC7A4 | -0.966347303 | ATAD3B | -1.167526301 |
| ZBBX | -0.966340595 | MFSD5 | -1.166900503 |
| OR52E2 | -0.965484195 | FAM209B | -1.166659981 |
| C15orf41 | -0.965187476 | SOX3 | -1.1660714 |
| GJC1 | -0.964735678 | FAM183A | -1.165952272 |
| SLC25A5 | -0.964460262 | RGS10 | -1.165285654 |
| HNRNPCL1 | -0.962960756 | CCDC125 | -1.165112361 |
| HNRNPA2B1 | -0.961640683 | TMEM230 | -1.164754052 |
| HELZ | -0.961255936 | TM6SF2 | -1.164689242 |
| HNRNPD | -0.961148313 | PHC3 | -1.164345153 |
| SNX22 | -0.960965128 | ALG8 | -1.1636855 |
| ANKLE2 | -0.960584879 | RPL38 | -1.163530585 |
| WDR24 | -0.960325608 | SMC5 | -1.162725855 |
| ATP6V1H | -0.960046498 | TECRL | -1.162608446 |
| RPS6 | -0.959802418 | INSM2 | -1.162511608 |
| ARPC2 | -0.959198251 | ANKFN1 | -1.162254029 |
| MRPL27 | -0.958820312 | HIST3H3 | -1.161849667 |
| COA5 | -0.95865868 | MEGF10 | -1.161822231 |

FIG. 45K

| | | | |
|---|---|---|---|
| OR13C5 | -0.958613032 | ALG10 | -1.160699223 |
| PADI4 | -0.957924378 | DKKL1 | -1.160593167 |
| PRPF38A | -0.95763203 | MPV17L | -1.160523288 |
| C8orf82 | -0.957027162 | SS18L2 | -1.160401447 |
| TOP2A | -0.956991206 | TMEM120B | -1.160003583 |
| USP39 | -0.954340951 | TMEM109 | -1.159426773 |
| WDR70 | -0.952987464 | OR52H1 | -1.159077488 |
| BRCA2 | -0.952182964 | PLA2G2E | -1.158794855 |
| MCM2 | -0.951805581 | ANKMY2 | -1.158296055 |
| IER5 | -0.951797441 | FOXD4L1 | -1.158115705 |
| AHSA1 | -0.951408637 | SH2D3A | -1.157904008 |
| GEMIN7 | -0.951372303 | CRTAP | -1.157674178 |
| EED | -0.950724816 | MARCKS | -1.15760582 |
| SMAD4 | -0.950573159 | DDX46 | -1.157570195 |
| MESDC2 | -0.950053433 | RPL13 | -1.157504332 |
| SLC22A25 | -0.949922009 | FAM216B | -1.157183413 |
| NSMCE1 | -0.949292453 | PPP4R2 | -1.157119162 |
| BAP1 | -0.948836345 | TSPAN16 | -1.157094764 |
| TMEM237 | -0.948441404 | UTP6 | -1.156869212 |
| NEU3 | -0.948069192 | PI3 | -1.156510368 |
| TEN1 | -0.94697411 | BRSK1 | -1.155649364 |
| SYS1 | -0.946634416 | TNNC2 | -1.15556236 |
| TMED10 | -0.946277895 | CCDC19 | -1.155391718 |
| KLF4 | -0.946216742 | FLYWCH2 | -1.155383306 |
| S100A10 | -0.94576215 | PTCH1 | -1.155025182 |
| C11orf57 | -0.945597045 | SHISA7 | -1.154703726 |
| FAM204A | -0.945399507 | KDM4C | -1.154270933 |
| UBL5 | -0.945324581 | ARHGAP36 | -1.15423169 |
| METTL16 | -0.945208816 | YDJC | -1.154229712 |
| GTF3C1 | -0.945069331 | SPTLC1 | -1.154192067 |
| ASNS | -0.944760908 | HMHB1 | -1.153717498 |
| PKMYT1 | -0.94465765 | TNNT3 | -1.153541832 |
| MRPL44 | -0.943978471 | TTC27 | -1.15316121 |
| NUP35 | -0.943646315 | IL6R | -1.153125602 |
| PPYR1 | -0.943328666 | SYVN1 | -1.152995283 |
| SMG5 | -0.942586637 | CTNNBIP1 | -1.152695365 |
| RNF217 | -0.941885759 | CRLF3 | -1.152200608 |
| CPSF4 | -0.941442272 | SYCE2 | -1.152198016 |
| AKAP10 | -0.940566385 | KIF12 | -1.152077246 |
| WEE1 | -0.939097678 | GEMIN4 | -1.151734538 |
| C3orf77 | -0.937721113 | USP54 | -1.151450973 |
| LGALS9C | -0.937476407 | RNPEP | -1.151140802 |
| SUZ12 | -0.937098269 | CATSPER1 | -1.151075373 |
| PSMA7 | -0.936080385 | LYSMD4 | -1.150886339 |
| ALDOA | -0.935866715 | PLOD1 | -1.150877531 |
| PAK1IP1 | -0.935775537 | SHROOM2 | -1.150659978 |
| SYMPK | -0.935542469 | C2orf69 | -1.150544498 |
| GNL3L | -0.935536653 | SYCN | -1.150379088 |
| TXNDC9 | -0.935104271 | PABPN1 | -1.150224404 |
| UBE3D | -0.935012347 | TARS | -1.149025971 |
| GLYCTK | -0.93464153 | NUPL1 | -1.148997097 |
| SLC3A2 | -0.934296036 | MAN2B2 | -1.148385262 |
| TAF7L | -0.933546227 | CRYAA | -1.148277098 |
| SMS | -0.933386778 | NDST2 | -1.147847842 |
| SAFB | -0.933374052 | MRPL36 | -1.14754419 |
| RP11-466G1: | -0.932142451 | OAS2 | -1.147355516 |
| MLKL | -0.931947868 | KRT20 | -1.147237746 |
| C18orf21 | -0.931878495 | RAX | -1.146544905 |
| CENPA | -0.931850229 | MED22 | -1.14647268 |
| SMARCB1 | -0.931804265 | PCDHB8 | -1.146301319 |
| RIOK1 | -0.931217515 | EXOSC5 | -1.146019271 |
| POP5 | -0.930830015 | MTHFD2 | -1.145860082 |
| SCAF11 | -0.930571845 | TMPRSS11BNL | -1.145855673 |
| SLC44A2 | -0.930391388 | THBD | -1.145684107 |
| GRWD1 | -0.930200191 | TCOF1 | -1.145635716 |
| DMAP1 | -0.929531228 | LCP2 | -1.14563327 |
| VRTN | -0.929439281 | DDX5 | -1.145354266 |
| NARFL | -0.929338565 | CFI | -1.145305361 |
| RNF135 | -0.928162601 | SERAC1 | -1.145252469 |
| SPC24 | -0.928075601 | KCTD8 | -1.145044577 |
| FAM63B | -0.927739551 | HCFC1 | -1.143604518 |

FIG. 45L

*LentiCRISPR* (pXPR_001 available through Addgene) *plasmid map & annotation key*

| | |
|---|---|
| Pink | BsmBI TypeIIs sites for cloning in 20bp sgRNA guide sequence after removing 1.8kb spacer sequence |
| Green | +85 chRNA sequence for sgRNA |
| Gray | EFS promoter sequence |
| Yellow | Human codon-optimized SpCas9 coding sequence |
| Red | P2A bicistronic linker/self-cleaving peptide |
| Blue | Puromycin resistance coding sequence |

Online plasmid map is available at the website bit.ly/pLentiCRISPR

```
>lentiCRISPR (pXPR_001)
TTAATGTAGTCTTATGCAATACTCTTGTAGTCTTGCAACATGGTAACGATGAGTTAGCAACATGCCTTACAAGGAGAG
AAAAAGCACCGTGCATGCCGATTGGTGGAAGTAAGGTGGTACGATCGTGCCTTATTAGGAAGGCAACAGACGGGTCTG
ACATGGATTGGACGAACCACTGAATTGCCGCATTGCAGAGATATTGTATTTAAGTGCCTAGCTCGATACATAAACGGG
TCTCTCTGGTTAGACCAGATCTGAGCCTGGGAGCTCTCTGGCTAACTAGGGAACCCACTGCTTAAGCCTCAATAAAGC
TTGCCTTGAGTGCTTCAAGTAGTGTGTGCCCGTCTGTTGTGTGACTCTGGTAACTAGAGATCCCTCAGACCCTTTTAG
TCAGTGTGGAAAATCTCTAGCAGTGGCGCCCGAACAGGGACTTGAAAGCGAAAGGGAAACCAGAGGAGCTCTCTCGAC
GCAGGACTCGGCTTGCTGAAGCGCGCACGGCAAGAGGCGAGGGGCGGCGACTGGTGAGTACGCCAAAAATTTTGACTA
GCGGAGGCTAGAAGGAGAGAGATGGGTGCGAGAGCGTCAGTATTAAGCGGGGGAGAATTAGATCGCGATGGGAAAAAA
TTCGGTTAAGGCCAGGGGGAAAGAAAAAATATAAATTAAAACATATAGTATGGGCAAGCAGGGAGCTAGAACGATTCG
CAGTTAATCCTGGCCTGTTAGAAACATCAGAAGGCTGTAGACAAATACTGGGACAGCTACAACCATCCCTTCAGACAG
GATCAGAAGAACTTAGATCATTATATAATACAGTAGCAACCCTCTATTGTGTGCATCAAAGGATAGAGATAAAAGACA
CCAAGGAAGCTTTAGACAAGATAGAGGAAGAGCAAAACAAAAGTAAGACCACCGCACAGCAAGCGGCCGCTGATCTTC
AGACCTGGAGGAGGAGATATGAGGGACAATTGGAGAAGTGAATTATATAAATATAAAGTAGTAAAAATTGAACCATTA
GGAGTAGCACCCACCAAGGCAAAGAGAAGAGTGGTGCAGAGAGAAAAAAGAGCAGTGGGAATAGGAGCTTTGTTCCTT
GGGTTCTTGGGAGCAGCAGGAAGCACTATGGGCGCAGCGTCAATGACGCTGACGGTACAGGCCAGACAATTATTGTCT
GGTATAGTGCAGCAGCAGAACAATTTGCTGAGGGCTATTGAGGCGCAACAGCATCTGTTGCAACTCACAGTCTGGGGC
ATCAAGCAGCTCCAGGCAAGAATCCTGGCTGTGGAAAGATACCTAAAGGATCAACAGCTCCTGGGGATTTGGGGTTGC
TCTGGAAAACTCATTTGCACCACTGCTGTGCCTTGGAATGCTAGTTGGAGTAATAAATCTCTGGAACAGATTTGGAAT
CACACGACCTGGATGGAGTGGGACAGAGAAATTAACAATTACACAAGCTTAATACACTCCTTAATTGAAGAATCGCAA
AACCAGCAAGAAAAGAATGAACAAGAATTATTGGAATTAGATAAATGGGCAAGTTTGTGGAATTGGTTTAACATAACA
AATTGGCTGTGGTATATAAAATTATTCATAATGATAGTAGGAGGCTTGGTAGGTTTAAGAATAGTTTTTGCTGTACTT
TCTATAGTGAATAGAGTTAGGCAGGGATATTCACCATTATCGTTTCAGACCCACCTCCCAACCCCGAGGGGACCCAGA
GAGGGCCTATTTCCCATGATTCCTTCATATTTGCATATACGATACAAGGCTGTTAGAGAGATAATTAGAATTAATTTG
ACTGTAAACACAAAGATATTAGTACAAAATACGTGACGTAGAAAGTAATAATTTCTTGGGTAGTTTGCAGTTTTAAAA
TTATGTTTTAAAATGGACTATCATATGCTTACCGTAACTTGAAAGTATTTCGATTTCTTGGCTTTATATATCTTGTGG
AAAGGACGAAACACCGGAGACGGTTGTAAATGAGCACACAAAATACACATGCTAAAATATTATATTCTATGACCTTTA
TAAAATCAACCAAAATCTTCTTTTTAATAACTTTAGTATCAATAATTAGAATTTTTATGTTCCTTTTTGCAAACTTTT
AATAAAAATGAGCAAAATAAAAAAACGCTAGTTTTAGTAACTCGCGTTGTTTTCTTCACCTTTAATAATAGCTACTCC
ACCACTTGTTCCTAAGCGGTCAGCTCCTGCTTCAATCATTTTTTGAGCATCTTCAAATGTTCTAACTCCACCAGCTGC
```

FIG. 46A

TTTAACTAAAGCATTGTCTTTAACAACTGACTTCATTAGTTTAACATCTTCAAATGTTGCACCTGATTTTGAAAATCC
TGTTGATGTTTTAACAAATTCTAATCCAGCTTCAACAGCTATTTCACAAGCTTTCATGATTTCTTCTTTTGTTAATAA
ACAATTTTCCATAATACATTTAACAACATGTGATCCAGCTGCTTTTTTTACAGCTTTCATGTCTTCTAAAACTAATTC
ATAATTTTTGTCTTTTAATGCACCAATATTTAATACCATATCAATTTCTGTTGCACCATCTTTAATTGCTTCAGAAAC
TTCGAATGCTTTTGTAGCTGTTGTGCATGCACCTAGAGGAAAACCTACAACATTTGTTATTCCTACATTTGTGCCTTT
TAATAATTCTTTACAATAGCTTGTTCAATATGAATTAACACAAACTGTTGCAAAATCAAATTCAATTGCTTCATCACA
TAATTGTTTAATTTCAGCTTTCGTAGCATCTTGTTTTAATAATGTGTGATCTATATATTTGTTTAGTTTCATTTTTTC
TCCTATATATTCATTTTTAATTTTAATTCTTTAATAATTTCGTCTACTTTAACTTTAGCGTTTTGAACAGATTCACCAACACCTATAAAATAAATTT
TTAGTTTAGGTTCAGTTCCACTTGGGCGAACAGCAAATCATGACTTATCTTCTAAATAAAATTTTAGTAAGTCTTGTCCTGGCATATT
ATACATTCCATCGATGTAGTCTTCAACATTAACAACTTTAAGTCCAGCAATTTGAGTTAAGGGTGTTGCTCTCAATGA
TTTCATTAATGGTTCAATTTTTAATTTCTTTTCTTCTGGTTTAAAATTCAAGTTTAAAGTGAAAGTGTAATATGCACC
CATTTCTTTAAATAAATCTTCTAAATAGTCTACTAATGTTTTATTTTGTTTTTTATAAAATCAAGCAGCCTCTGCTAT
TAATATAGAAGCTTGTATTCCATCTTTATCTCTAGCTGAGTCATCAATTACATATCCATAACTTTCTTCATAAGCAAA
AACAAAATTTAATCCGTTATCTTCTTCTTTAGCAATTTCTCTACCCATTCATTTAAATCCAGTTAAAGTTTTTACAAT
ATTAACTCCATATTTTTCATGAGCGATTCTATCACCCAAATCACTTGTTACAAAACTTGAATATAGAGCCGGATTTTT
TGGAATGCTATTTAAGCGTTTTAGATTTGATAATTTTCAATCAATTAAAATTGGTCCTGTTTGATTTCCATCTAATCT
TACAAAATGACCATCATGTTTTATTGCCATTCCAAATCTGTCAGCATCTGGGTCATTCATAATAATAATATCTGCATC
ATGTTTAATACCATATTCAAGCGGTATTTTTCATGCAGGATCAAATTCTGGATTTGGATTTACAACATTTTTAAATGT
TTCATCTTCAAATGCATGCTCTTCAACCTCAATAACGTTATATCCTGATTCACGTAATATTTTTGGGGTAAATTTAGT
TCCTGTTCCATTAACTGCGCTAAAAATAATTTTTAAATCTTTTTTAGCTTCTTGCTCTTTTTTGTACGTCTCTGTTTT
AGAGCTAGAAATAGCAAGTTAAAATAAGGCTAGTCCGTTATCAACTTGAAAAAGTGGCACCGAGTCGGTGCTTTTTTG
AATTCTAGATCTTGAGACAAATGGCAGTATTCATCCACAATTTTAAAAGAAAAGGGGGGATTGGGGGGTACAGTGCAG
GGGAAAGAATAGTAGACATAATAGCAACAGACATACAAACTAAAGAATTACAAAAACAAATTACAAAAATTCAAAATT
TTCGGGTTTATTACAGGGACAGCAGAGATCCACTTTGGCGCCGGCTCGAGTGGCTCCGGTGCCCGTCAGTGGGCAGAG
CGCACATCGCCCACAGTCCCCGAGAAGTTGGGGGGAGGGGTCGGCAATTGAACCGGTGCCTAGAGAAGGTGGCGCGGG
GTAAACTGGGAAAGTGATGTCGTGTACTGGCTCCGCCTTTTTCCCGAGGGTGGGGGAGAACCGTATATAAGTGCAGTA
GTCGCCGTGAACGTTCTTTTTCGCAACGGGTTTGCCGCCAGAACACAGGTGTCGTGACGCGGGATCCGCCACCATGGA
TTACAAAGACGATGACGATAAGATGGCCCCAAAGAAGAAGCGGAAGGTCGGTATCCACGGAGTCCCAGCAGCCGACAA
GAAGTACAGCATCGGCCTGGACATCGGCACCAACTCTGTGGGCTGGGCCGTGATCACCGACGAGTACAAGGTGCCCAG
CAAGAAATTCAAGGTGCTGGGCAACACCGACCGGCACAGCATCAAGAAGAACCTGATCGGAGCCCTGCTGTTCGACAG
CGGCGAAACAGCCGAGGCCACCCGGCTGAAGAGAACCGCCAGAAGAAGATACACCAGACGGAAGAACCGGATCTGCTA
TCTGCAAGAGATCTTCAGCAACGAGATGGCCAAGGTGGACGACAGCTTCTTCCACAGACTGGAAGAGTCCTTCCTGGT
GGAAGAGGATAAGAAGCACGAGCGGCACCCCATCTTCGGCAACATCGTGGACGAGGTGGCCTACCACGAGAAGTACCC
CACCATCTACCACCTGAGAAAGAAACTGGTGGACAGCACCGACAAGGCCGACCTGCGGCTGATCTATCTGGCCCTGGC
CCACATGATCAAGTTCCGGGGCCACTTCCTGATCGAGGGCGACCTGAACCCCGACAACAGCGACGTGGACAAGCTGTT
CATCCAGCTGGTGCAGACCTACAACCAGCTGTTCGAGGAAAACCCCATCAACGCCAGCGGCGTGGACGCCAAGGCCAT
CCTGTCTGCCAGACTGAGCAAGAGCAGACGGCTGGAAAATCTGATCGCCCAGCTGCCCGGCGAGAAGAAGAATGGCCT
GTTCGGCAACCTGATTGCCCTGAGCCTGGGCCTGACCCCCAACTTCAAGAGCAACTTCGACCTGGCCGAGGATGCCAA
ACTGCAGCTGAGCAAGGACACCTACGACGACGACCTGGACAACCTGCTGGCCCAGATCGGCGACCAGTACGCCGACCT
GTTTCTGGCCGCCAAGAACCTGTCCGACGCCATCCTGCTGAGCGACATCCTGAGAGTGAACACCGAGATCACCAAGGC
CCCCCTGAGCGCCTCTATGATCAAGAGATACGACGAGCACCACCAGGACCTGACCCTGCTGAAAGCTCTCGTGCGGCA

FIG. 46B

GCAGCTGCCTGAGAAGTACAAAGAGATTTTCTTCGACCAGAGCAAGAACGGCTACGCCGGCTACATTGACGGCGGAGC
CAGCCAGGAAGAGTTCTACAAGTTCATCAAGCCCATCCTGGAAAAGATGGACGGCACCGAGGAACTGCTCGTGAAGCT
GAACAGAGAGGACCTGCTGCGGAAGCAGCGGACCTTCGACAACGGCAGCATCCCCCACCAGATCCACCTGGGAGAGCT
GCACGCCATTCTGCGGCGGCAGGAAGATTTTTACCCATTCCTGAAGGACAACCGGGAAAAGATCGAGAAGATCCTGAC
CTTCCGCATCCCCTACTACGTGGGCCCTCTGGCCAGGGGAAACAGCAGATTCGCCTGGATGACCAGAAAGAGCGAGGA
AACCATCACCCCCTGGAACTTCGAGGAAGTGGTGGACAAGGGCGCTTCCGCCCAGAGCTTCATCGAGCGGATGACCAA
CTTCGATAAGAACCTGCCCAACGAGAAGGTGCTGCCCAAGCACAGCCTGCTGTACGAGTACTTCACCGTGTATAACGA
GCTGACCAAAGTGAAATACGTGACCGAGGGAATGAGAAAGCCCGCCTTCCTGAGCGGCGAGCAGAAAAAGGCCATCGT
GGACCTGCTGTTCAAGACCAACCGGAAAGTGACCGTGAAGCAGCTGAAAGAGGACTACTTCAAGAAAATCGAGTGCTT
CGACTCCGTGGAAATCTCCGGCGTGGAAGATCGGTTCAACGCCTCCCTGGGCACATACCACGATCTGCTGAAAATTAT
CAAGGACAAGGACTTCCTGGACAATGAGGAAAACGAGGACATTCTGGAAGATATCGTGCTGACCCTGACACTGTTTGA
GGACAGAGAGATGATCGAGGAACGGCTGAAAACCTATGCCCACCTGTTCGACGACAAAGTGATGAAGCAGCTGAAGCG
GCGGAGATACACCGGCTGGGGCAGGCTGAGCCGGAAGCTGATCAACGGCATCCGGGACAAGCAGTCCGGCAAGACAAT
CCTGGATTTCCTGAAGTCCGACGGCTTCGCCAACAGAAACTTCATGCAGCTGATCCACGACGACAGCCTGACCTTTAA
AGAGGACATCCAGAAAGCCCAGGTGTCCGGCCAGGGCGATAGCCTGCACGAGCACATTGCCAATCTGGCCGGCAGCCC
CGCCATTAAGAAGGGCATCCTGCAGACAGTGAAGGTGGTGGACGAGCTCGTGAAAGTGATGGGCCGGCACAAGCCCGA
GAACATCGTGATCGAAATGGCCAGAGAGAACCAGACCACCCAGAAGGGACAGAAGAACAGCCGCGAGAGAATGAAGCG
GATCGAAGAGGGCATCAAAGAGCTGGGCAGCCAGATCCTGAAAGAACACCCCGTGGAAAACACCCAGCTGCAGAACGA
GAAGCTGTACCTGTACTACCTGCAGAATGGGCGGGATATGTACGTGGACCAGGAACTGGACATCAACCGGCTGTCCGA
CTACGATGTGGACCATATCGTGCCTCAGAGCTTTCTGAAGGACGACTCCATCGACAACAAGGTGCTGACCAGAAGCGA
CAAGAACCGGGGCAAGAGCGACAACGTGCCCTCCGAAGAGGTCGTGAAGAAGATGAAGAACTACTGGCGGCAGCTGCT
GAACGCCAAGCTGATTACCCAGAGAAAGTTCGACAATCTGACCAAGGCCGAGAGAGGCGGCCTGAGCGAACTGGATAA
GGCCGGCTTCATCAAGAGACAGCTGGTGGAAACCCGGCAGATCACAAAGCACGTGGCACAGATCCTGGACTCCCGGAT
GAACACTAAGTACGACGAGAATGACAAGCTGATCCGGGAAGTGAAAGTGATCACCCTGAAGTCCAAGCTGGTGTCCGA
TTTCCGGAAGGATTTCCAGTTTTACAAAGTGCGCGAGATCAACAACTACCACCACGCCCACGACGCCTACCTGAACGC
CGTCGTGGGAACCGCCCTGATCAAAAAGTACCCTAAGCTGGAAAGCGAGTTCGTGTACGGCGACTACAAGGTGTACGA
CGTGCGGAAGATGATCGCCAAGAGCGAGCAGGAAATCGGCAAGGCTACCGCCAAGTACTTCTTCTACAGCAACATCAT
GAACTTTTTCAAGACCGAGATTACCCTGGCCAACGGCGAGATCCGGAAGCGGCCTCTGATCGAGACAAACGGCGAAAC
CGGGGAGATCGTGTGGGATAAGGGCCGGGATTTTGCCACCGTGCGGAAAGTGCTGAGCATGCCCCAAGTGAATATCGT
GAAAAAGACCGAGGTGCAGACAGGCGGCTTCAGCAAAGAGTCTATCCTGCCCAAGAGGAACAGCGATAAGCTGATCGC
CAGAAAGAAGGACTGGGACCCTAAGAAGTACGGCGGCTTCGACAGCCCCACCGTGGCCTATTCTGTGCTGGTGGTGGC
CAAAGTGGAAAAGGGCAAGTCCAAGAAACTGAAGAGTGTGAAAGAGCTGCTGGGGATCACCATCATGGAAAGAAGCAG
CTTCGAGAAGAATCCCATCGACTTTCTGGAAGCCAAGGGCTACAAAGAAGTGAAAAAGGACCTGATCATCAAGCTGCC
TAAGTACTCCCTGTTCGAGCTGGAAAACGGCCGGAAGAGAATGCTGGCCTCTGCCGGCGAACTGCAGAAGGGAAACGA
ACTGGCCCTGCCCTCCAAATATGTGAACTTCCTGTACCTGGCCAGCCACTATGAGAAGCTGAAGGGCTCCCCCGAGGA
TAATGAGCAGAAACAGCTGTTTGTGGAACAGCACAAGCACTACCTGGACGAGATCATCGAGCAGATCAGCGAGTTCTC
CAAGAGAGTGATCCTGGCCGACGCTAATCTGGACAAAGTGCTGTCCGCCTACAACAAGCACCGGGATAAGCCCATCAG
AGAGCAGGCCGAGAATATCATCCACCTGTTTACCCTGACCAATCTGGGAGCCCCTGCCGCCTTCAAGTACTTTGACAC
CACCATCGACCGGAAGAGGTACACCAGCACCAAAGAGGTGCTGGACGCCACCCTGATCCACCAGAGCATCACCGGCCT
GTACGAGACACGGATCGACCTGTCTCAGCTGGGAGGCGACAAGCGTCCTGCTGCTACTAAGAAAGCTGGTCAAGCTAA
GAAAAAGAAAGCTAGCGGCAGCGGCGCCACCAACTTCAGCCTGCTGAAGCAGGCCGGCGACGTGGAGGAGAACCCCGG

FIG. 46C

CCGGATGACCGAGTACAAGCCCACGGTGCGCCTCGCCACCCGCGACGACGTCCCCAGGGCCGTACGCACCCTCGCCGC
CGCGTTCGCCGACTACCCCGCCACGCGCCACACCGTCGATCCGGACCGCCACATCGAGCGGGTCACCGAGCTGCAAGA
ACTCTTCCTCACGCGCGTCGGGCTCGACATCGGCAAGGTGTGGGTCGCGGACGACGGCGCGGCCGTGGCGGTCTGGAC
CACGCCGGAGAGCGTCGAAGCGGGGGCGGTGTTCGCCGAGATCGGCCCGCGCATGGCCGAGTTGAGCGGTTCCCGGCT
GGCCGCGCAGCAACAGATGGAAGGCCTCCTGGCGCCGCACCGGCCCAAGGAGCCCGCGTGGTTCCTGGCCACCGTCGG
AGTCTCGCCCGACCACCAGGGCAAGGGTCTGGGCAGCGCCGTCGTGCTCCCCGGAGTGGAGGCGGCCGAGCGCGCCGG
GGTGCCCGCCTTCCTGGAGACCTCCGCGCCCCGCAACCTCCCCTTCTACGAGCGGCTCGGCTTCACCGTCACCGCCGA
CGTCGAGGTGCCCGAAGGACCGCGCACCTGGTGCATGACCCGCAAGCCCGGTGCCTGAACGCGTTAAGTCGACAATCA
ACCTCTGGATTACAAAATTTGTGAAAGATTGACTGGTATTCTTAACTATGTTGCTCCTTTTACGCTATGTGGATACGC
TGCTTTAATGCCTTTGTATCATGCTATTGCTTCCCGTATGGCTTTCATTTTCTCCTCCTTGTATAAATCCTGGTTGCT
GTCTCTTTATGAGGAGTTGTGGCCCGTTGTCAGGCAACGTGGCGTGGTGTGCACTGTGTTTGCTGACGCAACCCCCAC
TGGTTGGGGCATTGCCACCACCTGTCAGCTCCTTTCCGGGACTTTCGCTTTCCCCCTCCCTATTGCCACGGCGGAACT
CATCGCCGCCTGCCTTGCCCGCTGCTGGACAGGGGCTCGGCTGTTGGGCACTGACAATTCCGTGGTGTTGTCGGGGAA
ATCATCGTCCTTTCCTTGGCTGCTCGCCTGTGTTGCCACCTGGATTCTGCGCGGGACGTCCTTCTGCTACGTCCCTTC
GGCCCTCAATCCAGCGGACCTTCCTTCCCGCGGCCTGCTGCCGGCTCTGCGGCCTCTTCCGCGTCTTCGCCTTCGCCC
TCAGACGAGTCGGATCTCCCTTTGGGCCGCCTCCCCGCGTCGACTTTAAGACCAATGACTTACAAGGCAGCTGTAGAT
CTTAGCCACTTTTTAAAAGAAAAGGGGGGACTGGAAGGGCTAATTCACTCCCAACGAAGACAAGATCTGCTTTTTGCT
TGTACTGGGTCTCTCTGGTTAGACCAGATCTGAGCCTGGGAGCTCTCTGGCTAACTAGGGAACCCACTGCTTAAGCCT
CAATAAAGCTTGCCTTGAGTGCTTCAAGTAGTGTGTGCCCGTCTGTTGTGTGACTCTGGTAACTAGAGATCCCTCAGA
CCCTTTTAGTCAGTGTGGAAAATCTCTAGCAGTACGTATAGTAGTTCATGTCATCTTATTATTCAGTATTTATAACTT
GCAAAGAAATGAATATCAGAGAGTGAGAGGAACTTGTTTATTGCAGCTTATAATGGTTACAAATAAAGCAATAGCATC
ACAAATTTCACAAATAAAGCATTTTTTTCACTGCATTCTAGTTGTGGTTTGTCCAAACTCATCAATGTATCTTATCAT
GTCTGGCTCTAGCTATCCCGCCCCTAACTCCGCCCATCCCGCCCCTAACTCCGCCCAGTTCCGCCCATTCTCCGCCCC
ATGGCTGACTAATTTTTTTTATTTATGCAGAGGCCGAGGCCGCCTCGGCCTCTGAGCTATTCCAGAAGTAGTGAGGAG
GCTTTTTTGGAGGCCTAGGGACGTACCCAATTCGCCCTATAGTGAGTCGTATTACGCGCGCTCACTGGCCGTCGTTTT
ACAACGTCGTGACTGGGAAAACCCTGGCGTTACCCAACTTAATCGCCTTGCAGCACATCCCCCTTTCGCCAGCTGGCG
TAATAGCGAAGAGGCCCGCACCGATCGCCCTTCCCAACAGTTGCGCAGCCTGAATGGCGAATGGGACGCGCCCTGTAG
CGGCGCATTAAGCGCGGCGGGTGTGGTGGTTACGCGCAGCGTGACCGCTACACTTGCCAGCGCCCTAGCGCCCGCTCC
TTTCGCTTTCTTCCCTTCCTTTCTCGCCACGTTCGCCGGCTTTCCCCGTCAAGCTCTAAATCGGGGGCTCCCTTTAGG
GTTCCGATTTAGTGCTTTACGGCACCTCGACCCCAAAAAACTTGATTAGGGTGATGGTTCACGTAGTGGGCCATCGCC
CTGATAGACGGTTTTTCGCCCTTTGACGTTGGAGTCCACGTTCTTTAATAGTGGACTCTTGTTCCAAACTGGAACAAC
ACTCAACCCTATCTCGGTCTATTCTTTTGATTTATAAGGGATTTTGCCGATTTCGGCCTATTGGTTAAAAAATGAGCT
GATTTAACAAAAATTTAACGCGAATTTTAACAAAATATTAACGCTTACAATTTAGGTGGCACTTTTCGGGGAAATGTG
CGCGGAACCCCTATTTGTTTATTTTTCTAAATACATTCAAATATGTATCCGCTCATGAGACAATAACCCTGATAAATG
CTTCAATAATATTGAAAAAGGAAGAGTATGAGTATTCAACATTTCCGTGTCGCCCTTATTCCCTTTTTTGCGGCATTT
TGCCTTCCTGTTTTTGCTCACCCAGAAACGCTGGTGAAAGTAAAAGATGCTGAAGATCAGTTGGGTGCACGAGTGGGT
TACATCGAACTGGATCTCAACAGCGGTAAGATCCTTGAGAGTTTTCGCCCCGAAGAACGTTTTCCAATGATGAGCACT
TTTAAAGTTCTGCTATGTGGCGCGGTATTATCCCGTATTGACGCCGGGCAAGAGCAACTCGGTCGCCGCATACACTAT
TCTCAGAATGACTTGGTTGAGTACTCACCAGTCACAGAAAAGCATCTTACGGATGGCATGACAGTAAGAGAATTATGC
AGTGCTGCCATAACCATGAGTGATAACACTGCGGCCAACTTACTTCTGACAACGATCGGAGGACCGAAGGAGCTAACC
GCTTTTTTGCACAACATGGGGGATCATGTAACTCGCCTTGATCGTTGGGAACCGGAGCTGAATGAAGCCATACCAAAC

FIG. 46D

GACGAGCGTGACACCACGATGCCTGTAGCAATGGCAACAACGTTGCGCAAACTATTAACTGGCGAACTACTTACTCTA
GCTTCCCGGCAACAATTAATAGACTGGATGGAGGCGGATAAAGTTGCAGGACCACTTCTGCGCTCGGCCCTTCCGGCT
GGCTGGTTTATTGCTGATAAATCTGGAGCCGGTGAGCGTGGGTCTCGCGGTATCATTGCAGCACTGGGGCCAGATGGT
AAGCCCTCCCGTATCGTAGTTATCTACACGACGGGGAGTCAGGCAACTATGGATGAACGAAATAGACAGATCGCTGAG
ATAGGTGCCTCACTGATTAAGCATTGGTAACTGTCAGACCAAGTTTACTCATATATACTTTAGATTGATTTAAAACTT
CATTTTTAATTTAAAAGGATCTAGGTGAAGATCCTTTTTGATAATCTCATGACCAAAATCCCTTAACGTGAGTTTTCG
TTCCACTGAGCGTCAGACCCCGTAGAAAAGATCAAAGGATCTTCTTGAGATCCTTTTTTTCTGCGCGTAATCTGCTGC
TTGCAAACAAAAAAACCACCGCTACCAGCGGTGGTTTGTTTGCCGGATCAAGAGCTACCAACTCTTTTTCCGAAGGTA
ACTGGCTTCAGCAGAGCGCAGATACCAAATACTGTTCTTCTAGTGTAGCCGTAGTTAGGCCACCACTTCAAGAACTCT
GTAGCACCGCCTACATACCTCGCTCTGCTAATCCTGTTACCAGTGGCTGCTGCCAGTGGCGATAAGTCGTGTCTTACC
GGGTTGGACTCAAGACGATAGTTACCGGATAAGGCGCAGCGGTCGGGCTGAACGGGGGGTTCGTGCACACAGCCCAGC
TTGGAGCGAACGACCTACACCGAACTGAGATACCTACAGCGTGAGCTATGAGAAAGCGCCACGCTTCCCGAAGGGAGA
AAGGCGGACAGGTATCCGGTAAGCGGCAGGGTCGGAACAGGAGAGCGCACGAGGGAGCTTCCAGGGGGAAACGCCTGG
TATCTTTATAGTCCTGTCGGGTTTCGCCACCTCTGACTTGAGCGTCGATTTTTGTGATGCTCGTCAGGGGGGCGGAGC
CTATGGAAAAACGCCAGCAACGCGGCCTTTTTACGGTTCCTGGCCTTTTGCTGGCCTTTTGCTCACATGTTCTTTCCT
GCGTTATCCCCTGATTCTGTGGATAACCGTATTACCGCCTTTGAGTGAGCTGATACCGCTCGCCGCAGCCGAACGACC
GAGCGCAGCGAGTCAGTGAGCGAGGAAGCGGAAGAGCGCCCAATACGCAAACCGCCTCTCCCCGCGCGTTGGCCGATT
CATTAATGCAGCTGGCACGACAGGTTTCCCGACTGGAAAGCGGGCAGTGAGCGCAACGCAATTAATGTGAGTTAGCTC
ACTCATTAGGCACCCCAGGCTTTACACTTTATGCTTCCGGCTCGTATGTTGTGTGGAATTGTGAGCGGATAACAATTT
CACACAGGAAACAGCTATGACCATGATTACGCCAAGCGCGCAATTAACCCTCACTAAAGGGAACAAAAGCTGGAGCTG
CAAGC

FIG. 46E

<u>*LentiCRISPR* v2</u>

| | |
|---|---|
| Pink | BsmBI TypeIIs sites for cloning in 20bp sgRNA guide sequence after removing 1.8kb spacer sequence |
| Green | +85 chRNA sequence for sgRNA |
| Gray | EFS promoter sequence |
| Yellow | Human codon-optimized SpCas9 coding sequence |
| *Italics* | FLAG peptide tag |
| Red | P2A bicistronic linker/self-cleaving peptide |
| Blue | Puromycin resistance coding sequence |

GTCGACGGATCGGGAGATCTCCCGATCCCCTATGGTGCACTCTCAGTACAATCTGCTCTGATGCCGCATAGTTAAGCCAGTATCTGCTCCCTG
CTTGTGTGTTGGAGGTCGCTGAGTAGTGCGCGAGCAAAATTTAAGCTACAACAAGGCAAGGCTTGACCGACAATTGCATGAAGAATCTGCTTA
GGGTTAGGCGTTTTGCGCTGCTTCGCGATGTACGGGCCAGATATACGCGTTGACATTGATTATTGACTAGTTATTAATAGTAATCAATTACGG
GGTCATTAGTTCATAGCCCATATATGGAGTTCCGCGTTACATAACTTACGGTAAATGGCCCGCCTGGCTGACCGCCCAACGACCCCCGCCCAT
TGACGTCAATAATGACGTATGTTCCCATAGTAACGCCAATAGGGACTTTCCATTGACGTCAATGGGTGGAGTATTTACGGTAAACTGCCCACT
TGGCAGTACATCAAGTGTATCATATGCCAAGTACGCCCCCTATTGACGTCAATGACGGTAAATGGCCCGCCTGGCATTATGCCCAGTACATGA
CCTTATGGGACTTTCCTACTTGGCAGTACATCTACGTATTAGTCATCGCTATTACCATGGTGATGCGGTTTTGGCAGTACATCAATGGGCGTG
GATAGCGGTTTGACTCACGGGGATTTCCAAGTCTCCACCCCATTGACGTCAATGGGAGTTTGTTTTGGCACCAAAATCAACGGGACTTTCCAA
AATGTCGTAACAACTCCGCCCCATTGACGCAAATGGGCGGTAGGCGTGTACGGTGGGAGGTCTATATAAGCAGCGCGTTTTGCCTGTACTGGG
TCTCTCTGGTTAGACCAGATCTGAGCCTGGGAGCTCTCTGGCTAACTAGGGAACCCACTGCTTAAGCCTCAATAAAGCTTGCCTTGAGTGCTT
CAAGTAGTGTGTGCCCGTCTGTTGTGTGACTCTGGTAACTAGAGATCCCTCAGACCCTTTTAGTCAGTGTGGAAAATCTCTAGCAGTGGCGCC
CGAACAGGGACTTGAAAGCGAAAGGGAAACCAGAGGAGCTCTCTCGACGCAGGACTCGGCTTGCTGAAGCGCGCACGGCAAGAGGCGAGGGGC
GGCGACTGGTGAGTACGCCAAAAATTTTGACTAGCGGAGGCTAGAAGGAGAGAGATGGGTGCGAGAGCGTCAGTATTAAGCGGGGGAGAATTA
GATCGCGATGGGAAAAAATTCGGTTAAGGCCAGGGGGAAAGAAAAAATATAAATTAAAACATATAGTATGGGCAAGCAGGGAGCTAGAACGAT
TCGCAGTTAATCCTGGCCTGTTAGAAACATCAGAAGGCTGTAGACAAATACTGGGACAGCTACAACCATCCCTTCAGACAGGATCAGAAGAAC
TTAGATCATTATATAATACAGTAGCAACCCTCTATTGTGTGCATCAAAGGATAGAGATAAAAGACACCAAGGAAGCTTTAGACAAGATAGAGG
AAGAGCAAAACAAAAGTAAGACCACCGCACAGCAAGCGGCCGCTGATCTTCAGACCTGGAGGAGGAGATATGAGGGACAATTGGAGAAGTGAA
TTATATAAATATAAAGTAGTAAAAATTGAACCATTAGGAGTAGCACCCACCAAGGCAAAGAGAAGAGTGGTGCAGAGAGAAAAAAGAGCAGTG
GGAATAGGAGCTTTGTTCCTTGGGTTCTTGGGAGCAGCAGGAAGCACTATGGGCGCAGCGTCAATGACGCTGACGGTACAGGCCAGACAATTA
TTGTCTGGTATAGTGCAGCAGCAGAACAATTTGCTGAGGGCTATTGAGGCGCAACAGCATCTGTTGCAACTCACAGTCTGGGGCATCAAGCAG
CTCCAGGCAAGAATCCTGGCTGTGGAAAGATACCTAAAGGATCAACAGCTCCTGGGGATTTGGGGTTGCTCTGGAAAACTCATTTGCACCACT
GCTGTGCCTTGGAATGCTAGTTGGAGTAATAAATCTCTGGAACAGATTTGGAATCACACGACCTGGATGGAGTGGGACAGAGAAATTAACAAT
TACACAAGCTTAATACACTCCTTAATTGAAGAATCGCAAAACCAGCAAGAAAAGAATGAACAAGAATTATTGGAATTAGATAAATGGGCAAGT
TTGTGGAATTGGTTTAACATAACAAATTGGCTGTGGTATATAAAATTATTCATAATGATAGTAGGAGGCTTGGTAGGTTTAAGAATAGTTTTT
GCTGTACTTTCTATAGTGAATAGAGTTAGGCAGGGATATTCACCATTATCGTTTCAGACCCACCTCCCAACCCCGAGGGGACCCGACAGGCCC
GAAGGAATAGAAGAAGAAGGTGGAGAGAGAGACAGAGACAGATCCATTCGATTAGTGAACGGATCGGCACTGCGTGCGCCAATTCTGCAGACA
AATGGCAGTATTCATCCACAATTTTAAAAGAAAAGGGGGGATTGGGGGGTACAGTGCAGGGGAAAGAATAGTAGACATAATAGCAACAGACAT
ACAAACTAAAGAATTACAAAAACAAATTACAAAAATTCAAAATTTTCGGGTTTATTACAGGGACAGCAGAGATCCAGTTTGGTTAATTAAGGT
ACCGAGGGCCTATTTCCCATGATTCCTTCATATTTGCATATACGATACAAGGCTGTTAGAGAGATAATTAGAATTAATTTGACTGTAAACACA
AAGATATTAGTACAAAATACGTGACGTAGAAAGTAATAATTTCTTGGGTAGTTTGCAGTTTTAAAATTATGTTTTAAAATGGACTATCATATG
CTTACCGTAACTTGAAAGTATTTCGATTTCTTGGCTTTATATATCTTGTGGAAAGGACGAAACACCGGAGACGGTTGTAAATGAGCACACAAA
ATACACATGCTAAAATATTATATTCTATGACCTTTATAAAATCAACCAAAATCTTCTTTTTAATAACTTTAGTATCAATAATTAGAATTTTTA
TGTTCCTTTTTGCAAACTTTTAATAAAAATGAGCAAAATAAAAAAACGCTAGTTTTAGTAACTCGCGTTGTTTTCTTCACCTTTAATAATAGC
TACTCCACCACTTGTTCCTAAGCGGTCAGCTCCTGCTTCAATCATTTTTTGAGCATCTTCAAATGTTCTAACTCCACCAGCTGCTTTAACTAA
AGCATTGTCTTTAACAACTGACTTCATTAGTTTAACATCTTCAAATGTTGCACCTGATTTTGAAAATCCTGTTGATGTTTTAACAAATTCTAA
TCCAGCTTCAACAGCTATTTCACAAGCTTTCATGATTTCTTCTTTTGTTAATAAACAATTTTCCATAATACATTTAACAACATGTGATCCAGC
TGCTTTTTTTACAGCTTTCATGTCTTCTAAAACTAATTCATAATTTTTGTCTTTTAATGCACCAATATTTAATACCATATCAATTTCTGTTGC
ACCATCTTTAATTGCTTCAGAAACTTCGAATGCTTTTGTAGCTGTTGTGCATGCACCTAGAGGAAAACCTACAACATTTGTTATTCCTACATT

FIG. 49A

TGTGCCTTTTAATAATTCTTTACAATAGCTTGTTCAATATGAATTAACACAAACTGTTGCAAAATCAAATTCAATTGCTTCATCACATAATTG
TTTAATTTCAGCTTTCGTAGCATCTTGTTTTAATAATGTGTGATCTATATATTTGTTTAGTTTCATTTTTTCTCCTATATATTCATTTTTAAT
TTTAATTCTTTAATAATTTCGTCTACTTTAACTTTAGCGTTTTGAACAGATTCACCAACACCTATAAAATAAATTTTTAGTTTAGGTTCAGTT
CCACTTGGGCGAACAGCAAATCATGACTTATCTTCTAAATAAAATTTTAGTAAGTCTTGTCCTGGCATATTATACATTCCATCGATGTAGTCT
TCAACATTAACAACTTTAAGTCCAGCAATTTGAGTTAAGGGTGTTGCTCTCAATGATTTCATTAATGGTTCAATTTTTAATTTCTTTTCTTCT
GGTTTAAAATTCAAGTTTAAAGTGAAAGTGTAATATGCACCCATTTCTTTAAATAAATCTTCTAAATAGTCTACTAATGTTTTATTTTGTTTT
TTATAAAATCAAGCAGCCTCTGCTATTAATATAGAAGCTTGTATTCCATCTTTATCTCTAGCTGAGTCATCAATTACATATCCATAACTTTCT
TCATAAGCAAAAACAAAATTTAATCCGTTATCTTCTTCTTTAGCAATTTCTCTACCCATTCATTTAAATCCAGTTAAAGTTTTTACAATATTA
ACTCCATATTTTTCATGAGCGATTCTATCACCCAAATCACTTGTTACAAAACTTGAATATAGAGCCGGATTTTTTGGAATGCTATTTAAGCGT
TTTAGATTTGATAATTTTCAATCAATTAAAATTGGTCCTGTTTGATTTCCATCTAATCTTACAAAATGACCATCATGTTTTATTGCCATTCCA
AATCTGTCAGCATCTGGGTCATTCATAATAATAATATCTGCATCATGTTTAATACCATATTCAAGCGGTATTTTTCATGCAGGATCAAATTCT
GGATTTGGATTTACAACATTTTTAAATGTTTCATCTTCAAATGCATGCTCTTCAACCTCAATAACGTTATATCCTGATTCACGTAATATTTTT
GGGGTAAATTTAGTTCCTGTTCCATTAACTGCGCTAAAAATAATTTTTAAATCTTTTTTAGCTTCTTGCTCTTTTTTGTACGTCTCTGTTTTA
GAGCTAGAAATAGCAAGTTAAAATAAGGCTAGTCCGTTATCAACTTGAAAAAGTGGCACCGAGTCGGTGCTTTTTTGAATTCGCTAGCTAGGT
CTTGAAAGGAGTGGGAATTGGCTCCGGTGCCCGTCAGTGGGCAGAGCGCACATCGCCCACAGTCCCCGAGAAGTTGGGGGGAGGGGTCGGCAA
TTGATCCGGTGCCTAGAGAAGGTGGCGCGGGGTAAACTGGGAAAGTGATGTCGTGTACTGGCTCCGCCTTTTTCCCGAGGGTGGGGGAGAACC
GTATATAAGTGCAGTAGTCGCCGTGAACGTTCTTTTTCGCAACGGGTTTGCCGCCAGAACACAGGACCGGTTCTAGAGCGCTGCCACCATGGA
CAAGAAGTACAGCATCGGCCTGGACATCGGCACCAACTCTGTGGGCTGGGCCGTGATCACCGACGAGTACAAGGTGCCCAGCAAGAAATTCAA
GGTGCTGGGCAACACCGACCGGCACAGCATCAAGAAGAACCTGATCGGAGCCCTGCTGTTCGACAGCGGCGAAACAGCCGAGGCCACCCGGCT
GAAGAGAACCGCCAGAAGAAGATACACCAGACGGAAGAACCGGATCTGCTATCTGCAAGAGATCTTCAGCAACGAGATGGCCAAGGTGGACGA
CAGCTTCTTCCACAGACTGGAAGAGTCCTTCCTGGTGGAAGAGGATAAGAAGCACGAGCGGCACCCCATCTTCGGCAACATCGTGGACGAGGT
GGCCTACCACGAGAAGTACCCCACCATCTACCACCTGAGAAAGAAACTGGTGGACAGCACCGACAAGGCCGACCTGCGGCTGATCTATCTGGC
CCTGGCCCACATGATCAAGTTCCGGGGCCACTTCCTGATCGAGGGCGACCTGAACCCCGACAACAGCGACGTGGACAAGCTGTTCATCCAGCT
GGTGCAGACCTACAACCAGCTGTTCGAGGAAAACCCCATCAACGCCAGCGGCGTGGACGCCAAGGCCATCCTGTCTGCCAGACTGAGCAAGAG
CAGACGGCTGGAAAATCTGATCGCCCAGCTGCCCGGCGAGAAGAAGAATGGCCTGTTCGGAAACCTGATTGCCCTGAGCCTGGGCCTGACCCC
CAACTTCAAGAGCAACTTCGACCTGGCCGAGGATGCCAAACTGCAGCTGAGCAAGGACACCTACGACGACGACCTGGACAACCTGCTGGCCCA
GATCGGCGACCAGTACGCCGACCTGTTTCTGGCCGCCAAGAACCTGTCCGACGCCATCCTGCTGAGCGACATCCTGAGAGTGAACACCGAGAT
CACCAAGGCCCCCCTGAGCGCCTCTATGATCAAGAGATACGACGAGCACCACCAGGACCTGACCCTGCTGAAAGCTCTCGTGCGGCAGCAGCT
GCCTGAGAAGTACAAAGAGATTTTCTTCGACCAGAGCAAGAACGGCTACGCCGGCTACATTGACGGCGGAGCCAGCCAGGAAGAGTTCTACAA
GTTCATCAAGCCCATCCTGGAAAAGATGGACGGCACCGAGGAACTGCTCGTGAAGCTGAACAGAGAGGACCTGCTGCGGAAGCAGCGGACCTT
CGACAACGGCAGCATCCCCCACCAGATCCACCTGGGAGAGCTGCACGCCATTCTGCGGCGGCAGGAAGATTTTTACCCATTCCTGAAGGACAA
CCGGGAAAAGATCGAGAAGATCCTGACCTTCCGCATCCCCTACTACGTGGGCCCTCTGGCCAGGGGAAACAGCAGATTCGCCTGGATGACCAG
AAAGAGCGAGGAAACCATCACCCCCTGGAACTTCGAGGAAGTGGTGGACAAGGGCGCTTCCGCCCAGAGCTTCATCGAGCGGATGACCAACTT
CGATAAGAACCTGCCCAACGAGAAGGTGCTGCCCAAGCACAGCCTGCTGTACGAGTACTTCACCGTGTATAACGAGCTGACCAAAGTGAAATA
CGTGACCGAGGGAATGAGAAAGCCCGCCTTCCTGAGCGGCGAGCAGAAAAAGGCCATCGTGGACCTGCTGTTCAAGACCAACCGGAAAGTGAC
CGTGAAGCAGCTGAAAGAGGACTACTTCAAGAAAATCGAGTGCTTCGACTCCGTGGAAATCTCCGGCGTGGAAGATCGGTTCAACGCCTCCCT
GGGCACATACCACGATCTGCTGAAAATTATCAAGGACAAGGACTTCCTGGACAATGAGGAAAACGAGGACATTCTGGAAGATATCGTGCTGAC
CCTGACACTGTTTGAGGACAGAGAGATGATCGAGGAACGGCTGAAAACCTATGCCCACCTGTTCGACGACAAAGTGATGAAGCAGCTGAAGCG
GCGGAGATACACCGGCTGGGGCAGGCTGAGCCGGAAGCTGATCAACGGCATCCGGGACAAGCAGTCCGGCAAGACAATCCTGGATTTCCTGAA
GTCCGACGGCTTCGCCAACAGAAACTTCATGCAGCTGATCCACGACGACAGCCTGACCTTTAAAGAGGACATCCAGAAAGCCCAGGTGTCCGG
CCAGGGCGATAGCCTGCACGAGCACATTGCCAATCTGGCCGGCAGCCCCGCCATTAAGAAGGGCATCCTGCAGACAGTGAAGGTGGTGGACGA
GCTCGTGAAAGTGATGGGCCGGCACAAGCCCGAGAACATCGTGATCGAAATGGCCAGAGAGAACCAGACCACCCAGAAGGGACAGAAGAACAG
CCGCGAGAGAATGAAGCGGATCGAAGAGGGCATCAAAGAGCTGGGCAGCCAGATCCTGAAAGAACACCCCGTGGAAAACACCCAGCTGCAGAA
CGAGAAGCTGTACCTGTACTACCTGCAGAATGGGCGGGATATGTACGTGGACCAGGAACTGGACATCAACCGGCTGTCCGACTACGATGTGGA
CCATATCGTGCCTCAGAGCTTTCTGAAGGACGACTCCATCGACAACAAGGTGCTGACCAGAAGCGACAAGAACCGGGGCAAGAGCGACAACGT
GCCCTCCGAAGAGGTCGTGAAGAAGATGAAGAACTACTGGCGGCAGCTGCTGAACGCCAAGCTGATTACCCAGAGAAAGTTCGACAATCTGAC
CAAGGCCGAGAGAGGCGGCCTGAGCGAACTGGATAAGGCCGGCTTCATCAAGAGACAGCTGGTGGAAACCCGGCAGATCACAAAGCACGTGGC
ACAGATCCTGGACTCCCGGATGAACACTAAGTACGACGAGAATGACAAGCTGATCCGGGAAGTGAAAGTGATCACCCTGAAGTCCAAGCTGGT
GTCCGATTTCCGGAAGGATTTCCAGTTTTACAAAGTGCGCGAGATCAACAACTACCACCACGCCCACGACGCCTACCTGAACGCCGTCGTGGG

FIG. 49B

AACCGCCCTGATCAAAAAGTACCCTAAGCTGGAAAGCGAGTTCGTGTACGGCGACTACAAGGTGTACGACGTGCGGAAGATGATCGCCAAGAG
CGAGCAGGAAATCGGCAAGGCTACCGCCAAGTACTTCTTCTACAGCAACATCATGAACTTTTTCAAGACCGAGATTACCCTGGCCAACGGCGA
GATCCGGAAGCGGCCTCTGATCGAGACAAACGGCGAAACCGGGGAGATCGTGTGGGATAAGGGCCGGGATTTTGCCACCGTGCGGAAAGTGCT
GAGCATGCCCCAAGTGAATATCGTGAAAAAGACCGAGGTGCAGACAGGCGGCTTCAGCAAAGAGTCTATCCTGCCCAAGAGGAACAGCGATAA
GCTGATCGCCAGAAAGAAGGACTGGGACCCTAAGAAGTACGGCGGCTTCGACAGCCCCACCGTGGCCTATTCTGTGCTGGTGGTGGCCAAAGT
GGAAAAGGGCAAGTCCAAGAAACTGAAGAGTGTGAAAGAGCTGCTGGGGATCACCATCATGGAAAGAAGCAGCTTCGAGAAGAATCCCATCGA
CTTTCTGGAAGCCAAGGGCTACAAAGAAGTGAAAAAGGACCTGATCATCAAGCTGCCTAAGTACTCCCTGTTCGAGCTGGAAAACGGCCGGAA
GAGAATGCTGGCCTCTGCCGGCGAACTGCAGAAGGGAAACGAACTGGCCCTGCCCTCCAAATATGTGAACTTCCTGTACCTGGCCAGCCACTA
TGAGAAGCTGAAGGGCTCCCCCGAGGATAATGAGCAGAAACAGCTGTTTGTGGAACAGCACAAGCACTACCTGGACGAGATCATCGAGCAGAT
CAGCGAGTTCTCCAAGAGAGTGATCCTGGCCGACGCTAATCTGGACAAAGTGCTGTCCGCCTACAACAAGCACCGGGATAAGCCCATCAGAGA
GCAGGCCGAGAATATCATCCACCTGTTTACCCTGACCAATCTGGGAGCCCCTGCCGCCTTCAAGTACTTTGACACCACCATCGACCGGAAGAG
GTACACCAGCACCAAAGAGGTGCTGGACGCCACCCTGATCCACCAGAGCATCACCGGCCTGTACGAGACACGGATCGACCTGTCTCAGCTGGG
AGGCGACAAGCGACCTGCCGCCACAAAGAAGGCTGGACAGGCTAAGAAGAAGAAA*GATTACAAAGACGATGACGATAAG*GGATCCGGCGCAAC
AAACTTCTCTCTGCTGAAACAAGCCGGAGATGTCGAAGAGAATCCTGGACCGACCGAGTACAAGCCCACGGTGCGCCTCGCCACCCGCGACGA
CGTCCCCAGGGCCGTACGCACCCTCGCCGCCGCGTTCGCCGACTACCCCGCCACGCGCCACACCGTCGATCCGGACCGCCACATCGAGCGGGT
CACCGAGCTGCAAGAACTCTTCCTCACGCGCGTCGGGCTCGACATCGGCAAGGTGTGGGTCGCGGACGACGGCGCCGCGGTGGCGGTCTGGAC
CACGCCGGAGAGCGTCGAAGCGGGGGCGGTGTTCGCCGAGATCGGCCCGCGCATGGCCGAGTTGAGCGGTTCCCGGCTGGCCGCGCAGCAACA
GATGGAAGGCCTCCTGGCGCCGCACCGGCCCAAGGAGCCCGCGTGGTTCCTGGCCACCGTCGGAGTCTCGCCCGACCACCAGGGCAAGGGTCT
GGGCAGCGCCGTCGTGCTCCCCGGAGTGGAGGCGGCCGAGCGCGCCGGGGTGCCCGCCTTCCTGGAGACCTCCGCGCCCCGCAACCTCCCCTT
CTACGAGCGGCTCGGCTTCACCGTCACCGCCGACGTCGAGGTGCCCGAAGGACCGCGCACCTGGTGCATGACCCGCAAGCCCGGTGCCTGAAC
GCGTTAAGTCGACAATCAACCTCTGGATTACAAAATTTGTGAAAGATTGACTGGTATTCTTAACTATGTTGCTCCTTTTACGCTATGTGGATA
CGCTGCTTTAATGCCTTTGTATCATGCTATTGCTTCCCGTATGGCTTTCATTTTCTCCTCCTTGTATAAATCCTGGTTGCTGTCTCTTTATGA
GGAGTTGTGGCCCGTTGTCAGGCAACGTGGCGTGGTGTGCACTGTGTTTGCTGACGCAACCCCCACTGGTTGGGGCATTGCCACCACCTGTCA
GCTCCTTTCCGGGACTTTCGCTTTCCCCCTCCCTATTGCCACGGCGGAACTCATCGCCGCCTGCCTTGCCCGCTGCTGGACAGGGGCTCGGCT
GTTGGGCACTGACAATTCCGTGGTGTTGTCGGGGAAATCATCGTCCTTTCCTTGGCTGCTCGCCTGTGTTGCCACCTGGATTCTGCGCGGGAC
GTCCTTCTGCTACGTCCCTTCGGCCCTCAATCCAGCGGACCTTCCTTCCCGCGGCCTGCTGCCGGCTCTGCGGCCTCTTCCGCGTCTTCGCCT
TCGCCCTCAGACGAGTCGGATCTCCCTTTGGGCCGCCTCCCCGCGTCGACTTTAAGACCAATGACTTACAAGGCAGCTGTAGATCTTAGCCAC
TTTTTAAAAGAAAAGGGGGGACTGGAAGGGCTAATTCACTCCCAACGAAGACAAGATCTGCTTTTTGCTTGTACTGGGTCTCTCTGGTTAGAC
CAGATCTGAGCCTGGGAGCTCTCTGGCTAACTAGGGAACCCACTGCTTAAGCCTCAATAAAGCTTGCCTTGAGTGCTTCAAGTAGTGTGTGCC
CGTCTGTTGTGTGACTCTGGTAACTAGAGATCCCTCAGACCCTTTTAGTCAGTGTGGAAAATCTCTAGCAGGGCCCGTTTAAACCCGCTGATC
AGCCTCGACTGTGCCTTCTAGTTGCCAGCCATCTGTTGTTTGCCCCTCCCCCGTGCCTTCCTTGACCCTGGAAGGTGCCACTCCCACTGTCCT
TTCCTAATAAAATGAGGAAATTGCATCGCATTGTCTGAGTAGGTGTCATTCTATTCTGGGGGGTGGGGTGGGGCAGGACAGCAAGGGGGAGGA
TTGGGAAGACAATAGCAGGCATGCTGGGGATGCGGTGGGCTCTATGGCTTCTGAGGCGGAAAGAACCAGCTGGGGCTCTAGGGGGTATCCCCA
CGCGCCCTGTAGCGGCGCATTAAGCGCGGCGGGTGTGGTGGTTACGCGCAGCGTGACCGCTACACTTGCCAGCGCCCTAGCGCCCGCTCCTTT
CGCTTTCTTCCCTTCCTTTCTCGCCACGTTCGCCGGCTTTCCCCGTCAAGCTCTAAATCGGGGGCTCCCTTTAGGGTTCCGATTTAGTGCTTT
ACGGCACCTCGACCCCAAAAAACTTGATTAGGGTGATGGTTCACGTAGTGGGCCATCGCCCTGATAGACGGTTTTTCGCCCTTTGACGTTGGA
GTCCACGTTCTTTAATAGTGGACTCTTGTTCCAAACTGGAACAACACTCAACCCTATCTCGGTCTATTCTTTTGATTTATAAGGGATTTTGCC
GATTTCGGCCTATTGGTTAAAAAATGAGCTGATTTAACAAAAATTTAACGCGAATTAATTCTGTGGAATGTGTGTCAGTTAGGGTGTGGAAAG
TCCCCAGGCTCCCCAGCAGGCAGAAGTATGCAAAGCATGCATCTCAATTAGTCAGCAACCAGGTGTGGAAAGTCCCCAGGCTCCCCAGCAGGC
AGAAGTATGCAAAGCATGCATCTCAATTAGTCAGCAACCATAGTCCCGCCCCTAACTCCGCCCATCCCGCCCCTAACTCCGCCCAGTTCCGCC
CATTCTCCGCCCCATGGCTGACTAATTTTTTTTATTTATGCAGAGGCCGAGGCCGCCTCTGCCTCTGAGCTATTCCAGAAGTAGTGAGGAGGC
TTTTTTGGAGGCCTAGGCTTTTGCAAAAAGCTCCCGGGAGCTTGTATATCCATTTTCGGATCTGATCAGCACGTGTTGACAATTAATCATCGG
CATAGTATATCGGCATAGTATAATACGACAAGGTGAGGAACTAAACCATGGCCAAGTTGACCAGTGCCGTTCCGGTGCTCACCGCGCGCGACG
TCGCCGGAGCGGTCGAGTTCTGGACCGACCGGCTCGGGTTCTCCCGGGACTTCGTGGAGGACGACTTCGCCGGTGTGGTCCGGGACGACGTGA
CCCTGTTCATCAGCGCGGTCCAGGACCAGGTGGTGCCGGACAACACCCTGGCCTGGGTGTGGGTGCGCGGCCTGGACGAGCTGTACGCCGAGT
GGTCGGAGGTCGTGTCCACGAACTTCCGGGACGCCTCCGGGCCGGCCATGACCGAGATCGGCGAGCAGCCGTGGGGGCGGGAGTTCGCCCTGC
GCGACCCGGCCGGCAACTGCGTGCACTTCGTGGCCGAGGAGCAGGACTGACACGTGCTACGAGATTTCGATTCCACCGCCGCCTTCTATGAAA
GGTTGGGCTTCGGAATCGTTTTCCGGGACGCCGGCTGGATGATCCTCCAGCGCGGGGATCTCATGCTGGAGTTCTTCGCCCACCCCAACTTGT
TTATTGCAGCTTATAATGGTTACAAATAAAGCAATAGCATCACAAATTTCACAAATAAAGCATTTTTTTCACTGCATTCTAGTTGTGGTTTGT

FIG. 49C

CCAAACTCATCAATGTATCTTATCATGTCTGTATACCGTCGACCTCTAGCTAGAGCTTGGCGTAATCATGGTCATAGCTGTTTCCTGTGTGAA
ATTGTTATCCGCTCACAATTCCACACAACATACGAGCCGGAAGCATAAAGTGTAAAGCCTGGGGTGCCTAATGAGTGAGCTAACTCACATTAA
TTGCGTTGCGCTCACTGCCCGCTTTCCAGTCGGGAAACCTGTCGTGCCAGCTGCATTAATGAATCGGCCAACGCGCGGGGAGAGGCGGTTTGC
GTATTGGGCGCTCTTCCGCTTCCTCGCTCACTGACTCGCTGCGCTCGGTCGTTCGGCTGCGGCGAGCGGTATCAGCTCACTCAAAGGCGGTAA
TACGGTTATCCACAGAATCAGGGGATAACGCAGGAAAGAACATGTGAGCAAAAGGCCAGCAAAAGGCCAGGAACCGTAAAAAGGCCGCGTTGC
TGGCGTTTTTCCATAGGCTCCGCCCCCCTGACGAGCATCACAAAAATCGACGCTCAAGTCAGAGGTGGCGAAACCCGACAGGACTATAAAGAT
ACCAGGCGTTTCCCCCTGGAAGCTCCCTCGTGCGCTCTCCTGTTCCGACCCTGCCGCTTACCGGATACCTGTCCGCCTTTCTCCCTTCGGGAA
GCGTGGCGCTTTCTCATAGCTCACGCTGTAGGTATCTCAGTTCGGTGTAGGTCGTTCGCTCCAAGCTGGGCTGTGTGCACGAACCCCCCGTTC
AGCCCGACCGCTGCGCCTTATCCGGTAACTATCGTCTTGAGTCCAACCCGGTAAGACACGACTTATCGCCACTGGCAGCAGCCACTGGTAACA
GGATTAGCAGAGCGAGGTATGTAGGCGGTGCTACAGAGTTCTTGAAGTGGTGGCCTAACTACGGCTACACTAGAAGAACAGTATTTGGTATCT
GCGCTCTGCTGAAGCCAGTTACCTTCGGAAAAAGAGTTGGTAGCTCTTGATCCGGCAAACAAACCACCGCTGGTAGCGGTGGTTTTTTTGTTT
GCAAGCAGCAGATTACGCGCAGAAAAAAAGGATCTCAAGAAGATCCTTTGATCTTTTCTACGGGGTCTGACGCTCAGTGGAACGAAAACTCAC
GTTAAGGGATTTTGGTCATGAGATTATCAAAAAGGATCTTCACCTAGATCCTTTTAAATTAAAAATGAAGTTTTAAATCAATCTAAAGTATAT
ATGAGTAAACTTGGTCTGACAGTTACCAATGCTTAATCAGTGAGGCACCTATCTCAGCGATCTGTCTATTTCGTTCATCCATAGTTGCCTGAC
TCCCCGTCGTGTAGATAACTACGATACGGGAGGGCTTACCATCTGGCCCCAGTGCTGCAATGATACCGCGAGACCCACGCTCACCGGCTCCAG
ATTTATCAGCAATAAACCAGCCAGCCGGAAGGGCCGAGCGCAGAAGTGGTCCTGCAACTTTATCCGCCTCCATCCAGTCTATTAATTGTTGCC
GGGAAGCTAGAGTAAGTAGTTCGCCAGTTAATAGTTTGCGCAACGTTGTTGCCATTGCTACAGGCATCGTGGTGTCACGCTCGTCGTTTGGTA
TGGCTTCATTCAGCTCCGGTTCCCAACGATCAAGGCGAGTTACATGATCCCCCATGTTGTGCAAAAAAGCGGTTAGCTCCTTCGGTCCTCCGA
TCGTTGTCAGAAGTAAGTTGGCCGCAGTGTTATCACTCATGGTTATGGCAGCACTGCATAATTCTCTTACTGTCATGCCATCCGTAAGATGCT
TTTCTGTGACTGGTGAGTACTCAACCAAGTCATTCTGAGAATAGTGTATGCGGCGACCGAGTTGCTCTTGCCCGGCGTCAATACGGGATAATA
CCGCGCCACATAGCAGAACTTTAAAAGTGCTCATCATTGGAAAACGTTCTTCGGGGCGAAAACTCTCAAGGATCTTACCGCTGTTGAGATCCA
GTTCGATGTAACCCACTCGTGCACCCAACTGATCTTCAGCATCTTTTACTTTCACCAGCGTTTCTGGGTGAGCAAAAACAGGAAGGCAAAATG
CCGCAAAAAAGGGAATAAGGGCGACACGGAAATGTTGAATACTCATACTCTTCCTTTTTCAATATTATTGAAGCATTTATCAGGGTTATTGTC
TCATGAGCGGATACATATTTGAATGTATTTAGAAAAATAAACAAATAGGGGTTCCGCGCACATTTCCCCGAAAAGTGCCACCTGAC

FIG. 49D

<u>*lentiCas9-Blast*</u>

Gray EFS promoter sequence
Yellow Human codon-optimized SpCas9 coding sequence
*Italics* FLAG peptide tag
Red P2A bicistronic linker/self-cleaving peptide
Blue Blast resistance coding sequence GTCGACGGATCGGGAGATCTCCCGATCCCCTATGGTGCACTCTCAGTACAATCTGCTCTGATGCCGCATAGTTAAGCCAGTATCTGCTCCCTG
CTTGTGTGTTGGAGGTCGCTGAGTAGTGCGCGAGCAAAATTTAAGCTACAACAAGGCAAGGCTTGACCGACAATTGCATGAAGAATCTGCTTA
GGGTTAGGCGTTTTGCGCTGCTTCGCGATGTACGGGCCAGATATACGCGTTGACATTGATTATTGACTAGTTATTAATAGTAATCAATTACGG
GGTCATTAGTTCATAGCCCATATATGGAGTTCCGCGTTACATAACTTACGGTAAATGGCCCGCCTGGCTGACCGCCCAACGACCCCCGCCCAT
TGACGTCAATAATGACGTATGTTCCCATAGTAACGCCAATAGGGACTTTCCATTGACGTCAATGGGTGGAGTATTTACGGTAAACTGCCCACT
TGGCAGTACATCAAGTGTATCATATGCCAAGTACGCCCCCTATTGACGTCAATGACGGTAAATGGCCCGCCTGGCATTATGCCCAGTACATGA
CCTTATGGGACTTTCCTACTTGGCAGTACATCTACGTATTAGTCATCGCTATTACCATGGTGATGCGGTTTTGGCAGTACATCAATGGGCGTG
GATAGCGGTTTGACTCACGGGGATTTCCAAGTCTCCACCCCATTGACGTCAATGGGAGTTTGTTTTGGCACCAAAATCAACGGGACTTTCCAA
AATGTCGTAACAACTCCGCCCCATTGACGCAAATGGGCGGTAGGCGTGTACGGTGGGAGGTCTATATAAGCAGCGCGTTTTGCCTGTACTGGG
TCTCTCTGGTTAGACCAGATCTGAGCCTGGGAGCTCTCTGGCTAACTAGGGAACCCACTGCTTAAGCCTCAATAAAGCTTGCCTTGAGTGCTT
CAAGTAGTGTGTGCCCGTCTGTTGTGTGACTCTGGTAACTAGAGATCCCTCAGACCCTTTTAGTCAGTGTGGAAAATCTCTAGCAGTGGCGCC
CGAACAGGGACTTGAAAGCGAAAGGGAAACCAGAGGAGCTCTCTCGACGCAGGACTCGGCTTGCTGAAGCGCGCACGGCAAGAGGCGAGGGGC
GGCGACTGGTGAGTACGCCAAAAATTTTGACTAGCGGAGGCTAGAAGGAGAGAGATGGGTGCGAGAGCGTCAGTATTAAGCGGGGGAGAATTA
GATCGCGATGGGAAAAAATTCGGTTAAGGCCAGGGGGAAAGAAAAAATATAAATTAAAACATATAGTATGGGCAAGCAGGGAGCTAGAACGAT
TCGCAGTTAATCCTGGCCTGTTAGAAACATCAGAAGGCTGTAGACAAATACTGGGACAGCTACAACCATCCCTTCAGACAGGATCAGAAGAAC
TTAGATCATTATATAATACAGTAGCAACCCTCTATTGTGTGCATCAAAGGATAGAGATAAAAGACACCAAGGAAGCTTTAGACAAGATAGAGG
AAGAGCAAAACAAAAGTAAGACCACCGCACAGCAAGCGGCCGCTGATCTTCAGACCTGGAGGAGGAGATATGAGGGACAATTGGAGAAGTGAA
TTATATAAATATAAAGTAGTAAAAATTGAACCATTAGGAGTAGCACCCACCAAGGCAAAGAGAAGAGTGGTGCAGAGAGAAAAAAGAGCAGTG
GGAATAGGAGCTTTGTTCCTTGGGTTCTTGGGAGCAGCAGGAAGCACTATGGGCGCAGCGTCAATGACGCTGACGGTACAGGCCAGACAATTA
TTGTCTGGTATAGTGCAGCAGCAGAACAATTTGCTGAGGGCTATTGAGGCGCAACAGCATCTGTTGCAACTCACAGTCTGGGGCATCAAGCAG
CTCCAGGCAAGAATCCTGGCTGTGGAAAGATACCTAAAGGATCAACAGCTCCTGGGGATTTGGGGTTGCTCTGGAAAACTCATTTGCACCACT
GCTGTGCCTTGGAATGCTAGTTGGAGTAATAAATCTCTGGAACAGATTTGGAATCACACGACCTGGATGGAGTGGGACAGAGAAATTAACAAT
TACACAAGCTTAATACACTCCTTAATTGAAGAATCGCAAAACCAGCAAGAAAAGAATGAACAAGAATTATTGGAATTAGATAAATGGGCAAGT
TTGTGGAATTGGTTTAACATAACAAATTGGCTGTGGTATATAAAATTATTCATAATGATAGTAGGAGGCTTGGTAGGTTTAAGAATAGTTTTT
GCTGTACTTTCTATAGTGAATAGAGTTAGGCAGGGATATTCACCATTATCGTTTCAGACCCACCTCCCAACCCCGAGGGGACCCGACAGGCCC
GAAGGAATAGAAGAAGAAGGTGGAGAGAGAGACAGAGACAGATCCATTCGATTAGTGAACGGATCGGCACTGCGTGCGCCAATTCTGCAGACA
AATGGCAGTATTCATCCACAATTTTAAAAGAAAAGGGGGGATTGGGGGGTACAGTGCAGGGGAAAGAATAGTAGACATAATAGCAACAGACAT
ACAAACTAAAGAATTACAAAAACAAATTACAAAAATTCAAAATTTTCGGGTTTATTACAGGGACAGCAGAGATCCAGTTTGGTTAATTAAGCT
AGCTAGGTCTTGAAAGGAGTGGGAATTGGCTCCGGTGCCCGTCAGTGGGCAGAGCGCACATCGCCCACAGTCCCCGAGAAGTTGGGGGGAGGG
GTCGGCAATTGATCCGGTGCCTAGAGAAGGTGGCGCGGGGTAAACTGGGAAAGTGATGTCGTGTACTGGCTCCGCCTTTTTCCCGAGGGTGGG
GGAGAACCGTATATAAGTGCAGTAGTCGCCGTGAACGTTCTTTTTCGCAACGGGTTTGCCGCCAGAACACAGGACCGGTTCTAGAGCGCTGCC
ACCATGGACAAGAAGTACAGCATCGGCCTGGACATCGGCACCAACTCTGTGGGCTGGGCCGTGATCACCGACGAGTACAAGGTGCCCAGCAAG
AAATTCAAGGTGCTGGGCAACACCGACCGGCACAGCATCAAGAAGAACCTGATCGGAGCCCTGCTGTTCGACAGCGGCGAAACAGCCGAGGCC
ACCCGGCTGAAGAGAACCGCCAGAAGAAGATACACCAGACGGAAGAACCGGATCTGCTATCTGCAAGAGATCTTCAGCAACGAGATGGCCAAG
GTGGACGACAGCTTCTTCCACAGACTGGAAGAGTCCTTCCTGGTGGAAGAGGATAAGAAGCACGAGCGGCACCCCATCTTCGGCAACATCGTG
GACGAGGTGGCCTACCACGAGAAGTACCCCACCATCTACCACCTGAGAAAGAAACTGGTGGACAGCACCGACAAGGCCGACCTGCGGCTGATC
TATCTGGCCCTGGCCCACATGATCAAGTTCCGGGGCCACTTCCTGATCGAGGGCGACCTGAACCCCGACAACAGCGACGTGGACAAGCTGTTC
ATCCAGCTGGTGCAGACCTACAACCAGCTGTTCGAGGAAAACCCCATCAACGCCAGCGGCGTGGACGCCAAGGCCATCCTGTCTGCCAGACTG
AGCAAGAGCAGACGGCTGGAAAATCTGATCGCCCAGCTGCCCGGCGAGAAGAAGAATGGCCTGTTCGGAAACCTGATTGCCCTGAGCCTGGGC
CTGACCCCCAACTTCAAGAGCAACTTCGACCTGGCCGAGGATGCCAAACTGCAGCTGAGCAAGGACACCTACGACGACGACCTGGACAACCTG
CTGGCCCAGATCGGCGACCAGTACGCCGACCTGTTTCTGGCCGCCAAGAACCTGTCCGACGCCATCCTGCTGAGCGACATCCTGAGAGTGAAC

FIG. 50A

ACCGAGATCACCAAGGCCCCCCTGAGCGCCTCTATGATCAAGAGATACGACGAGCACCACCAGGACCTGACCCTGCTGAAAGCTCTCGTGCGG
CAGCAGCTGCCTGAGAAGTACAAAGAGATTTTCTTCGACCAGAGCAAGAACGGCTACGCCGGCTACATTGACGGCGGAGCCAGCCAGGAAGAG
TTCTACAAGTTCATCAAGCCCATCCTGGAAAAGATGGACGGCACCGAGGAACTGCTCGTGAAGCTGAACAGAGAGGACCTGCTGCGGAAGCAG
CGGACCTTCGACAACGGCAGCATCCCCCACCAGATCCACCTGGGAGAGCTGCACGCCATTCTGCGGCGGCAGGAAGATTTTTACCCATTCCTG
AAGGACAACCGGGAAAAGATCGAGAAGATCCTGACCTTCCGCATCCCCTACTACGTGGGCCCTCTGGCCAGGGGAAACAGCAGATTCGCCTGG
ATGACCAGAAAGAGCGAGGAAACCATCACCCCCTGGAACTTCGAGGAAGTGGTGGACAAGGGCGCTTCCGCCCAGAGCTTCATCGAGCGGATG
ACCAACTTCGATAAGAACCTGCCCAACGAGAAGGTGCTGCCCAAGCACAGCCTGCTGTACGAGTACTTCACCGTGTATAACGAGCTGACCAAA
GTGAAATACGTGACCGAGGGAATGAGAAAGCCCGCCTTCCTGAGCGGCGAGCAGAAAAAGGCCATCGTGGACCTGCTGTTCAAGACCAACCGG
AAAGTGACCGTGAAGCAGCTGAAAGAGGACTACTTCAAGAAAATCGAGTGCTTCGACTCCGTGGAAATCTCCGGCGTGGAAGATCGGTTCAAC
GCCTCCCTGGGCACATACCACGATCTGCTGAAAATTATCAAGGACAAGGACTTCCTGGACAATGAGGAAAACGAGGACATTCTGGAAGATATC
GTGCTGACCCTGACACTGTTTGAGGACAGAGAGATGATCGAGGAACGGCTGAAAACCTATGCCCACCTGTTCGACGACAAAGTGATGAAGCAG
CTGAAGCGGCGGAGATACACCGGCTGGGGCAGGCTGAGCCGGAAGCTGATCAACGGCATCCGGGACAAGCAGTCCGGCAAGACAATCCTGGAT
TTCCTGAAGTCCGACGGCTTCGCCAACAGAAACTTCATGCAGCTGATCCACGACGACAGCCTGACCTTTAAAGAGGACATCCAGAAAGCCCAG
GTGTCCGGCCAGGGCGATAGCCTGCACGAGCACATTGCCAATCTGGCCGGCAGCCCCGCCATTAAGAAGGGCATCCTGCAGACAGTGAAGGTG
GTGGACGAGCTCGTGAAAGTGATGGGCCGGCACAAGCCCGAGAACATCGTGATCGAAATGGCCAGAGAGAACCAGACCACCCAGAAGGGACAG
AAGAACAGCCGCGAGAGAATGAAGCGGATCGAAGAGGGCATCAAAGAGCTGGGCAGCCAGATCCTGAAAGAACACCCCGTGGAAAACACCCAG
CTGCAGAACGAGAAGCTGTACCTGTACTACCTGCAGAATGGGCGGGATATGTACGTGGACCAGGAACTGGACATCAACCGGCTGTCCGACTAC
GATGTGGACCATATCGTGCCTCAGAGCTTTCTGAAGGACGACTCCATCGACAACAAGGTGCTGACCAGAAGCGACAAGAACCGGGGCAAGAGC
GACAACGTGCCCTCCGAAGAGGTCGTGAAGAAGATGAAGAACTACTGGCGGCAGCTGCTGAACGCCAAGCTGATTACCCAGAGAAAGTTCGAC
AATCTGACCAAGGCCGAGAGAGGCGGCCTGAGCGAACTGGATAAGGCCGGCTTCATCAAGAGACAGCTGGTGGAAACCCGGCAGATCACAAAG
CACGTGGCACAGATCCTGGACTCCCGGATGAACACTAAGTACGACGAGAATGACAAGCTGATCCGGGAAGTGAAAGTGATCACCCTGAAGTCC
AAGCTGGTGTCCGATTTCCGGAAGGATTTCCAGTTTTACAAAGTGCGCGAGATCAACAACTACCACCACGCCCACGACGCCTACCTGAACGCC
GTCGTGGGAACCGCCCTGATCAAAAAGTACCCTAAGCTGGAAAGCGAGTTCGTGTACGGCGACTACAAGGTGTACGACGTGCGGAAGATGATC
GCCAAGAGCGAGCAGGAAATCGGCAAGGCTACCGCCAAGTACTTCTTCTACAGCAACATCATGAACTTTTTCAAGACCGAGATTACCCTGGCC
AACGGCGAGATCCGGAAGCGGCCTCTGATCGAGACAAACGGCGAAACCGGGGAGATCGTGTGGGATAAGGGCCGGGATTTTGCCACCGTGCGG
AAAGTGCTGAGCATGCCCCAAGTGAATATCGTGAAAAAGACCGAGGTGCAGACAGGCGGCTTCAGCAAAGAGTCTATCCTGCCCAAGAGGAAC
AGCGATAAGCTGATCGCCAGAAAGAAGGACTGGGACCCTAAGAAGTACGGCGGCTTCGACAGCCCCACCGTGGCCTATTCTGTGCTGGTGGTG
GCCAAAGTGGAAAAGGGCAAGTCCAAGAAACTGAAGAGTGTGAAAGAGCTGCTGGGGATCACCATCATGGAAAGAAGCAGCTTCGAGAAGAAT
CCCATCGACTTTCTGGAAGCCAAGGGCTACAAAGAAGTGAAAAAGGACCTGATCATCAAGCTGCCTAAGTACTCCCTGTTCGAGCTGGAAAAC
GGCCGGAAGAGAATGCTGGCCTCTGCCGGCGAACTGCAGAAGGGAAACGAACTGGCCCTGCCCTCCAAATATGTGAACTTCCTGTACCTGGCC
AGCCACTATGAGAAGCTGAAGGGCTCCCCCGAGGATAATGAGCAGAAACAGCTGTTTGTGGAACAGCACAAGCACTACCTGGACGAGATCATC
GAGCAGATCAGCGAGTTCTCCAAGAGAGTGATCCTGGCCGACGCTAATCTGGACAAAGTGCTGTCCGCCTACAACAAGCACCGGGATAAGCCC
ATCAGAGAGCAGGCCGAGAATATCATCCACCTGTTTACCCTGACCAATCTGGGAGCCCCTGCCGCCTTCAAGTACTTTGACACCACCATCGAC
CGGAAGAGGTACACCAGCACCAAAGAGGTGCTGGACGCCACCCTGATCCACCAGAGCATCACCGGCCTGTACGAGACACGGATCGACCTGTCT
CAGCTGGGAGGCGACAAGCGACCTGCCGCCACAAAGAAGGCTGGACAGGCTAAGAAGAAGAAA*GATTACAAAGACGATGACGATAAG*GGATCC
GGGCAAGAAACTTCTCTCTGCTGAAACAAGCCGGAGATGTCGAAGAGAATCCTGGACCGATGGCCAAGCCTTTGTCTCAAGAAGAATCCACC
CTCATTGAAAGAGCAACGGCTACAATCAACAGCATCCCCATCTCTGAAGACTACAGCGTCGCCAGCGCAGCTCTCTCTAGCGACGGCCGCATC
TTCACTGGTGTCAATGTATATCATTTTACTGGGGGACCTTGTGCAGAACTCGTGGTGCTGGGCACTGCTGCTGCTGCGGCAGCTGGCAACCTG
ACTTGTATCGTCGCGATCGGAAATGAGAACAGGGGCATCTTGAGCCCCTGCGGACGGTGCCGACAGGTGCTTCTCGATCTGCATCCTGGGATC
AAAGCCATAGTGAAGGACAGTGATGGACAGCCGACGGCAGTTGGGATTCGTGAATTGCTGCCCTCTGGTTATGTGTGGGAGGGCTAAGAATTC
GATATCAAGCTTATCGATAATCAACCTCTGGATTACAAAATTTGTGAAAGATTGACTGGTATTCTTAACTATGTTGCTCCTTTTACGCTATGT
GGATACGCTGCTTTAATGCCTTTGTATCATGCTATTGCTTCCCGTATGGCTTTCATTTTCTCCTCCTTGTATAAATCCTGGTTGCTGTCTCTT
TATGAGGAGTTGTGGCCCGTTGTCAGGCAACGTGGCGTGGTGTGCACTGTGTTTGCTGACGCAACCCCCACTGGTTGGGGCATTGCCACCACC
TGTCAGCTCCTTTCCGGGACTTTCGCTTTCCCCCTCCCTATTGCCACGGCGGAACTCATCGCCGCCTGCCTTGCCCGCTGCTGGACAGGGGCT
CGGCTGTTGGGCACTGACAATTCCGTGGTGTTGTCGGGGAAATCATCGTCCTTTCCTTGGCTGCTCGCCTGTGTTGCCACCTGGATTCTGCGC
GGGACGTCCTTCTGCTACGTCCCTTCGGCCCTCAATCCAGCGGACCTTCCTTCCCGCGGCCTGCTGCCGGCTCTGCGGCCTCTTCCGCGTCTT
CGCCTTCGCCCTCAGACGAGTCGGATCTCCCTTTGGGCCGCCTCCCCGCATCGATACCGTCGACCTCGAGACCTAGAAAAACATGGAGCAATC
ACAAGTAGCAATACAGCAGCTACCAATGCTGATTGTGCCTGGCTAGAAGCACAAGAGGAGGAGGAGGTGGGTTTTCCAGTCACACCTCAGGTA
CCTTTAAGACCAATGACTTACAAGGCAGCTGTAGATCTTAGCCACTTTTTAAAAGAAAAGGGGGGACTGGAAGGGCTAATTCACTCCCAACGA

FIG. 50B

AGACAAGATATCCTTGATCTGTGGATCTACCACACACAAGGCTACTTCCCTGATTGGCAGAACTACACACCAGGGCCAGGGATCAGATATCCA
CTGACCTTTGGATGGTGCTACAAGCTAGTACCAGTTGAGCAAGAGAAGGTAGAAGAAGCCAATGAAGGAGAGAACACCCGCTTGTTACACCCT
GTGAGCCTGCATGGGATGGATGACCCGGAGAGAGAAGTATTAGAGTGGAGGTTTGACAGCCGCCTAGCATTTCATCACATGGCCCGAGAGCTG
CATCCGGACTGTACTGGGTCTCTCTGGTTAGACCAGATCTGAGCCTGGGAGCTCTCTGGCTAACTAGGGAACCCACTGCTTAAGCCTCAATAA
AGCTTGCCTTGAGTGCTTCAAGTAGTGTGTGCCCGTCTGTTGTGTGACTCTGGTAACTAGAGATCCCTCAGACCCTTTTAGTCAGTGTGGAAA
ATCTCTAGCAGGGCCCGTTTAAACCCGCTGATCAGCCTCGACTGTGCCTTCTAGTTGCCAGCCATCTGTTGTTTGCCCCTCCCCCGTGCCTTC
CTTGACCCTGGAAGGTGCCACTCCCACTGTCCTTTCCTAATAAAATGAGGAAATTGCATCGCATTGTCTGAGTAGGTGTCATTCTATTCTGGG
GGGTGGGGTGGGGCAGGACAGCAAGGGGGAGGATTGGGAAGACAATAGCAGGCATGCTGGGGATGCGGTGGGCTCTATGGCTTCTGAGGCGGA
AAGAACCAGCTGGGGCTCTAGGGGGTATCCCCACGCGCCCTGTAGCGGCGCATTAAGCGCGGCGGGTGTGGTGGTTACGCGCAGCGTGACCGC
TACACTTGCCAGCGCCCTAGCGCCCGCTCCTTTCGCTTTCTTCCCTTCCTTTCTCGCCACGTTCGCCGGCTTTCCCCGTCAAGCTCTAAATCG
GGGGCTCCCTTTAGGGTTCCGATTTAGTGCTTTACGGCACCTCGACCCCAAAAAACTTGATTAGGGTGATGGTTCACGTAGTGGGCCATCGCC
CTGATAGACGGTTTTTCGCCCTTTGACGTTGGAGTCCACGTTCTTTAATAGTGGACTCTTGTTCCAAACTGGAACAACACTCAACCCTATCTC
GGTCTATTCTTTTGATTTATAAGGGATTTTGCCGATTTCGGCCTATTGGTTAAAAAATGAGCTGATTTAACAAAAATTTAACGCGAATTAATT
CTGTGGAATGTGTGTCAGTTAGGGTGTGGAAAGTCCCCAGGCTCCCCAGCAGGCAGAAGTATGCAAAGCATGCATCTCAATTAGTCAGCAACC
AGGTGTGGAAAGTCCCCAGGCTCCCCAGCAGGCAGAAGTATGCAAAGCATGCATCTCAATTAGTCAGCAACCATAGTCCCGCCCCTAACTCCG
CCCATCCCGCCCCTAACTCCGCCCAGTTCCGCCCATTCTCCGCCCCATGGCTGACTAATTTTTTTTATTTATGCAGAGGCCGAGGCCGCCTCT
GCCTCTGAGCTATTCCAGAAGTAGTGAGGAGGCTTTTTTGGAGGCCTAGGCTTTTGCAAAAAGCTCCCGGGAGCTTGTATATCCATTTTCGGA
TCTGATCAGCACGTGTTGACAATTAATCATCGGCATAGTATATCGGCATAGTATAATACGACAAGGTGAGGAACTAAACCATGGCCAAGTTGA
CCAGTGCCGTTCCGGTGCTCACCGCGCGCGACGTCGCCGGAGCGGTCGAGTTCTGGACCGACCGGCTCGGGTTCTCCCGGGACTTCGTGGAGG
ACGACTTCGCCGGTGTGGTCCGGGACGACGTGACCCTGTTCATCAGCGCGGTCCAGGACCAGGTGGTGCCGGACAACACCCTGGCCTGGGTGT
GGGTGCGCGGCCTGGACGAGCTGTACGCCGAGTGGTCGGAGGTCGTGTCCACGAACTTCCGGGACGCCTCCGGGCCGGCCATGACCGAGATCG
GCGAGCAGCCGTGGGGGCGGGAGTTCGCCCTGCGCGACCCGGCCGGCAACTGCGTGCACTTCGTGGCCGAGGAGCAGGACTGACACGTGCTAC
GAGATTTCGATTCCACCGCCGCCTTCTATGAAAGGTTGGGCTTCGGAATCGTTTTCCGGGACGCCGGCTGGATGATCCTCCAGCGCGGGGATC
TCATGCTGGAGTTCTTCGCCCACCCCAACTTGTTTATTGCAGCTTATAATGGTTACAAATAAAGCAATAGCATCACAAATTTCACAAATAAAG
CATTTTTTTCACTGCATTCTAGTTGTGGTTTGTCCAAACTCATCAATGTATCTTATCATGTCTGTATACCGTCGACCTCTAGCTAGAGCTTGG
CGTAATCATGGTCATAGCTGTTTCCTGTGTGAAATTGTTATCCGCTCACAATTCCACACAACATACGAGCCGGAAGCATAAAGTGTAAAGCCT
GGGGTGCCTAATGAGTGAGCTAACTCACATTAATTGCGTTGCGCTCACTGCCCGCTTTCCAGTCGGGAAACCTGTCGTGCCAGCTGCATTAAT
GAATCGGCCAACGCGCGGGGAGAGGCGGTTTGCGTATTGGGCGCTCTTCCGCTTCCTCGCTCACTGACTCGCTGCGCTCGGTCGTTCGGCTGC
GGCGAGCGGTATCAGCTCACTCAAAGGCGGTAATACGGTTATCCACAGAATCAGGGGATAACGCAGGAAAGAACATGTGAGCAAAAGGCCAGC
AAAAGGCCAGGAACCGTAAAAAGGCCGCGTTGCTGGCGTTTTTCCATAGGCTCCGCCCCCCTGACGAGCATCACAAAAATCGACGCTCAAGTC
AGAGGTGGCGAAACCCGACAGGACTATAAAGATACCAGGCGTTTCCCCCTGGAAGCTCCCTCGTGCGCTCTCCTGTTCCGACCCTGCCGCTTA
CCGGATACCTGTCCGCCTTTCTCCCTTCGGGAAGCGTGGCGCTTTCTCATAGCTCACGCTGTAGGTATCTCAGTTCGGTGTAGGTCGTTCGCT
CCAAGCTGGGCTGTGTGCACGAACCCCCCGTTCAGCCCGACCGCTGCGCCTTATCCGGTAACTATCGTCTTGAGTCCAACCCGGTAAGACACG
ACTTATCGCCACTGGCAGCAGCCACTGGTAACAGGATTAGCAGAGCGAGGTATGTAGGCGGTGCTACAGAGTTCTTGAAGTGGTGGCCTAACT
ACGGCTACACTAGAAGAACAGTATTTGGTATCTGCGCTCTGCTGAAGCCAGTTACCTTCGGAAAAAGAGTTGGTAGCTCTTGATCCGGCAAAC
AAACCACCGCTGGTAGCGGTGGTTTTTTTGTTTGCAAGCAGCAGATTACGCGCAGAAAAAAAGGATCTCAAGAAGATCCTTTGATCTTTTCTA
CGGGGTCTGACGCTCAGTGGAACGAAAACTCACGTTAAGGGATTTTGGTCATGAGATTATCAAAAAGGATCTTCACCTAGATCCTTTTAAATT
AAAAATGAAGTTTTAAATCAATCTAAAGTATATATGAGTAAACTTGGTCTGACAGTTACCAATGCTTAATCAGTGAGGCACCTATCTCAGCGA
TCTGTCTATTTCGTTCATCCATAGTTGCCTGACTCCCCGTCGTGTAGATAACTACGATACGGGAGGGCTTACCATCTGGCCCCAGTGCTGCAA
TGATACCGCGAGACCCACGCTCACCGGCTCCAGATTTATCAGCAATAAACCAGCCAGCCGGAAGGGCCGAGCGCAGAAGTGGTCCTGCAACTT
TATCCGCCTCCATCCAGTCTATTAATTGTTGCCGGGAAGCTAGAGTAAGTAGTTCGCCAGTTAATAGTTTGCGCAACGTTGTTGCCATTGCTA
CAGGCATCGTGGTGTCACGCTCGTCGTTTGGTATGGCTTCATTCAGCTCCGGTTCCCAACGATCAAGGCGAGTTACATGATCCCCCATGTTGT
GCAAAAAAGCGGTTAGCTCCTTCGGTCCTCCGATCGTTGTCAGAAGTAAGTTGGCCGCAGTGTTATCACTCATGGTTATGGCAGCACTGCATA
ATTCTCTTACTGTCATGCCATCCGTAAGATGCTTTTCTGTGACTGGTGAGTACTCAACCAAGTCATTCTGAGAATAGTGTATGCGGCGACCGA
GTTGCTCTTGCCCGGCGTCAATACGGGATAATACCGCGCCACATAGCAGAACTTTAAAAGTGCTCATCATTGGAAAACGTTCTTCGGGGCGAA
AACTCTCAAGGATCTTACCGCTGTTGAGATCCAGTTCGATGTAACCCACTCGTGCACCCAACTGATCTTCAGCATCTTTTACTTTCACCAGCG
TTTCTGGGTGAGCAAAAACAGGAAGGCAAAATGCCGCAAAAAAGGGAATAAGGGCGACACGGAAATGTTGAATACTCATACTCTTCCTTTTTC
AATATTATTGAAGCATTTATCAGGGTTATTGTCTCATGAGCGGATACATATTTGAATGTATTTAGAAAAATAAACAAATAGGGGTTCCGCGCA
CATTTCCCCGAAAAGTGCCACCTGAC

FIG. 50C

*lentiGuide-Puro*

| | |
|---|---|
| Pink | BsmBI TypeIIs sites for cloning in 20bp sgRNA guide sequence after removing 1.8kb spacer sequence |
| Green | +85 chRNA sequence for sgRNA |
| Gray | EF1a promoter sequence |
| Blue | Puromycin resistance coding sequence |

CCCGGGTGCAAAGATGGATAAAGTTTTAAACAGAGAGGAATCTTTGCAGCTAATGGACCTTCTAGGTCTTGAAAGGAGTGGGAATTGGCTCCG
GTGCCCGTCAGTGGGCAGAGCGCACATCGCCCACAGTCCCCGAGAAGTTGGGGGGAGGGGTCGGCAATTGATCCGGTGCCTAGAGAAGGTGGC
GCGGGGTAAACTGGGAAAGTGATGTCGTGTACTGGCTCCGCCTTTTTCCCGAGGGTGGGGGAGAACCGTATATAAGTGCAGTAGTCGCCGTGA
ACGTTCTTTTTCGCAACGGGTTTGCCGCCAGAACACAGGTAAGTGCCGTGTGTGGTTCCCGCGGGCCTGGCCTCTTTACGGGTTATGGCCCTT
GCGTGCCTTGAATTACTTCCACTGGCTGCAGTACGTGATTCTTGATCCCGAGCTTCGGGTTGGAAGTGGGTGGGAGAGTTCGAGGCCTTGCGC
TTAAGGAGCCCCTTCGCCTCGTGCTTGAGTTGAGGCCTGGCCTGGGCGCTGGGGCCGCCGCGTGCGAATCTGGTGGCACCTTCGCGCCTGTCT
CGCTGCTTTCGATAAGTCTCTAGCCATTTAAAATTTTTGATGACCTGCTGCGACGCTTTTTTTCTGGCAAGATAGTCTTGTAAATGCGGGCCA
AGATCTGCACACTGGTATTTCGGTTTTTGGGGCCGCGGGCGGCGACGGGGCCCGTGCGTCCCAGCGCACATGTTCGGCGAGGCGGGGCCTGCG
AGCGCGGCCACCGAGAATCGGACGGGGGTAGTCTCAAGCTGGCCGGCCTGCTCTGGTGCCTGGCCTCGCGCCGCCGTGTATCGCCCCGCCCTG
GGCGGCAAGGCTGGCCCGGTCGGCACCAGTTGCGTGAGCGGAAAGATGGCCGCTTCCCGGCCCTGCTGCAGGGAGCTCAAAATGGAGGACGCG
GCGCTCGGGAGAGCGGGCGGGTGAGTCACCCACACAAAGGAAAAGGGCCTTTCCGTCCTCAGCCGTCGCTTCATGTGACTCCACGGAGTACCG
GGCGCCGTCCAGGCACCTCGATTAGTTCTCGAGCTTTTGGAGTACGTCGTCTTTAGGTTGGGGGGAGGGGTTTTATGCGATGGAGTTTCCCCA
CACTGAGTGGGTGGAGACTGAAGTTAGGCCAGCTTGGCACTTGATGTAATTCTCCTTGGAATTTGCCCTTTTTGAGTTTGGATCTTGGTTCAT
TCTCAAGCCTCAGACAGTGGTTCAAAGTTTTTTTCTTCCATTTCAGGTGTCGTGACGTACGGCCACCATGACCGAGTACAAGCCCACGGTGCG
CCTCGCCACCCGCGACGACGTCCCCAGGGCCGTACGCACCCTCGCCGCCGCGTTCGCCGACTACCCCGCCACGCGCCACACCGTCGATCCGGA
CCGCCACATCGAGCGGGTCACCGAGCTGCAAGAACTCTTCCTCACGCGCGTCGGGCTCGACATCGGCAAGGTGTGGGTCGCGGACGACGGCGC
CGCCGTGGCGGTCTGGACCACGCCGGAGAGCGTCGAAGCGGGGGCGGTGTTCGCCGAGATCGGCCCGCGCATGGCCGAGTTGAGCGGTTCCCG
GCTGGCCGCGCAGCAACAGATGGAAGGCCTCCTGGCGCCGCACCGGCCCAAGGAGCCCGCGTGGTTCCTGGCCACCGTCGGAGTCTCGCCCGA
CCACCAGGGCAAGGGTCTGGGCAGCGCCGTCGTGCTCCCCGGAGTGGAGGCGGCCGAGCGCGCCGGGGTGCCCGCCTTCCTGGAGACCTCCGC
GCCCCGCAACCTCCCCTTCTACGAGCGGCTCGGCTTCACCGTCACCGCCGACGTCGAGGTGCCCGAAGGACCGCGCACCTGGTGCATGACCCG
CAAGCCCGGTGCCTGAACGCGTTAAGTCGACAATCAACCTCTGGATTACAAAATTTGTGAAAGATTGACTGGTATTCTTAACTATGTTGCTCC
TTTTACGCTATGTGGATACGCTGCTTTAATGCCTTTGTATCATGCTATTGCTTCCCGTATGGCTTTCATTTTCTCCTCCTTGTATAAATCCTG
GTTGCTGTCTCTTTATGAGGAGTTGTGGCCCGTTGTCAGGCAACGTGGCGTGGTGTGCACTGTGTTTGCTGACGCAACCCCCACTGGTTGGGG
CATTGCCACCACCTGTCAGCTCCTTTCCGGGACTTTCGCTTTCCCCCTCCCTATTGCCACGGCGGAACTCATCGCCGCCTGCCTTGCCCGCTG
CTGGACAGGGGCTCGGCTGTTGGGCACTGACAATTCCGTGGTGTTGTCGGGGAAATCATCGTCCTTTCCTTGGCTGCTCGCCTGTGTTGCCAC
CTGGATTCTGCGCGGGACGTCCTTCTGCTACGTCCCTTCGGCCCTCAATCCAGCGGACCTTCCTTCCCGCGGCCTGCTGCCGGCTCTGCGGCC
TCTTCCGCGTCTTCGCCTTCGCCCTCAGACGAGTCGGATCTCCCTTTGGGCCGCCTCCCCGCGTCGACTTTAAGACCAATGACTTACAAGGCA
GCTGTAGATCTTAGCCACTTTTTAAAAGAAAAGGGGGGACTGGAAGGGCTAATTCACTCCCAACGAAGACAAGATCTGCTTTTTGCTTGTACT
GGGTCTCTCTGGTTAGACCAGATCTGAGCCTGGGAGCTCTCTGGCTAACTAGGGAACCCACTGCTTAAGCCTCAATAAAGCTTGCCTTGAGTG
CTTCAAGTAGTGTGTGCCCGTCTGTTGTGTGACTCTGGTAACTAGAGATCCCTCAGACCCTTTTAGTCAGTGTGGAAAATCTCTAGCAGTACG
TATAGTAGTTCATGTCATCTTATTATTCAGTATTTATAACTTGCAAAGAAATGAATATCAGAGAGTGAGAGGAACTTGTTTATTGCAGCTTAT
AATGGTTACAAATAAAGCAATAGCATCACAAATTTCACAAATAAAGCATTTTTTTCACTGCATTCTAGTTGTGGTTTGTCCAAACTCATCAAT
GTATCTTATCATGTCTGGCTCTAGCTATCCCGCCCCTAACTCCGCCCATCCCGCCCCTAACTCCGCCCAGTTCCGCCCATTCTCCGCCCCATG
GCTGACTAATTTTTTTTATTTATGCAGAGGCCGAGGCCGCCTCGGCCTCTGAGCTATTCCAGAAGTAGTGAGGAGGCTTTTTTGGAGGCCTAG
GGACGTACCCAATTCGCCCTATAGTGAGTCGTATTACGCGCGCTCACTGGCCGTCGTTTTACAACGTCGTGACTGGGAAAACCCTGGCGTTAC
CCAACTTAATCGCCTTGCAGCACATCCCCCTTTCGCCAGCTGGCGTAATAGCGAAGAGGCCCGCACCGATCGCCCTTCCCAACAGTTGCGCAG
CCTGAATGGCGAATGGGACGCGCCCTGTAGCGGCGCATTAAGCGCGGCGGGTGTGGTGGTTACGCGCAGCGTGACCGCTACACTTGCCAGCGC
CCTAGCGCCCGCTCCTTTCGCTTTCTTCCCTTCCTTTCTCGCCACGTTCGCCGGCTTTCCCCGTCAAGCTCTAAATCGGGGGCTCCCTTTAGG
GTTCCGATTTAGTGCTTTACGGCACCTCGACCCCAAAAAACTTGATTAGGGTGATGGTTCACGTAGTGGGCCATCGCCCTGATAGACGGTTTT
TCGCCCTTTGACGTTGGAGTCCACGTTCTTTAATAGTGGACTCTTGTTCCAAACTGGAACAACACTCAACCCTATCTCGGTCTATTCTTTTGA
TTTATAAGGGATTTTGCCGATTTCGGCCTATTGGTTAAAAAATGAGCTGATTTAACAAAAATTTAACGCGAATTTTAACAAAATATTAACGCT

FIG. 51A

TACAATTTAGGTGGCACTTTTCGGGGAAATGTGCGCGGAACCCCTATTTGTTTATTTTTCTAAATACATTCAAATATGTATCCGCTCATGAGA
CAATAACCCTGATAAATGCTTCAATAATATTGAAAAAGGAAGAGTATGAGTATTCAACATTTCCGTGTCGCCCTTATTCCCTTTTTTGCGGCA
TTTTGCCTTCCTGTTTTTGCTCACCCAGAAACGCTGGTGAAAGTAAAAGATGCTGAAGATCAGTTGGGTGCACGAGTGGGTTACATCGAACTG
GATCTCAACAGCGGTAAGATCCTTGAGAGTTTTCGCCCCGAAGAACGTTTTCCAATGATGAGCACTTTTAAAGTTCTGCTATGTGGCGCGGTA
TTATCCCGTATTGACGCCGGGCAAGAGCAACTCGGTCGCCGCATACACTATTCTCAGAATGACTTGGTTGAGTACTCACCAGTCACAGAAAAG
CATCTTACGGATGGCATGACAGTAAGAGAATTATGCAGTGCTGCCATAACCATGAGTGATAACACTGCGGCCAACTTACTTCTGACAACGATC
GGAGGACCGAAGGAGCTAACCGCTTTTTTGCACAACATGGGGGATCATGTAACTCGCCTTGATCGTTGGGAACCGGAGCTGAATGAAGCCATA
CCAAACGACGAGCGTGACACCACGATGCCTGTAGCAATGGCAACAACGTTGCGCAAACTATTAACTGGCGAACTACTTACTCTAGCTTCCCGG
CAACAATTAATAGACTGGATGGAGGCGGATAAAGTTGCAGGACCACTTCTGCGCTCGGCCCTTCCGGCTGGCTGGTTTATTGCTGATAAATCT
GGAGCCGGTGAGCGTGGGTCTCGCGGTATCATTGCAGCACTGGGGCCAGATGGTAAGCCCTCCCGTATCGTAGTTATCTACACGACGGGGAGT
CAGGCAACTATGGATGAACGAAATAGACAGATCGCTGAGATAGGTGCCTCACTGATTAAGCATTGGTAACTGTCAGACCAAGTTTACTCATAT
ATACTTTAGATTGATTTAAAACTTCATTTTTAATTTAAAAGGATCTAGGTGAAGATCCTTTTTGATAATCTCATGACCAAAATCCCTTAACGT
GAGTTTTCGTTCCACTGAGCGTCAGACCCCGTAGAAAAGATCAAAGGATCTTCTTGAGATCCTTTTTTTCTGCGCGTAATCTGCTGCTTGCAA
ACAAAAAAACCACCGCTACCAGCGGTGGTTTGTTTGCCGGATCAAGAGCTACCAACTCTTTTTCCGAAGGTAACTGGCTTCAGCAGAGCGCAG
ATACCAAATACTGTTCTTCTAGTGTAGCCGTAGTTAGGCCACCACTTCAAGAACTCTGTAGCACCGCCTACATACCTCGCTCTGCTAATCCTG
TTACCAGTGGCTGCTGCCAGTGGCGATAAGTCGTGTCTTACCGGGTTGGACTCAAGACGATAGTTACCGGATAAGGCGCAGCGGTCGGGCTGA
ACGGGGGGTTCGTGCACACAGCCCAGCTTGGAGCGAACGACCTACACCGAACTGAGATACCTACAGCGTGAGCTATGAGAAAGCGCCACGCTT
CCCGAAGGGAGAAAGGCGGACAGGTATCCGGTAAGCGGCAGGGTCGGAACAGGAGAGCGCACGAGGGAGCTTCCAGGGGGAAACGCCTGGTAT
CTTTATAGTCCTGTCGGGTTTCGCCACCTCTGACTTGAGCGTCGATTTTTGTGATGCTCGTCAGGGGGGCGGAGCCTATGGAAAAACGCCAGC
AACGCGGCCTTTTTACGGTTCCTGGCCTTTTGCTGGCCTTTTGCTCACATGTTCTTTCCTGCGTTATCCCCTGATTCTGTGGATAACCGTATT
ACCGCCTTTGAGTGAGCTGATACCGCTCGCCGCAGCCGAACGACCGAGCGCAGCGAGTCAGTGAGCGAGGAAGCGGAAGAGCGCCCAATACGC
AAACCGCCTCTCCCCGCGCGTTGGCCGATTCATTAATGCAGCTGGCACGACAGGTTTCCCGACTGGAAAGCGGGCAGTGAGCGCAACGCAATT
AATGTGAGTTAGCTCACTCATTAGGCACCCCAGGCTTTACACTTTATGCTTCCGGCTCGTATGTTGTGTGGAATTGTGAGCGGATAACAATTT
CACACAGGAAACAGCTATGACCATGATTACGCCAAGCGCGCAATTAACCCTCACTAAAGGGAACAAAAGCTGGAGCTGCAAGCTTAATGTAGT
CTTATGCAATACTCTTGTAGTCTTGCAACATGGTAACGATGAGTTAGCAACATGCCTTACAAGGAGAGAAAAAGCACCGTGCATGCCGATTGG
TGGAAGTAAGGTGGTACGATCGTGCCTTATTAGGAAGGCAACAGACGGGTCTGACATGGATTGGACGAACCACTGAATTGCCGCATTGCAGAG
ATATTGTATTTAAGTGCCTAGCTCGATACATAAACGGGTCTCTCTGGTTAGACCAGATCTGAGCCTGGGAGCTCTCTGGCTAACTAGGGAACC
CACTGCTTAAGCCTCAATAAAGCTTGCCTTGAGTGCTTCAAGTAGTGTGTGCCCGTCTGTTGTGTGACTCTGGTAACTAGAGATCCCTCAGAC
CCTTTTAGTCAGTGTGGAAAATCTCTAGCAGTGGCGCCCGAACAGGGACTTGAAAGCGAAAGGGAAACCAGAGGAGCTCTCTCGACGCAGGAC
TCGGCTTGCTGAAGCGCGCACGGCAAGAGGCGAGGGGCGGCGACTGGTGAGTACGCCAAAAATTTTGACTAGCGGAGGCTAGAAGGAGAGAGA
TGGGTGCGAGAGCGTCAGTATTAAGCGGGGGAGAATTAGATCGCGATGGGAAAAAATTCGGTTAAGGCCAGGGGGAAAGAAAAAATATAAATT
AAAACATATAGTATGGGCAAGCAGGGAGCTAGAACGATTCGCAGTTAATCCTGGCCTGTTAGAAACATCAGAAGGCTGTAGACAAATACTGGG
ACAGCTACAACCATCCCTTCAGACAGGATCAGAAGAACTTAGATCATTATATAATACAGTAGCAACCCTCTATTGTGTGCATCAAAGGATAGA
GATAAAAGACACCAAGGAAGCTTTAGACAAGATAGAGGAAGAGCAAAACAAAAGTAAGACCACCGCACAGCAAGCGGCCGCTGATCTTCAGAC
CTGGAGGAGGAGATATGAGGGACAATTGGAGAAGTGAATTATATAAATATAAAGTAGTAAAAATTGAACCATTAGGAGTAGCACCCACCAAGG
CAAAGAGAAGAGTGGTGCAGAGAGAAAAAAGAGCAGTGGGAATAGGAGCTTTGTTCCTTGGGTTCTTGGGAGCAGCAGGAAGCACTATGGGCG
CAGCGTCAATGACGCTGACGGTACAGGCCAGACAATTATTGTCTGGTATAGTGCAGCAGCAGAACAATTTGCTGAGGGCTATTGAGGCGCAAC
AGCATCTGTTGCAACTCACAGTCTGGGGCATCAAGCAGCTCCAGGCAAGAATCCTGGCTGTGGAAAGATACCTAAAGGATCAACAGCTCCTGG
GGATTTGGGGTTGCTCTGGAAAACTCATTTGCACCACTGCTGTGCCTTGGAATGCTAGTTGGAGTAATAAATCTCTGGAACAGATTTGGAATC
ACACGACCTGGATGGAGTGGGACAGAGAAATTAACAATTACACAAGCTTAATACACTCCTTAATTGAAGAATCGCAAAACCAGCAAGAAAAGA
ATGAACAAGAATTATTGGAATTAGATAAATGGGCAAGTTTGTGGAATTGGTTTAACATAACAAATTGGCTGTGGTATATAAAATTATTCATAA
TGATAGTAGGAGGCTTGGTAGGTTTAAGAATAGTTTTTGCTGTACTTTCTATAGTGAATAGAGTTAGGCAGGGATATTCACCATTATCGTTTC
AGACCCACCTCCCAACCCCGAGGGGACCCAGAGAGGGCCTATTTCCCATGATTCCTTCATATTTGCATATACGATACAAGGCTGTTAGAGAGA
TAATTAGAATTAATTTGACTGTAAACACAAAGATATTAGTACAAAATACGTGACGTAGAAAGTAATAATTTCTTGGGTAGTTTGCAGTTTTAA
AATTATGTTTTAAAATGGACTATCATATGCTTACCGTAACTTGAAAGTATTTCGATTTCTTGGCTTTATATATCTTGTGGAAAGGACGAAACA
CCGGACACGGTTGTAAATGAGCACACAAAATACACATGCTAAAATATTATATTCTATGACCTTTATAAAATCAACCAAAATCTTCTTTTTAAT
AACTTTAGTATCAATAATTAGAATTTTTATGTTCCTTTTTGCAAACTTTTAATAAAAATGAGCAAAATAAAAAAACGCTAGTTTTAGTAACTC
GCGTTGTTTTCTTCACCTTTAATAATAGCTACTCCACCACTTGTTCCTAAGCGGTCAGCTCCTGCTTCAATCATTTTTTGAGCATCTTCAAAT
GTTCTAACTCCACCAGCTGCTTTAACTAAAGCATTGTCTTTAACAACTGACTTCATTAGTTTAACATCTTCAAATGTTGCACCTGATTTTGAA

FIG. 51B

AATCCTGTTGATGTTTTAACAAATTCTAATCCAGCTTCAACAGCTATTTCACAAGCTTTCATGATTTCTTCTTTTGTTAATAAACAATTTTCC
ATAATACATTTAACAACATGTGATCCAGCTGCTTTTTTTACAGCTTTCATGTCTTCTAAAACTAATTCATAATTTTTGTCTTTTAATGCACCA
ATATTTAATAGCATATCAATTTCTGTTGCACCATCTTTAATTGCTTCAGAAACTTCGAATGCTTTTGTAGCTGTTGTGCATGCACCTAGAGGA
AAACCTACAACATTTGTTATTCCTACATTTGTGCCTTTTAATAATTCTTTACAATAGCTTGTTCAATATGAATTAACACAAACTGTTGCAAAA
TCAAATTCAATTGCTTCATCACATAATTGTTTAATTTCAGCTTTCGTAGCATCTTGTTTTAATAATGTGTGATCTATATATTTGTTTAGTTTC
ATTTTTTCTCCTATATATTCATTTTTAATTTTAATTCTTTAATAATTTCGTCTACTTTAACTTTAGCGTTTTGAACAGATTCACCAACACCTA
TAAAATAAATTTTTAGTTTAGGTTCAGTTCCACTTGGGCGAACAGCAAATCATGACTTATCTTCTAAATAAAATTTTAGTAAGTCTTGTCCTG
GCATATTATACATTCCATCGATGTAGTCTTCAACATTAACAACTTTAAGTCCAGCAATTTGAGTTAAGGGTGTTGCTCTCAATGATTTCATTA
ATGGTTCAATTTTTAATTTCTTTTCTTCTGGTTTAAAATTCAAGTTTAAAGTGAAAGTGTAATATGCACCCATTTCTTTAAATAAATCTTCTA
AATAGTCTACTAATGTTTTATTTTGTTTTTTATAAAATCAAGCAGCCTCTGCTATTAATATAGAAGCTTGTATTCCATCTTTATCTCTAGCTG
AGTCATCAATTACATATCCATAACTTTCTTCATAAGCAAAAACAAAATTTAATCCGTTATCTTCTTCTTTAGCAATTTCTCTACCCATTCATT
TAAATCCAGTTAAAGTTTTTACAATATTAACTCCATATTTTTCATGAGCGATTCTATCACCCAAATCACTTGTTACAAAACTTGAATATAGAG
CCGGATTTTTTGGAATGCTATTTAAGCGTTTTAGATTTGATAATTTTCAATCAATTAAAATTGGTCCTGTTTGATTTCCATCTAATCTTACAA
AATGACCATCATGTTTTATTGCCATTCCAAATCTGTCAGCATCTGGGTCATTCATAATAATAATATCTGCATCATGTTTAATACCATATTCAA
GCGGTATTTTTCATGCAGGATCAAATTCTGGATTTGGATTTACAACATTTTTAAATGTTTCATCTTCAAATGCATGCTCTTCAACCTCAATAA
CGTTATATCCTGATTCACGTAATATTTTTGGGGTAAATTTAGTTCCTGTTCCATTAACTGCGCTAAAAATAATTTTTAAATCTTTTTTAGCTT
CTTGCTCTTTTTTGTACGTCTCTGTTTTAGAGCTAGAAATAGCAAGTTAAAATAAGGCTAGTCCGTTATCAACTTGAAAAAGTGGCACCGAGT
CGGTGCTTTTTTAAGCTTGGCGTAACTAGATCTTGAGACAAATGGCAGTATTCATCCACAATTTTAAAAGAAAAGGGGGGATTGGGGGGTACA
GTGCAGGGGAAAGAATAGTAGACATAATAGCAACAGACATACAAACTAAAGAATTACAAAAACAAATTACAAAAATTCAAAATTTTCGGGTTT
ATTACAGGGACAGCAGAGATCCACTTTGGCGCCGGCTCGAGGGGG

FIG. 51C

FUNCTIONAL GENOMICS USING CRISPR-Cas SYSTEMS, COMPOSITIONS, METHODS, SCREENS AND APPLICATIONS THEREOF

RELATED APPLICATIONS AND INCORPORATION BY REFERENCE

This application is a continuation of U.S. application Ser. No. 14/973,062, filed on Dec. 17, 2015, which is a continuation-in-part of International Application No. PCT/US14/041806, filed on Jun. 10, 2014, which claims priority to U.S. provisional patent applications 61/836,123, 61/960,777 and 61/995,636, filed on Jun. 17, 2013, Sep. 25, 2013 and Apr. 15, 2014 respectively, each incorporated herein by reference. This application is also a continuation of International Application No. PCT/US13/74800, filed Dec. 12, 2013. For purposes of the United States, this application also can be a continuation-in-part of PCT/US13/74800, filed Dec. 12, 2013; and Applicants reserve as permitted under US law to claim in the United States any right or benefit to U.S. provisional application 61/802,174, filed Mar. 15, 2013 and/or 61/736,527, filed Dec. 12, 2012, which are in the lineage of PCT/US13/74800, filed Dec. 12, 2013.

STATEMENT AS TO FEDERALLY SPONSORED RESEARCH

This invention was made with government support under Grant No. MH100706 awarded by the National Institutes of Health. The government has certain rights in the invention.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

The foregoing patent applications, from which this application claims priority, expressly refers to a lengthy table section. Copies of the Tables have been submitted in triplicate in compact disc form (i.e., "Copy 1," "Copy 2" and "Copy 3") with the USPTO on Apr. 15, 2014 in connection with the filing of U.S. provisional application 61/995,636 and are hereby incorporated herein by reference in their entirety, and may be employed in the practice of the invention. Each compact disc (CD), created Apr. 11, 2014, contains the following files:

Table 1_hKO 65K sgRNAs with off-target scores.txt, 3,883,008 bytes
Table 2A Human GeCKOv2 controls.txt, 53,248 bytes
Table 2B Human GeCKOv2 controls.txt, 77,824 bytes
Table 3_Human GeCKOv2 exons A.txt, 8,069,120 bytes
Table 4 Human GeCKOv2 exons B.txt, 8,081,408 bytes
Table 5_Human GeCKOv2 miRNAs.txt, 331,776 bytes
Table 6_Mouse GeCKOv2 controls.txt, 610,304 bytes
Table 7 Mouse GeCKOv2 exons A.txt, 8,650,752 bytes
Table 8 Mouse GeCKOv2 exons B.txt, 8,671,232 bytes
Table 9 Mouse GeCKOv2 miRNAs.txt, 208,896 bytes The disclosure in each of the foregoing US provisional patent applications is particularly incorporated herein by reference and particularly the disclosure of the CDs filed with 61/960,777 and 61/995,636 is particularly incorporated herein by reference in their entirety and is also included in this disclosure by way of the Biological Deposit(s) with the ATCC of plasmids/plasmid library(ies) containing nucleic acid molecules encoding selected guide sequences having the information set forth in U.S. provisional patent applications 61/960,777 and 61/995,636, namely, Deposit Nos: PTA-121339, PTA-121340, PTA-121341, PTA-121342, PTA-121343, deposited on Jun. 10, 2014, with the American Type Culture Collection on American Type Culture Collection (ATCC), 10801 University Boulevard, Manassas, VA 20110 USA, under and pursuant to the terms of the Budapest Treaty. Upon issuance of a patent, all restrictions upon the Deposit(s) will be irrevocably removed, and the Deposit(s) is/are intended to meet the requirements of 37 CFR §§ 1.801-1.809. The Deposit(s) will be maintained in the depository for a period of 30 years, or 5 years after the last request, or for the effective, enforceable life of the patent, whichever is longer, and will be replaced if necessary during that period; and the requirements of 37 CFR §§ 1.801-1.809 are are met.

SEQUENCE LISTING

The instant application contains a Sequence Listing which has been submitted electronically in ASCII format and is hereby incorporated by reference in its entirety. Said ASCII copy, created on May 29, 2018, is named 114203-5001_SL.txt and is 162,206 bytes in size.

FIELD OF THE INVENTION

The present invention generally relates to libraries, compositions, methods, applications, kits and screens used in functional genomics that focus on gene function in a cell and that may use vector systems and other aspects related to Clustered Regularly Interspaced Short Palindromic Repeats (CRISPR)-Cas systems and components thereof.

BACKGROUND OF THE INVENTION

Recent advances in genome sequencing techniques and analysis methods have significantly accelerated the ability to catalog and map genetic factors associated with a diverse range of biological functions and diseases. Functional genomics is a field of molecular biology that may be considered to utilize the vast wealth of data produced by genomic projects (such as genome sequencing projects) to describe gene (and protein) functions and interactions. Contrary to classical genomics, functional genomics focuses on the dynamic aspects such as gene transcription, translation, and protein-protein interactions, as opposed to the static aspects of the genomic information such as DNA sequence or structures, though these static aspects are very important and supplement one's understanding of cellular and molecular mechanisms. Functional genomics attempts to answer questions about the function of DNA at the levels of genes, RNA transcripts, and protein products. A key characteristic of functional genomics studies is a genome-wide approach to these questions, generally involving high-throughput methods rather than a more traditional "gene-by-gene" approach. Given the vast inventory of genes and genetic information it is advantageous to use genetic screens to provide information of what these genes do, what cellular pathways they are involved in and how any alteration in gene expression can result in particular biological process. Functional genomic screens attempt to characterize gene function in the context of living cells and hence are likely to generate biologically significant data. There are three key elements for a functional genomics screen: a good reagent to perturb the gene, a good tissue culture model and a good readout of cell state.

A reagent that has been used for perturbing genes in a number of functional genomics screens is RNA interference (RNAi). One can perform loss-of-function genetic screens and facilitate the identification of components of cellular signaling pathways utilizing RNAi. Gene silencing by RNAi in mammalian cells using small interfering RNAs (siRNAs) and short hairpin RNAs (shRNAs) has become a valuable genetic tool. Development of efficient and robust approaches to perform genome scale shRNA screens have been described in Luo B et al., "Highly parallel identification of essential genes in cancer cells" Proc Natl Acad Sci USA. 2008 Dec. 23; 105 (51):20380-5; Paddison P J et al., "A resource for large-scale RNA-interference-based screens in mammals" Nature. 2004 Mar. 25; 428(6981):427-31; Berns K et al., "A large-scale RNAi screen in human cells identifies new components of the p53 pathway" Nature. 2004 Mar. 25; 428(6981):431-7, the contents of all of which are incorporated by reference herein in their entirety.

However there are aspects of using shRNAs for functional genomic screens that are not advantageous. For example, there may be off-target effects for the shRNAs that limit spatial control. It is also important to note that using RNAi or other current technologies in functional genomics screens as mentioned herein results in a gene knockdown and not a gene knockout. Another minor factor that may be considered is the need for the continued expression of shRNA. Hence, there remains a need for new genome engineering technologies that are affordable, easy to set up, scalable, and amenable to knockout genes for de novo loss of function and afford spatial and temporal control with minimal off-target activity in a eukaryotic genome.

SUMMARY OF THE INVENTION

There exists a pressing need for alternative and robust systems and techniques for sequence targeting in functional genomic screens and other applications thereof. This invention addresses this need and provides related advantages. The CRISPR/Cas or the CRISPR-Cas system (both terms are used interchangeably throughout this application) does not require the generation of customized proteins (as in the case of technologies involving zinc finger proteins, meganucleases or transcription activator like effectors (TALEs)) to target specific sequences but rather a single Cas enzyme can be programmed by a short RNA molecule to recognize a specific DNA target, in other words the Cas enzyme can be recruited to a specific DNA target using said short RNA molecule. This enables parallel targeting of thousands of genomic loci using oligo library synthesis. Adding the CRISPR-Cas system to the repertoire of functional genomics tools and analysis methods may significantly simplify the methodology and accelerate the ability to catalog and map genetic factors associated with a diverse range of biological functions and diseases. The CRISPR-Cas system can be used effectively for gene targeting and knockout without deleterious effects in functional genomic screens and other applications thereof.

Aspects of the invention relate to synthesizing different unique 20 bp spacer or guide RNA sequences with which different genomic locations can be targeted with double strand breaks (DSBs) and indel mutations. It is this easy programmability that makes CRISPR an attractive targeted screening system. As with pooled shRNA libraries, array oligonucleotide synthesis technologies allow for parallel synthesis of thousands of targeting sequences that can be cloned en masse into a vector, e.g. a viral vector such as an AAV vector or a lentiviral vector, and produced as virus in a pool. This allows for targeting of the Cas9 nuclease by modification of a 20 nt RNA guide sequence and genetic perturbation on the level of the genome itself.

In one aspect, the invention provides a genome wide library comprising a plurality of unique CRISPR-Cas system guide sequences that are capable of targeting a plurality of target sequences in genomic loci, wherein said targeting results in a knockout of gene function. Aspects of the invention include the guide sequences listed in Tables 1, 3, 4, 5, 7, 8 or 9.

Aspects of the invention, including libraries, methods and kits also expressly include the library and guide sequences as described in "Genome-scale CRISPR-Cas9 knockout screening in human cells", Shalem O, Sanjana N E, Hartenian E, Shi X, Scott D A, Mikkelsen T S, Heckl D, Ebert B L, Root D E, Doench J G, Zhang F., Science. 2014 Jan. 3; 343(6166):84-7., including all and any disclosure thereof and all and any disclosure from the corresponding Supplementary materials available from the publisher, including Supplementary materials made available online.

Aspects of the invention, including libraries, methods and kits also expressly include the libraries and guide sequences as described on the addgene website, accessible at www.addgene.org/CRISPR/libraries/, under "Feng Zhang Lab (targets human genes)", including the GeCKO v1 and GeCKO v2 libraries. These libraries are alternatively referred to herein as GeCKO1 and GeCKO2. Those libraries are also disclosure in each of the priority U.S. provisional patent applications 61/960,777, 61/961,980, 61/963,643 and 61/995,636, and especially the CDs filed therewith, and the Budapest Treaty Biological Deposit(s) with the ATCC in connection with this application; namely, ATCC Deposit Nos: PTA-121339, PTA-121340, PTA-121341, PTA-121342, PTA-121343.

In one aspect, the invention provides a CRISPR library for use in a method of knocking out in parallel every gene in the genome. In one aspect, the library or libraries consist of specific sgRNA sequences for gene knock-out in either the human or mouse genome. In one aspect, each species-specific library is delivered as two half-libraries (e.g., A and B). In one aspect, when used together, the A and B libraries contain 6 sgRNAs per gene (3 sgRNAs in each half library). In one aspect, each library or half library may comprise up to 4 sgRNAs per microRNA ("miRNA"). In one aspect, each species-specific library comprises sgRNA specific for each of over 1000 miRNA per genome (e.g., 1864 in human, 1175 in mouse). In one aspect, each species-specific library comprises at least one, preferably at least 3, and most preferably at least 6 sgRNA specific to each gene in the targeted genome (e.g., 19,052 in human, 20,661 in mouse).

In one aspect, the GeCKO library is packaged in a viral vector. In one aspect, the GeCKO library is packaged in a lentivirus vector. In one aspect, the packaged GeCKO library is transduced at an MOI (multiplicity of infection) of about 10, of about 5, of about 3, of about 1 or of about less than 1, about less than 0.75, about less than 0.5, about less than 0.4, about less than 0.3, about less than 0.2 or about less than 0.1. In a further embodiment the cell is transduced with a multiplicity of infection (MOI) of 0.3-0.75, preferably, the MOI has a value close to 0.4, more preferably the MOI is 0.3 or 0.4. In one aspect, the MOI is about 0.3 or 0.4, thereby creating a panel of cells comprising about 1 CRISPR-Cas system chimeric RNA (chiRNA) per cell, after appropriate selection for successfully transfected/transduced cells, thereby providing a panel of cells comprising a cellular library with parallel knock outs of every gene in the genome.

In another aspect, the invention provides for a method of knocking out in parallel every gene in the genome, the method comprising contacting a population of cells with a composition comprising a vector system comprising one or more packaged vectors comprising a) a first regulatory element operably linked to a CRISPR-Cas system chimeric RNA (chiRNA) polynucleotide sequence that targets a DNA molecule encoding a gene product,
   wherein the polynucleotide sequence comprises
   (a) a guide sequence capable of hybridizing to a target sequence,
   (b) a tracr mate sequence, and
   (c) a tracr sequence, and
b) a second regulatory element operably linked to a sequence encoding a Cas protein and a selection marker, wherein components (a) and (b) are located on same or different vectors of the system,
wherein each cell is transfected with a single packaged vector,
selecting for successfully transfected cells,
wherein when transcribed, the tracr mate sequence hybridizes to the tracr sequence and the guide sequence directs sequence-specific binding of a CRISPR complex to a target sequence in the genomic loci of the DNA molecule encoding the gene product,
wherein the CRISPR complex comprises a CRISPR enzyme complexed with (1) the guide sequence that is hybridizable to the target sequence, and (2) the tracr mate sequence that is hybridized to the tracr sequence,
wherein the guide sequence is selected from the library of the invention,
wherein the guide RNAs target the genomic loci of the DNA molecule encoding the gene product and the CRISPR enzyme cleaves the genomic loci of the DNA molecule encoding the gene product and whereby each cell in the population of cells has a unique gene knocked out in parallel. In preferred embodiments, the cell is a eukaryotic cell. In further embodiments the vector is a lentivirus, a adenovirus or a AAV and/or the first regulatory element is a Pol III promoter such as a H1 promoter and a U6 promoter and/or the second regulatory element is a Pol II promoter selected from a doxycycline inducible promoter, a cell-type specific promoter and an EFS promoter, and/or the vector system comprises one vector and/or the CRISPR enzyme is Cas9.

The invention also encompasses methods of selecting individual cell knock outs that survive under a selective pressure, the method comprising contacting a population of cells with a composition comprising a vector system comprising one or more packaged vectors comprising a) a first regulatory element operably linked to a CRISPR-Cas system chimeric RNA (chiRNA) polynucleotide sequence that targets a DNA molecule encoding a gene product, wherein the polynucleotide sequence comprises
   (a) a guide sequence capable of hybridizing to a target sequence,
   (b) a tracr mate sequence, and
   (c) a tracr sequence, and
b) a second regulatory element operably linked to a Cas protein and a selection marker, wherein components (a) and (b) are located on same or different vectors of the system,
wherein each cell is transfected with a single packaged vector,
selecting for successfully transfected cells,
wherein when transcribed, the tracr mate sequence hybridizes to the tracr sequence and the guide sequence directs sequence-specific binding of a CRISPR complex to a target sequence in the genomic loci of the DNA molecule encoding the gene product,
wherein the CRISPR complex comprises a CRISPR enzyme complexed with (1) the guide sequence that is hybridizable to the target sequence, and (2) the tracr mate sequence that is hybridized to the tracr sequence,
wherein the guide sequence is selected from the library of the invention,
wherein the guide RNAs target the genomic loci of the DNA molecule encoding the gene product and the CRISPR enzyme cleaves the genomic loci of the DNA molecule encoding the gene product, whereby each cell in the population of cells has a unique gene knocked out in parallel,
applying the selective pressure,
and selecting the cells that survive under the selective pressure.

In preferred embodiments, the selective pressure is application of a drug, FACS sorting of cell markers or aging and/or the vector is a lentivirus, a adenovirus or a AAV and/or the first regulatory element is a Pol III promoter such as a H1 promoter and a U6 promoter and/or the second regulatory element is a Pol II promoter selected from a doxycycline inducible promoter, a cell-type specific promoter and an EFS promoter, and/or the vector system comprises one vector and/or the CRISPR enzyme is Cas9.

In other aspects, the invention encompasses methods of identifying the genetic basis of one or more medical symptoms exhibited by a subject, the method comprising obtaining a biological sample from the subject and isolating a population of cells having a first phenotype from the biological sample;
contacting the cells having the first phenotype with a composition comprising a vector system comprising one or more packaged vectors comprising
a) a first regulatory element operably linked to a CRISPR-Cas system chimeric RNA (chiRNA) polynucleotide sequence that targets a DNA molecule encoding a gene product,
   wherein the polynucleotide sequence comprises
   (a) a guide sequence capable of hybridizing to a target sequence,
   (b) a tracr mate sequence, and
   (c) a tracr sequence, and
b) a second regulatory element operably linked to a Cas protein and a selection marker,
wherein components (a) and (b) are located on same or different vectors of the system,
wherein each cell is transfected with a single packaged vector,
selecting for successfully transfected cells,
wherein when transcribed, the tracr mate sequence hybridizes to the tracr sequence and the guide sequence directs sequence-specific binding of a CRISPR complex to a target sequence in the genomic loci of the DNA molecule encoding the gene product, wherein the CRISPR complex comprises a CRISPR enzyme complexed with (1) the guide sequence that is hybridizable to the target sequence, and (2) the tracr mate sequence that is hybridized to the tracr sequence, wherein the guide sequence is selected from the library of the invention, wherein the guide RNAs target the genomic loci of the DNA molecule encoding the gene product and the CRISPR enzyme cleaves the genomic loci of the DNA molecule encoding the gene product, whereby each cell in the population of cells has a unique gene knocked out in parallel, applying the selective pressure, selecting the cells that survive under the selective pressure, determining the genomic loci of the DNA molecule that interacts with the first phenotype and identifying the genetic basis of the one or more medical symptoms exhibited by the subject.

In preferred embodiments, the selective pressure is application of a drug, FACS sorting of cell markers or aging and/or the vector is a lentivirus, a adenovirus or a AAV and/or the first regulatory element is a Pol III promoter such as a H1 promoter and a U6 promoter and/or the second regulatory element is a Pol II promoter selected from a doxycycline inducible promoter, a cell-type specific promoter and an EFS promoter, and/or the vector system comprises one vector and/or the CRISPR enzyme is Cas9.

The invention also comprehends kit comprising the library of the invention. In certain aspects, the kit comprises a single container comprising one or more vectors comprising the library of the invention. In other aspects, the kit comprises a single container comprising one or more plasmids comprising the library of the invention. The invention also comprehends kits comprising a panel comprising a selection of unique CRISPR-Cas system guide sequences from the library of the invention, wherein the selection is indicative of a particular physiological condition. In preferred embodiments, the targeting is of about 100 or more sequences, about 1000 or more sequences or about 20,000 or more sequences or the entire genome. In other embodiments a panel of target sequences is focused on a relevant or desirable pathway, such as an immune pathway or cell division.

In one aspect, the invention provides a genome wide library comprising a plurality of unique CRISPR-Cas system guide sequences that are capable of targeting a plurality of target sequences in genomic loci of a plurality of genes, wherein said targeting results in a knockout of gene function. In preferred embodiments of the invention the unique CRISPR-Cas system guide sequences are selected by an algorithm that predicts the efficacy of the guide sequences based on the primary nucleotide sequence of the guide sequence and/or by a heuristic that ranks the guide sequences based on off target scores. In certain embodiments of the invention, the guide sequences are capable of targeting a plurality of target sequences in genomic loci of a plurality of genes selected from the entire genome. In embodiments, the genes may represent a subset of the entire genome; for example, genes relating to a particular pathway (for example, an enzymatic pathway) or a particular disease or group of diseases or disorders may be selected. One or more of the genes may include a plurality of target sequences; that is, one gene may be targeted by a plurality of guide sequences. In certain embodiments, a knockout of gene function is not essential, and for certain applications, the invention may be practiced where said targeting results only in a knockdown of gene function. However, this is not preferred.

Aspects of the invention may include the guide sequences listed in Tables 1, 3, 4, 5, 7, 8 or 9 as provided in the compact discs created Apr. 11, 2014, as filed in connection with U.S. applications 61/960,777 and 61/995,636. In a further embodiment, the guide sequences target constitutive exons downstream of a start codon of the gene. In an advantageous embodiment, the guide sequences target either a first or a second exon of the gene. In yet another embodiment, the guide sequences target a non-transcribed strand of the genomic loci of the gene.

In another aspect, the invention provides for a method of knocking out in parallel every gene in the genome, the method comprising contacting a population of cells with a composition comprising a vector system comprising one or more packaged vectors comprising a) a first regulatory element operably linked to a CRISPR-Cas system chimeric RNA (chiRNA) polynucleotide sequence that targets a DNA molecule encoding a gene product, wherein the polynucleotide sequence comprises (a) a guide sequence capable of hybridizing to a target sequence, (b) a tracr mate sequence, and (c) a tracr sequence, and b) a second regulatory element operably linked to a Cas protein and a selection marker, wherein components (a) and (b) are located on same or different vectors of the system, wherein each cell is transduced with a single packaged vector, selecting for successfully transduced cells, wherein when transcribed, the tracr mate sequence hybridizes to the tracr sequence and the guide sequence directs sequence-specific binding of a CRISPR complex to a target sequence in the genomic loci of the DNA molecule encoding the gene product, wherein the CRISPR complex comprises a CRISPR enzyme complexed with (1) the guide sequence that is hybridizable to the target sequence, and (2) the tracr mate sequence that is hybridized to the tracr sequence, wherein the guide sequence is selected from the library of the invention, wherein the guide sequence targets the genomic loci of the DNA molecule encoding the gene product and the CRISPR enzyme cleaves the genomic loci of the DNA molecule encoding the gene product and whereby each cell in the population of cells has a unique gene knocked out in parallel. In preferred embodiments, the cell is a eukaryotic cell. The eukaryotic cell may be a plant or animal cell; for example, algae or microalgae; vertebrate, preferably mammalian, including murine, ungulate, primate, human; insect. In further embodiments the vector is a lentivirus, an adenovirus or an AAV and/or the first regulatory element is a Pol III promoter such as a H1 promoter and a U6 promoter and/or the second regulatory element is a Pol II promoter such as an EFS promoter or a doxycycline inducible promoter or a cell-type specific promoter as further described herein, and/or the vector system comprises one vector and/or the CRISPR enzyme is Cas9. In aspects of the invention the cell is a eukaryotic cell, preferably a human cell. In a further embodiment the cell is transduced with a multiplicity of infection (MOI)

of 0.3-0.75, preferably, the MOI has a value close to 0.4, more preferably the MOI is 0.3 or 0.4.

The invention also encompasses methods of selecting individual cell knock outs that survive under a selective pressure, the method comprising contacting a population of cells with a composition comprising a vector system comprising one or more packaged vectors comprising a) a first regulatory element operably linked to a CRISPR-Cas system chimeric RNA (chiRNA) polynucleotide sequence that targets a DNA molecule encoding a gene product, wherein the polynucleotide sequence comprises (a) a guide sequence capable of hybridizing to a target sequence, (b) a tracr mate sequence, and (c) a tracr sequence, and b) a second regulatory element operably linked to a Cas protein and a selection marker, wherein components (a) and (b) are located on same or different vectors of the system, wherein each cell is transduced with a single packaged vector, selecting for successfully transduced cells, wherein when transcribed, the tracr mate sequence hybridizes to the tracr sequence and the guide sequence directs sequence-specific binding of a CRISPR complex to a target sequence in the genomic loci of the DNA molecule encoding the gene product, wherein the CRISPR complex comprises a CRISPR enzyme complexed with (1) the guide sequence that is hybridizable to the target sequence, and (2) the tracr mate sequence that is hybridized to the tracr sequence, wherein the guide sequence is selected from the library of the invention, wherein the guide sequence targets the genomic loci of the DNA molecule encoding the gene product and the CRISPR enzyme cleaves the genomic loci of the DNA molecule encoding the gene product, whereby each cell in the population of cells has a unique gene knocked out in parallel, applying the selective pressure, and selecting the cells that survive under the selective pressure.

In preferred embodiments, the selective pressure is application of a drug, FACS sorting of cell markers or aging and/or the vector is a lentivirus, a adenovirus or a AAV and/or the first regulatory element is a Pol III promoter such as a H1 promoter and a U6 promoter and/or the second regulatory element is a Pol II promoter such as an EFS promoter or a doxycycline inducible promoter or a cell-type specific promoter, and/or the vector system comprises one vector and/or the CRISPR enzyme is Cas9. In a further embodiment the cell is transduced with a multiplicity of infection (MOI) of 0.3-0.75, preferably, the MOI has a value close to 0.4, more preferably the MOI is 0.3 or 0.4. In aspects of the invention the cell is a eukaryotic cell. The eukaryotic cell may be a plant or animal cell; for example, algae or microalgae; vertebrate, preferably mammalian, including murine, ungulate, primate, human; insect. Preferably the cell is a human cell. In preferred embodiments of the invention, the method further comprises extracting DNA and determining the depletion or enrichment of the guide sequences by deep sequencing.

In other aspects, the invention encompasses methods of identifying the genetic basis of one or more medical symptoms exhibited by a subject, the method comprising obtaining a biological sample from the subject and isolating a population of cells having a first phenotype from the biological sample;

contacting the cells having the first phenotype with a composition comprising a vector system comprising one or more packaged vectors comprising a) a first regulatory element operably linked to a CRISPR-Cas system chimeric RNA (chiRNA) polynucleotide sequence that targets a DNA molecule encoding a gene product, wherein the polynucleotide sequence comprises (a) a guide sequence capable of hybridizing to a target sequence, (b) a tracr mate sequence, and (c) a tracr sequence, and b) a second regulatory element operably linked to a Cas protein and a selection marker, wherein components (a) and (b) are located on same or different vectors of the system, wherein each cell is transduced with a single packaged vector, selecting for successfully transduced cells, wherein when transcribed, the tracr mate sequence hybridizes to the tracr sequence and the guide sequence directs sequence-specific binding of a CRISPR complex to a target sequence in the genomic loci of the DNA molecule encoding the gene product, wherein the CRISPR complex comprises a CRISPR enzyme complexed with (1) the guide sequence that is hybridizable to the target sequence, and (2) the tracr mate sequence that is hybridized to the tracr sequence, wherein the guide sequence is selected from the library of the invention, wherein the guide sequence targets the genomic loci of the DNA molecule encoding the gene product and the CRISPR enzyme cleaves the genomic loci of the DNA molecule encoding the gene product, whereby each cell in the population of cells has a unique gene knocked out in parallel, applying a selective pressure, selecting the cells that survive under the selective pressure, determining the genomic loci of the DNA molecule that interacts with the first phenotype and identifying the genetic basis of the one or more medical symptoms exhibited by the subject.

In preferred embodiments, the selective pressure is application of a drug, FACS sorting of cell markers or aging and/or the vector is a lentivirus, an adenovirus or an AAV and/or the first regulatory element is a Pol III promoter such as a H1 promoter and a U6 promoter and/or the second regulatory element is a Pol II promoter such as an EFS promoter or a doxycycline inducible promoter or a cell-type specific promoter, and/or the vector system comprises one vector and/or the CRISPR enzyme is Cas9. In a further embodiment the cell is transduced with a multiplicity of infection (MOI) of 0.3-0.75, preferably, the MOI has a value close to 0.4, more preferably the MOI is 0.3 or 0.4. In aspects of the invention the cell is a eukaryotic cell, preferably a human cell.

In an aspect, the library of the invention is a plasmid library. The plasmid library (preferably as further cloned into a delivery vector, such as lentivector) may be selected from the group consisting of:

(A) GeCKO1—library of sgRNA plasmids each encoding selected guide sequences and cloned into vector (lentiCRISPRv2)—ATCC Deposit No. PTA-121339;

(B) GeCKO2—half library A (human) sgRNA plasmids each encoding selected guide sequences and cloned into vector—ATCC Deposit No. PTA-121340;

(C) GeCKO2—half library B (human) of sgRNA plasmids each encoding selected guide sequences and cloned into vector—ATCC Deposit No. PTA-121341;

(D) GeCKO2—half library A (mouse) sgRNA plasmids each encoding selected guide sequences and cloned into vector—ATCC Deposit No. PTA-121342; and (E) GeCKO2—half library A (mouse) sgRNA plasmids each encoding selected guide sequences and cloned into vector—ATCC Deposit No. PTA-121343;

wherein "GeCKO" stands for Genome-scale CRISPR-Cas9 Knock Out". The various GeCKO libraries have been generated for targeting either human or mouse genomes and consist of a one vector system or a two vector system for delivery of short 20 bp sequences of the sgRNA with or without Cas9. The GeCKO1 library consists of specific sgRNA sequences for gene knock-out in either the human or mouse genome. The GeCKO2 libraries consist of specific sgRNA sequences for gene knock-out in either the human or mouse genome, wherein each species-specific library is delivered as two half-libraries (A and B). When used together, the A and B libraries contain 6 sgRNAs per gene (3 sgRNAs in each library) and may contain 4 sgRNAs per microRNA ("miRNA") for over 1000 miRNA per genome (1864 in human, 1175 in mouse). Any one or more GeCKO library may be used in any one of the methods or in any one of the kits of the present invention. The GeCKO libraries, and specifically each of (A) to (E), above, were deposited with the American Type Culture Collection (ATCC) on Jun. 10, 2014, and are further exemplified in ATCC Deposit Nos: PTA-121339, PTA-121340, PTA-121341, PTA-121342, PTA-121343, deposited on Jun. 10, 2014, as provided herein and in the compact discs created Apr. 11, 2014, as filed in connection with U.S. applications 61/960,777 and 61/995,636, including as the information set forth in those US applications and the compact discs filed therewith is presented herein via the ATCC Deposits.

In an aspect, the vector systems in the methods of the invention comprise one or more lentiviral vector(s). In a preferred embodiment, the one or more lentiviral vectors may comprise a codon optimized nuclear localization signal (NLS), a codon optimized P2A bicistronic linker sequence and an optimally placed U6 driven guide RNA cassette. In another aspect the vector system comprises two lentiviral vectors, wherein one lentiviral vector comprises the Cas9 enzyme and the other lentiviral vector comprises the guide RNA selected from the libraries of the invention. In an embodiment of the invention, each vector has a different selection marker, e.g. a different antibiotic resistance marker. The invention also comprehends kits comprising the libraries of the invention. In certain aspects, the kit comprises a single container comprising vectors comprising the library of the invention. In other aspects, the kit comprises a single container comprising plasmids comprising the library of the invention. The invention also comprehends kits comprising a panel comprising a selection of unique CRISPR-Cas system guide sequences from the library of the invention, wherein the selection is indicative of a particular physiological condition. In preferred embodiments, the targeting is of about 100 or more sequences, about 1000 or more sequences or about 20,000 or more sequences or the entire genome. In other embodiments a panel of target sequences is focused on a relevant or desirable pathway, such as an immune pathway or cell division.

In an aspect, the invention provides a non-human eukaryotic organism; preferably a multicellular eukaryotic organism, comprising a eukaryotic host cell according to any of the described embodiments in which a candidate gene is knocked down or knocked out. Preferably the gene is knocked out. In other aspects, the invention provides a eukaryotic organism; preferably a multicellular eukaryotic organism, comprising a eukaryotic host cell which has been altered according to any of the described embodiments. The organism in some embodiments of these aspects may be an animal; for example a mammal. Also, the organism may be an arthropod such as an insect. The organism also may be a plant. Further, the organism may be a fungus. In some embodiments, the invention provides a set of non-human eukaryotic organisms, each of which comprises a eukaryotic host cell according to any of the described embodiments in which a candidate gene is knocked down or knocked out. In preferred embodiments, the set comprises a plurality of organisms, in each of which a different gene is knocked down or knocked out.

In some embodiments, the CRISPR enzyme comprises one or more nuclear localization sequences of sufficient strength to drive accumulation of said CRISPR enzyme in a detectable amount in the nucleus of a eukaryotic cell. In some embodiments, the CRISPR enzyme is a type II CRISPR system enzyme. In some embodiments, the CRISPR enzyme is a Cas9 enzyme. In some embodiments, the Cas9 enzyme is *S. pneumoniae, S. pyogenes* or *S. thermophilus* Cas9, and may include mutated Cas9 derived from these organisms. The enzyme may be a Cas9 homolog or ortholog. In some embodiments, the CRISPR enzyme is codon-optimized for expression in a eukaryotic cell. In some embodiments, the CRISPR enzyme directs cleavage of one or two strands at the location of the target sequence. In one aspect, the CRISPR enzyme comprises at least one mutation in a catalytic domain. In one aspect, the CRISPR enzyme is a nickase. In some embodiments, the CRISPR enzyme lacks DNA strand cleavage activity. In some embodiments, the first regulatory element is a polymerase III promoter. In some embodiments, the second regulatory element is a polymerase II promoter. In some embodiments, the guide sequence is at least 15, 16, 17, 18, 19, 20, 25 nucleotides, or between 10-30, or between 15-25, or between 15-20 nucleotides in length. In an advantageous embodiment the guide sequence is 20 nucleotides in length.

As mentioned previously, a critical aspect of the invention is gene knock-out and not knock-down (which can be done with genome-wide siRNA or shRNA libraries). Applicants have provided the first demonstration of genome-wide knockouts that are barcoded and can be easily readout with next generation sequencing. Every single gene (or a subset of desired genes, for example, those relating to a particular enzymatic pathway or the like (e.g., including but not limited to pathways involved in signaling, metabolism, gene regulation, immune response, disease resistance, drug response and/or resistance, etc.) may be knocked OUT in parallel. This allows quantification of how well each gene KO confers a survival advantage with the selective pressure of the screen. In a preferred embodiment, the invention has advantageous pharmaceutical application, e.g., the invention may be harnessed to test how robust any new drug designed to kill cells (e.g. chemotherapeutic) is to mutations that KO genes. Cancers mutate at an exceedingly fast pace and the libraries and methods of the invention may be used in functional genomic screens to predict the ability of a chemotherapy to be robust to "escape mutations". (Refer to PLX data in BRAF V600E mutant A375 cells in Example 9.

Other mutations (e.g. NF1, NF2, and MED12) allow escape from the killing action of PLX.)

Aspects of the invention comprehend many types of screens and selection mechanisms can also be used with CRISPR screening. Screens for resistance to viral or bacterial pathogens may be used to identify genes that prevent infection or pathogen replication. As in drug resistance screens, survival after pathogen exposure provides strong selection. In cancer, negative selection CRISPR screens may identify "oncogene addictions" in specific cancer subtypes that can provide the foundation for molecular targeted therapies. For developmental studies, screening in human and mouse pluripotent cells may pinpoint genes required for pluripotency or for differentiation into distinct cell types. To distinguish cell types, fluorescent or cell surface marker reporters of gene expression may be used and cells may be sorted into groups based on expression level. Gene-based reporters of physiological states, such as activity-dependent transcription during repetitive neural firing or from antigen-based immune cell activation, may also be used. Any phenotype that is compatible with rapid sorting or separation may be harnessed for pooled screening. CRISPR screening may also be used as a diagnostic tool: With patient-derived iPS cells, genome-wide libraries may be used to examine multi-gene interactions (similar to synthetic lethal screens) or how different loss-of-functions mutations accumulated through aging or disease can interact with particular drug treatments.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention. These and other embodiments are disclosed or are obvious from and encompassed by, the following Detailed Description.

BRIEF DESCRIPTION OF THE DRAWINGS

The patent or application file contains at least one drawing executed in color. Copies of this patent or patent application publication with color drawing(s) will be provided by the Office upon request and payment of necessary fee.

FIG. 2A-2F shows an exemplary CRISPR system, a possible mechanism of action, an example adaptation for expression in eukaryotic cells, and results of tests assessing nuclear localization and CRISPR activity. FIG. 2C discloses SEQ ID NOS 79-80, respectively, in order of appearance. FIG. 2E discloses SEQ ID NOS 81-83, respectively, in order of appearance. FIG. 2F discloses SEQ ID NOS 84-88, respectively, in order of appearance.

FIG. 3A discloses SEQ ID NOS 89, 82 and 90-100, respectively, in order of appearance. FIG. 3C discloses SEQ ID NO: 89.

FIG. 4E discloses SEQ ID NO: 101. FIG. 4F discloses SEQ ID NOS 102-103, respectively, in order of appearance. FIG. 4G discloses SEQ ID NOS 104-108, respectively, in order of appearance.

FIG. 5 provides a table of protospacer sequences and summarizes modification efficiency results for protospacer targets designed based on exemplary *S. pyogenes* and *S. thermophilus* CRISPR systems with corresponding PAMs against loci in human and mouse genomes. Cells were transfected with Cas9 and either pre-crRNA/tracrRNA or chimeric RNA, and analyzed 72 hours after transfection. Percent indels are calculated based on Surveyor assay results from indicated cell lines (N=3 for all protospacer targets, errors are S.E.M., N.D. indicates not detectable using the Surveyor assay, and N.T. indicates not tested in this study). FIG. 5 discloses SEQ ID NOS 17, 16, 15, 109-114, 19, 18 and 115-119, respectively, in order of appearance.

FIG. 6A discloses SEQ ID NOS 120 and 121, respectively, in order of appearance.

FIG. 8A discloses SEQ ID NOS 122-124, respectively, in order of appearance. FIG. 8B discloses SEQ ID NOS 125-127, respectively, in order of appearance.

FIG. 9A-9C shows histograms of distances between adjacent *S. pyogenes* SF370 locus 1 PAM (NGG) (FIG. 9A) and *S. thermophilus* LMD9 locus 2 PAM (NNAGAAW) (FIG. 9B) in the human genome; and distances for each PAM by chromosome (Chr) (FIG. 9C).

FIG. 10B discloses SEQ ID NOS 128-129, respectively, in order of appearance. FIG. 10C discloses SEQ ID NO: 130.

FIG. 11A discloses SEQ ID NO: 131. FIG. 11B discloses SEQ ID NO: 132-134, respectively, in order of appearance.

FIG. 12A discloses SEQ ID NO: 135.

FIG. 15 provides a table of sequences for primers (SEQ ID NOS 138-147, respectively, in order of appearance) and probes (SEQ ID NOS 148-149, respectively, in order of appearance) used for Surveyor, RFLP, genomic sequencing, and Northern blot assays.

FIG. 16A discloses SEQ ID NO: 150)

FIG. 18 discloses SEQ ID NOS 151-229, respectively, in order of appearance.

FIG. 21C discloses SEQ ID NOS 230-232, 230, 233 and 232, respectively, in order of appearance. d, SURVEYOR assay for wildtype (wt) and nickase (D10A) SpCas9-mediated indels at the EMX1 target 1 locus (n=3). Arrows indicate positions of expected fragment sizes.

FIG. 22A discloses SEQ ID NOS 234-236, respectively, in order of appearance. FIG. 22B discloses SEQ ID NO: 237.

FIG. 29 shows design of sgRNAs to knock out EGFP. EGFP sequence (SEQ ID NO: 238) is shown with six different sgRNAs that were designed to target the coding sequence.

FIG. 42 discloses SEQ ID NOS 239-254, respectively, in order of appearance.

FIG. 43 discloses SEQ ID NOS 255-275, respectively, in order of appearance.

FIG. 44 discloses SEQ ID NOS 276-284 and 284-298, respectively, in order of appearance.

FIG. 45A-45L shows Top 1000 depleted genes for both A375 and HUES62. Mean depletion for each gene is given as the log 2 ratio of Day 14 vs. Day 3 representation (mean over sgRNAs for the gene).

FIG. 46A-46E shows the plasmid map (SEQ ID NO: 299) & annotation key for LentiCRISPR (pXPR_001 available through Addgene)

FIG. 49A-49D shows the plasmid map (SEQ ID NO: 300) & annotation key for LentiCRISPR v2 available through Addgene.

FIG. 50A-50C shows the plasmid map (SEQ ID NO: 301) & annotation key for LentiCas9-Blast available through Addgene.

FIG. 51A-51C shows the plasmid map (SEQ ID NO: 302) & annotation key for lentiGuide-Puro available through Addgene.

Figure 1:
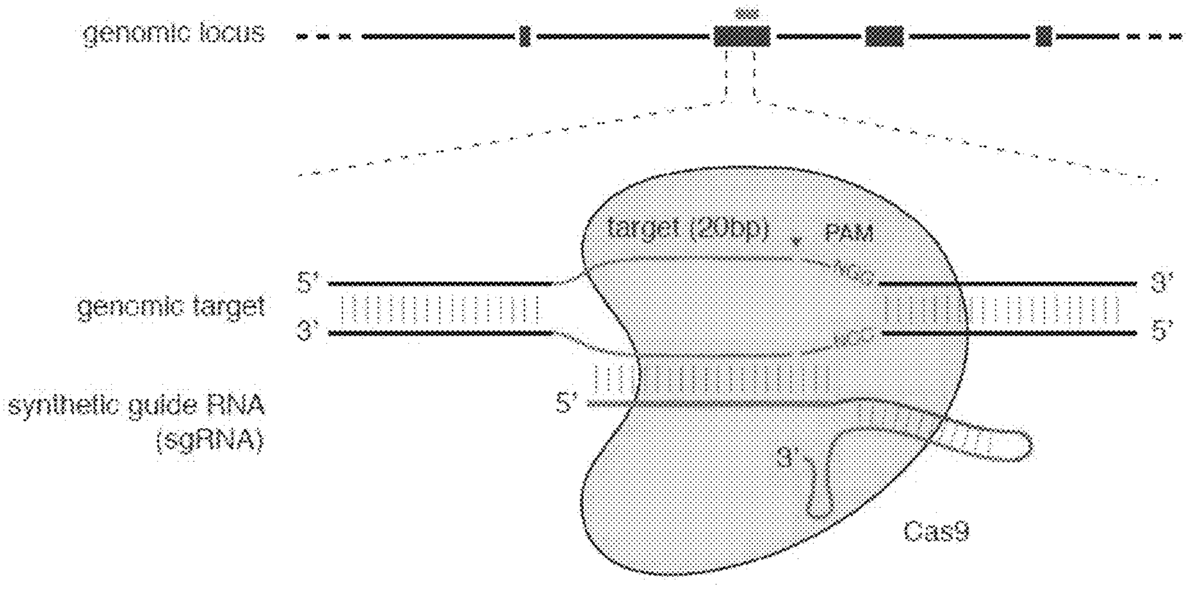
FIG. 1 shows a schematic model of the CRISPR system. The Cas9 nuclease from *Streptococcus pyogenes* (yellow) is targeted to genomic DNA by a synthetic guide RNA (sgRNA) consisting of a 20-nt guide sequence (blue) and a scaffold (red). The guide sequence base-pairs with the DNA target (blue), directly upstream of a requisite 5'-NGG protospacer adjacent motif (PAM; magenta), and Cas9 mediates a double-stranded break (DSB) ~3 bp upstream of the PAM (red triangle).

The figures herein are for illustrative purposes only and are not necessarily drawn to scale.

DETAILED DESCRIPTION OF THE INVENTION

With respect to general information on CRISPR-Cas Systems: Reference is also made to U.S. provisional patent applications 61/736,527, 61/748,427, 61/791,409 and 61/835,931, filed on Dec. 12, 2012, Jan. 2, 2013, Mar. 15, 2013 and Jun. 17, 2013, respectively. Reference is also made to U.S. provisional applications 61/757,972 and 61/768,959, filed on Jan. 29, 2013 and Feb. 25, 2013, respectively. Reference is also made to U.S. provisional patent applications 61/835,931, 61/835,936, 61/836,127, 61/836,101, 61/836,080 and 61/835,973, each filed Jun. 17, 2013. Each of these applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference in their entirety, and may be employed in the practice of the invention. All documents (e.g., these applications and the appln cited documents) are incorporated herein by reference to the same extent as if each individual document was specifically and individually indicated to be incorporated by reference.

Also with respect to general information on CRISPR-Cas Systems, mention is made of:

*Multiplex genome engineering using CRISPR/Cas systems*. Cong, L., Ran, F. A., Cox, D., Lin, S., Barretto, R., Habib, N., Hsu, P. D., Wu, X., Jiang, W., Marraffini, L. A., & Zhang, F. *Science* February 15; 339(6121): 819-23 (2013);

*RNA-guided editing of bacterial genomes using CRISPR-Cas systems*. Jiang W., Bikard D., Cox D., Zhang F, Marraffini L A. Nat Biotechnol March; 31(3):233-9 (2013);

*One-Step Generation of Mice Carrying Mutations in Multiple Genes by CRISPR/Cas—Mediated Genome Engineering*. Wang H., Yang H., Shivalila C S., Dawlaty M M., Cheng A W., Zhang F., Jaenisch R. Cell May 9; 153(4):910-8 (2013);

*Optical control of mammalian endogenous transcription and epigenetic states*. Konermann S, Brigham M D, Trevino A E, Hsu P D, Heidenreich M, Cong L, Platt R J, Scott D A, Church G M, Zhang F. Nature. 2013 Aug. 22; 500(7463):472-6. doi: 10.1038/Nature12466. Epub 2013 Aug. 23;

*Double Nicking by RNA-Guided CRISPR Cas9 for Enhanced Genome Editing Specificity*. Ran, F A., Hsu, P D., Lin, C Y., Gootenberg, J S., Konermann, S., Trevino, A E., Scott, D A., Inoue, A., Matoba, S., Zhang, Y., & Zhang, F. Cell August 28. pii: S0092-8674(13)01015-5. (2013);

*DNA targeting specificity of RNA-guided Cas9 nucleases*. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. *Nat Biotechnol* doi:10.1038/nbt.2647 (2013);

*Genome engineering using the CRISPR-Cas9 system*. Ran, F A., Hsu, P D., Wright, J., Agarwala, V., Scott, D A., Zhang, F. Nature Protocols November; 8(11):2281-308. (2013);

*Genome-Scale CRISPR-Cas9 Knockout Screening in Human Cells*. Shalem, O., Sanjana, N E., Hartenian, E., Shi, X., Scott, D A., Mikkelson, T., Heckl, D., Ebert, B L., Root, D E., Doench, J G., Zhang, F. *Science* December 12. (2013). [Epub ahead of print];

*Crystal structure of cas9 in complex with guide RNA and target DNA*. Nishimasu, H., Ran, F A., Hsu, P D., Konermann, S., Shehata, S I., Dohmae, N., Ishitani, R., Zhang, F., Nureki, O. *Cell February* 27. (2014). 156 (5):935-49;

*Genome-wide binding of the CRISPR endonuclease Cas9 in mammalian cells*. Wu X., Scott D A., Kriz A J., Chiu A C., Hsu P D., Dadon D B., Cheng A W., Trevino A E., Konermann S., Chen S., Jaenisch R., Zhang F., Sharp P A. *Nat Biotechnol*. (2014) Apr. 20. doi: 10.1038/nbt.2889, and

*Development and Applications of CRISPR-Cas9 for Genome Engineering*, Hsu et al, *Cell* 157, 1262-1278 (Jun. 5, 2014) (Hsu 2014), each of which is incorporated herein by reference, and discussed briefly below:

Cong et al. engineered type II CRISPR/Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR/Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA:Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli*, 65% that were recovered contained the mutation.

Konermann et al. addressed the need in the art for versatile and robust technologies that enable optical and chemical modulation of DNA-binding domains based CRISPR Cas9 enzyme and also Transcriptional Activator Like Effectors As discussed in the present specification, the Cas9 nuclease from the microbial CRISPR-Cas system is targeted to specific genomic loci by a 20 nt guide sequence, which can tolerate certain mismatches to the DNA target and thereby promote undesired off-target mutagenesis. To address this, Ran et al. described an approach that combined a Cas9 nickase mutant with paired guide RNAs to introduce targeted double-strand breaks. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and sgRNA can be titrated to minimize off-target modification. Additionally, to facilitate mammalian genome engineering applications, the authors reported providing a web-based software tool to guide the selection and validation of target sequences as well as off-target analyses.

Ran et al. described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knockout (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 A° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Hsu 2014 is a review article that discusses generally CRISPR-Cas9 history from yogurt to genome editing, including genetic screening of cells, that is in the information, data and findings of the applications in the lineage of this specification filed prior to Jun. 5, 2014. The general teachings of Hsu 2014 do not involve the specific models, animals of the instant specification.

Mention is also made of Cong et al, Supplementary Material . . . ", Science 339(6121), pp 1-25); Jinek et al, Science 337(6096), 17 Aug. 2012, pp 816-821; Gasiunas et al, PNAS 19(39), 25 Sep. 2012, pp E2579-2586; Shalem et al, Science 343(6166), pp 84-87 (2014); Haft et al, PLOS Computational Biology, Public Library of Science, vol. 1, no. 6, pp 474-83 (2005); and Wiedenheft et al, Nature 482(7385), pp 331-338 (2012), each of which, in their entirety, is hereby incorporated herein by reference, without any admission that these or any document cited herein is indeed prior art as to the instant invention.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non nucleotide components. A polynucleotide may be further modified after polymerization, such as by conjugation with a labeling component.

As used herein the term "candidate gene" refers to a cellular, viral, episomal, microbial, protozoal, fungal, animal, plant, chloroplastic, or mitochondrial gene. This term also refers to a microbial or viral gene that is part of a naturally occurring microbial or viral genome in a microbially or virally infected cell. The microbial or viral genome can be extrachromosomal or integrated into the host chromosome. This term also encompasses endogenous and exogenous genes, as well as cellular genes that are identified as ESTs. Often, the candidate genes of the invention are those for which the biological function is unknown. An assay of choice is used to determine whether or not the gene is associated with a selected phenotype upon regulation of candidate gene expression with systems of the invention. If the biological function is known, typically the candidate gene acts as a control gene, or is used to determine if one or more additional genes are associated with the same phenotype, or is used to determine if the gene participates with other genes in a particular phenotype.

A "selected phenotype" refers to any phenotype, e.g., any observable characteristic or functional effect that can be measured in an assay such as changes in cell growth, proliferation, morphology, enzyme function, signal transduction, expression patterns, downstream expression patterns, reporter gene activation, hormone release, growth factor release, neurotransmitter release, ligand binding, apoptosis, and product formation. Such assays include, e.g., transformation assays, e.g., changes in proliferation, anchorage dependence, growth factor dependence, foci formation, growth in soft agar, tumor proliferation in nude mice, and tumor vascularization in nude mice; apoptosis assays, e.g., DNA laddering and cell death, expression of genes involved in apoptosis; signal transduction assays, e.g., changes in intracellular calcium, cAMP, cGMP, IP3, changes in hormone and neurotransmitter release; receptor assays, e.g., estrogen receptor and cell growth; growth factor assays, e.g., EPO, hypoxia and erythrocyte colony forming units assays; enzyme product assays, e.g., FAD-2 induced oil desaturation; transcription assays, e.g., reporter gene assays; and protein production assays, e.g., VEGF ELISAs. A candidate gene is "associated with" a selected phenotype if modulation of gene expression of the candidate gene causes a change in the selected phenotype In aspects of the invention the terms "chimeric RNA", "chimeric guide RNA", "guide RNA", "single guide RNA" and "synthetic guide RNA" are used interchangeably and refer to the polynucleotide sequence comprising the guide sequence, the tracr sequence and the tracr mate sequence. The term "guide sequence" refers to the about 20 bp sequence within the guide RNA that specifies the target site and may be used interchangeably with the terms "guide" or "spacer". The term "tracr mate sequence" may also be used interchangeably with the term "direct repeat(s)". An exemplary CRISPR-Cas system is illustrated in FIG. 1.

As used herein the term "wild type" is a term of the art understood by skilled persons and means the typical form of an organism, strain, gene or characteristic as it occurs in nature as distinguished from mutant or variant forms.

As used herein the term "variant" should be taken to mean the exhibition of qualities that have a pattern that deviates from what occurs in nature.

The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature.

"Complementarity" refers to the ability of a nucleic acid to form hydrogen bond(s) with another nucleic acid sequence by either traditional Watson-Crick base pairing or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refers to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part I, Second Chapter "Overview of principles of hybridization and the strategy of nucleic acid probe assay", Elsevier, N.Y.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence.

As used herein, "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The terms "polypeptide", "peptide" and "protein" are used interchangeably herein to refer to polymers of amino acids of any length. The polymer may be linear or branched, it may comprise modified amino acids, and it may be interrupted by non amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

The terms "therapeutic agent", "therapeutic capable agent" or "treatment agent" are used interchangeably and refer to a molecule or compound that confers some beneficial effect upon administration to a subject. The beneficial effect includes enablement of diagnostic determinations; amelioration of a disease, symptom, disorder, or pathological condition; reducing or preventing the onset of a disease, symptom, disorder or condition; and generally counteracting a disease, symptom, disorder or pathological condition.

As used herein, "treatment" or "treating," or "palliating" or "ameliorating" are used interchangeably. These terms refer to an approach for obtaining beneficial or desired results including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested.

The term "effective amount" or "therapeutically effective amount" refers to the amount of an agent that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. The term also applies to a dose that will provide an image for detection by any one of the imaging methods described herein. The specific dose may vary depending on one or more of: the particular agent chosen, the dosing regimen to be followed, whether it is administered in combination with other compounds, timing of administration, the tissue to be imaged, and the physical delivery system in which it is carried.

The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

Several aspects of the invention relate to vector systems comprising one or more vectors, or vectors as such. Vectors can be designed for expression of CRISPR transcripts (e.g. nucleic acid transcripts, proteins, or enzymes) in prokaryotic or eukaryotic cells. For example, CRISPR transcripts can be expressed in bacterial cells such as *Escherichia coli*, insect cells (using baculovirus expression vectors), yeast cells, or mammalian cells. Suitable host cells are discussed further in Goeddel, GENE EXPRESSION TECHNOLOGY: METHODS IN ENZYMOLOGY 185, Academic Press, San Diego, Calif. (1990), the contents of which are incorporated herein by reference. Alternatively, the recombinant expression vector can be transcribed and translated in vitro, for example the lentiviral vectors encompassed in aspects of the invention may comprise a U6 RNA pol III promoter.

In general, and throughout this specification, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell).

The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g. 1, 2, 3, 4, 5, or more pol III promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1a promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.).

Some methods of the invention can include inducing expression. In some methods of the invention the organism or subject is a eukaryote (including mammal including human) or a non-human eukaryote or a non-human animal or a non-human mammal. In some methods of the invention the organism or subject is a plant. In some methods of the invention the organism or subject is a mammal or a non-human mammal. In some methods of the invention the organism or subject is algae. In some methods of the invention the viral vector is an AAV. In some methods of the invention the viral vector is a lentivirus-derived vector. In some methods of the invention the vector is an *Agrobacterium* Ti or Ri plasmid for use in plants. In some methods of the invention the CRISPR enzyme is a Cas9. In some methods of the invention the CRISPR enzyme comprises one or more mutations in one of the catalytic domains. In some methods of the invention the CRISPR enzyme is a Cas9 nickase. In some methods of the invention the expression of the guide sequence is under the control of the T7 promoter that is driven by the expression of T7 polymerase. In some methods of the invention the expression of the guide sequence is under the control of a U6 promoter.

Two ways to package Cas9 coding nucleic acid molecules, e.g., DNA, into viral vectors to mediate genome modification in vivo are preferred:

To Achieve NHEJ-Mediated Gene Knockout:

Single Virus Vector:

- Vector containing two or more expression cassettes:
- Promoter-Cas9 coding nucleic acid molecule-terminator
- Promoter-gRNA1-terminator
- Promoter-gRNA2-terminator
- Promoter-gRNA(N)-terminator (up to size limit of vector)

Double Virus Vector:

- Vector 1 containing one expression cassette for driving the expression of Cas9
- Promoter-Cas9 coding nucleic acid molecule-terminator
- Vector 2 containing one more expression cassettes for driving the expression of one or more guideRNAs
- Promoter-gRNA1-terminator
- Promoter-gRNA(N)-terminator (up to size limit of vector)

To Mediate Homology-Directed Repair:

- In addition to the single and double virus vector approaches described above, an additional vector is used to deliver a homology-direct repair template.

Promoters used to drive Cas9 coding nucleic acid molecule expression are matched to the cell or organism into which the vector is to be expressed. In the case of a eukaryotic organism or cell, various Pol II promoters are available. In one aspect of the invention, the choice of promoter used to drive Cas9 coding nucleic acid molecule expression can include:

- AAV ITR can serve as a promoter: this is advantageous for eliminating the need for an additional promoter element (which can take up space in the vector). The additional space freed up can be used to drive the expression of additional elements (gRNA, etc.). Also, ITR activity is relatively weaker, so can be used to reduce toxicity due to over expression of Cas9;
- For ubiquitous expression, can use promoters: CMV, CAG, CBh, PGK, SV40, Ferritin heavy or light chains, etc.;
- For cell-type specific expression, a variety of Pol II promoters are available. Exemplary promoters can be selected from one or more of the following nonlimiting list:
  - For brain expression, can use promoters: Synapsini for all neurons, CaMKIIalpha for excitatory neurons, GAD67 or GAD65 or VGAT for GABAergic neurons, etc.;
  - For liver expression, can use Albumin promoter;
  - For lung expression, can use SP-B;
  - For endothelial cells, can use ICAM;
  - For hematopoietic cells can use IFNbeta or CD45; and
  - For Osteoblasts can use OG-2;

Promoter Used to Drive Guide RNA can Include:

- Pol III promoters such as U6 or H1;
- T7 promoter that is driven by the expression of T7 polymerase;
- Use of Pol II promoter and intronic cassettes to express gRNA.

As to AAV, the AAV can be AAV1, AAV2, AAV5 or any combination thereof. One can select the AAV of the AAV with regard to the cells to be targeted; e.g., one can select AAV serotypes 1, 2, 5 or a hybrid or capsid AAV1, AAV2, AAV5 or any combination thereof for targeting brain or neuronal cells; and one can select AAV4 for targeting cardiac tissue. AAV8 is useful for delivery to the liver. The above promoters and vectors are preferred individually.

Advantageous vectors include vector systems derived from lentiviruses, adenoviruses and adeno-associated viruses, and types of such vectors can also be selected for targeting particular types of cells. In aspects on the invention the vectors may include but are not limited to packaged vectors. In other aspects of the invention a population of cells or host cells may be transduced with a vector with a low multiplicity of infection (MOI). As used herein the MOI is the ratio of infectious agents (e.g. phage or virus) to infection targets (e.g. cell). For example, when referring to a group of cells inoculated with infectious virus particles, the multiplicity of infection or MOI is the ratio of the number of infectious virus particles to the number of target cells present in a defined space (e.g. a well in a plate). In embodiments of the invention the cells are transduced with an MOI of 0.3-0.75 or 0.3-0.5; in preferred embodiments, the MOI has a value close to 0.4 and in more preferred embodiments the MOI is 0.3. In aspects of the invention the vector library of the invention may be applied to a well of a plate to attain a transduction efficiency of at least 20%, 30%, 40%, 50%, 60%, 70%, or 80%. In a preferred embodiment the transduction efficiency is approximately 30% wherein it may be approximately 370-400 cells per lentiCRISPR construct. In a more preferred embodiment, it may be 400 cells per lentiCRISPR construct.

Vectors may be introduced and propagated in a prokaryote. In some embodiments, a prokaryote is used to amplify copies of a vector to be introduced into a eukaryotic cell or as an intermediate vector in the production of a vector to be introduced into a eukaryotic cell (e.g. amplifying a plasmid as part of a viral vector packaging system). In some embodiments, a prokaryote is used to amplify copies of a vector and express one or more nucleic acids, such as to provide a source of one or more proteins for delivery to a host cell or host organism. Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, such as to the amino terminus of the recombinant protein. Such fusion vectors may serve one or more purposes, such as: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Example fusion expression vectors include pGEX (Pharmacia Biotech Inc; Smith and Johnson, 1988. Gene 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) Gene 69:301-315) and pET 11d (Studier et al., GENE EXPRESSION TECHNOLOGY: METHODS IN ENZYMOLOGY 185, Academic Press, San Diego, Calif. (1990) 60-89).

In some embodiments, a vector is a yeast expression vector. Examples of vectors for expression in yeast *Saccharomyces* cerevisae include pYepSec1 (Baldari, et al., 1987. *EMBO J.* 6: 229-234), pMFa (Kuijan and Herskowitz, 1982. *Cell* 30: 933-943), pJRY88 (Schultz et al., 1987. *Gene* 54: 113-123), pYES2 (Invitrogen Corporation, San Diego, Calif.), and picZ (InVitrogen Corp, San Diego, Calif.).

In some embodiments, a vector drives protein expression in insect cells using baculovirus expression vectors. Baculovirus vectors available for expression of proteins in cultured insect cells (e.g., SF9 cells) include the pAc series (Smith, et al., 1983. *Mol. Cell. Biol.* 3: 2156-2165) and the pVL series (Lucklow and Summers, 1989. *Virology* 170: 31-39).

In some embodiments, a vector is capable of driving expression of one or more sequences in mammalian cells using a mammalian expression vector. Examples of mammalian expression vectors include pCDM8 (Seed, 1987. *Nature* 329: 840) and pMT2PC (Kaufman, et al., 1987. *EMBO J.* 6: 187-195). When used in mammalian cells, the expression vector's control functions are typically provided by one or more regulatory elements. For example, commonly used promoters are derived from polyoma, adenovirus 2, cytomegalovirus, simian virus 40, and others disclosed herein and known in the art. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In some embodiments, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. *Genes Dev.* 1: 268-277), lymphoid-specific promoters (Calame and Eaton, 1988. *Adv. Immunol.* 43: 235-275), in particular promoters of T cell receptors (Winoto and Baltimore, 1989. *EMBO J.* 8: 729-733) and immunoglobulins (Baneiji, et al., 1983. *Cell* 33: 729-740; Queen and Baltimore, 1983. *Cell* 33: 741-748), neuron-specific promoters (e.g., the neurofilament promoter; Byrne and Ruddle, 1989. *Proc. Natl. Acad. Sci. USA* 86: 5473-5477), pancreas-specific promoters (Edlund, et al., 1985. *Science* 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. *Science* 249: 374-379) and the α-fetoprotein promoter (Campes and Tilghman, 1989. *Genes Dev.* 3: 537-546).

In some embodiments, a regulatory element is operably linked to one or more elements of a CRISPR system so as to drive expression of the one or more elements of the CRISPR system. In general, CRISPRs (Clustered Regularly Interspaced Short Palindromic Repeats), also known as SPIDRs (SPacer Interspersed Direct Repeats), constitute a family of DNA loci that are usually specific to a particular bacterial species. The CRISPR locus comprises a distinct class of interspersed short sequence repeats (SSRs) that were recognized in *E. coli* (Ishino et al., J. Bacteriol., 169:5429-5433 [1987]; and Nakata et al., J. Bacteriol., 171:3553-3556 [1989]), and associated genes. Similar interspersed SSRs have been identified in *Haloferax mediterranei, Streptococcus pyogenes, Anabaena*, and *Mycobacterium tuberculosis* (See, Groenen et al., Mol. Microbiol., 10:1057-1065 [1993]; Hoe et al., Emerg. Infect. Dis., 5:254-263 [1999]; Masepohl et al., Biochim. Biophys. Acta 1307:26-30 [1996]; and Mojica et al., Mol. Microbiol., 17:85-93 [1995]). The CRISPR loci typically differ from other SSRs by the structure of the repeats, which have been termed short regularly spaced repeats (SRSRs) (Janssen et al., OMICS J. Integ. Biol., 6:23-33 [2002]; and Mojica et al., Mol. Microbiol., 36:244-246 [2000]). In general, the repeats are short elements that occur in clusters that are regularly spaced by unique intervening sequences with a substantially constant length (Mojica et al., [2000], supra). Although the repeat sequences are highly conserved between strains, the number of interspersed repeats and the sequences of the spacer regions typically differ from strain to strain (van Embden et al., J. Bacteriol., 182:2393-2401 [2000]). CRISPR loci have been identified in more than 40 prokaryotes (See e.g., Jansen et al., Mol. Microbiol., 43:1565-1575 [2002]; and Mojica et al., [2005]) including, but not limited to Aeropyrum, *Pyrobaculum, Sulfolobus, Archaeoglobus, Halocarcula, Methanobacterium, Methanococcus, Methanosarcina, Methanopyrus, Pyrococcus, Picrophilus, Thermoplasma, Corynebacterium, Mycobacterium, Streptomyces, Aquifex, Porphyromonas, Chlorobium, Thermus, Bacillus, Listeria, Staphylococcus, Clostridium, Thermoanaerobacter, Mycoplasma, Fusobacterium, Azarcus, Chromobacterium, Neisseria, Nitrosomonas, Desulfovibrio, Geobacter, Myxococ-*

*cus, Campylobacter, Wolinella, Acinetobacter, Erwinia, Escherichia, Legionella, Methylococcus, Pasteurella, Photobacterium, Salmonella, Xanthomonas, Yersinia, Treponema*, and *Thermotoga.*

In aspects of the invention functional genomics screens allow for discovery of novel human and mammalian therapeutic applications, including the discovery of novel drugs, for, e.g., treatment of genetic diseases, cancer, fungal, protozoal, bacterial, and viral infection, ischemia, vascular disease, arthritis, immunological disorders, etc. As used herein assay systems may be used for a readout of cell state or changes in phenotype include, e.g., transformation assays, e.g., changes in proliferation, anchorage dependence, growth factor dependence, foci formation, growth in soft agar, tumor proliferation in nude mice, and tumor vascularization in nude mice; apoptosis assays, e.g., DNA laddering and cell death, expression of genes involved in apoptosis; signal transduction assays, e.g., changes in intracellular calcium, cAMP, cGMP, IP3, changes in hormone and neurotransmitter release; receptor assays, e.g., estrogen receptor and cell growth; growth factor assays, e.g., EPO, hypoxia and erythrocyte colony forming units assays; enzyme product assays, e.g., FAD-2 induced oil desaturation; transcription assays, e.g., reporter gene assays; and protein production assays, e.g., VEGF ELISAs.

Aspects of the invention relate to modulation of gene expression and modulation can be assayed by determining any parameter that is indirectly or directly affected by the expression of the target candidate gene. Such parameters include, e.g., changes in RNA or protein levels, changes in protein activity, changes in product levels, changes in downstream gene expression, changes in reporter gene transcription (luciferase, CAT, beta-galactosidase, beta-glucuronidase, GFP (see, e.g., Mistili & Spector, Nature Biotechnology 15:961-964 (1997)); changes in signal transduction, phosphorylation and dephosphorylation, receptor-ligand interactions, second messenger concentrations (e.g., cGMP, cAMP, IP3, and $Ca^{2+}$), cell growth, and neovascularization, etc., as described herein. These assays can be in vitro, in vivo, and ex vivo. Such functional effects can be measured by any means known to those skilled in the art, e.g., measurement of RNA or protein levels, measurement of RNA stability, identification of downstream or reporter gene expression, e.g., via chemiluminescence, fluorescence, calorimetric reactions, antibody binding, inducible markers, ligand binding assays; changes in intracellular second messengers such as cGMP and inositol triphosphate (IP3); changes in intracellular calcium levels; cytokine release, and the like, as described herein.

Several methods of DNA extraction and analysis are encompassed in the methods of the invention. As used herein "deep sequencing" indicates that the depth of the process is many times larger than the length of the sequence under study. Deep sequencing is encompassed in next generation sequencing methods which include but are not limited to single molecule real-time sequencing (Pacific Bio), Ion semiconductor (Ion torrent sequencing), Pyrosequencing (454), Sequencing by synthesis (Illumina), Sequencing by ligations (SOLiD sequencing) and Chain termination (Sanger sequencing).

To determine the level of gene expression modulated by the CRISPR-Cas system, cells contacted with the CRISPR-Cas system are compared to control cells, e.g., without the CRISPR-Cas system or with a non-specific CRISPR-Cas system, to examine the extent of inhibition or activation. Control samples may be assigned a relative gene expression activity value of 100%. Modulation/inhibition of gene expression is achieved when the gene expression activity value relative to the control is about 80%, preferably 50% (i.e., 0.5 times the activity of the control), more preferably 25%, more preferably 5-0%. Modulation/activation of gene expression is achieved when the gene expression activity value relative to the control is 110%, more preferably 150% (i.e., 1.5 times the activity of the control), more preferably 200-500%, more preferably 1000-2000% or more.

In general, "CRISPR system" or the "CRISPR-Cas system" refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or other sequences and transcripts from a CRISPR locus. In some embodiments, one or more elements of a CRISPR system is derived from a type I, type II, or type III CRISPR system. In some embodiments, one or more elements of a CRISPR system is derived from a particular organism comprising an endogenous CRISPR system, such as *Streptococcus pyogenes*. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. Full complementarity is not necessarily required, provided there is sufficient complementarity to cause hybridization and promote formation of a CRISPR complex. A target sequence may comprise any polynucleotide, such as DNA or RNA polynucleotides. In some embodiments, a target sequence is located in the nucleus or cytoplasm of a cell. In some embodiments, the target sequence may be within an organelle of a eukaryotic cell, for example, mitochondrion or chloroplast. A sequence or template that may be used for recombination into the targeted locus comprising the target sequences is referred to as an "editing template" or "editing polynucleotide" or "editing sequence". In aspects of the invention, an exogenous template polynucleotide may be referred to as an editing template. In an aspect of the invention the recombination is homologous recombination.

Typically, in the context of an endogenous CRISPR system, formation of a CRISPR complex (comprising a guide sequence hybridized to a target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. Without wishing to be bound by theory, the tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide sequence. In some embodiments, the tracr sequence has sufficient complementarity to a tracr mate sequence to hybridize and participate in formation of a CRISPR complex. As with the target sequence, it is believed that complete complementarity is not needed, provided there is sufficient to be functional. In some embodiments, the tracr sequence has at least 50%, 60%, 70%, 80%, 90%, 95% or 99% of sequence complementarity along the length of the tracr mate sequence when optimally aligned. In some embodiments, one or more vectors driving expression of one or more elements of a CRISPR system are introduced into a host cell such that expression of the elements of the CRISPR system direct formation of a CRISPR complex at one or more target sites. For example, a Cas enzyme, a guide sequence linked to a tracr-mate sequence, and a tracr sequence could each be operably linked to separate regulatory elements on separate vectors. Alternatively, two or more of the elements expressed from the same or different regulatory elements, may be combined in a single vector, with one or more additional vectors providing any components of the CRISPR system not included in the first vector. CRISPR system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding a CRISPR enzyme and one or more of the guide sequence, tracr mate sequence (optionally operably linked to the guide sequence), and a tracr sequence embedded within one or more intron sequences (e.g. each in a different intron, two or more in at least one intron, or all in a single intron). In some embodiments, the CRISPR enzyme, guide sequence, tracr mate sequence, and tracr sequence are operably linked to and expressed from the same promoter.

In some embodiments, a vector comprises one or more insertion sites, such as a restriction endonuclease recognition sequence (also referred to as a "cloning site"). In some embodiments, one or more insertion sites (e.g. about or more than about 1, 2, 3, 4, 5, 6, 7, 8, 9, 10, or more insertion sites) are located upstream and/or downstream of one or more sequence elements of one or more vectors. In some embodiments, a vector comprises an insertion site upstream of a tracr mate sequence, and optionally downstream of a regulatory element operably linked to the tracr mate sequence, such that following insertion of a guide sequence into the insertion site and upon expression the guide sequence directs sequence-specific binding of a CRISPR complex to a target sequence in a eukaryotic cell. In some embodiments, a vector comprises two or more insertion sites, each insertion site being located between two tracr mate sequences so as to allow insertion of a guide sequence at each site. In such an arrangement, the two or more guide sequences may comprise two or more copies of a single guide sequence, two or more different guide sequences, or combinations of these. When multiple different guide sequences are used, a single expression construct may be used to target CRISPR activity to multiple different, corresponding target sequences within a cell. For example, a single vector may comprise about or more than about 1, 2, 3, 4, 5, 6, 7, 8, 9, 10, 15, 20, or more guide sequences. In some embodiments, about or more than about 1, 2, 3, 4, 5, 6, 7, 8, 9, 10, or more such guide-sequence-containing vectors may be provided, and optionally delivered to a cell.

In some embodiments, a vector comprises a regulatory element operably linked to an enzyme-coding sequence encoding a CRISPR enzyme, such as a Cas protein. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. These enzymes are known; for example, the amino acid sequence of *S. pyogenes* Cas9 protein may be found in the SwissProt database under accession number Q99ZW2. In some embodiments, the unmodified CRISPR enzyme has DNA cleavage activity, such as Cas9. In some embodiments the CRISPR enzyme is Cas9, and may be Cas9 from *S. pyogenes* or *S. pneumoniae*. In some embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, a vector encodes a CRISPR enzyme that is mutated to with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand). Other examples of mutations that render Cas9 a nickase include, without limitation, H840A, N854A, and N863A. In aspects of the invention, nickases may be used for genome editing via homologous recombination, For example, FIG. 21 shows genome editing via homologous recombination. FIG. 21 (*a*) shows the schematic of SpCas9 nickase, with D10A mutation in the RuvC I catalytic domain. (b) Schematic representing homologous recombination (HR) at the human EMX1 locus using either sense or antisense single stranded oligonucleotides as repair templates. (c) Sequence of region modified by HR. d, SURVEYOR assay for wildtype (wt) and nickase (D10A) SpCas9-mediated indels at the EMX1 target 1 locus (n=3). Arrows indicate positions of expected fragment sizes.

In some embodiments, a Cas9 nickase may be used in combination with one or more guide sequence(s), e.g., two guide sequences, which target respectively sense and antisense strands of the DNA duplex of the gene target. This combination allows both strands to be nicked and used to induce NHEJ. Applicants have demonstrated (data not shown) the efficacy of two nickase targets (i.e., sgRNAs targeted at the same location but to different strands of DNA) in inducing mutagenic NHEJ. A single nickase (Cas9-D10A with a single sgRNA) is unable to induce NHEJ and create indels but Applicants have shown that double nickase (Cas9-D10A and two sgRNAs targeted to different strands at the same location) can do so in human embryonic stem cells (hESCs). The efficiency is about 50% of nuclease (i.e., regular Cas9 without D10 mutation) in hESCs.

As a further example, two or more catalytic domains of Cas9 (RuvC I, RuvC II, and RuvC III) may be mutated to produce a mutated Cas9 substantially lacking all DNA cleavage activity. In some embodiments, a D10A mutation is combined with one or more of H840A, N854A, or N863A mutations to produce a Cas9 enzyme substantially lacking all DNA cleavage activity. In some embodiments, a CRISPR enzyme is considered to substantially lack all DNA cleavage activity when the DNA cleavage activity of the mutated enzyme is less than about 25%, 10%, 5%, 1%, 0.1%, 0.01%, or lower with respect to its non-mutated form. Other mutations may be useful; where the Cas9 or other CRISPR enzyme is from a species other than *S. pyogenes*, mutations in corresponding amino acids may be made to achieve similar effects.

In some embodiments, an enzyme coding sequence encoding a CRISPR enzyme is codon optimized for expression in particular cells, such as eukaryotic cells. The eukaryotic cells may be those of or derived from a particular organism, such as a mammal, including but not limited to human, mouse, rat, rabbit, dog, or non-human primate. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database", and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, PA), are also available. In some embodiments, one or more codons (e.g. 1, 2, 3, 4, 5, 10, 15, 20, 25, 50, or more, or all codons) in a sequence encoding a CRISPR enzyme correspond to the most frequently used codon for a particular amino acid.

In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, ELAND (Illumina, San Diego, CA), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

A guide sequence may be selected to target any target sequence. In some embodiments, the target sequence is a sequence within a genome of a cell. Exemplary target sequences include those that are unique in the target genome. For example, for the *S. pyogenes* Cas9, a unique target sequence in a genome may include a Cas9 target site of the form MMMMMMMMNNNNNNNNNNNNXGG (SEQ ID NO: 303) where NNNNNNNNNNNNXGG (SEQ ID NO: 304) (N is A, G, T, or C; and X can be anything) has a single occurrence in the genome. A unique target sequence in a genome may include an *S. pyogenes* Cas9 target site of the form MMMMMMMMMNNNNNNNNNNNXGG (SEQ ID NO: 305) where NNNNNNNNNNNXGG (SEQ ID NO: 306) (N is A, G, T, or C; and X can be anything) has a single occurrence in the genome. For the *S. thermophilus* CRISPR1 Cas9, a unique target sequence in a genome may include a Cas9 target site of the form MMMMMMMMNNNNNNNNNNNNXXAGAAW (SEQ ID NO: 1) where NNNNNNNNNNNNXXAGAAW (N is A, G, T, or C; X can be anything; and W is A or T) (SEQ ID NO: 2) has a single occurrence in the genome. A unique target sequence in a genome may include an *S. thermophilus* CRISPR1 Cas9 target site of the form MMMMMMMMMNNNNNNNNNNNXXAGAAW (SEQ ID NO: 3) where NNNNNNNNNNNXXAGAAW (N is A, G, T, or C; X can be anything; and W is A or T) (SEQ ID NO: 4) has a single occurrence in the genome. For the *S. pyogenes* Cas9, a unique target sequence in a genome may include a Cas9 target site of the form MMMMMMMMNNNNNNNNNNNNXGGXG (SEQ ID NO: 307) where NNNNNNNNNNNNXGGXG (SEQ ID NO: 308) (N is A, G, T, or C; and X can be anything) has a single occurrence in the genome. A unique target sequence in a genome may include an *S. pyogenes* Cas9 target site of the form MMMMMMMMMNNNNNNNNNNNXGGXG (SEQ ID NO: 309) where NNNNNNNNNNNXGGXG (SEQ ID NO: 310) (N is A, G, T, or C; and X can be anything) has a single occurrence in the genome. In each of these sequences "M" may be A, G, T, or C, and need not be considered in identifying a sequence as unique.

In some embodiments, a guide sequence is selected to reduce the degree of secondary structure within the guide sequence. Secondary structure may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g. A. R. Gruber et al., 2008, Cell 106(1): 23-24; and PA Carr and GM Church, 2009, Nature Biotechnology 27(12): 1151-62). Further algorithms may be found in U.S. application Ser. No. 61/836,080; incorporated herein by reference.

In general, a tracr mate sequence includes any sequence that has sufficient complementarity with a tracr sequence to promote one or more of: (1) excision of a guide sequence flanked by tracr mate sequences in a cell containing the corresponding tracr sequence; and (2) formation of a CRISPR complex at a target sequence, wherein the CRISPR complex comprises the tracr mate sequence hybridized to the tracr sequence. In general, degree of complementarity is with reference to the optimal alignment of the tracr mate sequence and tracr sequence, along the length of the shorter of the two sequences. Optimal alignment may be determined by any suitable alignment algorithm, and may further account for secondary structures, such as self-complementarity within either the tracr sequence or tracr mate sequence.

In some embodiments, the degree of complementarity between the tracr sequence and tracr mate sequence along the length of the shorter of the two when optimally aligned is about or more than about 25%, 30%, 40%, 50%, 60%, 70%, 80%, 90%, 95%, 97.5%, 99%, or higher. Example illustrations of optimal alignment between a tracr sequence and a tracr mate sequence are provided in FIGS. 10B and 11B. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and tracr mate sequence are contained within a single transcript, such that hybridization between the two produces a transcript having a secondary structure, such as a hairpin. Preferred loop forming sequences for use in hairpin structures are four nucleotides in length, and most preferably have the sequence GAAA. However, longer or shorter loop sequences may be used, as may alternative sequences. The sequences preferably include a nucleotide triplet (for example, AAA), and an additional nucleotide (for example C or G). Examples of loop forming sequences include CAAA and AAAG. In an embodiment of the invention, the transcript or transcribed polynucleotide sequence has at least two or more hairpins. In preferred embodiments, the transcript has two, three, four or five hairpins. In a further embodiment of the invention, the transcript has at most five hairpins. In some embodiments, the single transcript further includes a transcription termination sequence; preferably this is a polyT sequence, for example six T nucleotides. Further non-limiting examples of single polynucleotides comprising a guide sequence, a tracr mate sequence, and a tracr sequence are as follows (listed 5' to 3'), where "N" represents a base of a guide sequence, the first block of lower case letters represent the tracr mate sequence, and the second block of lower case letters represent the tracr sequence, and the final poly-T sequence represents the transcription terminator: (1) NNNNNNNNNN NNNNNNNNNN gtttttgtac tctcaagatt taGAAAtaaa tcttgcagaa gctacaaaga taaggcttca tgccgaaatc aacaccctgt cattttatgg cagggtgttt tcgttattta aTTTTTT (SEQ ID NO: 5); (2) NNNNNNNNNN NNNNNNNNNN gtttttgtac tctcaGAAAt gcagaagcta caaagataag gcttcatgcc gaaatcaaca ccctgtcatt ttatggcagg gtgttttcgt tatttaaTTT TTT (SEQ ID NO: 6); (3) NNNNNNNNN NNNNNNNNNN Ngtttttgta ctctcaGAAA tgcagaagct acaaagata aggcttcatgccgaaatcaacaccctgtcattttatggcagggtgtTTTTTT (SEQ ID NO: 7); (4) NNNNNNNNNN NNNNNNNNNN gttttagagc taGAAAtagc aagttaaaat aaggctagtc cgttatcaac ttgaaaaagt ggcaccgagt cggtgcTTTT TT (SEQ ID NO: 8); (5) NNNNNNNNNN NNNNNNNNNN gttttagagc taGAAATAGc aagttaaaat aaggctagtccgttatcaacttgaaaaagtgTTTTTTT (SEQ ID NO: 9); and (6) NNNNNNNNNN NNNNNNNNNN gttttagagc tagAAATAGc aagttaaaat aaggctagtc cgttatca TTTTTTTT (SEQ ID NO: 10). In some embodiments, sequences (1) to (3) are used in combination with Cas9 from *S. thermophilus* CRISPR1. In some embodiments, sequences (4) to (6) are used in combination with Cas9 from *S. pyogenes*. In some embodiments, the tracr sequence is a separate transcript from a transcript comprising the tracr mate sequence (such as illustrated in the top portion of FIG. 11B).

In some embodiments, the CRISPR enzyme is part of a fusion protein comprising one or more heterologous protein domains (e.g. about or more than about 1, 2, 3, 4, 5, 6, 7, 8, 9, 10, or more domains in addition to the CRISPR enzyme). A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). A CRISPR enzyme may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4 DNA binding domain fusions, and herpes simplex virus (HSV) BP16 protein fusions. Additional domains that may form part of a fusion protein comprising a CRISPR enzyme are described in US20110059502, incorporated herein by reference. In some embodiments, a tagged CRISPR enzyme is used to identify the location of a target sequence.

In an aspect of the invention, a reporter gene which includes but is not limited to glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP), may be introduced into a cell to encode a gene product which serves as a marker by which to measure the alteration or modification of expression of the gene product. In a further embodiment of the invention, the DNA molecule encoding the gene product may be introduced into the cell via a vector. In a preferred embodiment of the invention the gene product is luciferase. In a further embodiment of the invention the expression of the gene product is decreased.

In some aspects, the invention provides methods comprising delivering one or more polynucleotides, such as or one or more vectors as described herein, one or more transcripts thereof, and/or one or proteins transcribed therefrom, to a host or target cell. In some aspects, the invention further provides cells produced by such methods, and organisms (such as animals, plants, or fungi) comprising or produced from such cells. In some embodiments, a CRISPR enzyme in combination with (and optionally complexed with) a guide sequence is delivered to a cell. Conventional viral and non-viral based gene transfer methods can be used to introduce nucleic acids in mammalian cells or target tissues. Such methods can be used to administer nucleic acids encoding components of a CRISPR system to cells in culture, or in a host organism. Non-viral vector delivery systems include DNA plasmids, RNA (e.g. a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell. For a review of gene therapy procedures, see Anderson, Science 256:808-813 (1992); Nabel & Felgner, TIBTECH 11:211-217 (1993); Mitani & Caskey, TIBTECH 11:162-166 (1993); Dillon, TIBTECH 11:167-175 (1993); Miller, Nature 357:455-460 (1992); Van Brunt, Biotechnology 6(10):1149-1154 (1988); Vigne, Restorative Neurology and Neuroscience 8:35-36 (1995); Kremer & Perricaudet, British Medical Bulletin 51(1):31-44 (1995); Haddada et al., in Current Topics in Microbiology and Immunology Doerfler and Böhm (eds) (1995); and Yu et al., Gene Therapy 1:13-26 (1994). Methods of non-viral delivery of nucleic acids include lipofection, nucleofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424; WO 91/16024. Delivery can be to cells (e.g. in vitro or ex vivo administration) or target tissues (e.g. in vivo administration).

The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids take advantage of highly evolved processes for targeting a virus to specific cells in the body and trafficking the viral payload to the nucleus. Viral vectors can be administered directly to patients (in vivo) or they can be used to treat cells in vitro, and the modified cells may optionally be administered to patients (ex vivo). Conventional viral based systems could include retroviral, lentivirus, adenoviral, adeno-associated and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al., J. Virol. 66:2731-2739 (1992); Johann et al., J. Virol. 66:1635-1640 (1992); Sommnerfelt et al., Virol. 176:58-59 (1990); Wilson et al., J. Virol. 63:2374-2378 (1989); Miller et al., J. Virol. 65:2220-2224 (1991); PCT/US94/05700). In applications where transient expression is preferred, adenoviral based systems may be used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors may also be used to transduce cells with target nucleic acids, e.g., in the in vitro production of nucleic acids and peptides, and for in vivo and ex vivo gene therapy procedures (see, e.g., West et al., Virology 160:38-47 (1987); U.S. Pat. No. 4,797,368; WO 93/24641; Kotin, Human Gene Therapy 5:793-801 (1994); Muzyczka, J. Clin. Invest. 94:1351 (1994). Construction of recombinant AAV vectors are described in a number of publications, including U.S. Pat. No. 5,173,414; Tratschin et al., Mol. Cell. Biol. 5:3251-3260 (1985); Tratschin, et al., Mol. Cell. Biol. 4:2072-2081 (1984); Hermonat & Muzyczka, PNAS 81:6466-6470 (1984); and Samulski et al., J. Virol. 63:03822-3828 (1989).

Packaging cells are typically used to form virus particles that are capable of infecting a host cell. Such cells include 293 cells, which package adenovirus, and ψ2 cells or PA317 cells, which package retrovirus. Viral vectors used in gene therapy are usually generated by producing a cell line that packages a nucleic acid vector into a viral particle. The vectors typically contain the minimal viral sequences required for packaging and subsequent integration into a host, other viral sequences being replaced by an expression cassette for the polynucleotide(s) to be expressed. The missing viral functions are typically supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences. The cell line may also be infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. Additional methods for the delivery of nucleic acids to cells are known to those skilled in the art. See, for example, US20030087817, incorporated herein by reference.

In some embodiments, a host cell is transiently or non-transiently transfected with one or more vectors described herein to arrive at a tissue culture model. In some embodiments, a cell is transfected as it naturally occurs in a subject. In some embodiments, a cell that is transfected is taken from a subject. In some embodiments, the cell is derived from cells taken from a subject, such as a cell line. A wide variety of cell lines for tissue culture models are known in the art. Examples of cell lines include, but are not limited to, C8161, CCRF-CEM, MOLT, mIMCD-3, NHDF, HeLa-S3, Huh1, Huh4, Huh7, HUVEC, HASMC, HEKn, HEKa, MiaPaCell, Panel, PC-3, TF1, CTLL-2, C1R, Rat6, CV1, RPTE, A10, T24, J82, A375, ARH-77, Calu1, SW480, SW620, SKOV3, SK-UT, CaCo2, P388D1, SEM-K2, WEHI-231, HB56, TIB55, Jurkat, J45.01, LRMB, Bcl-1, BC-3, IC21, DLD2, Raw264.7, NRK, NRK-52E, MRC5, MEF, Hep G2, HeLa B, HeLa T4, COS, COS-1, COS-6, COS-M6A, BS-C-1 monkey kidney epithelial, BALB/3T3 mouse embryo fibroblast, 3T3 Swiss, 3T3-L1, 132-d5 human fetal fibroblasts; 10.1 mouse fibroblasts, 293-T, 3T3, 721, 9L, A2780, A2780ADR, A2780cis, A172, A20, A253, A431, A-549, ALC, B16, B35, BCP-1 cells, BEAS-2B, bEnd.3, BHK-21, BR 293, BxPC3, C3H-10T1/2, C6/36, Ca1-27, CHO, CHO-7, CHO-IR, CHO-K1, CHO-K2, CHO-T, CHO Dhfr −/−, COR-L23, COR-L23/CPR, COR-L23/5010, COR-L23/R23, COS-7, COV-434, CML T1, CMT, CT26, D17, DH82, DU145, DuCaP, EL4, EM2, EM3, EMT6/AR1, EMT6/AR10.0, FM3, H1299, H69, HB54, HB55, HCA2, HEK-293, HeLa, Hepal c1c7, HL-60, HMEC, HT-29, Jurkat, JY cells, K562 cells, Ku812, KCL22, KG1, KYO1, LNCap, Ma-Mel 1-48, MC-38, MCF-7, MCF-10A, MDA-MB-231, MDA-MB-468, MDA-MB-435, MDCK II, MDCK II, MOR/0.2R, MONO-MAC 6, MTD-1A, MyEnd, NCI-H69/CPR, NCI-H69/LX10, NCI-H69/LX20, NCI-H69/LX4, NIH-3T3, NALM-1, NW-145, OPCN/OPCT cell lines, Peer, PNT-1A/PNT 2, RenCa, RIN-5F, RMA/RMAS, Saos-2 cells, Sf-9, SkBr3, T2, T-47D, T84, THP1 cell line, U373, U87, U937, VCaP, Vero cells, WM39, WT-49, X63, YAC-1, YAR, and transgenic varieties thereof. In a preferred embodiment of the invention the cells that relate to aspects of the invention are HEK293FT cells. Cell lines are available from a variety of sources known to those with skill in the art (see, e.g., the American Type Culture Collection (ATCC) (Manassas, Va.)). In some embodiments, a cell transfected with one or more vectors described herein is used to establish a new cell line comprising one or more vector-derived sequences. In some embodiments, a cell transiently transfected with the components of a CRISPR system as described herein (such as by transient transfection of one or more vectors, or transfection with RNA), and modified through the activity of a CRISPR complex, is used to establish a new cell line comprising cells containing the modification but lacking any other exogenous sequence. In some embodiments, cells transiently or non-transiently transfected with one or more vectors described herein, or cell lines derived from such cells are used in assessing one or more test compounds.

In some embodiments, one or more vectors described herein are used to transfect cells from a non-human transgenic animal or transgenic plant. In some embodiments, the transgenic animal is a mammal, such as a mouse, rat, or rabbit. In certain embodiments, the organism or subject is a plant. In certain embodiments, the organism or subject or plant is algae. Cells from transgenic animals are also provided, as are transgenic plants, especially crops and algae. The cells of a transgenic animal or plant may be useful in applications outside of providing a disease model. In this regard, cells from transgenic plants, especially pulses and tubers, and animals, especially mammals such as livestock (cows, sheep, goats and pigs), but also poultry and edible insects, are preferred.

In one aspect, the invention provides for methods of modifying a target polynucleotide in a eukaryotic cell, which may be in vivo, ex vivo or in vitro. In some embodiments, the method comprises sampling a cell or population of cells from a human or non-human animal or plant (including micro-algae), and modifying the cell or cells. Culturing may occur at any stage ex vivo. The cell or cells may even be re-introduced into the non-human animal or plant (including micro-algae).

In one aspect, the invention provides for methods of modifying a target polynucleotide in a eukaryotic cell. In some embodiments, the method comprises allowing a CRISPR complex to bind to the target polynucleotide to effect cleavage of said target polynucleotide thereby modifying the target polynucleotide, wherein the CRISPR complex comprises a CRISPR enzyme complexed with a guide sequence hybridized to a target sequence within said target polynucleotide, wherein said guide sequence is linked to a tracr mate sequence which in turn hybridizes to a tracr sequence.

In one aspect, the invention provides a method of modifying expression of a polynucleotide in a eukaryotic cell. In some embodiments, the method comprises allowing a CRISPR complex to bind to the polynucleotide such that said binding results in increased or decreased expression of said polynucleotide; wherein the CRISPR complex comprises a CRISPR enzyme complexed with a guide sequence hybridized to a target sequence within said polynucleotide, wherein said guide sequence is linked to a tracr mate sequence which in turn hybridizes to a tracr sequence.

With recent advances in crop genomics, the ability to use CRISPR-Cas systems to perform efficient and cost effective gene editing and manipulation will allow the rapid selection and comparison of single and and multiplexed genetic manipulations to transform such genomes for improved production and enhanced traits. In this regard reference is made to US patents and publications: U.S. Pat. No. 6,603,061—*Agrobacterium*-Mediated Plant Transformation Method; U.S. Pat. No. 7,868,149—Plant Genome Sequences and Uses Thereof and US 2009/0100536—Transgenic Plants with Enhanced Agronomic Traits, all the contents and disclosure of each of which are herein incorporated by reference in their entirety. In the practice of the invention, the contents and disclosure of Morrell et al "Crop genomics:advances and applications" Nat Rev Genet. 2011 Dec. 29; 13(2):85-96 are also herein incorporated by reference in their entirety. In some methods of the invention the vector is an *Agrobacterium* Ti or Ri plasmid for use in plants.

In plants, pathogens are often host-specific. For example, *Fusarium oxysporum* f. sp. *lycopersici* causes tomato wilt but attacks only tomato, and *F. oxysporum* f. *dianthii Puccinia graminis* f. sp. *tritici* attacks only wheat. Plants have existing and induced defenses to resist most pathogens. Mutations and recombination events across plant generations lead to genetic variability that gives rise to susceptibility or reduced susceptibility or resistance, especially as pathogens reproduce with more frequency than plants. In plants there can be non-host resistance, e.g., the host and pathogen are incompatible. There can also be Horizontal Resistance, e.g., partial resistance against all races of a pathogen, typically controlled by many genes and Vertical Resistance, e.g., complete resistance to some races of a pathogen but not to other races, typically controlled by a few genes. In a Gene-for-Gene level, plants and pathogens evolve together, and the genetic changes in one balance changes in other. Accordingly, using Natural Variability, breeders combine most useful genes for Yield, Quality, Uniformity, Hardiness, Resistance. The sources of resistance genes include native or foreign Varieties, Heirloom Varieties, Wild Plant Relatives, and Induced Mutations, e.g., treating plant material with mutagenic agents. Using the present invention, plant breeders are provided with a new tool to induce mutations. Accordingly, one skilled in the art can analyze the genome of sources of resistance genes, and in Varieties having desired characteristics or traits employ the present invention to induce the rise of resistance genes, with more precision than previous mutagenic agents and hence accelerate and improve plant breeding programs.

Screening can involve guide library synthesis, cloning of the guide RNA into a vector library to deliver the guides to cells, and the vector can include nucleic acid molecules to express Cas9 or the vector can be sequentially or co-delivered with one or more other vectors to deliver CRISPR-Cas9 system components, e.g., a second vector that contains nucleic acid molecules to express Cas9, or the cells can be otherwise engineered to express Cas9, whereby the CRISPR-cas system forms. The vector can be any suitable vector for delivery to the desired cell. Many such vectors are herein disclosed, including as to all cells mentioned herein; for instance, as to plants various vectors useful in the practice of the invention are also discussed in the context of crop genomics. The formed CRISPR-Cas9 system can give rise to mutations, e.g., breaks, or nicks, deletions, insertions, or substitutions. As members of the library may target different positions within the DNA of the cells, a library of cells, with potentially multiple genotypes arises. Such mutations may give rise to a desired phenotype. Thus, the library or libraries of cells are screened for selection of the desired phenotype. As to plants, CRISPR-Cas9 allows for targeted mutagenesis, e.g., CRISPR-Cas9 can be a mutagenic agent, plants expressing a desired phenotype from the mutation, e.g., reduced susceptibility or resistance to a pathogen or plant disease, are therefore better identified because the CRISPR-Cas9 system and the nature of the mutation can be correlated, e.g., based on the CRISPR-Cas9, e.g., guide sequence thereof, that induced a favorable mutation, one can appreciate where there was binding, and based on other aspects of the particular CRISPR-Cas9 system, the favorable mutation arising from CRISPR-Cas9 as a mutagenic agent can provide where and how the Cas9 of the system acted; and hence where and how, e.g., the nature of the mutation, is divined by screening using CRISPR-Cas9. Likewise, one can target particular portions of a cell, e.g., plant cell, genome by selection of a CRISPR-Cas9 library directed to portions of that genome, whereby a population having targeted mutations arises, and from the phenotypes of the cells, the skilled person can readily correlate the mutations made to the phenotypes observed, such that when a favorable phenotype is observed, the nature of the CRISPR-Cas9 can provide information as to binding and the nature of the mutation that gave rise to the favorable phenotype, and this can be useful to ascertain whether certain mutations can indeed give rise to favorable phenotypes. CRISPR-Cas9 can be used for revealing and engineering gene functions, including as to all cells mentioned herein, including, for instance plants (including microalgae). Accordingly, CRISPR-Cas9 libraries are a tool, including in creating or screening plant populations, e.g., plant or crop genetics, breeding. Moreover, as there are the GeCKO libraries corresponding to the mouse and human genomes, from this disclosure all that it presents to the knowledge in the art, Applicants believe one skilled in the art can create libraries analogous to the mouse and human GeCKO libraries for any plant without any undue experimentation.

In one aspect, the invention provides kits containing any one or more of the elements disclosed in the above methods and compositions. In some embodiments, the kit comprises a vector system and instructions for using the kit. In some embodiments, the vector system comprises (a) a first regulatory element operably linked to a tracr mate sequence and one or more insertion sites for inserting a guide sequence upstream of the tracr mate sequence, wherein when expressed, the guide sequence directs sequence-specific binding of a CRISPR complex to a target sequence in a eukaryotic cell, wherein the CRISPR complex comprises a CRISPR enzyme complexed with (1) the guide sequence that is hybridizable to the target sequence, and (2) the tracr mate sequence that is hybridized to the tracr sequence; and/or (b) a second regulatory element operably linked to an enzyme-coding sequence encoding said CRISPR enzyme comprising a nuclear localization sequence. Elements may be provided individually or in combinations, and may be provided in any suitable container, such as a vial, a bottle, or a tube. In some embodiments, the kit includes instructions in one or more languages, for example in more than one language.

In some embodiments, a kit comprises one or more reagents for use in a process utilizing one or more of the elements described herein. Reagents may be provided in any suitable container. For example, a kit may provide one or more reaction or storage buffers. Reagents may be provided in a form that is usable in a particular assay, or in a form that requires addition of one or more other components before use (e.g. in concentrate or lyophilized form). A buffer can be any buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In some embodiments, the buffer has a pH from about 7 to about 10. In some embodiments, the kit comprises one or more oligonucleotides corresponding to a guide sequence for insertion into a vector so as to operably link the guide sequence and a regulatory element. In some embodiments, the kit comprises a homologous recombination template polynucleotide.

In one aspect, the invention provides methods for using one or more elements of a CRISPR system. The CRISPR complex of the invention provides an effective means for modifying a target polynucleotide. The CRISPR complex of the invention has a wide variety of utility including modifying (e.g., deleting, inserting, translocating, inactivating, activating) a target polynucleotide in a multiplicity of cell types. As such the CRISPR complex of the invention has a broad spectrum of applications in, e.g., gene therapy, drug screening, disease diagnosis, and prognosis. An exemplary CRISPR complex comprises a CRISPR enzyme complexed with a guide sequence hybridized to a target sequence within the target polynucleotide. The guide sequence is linked to a tracr mate sequence, which in turn hybridizes to a tracr sequence.

The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA). Without wishing to be bound by theory, it is believed that the target sequence should be associated with a PAM (protospacer adjacent motif); that is, a short sequence recognized by the CRISPR complex. The precise sequence and length requirements for the PAM differ depending on the CRISPR enzyme used, but PAMs are typically 2-5 base pair sequences adjacent the protospacer (that is, the target sequence). Examples of PAM sequences are given in the examples below, and the skilled person will be able to identify further PAM sequences for use with a given CRISPR enzyme.

The target polynucleotide of a CRISPR complex may include a number of disease-associated genes and polynucleotides as well as signaling biochemical pathway-associated genes and polynucleotides as listed in U.S. provisional patent applications 61/736,527 and 61/748,427, both entitled SYSTEMS METHODS AND COMPOSITIONS FOR SEQUENCE MANIPULATION filed on Dec. 12, 2012 and Jan. 2, 2013, respectively, the contents of all of which are herein incorporated by reference in their entirety. The target polynucleotide of a CRISPR complex can be a gene of previously unknown function wherein its presence or absence in a screen (integrated barcode of the sgRNA) reveals details about its function. The target polynucleotide of a CRISPR complex may also be a gene whose interaction with the screening agent (e.g. drug or other selection agent) is discovered through its presence or absence in cells (barcode of the sgRNA) in the screen. Hence, in an aspect of the invention new drugs or pharmaceutical compositions may be tested for performance against all possible genetic KOs (or a subset of possible KOs; for example, genes associated with a particular enzymatic pathway) to understand how different organisms, e.g., humans (who carry different genetic KOs) might react to the drug and in which genetic background the drug might work better or worse.

Examples of genes and genomic loci that may be targeted by the CRISPR-Cas system guide RNA sequences described in Tables 1 and 10 (as provided in the compact discs created Apr. 11, 2014, as filed in connection with U.S. applications 61/960,777 and 61/995,636) may include but are not limited to sequences associated with a signaling biochemical pathway, e.g., a signaling biochemical pathway-associated gene or polynucleotide. Examples of target polynucleotides include a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease. The transcribed or translated products may be known or unknown, and may be at a normal or abnormal level.

Examples of disease-associated genes and polynucleotides are available from McKusick-Nathans Institute of Genetic Medicine, Johns Hopkins University (Baltimore, Md.) and National Center for Biotechnology Information, National Library of Medicine (Bethesda, Md.), available on the World Wide Web.

Examples of disease-associated genes and polynucleotides are listed in Tables A and B. Disease specific information is available from McKusick-Nathans Institute of Genetic Medicine, Johns Hopkins University (Baltimore, Md.) and National Center for Biotechnology Information, National Library of Medicine (Bethesda, Md.), available on the World Wide Web. Examples of signaling biochemical pathway-associated genes and polynucleotides are listed in Table C.

Mutations in these genes and pathways can result in production of improper proteins or proteins in improper amounts which affect function. Further examples of genes, diseases and proteins are hereby incorporated by reference from U.S. Provisional applications 61/736,527 and 61/748,427. Such genes, proteins and pathways may be the target polynucleotide of a CRISPR complex.

TABLE A

| DISEASE/DISORDERS | GENE(S) |
|---|---|
| Neoplasia | PTEN; ATM; ATR; EGFR; ERBB2; ERBB3; ERBB4; Notch1; Notch2; Notch3; Notch4; AKT; AKT2; AKT3; HIF; HIF1a; HIF3a; Met; HRG; Bcl2; PPAR alpha; PPAR gamma; WT1 (Wilms Tumor); FGF Receptor Family members (5 members: 1, 2, 3, 4, 5); CDKN2a; APC; RB (retinoblastoma); MEN1; VHL; BRCA1; BRCA2; AR (Androgen Receptor); TSG101; IGF; IGF Receptor; Igf1 (4 variants); Igf2 (3 variants); Igf 1 Receptor; Igf 2 Receptor; Bax; Bcl2; caspases family (9 members: 1, 2, 3, 4, 6, 7, 8, 9, 12); Kras; Apc |
| Age-related Macular Degeneration | Aber; Ccl2; Cc2; cp (ceruloplasmin); Timp3; cathepsinD; Vldlr; Ccr2 |
| Schizophrenia | Neuregulin1 (Nrg1); Erb4 (receptor for Neuregulin); Complexin1 (Cplx1); Tph1 Tryptophan hydroxylase; Tph2 Tryptophan hydroxylase 2; Neurexin 1; GSK3; GSK3a; GSK3b |
| Disorders | 5-HTT (Slc6a4); COMT; DRD (Drd1a); SLC6A3; DAOA; DTNBP1; Dao (Dao1) |
| Trinucleotide Repeat Disorders | HTT (Huntington's Dx); SBMA/SMAX1/AR (Kennedy's Dx); FXN/25 (Friedrich's Ataxia); ATX3 (Machado-Joseph's Dx); ATXN1 and ATXN2 (spinocerebellar ataxias); DMPK (myotonic dystrophy); Atrophin-1 and Atn1 (DRPLA Dx); CBP (Creb-BP-global instability); VLDLR (Alzheimer's); Atxn7; Atxn10 |

TABLE A-continued

| DISEASE/DISORDERS | GENE(S) |
|---|---|
| Fragile X Syndrome | FMR2; FXR1; FXR2; mGLUR5 |
| Secretase Related Disorders | APH-1 (alpha and beta); Presenilin (Psen1); nicastrin (Ncstn); PEN-2 |
| Others | Nos1; Parp1; Nat1; Nat2 |
| Prion-related disorders | Prp |
| ALS | SOD1; ALS2; STEX; FUS; TARDBP; VEGF (VEGF-a; VEGF-b; VEGF-c) |
| Drug addiction | Prkce (alcohol); Drd2; Drd4; ABAT (alcohol); GRIA2; Grm5; Grin1; Htr1b; Grin2a; Drd3; Pdyn; Gria1 (alcohol) |
| Autism | Mecp2; BZRAP1; MDGA2; Sema5A; Neurexin 1; Fragile X (FMR2 (AFF2); FXR1; FXR2; Mglur5) |
| Alzheimer's Disease | E1; CHIP; UCH; UBB; Tau; LRP; PICALM; Clusterin; PS1; SORL1; CR1; Vldlr; Uba1; Uba3; CHIP28 (Aqp1, Aquaporin 1); Uchl1; Uchl3; APP |
| Inflammation | IL-10; IL-1 (IL-1a; IL-1b); IL-13; IL-17 (IL-17a (CTLA8); IL-17b; IL-17c; IL-17d; IL-17f); II-23; Cx3cr1; ptpn22; TNFa; NOD2/CARD15 for IBD; IL-6; IL-12 (IL-12a; IL-12b); CTLA4; Cx3cl1 |
| Parkinson's Disease | x-Synuclein; DJ-1; LRRK2; Parkin; PINK1 |

TABLE B

| | |
|---|---|
| Blood and coagulation diseases and disorders | Anemia (CDAN1, CDA1, RPS19, DBA, PKLR, PK1, NT5C3, UMPH1, PSN1, RHAG, RH50A, NRAMP2, SPTB, ALAS2, ANH1, ASB, ABCB7, ABC7, ASAT); Bare lymphocyte syndrome (TAPBP, TPSN, TAP2, ABCB3, PSF2, RING11, MHC2TA, C2TA, RFX5, RFXAP, RFX5), Bleeding disorders (TBXA2R, P2RX1, P2X1); Factor H and factor H-like 1 (HF1, CFH, HUS); Factor V and factor VIII (MCFD2); Factor VII deficiency (F7); Factor X deficiency (F10); Factor XI deficiency (F11); Factor XII deficiency (F12, HAF); Factor XIIIA deficiency (F13A1, F13A); Factor XIIIB deficiency (F13B); Fanconi anemia (FANCA, FACA, FA1, FA, FAA, FAAP95, FAAP90, FLJ34064, FANCB, FANCC, FACC, BRCA2, FANCD1, FANCD2, FANCD, FACD, FAD, FANCE, FACE, FANCF, XRCC9, FANCG, BRIP1, BACH1, FANCJ, PHF9, FANCL, FANCM, KIAA1596); Hemophagocytic lymphohistiocytosis disorders (PRF1, HPLH2, UNC13D, MUNC13-4, HPLH3, HLH3, FHL3); Hemophilia A (F8, F8C, HEMA); Hemophilia B (F9, HEMB), Hemorrhagic disorders (PI, ATT, F5); Leukocyde deficiencies and disorders (ITGB2, CD18, LCAMB, LAD, EIF2B1, EIF2BA, EIF2B2, EIF2B3, EIF2B5, LVWM, CACH, CLE, EIF2B4); Sickle cell anemia (HBB); Thalassemia (HBA2, HBB, HBD, LCRB, HBA1). |
| Cell dysregulation and oncology diseases and disorders | B-cell non-Hodgkin lymphoma (BCL7A, BCL7); Leukemia (TAL1, TCL5, SCL, TAL2, FLT3, NBS1, NBS, ZNFN1A1, IK1, LYF1, HOXD4, HOX4B, BCR, CML, PHL, ALL, ARNT, KRAS2, RASK2, GMPS, AF10, ARHGEF12, LARG, KIAA0382, CALM, CLTH, CEBPA, CEBP, CHIC2, BTL, FLT3, KIT, PBT, LPP, NPM1, NUP214, D9S46E, CAN, CAIN, RUNX1, CBFA2, AML1, WHSC1L1, NSD3, FLT3, AF1Q, NPM1, NUMA1, ZNF145, PLZF, PML, MYL, STAT5B, AF10, CALM, CLTH, ARL11, ARLTS1, P2RX7, P2X7, BCR, CML, PHL, ALL, GRAF, NF1, VRNF, WSS, NFNS, PTPN11, PTP2C, SHP2, NS1, BCL2, CCND1, PRAD1, BCL1, TCRA, GATA1, GF1, ERYF1, NFE1, ABL1, NQO1, DIA4, NMOR1, NUP214, D9S46E, CAN, CAIN). |
| Inflammation and immune related diseases and disorders | AIDS (KIR3DL1, NKAT3, NKB1, AMB11, KIR3DS1, IFNG, CXCL12, SDF1); Autoimmune lymphoproliferative syndrome (TNFRSF6, APT1, FAS, CD95, ALPS1A); Combined immunodeficiency, (IL2RG, SCIDX1, SCIDX, IMD4); HIV-1 (CCL5, SCYA5, D17S136E, TCP228), HIV susceptibility or infection (IL10, CSIF, CMKBR2, CCR2, CMKBR5, CCCKR5 (CCR5)); Immunodeficiencies (CD3E, CD3G, AICDA, AID, HIGM2, TNFRSF5, CD40, UNG, DGU, HIGM4, TNFSF5, CD40LG, HIGM1, IGM, FOXP3, IPEX, AIID, XPID, PIDX, TNFRSF14B, TACI); Inflammation (IL-10, IL-1 (IL-1a, IL-1b), IL-13, IL-17 (IL-17a (CTLA8), IL-17b, IL-17c, IL-17d, IL-17f), II-23, Cx3cr1, ptpn22, TNFa, NOD2/CARD15 for IBD, IL-6, IL-12 (IL-12a, IL-12b), CTLA4, Cx3cl1); Severe combined immunodeficiencies (SCIDs)(JAK3, JAKL, DCLRE1C, ARTEMIS, SCIDA, RAG1, RAG2, ADA, PTPRC, CD45, LCA, IL7R, CD3D, T3D, IL2RG, SCIDX1, SCIDX, IMD4). |
| Metabolic, liver, kidney and protein diseases and disorders | Amyloid neuropathy (TTR, PALB); Amyloidosis (APOA1, APP, AAA, CVAP, AD1, GSN, FGA, LYZ, TTR, PALB); Cirrhosis (KRT18, KRT8, CIRH1A, NAIC, TEX292, KIAA1988); Cystic fibrosis (CFTR, ABCC7, CF, MRP7); Glycogen storage diseases (SLC2A2, GLUT2, G6PC, G6PT, G6PT1, GAA, LAMP2, LAMPB, AGL, GDE, GBE1, GYS2, PYGL, PFKM); Hepatic adenoma, 142330 (TCF1, HNF1A, MODY3), Hepatic failure, early onset, and neurologic disorder (SCOD1, SCO1), Hepatic lipase deficiency (LIPC), Hepatoblastoma, cancer and |

TABLE B-continued

| | |
|---|---|
| | carcinomas (CTNNB1, PDGFRL, PDGRL, PRLTS, AXIN1, AXIN, CTNNB1, TP53, P53, LFS1, IGF2R, MPRI, MET, CASP8, MCH5; Medullary cystic kidney disease (UMOD, HNFJ, FJHN, MCKD2, ADMCKD2); Phenylketonuria (PAH, PKU1, QDPR, DHPR, PTS); Polycystic kidney and hepatic disease (FCYT, PKHD1, ARPKD, PKD1, PKD2, PKD4, PKDTS, PRKCSH, G19P1, PCLD, SEC63). |
| Muscular/Skeletal diseases and disorders | Becker muscular dystrophy (DMD, BMD, MYF6), Duchenne Muscular Dystrophy (DMD, BMD); Emery-Dreifuss muscular dystrophy (LMNA, LMN1, EMD2, FPLD, CMD1A, HGPS, LGMD1B, LMNA, LMN1, EMD2, FPLD, CMD1A); Facioscapulohumeral muscular dystrophy (FSHMD1A, FSHD1A); Muscular dystrophy (FKRP, MDC1C, LGMD2I, LAMA2, LAMM, LARGE, KIAA0609, MDC1D, FCMD, TTID, MYOT, CAPN3, CANP3, DYSF, LGMD2B, SGCG, LGMD2C, DMDA1, SCG3, SGCA, ADL, DAG2, LGMD2D, DMDA2, SGCB, LGMD2E, SGCD, SGD, LGMD2F, CMD1L, TCAP, LGMD2G, CMD1N, TRIM32, HT2A, LGMD2H, FKRP, MDC1C, LGMD2I, TTN, CMD1G, TMD, LGMD2J, POMT1, CAV3, LGMD1C, SEPN1, SELN, RSMD1, PLEC1, PLTN, EBS1); Osteopetrosis (LRP5, BMND1, LRP7, LR3, OPPG, VBCH2, CLCN7, CLC7, OPTA2, OSTM1, GL, TCIRG1, TIRC7, OC116, OPTB1); Muscular atrophy (VAPB, VAPC, ALS8, SMN1, SMA1, SMA2, SMA3, SMA4, BSCL2, SPG17, GARS, SMAD1, CMT2D, HEXB, IGHMBP2, SMUBP2, CATF1, SMARD1). |
| Neurological and neuronal diseases and disorders | ALS (SOD1, ALS2, STEX, FUS, TARDBP, VEGF (VEGF-a, VEGF-b, VEGF-c); Alzheimer disease (APP, AAA, CVAP, AD1, APOE, AD2, PSEN2, AD4, STM2, APBB2, FE65L1, NOS3, PLAU, URK, ACE, DCP1, ACE1, MPO, PACIP1, PAXIP1L, PTIP, A2M, BLMH, BMH, PSEN1, AD3); Autism (Mecp2, BZRAP1, MDGA2, Sema5A, Neurexin 1, GLO1, MECP2, RTT, PPMX, MRX16, MRX79, NLGN3, NLGN4, KIAA1260, AUTSX2); Fragile X Syndrome (FMR2, FXR1, FXR2, mGLUR5); Huntington's disease and disease like disorders (HD, IT15, PRNP, PRIP, JPH3, JP3, HDL2, TBP, SCA17); Parkinson disease (NR4A2, NURR1, NOT, TINUR, SNCAIP, TBP, SCA17, SNCA, NACP, PARK1, PARK4, DJ1, PARK7, LRRK2, PARK8, PINK1, PARK6, UCHL1, PARK5, SNCA, NACP, PARK1, PARK4, PRKN, PARK2, PDJ, DBH, NDUFV2); Rett syndrome (MECP2, RTT, PPMX, MRX16, MRX79, CDKL5, STK9, MECP2, RTT, PPMX, MRX16, MRX79, x-Synuclein, DJ-1); Schizophrenia (Neuregulin1 (Nrg1), Erb4 (receptor for Neuregulin), Complexin1 (Cplx1), Tph1 Tryptophan hydroxylase, Tph2, Tryptophan hydroxylase 2, Neurexin 1, GSK3, GSK3a, GSK3b, 5-HTT (Slc6a4), COMT, DRD (Drd1a), SLC6A3, DAOA, DTNBP1, Dao (Dao1)); Secretase Related Disorders (APH-1 (alpha and beta), Presenilin (Psen1), nicastrin, (Ncstn), PEN-2, Nos1, Parp1, Nat1, Nat2); Trinucleotide Repeat Disorders (HTT (Huntington's Dx), SBMA/SMAX1/AR (Kennedy's Dx), FXN/X25 (Friedrich's Ataxia), ATX3 (Machado-Joseph's Dx), ATXN1 and ATXN2 (spinocerebellar ataxias), DMPK (myotonic dystrophy), Atrophin-1 and Atn1 (DRPLA Dx), CBP (Creb-BP-global instability), VLDLR (Alzheimer's), Atxn7, Atxn10). |
| Occular diseases and disorders | Age-related macular degeneration (Abcr, Ccl2, Cc2, cp (ceruloplasmin), Timp3, cathepsinD, Vldlr, Ccr2); Cataract (CRYAA, CRYA1, CRYBB2, CRYB2, PITX3, BFSP2, CP49, CP47, CRYAA, CRYA1, PAX6, AN2, MGDA, CRYBA1, CRYB1, CRYGC, CRYG3, CCL, LIM2, MP19, CRYGD, CRYG4, BFSP2, CP49, CP47, HSF4, CTM, HSF4, CTM, MIP, AQP0, CRYAB, CRYA2, CTPP2, CRYBB1, CRYGD, CRYG4, CRYBB2, CRYB2, CRYGC, CRYG3, CCL, CRYAA, CRYA1, GJA8, CX50, CAE1, GJA3, CX46, CZP3, CAE3, CCM1, CAM, KRIT1); Corneal clouding and dystrophy (APOA1, TGFBI, CSD2, CDGG1, CSD, BIGH3, CDG2, TACSTD2, TROP2, M1S1, VSX1, RINX, PPCD, PPD, KTCN, COL8A2, FECD, PPCD2, PIP5K3, CFD); Cornea plana congenital (KERA, CNA2); Glaucoma (MYOC, TIGR, GLC1A, JOAG, GPOA, OPTN, GLC1E, FIP2, HYPL, NRP, CYP1B1, GLC3A, OPA1, NTG, NPG, CYP1B1, GLC3A); Leber congenital amaurosis (CRB1, RP12, CRX, CORD2, CRD, RPGRIP1, LCA6, CORD9, RPE65, RP20, AIPL1, LCA4, GUCY2D, GUC2D, LCA1, CORD6, RDH12, LCA3); Macular dystrophy (ELOVL4, ADMD, STGD2, STGD3, RDS, RP7, PRPH2, PRPH, AVMD, AOFMD, VMD2). |

TABLE C

| CELLULAR FUNCTION | GENES |
|---|---|
| PI3K/AKT Signaling | PRKCE; ITGAM; ITGA5; IRAK1; PRKAA2; EIF2AK2; PTEN; EIF4E; PRKCZ; GRK6; MAPK1; TSC1; PLK1; AKT2; IKBKB; PIK3CA; CDK8; CDKN1B; NFKB2; BCL2; PIK3CB; PPP2R1A; MAPK8; BCL2L1; MAPK3; TSC2; ITGA1; KRAS; EIF4EBP1; RELA; PRKCD; NOS3; |

TABLE C-continued

| CELLULAR FUNCTION | GENES |
|---|---|
| | PRKAA1; MAPK9; CDK2; PPP2CA; PIM1; ITGB7; YWHAZ; ILK; TP53; RAF1; IKBKG; RELB; DYRK1A; CDKN1A; ITGB1; MAP2K2; JAK1; AKT1; JAK2; PIK3R1; CHUK; PDPK1; PPP2R5C; CTNNB1; MAP2K1; NFKB1; PAK3; ITGB3; CCND1; GSK3A; FRAP1; SFN; ITGA2; TTK; CSNK1A1; BRAF; GSK3B; AKT3; FOXO1; SGK; HSP90AA1; RPS6KB1 |
| ERK/MAPK Signaling | PRKCE; ITGAM; ITGA5; HSPB1; IRAK1; PRKAA2; EIF2AK2; RAC1; RAP1A; TLN1; EIF4E; ELK1; GRK6; MAPK1; RAC2; PLK1; AKT2; PIK3CA; CDK8; CREB1; PRKCI; PTK2; FOS; RPS6KA4; PIK3CB; PPP2R1A; PIK3C3; MAPK8; MAPK3; ITGA1; ETS1; KRAS; MYCN; EIF4EBP1; PPARG; PRKCD; PRKAA1; MAPK9; SRC; CDK2; PPP2CA; PIM1; PIK3C2A; ITGB7; YWHAZ; PPP1CC; KSR1; PXN; RAF1; FYN; DYRK1A; ITGB1; MAP2K2; PAK4; PIK3R1; STAT3; PPP2R5C; MAP2K1; PAK3; ITGB3; ESR1; ITGA2; MYC; TTK; CSNK1A1; CRKL; BRAF; ATF4; PRKCA; SRF; STAT1; SGK |
| Glucocorticoid Receptor Signaling | RAC1; TAF4B; EP300; SMAD2; TRAF6; PCAF; ELK1; MAPK1; SMAD3; AKT2; IKBKB; NCOR2; UBE2I; PIK3CA; CREB1; FOS; HSPA5; NFKB2; BCL2; MAP3K14; STAT5B; PIK3CB; PIK3C3; MAPK8; BCL2L1; MAPK3; TSC22D3; MAPK10; NRIP1; KRAS; MAPK13; RELA; STAT5A; MAPK9; NOS2A; PBX1; NR3C1; PIK3C2A; CDKN1C; TRAF2; SERPINE1; NCOA3; MAPK14; TNF; RAF1; IKBKG; MAP3K7; CREBBP; CDKN1A; MAP2K2; JAK1; IL8; NCOA2; AKT1; JAK2; PIK3R1; CHUK; STAT3; MAP2K1; NFKB1; TGFBR1; ESR1; SMAD4; CEBPB; JUN; AR; AKT3; CCL2; MMP1; STAT1; IL6; HSP90AA1 |
| Axonal Guidance Signaling | PRKCE; ITGAM; ROCK1; ITGA5; CXCR4; ADAM12; IGF1; RAC1; RAP1A; EIF4E; PRKCZ; NRP1; NTRK2; ARHGEF7; SMO; ROCK2; MAPK1; PGF; RAC2; PTPN11; GNAS; AKT2; PIK3CA; ERBB2; PRKCI; PTK2; CFL1; GNAQ; PIK3CB; CXCL12; PIK3C3; WNT11; PRKD1; GNB2L1; ABL1; MAPK3; ITGA1; KRAS; RHOA; PRKCD; PIK3C2A; ITGB7; GLI2; PXN; VASP; RAF1; FYN; ITGB1; MAP2K2; PAK4; ADAM17; AKT1; PIK3R1; GLI1; WNT5A; ADAM10; MAP2K1; PAK3; ITGB3; CDC42; VEGFA; ITGA2; EPHA8; CRKL; RND1; GSK3B; AKT3; PRKCA |
| Ephrin Receptor Signaling | PRKCE; ITGAM; ROCK1; ITGA5; CXCR4; IRAK1; PRKAA2; EIF2AK2; RAC1; RAP1A; GRK6; ROCK2; MAPK1; PGF; RAC2; PTPN11; GNAS; PLK1; AKT2; DOK1; CDK8; CREB1; PTK2; CFL1; GNAQ; MAP3K14; CXCL12; MAPK8; GNB2L1; ABL1; MAPK3; ITGA1; KRAS; RHOA; PRKCD; PRKAA1; MAPK9; SRC; CDK2; PIM1; ITGB7; PXN; RAF1; FYN; DYRK1A; ITGB1; MAP2K2; PAK4; AKT1; JAK2; STAT3; ADAM10; MAP2K1; PAK3; ITGB3; CDC42; VEGFA; ITGA2; EPHA8; TTK; CSNK1A1; CRKL; BRAF; PTPN13; ATF4; AKT3; SGK |
| Actin Cytoskeleton Signaling | ACTN4; PRKCE; ITGAM; ROCK1; ITGA5; IRAK1; PRKAA2; EIF2AK2; RAC1; INS; ARHGEF7; GRK6; ROCK2; MAPK1; RAC2; PLK1; AKT2; PIK3CA; CDK8; PTK2; CFL1; PIK3CB; MYH9; DIAPH1; PIK3C3; MAPK8; F2R; MAPK3; SLC9A1; ITGA1; KRAS; RHOA; PRKCD; PRKAA1; MAPK9; CDK2; PIM1; PIK3C2A; ITGB7; PPP1CC; PXN; VIL2; RAF1; GSN; DYRK1A; ITGB1; MAP2K2; PAK4; PIP5K1A; PIK3R1; MAP2K1; PAK3; ITGB3; CDC42; APC; ITGA2; TTK; CSNK1A1; CRKL; BRAF; VAV3; SGK |
| Huntington's Disease Signaling | PRKCE; IGF1; EP300; RCOR1; PRKCZ; HDAC4; TGM2; MAPK1; CAPNS1; AKT2; EGFR; NCOR2; SP1; CAPN2; PIK3CA; HDAC5; CREB1; PRKCI; HSPA5; REST; GNAQ; PIK3CB; PIK3C3; MAPK8; IGF1R; PRKD1; GNB2L1; BCL2L1; CAPN1; MAPK3; CASP8; HDAC2; HDAC7A; PRKCD; HDAC11; MAPK9; HDAC9; PIK3C2A; HDAC3; TP53; CASP9; CREBBP; AKT1; PIK3R1; PDPK1; CASP1; APAF1; FRAP1; CASP2; JUN; BAX; ATF4; AKT3; PRKCA; CLTC; SGK; HDAC6; CASP3 |
| Apoptosis Signaling | PRKCE; ROCK1; BID; IRAK1; PRKAA2; EIF2AK2; BAK1; BIRC4; GRK6; MAPK1; CAPNS1; PLK1; AKT2; IKBKB; CAPN2; CDK8; FAS; NFKB2; BCL2; MAP3K14; MAPK8; BCL2L1; CAPN1; MAPK3; CASP8; KRAS; RELA; |

TABLE C-continued

| CELLULAR FUNCTION | GENES |
|---|---|
| | PRKCD; PRKAA1; MAPK9; CDK2; PIM1; TP53; TNF; RAF1; IKBKG; RELB; CASP9; DYRK1A; MAP2K2; CHUK; APAF1; MAP2K1; NFKB1; PAK3; LMNA; CASP2; BIRC2; TTK; CSNK1A1; BRAF; BAX; PRKCA; SGK; CASP3; BIRC3; PARP1 |
| B Cell Receptor Signaling | RAC1; PTEN; LYN; ELK1; MAPK1; RAC2; PTPN11; AKT2; IKBKB; PIK3CA; CREB1; SYK; NFKB2; CAMK2A; MAP3K14; PIK3CB; PIK3C3; MAPK8; BCL2L1; ABL1; MAPK3; ETS1; KRAS; MAPK13; RELA; PTPN6; MAPK9; EGR1; PIK3C2A; BTK; MAPK14; RAF1; IKBKG; RELB; MAP3K7; MAP2K2; AKT1; PIK3R1; CHUK; MAP2K1; NFKB1; CDC42; GSK3A; FRAP1; BCL6; BCL10; JUN; GSK3B; ATF4; AKT3; VAV3; RPS6KB1 |
| Leukocyte Extravasation Signaling | ACTN4; CD44; PRKCE; ITGAM; ROCK1; CXCR4; CYBA; RAC1; RAP1A; PRKCZ; ROCK2; RAC2; PTPN11; MMP14; PIK3CA; PRKCI; PTK2; PIK3CB; CXCL12; PIK3C3; MAPK8; PRKD1; ABL1; MAPK10; CYBB; MAPK13; RHOA; PRKCD; MAPK9; SRC; PIK3C2A; BTK; MAPK14; NOX1; PXN; VIL2; VASP; ITGB1; MAP2K2; CTNND1; PIK3R1; CTNNB1; CLDN1; CDC42; F11R; ITK; CRKL; VAV3; CTTN; PRKCA; MMP1; MMP9 |
| Integrin Signaling | ACTN4; ITGAM; ROCK1; ITGA5; RAC1; PTEN; RAP1A; TLN1; ARHGEF7; MAPK1; RAC2; CAPNS1; AKT2; CAPN2; PIK3CA; PTK2; PIK3CB; PIK3C3; MAPK8; CAV1; CAPN1; ABL1; MAPK3; ITGA1; KRAS; RHOA; SRC; PIK3C2A; ITGB7; PPP1CC; ILK; PXN; VASP; RAF1; FYN; ITGB1; MAP2K2; PAK4; AKT1; PIK3R1; TNK2; MAP2K1; PAK3; ITGB3; CDC42; RND3; ITGA2; CRKL; BRAF; GSK3B; AKT3 |
| Acute Phase Response Signaling | IRAK1; SOD2; MYD88; TRAF6; ELK1; MAPK1; PTPN11; AKT2; IKBKB; PIK3CA; FOS; NFKB2; MAP3K14; PIK3CB; MAPK8; RIPK1; MAPK3; IL6ST; KRAS; MAPK13; IL6R; RELA; SOCS1; MAPK9; FTL; NR3C1; TRAF2; SERPINE1; MAPK14; TNF; RAF1; PDK1; IKBKG; RELB; MAP3K7; MAP2K2; AKT1; JAK2; PIK3R1; CHUK; STAT3; MAP2K1; NFKB1; FRAP1; CEBPB; JUN; AKT3; IL1R1; IL6 |
| PTEN Signaling | ITGAM; ITGA5; RAC1; PTEN; PRKCZ; BCL2L11; MAPK1; RAC2; AKT2; EGFR; IKBKB; CBL; PIK3CA; CDKN1B; PTK2; NFKB2; BCL2; PIK3CB; BCL2L1; MAPK3; ITGA1; KRAS; ITGB7; ILK; PDGFRB; INSR; RAF1; IKBKG; CASP9; CDKN1A; ITGB1; MAP2K2; AKT1; PIK3R1; CHUK; PDGFRA; PDPK1; MAP2K1; NFKB1; ITGB3; CDC42; CCND1; GSK3A; ITGA2; GSK3B; AKT3; FOXO1; CASP3; RPS6KB1 |
| p53 Signaling | PTEN; EP300; BBC3; PCAF; FASN; BRCA1; GADD45A; BIRC5; AKT2; PIK3CA; CHEK1; TP53INP1; BCL2; PIK3CB; PIK3C3; MAPK8; THBS1; ATR; BCL2L1; E2F1; PMAIP1; CHEK2; TNFRSF10B; TP73; RB1; HDAC9; CDK2; PIK3C2A; MAPK14; TP53; LRDD; CDKN1A; HIPK2; AKT1; PIK3R1; RRM2B; APAF1; CTNNB1; SIRT1; CCND1; PRKDC; ATM; SFN; CDKN2A; JUN; SNAI2; GSK3B; BAX; AKT3 |
| Aryl Hydrocarbon Receptor Signaling | HSPB1; EP300; FASN; TGM2; RXRA; MAPK1; NQO1; NCOR2; SP1; ARNT; CDKN1B; FOS; CHEK1; SMARCA4; NFKB2; MAPK8; ALDH1A1; ATR; E2F1; MAPK3; NRIP1; CHEK2; RELA; TP73; GSTP1; RB1; SRC; CDK2; AHR; NFE2L2; NCOA3; TP53; TNF; CDKN1A; NCOA2; APAF1; NFKB1; CCND1; ATM; ESR1; CDKN2A; MYC; JUN; ESR2; BAX; IL6; CYP1B1; HSP90AA1 |
| Xenobiotic Metabolism Signaling | PRKCE; EP300; PRKCZ; RXRA; MAPK1; NQO1; NCOR2; PIK3CA; ARNT; PRKCI; NFKB2; CAMK2A; PIK3CB; PPP2R1A; PIK3C3; MAPK8; PRKD1; ALDH1A1; MAPK3; NRIP1; KRAS; MAPK13; PRKCD; GSTP1; MAPK9; NOS2A; ABCB1; AHR; PPP2CA; FTL; NFE2L2; PIK3C2A; PPARGC1A; MAPK14; TNF; RAF1; CREBBP; MAP2K2; PIK3R1; PPP2R5C; MAP2K1; NFKB1; KEAP1; PRKCA; EIF2AK3; IL6; CYP1B1; HSP90AA1 |
| SAPK/JNK Signaling | PRKCE; IRAK1; PRKAA2; EIF2AK2; RAC1; ELK1; GRK6; MAPK1; GADD45A; RAC2; PLK1; AKT2; PIK3CA; FADD; CDK8; PIK3CB; PIK3C3; MAPK8; RIPK1; GNB2L1; IRS1; MAPK3; MAPK10; DAXX; KRAS; PRKCD; PRKAA1; MAPK9; CDK2; PIM1; PIK3C2A; |

TABLE C-continued

| CELLULAR FUNCTION | GENES |
|---|---|
| | TRAF2; TP53; LCK; MAP3K7; DYRK1A; MAP2K2; PIK3R1; MAP2K1; PAK3; CDC42; JUN; TTK; CSNK1A1; CRKL; BRAF; SGK |
| PPAr/RXR Signaling | PRKAA2; EP300; INS; SMAD2; TRAF6; PPARA; FASN; RXRA; MAPK1; SMAD3; GNAS; IKBKB; NCOR2; ABCA1; GNAQ; NFKB2; MAP3K14; STAT5B; MAPK8; IRS1; MAPK3; KRAS; RELA; PRKAA1; PPARGC1A; NCOA3; MAPK14; INSR; RAF1; IKBKG; RELB; MAP3K7; CREBBP; MAP2K2; JAK2; CHUK; MAP2K1; NFKB1; TGFBR1; SMAD4; JUN; IL1R1; PRKCA; IL6; HSP90AA1; ADIPOQ |
| NF-KB Signaling | IRAK1; EIF2AK2; EP300; INS; MYD88; PRKCZ; TRAF6; TBK1; AKT2; EGFR; IKBKB; PIK3CA; BTRC; NFKB2; MAP3K14; PIK3CB; PIK3C3; MAPK8; RIPK1; HDAC2; KRAS; RELA; PIK3C2A; TRAF2; TLR4; PDGFRB; TNF; INSR; LCK; IKBKG; RELB; MAP3K7; CREBBP; AKT1; PIK3R1; CHUK; PDGFRA; NFKB1; TLR2; BCL10; GSK3B; AKT3; TNFAIP3; IL1R1 |
| Neuregulin Signaling | ERBB4; PRKCE; ITGAM; ITGA5; PTEN; PRKCZ; ELK1; MAPK1; PTPN11; AKT2; EGFR; ERBB2; PRKCI; CDKN1B; STAT5B; PRKD1; MAPK3; ITGA1; KRAS; PRKCD; STAT5A; SRC; ITGB7; RAF1; ITGB1; MAP2K2; ADAM17; AKT1; PIK3R1; PDPK1; MAP2K1; ITGB3; EREG; FRAP1; PSEN1; ITGA2; MYC; NRG1; CRKL; AKT3; PRKCA; HSP90AA1; RPS6KB1 |
| Wnt & Beta catenin Signaling | CD44; EP300; LRP6; DVL3; CSNK1E; GJA1; SMO; AKT2; PIN1; CDH1; BTRC; GNAQ; MARK2; PPP2R1A; WNT11; SRC; DKK1; PPP2CA; SOX6; SFRP2; ILK; LEF1; SOX9; TP53; MAP3K7; CREBBP; TCF7L2; AKT1; PPP2R5C; WNT5A; LRP5; CTNNB1; TGFBR1; CCND1; GSK3A; DVL1; APC; CDKN2A; MYC; CSNK1A1; GSK3B; AKT3; SOX2 |
| Insulin Receptor Signaling | PTEN; INS; EIF4E; PTPN1; PRKCZ; MAPK1; TSC1; PTPN11; AKT2; CBL; PIK3CA; PRKCI; PIK3CB; PIK3C3; MAPK8; IRS1; MAPK3; TSC2; KRAS; EIF4EBP1; SLC2A4; PIK3C2A; PPP1CC; INSR; RAF1; FYN; MAP2K2; JAK1; AKT1; JAK2; PIK3R1; PDPK1; MAP2K1; GSK3A; FRAP1; CRKL; GSK3B; AKT3; FOXO1; SGK; RPS6KB1 |
| IL-6 Signaling | HSPB1; TRAF6; MAPKAPK2; ELK1; MAPK1; PTPN11; IKBKB; FOS; NFKB2; MAP3K14; MAPK8; MAPK3; MAPK10; IL6ST; KRAS; MAPK13; IL6R; RELA; SOCS1; MAPK9; ABCB1; TRAF2; MAPK14; TNF; RAF1; IKBKG; RELB; MAP3K7; MAP2K2; IL8; JAK2; CHUK; STAT3; MAP2K1; NFKB1; CEBPB; JUN; IL1R1; SRF; IL6 |
| Hepatic Cholestasis | PRKCE; IRAK1; INS; MYD88; PRKCZ; TRAF6; PPARA; RXRA; IKBKB; PRKCI; NFKB2; MAP3K14; MAPK8; PRKD1; MAPK10; RELA; PRKCD; MAPK9; ABCB1; TRAF2; TLR4; TNF; INSR; IKBKG; RELB; MAP3K7; IL8; CHUK; NR1H2; TJP2; NFKB1; ESR1; SREBF1; FGFR4; JUN; IL1R1; PRKCA; IL6 |
| IGF-1 Signaling | IGF1; PRKCZ; ELK1; MAPK1; PTPN11; NEDD4; AKT2; PIK3CA; PRKCI; PTK2; FOS; PIK3CB; PIK3C3; MAPK8; IGF1R; IRS1; MAPK3; IGFBP7; KRAS; PIK3C2A; YWHAZ; PXN; RAF1; CASP9; MAP2K2; AKT1; PIK3R1; PDPK1; MAP2K1; IGFBP2; SFN; JUN; CYR61; AKT3; FOXO1; SRF; CTGF; RPS6KB1 |
| NRF2-mediated Oxidative Stress Response | PRKCE; EP300; SOD2; PRKCZ; MAPK1; SQSTM1; NQO1; PIK3CA; PRKCI; FOS; PIK3CB; PIK3C3; MAPK8; PRKD1; MAPK3; KRAS; PRKCD; GSTP1; MAPK9; FTL; NFE2L2; PIK3C2A; MAPK14; RAF1; MAP3K7; CREBBP; MAP2K2; AKT1; PIK3R1; MAP2K1, PPIB; JUN; KEAP1; GSK3B; ATF4; PRKCA; EIF2AK3; HSP90AA1 |
| Hepatic Fibrosis/Hepatic Stellate Cell Activation | EDN1; IGF1; KDR; FLT1; SMAD2; FGFR1; MET; PGF; SMAD3; EGFR; FAS; CSF1; NFKB2; BCL2; MYH9; IGF1R; IL6R; RELA; TLR4; PDGFRB; TNF; RELB; IL8; PDGFRA; NFKB1; TGFBR1; SMAD4; VEGFA; BAX; IL1R1; CCL2; HGF; MMP1; STAT1; IL6; CTGF; MMP9 |
| PPAR Signaling | EP300; INS; TRAF6; PPARA; RXRA; MAPK1; IKBKB; NCOR2; FOS; NFKB2; MAP3K14; STAT5B; MAPK3; NRIP1; KRAS; PPARG; RELA; STAT5A; TRAF2; PPARGC1A; PDGFRB; TNF; INSR; RAF1; IKBKG; RELB; MAP3K7; CREBBP; MAP2K2; CHUK; PDGFRA; MAP2K1; NFKB1; JUN; IL1R1; HSP90AA1 |

TABLE C-continued

| CELLULAR FUNCTION | GENES |
|---|---|
| Fc Epsilon RI Signaling | PRKCE; RAC1; PRKCZ; LYN; MAPK1; RAC2; PTPN11; AKT2; PIK3CA; SYK; PRKCI; PIK3CB; PIK3C3; MAPK8; PRKD1; MAPK3; MAPK10; KRAS; MAPK13; PRKCD; MAPK9; PIK3C2A; BTK; MAPK14; TNF; RAF1; FYN; MAP2K2; AKT1; PIK3R1; PDPK1; MAP2K1; AKT3; VAV3; PRKCA |
| G-Protein Coupled Receptor Signaling | PRKCE; RAP1A; RGS16; MAPK1; GNAS; AKT2; IKBKB; PIK3CA; CREB1; GNAQ; NFKB2; CAMK2A; PIK3CB; PIK3C3; MAPK3; KRAS; RELA; SRC; PIK3C2A; RAF1; IKBKG; RELB; FYN; MAP2K2; AKT1; PIK3R1; CHUK; PDPK1; STAT3; MAP2K1; NFKB1; BRAF; ATF4; AKT3; PRKCA |
| Inositol Phosphate Metabolism | PRKCE; IRAK1; PRKAA2; EIF2AK2; PTEN; GRK6; MAPK1; PLK1; AKT2; PIK3CA; CDK8; PIK3CB; PIK3C3; MAPK8; MAPK3; PRKCD; PRKAA1; MAPK9; CDK2; PIM1; PIK3C2A; DYRK1A; MAP2K2; PIP5K1A; PIK3R1; MAP2K1; PAK3; ATM; TTK; CSNK1A1; BRAF; SGK |
| PDGF Signaling | EIF2AK2; ELK1; ABL2; MAPK1; PIK3CA; FOS; PIK3CB; PIK3C3; MAPK8; CAV1; ABL1; MAPK3; KRAS; SRC; PIK3C2A; PDGFRB; RAF1; MAP2K2; JAK1; JAK2; PIK3R1; PDGFRA; STAT3; SPHK1; MAP2K1; MYC; JUN; CRKL; PRKCA; SRF; STAT1; SPHK2 |
| VEGF Signaling | ACTN4; ROCK1; KDR; FLT1; ROCK2; MAPK1; PGF; AKT2; PIK3CA; ARNT; PTK2; BCL2; PIK3CB; PIK3C3; BCL2L1; MAPK3; KRAS; HIF1A; NOS3; PIK3C2A; PXN; RAF1; MAP2K2; ELAVL1; AKT1; PIK3R1; MAP2K1; SFN; VEGFA; AKT3; FOXO1; PRKCA |
| Natural Killer Cell Signaling | PRKCE; RAC1; PRKCZ; MAPK1; RAC2; PTPN11; KIR2DL3; AKT2; PIK3CA; SYK; PRKCI; PIK3CB; PIK3C3; PRKD1; MAPK3; KRAS; PRKCD; PTPN6; PIK3C2A; LCK; RAF1; FYN; MAP2K2; PAK4; AKT1; PIK3R1; MAP2K1; PAK3; AKT3; VAV3; PRKCA |
| Cell Cycle: G1/S Checkpoint Regulation | HDAC4; SMAD3; SUV39H1; HDAC5; CDKN1B; BTRC; ATR; ABL1; E2F1; HDAC2; HDAC7A; RB1; HDAC11; HDAC9; CDK2; E2F2; HDAC3; TP53; CDKN1A; CCND1; E2F4; ATM; RBL2; SMAD4; CDKN2A; MYC; NRG1; GSK3B; RBL1; HDAC6 |
| T Cell Receptor Signaling | RAC1; ELK1; MAPK1; IKBKB; CBL; PIK3CA; FOS; NFKB2; PIK3CB; PIK3C3; MAPK8; MAPK3; KRAS; RELA; PIK3C2A; BTK; LCK; RAF1; IKBKG; RELB; FYN; MAP2K2; PIK3R1; CHUK; MAP2K1; NFKB1; ITK; BCL10; JUN; VAV3 |
| Death Receptor Signaling | CRADD; HSPB1; BID; BIRC4; TBK1; IKBKB; FADD; FAS; NFKB2; BCL2; MAP3K14; MAPK8; RIPK1; CASP8; DAXX; TNFRSF10B; RELA; TRAF2; TNF; IKBKG; RELB; CASP9; CHUK; APAF1; NFKB1; CASP2; BIRC2; CASP3; BIRC3 |
| FGF Signaling | RAC1; FGFR1; MET; MAPKAPK2; MAPK1; PTPN11; AKT2; PIK3CA; CREB1; PIK3CB; PIK3C3; MAPK8; MAPK3; MAPK13; PTPN6; PIK3C2A; MAPK14; RAF1; AKT1; PIK3R1; STAT3; MAP2K1; FGFR4; CRKL; ATF4; AKT3; PRKCA; HGF |
| GM-CSF Signaling | LYN; ELK1; MAPK1; PTPN11; AKT2; PIK3CA; CAMK2A; STAT5B; PIK3CB; PIK3C3; GNB2L1; BCL2L1; MAPK3; ETS1; KRAS; RUNX1; PIM1; PIK3C2A; RAF1; MAP2K2; AKT1; JAK2; PIK3R1; STAT3; MAP2K1; CCND1; AKT3; STAT1 |
| Amyotrophic Lateral Sclerosis Signaling | BID; IGF1; RAC1; BIRC4; PGF; CAPNS1; CAPN2; PIK3CA; BCL2; PIK3CB; PIK3C3; BCL2L1; CAPN1; PIK3C2A; TP53; CASP9; PIK3R1; RAB5A; CASP1; APAF1; VEGFA; BIRC2; BAX; AKT3; CASP3; BIRC3 |
| JAK/Stat Signaling | PTPN1; MAPK1; PTPN11; AKT2; PIK3CA; STAT5B; PIK3CB; PIK3C3; MAPK3; KRAS; SOCS1; STAT5A; PTPN6; PIK3C2A; RAF1; CDKN1A; MAP2K2; JAK1; AKT1; JAK2; PIK3R1; STAT3; MAP2K1; FRAP1; AKT3; STAT1 |
| Nicotinate and Nicotinamide Metabolism | PRKCE; IRAK1; PRKAA2; EIF2AK2; GRK6; MAPK1; PLK1; AKT2; CDK8; MAPK8; MAPK3; PRKCD; PRKAA1; PBEF1; MAPK9; CDK2; PIM1; DYRK1A; MAP2K2; MAP2K1; PAK3; NT5E; TTK; CSNK1A1; BRAF; SGK |
| Chemokine Signaling | CXCR4; ROCK2; MAPK1; PTK2; FOS; CFL1; GNAQ; CAMK2A; CXCL12; MAPK8; MAPK3; KRAS; MAPK13; RHOA; CCR3; SRC; PPP1CC; MAPK14; NOX1; RAF1; MAP2K2; MAP2K1; JUN; CCL2; PRKCA |

TABLE C-continued

| CELLULAR FUNCTION | GENES |
|---|---|
| IL-2 Signaling | ELK1; MAPK1; PTPN11; AKT2; PIK3CA; SYK; FOS; STAT5B; PIK3CB; PIK3C3; MAPK8; MAPK3; KRAS; SOCS1; STAT5A; PIK3C2A; LCK; RAF1; MAP2K2; JAK1; AKT1; PIK3R1; MAP2K1; JUN; AKT3 |
| Synaptic Long Term Depression | PRKCE; IGF1; PRKCZ; PRDX6; LYN; MAPK1; GNAS; PRKCI; GNAQ; PPP2R1A; IGF1R; PRKD1; MAPK3; KRAS; GRN; PRKCD; NOS3; NOS2A; PPP2CA; YWHAZ; RAF1; MAP2K2; PPP2R5C; MAP2K1; PRKCA |
| Estrogen Receptor Signaling | TAF4B; EP300; CARM1; PCAF; MAPK1; NCOR2; SMARCA4; MAPK3; NRIP1; KRAS; SRC; NR3C1; HDAC3; PPARGC1A; RBM9; NCOA3; RAF1; CREBBP; MAP2K2; NCOA2; MAP2K1; PRKDC; ESR1; ESR2 |
| Protein Ubiquitination Pathway | TRAF6; SMURF1; BIRC4; BRCA1; UCHL1; NEDD4; CBL; UBE2I; BTRC; HSPA5; USP7; USP10; FBW7; USP9X; STUB1; USP22; B2M; BIRC2; PARK2; USP8; USP1; VHL; HSP90AA1; BIRC3 |
| IL-10 Signaling | TRAF6; CCR1; ELK1; IKBKB; SP1; FOS; NFKB2; MAP3K14; MAPK8; MAPK13; RELA; MAPK14; TNF; IKBKG; RELB; MAP3K7; JAK1; CHUK; STAT3; NFKB1; JUN; IL1R1; IL6 |
| VDR/RXR Activation | PRKCE; EP300; PRKCZ; RXRA; GADD45A; HES1; NCOR2; SP1; PRKCI; CDKN1B; PRKD1; PRKCD; RUNX2; KLF4; YY1; NCOA3; CDKN1A; NCOA2; SPP1; LRP5; CEBPB; FOXO1; PRKCA |
| TGF-beta Signaling | EP300; SMAD2; SMURF1; MAPK1; SMAD3; SMAD1; FOS; MAPK8; MAPK3; KRAS; MAPK9; RUNX2; SERPINE1; RAF1; MAP3K7; CREBBP; MAP2K2; MAP2K1; TGFBR1; SMAD4; JUN; SMAD5 |
| Toll-like Receptor Signaling | IRAK1; EIF2AK2; MYD88; TRAF6; PPARA; ELK1; IKBKB; FOS; NFKB2; MAP3K14; MAPK8; MAPK13; RELA; TLR4; MAPK14; IKBKG; RELB; MAP3K7; CHUK; NFKB1; TLR2; JUN |
| p38 MAPK Signaling | HSPB1; IRAK1; TRAF6; MAPKAPK2; ELK1; FADD; FAS; CREB1; DDIT3; RPS6KA4; DAXX; MAPK13; TRAF2; MAPK14; TNF; MAP3K7; TGFBR1; MYC; ATF4; IL1R1; SRF; STAT1 |
| Neurotrophin/TRK Signaling | NTRK2; MAPK1; PTPN11; PIK3CA; CREB1; FOS; PIK3CB; PIK3C3; MAPK8; MAPK3; KRAS; PIK3C2A; RAF1; MAP2K2; AKT1; PIK3R1; PDPK1; MAP2K1; CDC42; JUN; ATF4 |
| FXR/RXR Activation | INS; PPARA; FASN; RXRA; AKT2; SDC1; MAPK8; APOB; MAPK10; PPARG; MTTP; MAPK9; PPARGC1A; TNF; CREBBP; AKT1; SREBF1; FGFR4; AKT3; FOXO1 |
| Synaptic Long Term Potentiation | PRKCE; RAP1A; EP300; PRKCZ; MAPK1; CREB1; PRKCI; GNAQ; CAM1K2A; PRKD1; MAPK3; KRAS; PRKCD; PPP1CC; RAF1; CREBBP; MAP2K2; MAP2K1; ATF4; PRKCA |
| Calcium Signaling | RAP1A; EP300; HDAC4; MAPK1; HDAC5; CREB1; CAMK2A; MYH9; MAPK3; HDAC2; HDAC7A; HDAC11; HDAC9; HDAC3; CREBBP; CALR; CAMKK2; ATF4; HDAC6 |
| EGF Signaling | ELK1; MAPK1; EGFR; PIK3CA; FOS; PIK3CB; PIK3C3; MAPK8; MAPK3; PIK3C2A, RAF1; JAK1; PIK3R1; STAT3; MAP2K1; JUN; PRKCA; SRF; STAT1 |
| Hypoxia Signaling in the Cardiovascular System | EDN1; PTEN; EP300; NQO1; UBE2I; CREB1; ARNT; HIF1A; SLC2A4; NOS3; TP53; LDHA; AKT1; ATM; VEGFA; JUN; ATF4; VHL; HSP90AA1 |
| LPS/IL-1 Mediated Inhibition of RXR Function | IRAK1; MYD88; TRAF6; PPARA; RXRA; ABCA1; MAPK8; ALDH1A1; GSTP1; MAPK9; ABCB1; TRAF2; TLR4; TNF; MAP3K7; NR1H2; SREBF1; JUN; IL1R1 |
| LXR/RXR Activation | FASN; RXRA; NCOR2; ABCA1; NFKB2; IRF3; RELA; NOS2A; TLR4; TNF; RELB; LDLR; NR1H2; NFKB1; SREBF1; IL1R1; CCL2; IL6; MMP9 |
| Amyloid Processing | PRKCE; CSNK1E; MAPK1; CAPNS1; AKT2; CAPN2; CAPN1; MAPK3; MAPK13; MAPT; MAPK14; AKT1; PSEN1; CSNK1A1; GSK3B; AKT3; APP |
| IL-4 Signaling | AKT2; PIK3CA; PIK3CB; PIK3C3; IRS1; KRAS; SOCS1; PTPN6; NR3C1; PIK3C2A; JAK1; AKT1; JAK2; PIK3R1; FRAP1; AKT3; RPS6KB1 |
| Cell Cycle: G2/M DNA Damage Checkpoint Regulation | EP300; PCAF; BRCA1; GADD45A; PLK1; BTRC; CHEK1; ATR; CHEK2; YWHAZ; TP53; CDKN1A; PRKDC; ATM; SFN; CDKN2A |
| Nitric Oxide Signaling in the | KDR; FLT1; PGF; AKT2; PIK3CA; PIK3CB; PIK3C3; |

TABLE C-continued

| CELLULAR FUNCTION | GENES |
|---|---|
| Cardiovascular System | CAV1; PRKCD; NOS3; PIK3C2A; AKT1; PIK3R1; VEGFA; AKT3; HSP90AA1 |
| Purine Metabolism | NME2; SMARCA4; MYH9; RRM2; ADAR; EIF2AK4; PKM2; ENTPD1; RAD51; RRM2B; TJP2; RAD51C; NT5E; POLD1; NME1 |
| cAMP-mediated Signaling | RAP1A; MAPK1; GNAS; CREB1; CAMK2A; MAPK3; SRC; RAF1; MAP2K2; STAT3; MAP2K1; BRAF; ATF4 |
| Mitochondrial Dysfunction | SOD2; MAPK8; CASP8; MAPK10; MAPK9; CASP9; PARK7; PSEN1; PARK2; APP; CASP3 |
| Notch Signaling | HES1; JAG1; NUMB; NOTCH4; ADAM17; NOTCH2; PSEN1; NOTCH3; NOTCH1; DLL4 |
| Endoplasmic Reticulum Stress Pathway | HSPA5; MAPK8; XBP1; TRAF2; ATF6; CASP9; ATF4; EIF2AK3; CASP3 |
| Pyrimidine Metabolism | NME2; AICDA; RRM2; EIF2AK4; ENTPD1; RRM2B; NT5E; POLD1; NME1 |
| Parkinson's Signaling | UCHL1; MAPK8; MAPK13; MAPK14; CASP9; PARK7; PARK2; CASP3 |
| Cardiac & Beta Adrenergic Signaling | GNAS; GNAQ; PPP2R1A; GNB2L1; PPP2CA; PPP1CC; PPP2R5C |
| Glycolysis/Gluconeogenesis | HK2; GCK; GPI; ALDH1A1; PKM2; LDHA; HK1 |
| Interferon Signaling | IRF1; SOCS1; JAK1; JAK2; IFITM1; STAT1; IFIT3 |
| Sonic Hedgehog Signaling | ARRB2; SMO; GLI2; DYRK1A; GLI1; GSK3B; DYRK1B |
| Glycerophospholipid Metabolism | PLD1; GRN; GPAM; YWHAZ; SPHK1; SPHK2 |
| Phospholipid Degradation | PRDX6; PLD1; GRN; YWHAZ; SPHK1; SPHK2 |
| Tryptophan Metabolism | SIAH2; PRMT5; NEDD4; ALDH1A1; CYP1B1; SIAH1 |
| Lysine Degradation | SUV39H1; EHMT2; NSD1; SETD7; PPP2R5C |
| Nucleotide Excision Repair Pathway | ERCC5; ERCC4; XPA; XPC; ERCC1 |
| Starch and Sucrose Metabolism | UCHL1; HK2; GCK; GPI; HK1 |
| Aminosugars Metabolism | NQO1; HK2; GCK; HK1 |
| Arachidonic Acid Metabolism | PRDX6; GRN; YWHAZ; CYP1B1 |
| Circadian Rhythm Signaling | CSNK1E; CREB1; ATF4; NR1D1 |
| Coagulation System | BDKRB1; F2R; SERPINE1; F3 |
| Dopamine Receptor Signaling | PPP2R1A; PPP2CA; PPP1CC; PPP2R5C |
| Glutathione Metabolism | IDH2; GSTP1; ANPEP; IDH1 |
| Glycerolipid Metabolism | ALDH1A1; GPAM; SPHK1; SPHK2 |
| Linoleic Acid Metabolism | PRDX6; GRN; YWHAZ; CYP1B1 |
| Methionine Metabolism | DNMT1; DNWIT3B; AHCY; DNMT3A |
| Pyruvate Metabolism | GLO1; ALDH1A1; PKM2; LDHA |
| Arginine and Proline Metabolism | ALDH1A1; NOS3; NOS2A |
| Eicosanoid Signaling | PRDX6; GRN; YWHAZ |
| Fructose and Mannose Metabolism | HK2; GCK; HK1 |
| Galactose Metabolism | HK2; GCK; HK1 |
| Stilbene, Coumarine and Lignin Biosynthesis | PRDX6; PRDX1; TYR |
| Antigen Presentation Pathway | CALR; B2M |
| Biosynthesis of Steroids | NQO1; DHCR7 |
| Butanoate Metabolism | ALDH1A1; NLGN1 |
| Citrate Cycle | IDH2; IDH1 |
| Fatty Acid Metabolism | ALDH1A1; CYP1B1 |
| Glycerophospholipid Metabolism | PRDX6; CHKA |
| Histidine Metabolism | PRMT5; ALDH1A1 |
| Inositol Metabolism | ERO1L; APEX1 |
| Metabolism of Xenobiotics by Cytochrome p450 | GSTP1; CYP1B1 |
| Methane Metabolism | PRDX6; PRDX1 |
| Phenylalanine Metabolism | PRDX6; PRDX1 |

TABLE C-continued

| CELLULAR FUNCTION | GENES |
|---|---|
| Propanoate Metabolism | ALDH1A1; LDHA |
| Selenoamino Acid Metabolism | PRMT5; AHCY |
| Sphingolipid Metabolism | SPHK1; SPHK2 |
| Aminophosphonate Metabolism | PRMT5 |
| Androgen and Estrogen Metabolism | PRMT5 |
| Ascorbate and Aldarate Metabolism | ALDH1A1 |
| Bile Acid Biosynthesis | ALDH1A1 |
| Cysteine Metabolism | LDHA |
| Fatty Acid Biosynthesis | FASN |
| Glutamate Receptor Signaling | GNB2L1 |
| NRF2-mediated Oxidative Stress Response | PRDX1 |
| Pentose Phosphate Pathway | GPI |
| Pentose and Glucuronate Interconversions | UCHL1 |
| Retinol Metabolism | ALDH1A1 |
| Riboflavin Metabolism | TYR |
| Tyrosine Metabolism | PRMT5, TYR |
| Ubiquinone Biosynthesis | PRMT5 |
| Valine, Leucine and Isoleucine Degradation | ALDH1A1 |
| Glycine, Serine and Threonine Metabolism | CHKA |
| Lysine Degradation | ALDH1A1 |
| Pain/Taste | TRPM5; TRPA1 |
| Pain | TRPM7; TRPC5; TRPC6; TRPC1; Cnr1; cnr2; Grk2; Trpa1; Pomc; Cgrp; Crf; Pka; Era; Nr2b; TRPM5; Prkaca; Prkacb; Prkar1a; Prkar2a |
| Mitochondrial Function | AIF; CytC; SMAC (Diablo); Aifm-1; Aifm-2 |
| Developmental Neurology | BMP-4; Chordin (Chrd); Noggin (Nog); WNT (Wnt2; Wnt2b; Wnt3a; Wnt4; Wnt5a; Wnt6; Wnt7b; Wnt8b; Wnt9a; Wnt9b; Wnt10a; Wnt10b; Wnt16); beta-catenin; Dkk-1; Frizzled related proteins; Otx-2; Gbx2; FGF-8; Reelin; Dab1; unc-86 (Pou4f1 or Brn3a); Numb; Reln |

Embodiments of the invention also relate to methods and compositions related to knocking out genes, amplifying genes and repairing particular mutations associated with DNA repeat instability and neurological disorders (Robert D. Wells, Tetsuo Ashizawa, Genetic Instabilities and Neurological Diseases, Second Edition, Academic Press, Oct. 13, 2011—Medical). Specific aspects of tandem repeat sequences have been found to be responsible for more than twenty human diseases (New insights into repeat instability: role of RNA•DNA hybrids. McIvor E I, Polak U, Napierala M. RNA Biol. 2010 September-October; 7(5):551-8). The CRISPR-Cas system may be harnessed to correct these defects of genomic instability.

A further aspect of the invention relates to utilizing the CRISPR-Cas system for correcting defects in the EMP2A and EMP2B genes that have been identified to be associated with Lafora disease. Lafora disease is an autosomal recessive condition which is characterized by progressive myoclonus epilepsy which may start as epileptic seizures in adolescence. A few cases of the disease may be caused by mutations in genes yet to be identified. The disease causes seizures, muscle spasms, difficulty walking, dementia, and eventually death. There is currently no therapy that has proven effective against disease progression. Other genetic abnormalities associated with epilepsy may also be targeted by the CRISPR-Cas system and the underlying genetics is further described in Genetics of Epilepsy and Genetic Epilepsies, edited by Giuliano Avanzini, Jeffrey L. Noebels, Mariani Foundation Paediatric Neurology:20; 2009).

In yet another aspect of the invention, the CRISPR-Cas system may be used to correct ocular defects that arise from several genetic mutations further described in Genetic Diseases of the Eye, Second Edition, edited by Elias I. Traboulsi, Oxford University Press, 2012.

Several further aspects of the invention relate to correcting defects associated with a wide range of genetic diseases which are further described on the website of the National Institutes of Health under the topic subsection Genetic Disorders (website at health.nih.gov/topic/GeneticDisorders). The genetic brain diseases may include but are not limited to Adrenoleukodystrophy, Agenesis of the Corpus Callosum, Aicardi Syndrome, Alpers' Disease, Alzheimer's Disease, Barth Syndrome, Batten Disease, CADASIL, Cerebellar Degeneration, Fabry's Disease, Gerstmann-Straussler-Scheinker Disease, Huntington's Disease and other Triplet Repeat Disorders, Leigh's Disease, Lesch-Nyhan Syndrome, Menkes Disease, Mitochondrial Myopathies and NINDS Colpocephaly. These diseases are further described on the website of the National Institutes of Health under the subsection Genetic Brain Disorders.

In some embodiments, the condition may be neoplasia. In some embodiments, where the condition is neoplasia, the genes to be targeted are any of those listed in Table A (in this case PTEN asn so forth). In some embodiments, the condition may be Age-related Macular Degeneration. In some embodiments, the condition may be a Schizophrenic Disorder. In some embodiments, the condition may be a Trinucleotide Repeat Disorder. In some embodiments, the condition may be Fragile X Syndrome. In some embodiments, the condition may be a Secretase Related Disorder. In some embodiments, the condition may be a Prion-related disorder. In some embodiments, the condition may be ALS. In some embodiments, the condition may be a drug addiction. In some embodiments, the condition may be Autism. In some embodiments, the condition may be Alzheimer's Disease. In some embodiments, the condition may be inflammation. In some embodiments, the condition may be Parkinson's Disease.

Examples of proteins associated with Parkinson's disease include but are not limited to α-synuclein, DJ-1, LRRK2, PINK1, Parkin, UCHL1, Synphilin-1, and NURR1. Examples of addiction-related proteins may include ABAT for example.

Examples of inflammation-related proteins may include the monocyte chemoattractant protein-1 (MCP1) encoded by the Ccr2 gene, the C-C chemokine receptor type 5 (CCR5) encoded by the Ccr5 gene, the IgG receptor IIB (FCGR2b, also termed CD32) encoded by the Fcgr2b gene, or the Fc epsilon Rig (FCER1g) protein encoded by the Fcer1g gene, for example.

Examples of cardiovascular diseases associated proteins may include IL1B (interleukin 1, beta), XDH (xanthine dehydrogenase), TP53 (tumor protein p53), PTGIS (prostaglandin 12 (prostacyclin) synthase), MB (myoglobin), IL4 (interleukin 4), ANGPT1 (angiopoietin 1), ABCG8 (ATP-binding cassette, sub-family G (WHITE), member 8), or CTSK (cathepsin K), for example.

Examples of Alzheimer's disease associated proteins may include the very low density lipoprotein receptor protein (VLDLR) encoded by the VLDLR gene, the ubiquitin-like modifier activating enzyme 1 (UBA1) encoded by the UBA1 gene, or the NEDD8-activating enzyme E1 catalytic subunit protein (UBE1C) encoded by the UBA3 gene, for example.

Examples of proteins associated Autism Spectrum Disorder may include the benzodiazapine receptor (peripheral) associated protein 1 (BZRAP1) encoded by the BZRAP1 gene, the AF4/FMR2 family member 2 protein (AFF2) encoded by the AFF2 gene (also termed MFR2), the fragile X mental retardation autosomal homolog 1 protein (FXR1) encoded by the FXR1 gene, or the fragile X mental retardation autosomal homolog 2 protein (FXR2) encoded by the FXR2 gene, for example.

Examples of proteins associated Macular Degeneration may include the ATP-binding cassette, sub-family A (ABC1) member 4 protein (ABCA4) encoded by the ABCR gene, the apolipoprotein E protein (APOE) encoded by the APOE gene, or the chemokine (C-C motif) Ligand 2 protein (CCL2) encoded by the CCL2 gene, for example.

Examples of proteins associated Schizophrenia may include NRG1, ErbB4, CPLX1, TPH1, TPH2, NRXN1, GSK3A, BDNF, DISC1, GSK3B, and combinations thereof.

Examples of proteins involved in tumor suppression may include ATM (ataxia telangiectasia mutated), ATR (ataxia telangiectasia and Rad3 related), EGFR (epidermal growth factor receptor), ERBB2 (v-erb-b2 erythroblastic leukemia viral oncogene homolog 2), ERBB3 (v-erb-b2 erythroblastic leukemia viral oncogene homolog 3), ERBB4 (v-erb-b2 erythroblastic leukemia viral oncogene homolog 4), Notch 1, Notch2, Notch 3, or Notch 4, for example.

Examples of proteins associated with a secretase disorder may include PSENEN (presenilin enhancer 2 homolog (*C. elegans*)), CTSB (cathepsin B), PSEN1 (presenilin 1), APP (amyloid beta (A4) precursor protein), APH1B (anterior pharynx defective 1 homolog B (*C. elegans*)), PSEN2 (presenilin 2 (Alzheimer disease 4)), or BACE1 (beta-site APP-cleaving enzyme 1), for example.

Examples of proteins associated with Amyotrophic Lateral Sclerosis may include SOD1 (superoxide dismutase 1), ALS2 (amyotrophic lateral sclerosis 2), FUS (fused in sarcoma), TARDBP (TAR DNA binding protein), VAGFA (vascular endothelial growth factor A), VAGFB (vascular endothelial growth factor B), and VAGFC (vascular endothelial growth factor C), and any combination thereof.

Examples of proteins associated with prion diseases may include SOD1 (superoxide dismutase 1), ALS2 (amyotrophic lateral sclerosis 2), FUS (fused in sarcoma), TARDBP (TAR DNA binding protein), VAGFA (vascular endothelial growth factor A), VAGFB (vascular endothelial growth factor B), and VAGFC (vascular endothelial growth factor C), and any combination thereof.

Examples of proteins related to neurodegenerative conditions in prion disorders may include A2M (Alpha-2-Macroglobulin), AATF (Apoptosis antagonizing transcription factor), ACPP (Acid phosphatase prostate), ACTA2 (Actin alpha 2 smooth muscle aorta), ADAM22 (ADAM metallopeptidase domain), ADORA3 (Adenosine A3 receptor), or ADRA1D (Alpha-1D adrenergic receptor for Alpha-1D adrenoreceptor), for example.

Examples of proteins associated with Immunodeficiency may include A2M [alpha-2-macroglobulin]; AANAT [arylalkylamine N-acetyltransferase]; ABCA1 [ATP-binding cassette, sub-family A (ABC1), member 1]; ABCA2 [ATP-binding cassette, sub-family A (ABC1), member 2]; or ABCA3 [ATP-binding cassette, sub-family A (ABC1), member 3]; for example.

Examples of proteins associated with Trinucleotide Repeat Disorders include AR (androgen receptor), FMR1 (fragile X mental retardation 1), HTT (huntingtin), or DMPK (dystrophia myotonica-protein kinase), FXN (frataxin), ATXN2 (ataxin 2), for example.

Examples of proteins associated with Neurotransmission Disorders include SST (somatostatin), NOS1 (nitric oxide synthase 1 (neuronal)), ADRA2A (adrenergic, alpha-2A-, receptor), ADRA2C (adrenergic, alpha-2C-, receptor), TACR1 (tachykinin receptor 1), or HTR2c (5-hydroxytryptamine (serotonin) receptor 2C), for example.

Examples of neurodevelopmental-associated sequences include A2BP1 [ataxin 2-binding protein 1], AADAT [aminoadipate aminotransferase], AANAT [arylalkylamine N-acetyltransferase], ABAT [4-aminobutyrate aminotransferase], ABCA1 [ATP-binding cassette, sub-family A (ABC1), member 1], or ABCA13 [ATP-binding cassette, sub-family A (ABC1), member 13], for example.

Further examples of preferred conditions treatable with the present system include may be selected from: Aicardi-Goutieres Syndrome; Alexander Disease; Allan-Herndon-Dudley Syndrome; POLG-Related Disorders; Alpha-Mannosidosis (Type II and III); Alström Syndrome; Angelman; Syndrome; Ataxia-Telangiectasia; Neuronal Ceroid-Lipofuscinoses; Beta-Thalassemia; Bilateral Optic Atrophy and (Infantile) Optic Atrophy Type 1; Retinoblastoma (bilateral); Canavan Disease; Cerebrooculofacioskeletal Syndrome 1 [COFS1]; Cerebrotendinous Xanthomatosis; Cornelia de Lange Syndrome; MAPT-Related Disorders; Genetic Prion Diseases; Dravet Syndrome; Early-Onset Familial Alzheimer Disease; Friedreich Ataxia [FRDA]; Fryns Syndrome; Fucosidosis; Fukuyama Congenital Muscular Dystrophy; Galactosialidosis; Gaucher Disease; Organic Acidemias; Hemophagocytic Lymphohistiocytosis; Hutchinson-Gilford Progeria Syndrome; Mucolipidosis II; Infantile Free Sialic Acid Storage Disease; PLA2G6-Associated Neurodegeneration; Jervell and Lange-Nielsen Syndrome; Junctional Epidermolysis Bullosa; Huntington Disease; Krabbe Disease (Infantile); Mitochondrial DNA-Associated Leigh Syndrome and NARP; Lesch-Nyhan Syndrome; LIS1-Associated Lissencephaly; Lowe Syndrome; Maple Syrup Urine Disease; MECP2 Duplication Syndrome; ATP7A-Related Copper Transport Disorders; LAMA2-Related Muscular Dystrophy; Arylsulfatase A Deficiency; Mucopolysaccharidosis Types I, II or III; Peroxisome Biogenesis Disorders, Zellweger Syndrome Spectrum; Neurodegeneration with Brain Iron Accumulation Disorders; Acid Sphingomyelinase Deficiency; Niemann-Pick Disease Type C; Glycine Encephalopathy; ARX-Related Disorders; Urea Cycle Disorders; COL1A1/2-Related Osteogenesis Imperfecta; Mitochondrial DNA Deletion Syndromes; PLP1-Related Disorders; Perry Syndrome; Phelan-McDermid Syndrome; Glycogen Storage Disease Type II (Pompe Disease) (Infantile); MAPT-Related Disorders; MECP2-Related Disorders; Rhizomelic Chondrodysplasia *Punctata* Type 1; Roberts Syndrome; Sandhoff Disease; Schindler Disease—Type 1; Adenosine Deaminase Deficiency; Smith-Lemli-Opitz Syndrome; Spinal Muscular Atrophy; Infantile-Onset Spinocerebellar Ataxia; Hexosaminidase A Deficiency; Thanatophoric Dysplasia Type 1; Collagen Type VI-Related Disorders; Usher Syndrome Type I; Congenital Muscular Dystrophy; Wolf-Hirschhorn Syndrome; Lysosomal Acid Lipase Deficiency; and Xeroderma Pigmentosum.

As will be apparent, it is envisaged that the present system can be used to target any polynucleotide sequence of interest. Some examples of conditions or diseases that might be usefully treated using the present system are included in the Tables above and examples of genes currently associated with those conditions are also provided there. However, the genes exemplified are not exhaustive.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1: CRISPR Complex Activity in the Nucleus of a Eukaryotic Cell

Figure 2A:
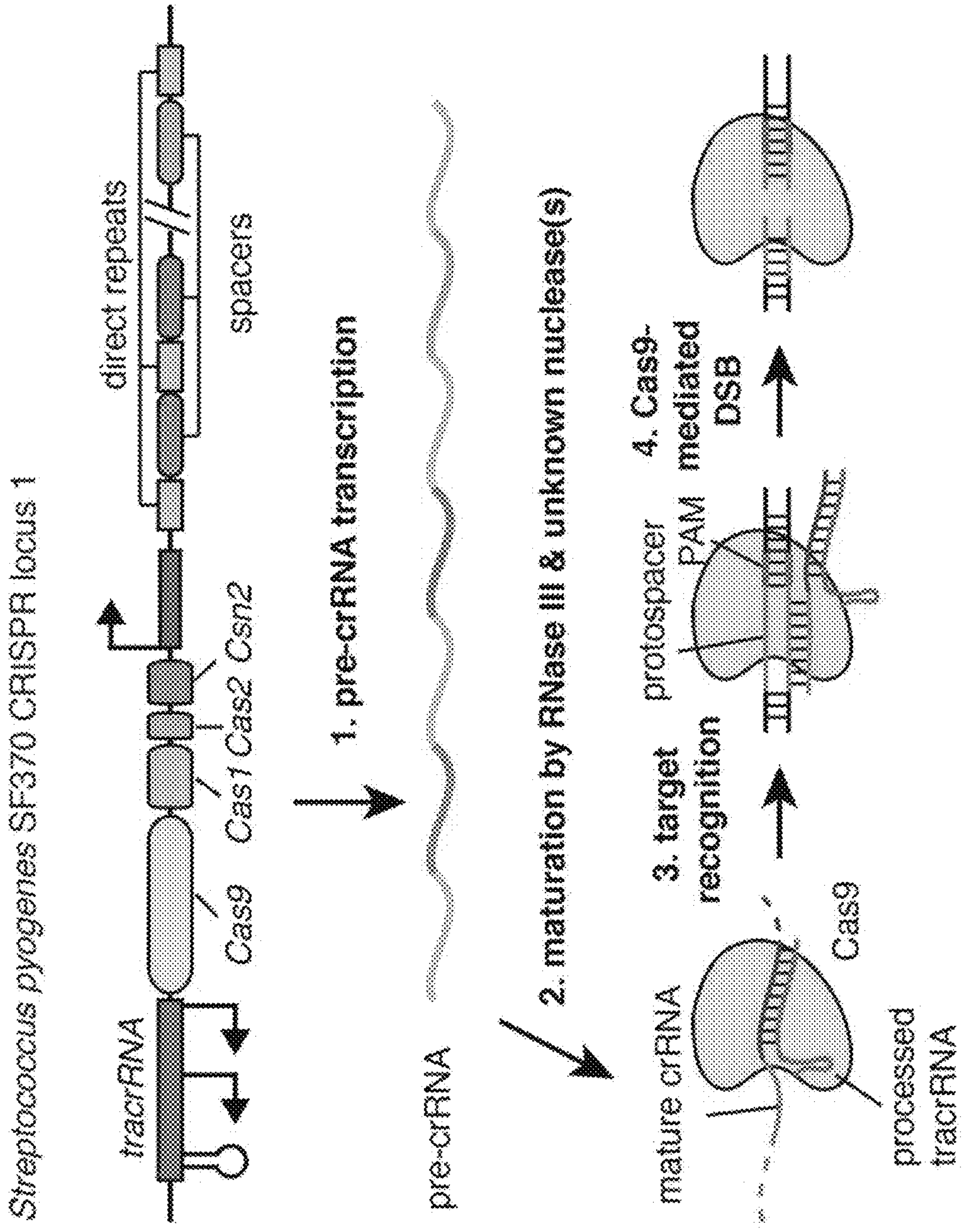
Figure 2B:
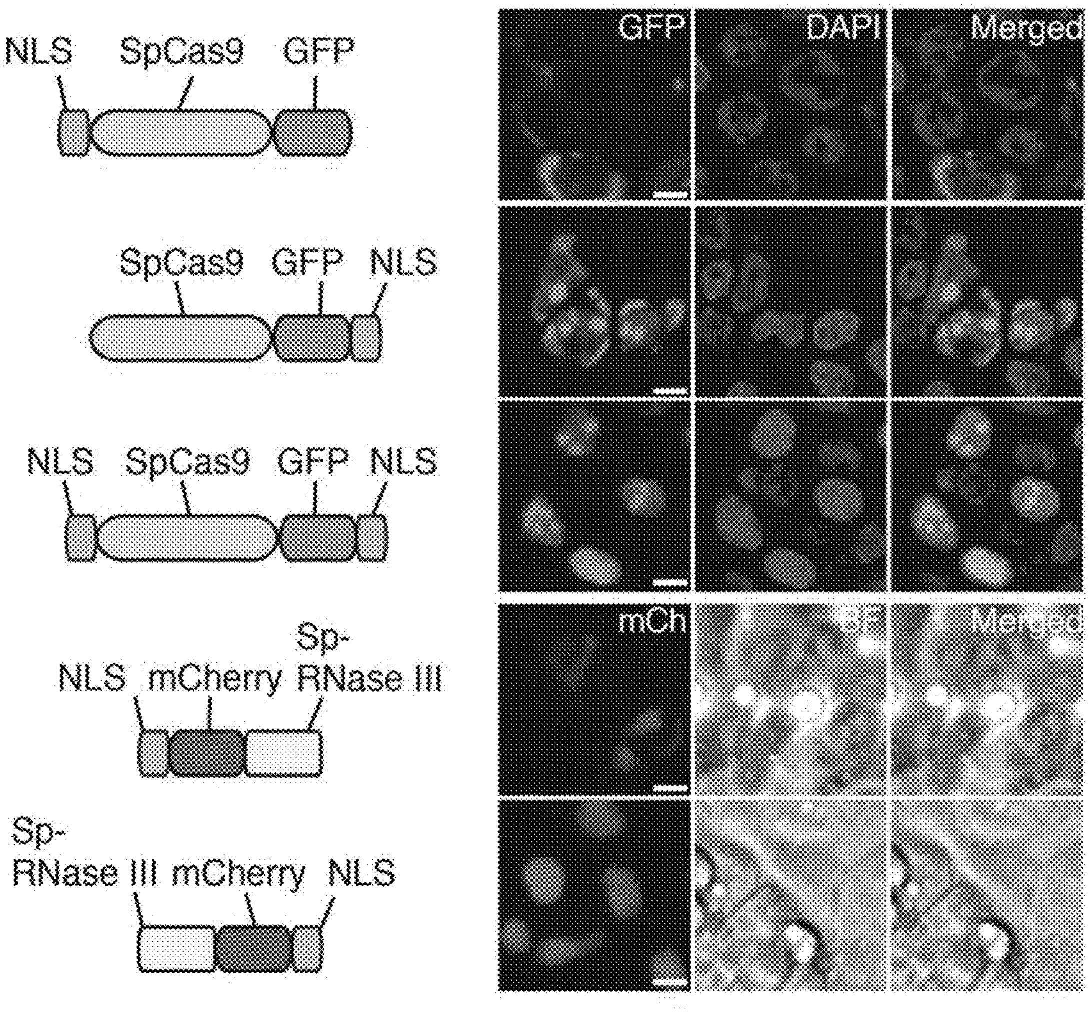

An example type II CRISPR system is the type II CRISPR locus from *Streptococcus pyogenes* SF370, which contains a cluster of four genes Cas9, Cas1, Cas2, and Csn1, as well as two non-coding RNA elements, tracrRNA and a characteristic array of repetitive sequences (direct repeats) interspaced by short stretches of non-repetitive sequences (spacers, about 30 bp each). In this system, targeted DNA double-strand break (DSB) is generated in four sequential steps (FIG. 2A). First, two non-coding RNAs, the pre-crRNA array and tracrRNA, are transcribed from the CRISPR locus. Second, tracrRNA hybridizes to the direct repeats of pre-crRNA, which is then processed into mature crRNAs containing individual spacer sequences. Third, the mature crRNA:tracrRNA complex directs Cas9 to the DNA target consisting of the protospacer and the corresponding PAM via heteroduplex formation between the spacer region of the crRNA and the protospacer DNA. Finally, Cas9 mediates cleavage of target DNA upstream of PAM to create a DSB within the protospacer (FIG. 2A). This example describes an example process for adapting this RNA-programmable nuclease system to direct CRISPR complex activity in the nuclei of eukaryotic cells.

Cell Culture and Transfection

Human embryonic kidney (HEK) cell line HEK 293FT (LIFE TECHNOLOGIES®) was maintained in Dulbecco's modified Eagle's Medium (DMEM) supplemented with 10% fetal bovine serum (HyClone), 2 mM GlutaMAX (LIFE TECHNOLOGIES®), 100U/mL penicillin, and 100 μg/mL streptomycin at 37° C. with 5% $CO_2$ incubation. Mouse neuro2A (N2A) cell line (ATCC) was maintained with DMEM supplemented with 5% fetal bovine serum (HyClone), 2 mM GlutaMAX (LIFE TECHNOLOGIES®), 100U/mL penicillin, and 100 μg/mL streptomycin at 37° C. with 5% $CO_2$.

HEK 293FT or N2A cells were seeded into 24-well plates (CORNING®) one day prior to transfection at a density of 200,000 cells per well. Cells were transfected using LIPOFECTAMINE® 2000 (LIFE TECHNOLOGIES®) following the manufacturer's recommended protocol. For each well of a 24-well plate a total of 800 ng of plasmids were used.

Surveyor Assay and Sequencing Analysis for Genome Modification

HEK 293FT or N2A cells were transfected with plasmid DNA as described above. After transfection, the cells were incubated at 37° C. for 72 hours before genomic DNA extraction. Genomic DNA was extracted using the QuickExtract DNA extraction kit (Epicentre) following the manufacturer's protocol. Briefly, cells were resuspended in QuickExtract solution and incubated at 65° C. for 15 minutes and 98° C. for 10 minutes. Extracted genomic DNA was immediately processed or stored at −20° C.

Figure 7:
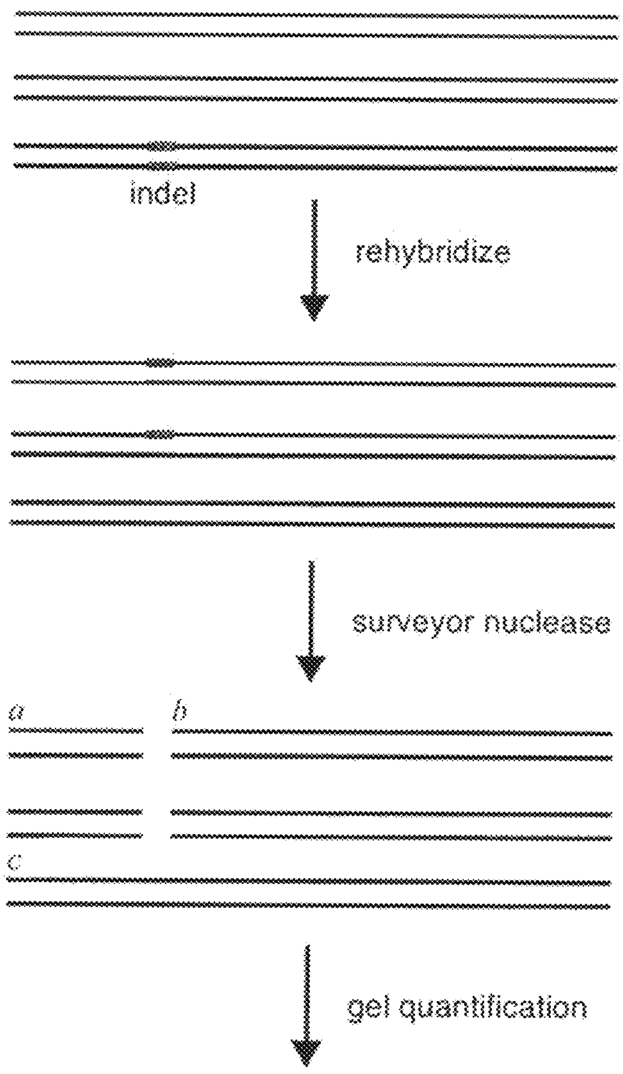
FIG. 7 shows a schematic of a surveyor nuclease assay for detection of double strand break-induced micro-insertions and micro-deletions.

The genomic region surrounding a CRISPR target site for each gene was PCR amplified, and products were purified using QIAQUICK® Spin Column (QIAGEN®) following manufacturer's protocol. A total of 400 ng of the purified PCR products were mixed with 2 μl 10× Taq polymerase PCR buffer (Enzymatics) and ultrapure water to a final volume of 20 μl, and subjected to a re-annealing process to enable heteroduplex formation: 95° C. for 10 min, 95° C. to 85° C. ramping at −2° C./s, 85° C. to 25° C. at −0.25° C./s, and 25° C. hold for 1 minute. After re-annealing, products were treated with Surveyor nuclease and Surveyor enhancer S (TRANSGENOMICS®) following the manufacturer's recommended protocol, and analyzed on 4-20% Novex TBE poly-acrylamide gels (LIFE TECHNOLOGIES®). Gels were stained with SYBR Gold DNA stain (LIFE TECHNOLOGIES®) for 30 minutes and imaged with a Gel Doc gel imaging system (Bio-rad). Quantification was based on relative band intensities, as a measure of the fraction of cleaved DNA. FIG. 7 provides a schematic illustration of this Surveyor assay.

Restriction Fragment Length Polymorphism Assay for Detection of Homologous Recombination.

HEK 293FT and N2A cells were transfected with plasmid DNA, and incubated at 37° C. for 72 hours before genomic DNA extraction as described above. The target genomic region was PCR amplified using primers outside the homology arms of the homologous recombination (HR) template. PCR products were separated on a 1% agarose gel and extracted with MinElute GelExtraction Kit (QIAGEN®). Purified products were digested with HindIII (Fermentas) and analyzed on a 6% Novex TBE poly-acrylamide gel (LIFE TECHNOLOGIES®).

RNA Secondary Structure Prediction and Analysis

RNA secondary structure prediction was performed using the online webserver RNAfold developed at Institute for Theoretical Chemistry at the University of Vienna, using the centroid structure prediction algorithm (see e.g. A. R. Gruber et al., 2008, Cell 106(1): 23-24; and PA Carr and GM Church, 2009, Nature Biotechnology 27(12): 1151-62).

RNA Purification

HEK 293FT cells were maintained and transfected as stated above. Cells were harvested by trypsinization followed by washing in phosphate buffered saline (PBS). Total cell RNA was extracted with TRI reagent (SigmaSIGMA®) following manufacturer's protocol. Extracted total RNA was quantified using Naonodrop (Thermo Scientific) and normalized to same concentration.

Northern Blot Analysis of crRNA and tracrRNA Expression in Mammalian Cells

RNAs were mixed with equal volumes of 2× loading buffer (Ambion), heated to 95° C. for 5 min, chilled on ice for 1 min, and then loaded onto 8% denaturing polyacrylamide gels (SequaGel, National Diagnostics) after pre-running the gel for at least 30 minutes. The samples were electrophoresed for 1.5 hours at 40 W limit. Afterwards, the RNA was transferred to Hybond N+ membrane (GE Healthcare) at 300 mA in a semi-dry transfer apparatus (Bio-rad) at room temperature for 1.5 hours. The RNA was crosslinked to the membrane using autocrosslink button on Stratagene UV Crosslinker the Stratalinker (Stratagene). The membrane was pre-hybridized in ULTRAhyb-Oligo Hybridization Buffer (Ambion) for 30 min with rotation at 42° C., and probes were then added and hybridized overnight. Probes were ordered from IDT and labeled with [gamma-$^{32}$P] ATP (Perkin Elmer) with T4 polynucleotide kinase (New England Biolabs). The membrane was washed once with pre-warmed (42° C.) 2×SSC, 0.5% SDS for 1 min followed by two 30 minute washes at 42° C. The membrane was exposed to a phosphor screen for one hour or overnight at room temperature and then scanned with a phosphorimager (Typhoon).

Bacterial CRISPR System Construction and Evaluation

Figure 6A:
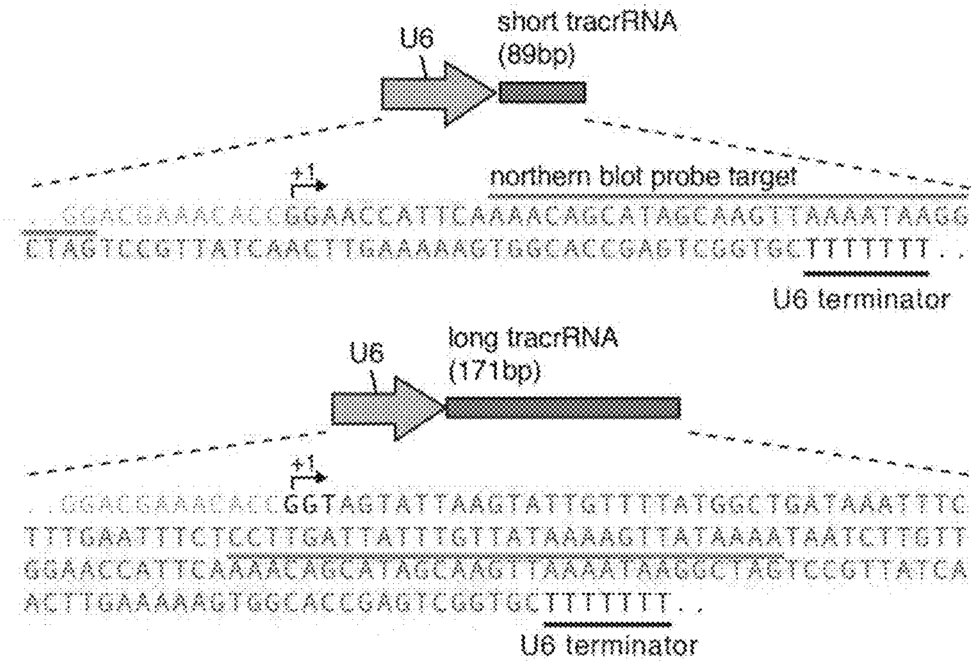
FIG. 6A-6C shows a comparison of different tracrRNA transcripts for Cas9-mediated gene targeting.
Figure 6B:
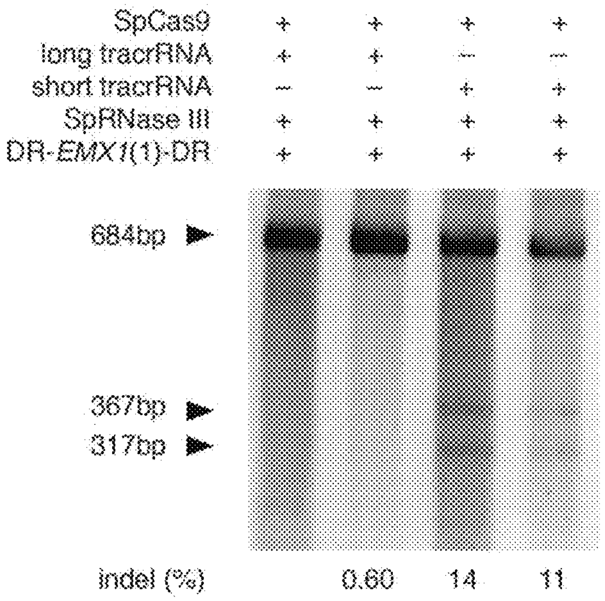
Figure 6C:
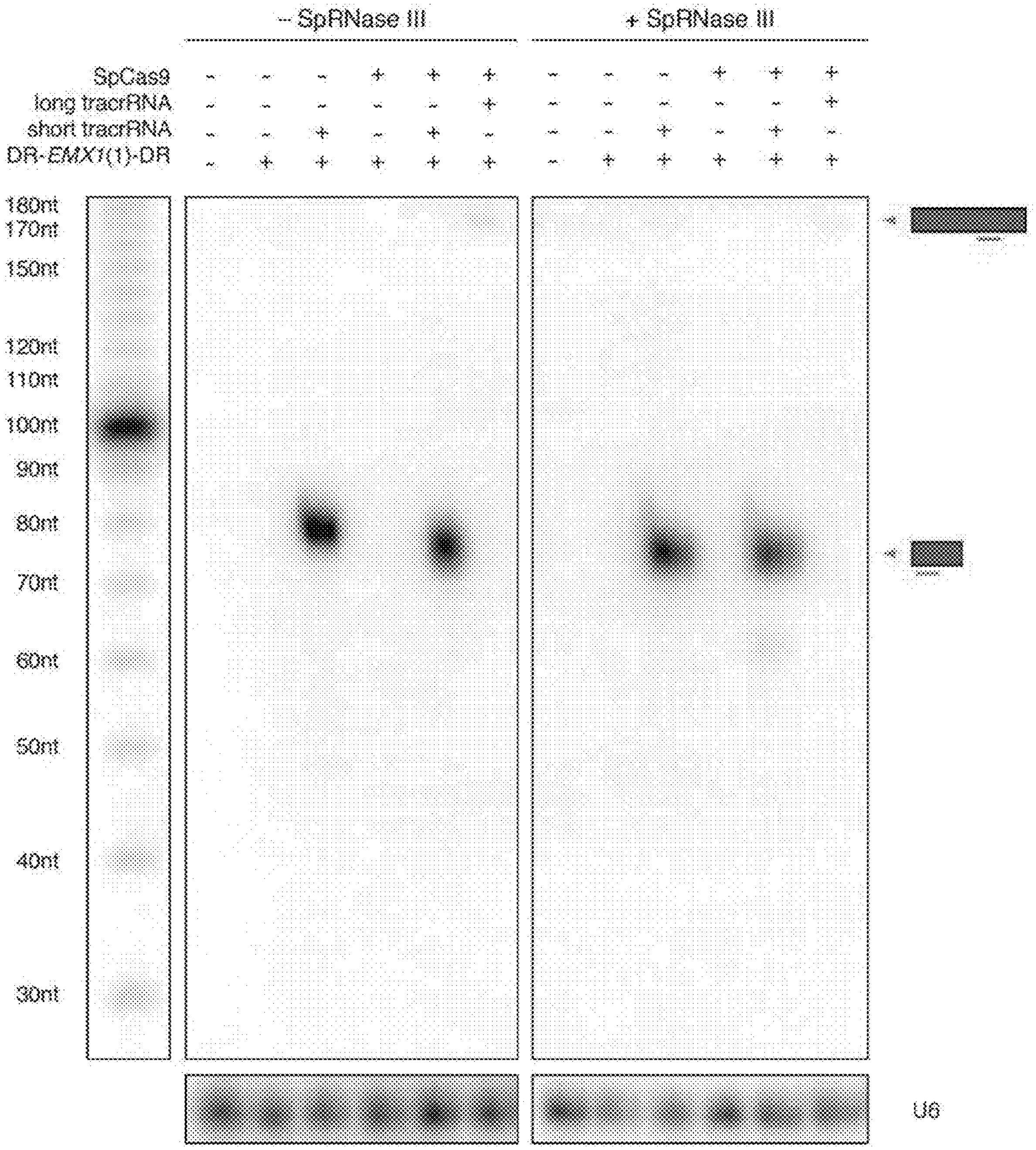

CRISPR locus elements, including tracrRNA, Cas9, and leader were PCR amplified from *Streptococcus pyogenes* SF370 genomic DNA with flanking homology arms for GIBSON® Assembly. Two BsaI type IIS sites were introduced in between two direct repeats to facilitate easy insertion of spacers (FIG. 8). PCR products were cloned into EcoRV-digested pACYC184 downstream of the tet promoter using GIBSON® Assembly Master Mix (NEB®). Other endogenous CRISPR system elements were omitted, with the exception of the last 50 bp of Csn2. Oligos (Integrated DNA Technology) encoding spacers with complimentary overhangs were cloned into the BsaI-digested vector pDC000 (NEB®) and then ligated with T7 ligase (Enzymatics) to generate pCRISPR plasmids. Challenge plasmids containing spacers with PAM expression in mammalian cells (expression constructs illustrated in FIG. 6A, with functionality as determined by results of the Surveyor assay shown in FIG. 6B). Transcription start sites are marked as +1, and transcription terminator and the sequence probed by northern blot are also indicated. Expression of processed tracrRNA was also confirmed by Northern blot. FIG. 6C shows results of a Northern blot analysis of total RNA extracted from 293FT cells transfected with U6 expression constructs carrying long or short tracrRNA, as well as SpCas9 and DR-EMX1(1)-DR. Left and right panels are from 293FT cells transfected without or with SpRNase III, respectively. U6 indicate loading control blotted with a probe targeting human U6 snRNA. Transfection of the short tracrRNA expression construct led to abundant levels of the processed form of tracrRNA (~75 bp). Very low amounts of long tracrRNA are detected on the Northern blot.

Figure 2C:
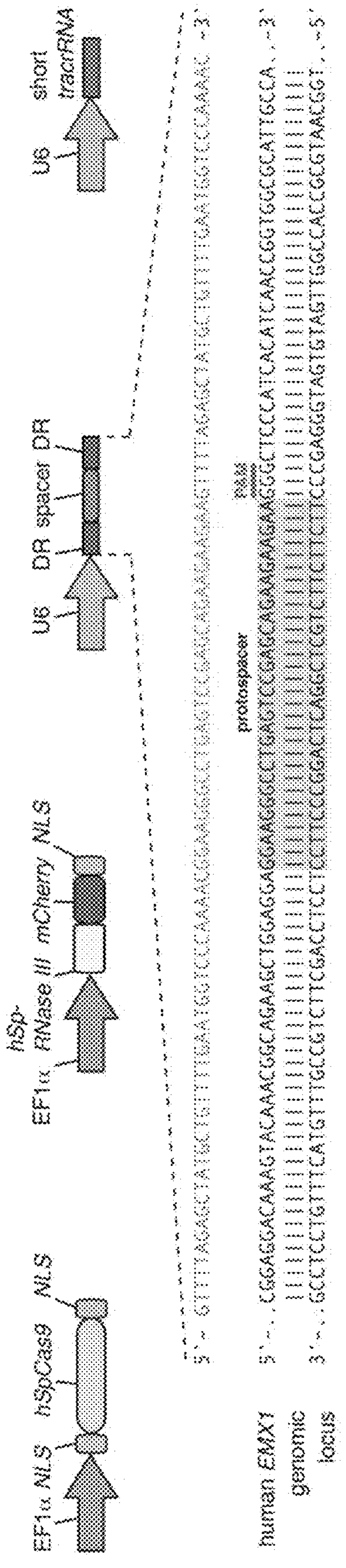

To promote precise transcriptional initiation, the RNA polymerase III-based U6 promoter was selected to drive the expression of tracrRNA (FIG. 2C). Similarly, a U6 promoter-based construct was developed to express a pre-crRNA array consisting of a single spacer flanked by two direct repeats (DRs, also encompassed by the term "tracr-mate sequences"; FIG. 2C). The initial spacer was designed to target a 33-base-pair (bp) target site (30-bp protospacer plus a 3-bp CRISPR motif (PAM) sequence satisfying the NGG recognition motif of Cas9) in the human EMX1 locus (FIG. 2C), a key gene in the development of the cerebral cortex.

Figure 2D:
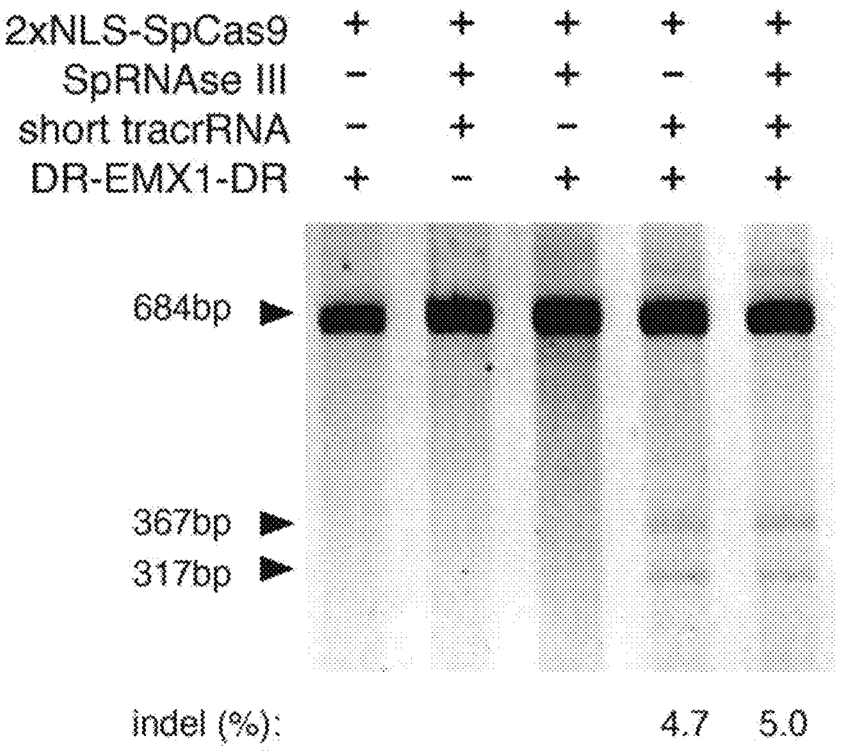

To test whether heterologous expression of the CRISPR system (SpCas9, SpRNase III, tracrRNA, and pre-crRNA) in mammalian cells can achieve targeted cleavage of mammalian chromosomes, HEK 293FT cells were transfected with combinations of CRISPR components. Since DSBs in mammalian nuclei are partially repaired by the non-homologous end joining (NHEJ) pathway, which leads to the formation of indels, the Surveyor assay was used to detect potential cleavage activity at the target EMX1 locus (FIG. 7) (see e.g. Guschin et al., 2010, Methods Mol Biol 649: 247). Co-transfection of all four CRISPR components was able to induce up to 5.0% cleavage in the protospacer (see FIG. 2D). Co-transfection of all CRISPR components minus SpRNase III also induced up to 4.7% indel in the protospacer, suggesting that there may be endogenous mammalian RNases that are capable of assisting with crRNA maturation, such as for example the related Dicer and Drosha enzymes. Removing any of the remaining three components abolished the genome cleavage activity of the CRISPR system (FIG. 2D). Sanger sequencing of amplicons containing the target locus verified the cleavage activity: in 43 sequenced clones, 5 mutated alleles (11.6%) were found. Similar experiments using a variety of guide sequences produced indel percentages as high as 29% (see FIGS. 3-6, 10, and 11). These results define a three-component system for efficient CRISPR-mediated genome modification in mammalian cells. To optimize the cleavage efficiency, Applicants also tested whether different isoforms of tracrRNA affected the cleavage efficiency and found that, in this example system, only the short (89-bp) transcript form was able to mediate cleavage of the human EMX1 genomic locus (FIG. 6B).

Figure 12A:
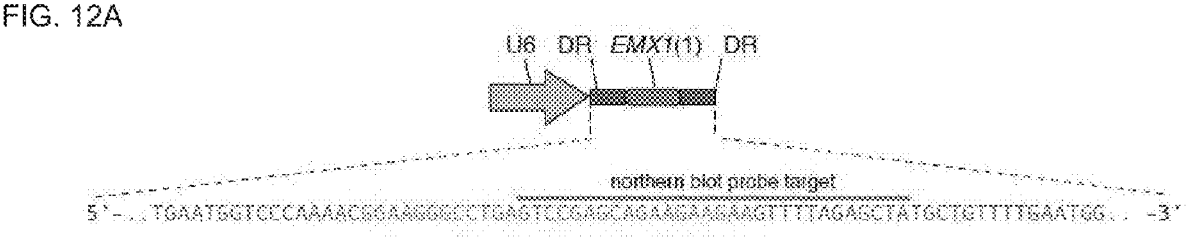
FIG. 12A-12B shows the results of a Northern blot analysis of crRNA processing in mammalian cells.
Figure 12B:
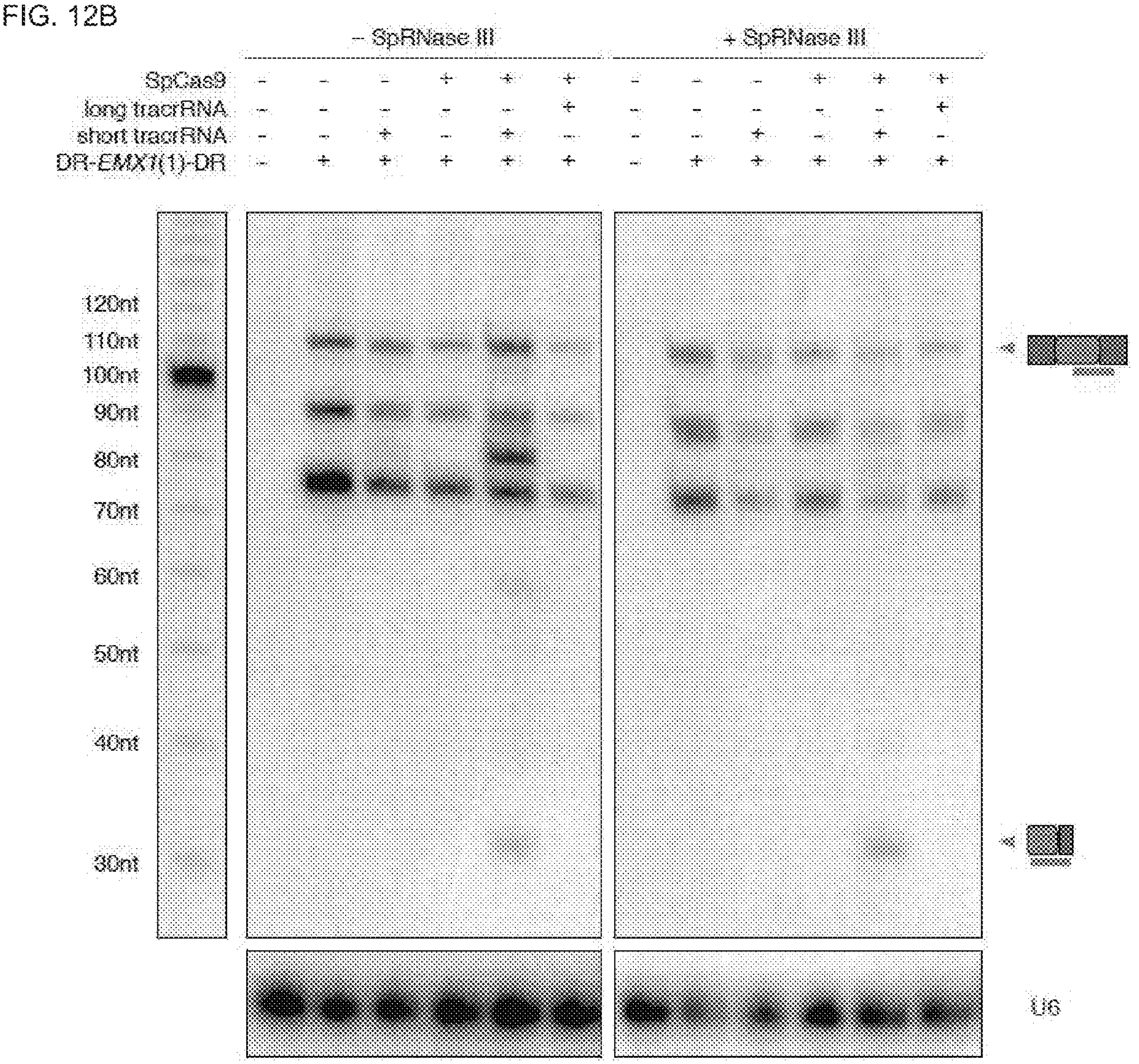

FIG. 12 provides an additional Northern blot analysis of crRNA processing in mammalian cells. FIG. 12A illustrates a schematic showing the expression vector for a single spacer flanked by two direct repeats (DR-EMX1(1)-DR). The 30 bp spacer targeting the human EMX1 locus protospacer 1 (see FIG. 6) and the direct repeat sequences are shown in the sequence beneath FIG. 12A. The line indicates the region whose reverse-complement sequence was used to generate Northern blot probes for EMX1(1) crRNA detection. FIG. 12B shows a Northern blot analysis of total RNA extracted from 293FT cells transfected with U6 expression constructs carrying DR-EMX1(1)-DR. Left and right panels are from 293FT cells transfected without or with SpRNase III respectively. DR-EMX1(1)-DR was processed into mature crRNAs only in the presence of SpCas9 and short tracrRNA and was not dependent on the presence of SpRNase III. The mature crRNA detected from transfected 293FT total RNA is ~33 bp and is shorter than the 39-42 bp mature crRNA from *S. pyogenes*. These results demonstrate that a CRISPR system can be transplanted into eukaryotic cells and reprogrammed to facilitate cleavage of endogenous mammalian target polynucleotides.

FIG. 2 illustrates the bacterial CRISPR system described in this example. FIG. 2A illustrates a schematic showing the CRISPR locus 1 from *Streptococcus pyogenes* SF370 and a proposed mechanism of CRISPR-mediated DNA cleavage by this system. Mature crRNA processed from the direct repeat-spacer array directs Cas9 to genomic targets consisting of complimentary protospacers and a protospacer-adjacent motif (PAM). Upon target-spacer base pairing, Cas9 mediates a double-strand break in the target DNA. FIG. 2B illustrates engineering of *S. pyogenes* Cas9 (SpCas9) and RNase III (SpRNase III) with nuclear localization signals (NLSs) to enable import into the mammalian nucleus. FIG. 2C illustrates mammalian expression of SpCas9 and SpRNase III driven by the constitutive EF1a promoter and tracrRNA and pre-crRNA array (DR-Spacer-DR) driven by the RNA Pol3 promoter U6 to promote precise transcription initiation and termination. A protospacer from the human EMX1 locus with a satisfactory PAM sequence is used as the spacer in the pre-crRNA array. FIG. 2D illustrates surveyor nuclease assay for SpCas9-mediated minor insertions and deletions. SpCas9 was expressed with and without SpRNase III, tracrRNA, and a pre-crRNA array carrying the EMX1-target spacer. FIG. 2E illustrates a schematic representation of base pairing between target locus and EMX1-targeting crRNA, as well as an example chromatogram showing a micro deletion adjacent to the SpCas9 cleavage site. FIG. 2F illustrates mutated alleles identified from sequencing analysis of 43 clonal amplicons showing a variety of micro insertions and deletions. Dashes indicate deleted bases, and non-aligned or mismatched bases indicate insertions or mutations. Scale bar=10 μm.

Figure 8A:
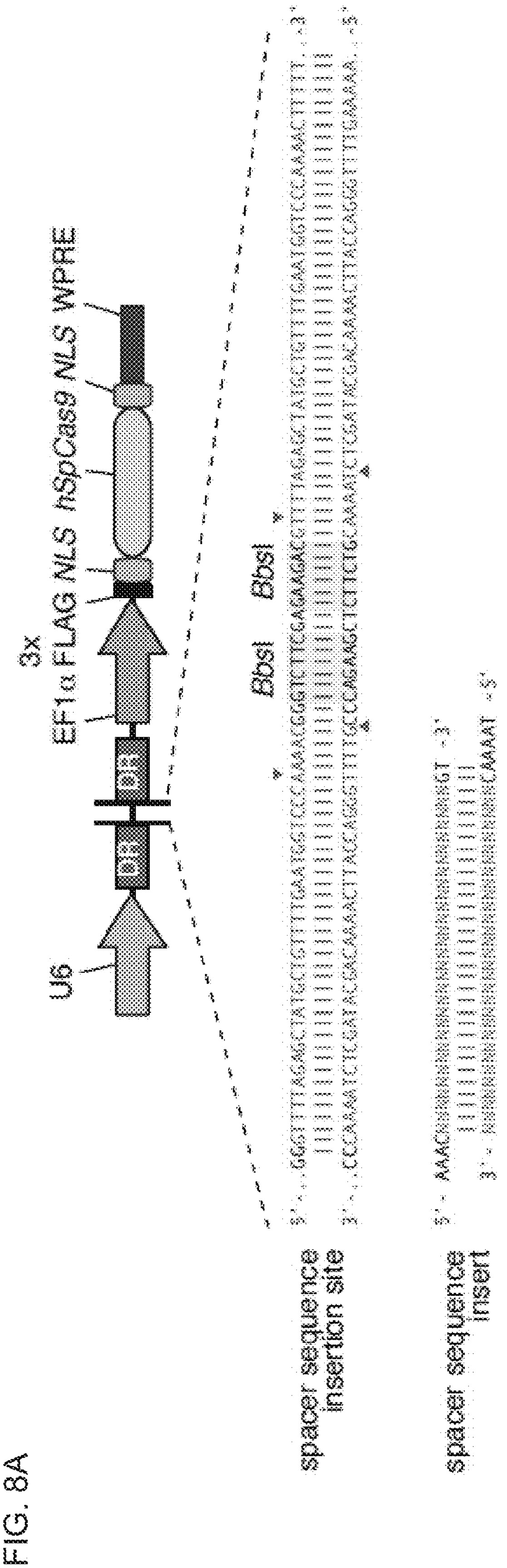
FIG. 8A-8B shows exemplary bicistronic expression vectors for expression of CRISPR system elements in eukaryotic cells.
Figure 8B:
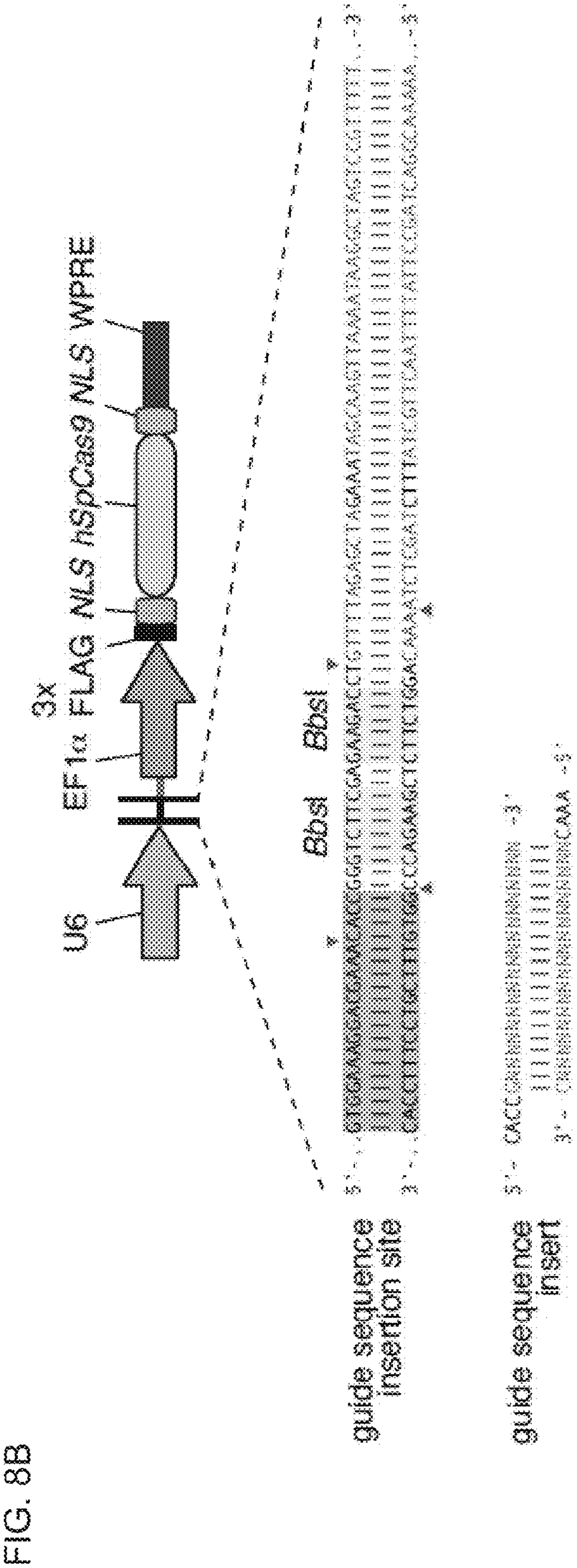

To further simplify the three-component system, a chimeric crRNA-tracrRNA hybrid design was adapted, where a mature crRNA (comprising a guide sequence) may be fused to a partial tracrRNA via a stem-loop to mimic the natural crRNA:tracrRNA duplex. To increase co-delivery efficiency, a bicistronic expression vector was created to drive co-expression of a chimeric RNA and SpCas9 in transfected cells. In parallel, the bicistronic vectors were used to express a pre-crRNA (DR-guide sequence-DR) with SpCas9, to induce processing into crRNA with a separately expressed tracrRNA (compare FIG. 11B top and bottom). FIG. 8 provides schematic illustrations of bicistronic expression vectors for pre-crRNA array (FIG. 8A) or chimeric crRNA (represented by the short line downstream of the guide sequence insertion site and upstream of the EF1α promoter in FIG. 8B) with hSpCas9, showing location of various elements and the point of guide sequence insertion. The expanded sequence around the location of the guide sequence insertion site in FIG. 8B also shows a partial DR sequence (GTTTTAGAGCTA) (SEQ ID NO: 11) and a partial tracrRNA sequence (TAGCAAGTTAAAATAAGGCTAGTCCGTTTTT)(SEQ ID NO: 12). Guide sequences can be inserted between BbsI sites using annealed oligonucleotides. Sequence designs for the oligonucleotides are shown below the schematic illustrations in FIG. 8, with appropriate ligation adapters indicated. WPRE represents the Woodchuck hepatitis virus post-transcriptional regulatory element. The efficiency of chimeric RNA-mediated cleavage was tested by targeting the same EMX1 locus described above. Using both Surveyor assay and Sanger sequencing of amplicons, Applicants confirmed that the chimeric RNA design facilitates cleavage of human EMX1 locus with approximately a 4.7% modification rate (FIG. 3).

Figure 13A:
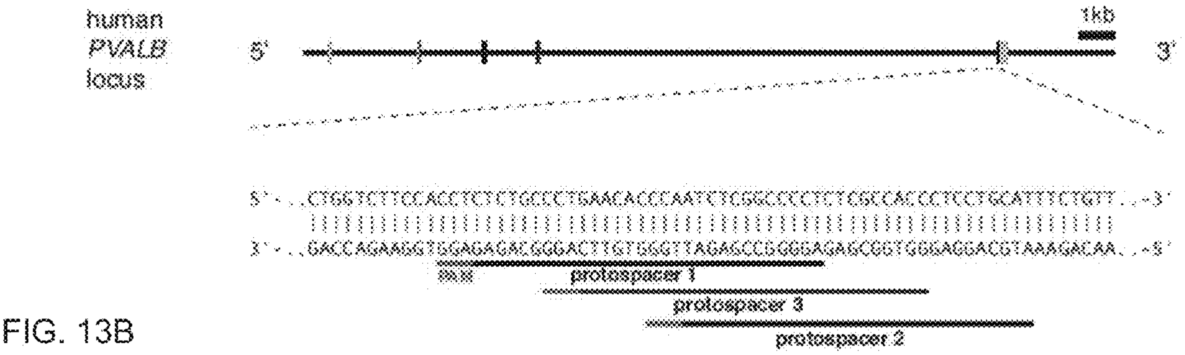
FIG. 13A-13B shows an exemplary selection of protospacers in the human PVALB (SEQ ID NO: 136) and mouse Th loci (SEQ ID NO: 137).
Figure 13B:
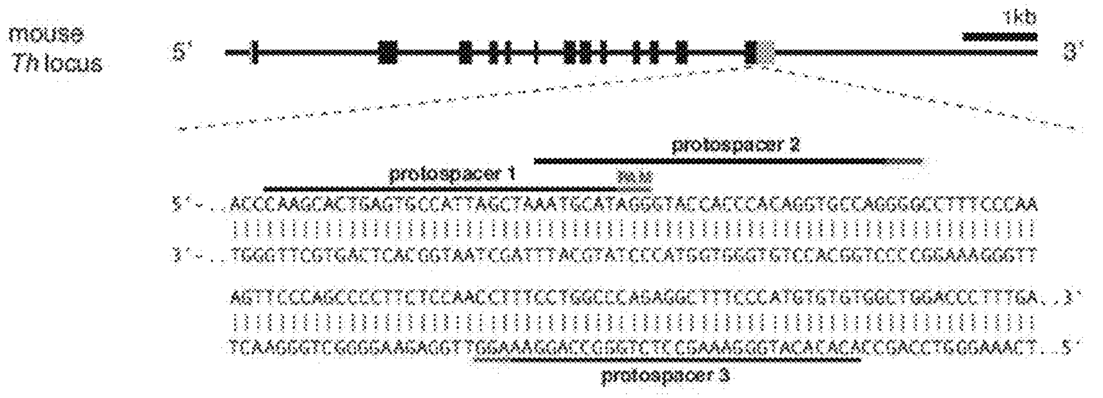

Generalizability of CRISPR-mediated cleavage in eukaryotic cells was tested by targeting additional genomic loci in both human and mouse cells by designing chimeric RNA targeting multiple sites in the human EMX1 and PVALB, as well as the mouse Th loci. FIG. 13 illustrates the selection of some additional targeted protospacers in human PVALB (FIG. 13A) and mouse Th (FIG. 13B) loci. Schematics of the gene loci and the location of three protospacers within the last exon of each are provided. The underlined sequences include 30 bp of protospacer sequence and 3 bp at the 3' end corresponding to the PAM sequences. Protospacers on the sense and anti-sense strands are indicated above and below the DNA sequences, respectively. A modification rate of 6.3% and 0.75% was achieved for the human PVALB and mouse Th loci respectively, demonstrating the broad applicability of the CRISPR system in modifying different loci across multiple organisms (FIG. 5). While cleavage was only detected with one out of three spacers for each locus using the chimeric constructs, all target sequences were cleaved with efficiency of indel production reaching 27% when using the co-expressed pre-crRNA arrangement (FIGS. 6 and 13).

Figures 11A, 11B, 11C:
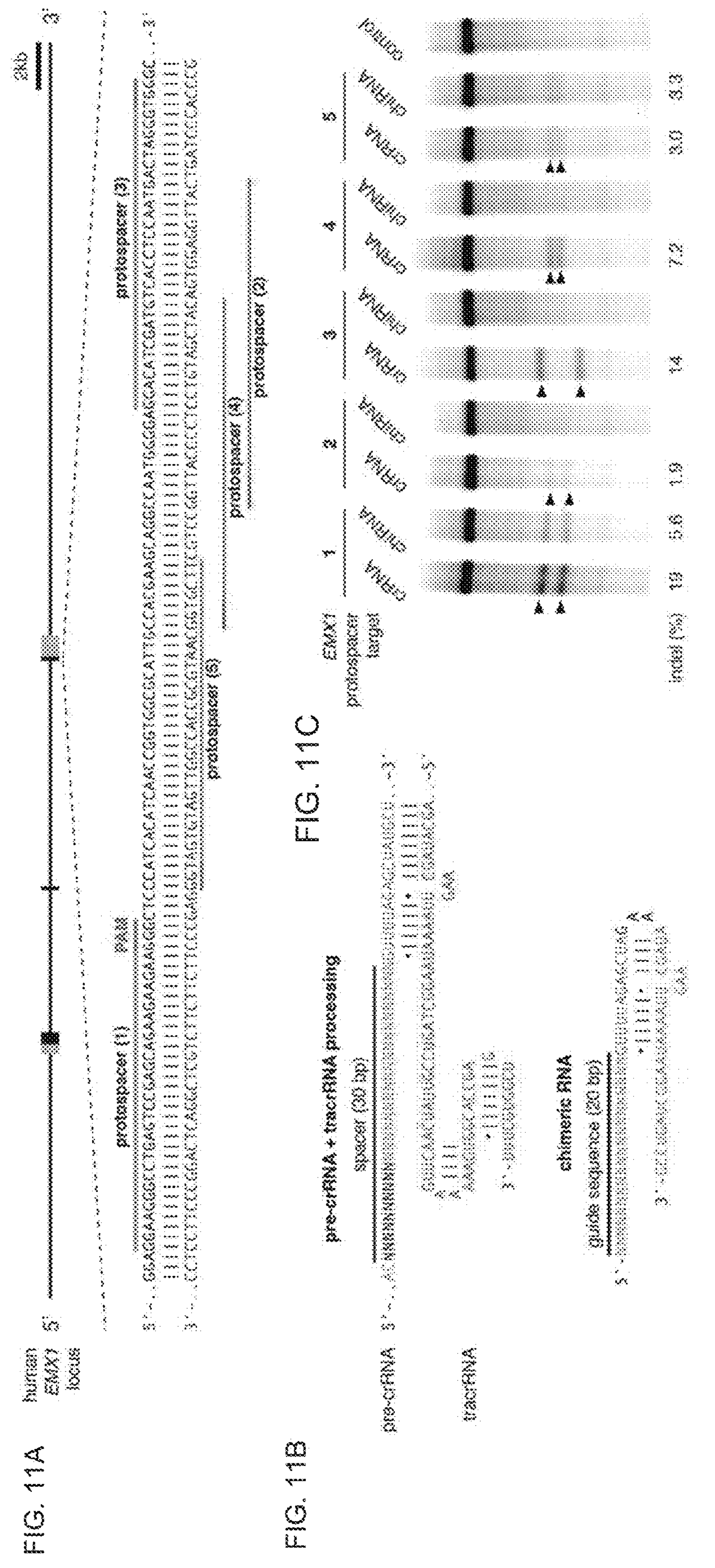
FIG. 11A-11C shows exemplary manipulations of a CRISPR system for targeting of genomic loci in mammalian cells.

FIG. 11 provides a further illustration that SpCas9 can be reprogrammed to target multiple genomic loci in mammalian cells. FIG. 11A provides a schematic of the human EMX1 locus showing the location of five protospacers, indicated by the underlined sequences. FIG. 11B provides a schematic of the pre-crRNA/trcrRNA complex showing hybridization between the direct repeat region of the pre-crRNA and tracrRNA (top), and a schematic of a chimeric RNA design comprising a 20 bp guide sequence, and tracr mate and tracr sequences consisting of partial direct repeat and tracrRNA sequences hybridized in a hairpin structure (bottom). Results of a Surveyor assay comparing the efficacy of Cas9-mediated cleavage at five protospacers in the human EMX1 locus is illustrated in FIG. 11C. Each protospacer is targeted using either processed pre-crRNA/tracrRNA complex (crRNA) or chimeric RNA (chiRNA).

Since the secondary structure of RNA can be crucial for intermolecular interactions, a structure prediction algorithm based on minimum free energy and Boltzmann-weighted structure ensemble was used to compare the putative secondary structure of all guide sequences used in the genome targeting experiment (see e.g. Gruber et al., 2008, Nucleic Acids Research, 36: W70). Analysis revealed that in most cases, the effective guide sequences in the chimeric crRNA context were substantially free of secondary structure motifs, whereas the ineffective guide sequences were more likely to form internal secondary structures that could prevent base pairing with the target protospacer DNA. It is thus possible that variability in the spacer secondary structure might impact the efficiency of CRISPR-mediated interference when using a chimeric crRNA.

Figure 22A:
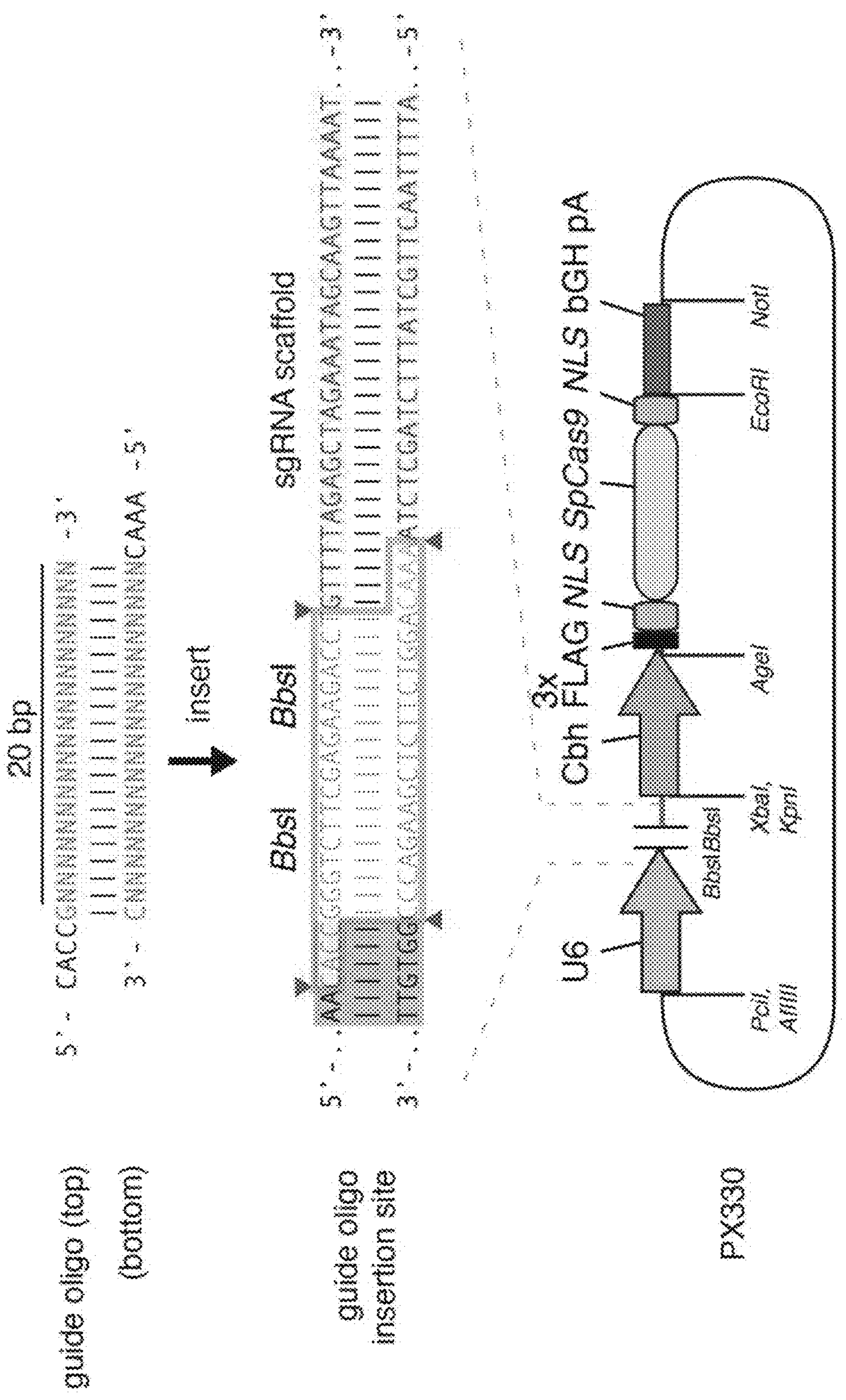
FIG. 22A-22B shows single vector designs for SpCas9.
Figure 22B:
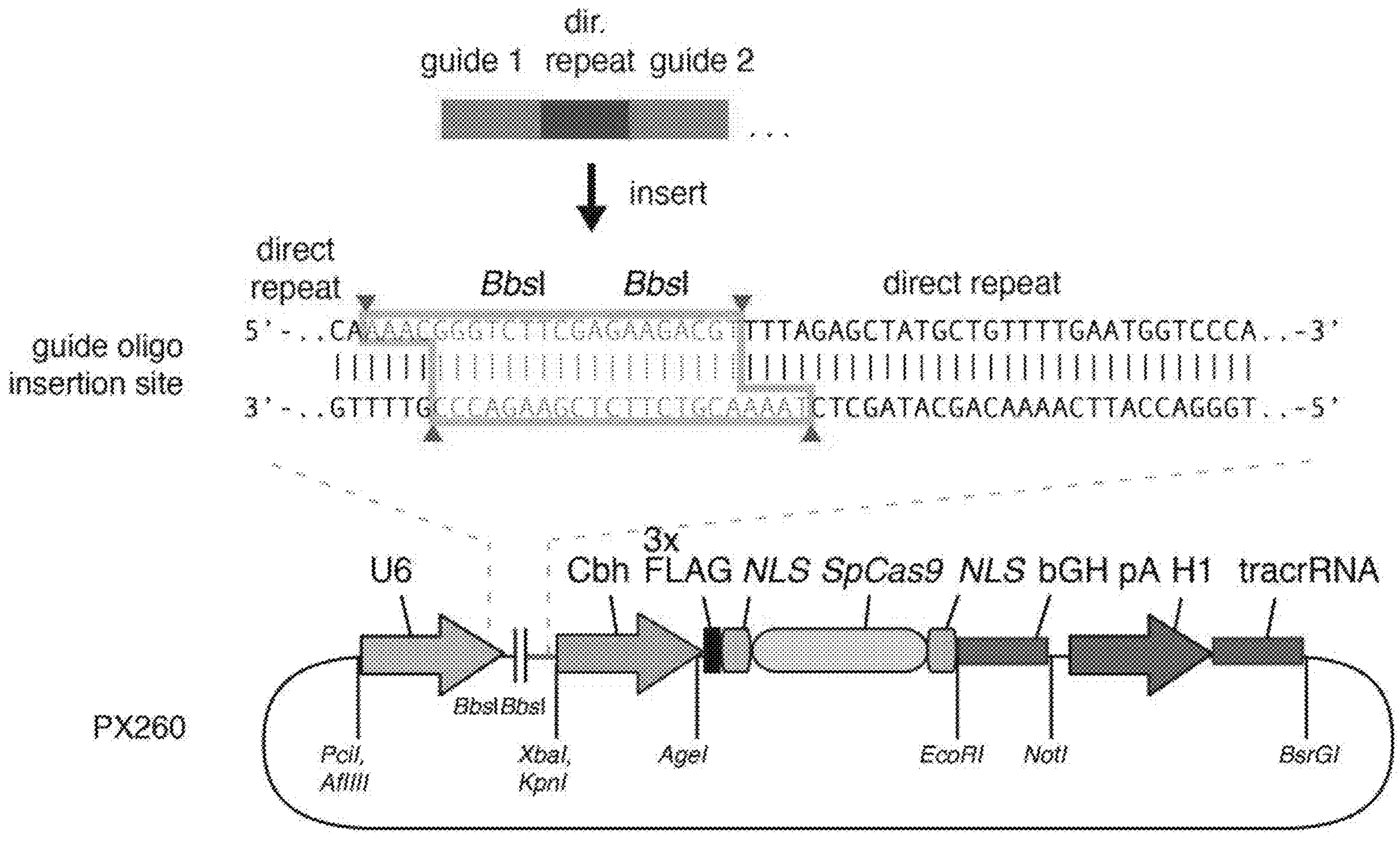
Figure 23A:
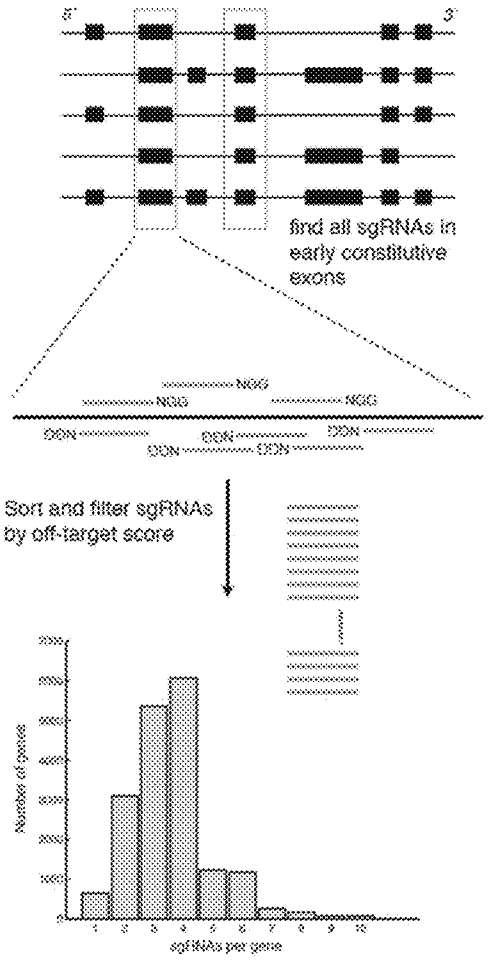
FIG. 23A-23D shows A) Design of sgRNAs for functional knock-out of all coding genes in the human genome. Early constitutive exons for genes are identified using Illumina Human BodyMap 2.0 and NCBI CCDS datasets. sgRNAs are ranked by an off-target score using a metric that includes the number of off-targets in the genome and the type of mutations (distance from PAM and clustering) to evaluate off-target cutting. The best sgRNA (lowest off-target score) in each exon are included in the library. Most genes have 3 or 4 sgRNAs targeting early exons. B) Individual sgRNAs are synthesized using array synthesis of ssDNAs and then PCR amplified as dsDNA. These dsDNAs are cloned into the lentiviral transfer plasmid after a U6 promoter; this vector also contains a EFS promoter driving Cas9 and puromycin resistance. The pooled library is packaged into lentiviral particles in HEK 293FT cells via co-transfection with pVSVg and psPAX2. To begin the screen, cells to be screened are infected at a MOI between 0.3 to 0.5 to ensure that each cell receives only 1 viral construct. In aspects of the invention, the MOI may be between 0.3 to 0.75. After 24 hours, cells are selected via puromycin so that only cells transduced with a CRISPR construct are preserved. C) Different sgRNA targeting the initial part of EGFP are cloned into the Cas9-2A-Puro lentiviral vector and packaged into virus. Distribution of EGFP fluorescence is shown for 293 Ts expressing EGFP after transduction with each EGFP-targeting sgRNA, a Cas9-only virus, or uninfected control cells. D) States NGS indel data on EGFP cells.
Figure 23B:
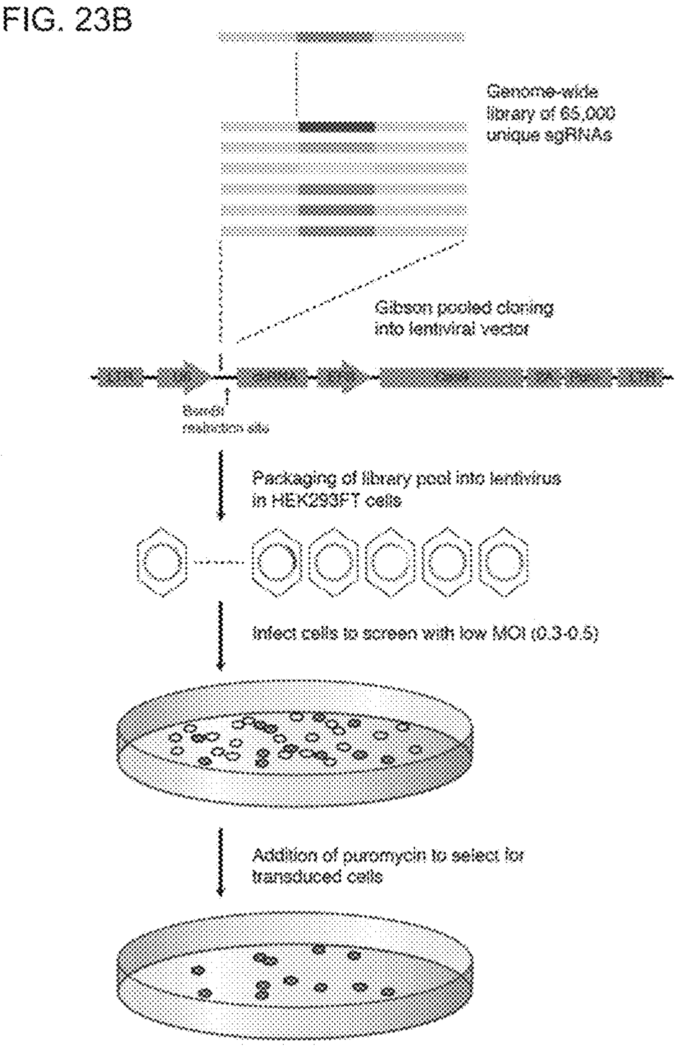
Figures 23C, 23D:
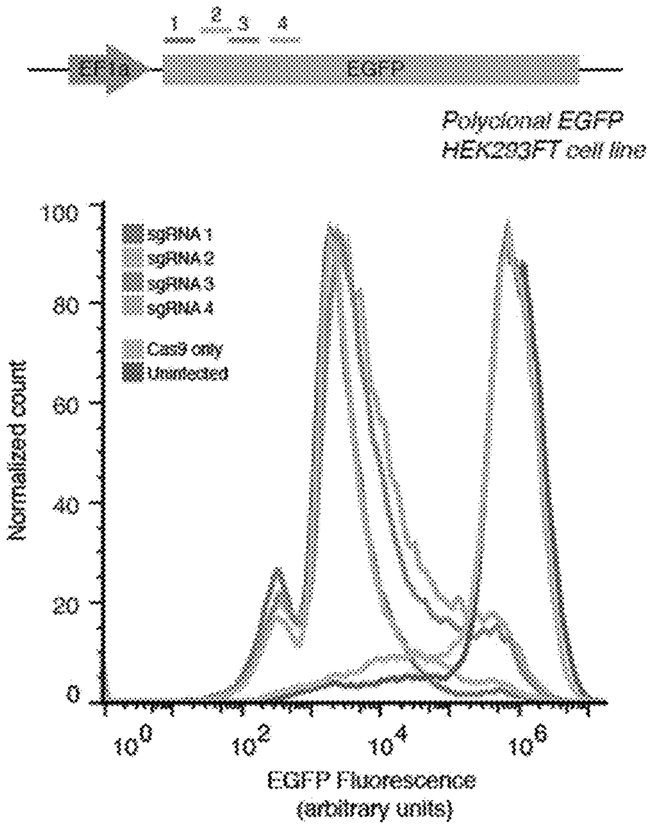
Figure 24A:
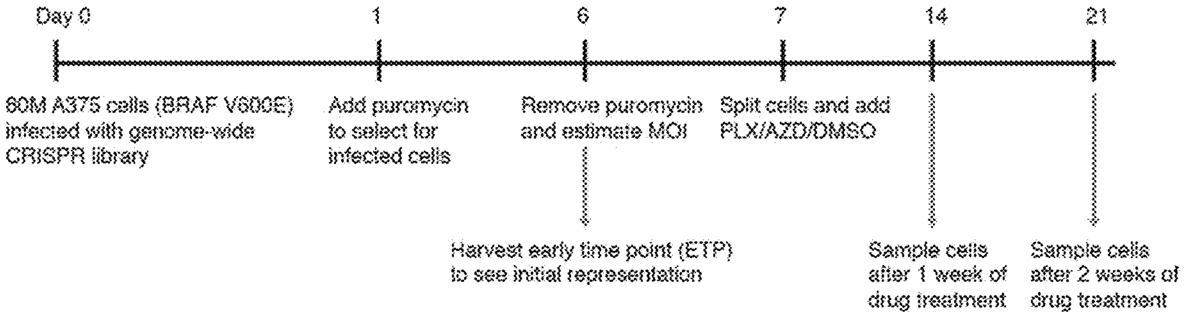
FIG. 24A-24F shows A) Timeline of Vemurafenib (PLX) resistance screen in A375 cells. B) Scatterplot of individual sgRNA abundances from biological replicates of DMSO treatment. C) Scatterplot of individual sgRNA abundances from biological replicates of PLX treatment. D) Boxplot showing the distribution of reads from different sgRNA. PLX has a statistically significant decrease in the average number of reads per sgRNA with an increase in the number in reads for the most abundant sgRNAs. E) Scatterplot of individual sgRNA abundances in PLX vs. DMSO treatment. F) Mapping of sgRNAs to genes and the calculating the median sgRNA enrichment value. By calculating an empirical distribution of p-values, a few gene knock outs display significant enrichment after PLX treatment, such as NF2, NF1, MED12, and MED15.
Figure 24B:
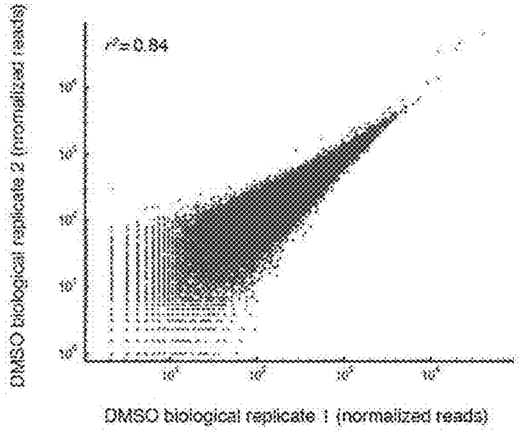
Figure 24C:
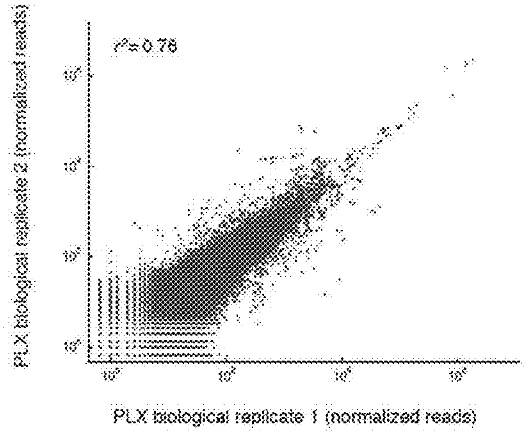
Figure 24D:
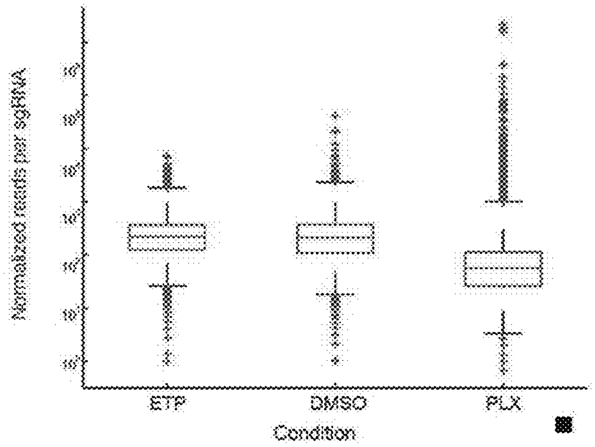
Figure 24E:
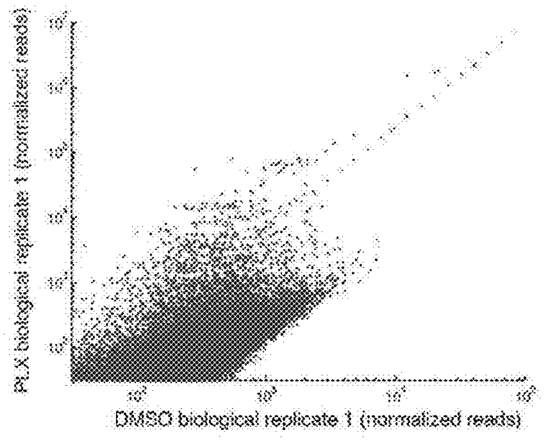
Figure 24F:
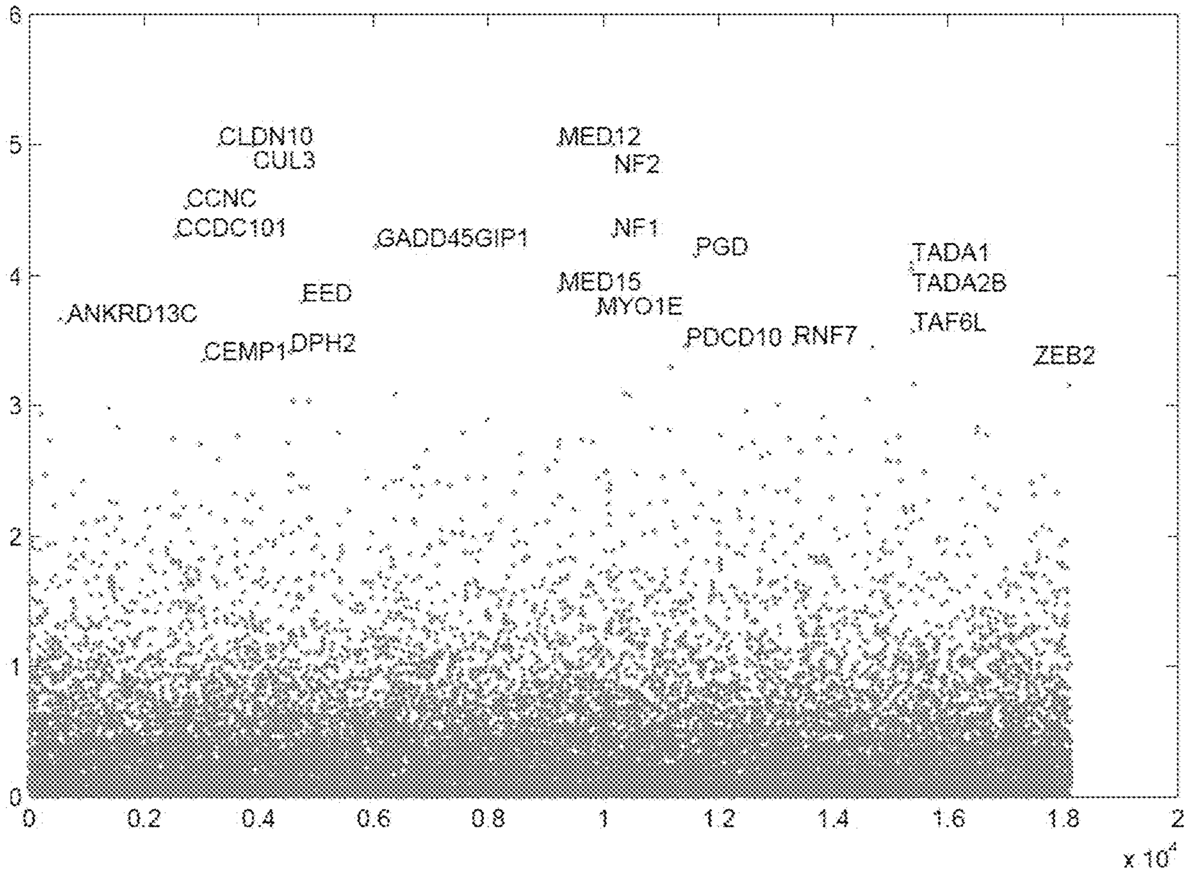

Further vector designs for SpCas9 are shown in FIG. 22, which illustrates single expression vectors incorporating a U6 promoter linked to an insertion site for a guide oligo, and a Cbh promoter linked to SpCas9 coding sequence. The vector shown in FIG. 22*b* includes a tracrRNA coding sequence linked to an H1 promoter.

Figure 3A:
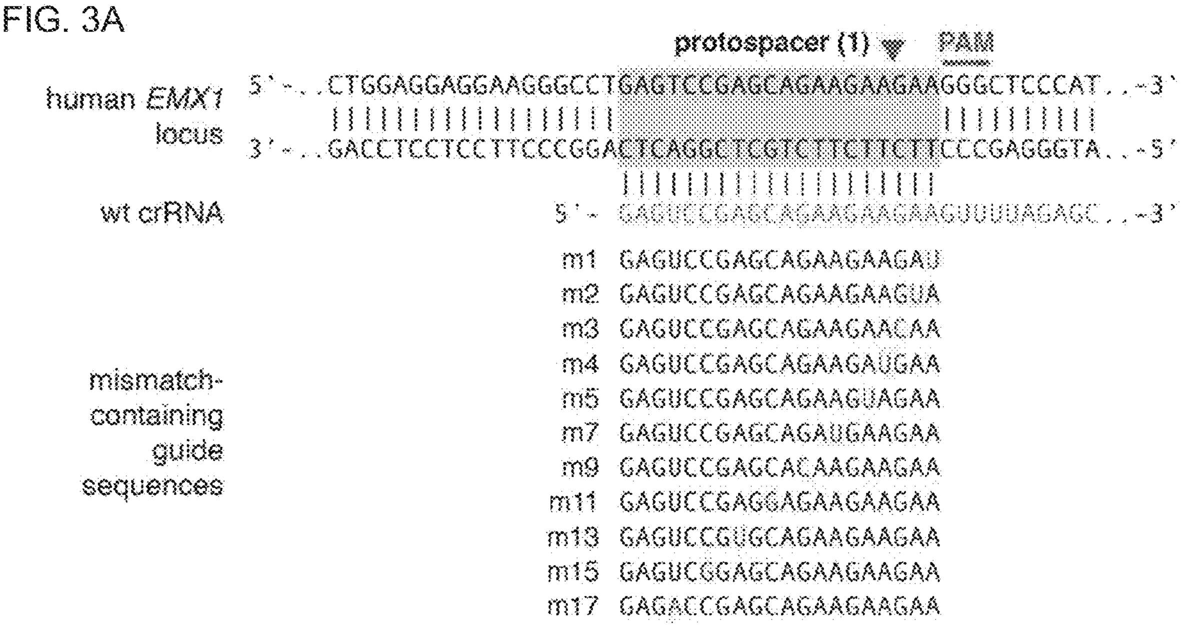
FIG. 3A-3D shows results of an evaluation of SpCas9 specificity for an example target.
Figure 3B:
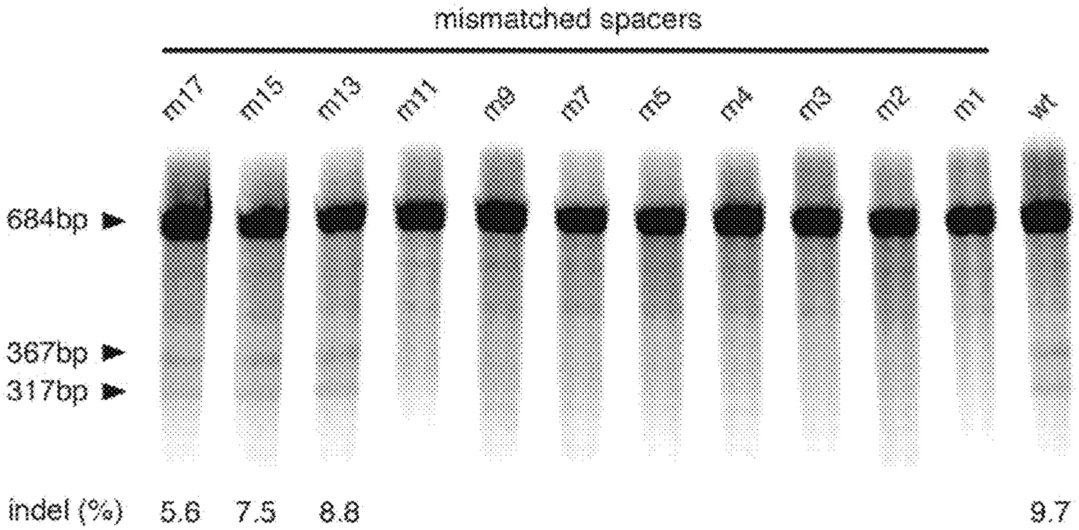
Figure 3C:
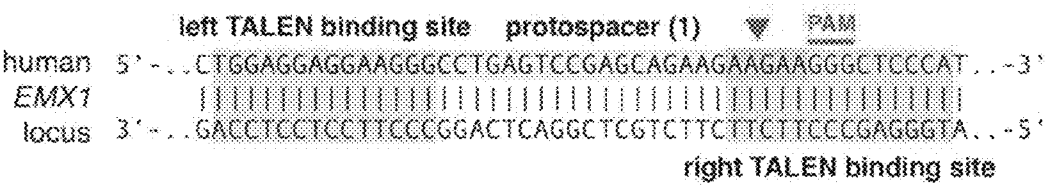

In the bacterial assay, all spacers facilitated efficient CRISPR interference (FIG. 3C). These results suggest that there may be additional factors affecting the efficiency of CRISPR activity in mammalian cells.

Figure 3D:
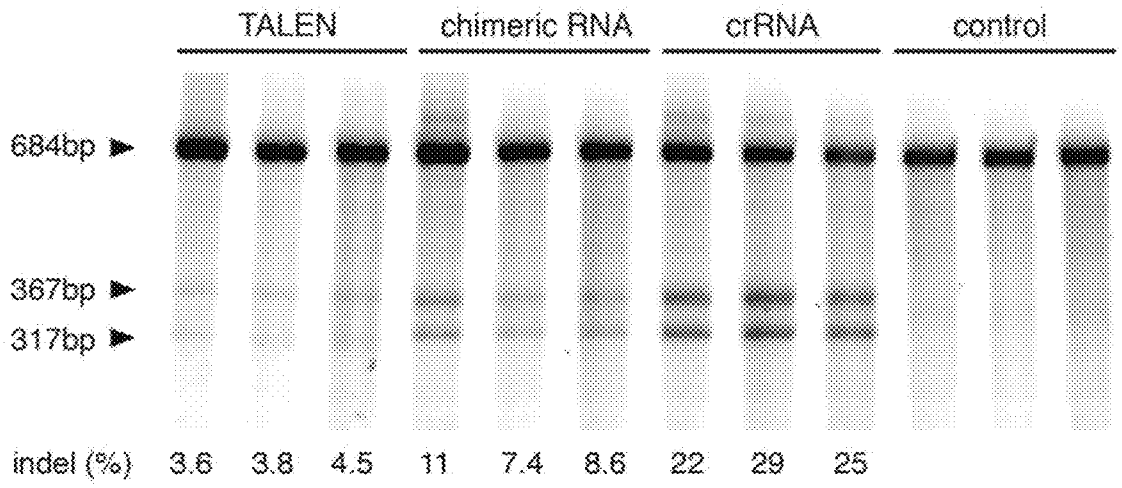

To investigate the specificity of CRISPR-mediated cleavage, the effect of single-nucleotide mutations in the guide sequence on protospacer cleavage in the mammalian genome was analyzed using a series of EMX1-targeting chimeric crRNAs with single point mutations (FIG. 3A). FIG. 3B illustrates results of a Surveyor nuclease assay comparing the cleavage efficiency of Cas9 when paired with different mutant chimeric RNAs. Single-base mismatch up to 12-bp 5' of the PAM substantially abrogated genomic cleavage by SpCas9, whereas spacers with mutations at farther upstream positions retained activity against the original protospacer target (FIG. 3B). In addition to the PAM, SpCas9 has single-base specificity within the last 12-bp of the spacer. Furthermore, CRISPR is able to mediate genomic cleavage as efficiently as a pair of TALE nucleases (TALEN) targeting the same EMX1 protospacer. FIG. 3C provides a schematic showing the design of TALENs targeting EMX1, and FIG. 3D shows a Surveyor gel comparing the efficiency of TALEN and Cas9 (n=3).

Figure 4A:
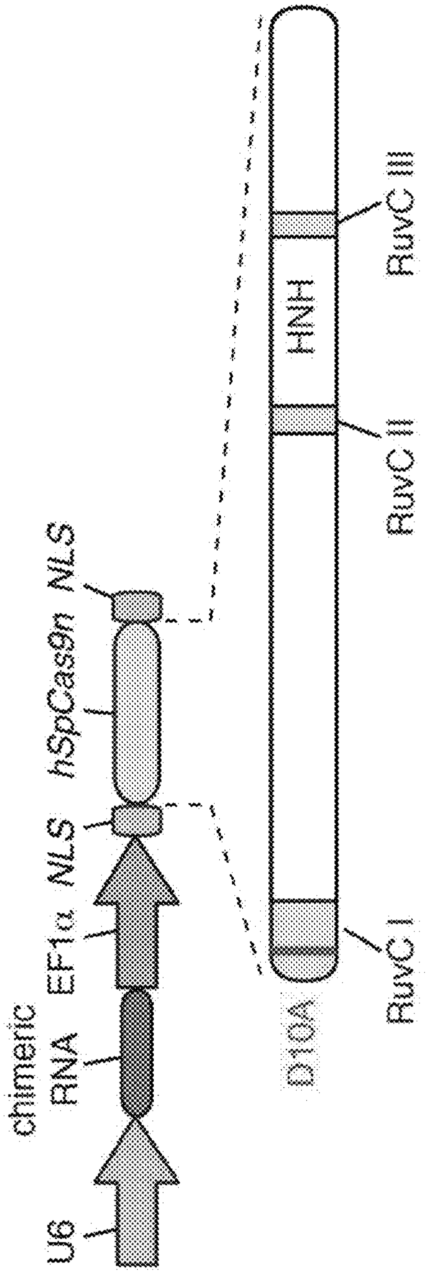
FIG. 4A-4G show an exemplary vector system and results for its use in directing homologous recombination in eukaryotic cells.
Figure 4B:
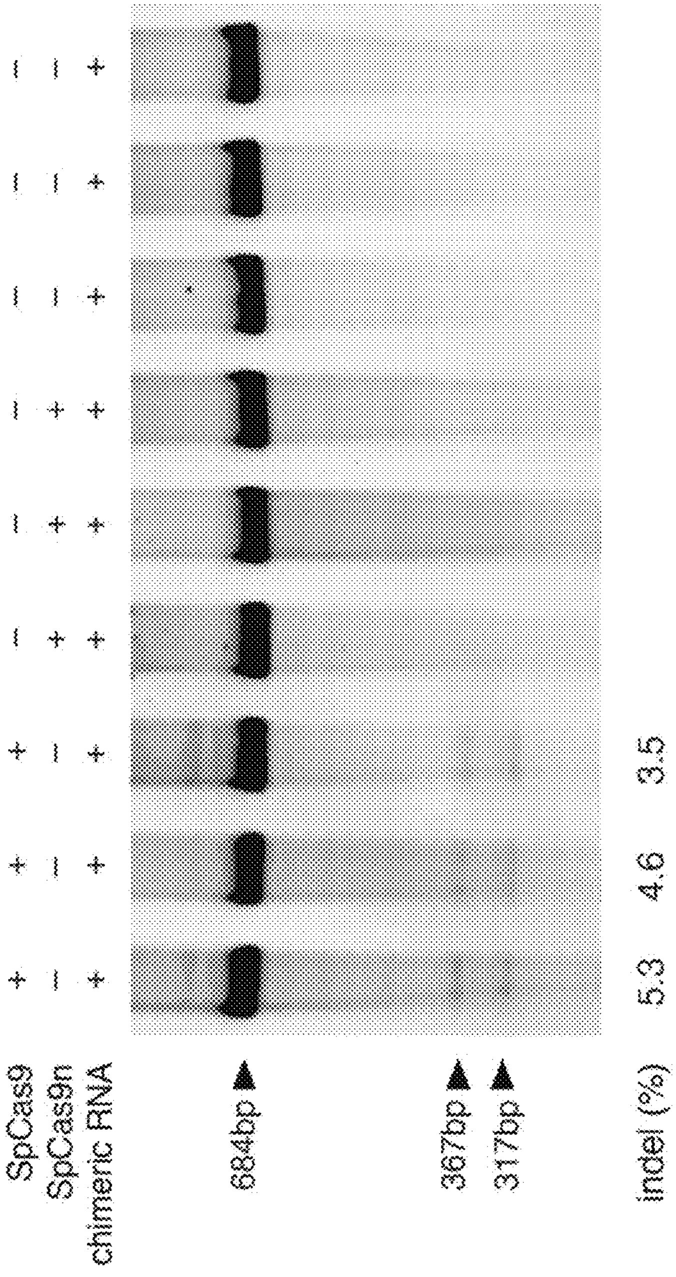
Figure 4C:
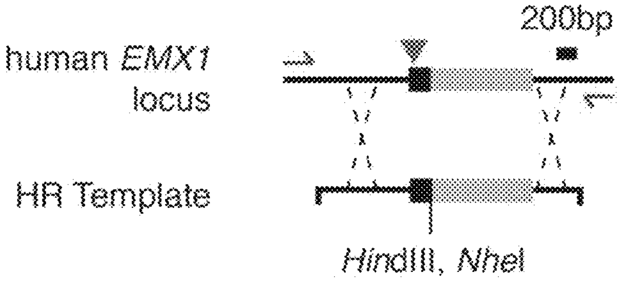
Figure 4D:
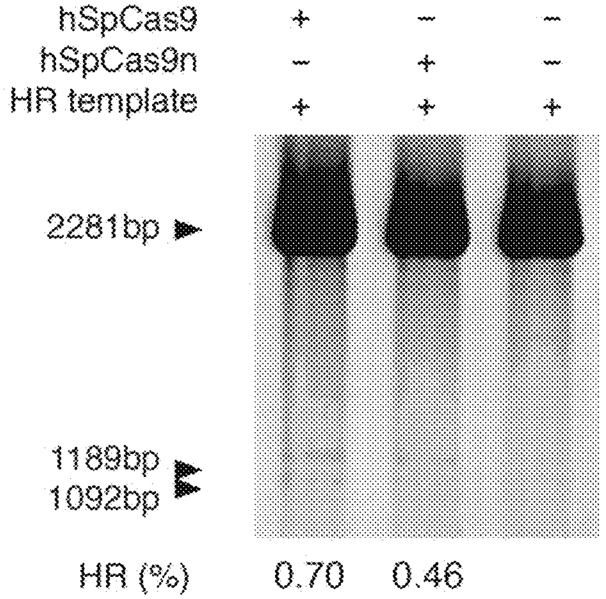
Figure 4E:
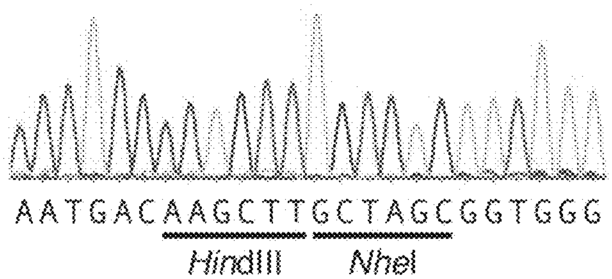

Having established a set of components for achieving CRISPR-mediated gene editing in mammalian cells through the error-prone NHEJ mechanism, the ability of CRISPR to stimulate homologous recombination (HR), a high fidelity gene repair pathway for making precise edits in the genome, was tested. The wild type SpCas9 is able to mediate site-specific DSBs, which can be repaired through both NHEJ and HR. In addition, an aspartate-to-alanine substitution (D10A) in the RuvC I catalytic domain of SpCas9 was engineered to convert the nuclease into a nickase (SpCas9n; illustrated in FIG. 4A) (see e.g. Sapranausaks et al., 2011, Nucleic Acids Research, 39: 9275; Gasiunas et al., 2012, Proc. Natl. Acad. Sci. USA, 109:E2579), such that nicked genomic DNA undergoes the high-fidelity homology-directed repair (HDR). Surveyor assay confirmed that SpCas9n does not generate indels at the EMX1 protospacer target. As illustrated in FIG. 4B, co-expression of EMX1-targeting chimeric crRNA with SpCas9 produced indels in the target site, whereas co-expression with SpCas9n did not (n=3). Moreover, sequencing of 327 amplicons did not detect any indels induced by SpCas9n. The same locus was selected to test CRISPR-mediated HR by co-transfecting HEK 293FT cells with the chimeric RNA targeting EMX1, hSpCas9 or hSpCas9n, as well as a HR template to introduce a pair of restriction sites (HindIII and NheI) near the protospacer. FIG. 4C provides a schematic illustration of the HR strategy, with relative locations of recombination points and primer annealing sequences (arrows). SpCas9 and SpCas9n indeed catalyzed integration of the HR template into the EMX1 locus. PCR amplification of the target region followed by restriction digest with HindIII revealed cleavage products corresponding to expected fragment sizes (arrows in restriction fragment length polymorphism gel analysis shown in FIG. 4D), with SpCas9 and SpCas9n mediating similar levels of HR efficiencies. Applicants further verified HR using Sanger sequencing of genomic amplicons (FIG. 4E). These results demonstrate the utility of CRISPR for facilitating targeted gene insertion in the mammalian genome. Given the 14-bp (12-bp from the spacer and 2-bp from the PAM) target specificity of the wild type SpCas9, the availability of a nickase can significantly reduce the likelihood of off-target modifications, since single strand breaks are not substrates for the error-prone NHEJ pathway.

Figure 4F:
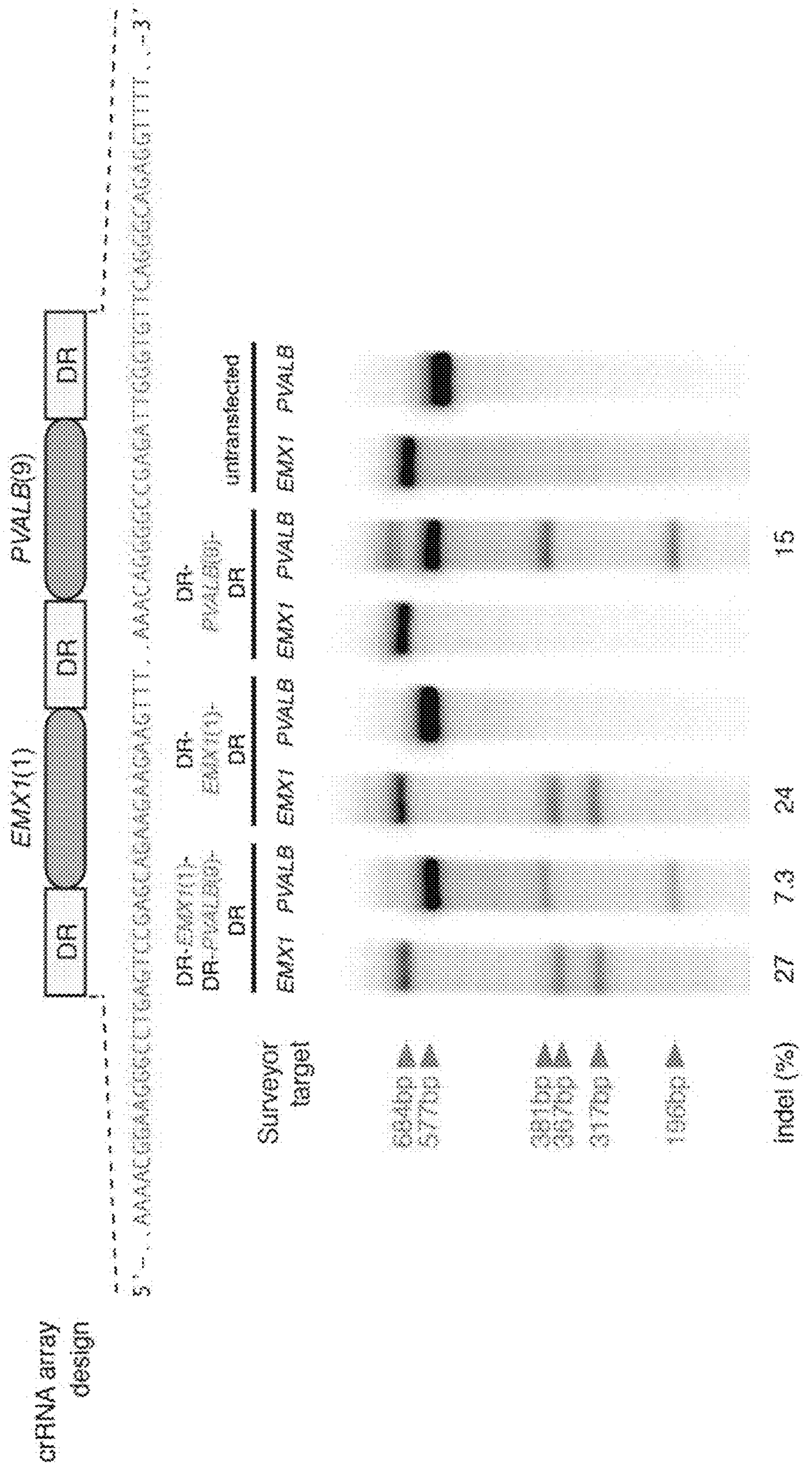
Figure 4G:
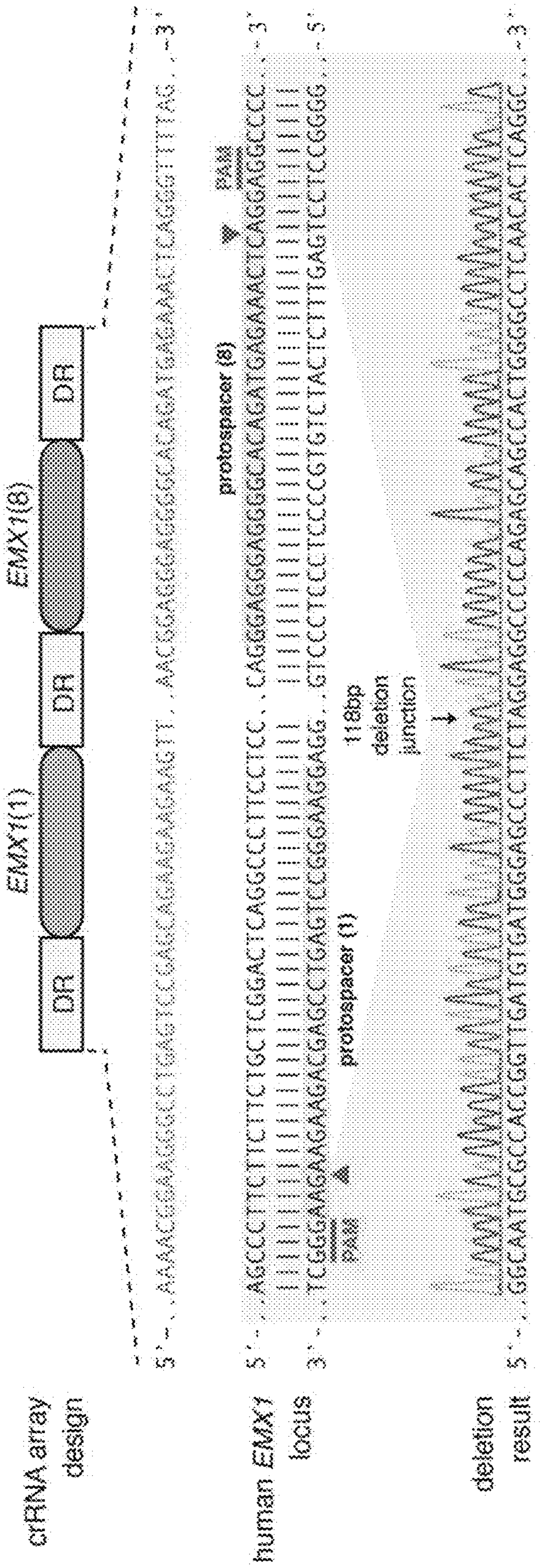

Expression constructs mimicking the natural architecture of CRISPR loci with arrayed spacers (FIG. 2A) were constructed to test the possibility of multiplexed sequence targeting. Using a single CRISPR array encoding a pair of EMX1- and PVALB-targeting spacers, efficient cleavage at both loci was detected (FIG. 4F, showing both a schematic design of the crRNA array and a Surveyor blot showing efficient mediation of cleavage). Targeted deletion of larger genomic regions through concurrent DSBs using spacers against two targets within EMX1 spaced by 119 bp was also tested, and a 1.6% deletion efficacy (3 out of 182 amplicons; FIG. 4G) was detected. This demonstrates that the CRISPR system can mediate multiplexed editing within a single genome.

Example 2: CRISPR System Modifications and Alternatives

Figures 10A, 10B, 10C:
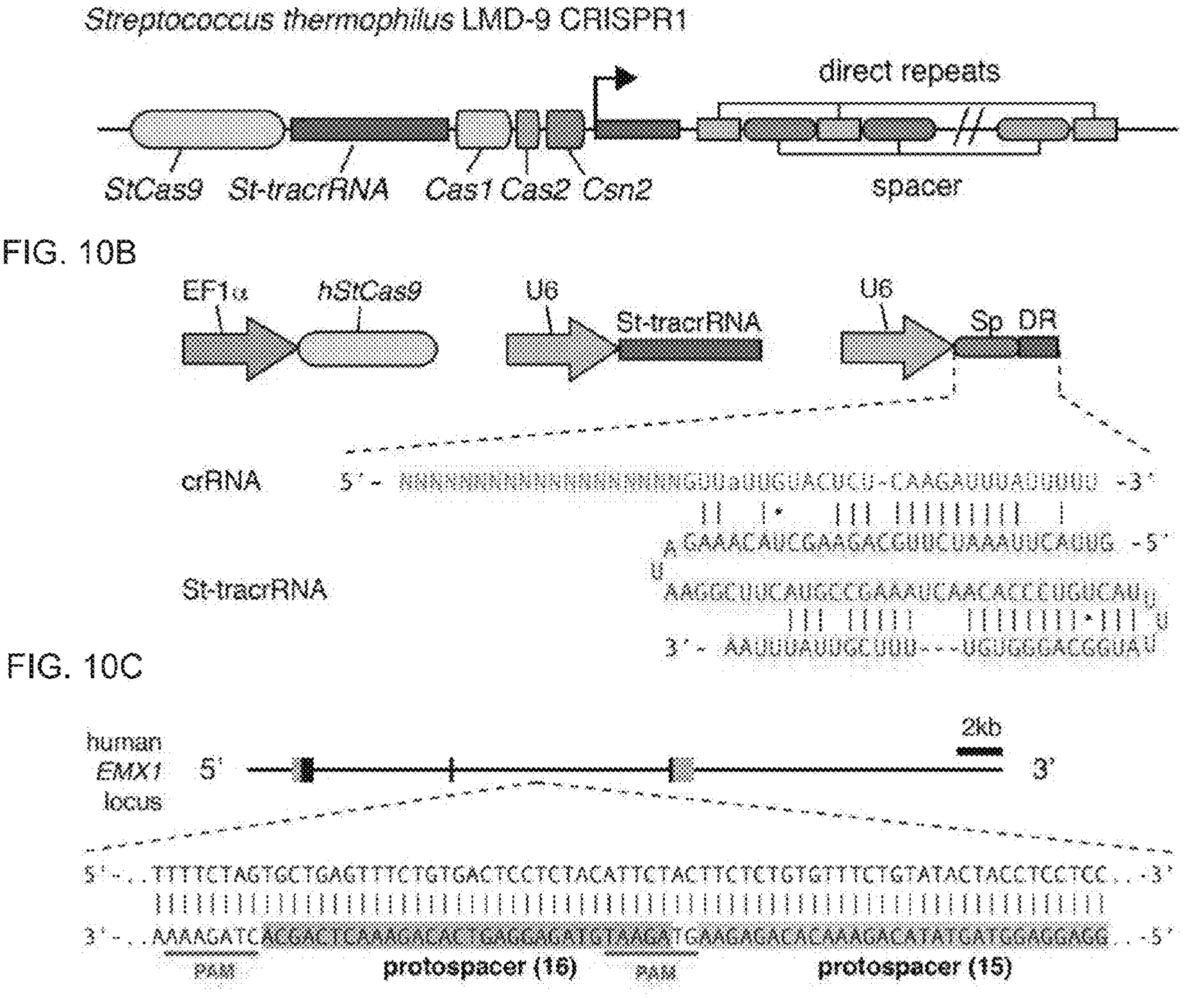
FIG. 10A-10D shows an exemplary CRISPR system, an example adaptation for expression in eukaryotic cells, and results of tests assessing CRISPR activity.
Figure 10D:
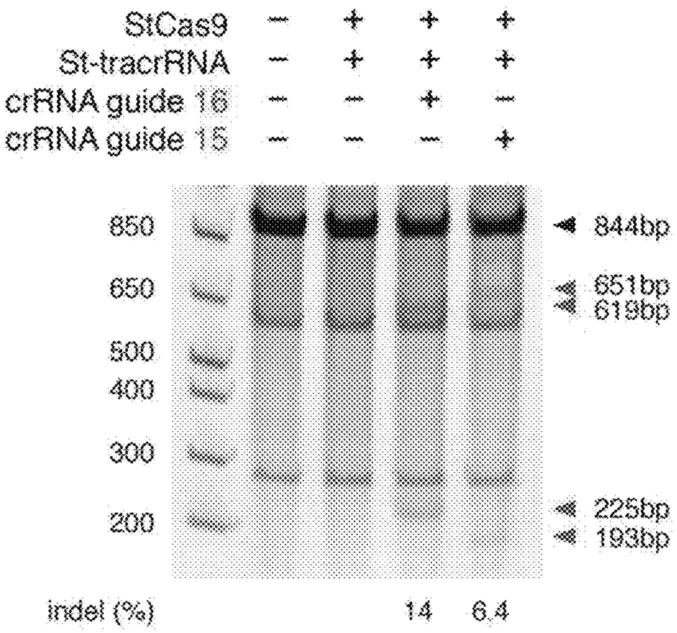
Figure 14:
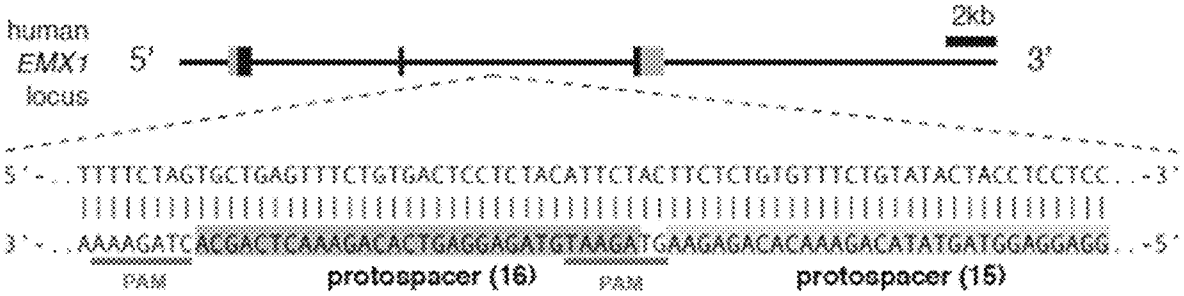
FIG. 14 shows example protospacer and corresponding PAM sequence targets of the *S. thermophilus* CRISPR system in the human EMX1 locus (SEQ ID NO: 130).

The ability to use RNA to program sequence-specific DNA cleavage defines a new class of genome engineering tools for a variety of research and industrial applications. Several aspects of the CRISPR system can be further improved to increase the efficiency and versatility of CRISPR targeting. Optimal Cas9 activity may depend on the availability of free $Mg^{2+}$ at levels higher than that present in the mammalian nucleus (see e.g. Jinek et al., 2012, Science, 337:816), and the preference for an NGG motif immediately downstream of the protospacer restricts the ability to target on average every 12-bp in the human genome (FIG. 9, evaluating both plus and minus strands of human chromosomal sequences). Some of these constraints can be overcome by exploring the diversity of CRISPR loci across the microbial metagenome (see e.g. Makarova et al., 2011, Nat Rev Microbiol, 9:467). Other CRISPR loci may be transplanted into the mammalian cellular milieu by a process similar to that described in Example 1. For example, FIG. 10 illustrates adaptation of the Type II CRISPR system from CRISPR 1 of *Streptococcus thermophilus* LMD-9 for heterologous expression in mammalian cells to achieve CRISPR-mediated genome editing. FIG. 10A provides a Schematic illustration of CRISPR 1 from *S. thermophilus* LMD-9. FIG. 10B illustrates the design of an expression system for the *S. thermophilus* CRISPR system. Human codon-optimized hStCas9 is expressed using a constitutive EF1a promoter. Mature versions of tracrRNA and crRNA are expressed using the U6 promoter to promote precise transcription initiation. Sequences from the mature crRNA and tracrRNA are illustrated. A single base indicated by the lower case "a" in the crRNA sequence is used to remove the polyU sequence, which serves as a RNA polIII transcriptional terminator. FIG. 10C provides a schematic showing guide sequences targeting the human EMX1 locus. FIG. 10D shows the results of hStCas9-mediated cleavage in the target locus using the Surveyor assay. RNA guide spacers 1 and 2 induced 14% and 6.4%, respectively. Statistical analysis of cleavage activity across biological replica at these two protospacer sites is also provided in FIG. 5. FIG. 14 provides a schematic of additional protospacer and corresponding PAM sequence targets of the *S. thermophilus* CRISPR system in the human EMX1 locus. Two protospacer sequences are highlighted and their corresponding PAM sequences satisfying NNAGAAW motif are indicated by underlining 3' with respect to the corresponding highlighted sequence. Both protospacers target the anti-sense strand.

Example 3: Sample Target Sequence Selection Algorithm

A software program is designed to identify candidate CRISPR target sequences on both strands of an input DNA sequence based on desired guide sequence length and a CRISPR motif sequence (PAM) for a specified CRISPR enzyme. For example, target sites for Cas9 from *S. pyogenes*, with PAM sequences NGG, may be identified by searching for 5'-$N_x$-NGG-3' both on the input sequence and on the reverse-complement of the input. Likewise, target sites for Cas9 of *S. thermophilus* CRISPR1, with PAM sequence NNAGAAW, may be identified by searching for 5'-$N_x$-NNAGAAW-3' (SEQ ID NO: 13) both on the input sequence and on the reverse-complement of the input. Likewise, target sites for Cas9 of *S. thermophilus* CRISPR3, with PAM sequence NGGNG, may be identified by searching for 5'-$N_x$-NGGNG-3' both on the input sequence and on the reverse-complement of the input. The value "x" in $N_x$ may be fixed by the program or specified by the user, such as 20.

Figure 18:
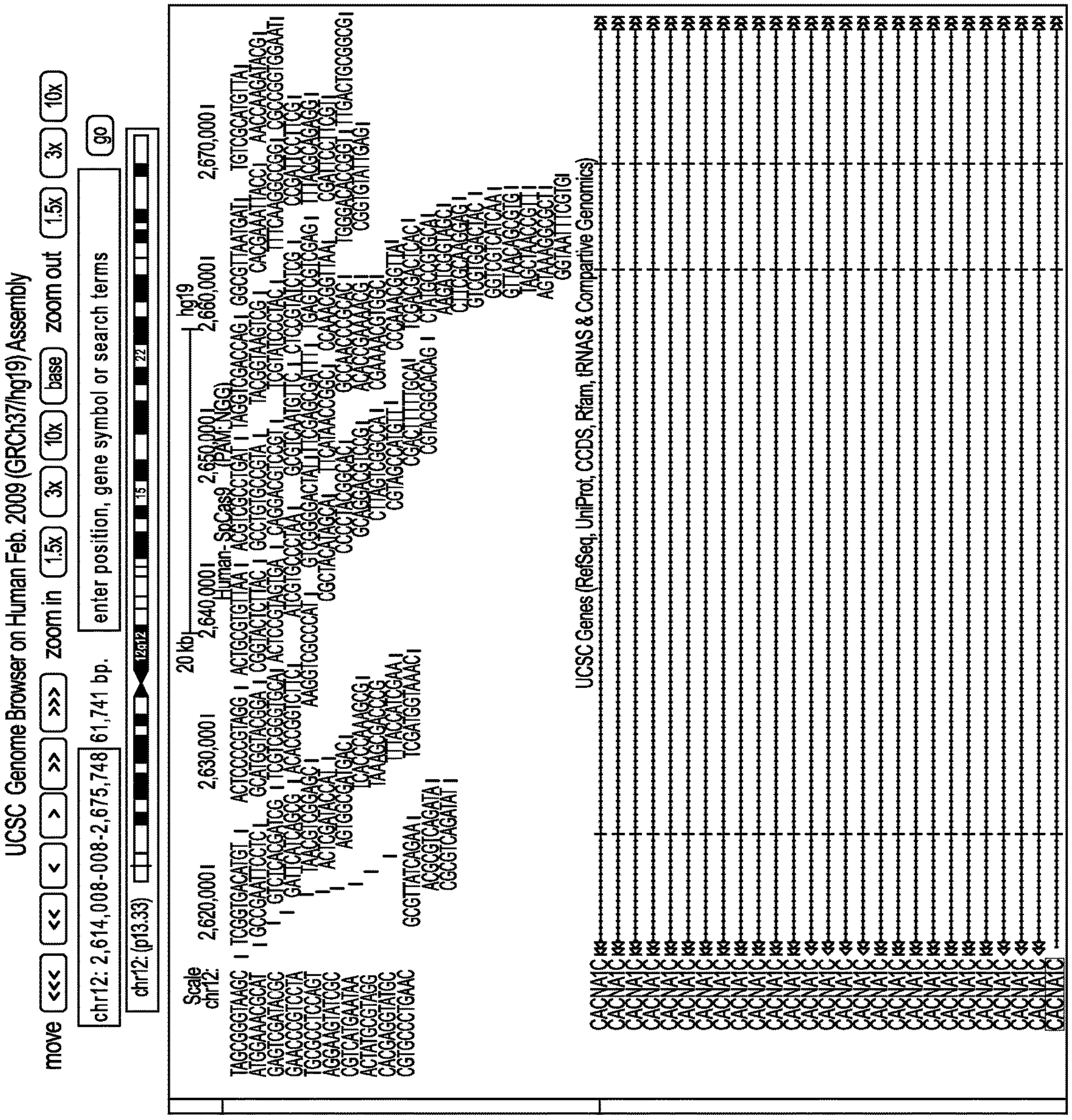
FIG. 18 shows an exemplary visualization of some *S. pyogenes* Cas9 target sites in the human genome using the UCSC genome browser.
Figure 19A:
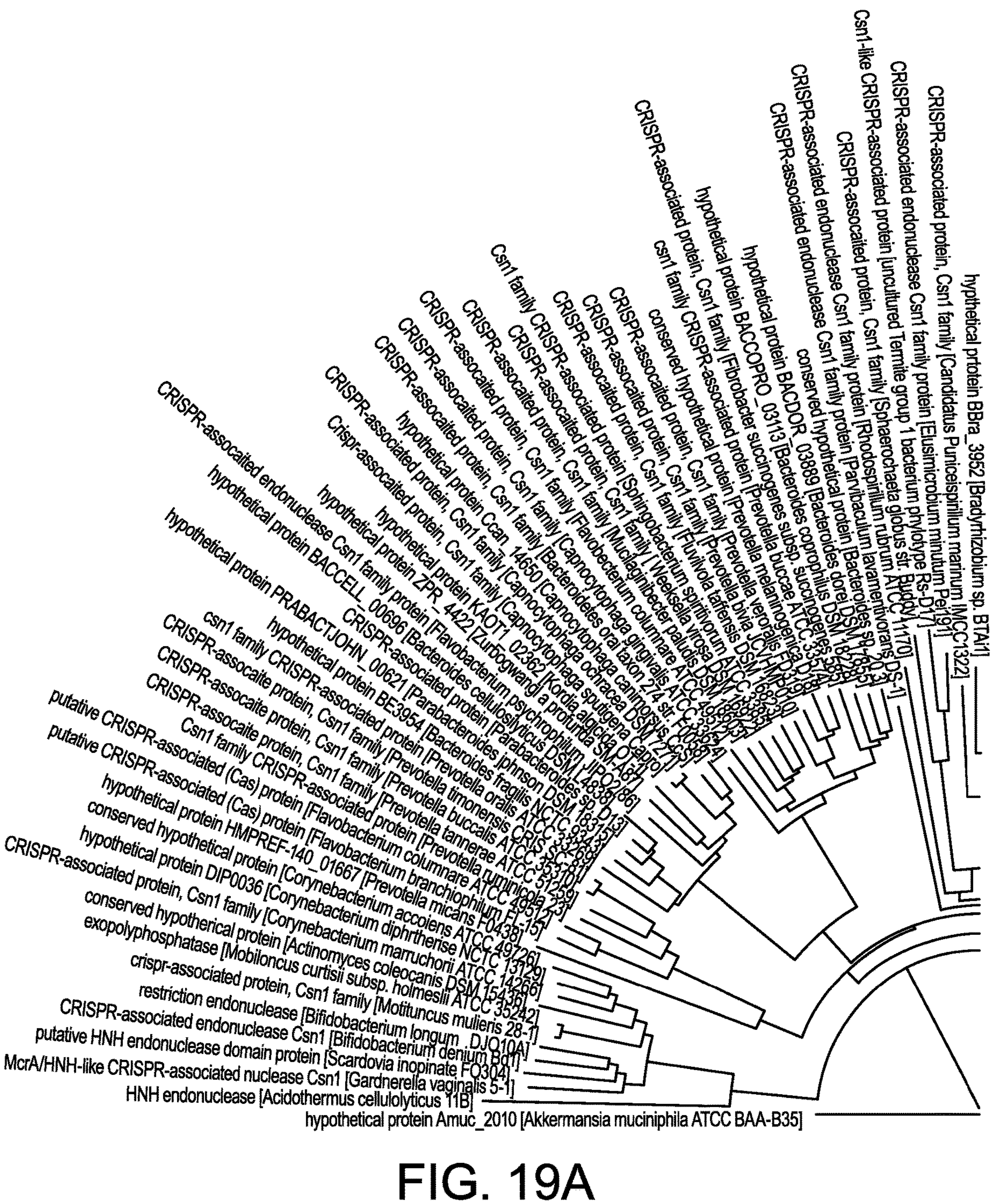
FIG. 19A-19D shows a circular depiction of the phylogenetic analysis revealing five families of Cas9s, including three groups of large Cas9s (~1400 amino acids) and two of small Cas9s (~1100 amino acids).
Figure 19B:
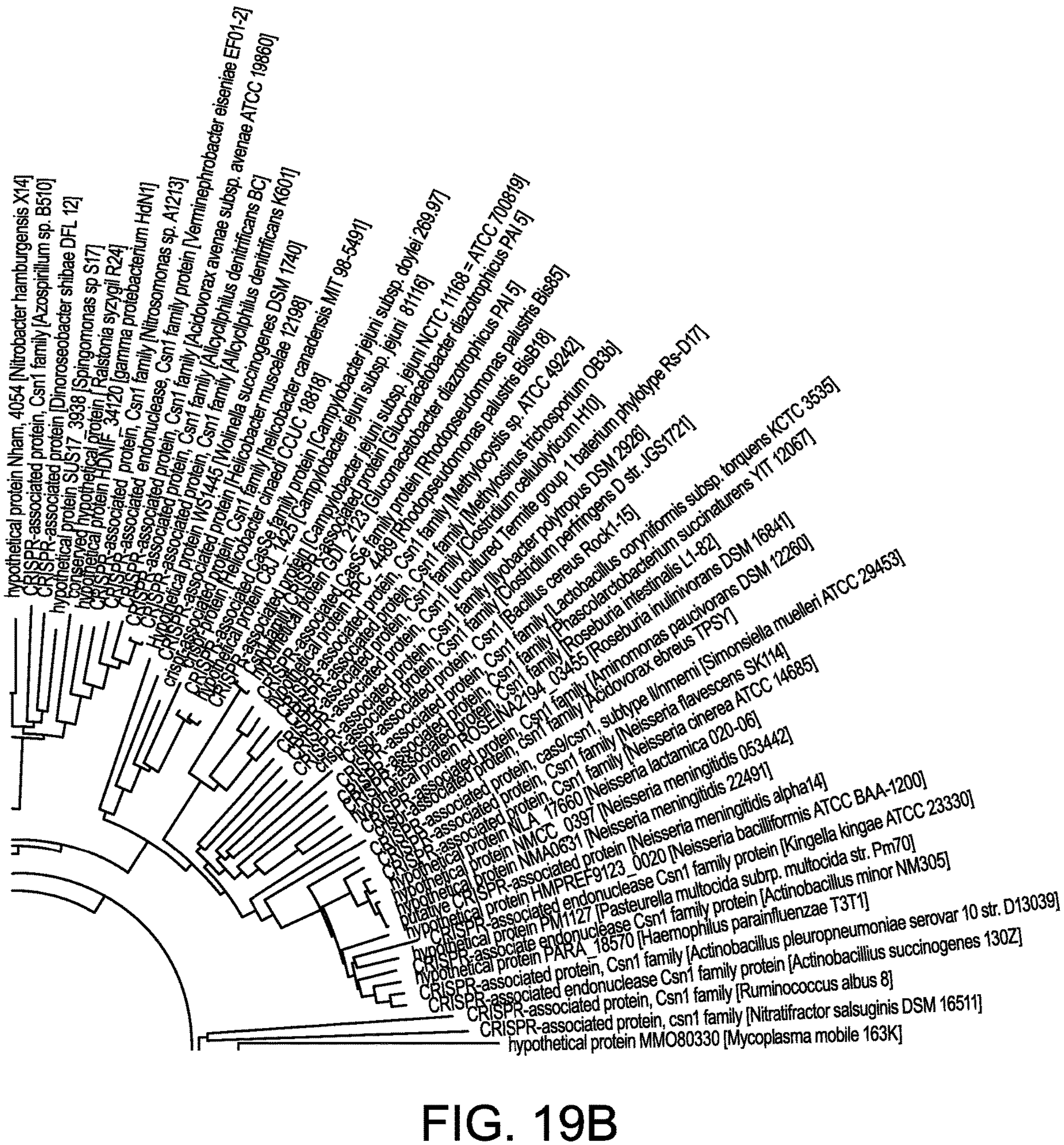
Figure 19C:
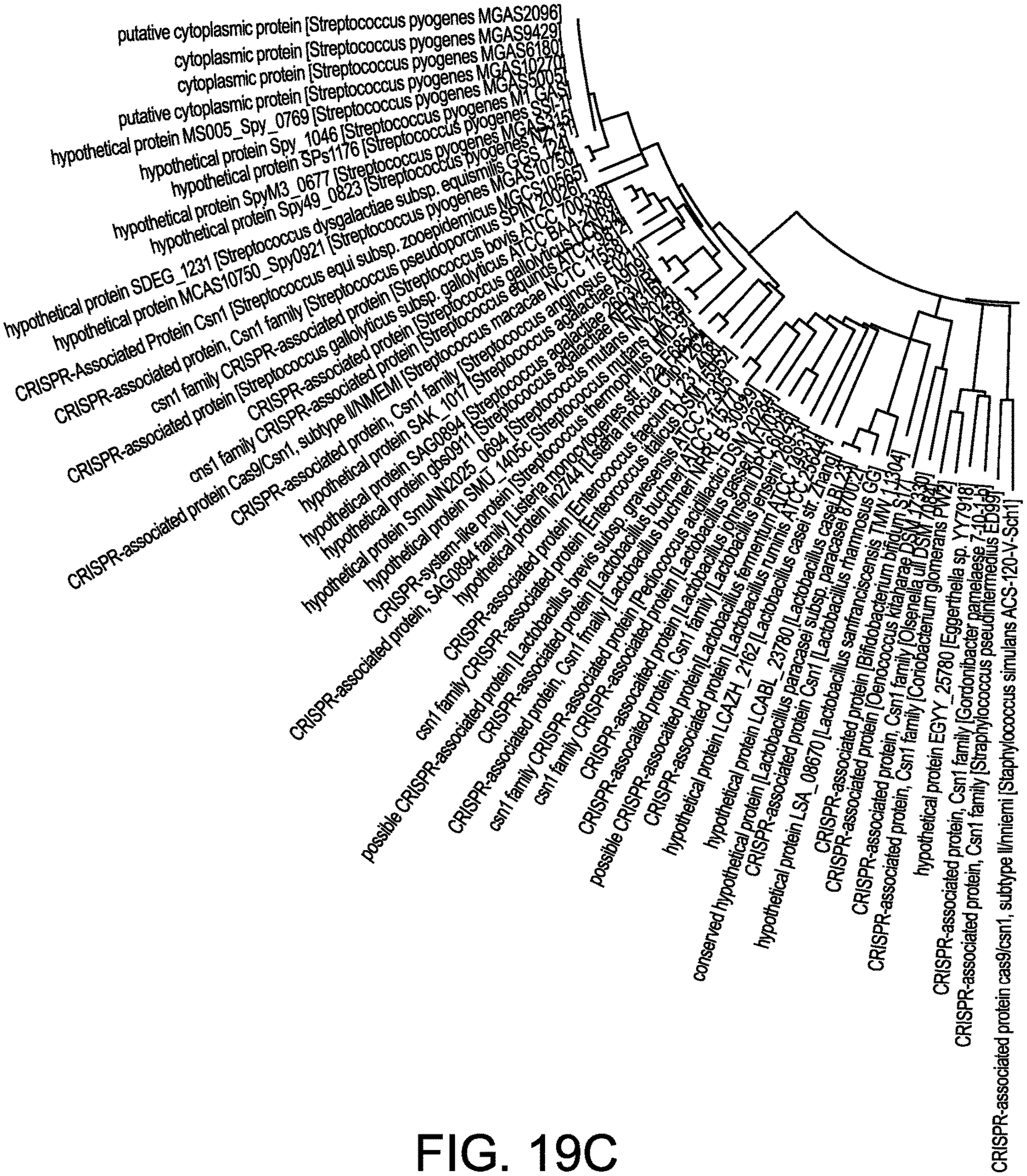
Figure 19D:
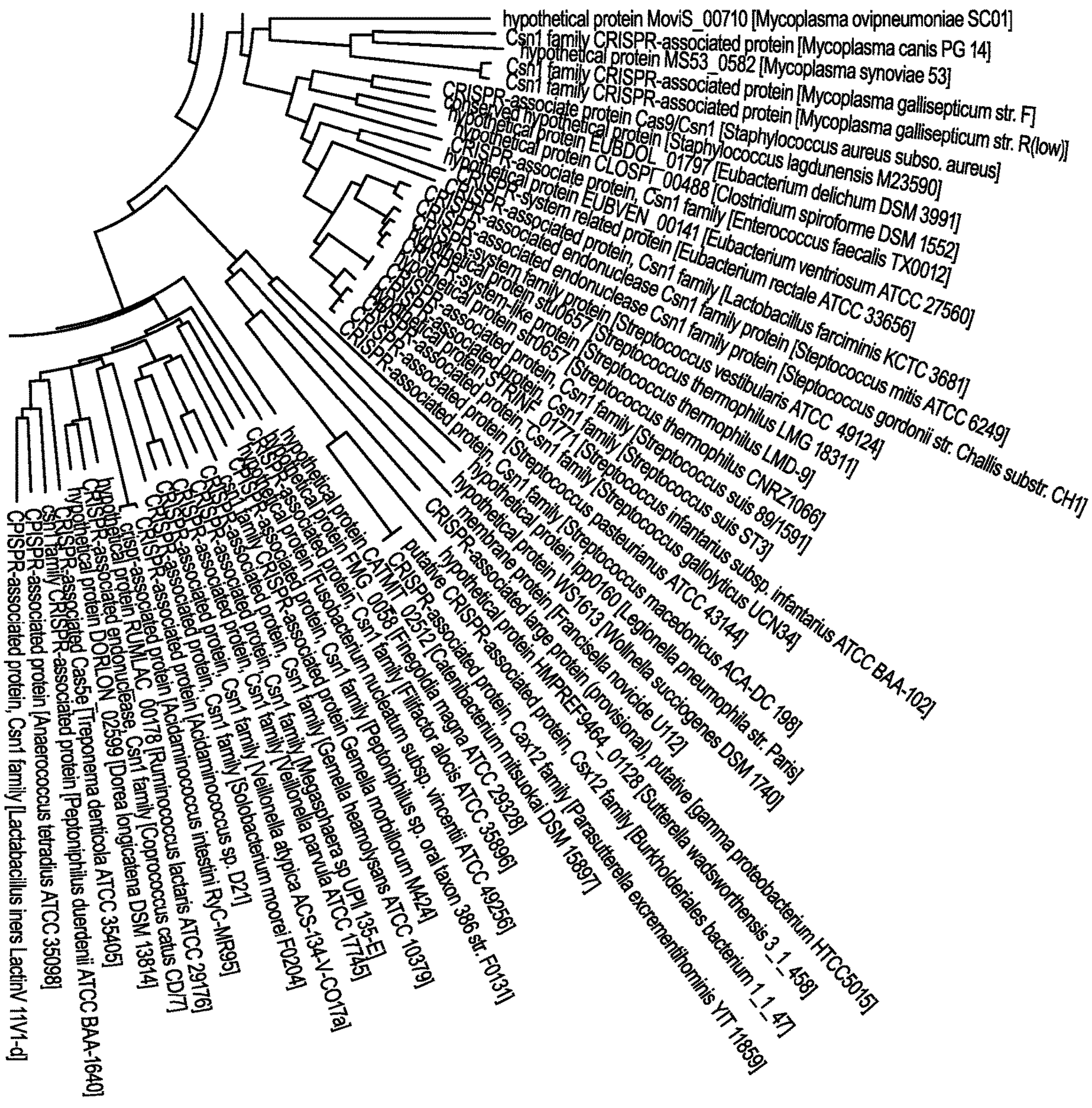
Figure 20A:
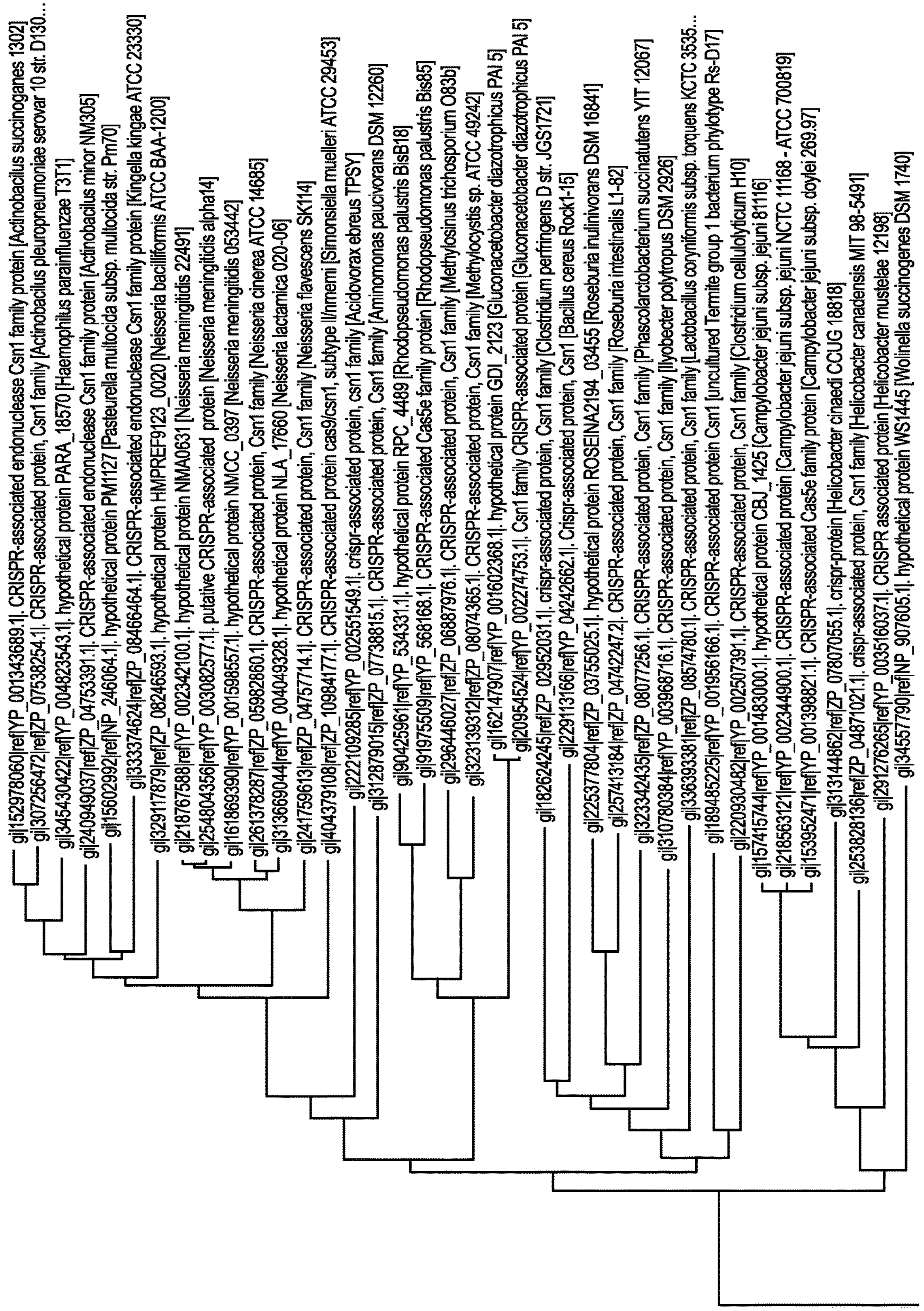
FIG. 20A-20F shows the linear depiction of the phylogenetic analysis revealing five families of Cas9s, including three groups of large Cas9s (~1400 amino acids) and two of small Cas9s (~1100 amino acids).
Figure 20B:
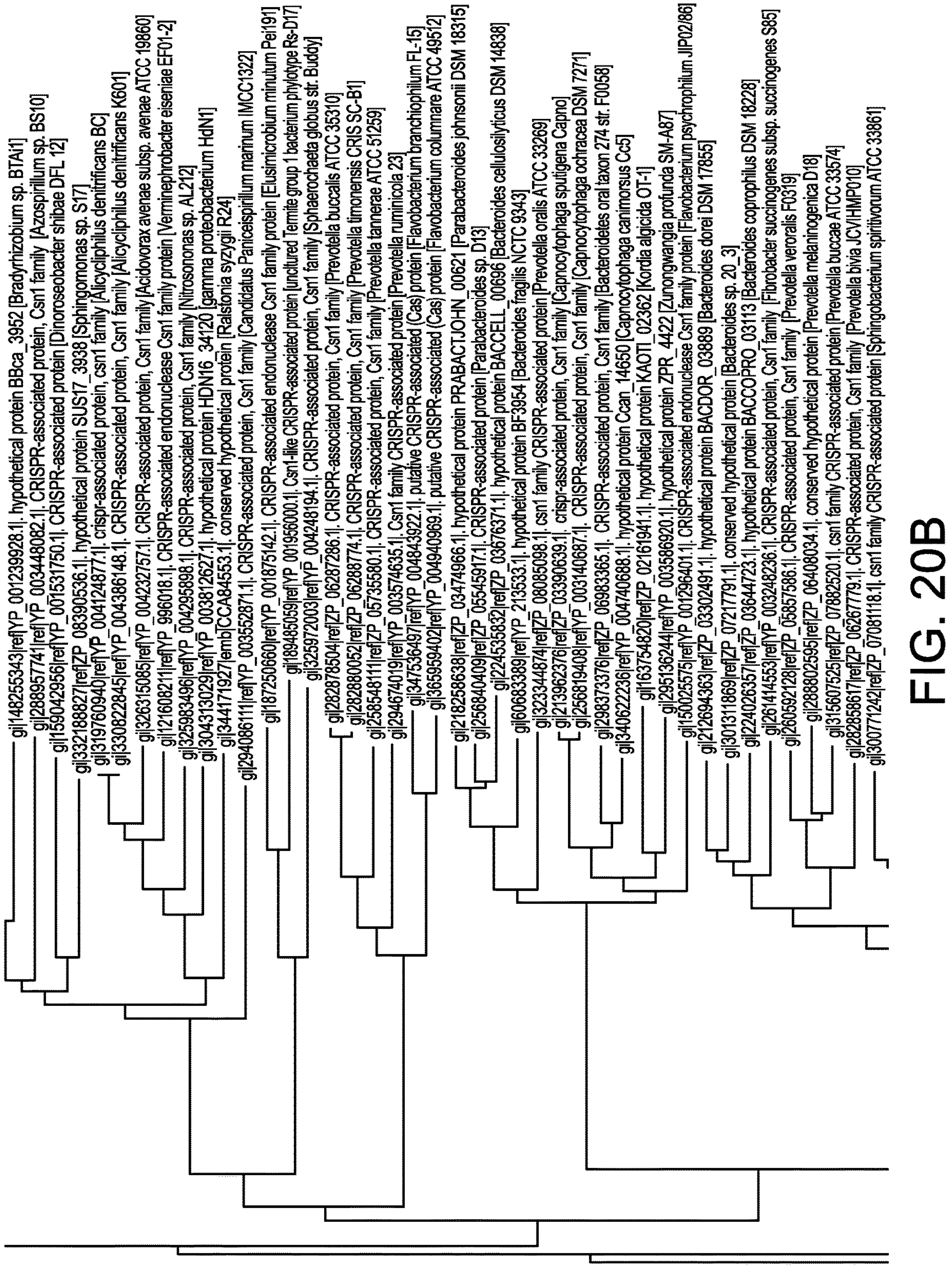
Figure 20C:
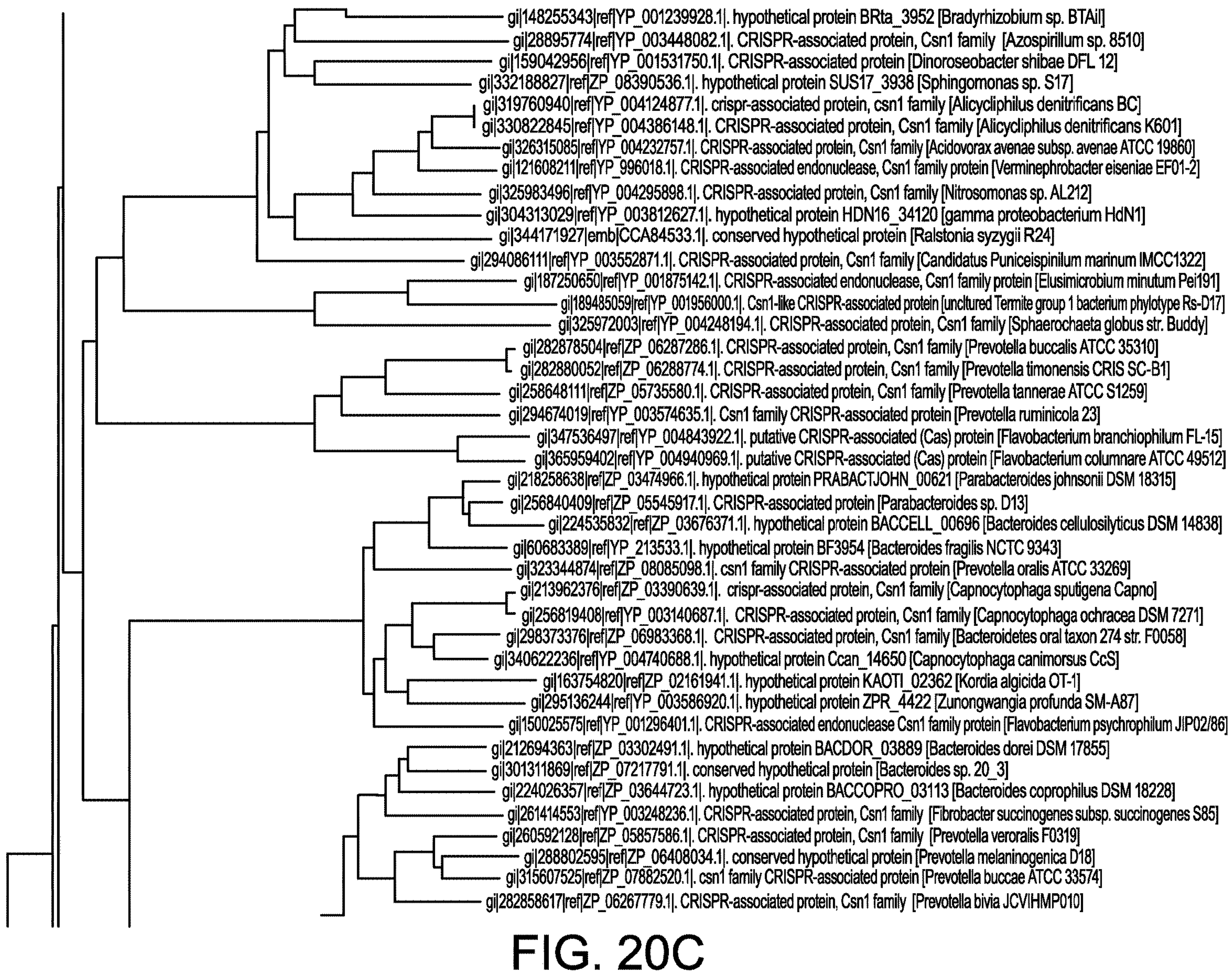
Figure 20D:
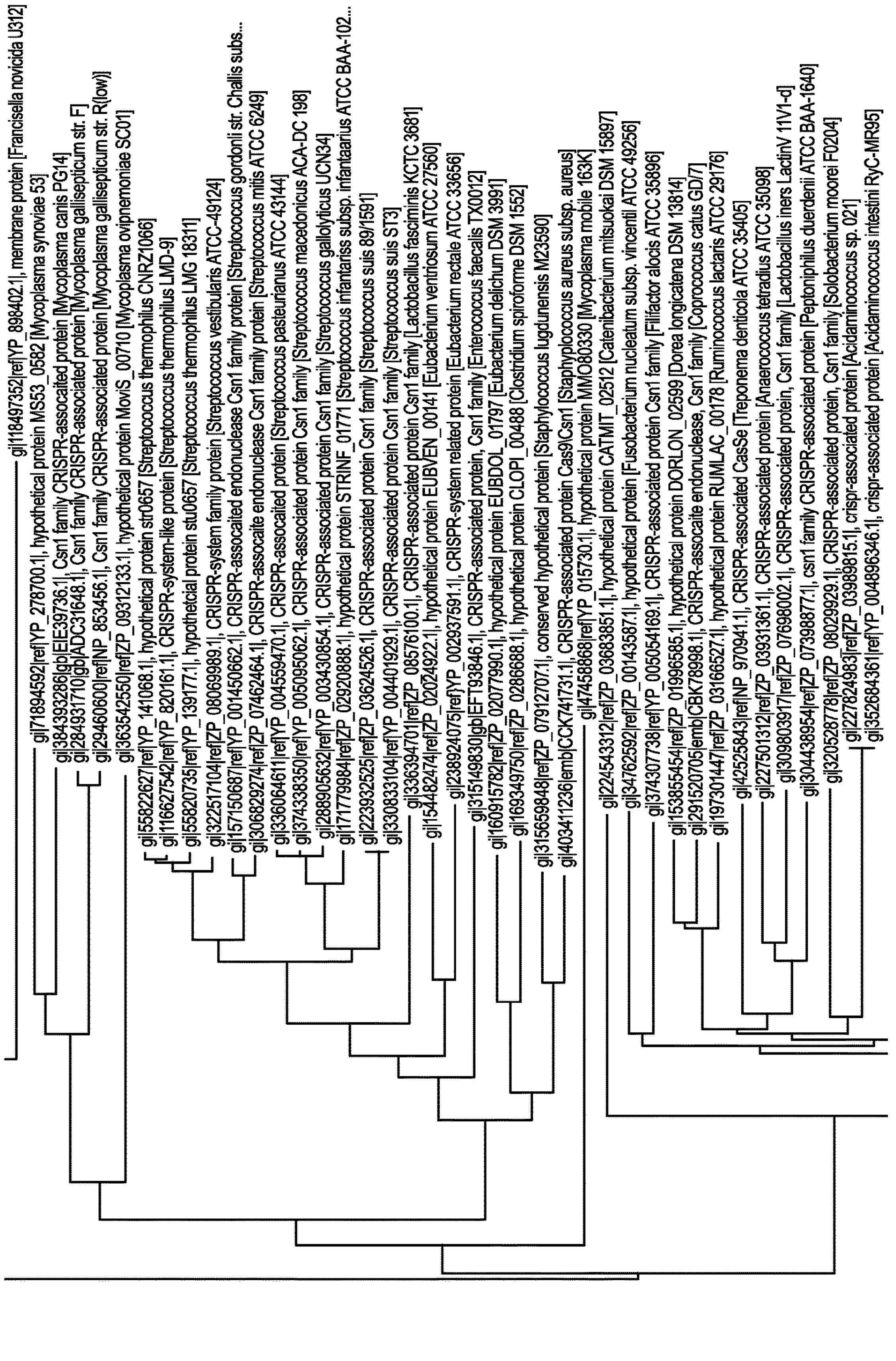
Figure 20E:
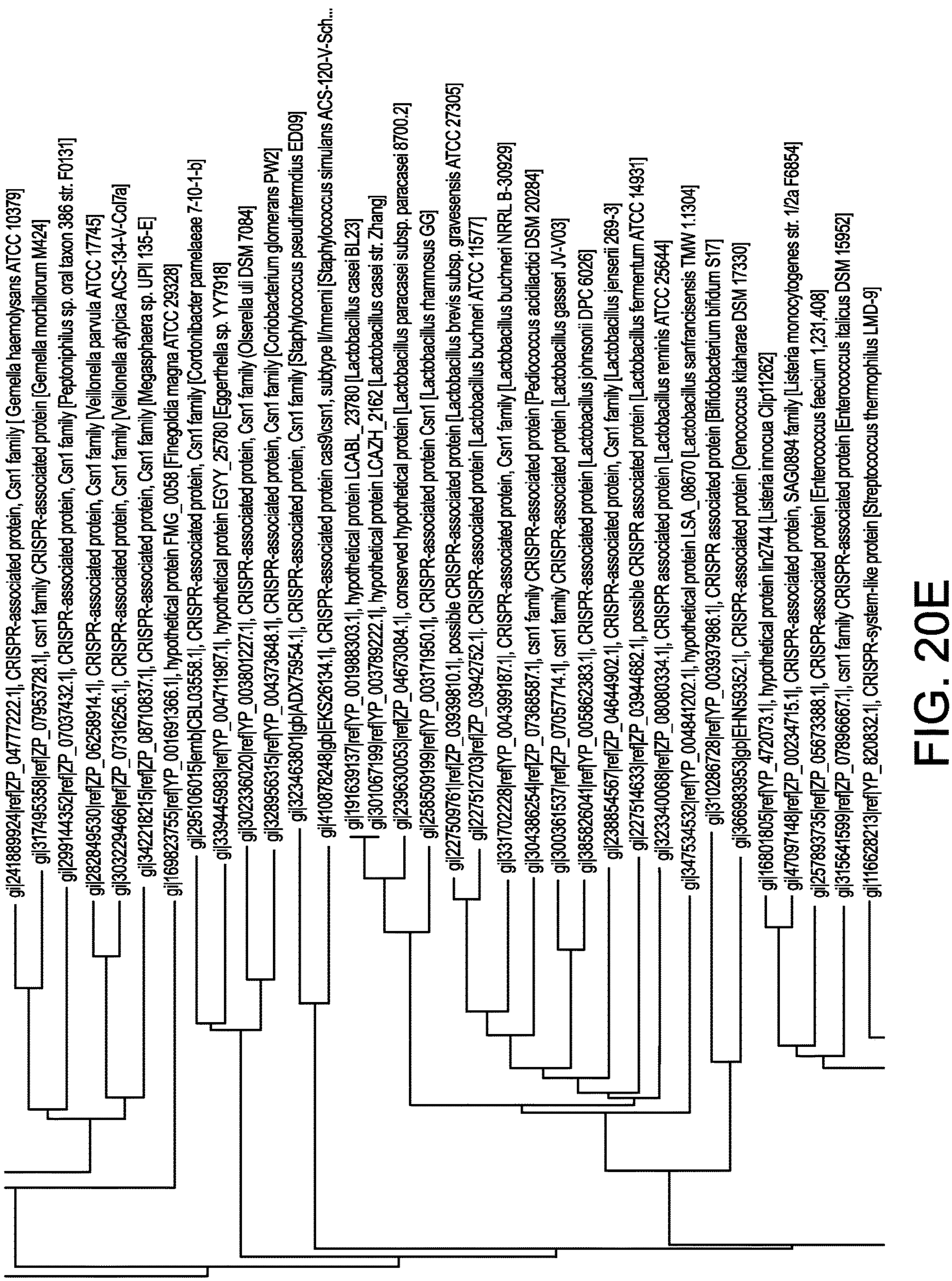
Figure 20F:
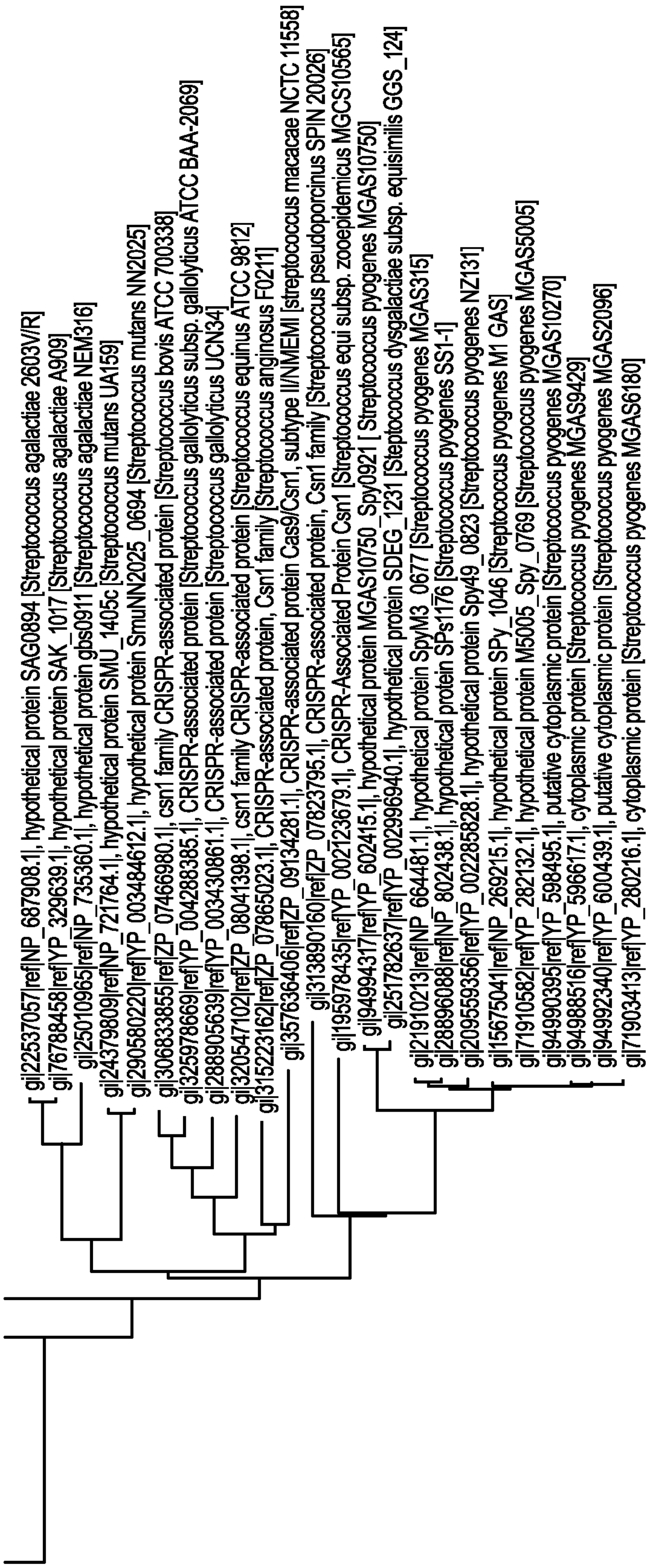
Figure 21A:
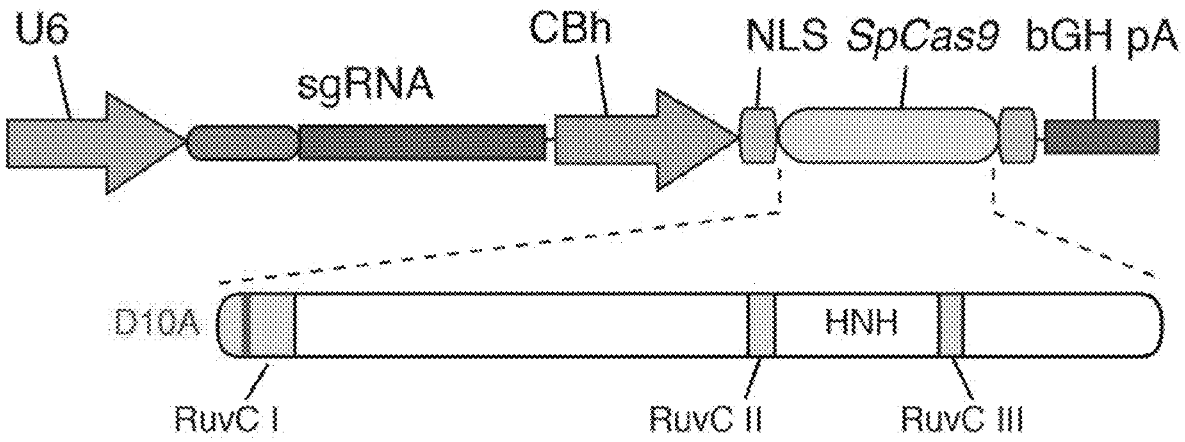
FIG. 21A-21D (a-d) shows genome editing via homologous recombination. (a) Schematic of SpCas9 nickase, with D10A mutation in the RuvC I catalytic domain. (b) Schematic representing homologous recombination (HR) at the human EMX1 locus using either sense or antisense single stranded oligonucleotides as repair templates. Red arrow above indicates sgRNA cleavage site; PCR primers for genotyping (Tables J and K) are indicated as arrows in right panel. (c) Sequence of region modified by HR.
Figure 21B:
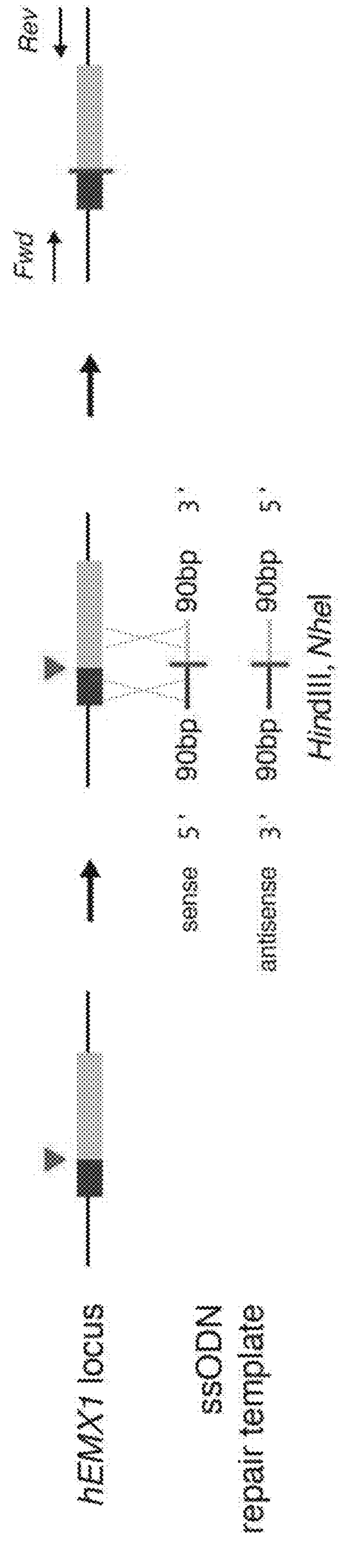
Figure 21C:
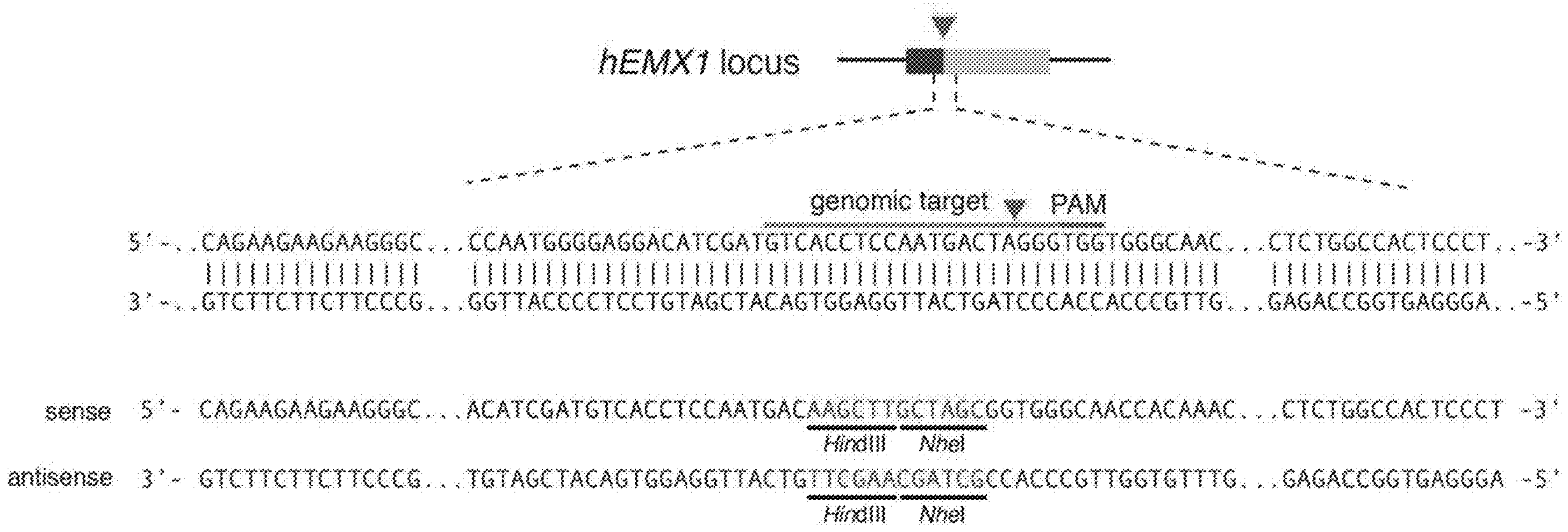
Figure 21D:
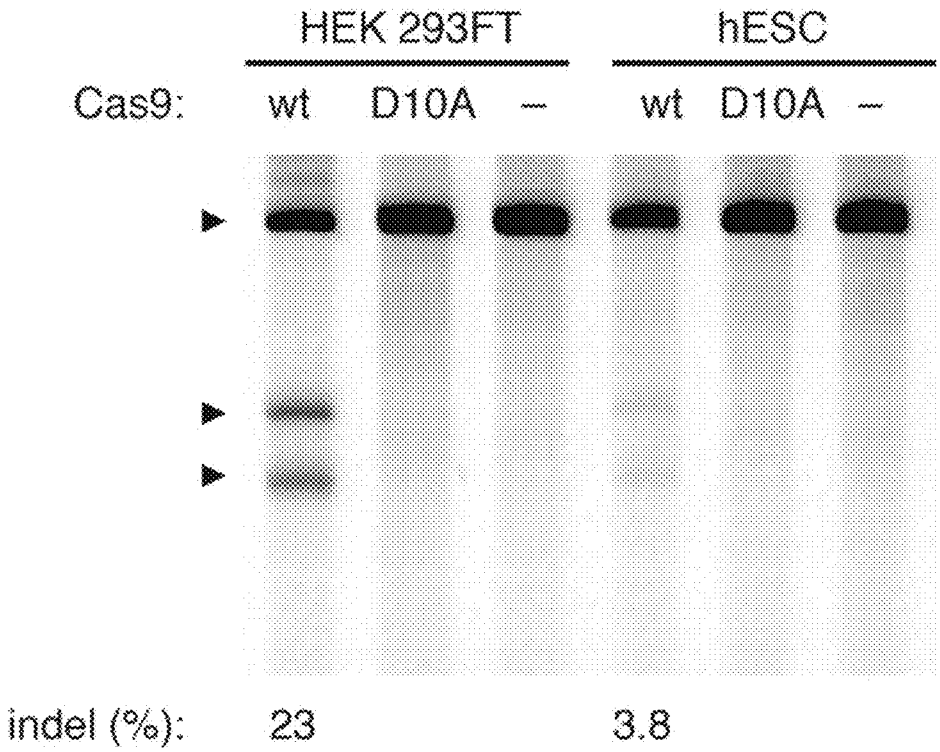

Since multiple occurrences in the genome of the DNA target site may lead to nonspecific genome editing, after identifying all potential sites, the program filters out sequences based on the number of times they appear in the relevant reference genome. For those CRISPR enzymes for which sequence specificity is determined by a 'seed' sequence, such as the 11-12 bp 5' from the PAM sequence, including the PAM sequence itself, the filtering step may be based on the seed sequence. Thus, to avoid editing at additional genomic loci, results are filtered based on the number of occurrences of the seed:PAM sequence in the relevant genome. The user may be allowed to choose the length of the seed sequence. The user may also be allowed to specify the number of occurrences of the seed:PAM sequence in a genome for purposes of passing the filter. The default is to screen for unique sequences. Filtration level is altered by changing both the length of the seed sequence and the number of occurrences of the sequence in the genome. The program may in addition or alternatively provide the sequence of a guide sequence complementary to the reported target sequence(s) by providing the reverse complement of the identified target sequence(s). An example visualization of some target sites in the human genome is provided in FIG. 18.

Further details of methods and algorithms to optimize sequence selection can be found in U.S. application Ser. No. 61/064,798; incorporated herein by reference.

Example 4: Evaluation of Multiple Chimeric crRNA-tracrRNA Hybrids

Figure 16A:
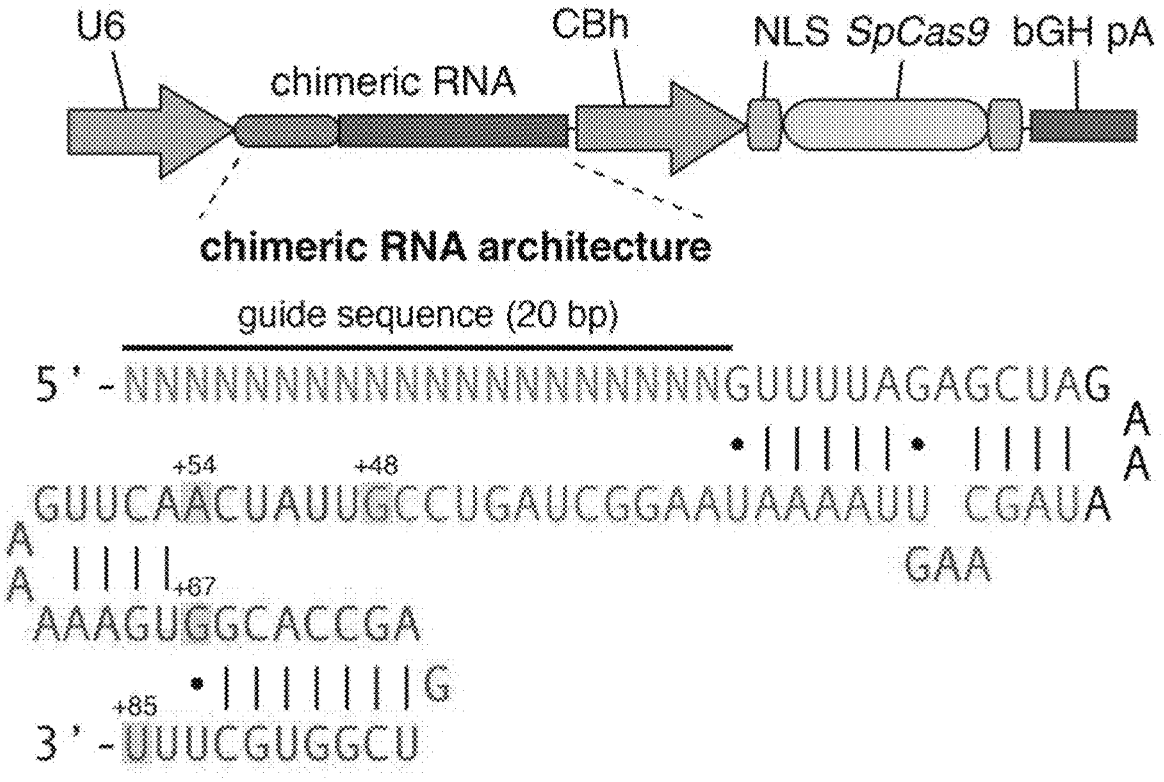
FIG. 16A-16C shows exemplary manipulation of a CRISPR system with chimeric RNAs and results of SURVEYOR assays for system activity in eukaryotic cells.
Figure 16B:
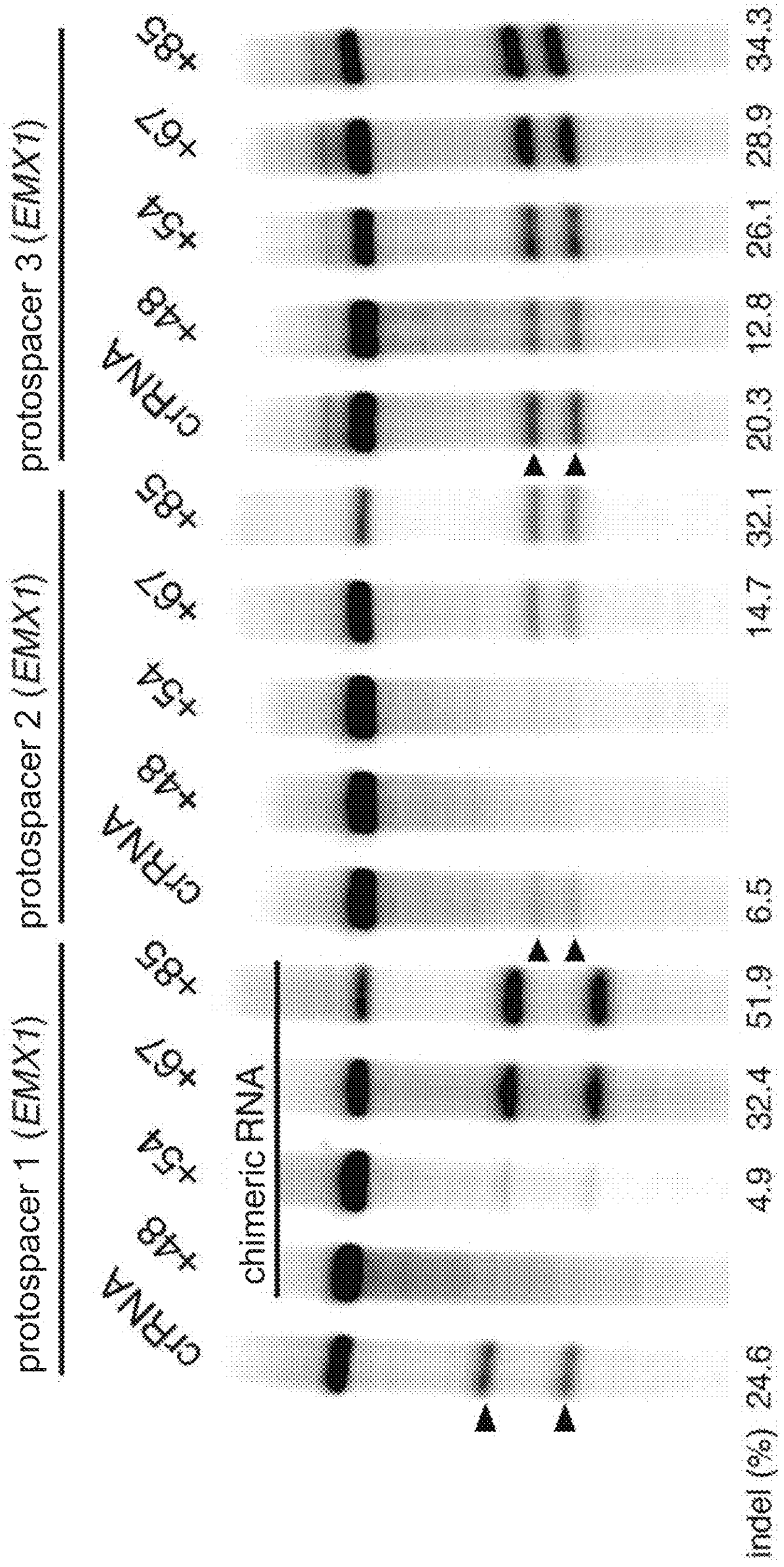
Figure 16C:
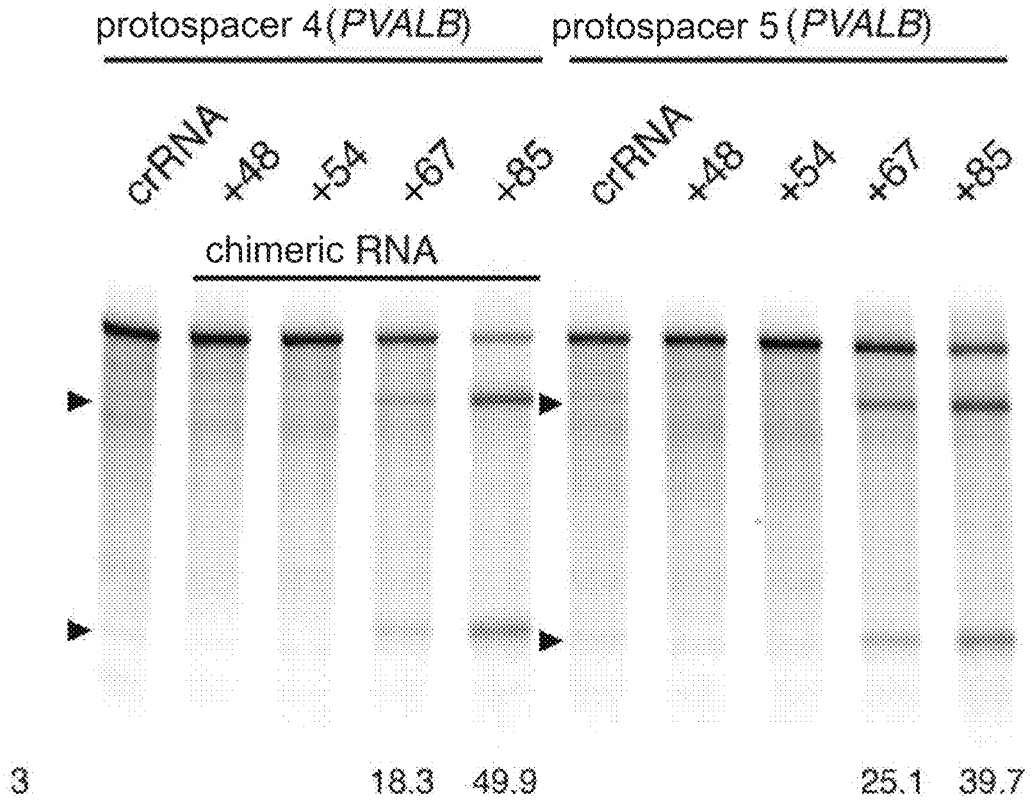

This example describes results obtained for chimeric RNAs (chiRNAs; comprising a guide sequence, a tracr mate sequence, and a tracr sequence in a single transcript) having tracr sequences that incorporate different lengths of wild-type tracrRNA sequence. FIG. 16*a* illustrates a schematic of a bicistronic expression vector for chimeric RNA and Cas9. Cas9 is driven by the CBh promoter and the chimeric RNA is driven by a U6 promoter. The chimeric guide RNA consists of a 20 bp guide sequence (Ns) joined to the tracr sequence (running from the first "U" of the lower strand to the end of the transcript), which is truncated at various positions as indicated. The guide and tracr sequences are separated by the tracr-mate sequence GUUUUAGAGCUA (SEQ ID NO: 14) followed by the loop sequence GAAA. Results of SURVEYOR assays for Cas9-mediated indels at the human EMX1 and PVALB loci are illustrated in FIGS. 16*b* and 16*c*, respectively. Arrows indicate the expected SURVEYOR fragments. ChiRNAs are indicated by their "+n" designation, and crRNA refers to a hybrid RNA where guide and tracr sequences are expressed as separate transcripts. Quantification of these results, performed in triplicate, are illustrated by histogram in FIGS. 17*a* and 17*b*, corresponding to FIGS. 16*b* and 16*c*, respectively ("N.D." indicates no indels detected). Protospacer IDs and their corresponding genomic target, protospacer sequence, PAM sequence, and strand location are provided in Table D. Guide sequences were designed to be complementary to the entire protospacer sequence in the case of separate transcripts in the hybrid system, or only to the underlined portion in the case of chimeric RNAs.

TABLE D (SEQ ID NOs: 15-19, respectively, in order of appearance)

| protospacer ID | genomic target | protospacer sequence (5' to 3') | PAM | strand |
|---|---|---|---|---|
| 1 | EMX1 | GGACATCGAT<u>GTCACCTCCAATGACTAGGG</u> | TGG | + |
| 2 | EMX1 | CATTGGAGGT<u>GACATCGATGTCCTCCCCAT</u> | TGG | - |
| 3 | EMX1 | GGAAGGGCCT<u>GAGTCCGAGCAGAAGAAGAA</u> | GGG | + |
| 4 | PVALB | GGTGGCGAGA<u>GGGGCCGAGATTGGGTGTTC</u> | AGG | + |
| 5 | PVALB | ATGCAGGAGG<u>GTGGCGAGAGGGGCCGAGAT</u> | TGG | + |

Further details to optimize guide sequences can be found in U.S. application Ser. No. 61/836,127; incorporated herein by reference.

Figure 17B:
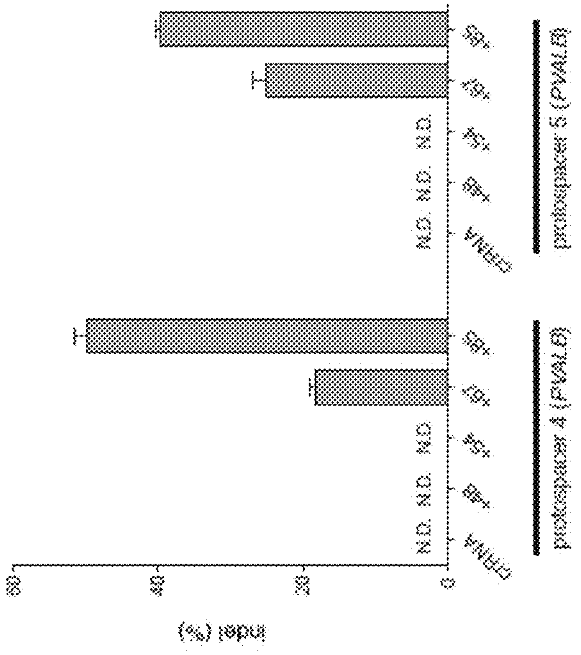
FIG. 17A-17B shows a graphical representation of the results of SURVEYOR assays for CRISPR system activity in eukaryotic cells.
Figure 17A:
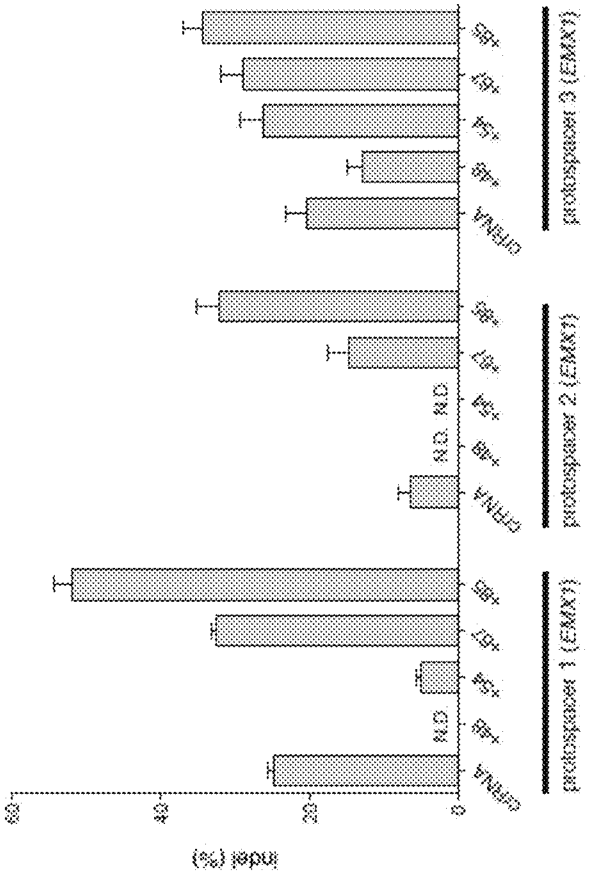

Initially, three sites within the EMX1 locus in human HEK 293FT cells were targeted. Genome modification efficiency of each chiRNA was assessed using the SURVEYOR nuclease assay, which detects mutations resulting from DNA double-strand breaks (DSBs) and their subsequent repair by the non-homologous end joining (NHEJ) DNA damage repair pathway. Constructs designated chiRNA(+n) indicate that up to the +n nucleotide of wild-type tracrRNA is included in the chimeric RNA construct, with values of 48, 54, 67, and 85 used for n. Chimeric RNAs containing longer fragments of wild-type tracrRNA (chiRNA(+67) and chiRNA(+85)) mediated DNA cleavage at all three EMX1 target sites, with chiRNA(+85) in particular demonstrating significantly higher levels of DNA cleavage than the corresponding crRNA/tracrRNA hybrids that expressed guide and tracr sequences in separate transcripts (FIGS. 16*b* and 17*a*). Two sites in the PVALB locus that yielded no detectable cleavage using the hybrid system (guide sequence and tracr sequence expressed as separate transcripts) were also targeted using chiRNAs. chiRNA(+67) and chiRNA(+85) were able to mediate significant cleavage at the two PVALB protospacers (FIGS. 16*c* and 17*b*).

For all five targets in the EMX1 and PVALB loci, a consistent increase in genome modification efficiency with increasing tracr sequence length was observed. Without wishing to be bound by any theory, the secondary structure formed by the 3' end of the tracrRNA may play a role in enhancing the rate of CRISPR complex formation.

Example 5: Cas9 Diversity

The CRISPR-Cas system is an adaptive immune mechanism against invading exogenous DNA employed by diverse species across bacteria and archaea. The type II CRISPR-Cas9 system consists of a set of genes encoding proteins responsible for the "acquisition" of foreign DNA into the CRISPR locus, as well as a set of genes encoding the "execution" of the DNA cleavage mechanism; these include the DNA nuclease (Cas9), a non-coding transactivating cr-RNA (tracrRNA), and an array of foreign DNA-derived spacers flanked by direct repeats (crRNAs). Upon maturation by Cas9, the tracRNA and crRNA duplex guide the Cas9 nuclease to a target DNA sequence specified by the spacer guide sequences, and mediates double-stranded breaks in the DNA near a short sequence motif in the target DNA that is required for cleavage and specific to each CRISPR-Cas system. The type II CRISPR-Cas systems are found throughout the bacterial kingdom and highly diverse in in Cas9 protein sequence and size, tracrRNA and crRNA direct repeat sequence, genome organization of these elements, and the motif requirement for target cleavage. One species may have multiple distinct CRISPR-Cas systems.

Applicants evaluated 207 putative Cas9s from bacterial species identified based on sequence homology to known Cas9s and structures orthologous to known subdomains, including the HNH endonuclease domain and the RuvC endonuclease domains [information from the Eugene Koonin and Kira Makarova]. Phylogenetic analysis based on the protein sequence conservation of this set revealed five families of Cas9s, including three groups of large Cas9s (~1400 amino acids) and two of small Cas9s (~1100 amino acids) (see FIGS. 19 and 20A-F). Further details of Cas9s and mutations of the Cas9 enzyme to convert into a nickase or DNA binding protein and use of same with altered functionality can be found in U.S. application Ser. Nos. 61/836,101 and 61/835,936 incorporated herein by reference.

Example 6: Cas9 Orthologs

Applicants analyzed Cas9 orthologs to identify the relevant PAM sequences and the corresponding chimeric guide RNA. Having an expanded set of PAMs provides broader targeting across the genome and also significantly increases the number of unique target sites and provides potential for identifying novel Cas9s with increased levels of specificity in the genome.

The specificity of Cas9 orthologs can be evaluated by testing the ability of each Cas9 to tolerate mismatches between the guide RNA and its DNA target. For example, the specificity of SpCas9 has been characterized by testing the effect of mutations in the guide RNA on cleavage efficiency. Libraries of guide RNAs were made with single or multiple mismatches between the guide sequence and the target DNA. Based on these findings, target sites for SpCas9 can be selected based on the following guidelines:

To maximize SpCas9 specificity for editing a particular gene, one should choose a target site within the locus of interest such that potential 'off-target' genomic sequences abide by the following four constraints: First and foremost, they should not be followed by a PAM with either 5'-NGG or NAG sequences. Second, their global sequence similarity to the target sequence should be minimized. Third, a maximal number of mismatches should lie within the PAM-proximal region of the off-target site. Finally, a maximal number of mismatches should be consecutive or spaced less than four bases apart.

Similar methods can be used to evaluate the specificity of other Cas9 orthologs and to establish criteria for the selection of specific target sites within the genomes of target species. As mentioned previously phylogenetic analysis based on the protein sequence conservation of this set revealed five families of Cas9s, including three groups of large Cas9s (~1400 amino acids) and two of small Cas9s (~100 amino acids) (see FIGS. 19 and 20A-F). Further details on Cas orthologs can be found in U.S. application Serial Nos 61/836,101 and 61/835,936 incorporated herein by reference.

Example 7: Engineering of Plants (Micro-Algae) Using Cas9 to Target and Manipulate Plant Genes Methods of Delivering Cas9

- Method 1: Applicants deliver Cas9 and guide RNA using a vector that expresses Cas9 under the control of a constitutive promoter such as Hsp70A-Rbc S2 or Beta2-tubulin.
- Method 2: Applicants deliver Cas9 and T7 polymerase using vectors that expresses Cas9 and T7 polymerase under the control of a constitutive promoter such as Hsp70A-Rbc S2 or Beta2-tubulin. Guide RNA will be delivered using a vector containing T7 promoter driving the guide RNA.
- Method 3: Applicants deliver Cas9 mRNA and in vitro transcribed guide RNA to algae cells. RNA can be in vitro transcribed. Cas9 mRNA will consist of the coding region for Cas9 as well as 3'UTR from Cop1 to ensure stabilization of the Cas9 mRNA.

For Homologous recombination, Applicants provide an additional homology directed repair template.

Sequence for a cassette driving the expression of Cas9 under the control of beta-2 tubulin promoter, followed by the 3' UTR of Cop1.

```
(SEQ ID NO: 20)
TCTTTCTTGCGCTATGACACTTCCAGCAAAAGGTA

GGGCGGGCTGCGAGACGGCTTCCCGGCGCTGCATG

CAACACCGATGATGCTTCGACCCCCCGAAGCTCCT

TCGGGGCTGCATGGGCGCTCCGATGCCGCTCCAGG

GCGAGCGCTGTTTAAATAGCCAGGCCCCCGATTGC

AAAGACATTATAGCGAGCTACCAAAGCCATATTCA

AACACCTAGATCACTACCACTTCTACACAGGCCAC

TCGAGCTTGTGATCGCACTCCGCTAAGGGGGCGCC

TCTTCCTCTTCGTTTCAGTCACAACCCGCAAACAT

GTACCCATACGATGTTCCAGATTACGCTTCGCCGA

AGAAAAAGCGCAAGGTCGAAGCGTCCGACAAGAAG

TACAGCATCGGCCTGGACATCGGCACCAACTCTGT
```

GGGCTGGGCCGTGATCACCGACGAGTACAAGGTGC
CCAGCAAGAAATTCAAGGTGCTGGGCAACACCGAC
CGGCACAGCATCAAGAAGAACCTGATCGGAGCCCT
GCTGTTCGACAGCGGCGAAACAGCCGAGGCCACCC
GGCTGAAGAGAACCGCCAGAAGAAGATACACCAGA
CGGAAGAACCGGATCTGCTATCTGCAAGAGATCTT
CAGCAACGAGATGGCCAAGGTGGACGACAGCTTCT
TCCACAGACTGGAAGAGTCCTTCCTGGTGGAAGAG
GATAAGAAGCACGAGCGGCACCCCATCTTCGGCAA
CATCGTGGACGAGGTGGCCTACCACGAGAAGTACC
CCACCATCTACCACCTGAGAAAGAAACTGGTGGAC
AGCACCGACAAGGCCGACCTGCGGCTGATCTATCT
GGCCCTGGCCCACATGATCAAGTTCCGGGGCCACT
TCCTGATCGAGGGCGACCTGAACCCCGACAACAGC
GACGTGGACAAGCTGTTCATCCAGCTGGTGCAGAC
CTACAACCAGCTGTTCGAGGAAAACCCCATCAACG
CCAGCGGCGTGGACGCCAAGGCCATCCTGTCTGCC
AGACTGAGCAAGAGCAGACGGCTGGAAAATCTGAT
CGCCCAGCTGCCCGGCGAGAAGAAGAATGGCCTGT
TCGGCAACCTGATTGCCCTGAGCCTGGGCCTGACC
CCCAACTTCAAGAGCAACTTCGACCTGGCCGAGGA
TGCCAAACTGCAGCTGAGCAAGGACACCTACGACG
ACGACCTGGACAACCTGCTGGCCCAGATCGGCGAC
CAGTACGCCGACCTGTTTCTGGCCGCCAAGAACCT
GTCCGACGCCATCCTGCTGAGCGACATCCTGAGAG
TGAACACCGAGATCACCAAGGCCCCCCTGAGCGCC
TCTATGATCAAGAGATACGACGAGCACCACCAGGA
CCTGACCCTGCTGAAAGCTCTCGTGCGGCAGCAGC
TGCCTGAGAAGTACAAAGAGATTTTCTTCGACCAG
AGCAAGAACGGCTACGCCGGCTACATTGACGGCGG
AGCCAGCCAGGAAGAGTTCTACAAGTTCATCAAGC
CCATCCTGGAAAAGATGGACGGCACCGAGGAACTG
CTCGTGAAGCTGAACAGAGAGGACCTGCTGCGGAA
GCAGCGGACCTTCGACAACGGCAGCATCCCCCACC
AGATCCACCTGGGAGAGCTGCACGCCATTCTGCGG
CGGCAGGAAGATTTTTACCCATTCCTGAAGGACAA
CCGGGAAAAGATCGAGAAGATCCTGACCTTCCGCA
TCCCCTACTACGTGGGCCCTCTGGCCAGGGGAAAC
AGCAGATTCGCCTGGATGACCAGAAAGAGCGAGGA
AACCATCACCCCCTGGAACTTCGAGGAAGTGGTGG
ACAAGGGCGCTTCCGCCCAGAGCTTCATCGAGCGG

ATGACCAACTTCGATAAGAACCTGCCCAACGAGAA
GGTGCTGCCCAAGCACAGCCTGCTGTACGAGTACT
TCACCGTGTATAACGAGCTGACCAAAGTGAAATAC
GTGACCGAGGGAATGAGAAAGCCCGCCTTCCTGAG
CGGCGAGCAGAAAAAGGCCATCGTGGACCTGCTGT
TCAAGACCAACCGGAAAGTGACCGTGAAGCAGCTG
AAAGAGGACTACTTCAAGAAAATCGAGTGCTTCGA
CTCCGTGGAAATCTCCGGCGTGGAAGATCGGTTCA
ACGCCTCCCTGGGCACATACCACGATCTGCTGAAA
ATTATCAAGGACAAGGACTTCCTGGACAATGAGGA
AAACGAGGACATTCTGGAAGATATCGTGCTGACCC
TGACACTGTTTGAGGACAGAGAGATGATCGAGGAA
CGGCTGAAAACCTATGCCCACCTGTTCGACGACAA
AGTGATGAAGCAGCTGAAGCGGCGGAGATACACCG
GCTGGGGCAGGCTGAGCCGGAAGCTGATCAACGGC
ATCCGGGACAAGCAGTCCGGCAAGACAATCCTGGA
TTTCCTGAAGTCCGACGGCTTCGCCAACAGAAACT
TCATGCAGCTGATCCACGACGACAGCCTGACCTTT
AAAGAGGACATCCAGAAAGCCCAGGTGTCCGGCCA
GGGCGATAGCCTGCACGAGCACATTGCCAATCTGG
CCGGCAGCCCCGCCATTAAGAAGGGCATCCTGCAG
ACAGTGAAGGTGGTGGACGAGCTCGTGAAAGTGAT
GGGCCGGCACAAGCCCGAGAACATCGTGATCGAAA
TGGCCAGAGAGAACCAGACCACCCAGAAGGGACAG
AAGAACAGCCGCGAGAGAATGAAGCGGATCGAAGA
GGGCATCAAAGAGCTGGGCAGCCAGATCCTGAAAG
AACACCCCGTGGAAAACACCCAGCTGCAGAACGAG
AAGCTGTACCTGTACTACCTGCAGAATGGGCGGGA
TATGTACGTGGACCAGGAACTGGACATCAACCGGC
TGTCCGACTACGATGTGGACCATATCGTGCCTCAG
AGCTTTCTGAAGGACGACTCCATCGACAACAAGGT
GCTGACCAGAAGCGACAAGAACCGGGGCAAGAGCG
ACAACGTGCCCTCCGAAGAGGTCGTGAAGAAGATG
AAGAACTACTGGCGGCAGCTGCTGAACGCCAAGCT
GATTACCCAGAGAAAGTTCGACAATCTGACCAAGG
CCGAGAGAGGCGGCCTGAGCGAACTGGATAAGGCC
GGCTTCATCAAGAGACAGCTGGTGGAAACCCGGCA
GATCACAAAGCACGTGGCACAGATCCTGGACTCCC
GGATGAACACTAAGTACGACGAGAATGACAAGCTG
ATCCGGGAAGTGAAAGTGATCACCCTGAAGTCCAA

-continued

GCTGGTGTCCGATTTCCGGAAGGATTTCCAGTTTT

ACAAAGTGCGCGAGATCAACAACTACCACCACGCC

CACGACGCCTACCTGAACGCCGTCGTGGGAACCGC

CCTGATCAAAAAGTACCCTAAGCTGGAAAGCGAGT

TCGTGTACGGCGACTACAAGGTGTACGACGTGCGG

AAGATGATCGCCAAGAGCGAGCAGGAAATCGGCAA

GGCTACCGCCAAGTACTTCTTCTACAGCAACATCA

TGAACTTTTTCAAGACCGAGATTACCCTGGCCAAC

GGCGAGATCCGGAAGCGGCCTCTGATCGAGACAAA

CGGCGAAACCGGGGAGATCGTGTGGGATAAGGGCC

GGGATTTTGCCACCGTGCGGAAAGTGCTGAGCATG

CCCCAAGTGAATATCGTGAAAAAGACCGAGGTGCA

GACAGGCGGCTTCAGCAAAGAGTCTATCCTGCCCA

AGAGGAACAGCGATAAGCTGATCGCCAGAAAGAAG

GACTGGGACCCTAAGAAGTACGGCGGCTTCGACAG

CCCCACCGTGGCCTATTCTGTGCTGGTGGTGGCCA

AAGTGGAAAAGGGCAAGTCCAAGAAACTGAAGAGT

GTGAAAGAGCTGCTGGGGATCACCATCATGGAAAG

AAGCAGCTTCGAGAAGAATCCCATCGACTTTCTGG

AAGCCAAGGGCTACAAAGAAGTGAAAAAGGACCTG

ATCATCAAGCTGCCTAAGTACTCCCTGTTCGAGCT

GGAAAACGGCCGGAAGAGAATGCTGGCCTCTGCCG

GCGAACTGCAGAAGGGAAACGAACTGGCCCTGCCC

TCCAAATATGTGAACTTCCTGTACCTGGCCAGCCA

CTATGAGAAGCTGAAGGGCTCCCCCGAGGATAATG

AGCAGAAACAGCTGTTTGTGGAACAGCACAAGCAC

TACCTGGACGAGATCATCGAGCAGATCAGCGAGTT

CTCCAAGAGAGTGATCCTGGCCGACGCTAATCTGG

ACAAAGTGCTGTCCGCCTACAACAAGCACCGGGAT

AAGCCCATCAGAGAGCAGGCCGAGAATATCATCCA

CCTGTTTACCCTGACCAATCTGGGAGCCCCTGCCG

CCTTCAAGTACTTTGACACCACCATCGACCGGAAG

AGGTACACCAGCACCAAAGAGGTGCTGGACGCCAC

CCTGATCCACCAGAGCATCACCGGCCTGTACGAGA

CACGGATCGACCTGTCTCAGCTGGGAGGCGACAGC

CCCAAGAAGAAGAGAAAGGTGGAGGCCAGCTAAGG

ATCCGGCAAGACTGGCCCCGCTTGGCAACGCAACA

GTGAGCCCCTCCCTAGTGTGTTTGGGGATGTGACT

ATGTATTCGTGTGTTGGCCAACGGGTCAACCCGAA

CAGATTGATACCCGCCTTGGCATTTCCTGTCAGAA

TGTAACGTCAGTTGATGGTACT

Sequence for a cassette driving the expression of T7 polymerase under the control of beta-2 tubulin promoter, followed by the 3' UTR of Cop 1:

(SEQ ID NO: 21)

TCTTTCTTGCGCTATGACACTTCCAGCAAAAGGTA

GGGCGGGCTGCGAGACGGCTTCCCGGCGCTGCATG

CAACACCGATGATGCTTCGACCCCCCGAAGCTCCT

TCGGGGCTGCATGGGCGCTCCGATGCCGCTCCAGG

GCGAGCGCTGTTTAAATAGCCAGGCCCCCGATTGC

AAAGACATTATAGCGAGCTACCAAAGCCATATTCA

AACACCTAGATCACTACCACTTCTACACAGGCCAC

TCGAGCTTGTGATCGCACTCCGCTAAGGGGGCGCC

TCTTCCTCTTCGTTTCAGTCACAACCCGCAAACat gcctaagaagaagaggaaggttaacacgattaaca tcgctaagaacgacttctctgacatcgaactggct gctatcccgttcaacactctggctgaccattacgg tgagcgtttagctcgcgaacagttggcccttgagc atgagtcttacgagatgggtgaagcacgcttccgc aagatgtttgagcgtcaacttaaagctggtgaggt tgcggataacgctgccgccaagcctctcatcacta ccctactccctaagatgattgcacgcatcaacgac tggtttgaggaagtgaaagctaagcgcggcaagcg cccgacagccttccagttcctgcaagaaatcaagc cggaagccgtagcgtacatcaccattaagaccact ctggcttgcctaaccagtgctgacaatacaaccgt tcaggctgtagcaagcgcaatcggtcgggccattg aggacgaggctcgcttcggtcgtatccgtgacctt gaagctaagcacttcaagaaaaacgttgaggaaca actcaacaagcgcgtagggcacgtctacaagaaag catttatgcaagttgtcgaggctgacatgctctct aagggtctactcggtggcgaggcgtggtcttcgtg gcataaggaagactctattcatgtaggagtacgct gcatcgagatgctcattgagtcaaccggaatggtt agcttacaccgccaaaatgctggcgtagtaggtca agactctgagactatcgaactcgcacctgaatacg ctgaggctatcgcaacccgtgcaggtgcgctggct ggcatctctccgatgttccaaccttgcgtagttcc tcctaagccgtggactggcattactggtggtggct attgggctaacggtcgtcgtcctctggcgctggtg cgtactcacagtaagaaagcactgatgcgctacga agacgtttacatgcctgaggtgtacaaagcgatta acattgcgcaaaacaccgcatggaaaatcaacaag -continued aaagtcctagcggtcgccaacgtaatcaccaagtg gaagcattgtccggtcgaggacatccctgcgattg agcgtgaagaactcccgatgaaaccggaagacatc gacatgaatcctgaggctctcaccgcgtggaaacg tgctgccgctgctgtgtaccgcaaggacaaggctc gcaagtctcgccgtatcagccttgagttcatgctt gagcaagccaataagtttgctaaccataaggccat ctggttcccttacaacatggactggcgcggtcgtg tttacgctgtgtcaatgttcaacccgcaaggtaac gatatgaccaaaggactgcttacgctggcgaaagg taaaccaatcggtaaggaaggttactactggctga aaatccacggtgcaaactgtgcgggtgtcgacaag gttccgttccctgagcgcatcaagttcattgagga aaaccacgagaacatcatggcttgcgctaagtctc cactggagaacacttggtgggctgagcaagattct ccgttctgcttccttgcgttctgctttgagtacgc tggggtacagcaccacggcctgagctataactgct cccttccgctggcgtttgacgggtcttgctctggc atccagcacttctccgcgatgctccgagatgaggt aggtggtcgcgcggttaacttgcttcctagtgaaa ccgttcaggacatctacgggattgttgctaagaaa gtcaacgagattctacaagcagacgcaatcaatgg gaccgataacgaagtagttaccgtgaccgatgaga acactggtgaaatctctgagaaagtcaagctgggc actaaggcactggctggtcaatggctggcttacgg tgttactcgcagtgtgactaagcgttcagtcatga cgctggcttacgggtccaaagagttcggcttccgt caacaagtgctggaagataccattcagccagctat tgattccggcaagggtctgatgttcactcagccga atcaggctgctggatacatggctaagctgatttgg gaatctgtgagcgtgacggtggtagctgcggttga agcaatgaactggcttaagtctgctgctaagctgc tggctgctgaggtcaaagataagaagactggagag attcttcgcaagcgttgcgctgtgcattgggtaac tcctgatggtttccctgtgtggcaggaatacaaga agcctattcagacgcgcttgaacctgatgttcctc ggtcagttccgcttacagcctaccattaacaccaa caaagatagcgagattgatgcacacaaacaggagt ctggtatcgctcctaactttgtacacagccaagac ggtagccaccttcgtaagactgtagtgtgggcaca -continued cgagaagtacggaatcgaatcttttgcactgattc acgactccttcggtacgattccggctgacgctgcg aacctgttcaaagcagtgcgcgaaactatggttga cacatatgagtcttgtgatgtactggctgatttct acgaccagttcgctgaccagttgcacgagtctcaa ttggacaaaatgccagcacttccggctaaaggtaa cttgaacctccgtgacatcttagagtcggacttcg cgttcgcgtaaGGATCCGGCAAGACTGGCCCCGCT

TGGCAACGCAACAGTGAGCCCCTCCCTAGTGTGTT

TGGGGATGTGACTATGTATTCGTGTGTTGGCCAAC

GGGTCAACCCGAACAGATTGATACCCGCCTTGGCA

TTTCCTGTCAGAATGTAACGTCAGTTGATGGTACT

Sequence of guide RNA driven by the T7 promoter (T7 promoter, Ns represent targeting sequence):

(SEQ ID NO: 22)

gaaatTAATACGACTCACTATANNNNNNNNNNNNNNNNNNNNgttttaga
gctaGAAAtagcaagttaaaataaggctagtccgttatcaacttgaaaaa
gtggcaccgagtcggtgcttttttt Gene Delivery:

*Chlamydomonas reinhardtii* strain CC-124 and CC-125 from the *Chlamydomonas* Resource Center will be used for electroporation. Electroporation protocol follows standard recommended protocol from the GeneArt *Chlamydomonas* Engineering kit. Also, Applicants generate a line of *Chlamydomonas reinhardtii* that expresses Cas9 constitutively. This can be done by using pChlamy1 (linearized using PvuI) and selecting for hygromycin resistant colonies. Sequence for pChlamy1 containing Cas9 is below. In this way to achieve gene knockout one simply needs to deliver RNA for the guideRNA. For homologous recombination Applicants deliver guideRNA as well as a linearized homologous recombination template.

pChlamy1-Cas9:

(SEQ ID NO: 23)

TGCGGTATTTCACACCGCATCAGGTGGCACTTTTC

GGGGAAATGTGCGCGGAACCCCTATTTGTTTATTT

TTCTAAATACATTCAAATATGTATCCGCTCATGAG

ATTATCAAAAAGGATCTTCACCTAGATCCTTTTAA

ATTAAAAATGAAGTTTTAAATCAATCTAAAGTATA

TATGAGTAAACTTGGTCTGACAGTTACCAATGCTT

AATCAGTGAGGCACCTATCTCAGCGATCTGTCTAT

TTCGTTCATCCATAGTTGCCTGACTCCCCGTCGTG

TAGATAACTACGATACGGGAGGGCTTACCATCTGG

CCCCAGTGCTGCAATGATACCGCGAGACCCACGCT

CACCGGCTCCAGATTTATCAGCAATAAACCAGCCA

GCCGGAAGGGCCGAGCGCAGAAGTGGTCCTGCAAC

TTTATCCGCCTCCATCCAGTCTATTAATTGTTGCC

-continued

GGGAAGCTAGAGTAAGTAGTTCGCCAGTTAATAGT
TTGCGCAACGTTGTTGCCATTGCTACAGGCATCGT
GGTGTCACGCTCGTCGTTTGGTATGGCTTCATTCA
GCTCCGGTTCCCAACGATCAAGGCGAGTTACATGA
TCCCCCATGTTGTGCAAAAAAGCGGTTAGCTCCTT
CGGTCCTCCGATCGTTGTCAGAAGTAAGTTGGCCG
CAGTGTTATCACTCATGGTTATGGCAGCACTGCAT
AATTCTCTTACTGTCATGCCATCCGTAAGATGCTT
TTCTGTGACTGGTGAGTACTCAACCAAGTCATTCT
GAGAATAGTGTATGCGGCGACCGAGTTGCTCTTGC
CCGGCGTCAATACGGGATAATACCGCGCCACATAG
CAGAACTTTAAAAGTGCTCATCATTGGAAAACGTT
CTTCGGGGCGAAAACTCTCAAGGATCTTACCGCTG
TTGAGATCCAGTTCGATGTAACCCACTCGTGCACC
CAACTGATCTTCAGCATCTTTTACTTTCACCAGCG
TTTCTGGGTGAGCAAAAACAGGAAGGCAAAATGCC
GCAAAAAAGGGAATAAGGGCGACACGGAAATGTTG
AATACTCATACTCTTCCTTTTTCAATATTATTGAA
GCATTTATCAGGGTTATTGTCTCATGACCAAAATC
CCTTAACGTGAGTTTTCGTTCCACTGAGCGTCAGA
CCCCGTAGAAAAGATCAAAGGATCTTCTTGAGATC
CTTTTTTTCTGCGCGTAATCTGCTGCTTGCAAACA
AAAAAACCACCGCTACCAGCGGTGGTTTGTTTGCC
GGATCAAGAGCTACCAACTCTTTTTCCGAAGGTAA
CTGGCTTCAGCAGAGCGCAGATACCAAATACTGTT
CTTCTAGTGTAGCCGTAGTTAGGCCACCACTTCAA
GAACTCTGTAGCACCGCCTACATACCTCGCTCTGC
TAATCCTGTTACCAGTGGCTGTTGCCAGTGGCGAT
AAGTCGTGTCTTACCGGGTTGGACTCAAGACGATA
GTTACCGGATAAGGCGCAGCGGTCGGGCTGAACGG
GGGGTTCGTGCACACAGCCCAGCTTGGAGCGAACG
ACCTACACCGAACTGAGATACCTACAGCGTGAGCT
ATGAGAAAGCGCCACGCTTCCCGAAGGGAGAAAGG
CGGACAGGTATCCGGTAAGCGGCAGGGTCGGAACA
GGAGAGCGCACGAGGGAGCTTCCAGGGGGAAACGC
CTGGTATCTTTATAGTCCTGTCGGGTTTCGCCACC
TCTGACTTGAGCGTCGATTTTTGTGATGCTCGTCA
GGGGGGCGGAGCCTATGGAAAAACGCCAGCAACGC
GGCCTTTTTACGGTTCCTGGCCTTTTGCTGGCCTT
TTGCTCACATGTTCTTTCCTGCGTTATCCCCTGAT

-continued

TCTGTGGATAACCGTATTACCGCCTTTGAGTGAGC
TGATACCGCTCGCCGCAGCCGAACGACCGAGCGCA
GCGAGTCAGTGAGCGAGGAAGCGGTCGCTGAGGCT
TGACATGATTGGTGCGTATGTTTGTATGAAGCTAC
AGGACTGATTTGGCGGGCTATGAGGGCGGGGGAAG
CTCTGGAAGGGCCGCGATGGGGCGCGCGGCGTCCA
GAAGGCGCCATACGGCCCGCTGGCGGCACCCATCC
GGTATAAAAGCCCGCGACCCCGAACGGTGACCTCC
ACTTTCAGCGACAAACGAGCACTTATACATACGCG
ACTATTCTGCCGCTATACATAACCACTCAGCTAGC
TTAAGATCCCATCAAGCTTGCATGCCGGGCGCGCC
AGAAGGAGCGCAGCCAAACCAGGATGATGTTTGAT
GGGGTATTTGAGCACTTGCAACCCTTATCCGGAAG
CCCCCTGGCCCACAAAGGCTAGGCGCCAATGCAAG
CAGTTCGCATGCAGCCCCTGGAGCGGTGCCCTCCT
GATAAACCGGCCAGGGGGCCTATGTTCTTTACTTT
TTTACAAGAGAAGTCACTCAACATCTTAAAATGGC
CAGGTGAGTCGACGAGCAAGCCCGGCGGATCAGGC
AGCGTGCTTGCAGATTTGACTTGCAACGCCCGCAT
TGTGTCGACGAAGGCTTTTGGCTCCTCTGTCGCTG
TCTCAAGCAGCATCTAACCCTGCGTCGCCGTTTCC
ATTTGCAGGAGATTCGAGGTACCATGTACCCATAC
GATGTTCCAGATTACGCTTCGCCGAAGAAAAAGCG
CAAGGTCGAAGCGTCCGACAAGAAGTACAGCATCG
GCCTGGACATCGGCACCAACTCTGTGGGCTGGGCC
GTGATCACCGACGAGTACAAGGTGCCCAGCAAGAA
ATTCAAGGTGCTGGGCAACACCGACCGGCACAGCA
TCAAGAAGAACCTGATCGGAGCCCTGCTGTTCGAC
AGCGGCGAAACAGCCGAGGCCACCCGGCTGAAGAG
AACCGCCAGAAGAAGATACACCAGACGGAAGAACC
GGATCTGCTATCTGCAAGAGATCTTCAGCAACGAG
ATGGCCAAGGTGGACGACAGCTTCTTCCACAGACT
GGAAGAGTCCTTCCTGGTGGAAGAGGATAAGAAGC
ACGAGCGGCACCCCATCTTCGGCAACATCGTGGAC
GAGGTGGCCTACCACGAGAAGTACCCCACCATCTA
CCACCTGAGAAAGAAACTGGTGGACAGCACCGACA
AGGCCGACCTGCGGCTGATCTATCTGGCCCTGGCC
CACATGATCAAGTTCCGGGGCCACTTCCTGATCGA
GGGCGACCTGAACCCCGACAACAGCGACGTGGACA
AGCTGTTCATCCAGCTGGTGCAGACCTACAACCAG
CTGTTCGAGGAAAACCCCATCAACGCCAGCGGCGT

-continued

GGACGCCAAGGCCATCCTGTCTGCCAGACTGAGCA

AGAGCAGACGGCTGGAAAATCTGATCGCCCAGCTG

CCCGGCGAGAAGAAGAATGGCCTGTTCGGCAACCT

GATTGCCCTGAGCCTGGGCCTGACCCCCAACTTCA

AGAGCAACTTCGACCTGGCCGAGGATGCCAAACTG

CAGCTGAGCAAGGACACCTACGACGACGACCTGGA

CAACCTGCTGGCCCAGATCGGCGACCAGTACGCCG

ACCTGTTTCTGGCCGCCAAGAACCTGTCCGACGCC

ATCCTGCTGAGCGACATCCTGAGAGTGAACACCGA

GATCACCAAGGCCCCCCTGAGCGCCTCTATGATCA

AGAGATACGACGAGCACCACCAGGACCTGACCCTG

CTGAAAGCTCTCGTGCGGCAGCAGCTGCCTGAGAA

GTACAAAGAGATTTTCTTCGACCAGAGCAAGAACG

GCTACGCCGGCTACATTGACGGCGGAGCCAGCCAG

GAAGAGTTCTACAAGTTCATCAAGCCCATCCTGGA

AAAGATGGACGGCACCGAGGAACTGCTCGTGAAGC

TGAACAGAGAGGACCTGCTGCGGAAGCAGCGGACC

TTCGACAACGGCAGCATCCCCCACCAGATCCACCT

GGGAGAGCTGCACGCCATTCTGCGGCGGCAGGAAG

ATTTTTACCCATTCCTGAAGGACAACCGGGAAAAG

ATCGAGAAGATCCTGACCTTCCGCATCCCCTACTA

CGTGGGCCCTCTGGCCAGGGGAAACAGCAGATTCG

CCTGGATGACCAGAAAGAGCGAGGAAACCATCACC

CCCTGGAACTTCGAGGAAGTGGTGGACAAGGGCGC

TTCCGCCCAGAGCTTCATCGAGCGGATGACCAACT

TCGATAAGAACCTGCCCAACGAGAAGGTGCTGCCC

AAGCACAGCCTGCTGTACGAGTACTTCACCGTGTA

TAACGAGCTGACCAAAGTGAAATACGTGACCGAGG

GAATGAGAAAGCCCGCCTTCCTGAGCGGCGAGCAG

AAAAAGGCCATCGTGGACCTGCTGTTCAAGACCAA

CCGGAAAGTGACCGTGAAGCAGCTGAAAGAGGACT

ACTTCAAGAAAATCGAGTGCTTCGACTCCGTGGAA

ATCTCCGGCGTGGAAGATCGGTTCAACGCCTCCCT

GGGCACATACCACGATCTGCTGAAAATTATCAAGG

ACAAGGACTTCCTGGACAATGAGGAAAACGAGGAC

ATTCTGGAAGATATCGTGCTGACCCTGACACTGTT

TGAGGACAGAGAGATGATCGAGGAACGGCTGAAAA

CCTATGCCCACCTGTTCGACGACAAAGTGATGAAG

CAGCTGAAGCGGCGGAGATACACCGGCTGGGGCAG

GCTGAGCCGGAAGCTGATCAACGGCATCCGGGACA

-continued

AGCAGTCCGGCAAGACAATCCTGGATTTCCTGAAG

TCCGACGGCTTCGCCAACAGAAACTTCATGCAGCT

GATCCACGACGACAGCCTGACCTTTAAAGAGGACA

TCCAGAAAGCCCAGGTGTCCGGCCAGGGCGATAGC

CTGCACGAGCACATTGCCAATCTGGCCGGCAGCCC

CGCCATTAAGAAGGGCATCCTGCAGACAGTGAAGG

TGGTGGACGAGCTCGTGAAAGTGATGGGCCGGCAC

AAGCCCGAGAACATCGTGATCGAAATGGCCAGAGA

GAACCAGACCACCCAGAAGGGACAGAAGAACAGCC

GCGAGAGAATGAAGCGGATCGAAGAGGGCATCAAA

GAGCTGGGCAGCCAGATCCTGAAAGAACACCCCGT

GGAAAACACCCAGCTGCAGAACGAGAAGCTGTACC

TGTACTACCTGCAGAATGGGCGGGATATGTACGTG

GACCAGGAACTGGACATCAACCGGCTGTCCGACTA

CGATGTGGACCATATCGTGCCTCAGAGCTTTCTGA

AGGACGACTCCATCGACAACAAGGTGCTGACCAGA

AGCGACAAGAACCGGGGCAAGAGCGACAACGTGCC

CTCCGAAGAGGTCGTGAAGAAGATGAAGAACTACT

GGCGGCAGCTGCTGAACGCCAAGCTGATTACCCAG

AGAAAGTTCGACAATCTGACCAAGGCCGAGAGAGG

CGGCCTGAGCGAACTGGATAAGGCCGGCTTCATCA

AGAGACAGCTGGTGGAAACCCGGCAGATCACAAAG

CACGTGGCACAGATCCTGGACTCCCGGATGAACAC

TAAGTACGACGAGAATGACAAGCTGATCCGGGAAG

TGAAAGTGATCACCCTGAAGTCCAAGCTGGTGTCC

GATTTCCGGAAGGATTTCCAGTTTTACAAAGTGCG

CGAGATCAACAACTACCACCACGCCCACGACGCCT

ACCTGAACGCCGTCGTGGGAACCGCCCTGATCAAA

AAGTACCCTAAGCTGGAAAGCGAGTTCGTGTACGG

CGACTACAAGGTGTACGACGTGCGGAAGATGATCG

CCAAGAGCGAGCAGGAAATCGGCAAGGCTACCGCC

AAGTACTTCTTCTACAGCAACATCATGAACTTTTT

CAAGACCGAGATTACCCTGGCCAACGGCGAGATCC

GGAAGCGGCCTCTGATCGAGACAAACGGCGAAACC

GGGGAGATCGTGTGGGATAAGGGCCGGGATTTTGC

CACCGTGCGGAAAGTGCTGAGCATGCCCCAAGTGA

ATATCGTGAAAAAGACCGAGGTGCAGACAGGCGGC

TTCAGCAAAGAGTCTATCCTGCCCAAGAGGAACAG

CGATAAGCTGATCGCCAGAAAGAAGGACTGGGACC

CTAAGAAGTACGGCGGCTTCGACAGCCCCACCGTG

GCCTATTCTGTGCTGGTGGTGGCCAAAGTGGAAAA

-continued

GGGCAAGTCCAAGAAACTGAAGAGTGTGAAAGAGC

TGCTGGGGATCACCATCATGGAAAGAAGCAGCTTC

GAGAAGAATCCCATCGACTTTCTGGAAGCCAAGGG

CTACAAAGAAGTGAAAAAGGACCTGATCATCAAGC

TGCCTAAGTACTCCCTGTTCGAGCTGGAAAACGGC

CGGAAGAGAATGCTGGCCTCTGCCGGCGAACTGCA

GAAGGGAAACGAACTGGCCCTGCCCTCCAAATATG

TGAACTTCCTGTACCTGGCCAGCCACTATGAGAAG

CTGAAGGGCTCCCCCGAGGATAATGAGCAGAAACA

GCTGTTTGTGGAACAGCACAAGCACTACCTGGACG

AGATCATCGAGCAGATCAGCGAGTTCTCCAAGAGA

GTGATCCTGGCCGACGCTAATCTGGACAAAGTGCT

GTCCGCCTACAACAAGCACCGGGATAAGCCCATCA

GAGAGCAGGCCGAGAATATCATCCACCTGTTTACC

CTGACCAATCTGGGAGCCCCTGCCGCCTTCAAGTA

CTTTGACACCACCATCGACCGGAAGAGGTACACCA

GCACCAAAGAGGTGCTGGACGCCACCCTGATCCAC

CAGAGCATCACCGGCCTGTACGAGACACGGATCGA

CCTGTCTCAGCTGGGAGGCGACAGCCCCAAGAAGA

AGAGAAAGGTGGAGGCCAGCTAACATATGATTCGA

ATGTCTTTCTTGCGCTATGACACTTCCAGCAAAAG

GTAGGGCGGGCTGCGAGACGGCTTCCCGGCGCTGC

ATGCAACACCGATGATGCTTCGACCCCCCGAAGCT

CCTTCGGGGCTGCATGGGCGCTCCGATGCCGCTCC

AGGGCGAGCGCTGTTTAAATAGCCAGGCCCCCGAT

TGCAAAGACATTATAGCGAGCTACCAAAGCCATAT

TCAAACACCTAGATCACTACCACTTCTACACAGGC

CACTCGAGCTTGTGATCGCACTCCGCTAAGGGGGC

GCCTCTTCCTCTTCGTTTCAGTCACAACCCGCAAA

CATGACACAAGAATCCCTGTTACTTCTCGACCGTA

TTGATTCGGATGATTCCTACGCGAGCCTGCGGAAC

GACCAGGAATTCTGGGAGGTGAGTCGACGAGCAAG

CCCGGCGGATCAGGCAGCGTGCTTGCAGATTTGAC

TTGCAACGCCCGCATTGTGTCGACGAAGGCTTTTG

GCTCCTCTGTCGCTGTCTCAAGCAGCATCTAACCC

TGCGTCGCCGTTTCCATTTGCAGCCGCTGGCCCGC

CGAGCCCTGGAGGAGCTCGGGCTGCCGGTGCCGCC

GGTGCTGCGGGTGCCCGGCGAGAGCACCAACCCCG

TACTGGTCGGCGAGCCCGGCCCGGTGATCAAGCTG

TTCGGCGAGCACTGGTGCGGTCCGGAGAGCCTCGC

-continued

GTCGGAGTCGGAGGCGTACGCGGTCCTGGCGGACG

CCCCGGTGCCGGTGCCCCGCCTCCTCGGCCGCGGC

GAGCTGCGGCCCGGCACCGGAGCCTGGCCGTGGCC

CTACCTGGTGATGAGCCGGATGACCGGCACCACCT

GGCGGTCCGCGATGGACGGCACGACCGACCGGAAC

GCGCTGCTCGCCCTGGCCCGCGAACTCGGCCGGGT

GCTCGGCCGGCTGCACAGGGTGCCGCTGACCGGGA

ACACCGTGCTCACCCCCCATTCCGAGGTCTTCCCG

GAACTGCTGCGGGAACGCCGCGCGGCGACCGTCGA

GGACCACCGCGGGTGGGGCTACCTCTCGCCCCGGC

TGCTGGACCGCCTGGAGGACTGGCTGCCGGACGTG

GACACGCTGCTGGCCGGCCGCGAACCCCGGTTCGT

CCACGGCGACCTGCACGGGACCAACATCTTCGTGG

ACCTGGCCGCGACCGAGGTCACCGGGATCGTCGAC

TTCACCGACGTCTATGCGGGAGACTCCCGCTACAG

CCTGGTGCAACTGCATCTCAACGCCTTCCGGGGCG

ACCGCGAGATCCTGGCCGCGCTGCTCGACGGGGCG

CAGTGGAAGCGGACCGAGGACTTCGCCCGCGAACT

GCTCGCCTTCACCTTCCTGCACGACTTCGAGGTGT

TCGAGGAGACCCCGCTGGATCTCTCCGGCTTCACC

GATCCGGAGGAACTGGCGCAGTTCCTCTGGGGGCC

GCCGGACACCGCCCCCGGCGCCTGATAAGGATCCG

GCAAGACTGGCCCCGCTTGGCAACGCAACAGTGAG

CCCCTCCCTAGTGTGTTTGGGGATGTGACTATGTA

TTCGTGTGTTGGCCAACGGGTCAACCCGAACAGAT

TGATACCCGCCTTGGCATTTCCTGTCAGAATGTAA

CGTCAGTTGATGGTACT.

For all modified *Chlamydomonas reinhardtii* cells, Applicants use PCR, SURVEYOR nuclease assay, and DNA sequencing to verify successful modification.

Example 8: Selection of Guide RNA Sequences for Targeting a Given Gene Using a CRISPR-Cas System Applicants used HumanBody 2.0 expression data from Illumina to calculate for each exon the percent of "constitutiveness". The term "constitutiveness" as used herein relates to how many times the exon is not spliced out across different tissues. From this analysis, Applicants compiled a list of constitutive exons that are expressed across all measured tissues. Applicants then intersected this data with NCBI CCDS database (available at the website ncbi.nlm.nih.gov/CCDS/) and take CCDS exons which are 98% covered with a constitutive exon from as previously determined.

For each CCDS entry, Applicants took the two earliest constitutive exons. If there are not enough constitutive exons in this gene or no data Applicants added exon 2, 3 or both to get to 2 unique exons.

For each candidate exon Applicants found all the possible *S. pyogenes* sgRNA guide sequences (or guide sequence) of the form (N)20NGG. Applicants calculated an off target score for each guide sequence as follows:

(a) Applicants used a short-read aligner and mapped each 20mer guide sequence to the genome to find all the sequences that are similar to it allowing up to 3 mismatches.

(b) At this point if a guide has a match to a sequence in the genome with zero (perfect match) or one base mismatch it is discarded.

(c) For the other guide (closest off target is with two or more mismatches), Applicants calculated the following off target score:

$$OS = \sum_{off\ targets} (\text{sum min location})\left(\frac{D(\text{mm})}{D(\text{max})}\right)$$

where:

sum mm location=sum of the mis-match locations from 3' to 5'.

The PAM (NGG) proximal base is 1 and the PAM distal base is 20.

D(mm)=distance in bp between mismatch locations.

D(max)=maximal possible distance between 2 or 3 mismatches.

Applicants then sort the guide sequences for each gene by off target score, take the two best for each gene up to a off target score of 400. Applicants then iteratively added guide sequences to genes choosing the next best guide sequence for each gene until the whole list of guide sequences contained 65017 guide sequences.

Example 9: Genome Scale CRISPR-Cas9 Knockout Screening in Human Cells

The simplicity of programming the CRISPR-associated nuclease Cas9 to modify specific genomic loci suggests a new way to interrogate gene function on the genome-wide scale. Applicants showed that lentiviral delivery of a genome-scale CRISPR-Cas9 knockout (GeCKO) library targeting 18,080 genes with 64,751 unique guide sequences enables both negative and positive selection screening in human cells. First, Applicants used the GeCKO library to identify genes essential for cell viability in cancer and pluripotent stem cells. Next, in a melanoma model, Applicants screened for candidate genes whose loss is involved in resistance to vemurafenib, a therapeutic that inhibits mutant protein kinase BRAF. Applicants' highest-ranking gene candidates include the previously-validated genes NF1 and MED12 as well as novel candidate genes (NF2, CUL3, TADA2B and TADA1). Notably, Applicants observed a high level of consistency between independent guide RNAs targeting the same gene and a high rate of validation, demonstrating the promise of genome-scale screening with Cas9.

A major goal since the completion of the Human Genome Project is the functional characterization of all annotated genetic elements in normal biological processes and disease. Genome-scale loss-of-function screens have provided a wealth of information in diverse model systems. In mammalian cells, RNA interference (RNAi) is the predominant method for genome-wide loss-of-function screening, but its utility is limited by the inherent incompleteness of protein depletion by RNAi and confounding off-target effects.

The RNA-guided CRISPR (clustered regularly interspaced short palindrome repeats)-associated nuclease Cas9 provides an effective means of introducing targeted loss-of function mutations at specific sites in the genome. Cas9 can be programmed to induce DNA double strand breaks (DSBs) at specific genomic loci through a synthetic single guide RNA (sgRNA), which when targeted to coding regions of genes can create frame shift indel mutations that result in a loss-of-function allele. Because the targeting specificity of Cas9 is conferred by short guide sequences, which can be easily generated at large scale by array-based oligonucleotide library synthesis, Applicants explored the potential of Cas9 for pooled genome-scale functional screening.

Figure 25A:
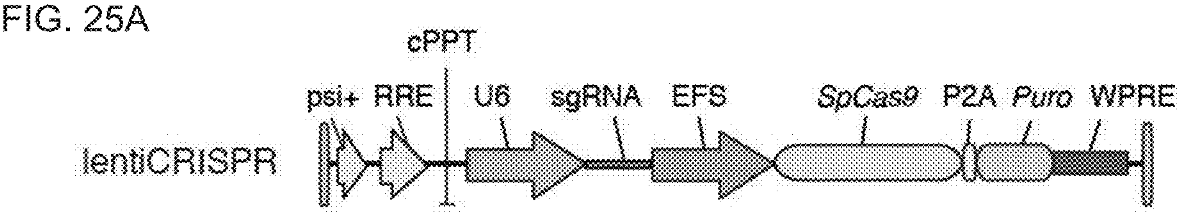
FIG. 25A-25C shows lentiviral delivery of Cas9 and sgRNA provides efficient depletion of target genes. (A) Lentiviral expression vector for Cas9 and sgRNA (lentiCRISPR). Puromycin selection marker (puro), psi packaging signal (psi+), rev response element (RRE), central polypurine tract (cPPT), and posttranscriptional regulatory element (WPRE). (B) Distribution of fluorescence from 293T-EGFP cells transduced by EGFP-targeting lentiCRISPR (sgRNAs 1-6, outlined peaks) and Cas9-only (green-shaded peak) vectors, and non-fluorescent 293T cells (grey shaded peak). (C) Distribution of fluorescence from 293T-EGFP cells transduced by EGFP-targeting shRNA (shRNAs 1-4, outlined peaks) and control shRNA (green-shaded peak) vectors, and non-fluorescent 293T cells (grey shaded peak).

Lentiviral vectors are commonly used for delivery of pooled short hairpin RNAs (shRNAs) in RNAi since they can be easily titrated to control transgene copy number, and are stably maintained as genomic integrants during subsequent cell replication. Therefore Applicants designed a single lentiviral vector to deliver Cas9, a puromycin selection marker, and a sgRNA into target cells (lentiCRISPR, FIGS. 25A and 46). The ability to simultaneously deliver Cas9 and sgRNA through a single vector enables application to any cell type of interest, without the need to first generate cell lines that express Cas9.

Figure 25B:
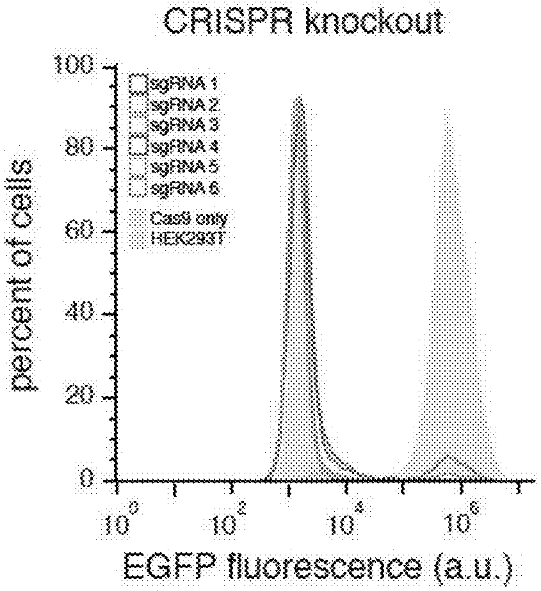
Figure 25C:
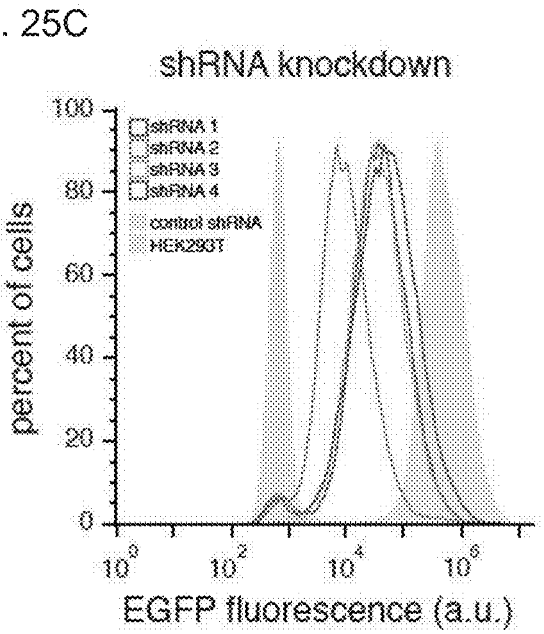
Figure 30A:
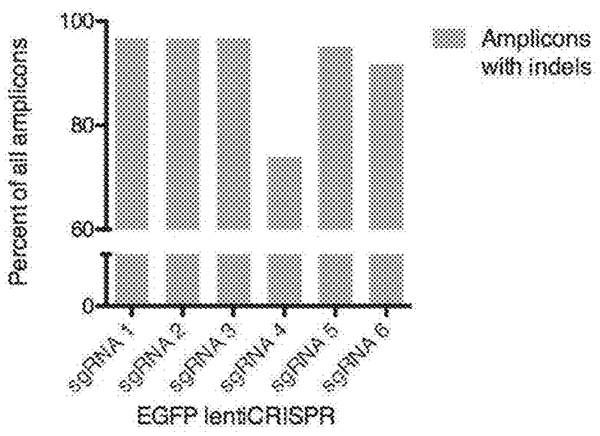
FIG. 30A-30B shows deep sequencing for indel analysis of EGFP locus after lentiCRISPR modification. (A) Deep-sequencing of genomic DNA from HEK293T-EGFP cells that were infected with EGFP-targeting lentiCRISPRs shows that most amplicons have insertion or deletion (indel) mutations. Genomic DNA was extracted from cells on day 11 post-infection. For each lentiCRISPR, $1\text{-}2\times10^4$ reads were used for the analysis. (B) Distribution of types of indel mutations. lentiCRISPR transduction leads to both frameshift and in-frame indel mutations.
Figure 30B:
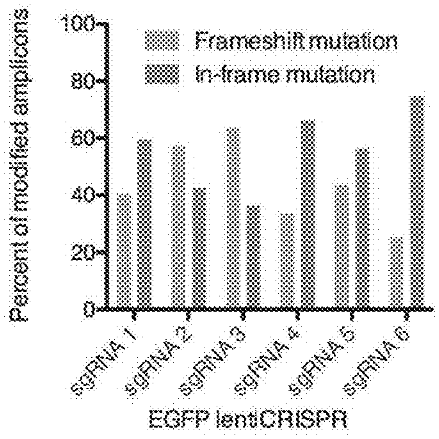

To determine the efficacy of gene knockout by lentiCRISPR transduction, Applicants tested six sgRNAs targeting enhanced green fluorescent protein (EGFP) in a HEK293T cell line containing a single-copy of EGFP (FIG. 29). After transduction at a low multiplicity of infection (MOI=0.3) followed by selection with puromycin, lentiCRISPRs abolished EGFP fluorescence in 93±8% (mean±s.d.) of cells after 11 days (FIG. 25B). Deep sequencing of the EGFP locus revealed a 92±9% indel frequency ($n \geq 10^4$ sequencing reads per condition; FIG. 30). In contrast, transduction of cells with lentiviral vectors expressing EGFP-targeting shRNA led to incomplete knockdown of EGFP fluorescence (FIG. 25C).

Given the high efficacy of gene knockout by lentiCRISPR, Applicants tested the feasibility of conducting genome-scale CRISPR knockout (GeCKO) screening with a pooled lentiCRISPR library. Applicants designed a library of sgRNAs targeting 5' constitutive exons (FIG. 26A) of 18,080 genes in the human genome with an average coverage of 3-4 sgRNAs per gene (Table 1); and each target site was selected to minimize off-target modification as described herein.

Figure 26A:
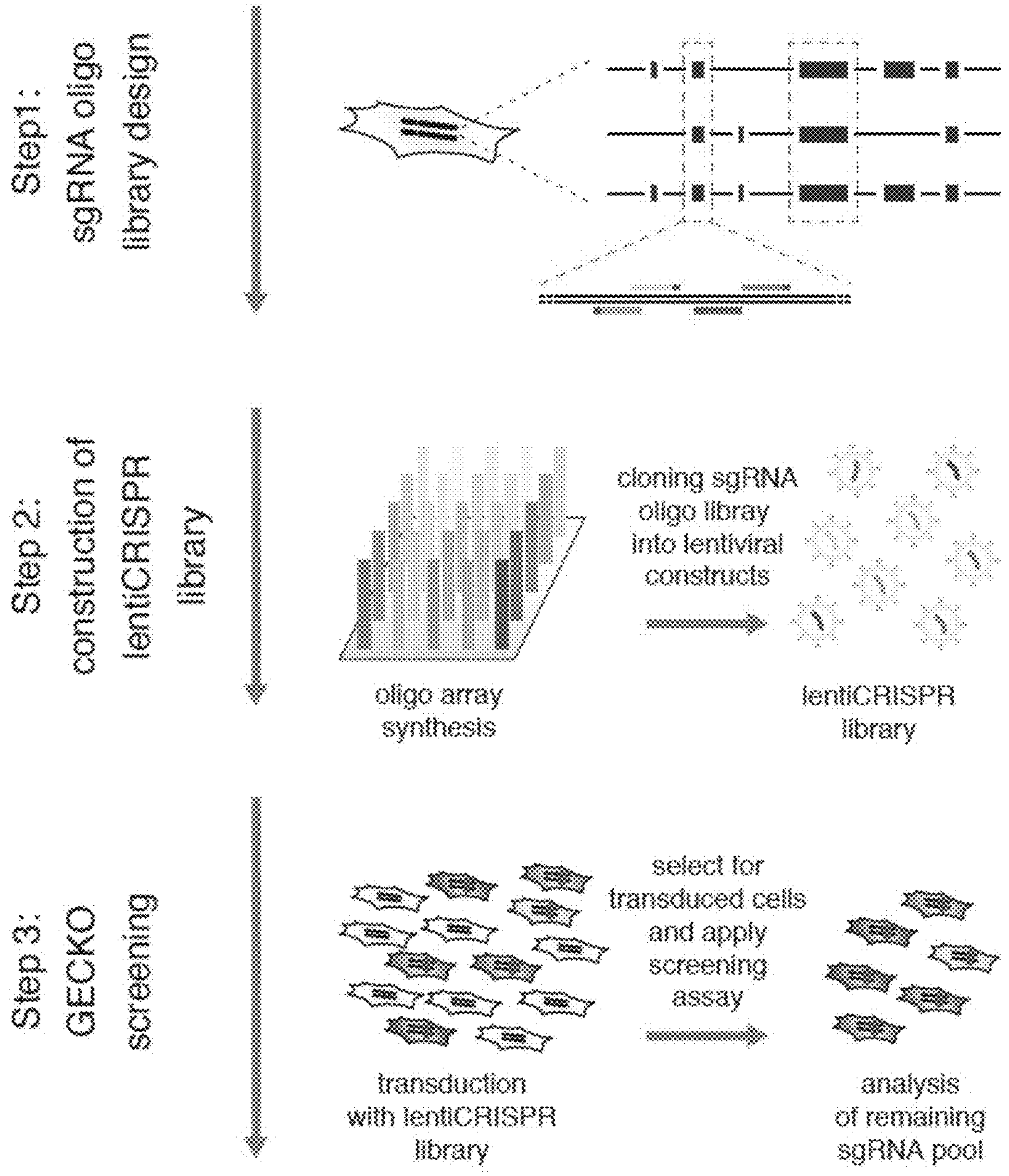
FIG. 26A-26E shows GeCKO library design and application for genome-scale negative selection screening. (A) Design of sgRNA library for genome-scale knockout of coding sequences in human cells (supplementary discussion). (B), (C) Cumulative frequency of sgRNAs 3 and 14 days post transduction in A375 and hES cells respectively. Shift in the 14 day curve represents the depletion in a subset of sgRNAs. (D), (E) Five most significantly depleted gene sets in A375 cells (nominal $p<10^{-5}$, FDR-corrected $q<10^{-5}$) and HUES62 cells (nominal $p<10^{-5}$, FDR-corrected $q<10^{3}$) identified by Gene Set Enrichment Analysis (GSEA).
Figure 26B:
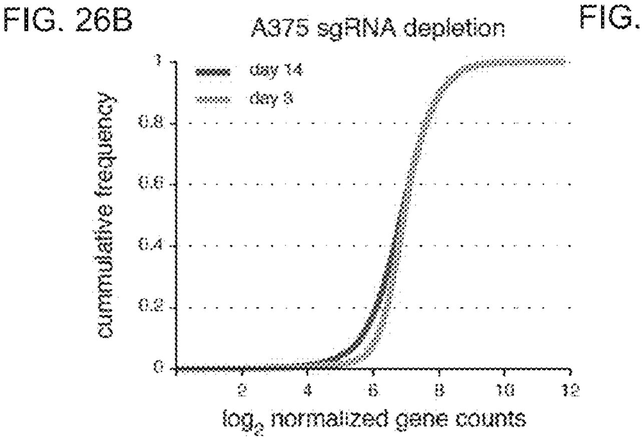
Figure 26C:
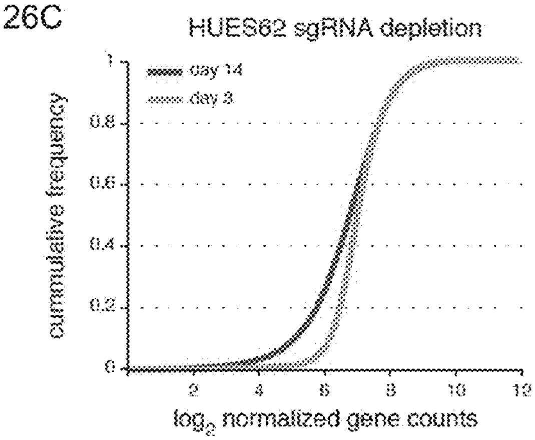
Figure 26D:
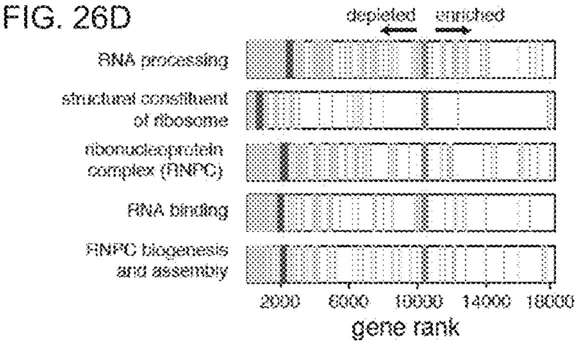
Figure 26E:
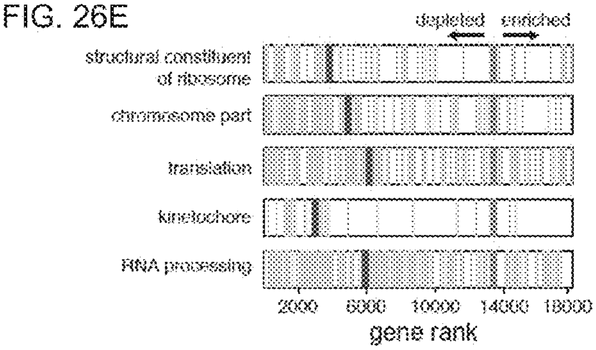
Figure 31:
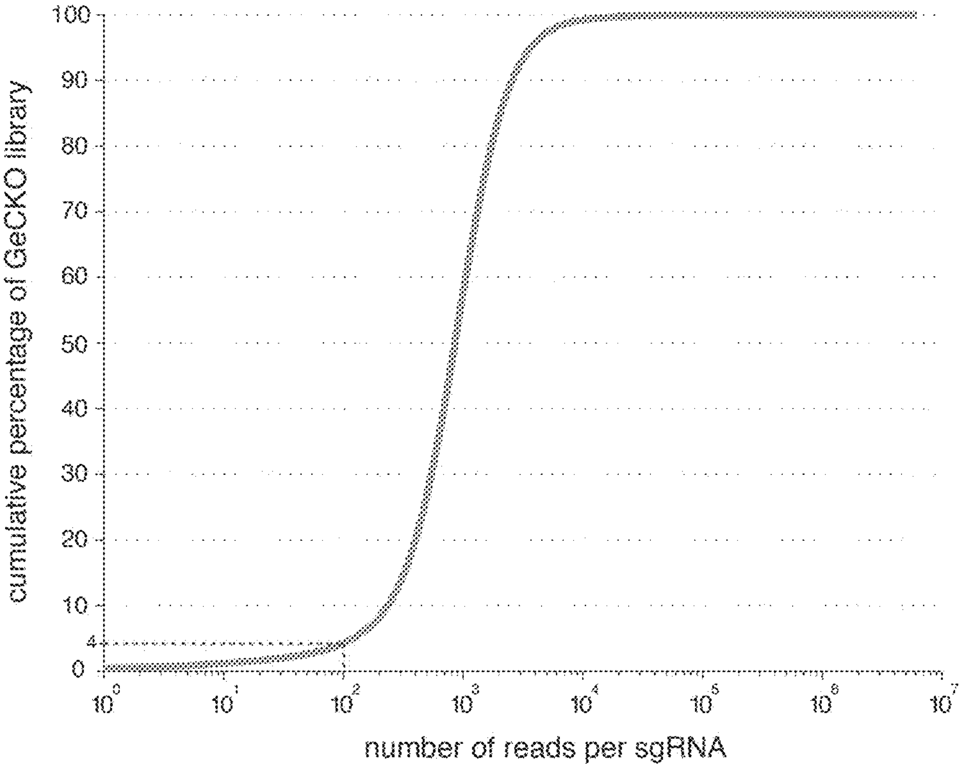
FIG. 31 shows Read coverage per sgRNA in a single experiment. Cumulative distribution of the number of reads per sgRNA in a single A375 experiment. The red line indicates that less than 4% of the sgRNAs are covered by less than 100 reads.
Figure 32:
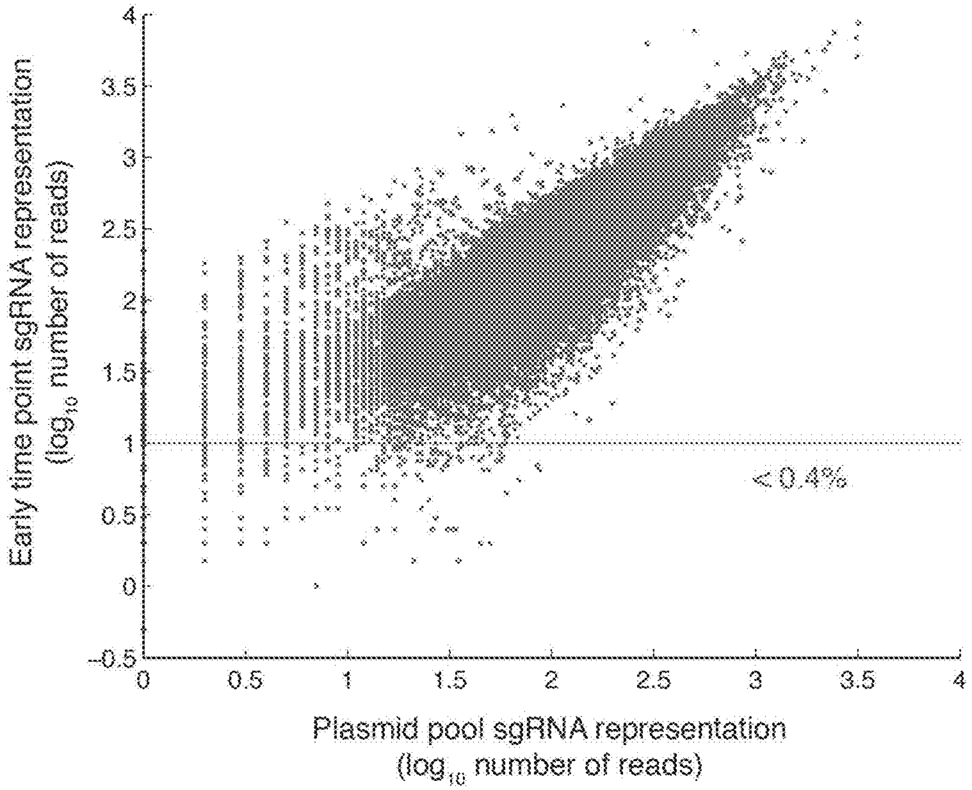
FIG. 32 shows Comparison of sgRNA representation between the plasmid pool to an early time point (day 7). Scatter plot of sgRNA representation ($\log_{10}$ number of reads) between the plasmid pool before virus production to a cell population 7 days post infection. Red line indicates that less than 0.4% of sgRNA have undetectable representation (less than 10 reads).
Figure 33A:
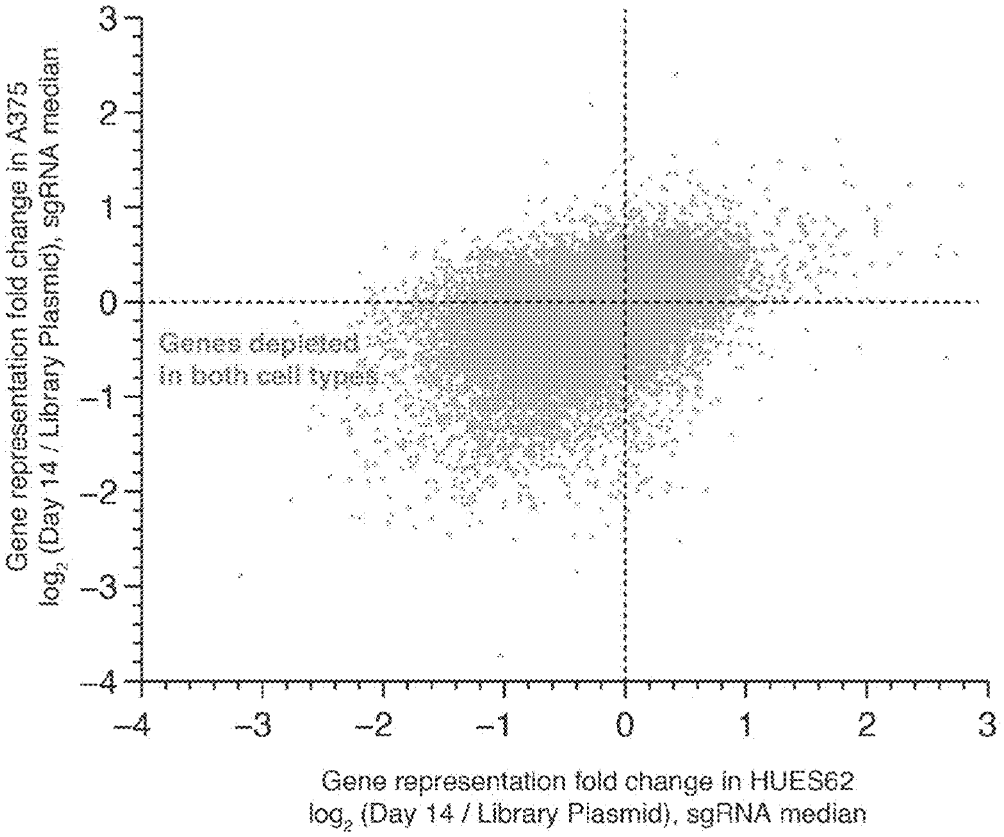
FIG. 33A-33C shows Comparison of gene and gene category depletion between A375 melanoma and HUES62 human ES cells. (A) Scatter plot of gene enrichment/depletion as log 2 fold change of each gene between cells 14 days post-transduction and initial library plasmid in A375 melanoma cells and HUES62 hES cells. Gene enrichment/depletion was calculated using RIGER analysis of individual sgRNA depletion. Lower left quadrant contains genes depleted in both A375 and HUES62 cells. (B) Overlap between the top 1000 most depleted genes in each cell type. (C) Overlap between the top 100 most depleted Gene Ontology (GO) categories for each cell type as ranked by Gene Set Enrichment Analysis (GSEA) on the gene enrichment/depletion values.
Figure 33B:
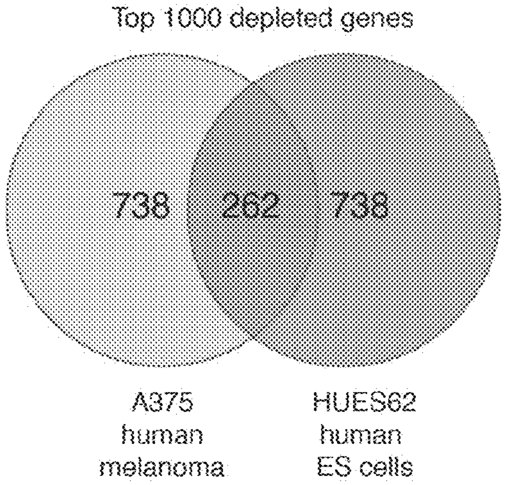
Figure 33C:
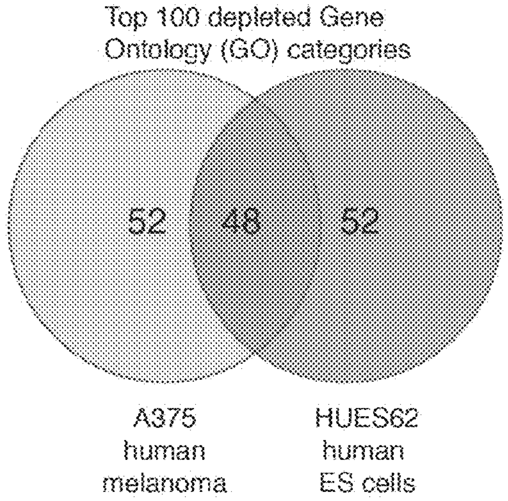

To test the efficacy of the full GeCKO library at achieving knockout of endogenous gene targets, Applicants conducted a negative selection screen by profiling the depletion of sgRNAs targeting essential survival genes (FIG. 26A). Applicants transduced the human melanoma cell line A375 and the human stem cell line HUES62 with the GeCKO library at a MOI of 0.3. As expected, deep sequencing (FIG. 31, 32) 14 days post-transduction revealed a significant reduction in the diversity of sgRNAs in the surviving A375 and HUES62 cells (FIG. 26B, C; Wilcoxon rank sum test, $p<10^{-10}$ for both cell types). Gene set enrichment analysis (GSEA) indicated that most of the depleted sgRNAs targeted essential genes such as ribosomal structural constituents (FIG. 26D, E, and Tables E, F). The overlap in highly depleted genes and functional gene categories between the two cell lines (FIG. 33) indicates that GeCKO can identify essential genes and that enrichment analysis of depleted sgRNAs can pinpoint gene targets in negative selection screens.

TABLE E

Gene Set Enrichment Analysis output for negative selection of essential genes in A375 cells after 14 additional days in culture. For the analysis, the ALL Gene Ontology set was used from the Molecular Signatures Database (MSigDB) with a minimum set size of 50 and max set size of 300.

| NAME | SIZE | ES | NES | NOMp | FDRq | FWERp | RANK AT MAX |
|---|---|---|---|---|---|---|---|
| RNA_PROCESSING | 165 | 0.39 | 5.78 | 0 | 0 | 0 | 2823 |
| STRUCTURAL_CONSTITUENT_OF_RIBOSOME | 71 | 0.58 | 5.68 | 0 | 0 | 0 | 2753 |
| RIBONUCLEOPROTEIN_COMPLEX | 138 | 0.4 | 5.51 | 0 | 0 | 0 | 3865 |
| RNA_BINDING | 241 | 0.29 | 5.21 | 0 | 0 | 0 | 4664 |
| RIBONUCLEOPROTEIN_COMPLEX_BIOGENESIS_AND_ASSEMBLY | 81 | 0.45 | 4.67 | 0 | 0 | 0 | 2979 |
| NUCLEOPLASM | 271 | 0.24 | 4.62 | 0 | 0 | 0 | 4928 |
| RNA_SPLICING | 86 | 0.42 | 4.61 | 0 | 0 | 0 | 2768 |
| NUCLEOLUS | 120 | 0.36 | 4.56 | 0 | 0 | 0 | 5363 |
| NUCLEOPLASM_PART | 206 | 0.26 | 4.41 | 0 | 0 | 0 | 4047 |
| MRNA_METABOLIC_PROCESS | 79 | 0.42 | 4.25 | 0 | 0 | 0 | 4596 |
| MRNA_PROCESSING_GO_0006397 | 70 | 0.42 | 4.13 | 0 | 0 | 0 | 4596 |
| TRANSLATION | 166 | 0.27 | 4.09 | 0 | 0 | 0 | 1815 |
| DNA_METABOLIC_PROCESS | 250 | 0.21 | 3.86 | 0 | 0 | 0 | 6569 |
| BIOPOLYMER_CATABOLIC_PROCESS | 112 | 0.29 | 3.63 | 0 | 0 | 0 | 6456 |
| CHROMOSOMAL_PART | 93 | 0.32 | 3.61 | 0 | 0 | 0 | 4006 |
| PROTEIN_RNA_COMPLEX_ASSEMBLY | 62 | 0.38 | 3.6 | 0 | 0 | 0 | 2979 |
| DNA_DIRECTED_RNA_POLYMERASEII_HOLOENZYME | 65 | 0.38 | 3.6 | 0 | 0 | 0 | 3367 |
| MACROMOLECULE_CATABOLIC_PROCESS | 130 | 0.26 | 3.56 | 0 | 0 | 0 | 6456 |
| ORGANELLE_MEMBRANE | 287 | 0.18 | 3.56 | 0 | 0 | 0 | 7993 |
| CHROMOSOME | 119 | 0.28 | 3.54 | 0 | 0 | 0 | 3434 |
| DNA_REPLICATION | 99 | 0.3 | 3.53 | 0 | 0 | 0 | 3471 |
| MITOCHONDRIAL_PART | 138 | 0.26 | 3.52 | 0 | 0 | 0 | 5678 |
| ORGANELLE_ENVELOPE | 164 | 0.23 | 3.47 | 0 | 0 | 0 | 6682 |
| STRUCTURAL_MOLECULE_ACTIVITY | 218 | 0.2 | 3.43 | 0 | 0 | 0 | 4049 |
| ENVELOPE | 164 | 0.23 | 3.34 | 0 | 0 | 0 | 6682 |
| MACROMOLECULAR_COMPLEX_ASSEMBLY | 267 | 0.17 | 3.21 | 0 | 0 | 0 | 3419 |
| MITOSIS | 80 | 0.3 | 3.2 | 0 | 0 | 0 | 3551 |
| CELLULAR_COMPONENT_ASSEMBLY | 284 | 0.16 | 3.1 | 0 | 0 | 0 | 3419 |
| M_PHASE_OF_MITOTIC_CELL_CYCLE | 83 | 0.29 | 3.08 | 0 | 0 | 0 | 3551 |
| CELLULAR_MACROMOLECULE_CATABOLIC_PROCESS | 99 | 0.26 | 3.06 | 0 | 0 | 0 | 6249 |
| MICROTUBULE_CYTOSKELETON | 146 | 0.22 | 3.05 | 0 | 0 | 0 | 4125 |
| CELL_CYCLE_PROCESS | 190 | 0.19 | 3.01 | 0 | 0 | 0 | 4125 |
| RESPONSE_TO_ENDOGENOUS_STIMULUS | 192 | 0.18 | 2.93 | 0 | 0 | 0 | 7033 |
| RESPONSE_TO_DNA_DAMAGE_STIMULUS | 157 | 0.2 | 2.92 | 0 | 0 | 0 | 6569 |
| DNA_REPAIR | 121 | 0.23 | 2.92 | 0 | 0 | 0 | 6569 |
| MITOCHONDRIAL_ENVELOPE | 93 | 0.25 | 2.91 | 0 | 0 | 0 | 8216 |
| MITOCHONDRIAL_MEMBRANE | 82 | 0.27 | 2.91 | 0 | 0 | 0 | 8216 |
| CELL_CYCLE_PHASE | 168 | 0.19 | 2.88 | 0 | 2.82E−05 | 0.001 | 4070 |
| M_PHASE | 112 | 0.23 | 2.86 | 0 | 2.75E−05 | 0.001 | 3938 |
| PROTEIN_CATABOLIC_PROCESS | 67 | 0.3 | 2.86 | 0 | 2.68E−05 | 0.001 | 6456 |
| MICROTUBULE_ORGANIZING_CENTER | 65 | 0.3 | 2.85 | 0 | 2.61E−05 | 0.001 | 5445 |
| ORGANELLE_INNER_MEMBRANE | 72 | 0.28 | 2.78 | 0 | 7.79E−05 | 0.003 | 8154 |
| MITOCHONDRIAL_INNER_MEMBRANE | 64 | 0.3 | 2.77 | 0 | 7.61E−05 | 0.003 | 8154 |
| MITOTIC_CELL_CYCLE | 151 | 0.19 | 2.76 | 0 | 9.95E−05 | 0.004 | 2454 |
| DNA_DEPENDENT_DNA_REPLICATION | 53 | 0.31 | 2.73 | 0 | 1.22E−04 | 0.005 | 3170 |
| ATPASE_ACTIVITY | 110 | 0.22 | 2.68 | 0 | 1.88E−04 | 0.008 | 5581 |
| PROTEIN_FOLDING | 55 | 0.3 | 2.67 | 0 | 2.07E−04 | 0.009 | 7936 |
| CYTOSKELETAL_PART | 224 | 0.16 | 2.64 | 0 | 2.03E−04 | 0.009 | 4745 |
| CELLULAR_PROTEIN_CATABOLIC_PROCESS | 57 | 0.29 | 2.6 | 0 | 2.22E−04 | 0.01 | 6456 |
| NUCLEOSIDE_TRIPHOSPHATASE_ACTIVITY | 205 | 0.15 | 2.59 | 0 | 3.06E−04 | 0.014 | 6559 |
| ENDOMEMBRANE_SYSTEM | 211 | 0.15 | 2.57 | 0 | 3.62E−04 | 0.017 | 7971 |
| TRANSCRIPTION_FACTOR_COMPLEX | 89 | 0.23 | 2.57 | 0 | 3.55E−04 | 0.017 | 9975 |
| PYROPHOSPHATASE_ACTIVITY | 219 | 0.15 | 2.54 | 0 | 4.90E−04 | 0.024 | 6559 |
| HYDROLASE_ACTIVITY_ACTING_ON_ACID_ANHYDRIDES | 221 | 0.15 | 2.53 | 0 | 5.21E−04 | 0.026 | 6559 |
| REGULATION_OF_CELL_CYCLE | 175 | 0.16 | 2.53 | 0 | 5.12E−04 | 0.026 | 3551 |
| NUCLEAR_ENVELOPE | 72 | 0.25 | 2.51 | 0 | 6.23E−04 | 0.032 | 6682 |
| CENTROSOME | 56 | 0.29 | 2.51 | 0 | 6.12E−04 | 0.032 | 5445 |
| INTRACELLULAR_TRANSPORT | 271 | 0.13 | 2.48 | 0 | 7.09E−04 | 0.038 | 7734 |
| CATABOLIC_PROCESS | 218 | 0.14 | 2.45 | 0 | 9.14E−04 | 0.049 | 3576 |
| LIGASE_ACTIVITY | 94 | 0.22 | 2.44 | 0 | 9.17E−04 | 0.05 | 6249 |
| ATPASE_ACTIVITY_COUPLED | 91 | 0.22 | 2.39 | 0 | 0.00138 | 0.076 | 5581 |
| CELLULAR_CATABOLIC_PROCESS | 206 | 0.14 | 2.38 | 0 | 0.00141 | 0.079 | 3576 |
| MITOCHONDRIAL_MEMBRANE_PART | 50 | 0.27 | 2.32 | 0 | 0.00218 | 0.121 | 7993 |
| NUCLEASE_ACTIVITY | 55 | 0.26 | 2.31 | 0.002 | 0.00232 | 0.129 | 6720 |
| CHROMOSOME_ORGANIZATION_AND_BIOGENESIS | 122 | 0.18 | 2.3 | 0 | 0.00246 | 0.14 | 4623 |
| MACROMOLECULE_LOCALIZATION | 230 | 0.13 | 2.21 | 0 | 0.00434 | 0.23 | 7886 |
| NUCLEAR_MEMBRANE | 50 | 0.25 | 2.04 | 0.002 | 0.01183 | 0.519 | 6682 |
| REGULATION_OF_PROTEIN_METABOLIC_PROCESS | 165 | 0.14 | 2.03 | 0 | 0.01208 | 0.531 | 8311 |
| LIGASE_ACTIVITY_FORMING_CARBON_NITROGEN_BONDS | 67 | 0.2 | 1.98 | 0.002 | 0.01638 | 0.65 | 6249 |
| KINASE_BINDING | 68 | 0.2 | 1.92 | 0.009 | 0.02197 | 0.739 | 9808 |
| PEPTIDYL_AMINO_ACID_MODIFICATION | 62 | 0.2 | 1.88 | 0.011 | 0.02821 | 0.827 | 12915 |
| ESTABLISHMENT_OF_PROTEIN_LOCALIZATION | 185 | 0.12 | 1.87 | 0.014 | 0.02952 | 0.851 | 8072 |
| ENZYME_BINDING | 174 | 0.12 | 1.86 | 0.008 | 0.02965 | 0.855 | 10013 |

TABLE E-continued

Gene Set Enrichment Analysis output for negative selection of essential genes in A375 cells after 14 additional days in culture. For the analysis, the ALL Gene Ontology set was used from the Molecular Signatures Database (MSigDB) with a minimum set size of 50 and max set size of 300.

| NAME | SIZE | ES | NES | NOMp | FDRq | FWERp | RANK AT MAX |
|---|---|---|---|---|---|---|---|
| REGULATION_OF_TRANSCRIPTION_FROM_RNA_POLYMERASE_I_PROMOTER | 283 | 0.1 | 1.85 | 0.006 | 0.0316 | 0.875 | 4713 |
| COFACTOR_METABOLIC_PROCESS | 54 | 0.21 | 1.83 | 0.008 | 0.03423 | 0.894 | 10520 |
| REGULATION_OF_CELLULAR_PROTEIN_METABOLIC_PROCESS | 155 | 0.12 | 1.82 | 0.006 | 0.03515 | 0.902 | 8311 |
| RNA_POLYMERASE_II_TRANSCRIPTION_FACTOR_ACTIVITY | 179 | 0.12 | 1.8 | 0.012 | 0.03919 | 0.929 | 4869 |
| TRANSFERASE_ACTIVITY_TRANSFERRING_ACYL_GROUPS | 59 | 0.2 | 1.78 | 0.006 | 0.04205 | 0.94 | 5002 |
| PROTEIN_LOCALIZATION | 209 | 0.11 | 1.78 | 0.016 | 0.04372 | 0.948 | 7886 |
| SMALL_CONJUGATING_PROTEIN_LIGASE_ACTIVITY | 51 | 0.21 | 1.76 | 0.025 | 0.04791 | 0.962 | 12441 |
| CYTOSOL | 199 | 0.11 | 1.75 | 0.024 | 0.05038 | 0.97 | 4982 |
| REGULATION_OF_CELLULAR_COMPONENT_ORGANIZATION_AND_BIOGENESIS | 117 | 0.14 | 1.74 | 0.017 | 0.05232 | 0.977 | 4133 |
| POSITIVE_REGULATION_OF_CELLULAR_METABOLIC_PROCESS | 224 | 0.1 | 1.73 | 0.034 | 0.05359 | 0.981 | 4250 |
| ACID_AMINO_ACID_LIGASE_ACTIVITY | 57 | 0.2 | 1.73 | 0.021 | 0.05354 | 0.982 | 6249 |
| INTRACELLULAR_PROTEIN_TRANSPORT | 141 | 0.12 | 1.72 | 0.023 | 0.05523 | 0.984 | 6698 |
| PROTEIN_KINASE_BINDING | 60 | 0.19 | 1.72 | 0.022 | 0.05481 | 0.984 | 9808 |
| INTRINSIC_TO_ORGANELLE_MEMBRANE | 51 | 0.2 | 1.72 | 0.02 | 0.05486 | 0.985 | 7971 |
| POSITIVE_REGULATION_OF_RNA_METABOLIC_PROCESS | 119 | 0.13 | 1.71 | 0.024 | 0.0559 | 0.986 | 4250 |
| INTERPHASE | 68 | 0.17 | 1.7 | 0.026 | 0.05724 | 0.987 | 4070 |
| PROTEIN_TRANSPORT | 152 | 0.12 | 1.69 | 0.022 | 0.06056 | 0.988 | 8072 |
| ESTABLISHMENT_AND_OR_MAINTENANCE_OF_CHROMATIN_ARCHITECTURE | 76 | 0.17 | 1.69 | 0.03 | 0.06152 | 0.99 | 5256 |
| POSITIVE_REGULATION_OF_NUCLEOBASENUCLEOSIDENUCLEOTIDE_AND_NUCLEIC_ACID_METABOLIC_PROCESS | 153 | 0.12 | 1.68 | 0.031 | 0.06336 | 0.992 | 4250 |
| ENDOPLASMIC_RETICULUM | 278 | 0.09 | 1.68 | 0.026 | 0.06293 | 0.992 | 7817 |
| POSITIVE_REGULATION_OF_TRANSCRIPTIONDNA_DEPENDENT | 117 | 0.13 | 1.67 | 0.024 | 0.06531 | 0.993 | 4250 |
| POSITIVE_REGULATION_OF_METABOLIC_PROCESS | 230 | 0.09 | 1.65 | 0.028 | 0.06918 | 0.997 | 4250 |
| TRANSCRIPTION_ACTIVATOR_ACTIVITY | 170 | 0.11 | 1.65 | 0.039 | 0.07019 | 0.998 | 4537 |
| POSITIVE_REGULATION_OF_TRANSCRIPTION_FROM_RNA_POLYMERASE_II_PROMOTER | 64 | 0.17 | 1.63 | 0.025 | 0.07401 | 0.998 | 4250 |
| NUCLEOBASENUCLEOSIDE_AND_NUCLEOTIDE_METABOLIC_PROCESS | 51 | 0.19 | 1.63 | 0.037 | 0.07477 | 0.999 | 5750 |
| SMALL_PROTEIN_CONJUGATING_ENZYME_ACTIVITY | 52 | 0.19 | 1.62 | 0.027 | 0.07592 | 0.999 | 12441 |
| ENDOPLASMIC_RETICULUM_MEMBRANE | 81 | 0.15 | 1.61 | 0.041 | 0.08117 | 0.999 | 6591 |
| POSITIVE_REGULATION_OF_TRANSCRIPTION | 143 | 0.11 | 1.59 | 0.051 | 0.08681 | 0.999 | 4250 |
| NUCLEAR_ENVELOPE_ENDOPLASMIC_RETICULUM_NETWORK | 90 | 0.14 | 1.59 | 0.039 | 0.08705 | 0.999 | 6591 |
| NUCLEAR_TRANSPORT | 86 | 0.15 | 1.58 | 0.04 | 0.09042 | 1 | 7204 |
| ENDOPLASMIC_RETICULUM_PART | 92 | 0.14 | 1.57 | 0.042 | 0.09295 | 1 | 6669 |
| TRANSCRIPTION_COACTIVATOR_ACTIVITY | 120 | 0.12 | 1.57 | 0.044 | 0.09258 | 1 | 4536 |
| NUCLEOCYTOPLASMIC_TRANSPORT | 85 | 0.14 | 1.56 | 0.042 | 0.09541 | 1 | 7204 |
| PROTEIN_C_TERMINUS_BINDING | 70 | 0.16 | 1.56 | 0.051 | 0.09668 | 1 | 12272 |
| NUCLEAR_CHROMOSOME | 51 | 0.18 | 1.54 | 0.062 | 0.10619 | 1 | 3434 |
| PROTEOLYSIS | 184 | 0.1 | 1.52 | 0.066 | 0.11481 | 1 | 6570 |
| CHROMATIN_MODIFICATION | 54 | 0.18 | 1.51 | 0.057 | 0.11578 | 1 | 3790 |
| INTERPHASE_OF_MITOTIC_CELL_CYCLE | 62 | 0.16 | 1.46 | 0.093 | 0.1459 | 1 | 4070 |
| HYDROLASE_ACTIVITY_ACTING_ON_ESTER_BONDS | 263 | 0.08 | 1.42 | 0.08 | 0.17096 | 1 | 10388 |
| GOLGI_APPARATUS_PART | 94 | 0.12 | 1.41 | 0.078 | 0.17588 | 1 | 10008 |
| TRANSCRIPTION_COFACTOR_ACTIVITY | 219 | 0.08 | 1.39 | 0.095 | 0.19304 | 1 | 4536 |
| PROTEIN_IMPORT | 62 | 0.15 | 1.39 | 0.121 | 0.19213 | 1 | 7185 |
| TRANSCRIPTION_FACTOR_BINDING | 298 | 0.07 | 1.37 | 0.111 | 0.20094 | 1 | 4802 |
| PROTEIN_HETERODIMERIZATION_ACTIVITY | 75 | 0.13 | 1.37 | 0.117 | 0.20087 | 1 | 7886 |
| MICROTUBULE_BASED_PROCESS | 76 | 0.13 | 1.34 | 0.146 | 0.22731 | 1 | 2409 |
| POSITIVE_REGULATION_OF_PROTEIN_METABOLIC_PROCESS | 72 | 0.13 | 1.32 | 0.144 | 0.24339 | 1 | 7879 |
| OXIDOREDUCTASE_ACTIVITY | 282 | 0.07 | 1.32 | 0.145 | 0.24362 | 1 | 9653 |
| PROTEIN_TARGETING | 108 | 0.11 | 1.31 | 0.158 | 0.24756 | 1 | 2572 |
| PHOSPHORIC_ESTER_HYDROLASE_ACTIVITY | 149 | 0.09 | 1.3 | 0.149 | 0.25681 | 1 | 10507 |
| GENERATION_OF_PRECURSOR_METABOLITES_AND_ENERGY | 122 | 0.1 | 1.29 | 0.175 | 0.263 | 1 | 10168 |
| GTPASE_ACTIVITY | 94 | 0.11 | 1.28 | 0.17 | 0.27137 | 1 | 6559 |
| REGULATION_OF_TRANSLATION | 89 | 0.12 | 1.28 | 0.182 | 0.26987 | 1 | 12650 |
| ANION_TRANSMEMBRANE_TRANSPORTER_ACTIVITY | 59 | 0.14 | 1.27 | 0.155 | 0.27786 | 1 | 14818 |
| INORGANIC_CATION_TRANSMEMBRANE_TRANSPORTER_ACTIVITY | 56 | 0.14 | 1.25 | 0.203 | 0.29417 | 1 | 6084 |
| ALCOHOL_METABOLIC_PROCESS | 87 | 0.11 | 1.24 | 0.198 | 0.3057 | 1 | 5002 |
| SMALL_GTPASE_REGULATOR_ACTIVITY | 67 | 0.13 | 1.22 | 0.212 | 0.32345 | 1 | 9244 |
| CYTOSKELETAL_PROTEIN_BINDING | 155 | 0.08 | 1.22 | 0.208 | 0.32316 | 1 | 3830 |
| PROTEIN_DOMAIN_SPECIFIC_BINDING | 70 | 0.13 | 1.22 | 0.214 | 0.32228 | 1 | 10281 |
| PROTEIN_DIMERIZATION_ACTIVITY | 177 | 0.08 | 1.21 | 0.231 | 0.32627 | 1 | 14919 |
| STRUCTURE_SPECIFIC_DNA_BINDING | 54 | 0.14 | 1.21 | 0.243 | 0.32383 | 1 | 7121 |
| GOLGI_APPARATUS | 216 | 0.07 | 1.21 | 0.22 | 0.32532 | 1 | 7875 |
| SEQUENCE_SPECIFIC_DNA_BINDING | 57 | 0.13 | 1.21 | 0.215 | 0.3236 | 1 | 11740 |
| POSITIVE_REGULATION_OF_CELLULAR_PROTEIN_METABOLIC_PROCESS | 70 | 0.12 | 1.19 | 0.247 | 0.34325 | 1 | 7879 |

TABLE E-continued

Gene Set Enrichment Analysis output for negative selection of essential genes in A375 cells after 14 additional days in culture. For the analysis, the ALL Gene Ontology set was used from the Molecular Signatures Database (MSigDB) with a minimum set size of 50 and max set size of 300.

| NAME | SIZE | ES | NES | NOMp | FDRq | FWERp | RANK AT MAX |
|---|---|---|---|---|---|---|---|
| CARBOHYDRATE_METABOLIC_PROCESS | 177 | 0.08 | 1.19 | 0.217 | 0.34568 | 1 | 10067 |
| GTPASE_REGULATOR_ACTIVITY | 122 | 0.09 | 1.18 | 0.232 | 0.35845 | 1 | 9407 |
| SECRETION_BY_CELL | 112 | 0.09 | 1.17 | 0.243 | 0.36174 | 1 | 7757 |
| SECRETION | 174 | 0.08 | 1.16 | 0.269 | 0.37594 | 1 | 7820 |
| PHOSPHORIC_MONOESTER_HYDROLASE_ACTIVITY | 108 | 0.1 | 1.16 | 0.283 | 0.37476 | 1 | 9922 |
| CYTOSKELETON_ORGANIZATION_AND_BIOGENESIS | 199 | 0.07 | 1.15 | 0.275 | 0.38345 | 1 | 8398 |
| PROTEIN_COMPLEX_BINDING | 53 | 0.13 | 1.13 | 0.298 | 0.39885 | 1 | 14915 |
| RESPONSE_TO_OTHER_ORGANISM | 78 | 0.11 | 1.12 | 0.301 | 0.41053 | 1 | 10042 |
| SECRETORY_PATHWAY | 80 | 0.11 | 1.11 | 0.285 | 0.41916 | 1 | 6638 |
| PROTEIN_COMPLEX_ASSEMBLY | 160 | 0.07 | 1.09 | 0.329 | 0.45045 | 1 | 2284 |
| NUCLEOTIDE_BINDING | 213 | 0.06 | 1.09 | 0.334 | 0.44914 | 1 | 5253 |
| GLYCOPROTEIN_BIOSYNTHETIC_PROCESS | 74 | 0.11 | 1.07 | 0.347 | 0.46709 | 1 | 9904 |
| RESPONSE_TO_BIOTIC_STIMULUS | 112 | 0.09 | 1.07 | 0.358 | 0.46716 | 1 | 11595 |
| DEPHOSPHORYLATION | 68 | 0.11 | 1.06 | 0.354 | 0.48637 | 1 | 3576 |
| NEGATIVE_REGULATION_OF_NUCLEOBASENUCLEOSIDENUCLEOTIDE_AND_NUCLEIC_ACID_METABOLIC_PROCESS | 208 | 0.06 | 1.04 | 0.398 | 0.51567 | 1 | 3307 |
| CARBOXYLIC_ACID_METABOLIC_PROCESS | 176 | 0.07 | 1.02 | 0.409 | 0.53327 | 1 | 13899 |
| RESPONSE_TO_ABIOTIC_STIMULUS | 81 | 0.1 | 1.01 | 0.437 | 0.55167 | 1 | 2485 |
| RAS_PROTEIN_SIGNAL_TRANSDUCTION | 64 | 0.11 | 0.99 | 0.459 | 0.56979 | 1 | 11509 |
| ACTIN_BINDING | 76 | 0.1 | 0.99 | 0.456 | 0.57185 | 1 | 11233 |
| PROTEIN_AMINO_ACID_DEPHOSPHORYLATION | 61 | 0.11 | 0.99 | 0.467 | 0.57088 | 1 | 3369 |
| APOPTOTIC_PROGRAM | 57 | 0.11 | 0.99 | 0.467 | 0.5697 | 1 | 12804 |
| STRUCTURAL_CONSTITUENT_OF_CYTOSKELETON | 54 | 0.11 | 0.98 | 0.464 | 0.57267 | 1 | 5005 |
| ENZYME_INHIBITOR_ACTIVITY | 118 | 0.08 | 0.97 | 0.484 | 0.59056 | 1 | 9572 |
| POSITIVE_REGULATION_OF_I_KAPPAB_KINASE_NF_KAPPAB_CASCADE | 84 | 0.09 | 0.96 | 0.475 | 0.59815 | 1 | 14222 |
| ORGANIC_ACID_METABOLIC_PROCESS | 178 | 0.06 | 0.96 | 0.487 | 0.59493 | 1 | 13899 |
| MONOCARBOXYLIC_ACID_METABOLIC_PROCESS | 87 | 0.09 | 0.96 | 0.516 | 0.59446 | 1 | 13681 |
| NEGATIVE_REGULATION_OF_CELLULAR_METABOLIC_PROCESS | 255 | 0.05 | 0.95 | 0.5 | 0.60411 | 1 | 3307 |
| GLYCOPROTEIN_METABOLIC_PROCESS | 90 | 0.09 | 0.95 | 0.507 | 0.60702 | 1 | 11014 |
| NEGATIVE_REGULATION_OF_METABOLIC_PROCESS | 257 | 0.05 | 0.94 | 0.502 | 0.61476 | 1 | 3307 |
| SMALL_GTPASE_MEDIATED_SIGNAL_TRANSDUCTION | 85 | 0.09 | 0.94 | 0.499 | 0.61255 | 1 | 11509 |
| PROTEIN_HOMODIMERIZATION_ACTIVITY | 118 | 0.07 | 0.94 | 0.515 | 0.6163 | 1 | 14919 |
| POSITIVE_REGULATION_OF_SIGNAL_TRANSDUCTION | 120 | 0.07 | 0.94 | 0.53 | 0.61278 | 1 | 15308 |
| RESPONSE_TO_RADIATION | 55 | 0.11 | 0.93 | 0.527 | 0.61353 | 1 | 2360 |
| CELLULAR_CARBOHYDRATE_METABOLIC_PROCESS | 124 | 0.07 | 0.91 | 0.552 | 0.64116 | 1 | 4663 |
| REGULATION_OF_I_KAPPAB_KINASE_NF_KAPPAB_CASCADE | 90 | 0.08 | 0.91 | 0.565 | 0.65121 | 1 | 15690 |
| LIPID_BIOSYNTHETIC_PROCESS | 96 | 0.08 | 0.88 | 0.581 | 0.69681 | 1 | 10784 |
| PURINE_NUCLEOTIDE_BINDING | 200 | 0.05 | 0.86 | 0.661 | 0.7253 | 1 | 15565 |
| PURINE_RIBONUCLEOTIDE_BINDING | 194 | 0.05 | 0.84 | 0.663 | 0.75173 | 1 | 5186 |
| AMINO_ACID_METABOLIC_PROCESS | 77 | 0.08 | 0.82 | 0.691 | 0.77186 | 1 | 12986 |
| PHOSPHOPROTEIN_PHOSPHATASE_ACTIVITY | 79 | 0.08 | 0.82 | 0.721 | 0.76882 | 1 | 3369 |
| ATP_BINDING | 149 | 0.05 | 0.8 | 0.729 | 0.79992 | 1 | 15510 |
| ADENYL_NUCLEOTIDE_BINDING | 162 | 0.05 | 0.78 | 0.752 | 0.81705 | 1 | 15539 |
| ELECTRON_TRANSPORT_GO_0006118 | 51 | 0.09 | 0.76 | 0.766 | 0.85094 | 1 | 9279 |
| MULTI_ORGANISM_PROCESS | 153 | 0.05 | 0.75 | 0.792 | 0.857 | 1 | 13249 |
| ADENYL_RIBONUCLEOTIDE_BINDING | 156 | 0.05 | 0.74 | 0.794 | 0.87127 | 1 | 15539 |
| REGULATION_OF_BINDING | 56 | 0.08 | 0.74 | 0.782 | 0.86663 | 1 | 5256 |
| IDENTICAL_PROTEIN_BINDING | 297 | 0.04 | 0.73 | 0.819 | 0.8703 | 1 | 14671 |
| REGULATION_OF_GROWTH | 54 | 0.08 | 0.71 | 0.824 | 0.89318 | 1 | 9818 |
| OXIDOREDUCTASE_ACTIVITY_ACTING_ON_CH_OH_GROUP_OF_DONORS | 61 | 0.08 | 0.71 | 0.83 | 0.89082 | 1 | 2727 |
| ELECTRON_CARRIER_ACTIVITY | 78 | 0.07 | 0.7 | 0.867 | 0.90169 | 1 | 13510 |
| GROWTH | 72 | 0.07 | 0.67 | 0.883 | 0.9323 | 1 | 2784 |
| CYSTEINE_TYPE_PEPTIDASE_ACTIVITY | 54 | 0.08 | 0.66 | 0.87 | 0.93021 | 1 | 7915 |
| HEMOPOIESIS | 71 | 0.07 | 0.65 | 0.905 | 0.94316 | 1 | 9936 |
| PROTEIN_AMINO_ACID_PHOSPHORYLATION | 268 | 0.03 | 0.64 | 0.89 | 0.94752 | 1 | 6898 |
| TRANSITION_METAL_ION_BINDING | 106 | 0.05 | 0.62 | 0.933 | 0.95526 | 1 | 4837 |
| ACTIN_CYTOSKELETON | 125 | 0.04 | 0.56 | 0.978 | 0.99424 | 1 | 10554 |
| AMINO_ACID_AND_DERIVATIVE_METABOLIC_PROCESS | 99 | 0.05 | 0.55 | 0.96 | 0.99288 | 1 | 13079 |
| NEGATIVE_REGULATION_OF_RNA_METABOLIC_PROCESS | 129 | 0.04 | 0.55 | 0.972 | 0.98941 | 1 | 7189 |
| REGULATION_OF_RESPONSE_TO_STIMULUS | 59 | 0.06 | 0.51 | 0.99 | 0.99725 | 1 | 7791 |
| ENZYME_ACTIVATOR_ACTIVITY | 120 | 0.04 | 0.49 | 0.996 | 0.9967 | 1 | 13202 |
| NITROGEN_COMPOUND_METABOLIC_PROCESS | 151 | 0.03 | 0.49 | 0.992 | 0.99283 | 1 | 16617 |

TABLE F

Gene Set Enrichment Analysis output for negative selection of essential genes in HUES62 hES cells after 14 additional days in culture. For the analysis, the ALL Gene Ontology set was used from from the Moleular Signatures Database (MSigDB) with a minimum set size of 50 and max set size of 300.

| NAME | SIZE | ES | NES | NOMp | FDRq | FWERp | RANK AT MAX |
|---|---|---|---|---|---|---|---|
| RIBONUCLEOPROTEIN_COMPLEX_BIOGENESIS_AND_ASSEMBLY | 73 | 0.2 | 2.3 | 0 | 0.142 | 0.121 | 4298 |
| RNA_POLYMERASE_II_TRANSCRIPTION_FACTOR_ACTIVITY | 162 | 0.1 | 2.1 | 0 | 0.222 | 0.329 | 3199 |
| RNA_SPLICING | 76 | 0.2 | 2.1 | 0.006 | 0.204 | 0.416 | 6793 |
| RNA_PROCESSING | 144 | 0.1 | 2 | 0.004 | 0.219 | 0.534 | 5451 |
| PROTEIN_RNA_COMPLEX_ASSEMBLY | 57 | 0.2 | 2 | 0.006 | 0.189 | 0.563 | 4298 |
| MITOSIS | 71 | 0.2 | 1.9 | 0.008 | 0.244 | 0.716 | 5678 |
| M_PHASE_OF_MITOTIC_CELL_CYCLE | 74 | 0.2 | 1.9 | 0.01 | 0.255 | 0.788 | 5678 |
| REPRODUCTIVE_PROCESS | 137 | 0.1 | 1.8 | 0.019 | 0.414 | 0.947 | 6727 |
| MITOTIC_CELL_CYCLE | 137 | 0.1 | 1.8 | 0.019 | 0.403 | 0.958 | 8284 |
| REGULATION_OF_CELL_CYCLE | 157 | 0.1 | 1.7 | 0.039 | 0.647 | 0.995 | 9226 |
| RIBONUCLEOPROTEIN_COMPLEX | 115 | 0.1 | 1.6 | 0.043 | 0.717 | 0.998 | 6653 |
| MACROMOLECULAR_COMPLEX_ASSEMBLY | 242 | 0.1 | 1.6 | 0.03 | 0.691 | 1 | 4562 |
| TRANSLATION | 147 | 0.1 | 1.6 | 0.05 | 0.671 | 1 | 7108 |
| DNA_DIRECTED_RNA_POLYMERASEII_HOLOENZYME | 57 | 0.2 | 1.6 | 0.049 | 0.631 | 1 | 5123 |
| CHROMOSOMAL_PART | 77 | 0.1 | 1.6 | 0.063 | 0.701 | 1 | 8719 |
| CELLULAR_COMPONENT_ASSEMBLY | 257 | 0.1 | 1.5 | 0.062 | 0.688 | 1 | 4562 |
| RNA_BINDING | 216 | 0.1 | 1.5 | 0.056 | 0.696 | 1 | 5522 |
| M_PHASE | 101 | 0.1 | 1.5 | 0.08 | 0.687 | 1 | 8489 |
| MRNA_PROCESSING_GO_0006397 | 63 | 0.2 | 1.5 | 0.068 | 0.663 | 1 | 4298 |
| REPRODUCTION | 226 | 0.1 | 1.5 | 0.053 | 0.632 | 1 | 6759 |
| MRNA_METABOLIC_PROCESS | 71 | 0.1 | 1.5 | 0.086 | 0.732 | 1 | 6950 |
| REGULATION_OF_KINASE_ACTIVITY | 133 | 0.1 | 1.5 | 0.083 | 0.733 | 1 | 7168 |
| ENZYME_BINDING | 154 | 0.1 | 1.4 | 0.087 | 0.735 | 1 | 10360 |
| REGULATION_OF_PROTEIN_KINASE_ACTIVITY | 131 | 0.1 | 1.4 | 0.1 | 0.773 | 1 | 7168 |
| NUCLEOLUS | 94 | 0.1 | 1.4 | 0.113 | 0.764 | 1 | 7137 |
| TRANSCRIPTION_FACTOR_COMPLEX | 81 | 0.1 | 1.4 | 0.113 | 0.742 | 1 | 8392 |
| CHROMOSOME | 102 | 0.1 | 1.4 | 0.091 | 0.721 | 1 | 2248 |
| STRUCTURAL_CONSTITUENT_OF_RIBOSOME | 60 | 0.2 | 1.4 | 0.098 | 0.709 | 1 | 10943 |
| CELL_ACTIVATION | 71 | 0.1 | 1.4 | 0.114 | 0.701 | 1 | 6829 |
| CELL_CYCLE_PHASE | 153 | 0.1 | 1.4 | 0.093 | 0.713 | 1 | 8333 |
| POSITIVE_REGULATION_OF_TRANSCRIPTION | 131 | 0.1 | 1.4 | 0.11 | 0.701 | 1 | 8116 |
| TRANSMISSION_OF_NERVE_IMPULSE | 170 | 0.1 | 1.4 | 0.12 | 0.699 | 1 | 11366 |
| APOPTOTIC_PROGRAM | 51 | 0.2 | 1.4 | 0.12 | 0.692 | 1 | 5013 |
| DNA_METABOLIC_PROCESS | 219 | 0.1 | 1.4 | 0.117 | 0.676 | 1 | 9608 |
| POSITIVE_REGULATION_OF_CELLULAR_METABOLIC_PROCESS | 204 | 0.1 | 1.3 | 0.146 | 0.745 | 1 | 8687 |
| MICROTUBULE_CYTOSKELETON | 132 | 0.1 | 1.3 | 0.142 | 0.739 | 1 | 1731 |
| KINASE_BINDING | 61 | 0.1 | 1.3 | 0.142 | 0.726 | 1 | 10359 |
| REGULATION_OF_TRANSFERASE_ACTIVITY | 137 | 0.1 | 1.3 | 0.138 | 0.711 | 1 | 7168 |
| LYMPHOCYTE_ACTIVATION | 56 | 0.1 | 1.3 | 0.151 | 0.693 | 1 | 6829 |
| MACROMOLECULE_CATABOLIC_PROCESS | 116 | 0.1 | 1.3 | 0.145 | 0.68 | 1 | 13196 |
| LEUKOCYTE_ACTIVATION | 64 | 0.1 | 1.3 | 0.17 | 0.71 | 1 | 6829 |
| POSITIVE_REGULATION_OF_METABOLIC_PROCESS | 210 | 0.1 | 1.3 | 0.181 | 0.716 | 1 | 8687 |
| PROTEIN_KINASE_BINDING | 53 | 0.2 | 1.3 | 0.142 | 0.703 | 1 | 7909 |
| RESPONSE_TO_ENDOGENOUS_STIMULUS | 174 | 0.1 | 1.3 | 0.163 | 0.693 | 1 | 9799 |
| CELLULAR_MACROMOLECULE_CATABOLIC_PROCESS | 87 | 0.1 | 1.3 | 0.156 | 0.691 | 1 | 12929 |
| BIOPOLYMER_CATABOLIC_PROCESS | 103 | 0.1 | 1.3 | 0.185 | 0.697 | 1 | 6589 |
| POSITIVE_REGULATION_OF_ NUCLEOBASENUCLEOSIDENUCLEOTIDE_AND_ NUCLEIC_ACID_METABOLIC_PROCESS | 141 | 0.1 | 1.3 | 0.18 | 0.692 | 1 | 8116 |
| ANION_TRANSMEMBRANE_TRANSPORTER_ACTIVITY | 56 | 0.1 | 1.3 | 0.177 | 0.702 | 1 | 6320 |
| CELL_PROJECTION | 94 | 0.1 | 1.3 | 0.2 | 0.691 | 1 | 7993 |
| SYNAPTIC_TRANSMISSION | 156 | 0.1 | 1.2 | 0.193 | 0.767 | 1 | 11366 |
| CARBOHYDRATE_BINDING | 61 | 0.1 | 1.2 | 0.192 | 0.757 | 1 | 2825 |
| CYTOKINE_PRODUCTION | 65 | 0.1 | 1.2 | 0.189 | 0.752 | 1 | 9817 |
| PROTEIN_CATABOLIC_PROCESS | 61 | 0.1 | 1.2 | 0.222 | 0.758 | 1 | 13196 |
| PHOSPHORIC_ESTER_HYDROLASE_ACTIVITY | 141 | 0.1 | 1.2 | 0.2 | 0.754 | 1 | 12864 |
| PROTEIN_TYROSINE_KINASE_ACTIVITY | 54 | 0.1 | 1.2 | 0.198 | 0.745 | 1 | 5783 |
| CALCIUM_ION_BINDING | 89 | 0.1 | 1.2 | 0.215 | 0.77 | 1 | 7829 |
| PHOSPHOTRANSFERASE_ACTIVITY_ALCOHOL_GROUP_AS_ ACCEPTOR | 299 | 0.1 | 1.2 | 0.238 | 0.764 | 1 | 7371 |
| REGULATION_OF_CELL_PROLIFERATION | 273 | 0.1 | 1.2 | 0.235 | 0.774 | 1 | 8412 |
| CENTRAL_NERVOUS_SYSTEM_DEVELOPMENT | 112 | 0.1 | 1.2 | 0.256 | 0.821 | 1 | 7866 |
| REGULATION_OF_SIGNAL_TRANSDUCTION | 195 | 0.1 | 1.2 | 0.246 | 0.831 | 1 | 9366 |
| POSITIVE_REGULATION_OF_TRANSCRIPTIONDNA_ DEPENDENT | 108 | 0.1 | 1.2 | 0.247 | 0.82 | 1 | 8055 |
| POSITIVE_REGULATION_OF_DEVELOPMENTAL_PROCESS | 195 | 0.1 | 1.2 | 0.259 | 0.834 | 1 | 12108 |
| POSITIVE_REGULATION_OF_RNA_METABOLIC_PROCESS | 110 | 0.1 | 1.2 | 0.279 | 0.829 | 1 | 8055 |
| PHOSPHORIC_MONOESTER_HYDROLASE_ACTIVITY | 103 | 0.1 | 1.1 | 0.275 | 0.826 | 1 | 12864 |
| NEGATIVE_REGULATION_OF_CELL_PROLIFERATION | 135 | 0.1 | 1.1 | 0.279 | 0.818 | 1 | 8723 |
| TRANSCRIPTION_ACTIVATOR_ACTIVITY | 156 | 0.1 | 1.1 | 0.297 | 0.829 | 1 | 10875 |
| DNA_REPLICATION | 82 | 0.1 | 1.1 | 0.306 | 0.843 | 1 | 6359 |
| MONOCARBOXYLIC_ACID_METABOLIC_PROCESS | 77 | 0.1 | 1.1 | 0.3 | 0.839 | 1 | 13160 |

TABLE F-continued

Gene Set Enrichment Analysis output for negative selection of essential genes in HUES62 hES cells after 14 additional days in culture. For the analysis, the ALL Gene Ontology set was used from from the Moleular Signatures Database (MSigDB) with a minimum set size of 50 and max set size of 300.

| NAME | SIZE | ES | NES | NOMp | FDRq | FWERp | RANK AT MAX |
|---|---|---|---|---|---|---|---|
| NUCLEOPLASM_PART | 184 | 0.1 | 1.1 | 0.311 | 0.83 | 1 | 2383 |
| POSITIVE_REGULATION_OF_TRANSFERASE_ACTIVITY | 71 | 0.1 | 1.1 | 0.296 | 0.818 | 1 | 5202 |
| NEGATIVE_REGULATION_OF_METABOLIC_PROCESS | 232 | 0.1 | 1.1 | 0.311 | 0.831 | 1 | 5603 |
| MAPKKK_CASCADE_GO_0000165 | 87 | 0.1 | 1.1 | 0.339 | 0.835 | 1 | 5783 |
| MICROTUBULE_ORGANIZING_CENTER | 56 | 0.1 | 1.1 | 0.321 | 0.831 | 1 | 1731 |
| NEGATIVE_REGULATION_OF_CELLULAR_METABOLIC_PROCESS | 230 | 0.1 | 1.1 | 0.314 | 0.822 | 1 | 5603 |
| CELL_CYCLE_GO_0007049 | 273 | 0.1 | 1.1 | 0.322 | 0.815 | 1 | 8333 |
| PHOSPHORYLATION | 282 | 0.1 | 1.1 | 0.318 | 0.807 | 1 | 11887 |
| CELLULAR_PROTEIN_CATABOLIC_PROCESS | 51 | 0.1 | 1.1 | 0.341 | 0.821 | 1 | 12860 |
| MEMBRANE_ORGANIZATION_AND_BIOGENESIS | 124 | 0.1 | 1.1 | 0.329 | 0.818 | 1 | 3729 |
| PROTEINACEOUS_EXTRACELLULAR_MATRIX | 85 | 0.1 | 1.1 | 0.327 | 0.84 | 1 | 12100 |
| PROTEIN_DIMERIZATION_ACTIVITY | 160 | 0.1 | 1.1 | 0.351 | 0.837 | 1 | 9757 |
| G_PROTEIN_SIGNALING_COUPLED_TO_CAMP_NUCLEOTIDE_SECOND_MESSENGER | 58 | 0.1 | 1.1 | 0.365 | 0.831 | 1 | 4757 |
| ACID_AMINO_ACID_LIGASE_ACTIVITY | 53 | 0.1 | 1.1 | 0.364 | 0.83 | 1 | 5009 |
| EXTRACELLULAR_MATRIX | 85 | 0.1 | 1.1 | 0.335 | 0.828 | 1 | 12100 |
| NEGATIVE_REGULATION_OF_CELL_CYCLE | 67 | 0.1 | 1.1 | 0.385 | 0.837 | 1 | 13433 |
| DNA_REPAIR | 108 | 0.1 | 1.1 | 0.343 | 0.827 | 1 | 9370 |
| VESICLE_MEDIATED_TRANSPORT | 175 | 0.1 | 1.1 | 0.375 | 0.826 | 1 | 3962 |
| ORGANELLE_MEMBRANE | 262 | 0.1 | 1.1 | 0.335 | 0.823 | 1 | 11505 |
| PURINE_NUCLEOTIDE_BINDING | 183 | 0.1 | 1.1 | 0.349 | 0.824 | 1 | 5664 |
| CYTOSKELETAL_PART | 206 | 0.1 | 1 | 0.372 | 0.819 | 1 | 1731 |
| CYTOSOL | 183 | 0.1 | 1 | 0.369 | 0.828 | 1 | 12199 |
| PURINE_RIBONUCLEOTIDE_BINDING | 178 | 0.1 | 1 | 0.398 | 0.825 | 1 | 5664 |
| SEXUAL_REPRODUCTION | 117 | 0.1 | 1 | 0.396 | 0.842 | 1 | 12380 |
| ZINC_ION_BINDING | 76 | 0.1 | 1 | 0.395 | 0.836 | 1 | 2628 |
| CELL_CYCLE_PROCESS | 172 | 0.1 | 1 | 0.416 | 0.864 | 1 | 8333 |
| IDENTICAL_PROTEIN_BINDING | 265 | 0.1 | 1 | 0.421 | 0.861 | 1 | 2850 |
| LIGASE_ACTIVITY_FORMING_CARBON_NITROGEN_BONDS | 63 | 0.1 | 1 | 0.441 | 0.855 | 1 | 5120 |
| ANTI_APOPTOSIS | 105 | 0.1 | 1 | 0.444 | 0.852 | 1 | 4654 |
| SMALL_GTPASE_MEDIATED_SIGNAL_TRANSDUCTION | 78 | 0.1 | 1 | 0.453 | 0.854 | 1 | 10865 |
| CAMP_MEDIATED_SIGNALING | 59 | 0.1 | 1 | 0.418 | 0.857 | 1 | 4757 |
| REGULATION_OF_PROTEIN_METABOLIC_PROCESS | 154 | 0.1 | 1 | 0.467 | 0.855 | 1 | 3729 |
| TRANSCRIPTION_COACTIVATOR_ACTIVITY | 109 | 0.1 | 1 | 0.477 | 0.869 | 1 | 12523 |
| NUCLEAR_ENVELOPE | 62 | 0.1 | 1 | 0.464 | 0.871 | 1 | 2228 |
| OXIDOREDUCTASE_ACTIVITY | 257 | 0.1 | 1 | 0.458 | 0.871 | 1 | 6094 |
| ENZYME_REGULATOR_ACTIVITY | 279 | 0 | 1 | 0.478 | 0.884 | 1 | 12824 |
| EXTRACELLULAR_MATRIX_PART | 50 | 0.1 | 1 | 0.498 | 0.881 | 1 | 12058 |
| CATABOLIC_PROCESS | 200 | 0.1 | 1 | 0.49 | 0.894 | 1 | 13541 |
| NEUROGENESIS | 83 | 0.1 | 0.9 | 0.526 | 0.91 | 1 | 12169 |
| CYTOSKELETON_ORGANIZATION_AND_BIOGENESIS | 182 | 0.1 | 0.9 | 0.508 | 0.912 | 1 | 8813 |
| MACROMOLECULE_BIOSYNTHETIC_PROCESS | 276 | 0 | 0.9 | 0.511 | 0.912 | 1 | 12108 |
| CARBOHYDRATE_METABOLIC_PROCESS | 160 | 0.1 | 0.9 | 0.509 | 0.91 | 1 | 12203 |
| ACTIN_CYTOSKELETON_ORGANIZATION_AND_BIOGENESIS | 89 | 0.1 | 0.9 | 0.508 | 0.903 | 1 | 8813 |
| PROTEIN_DOMAIN_SPECIFIC_BINDING | 64 | 0.1 | 0.9 | 0.523 | 0.908 | 1 | 12290 |
| CATION_BINDING | 181 | 0.1 | 0.9 | 0.539 | 0.905 | 1 | 12366 |
| PROTEIN_C_TERMINUS_BINDING | 61 | 0.1 | 0.9 | 0.532 | 0.907 | 1 | 5785 |
| TRANSCRIPTION_FACTOR_BINDING | 271 | 0 | 0.9 | 0.543 | 0.9 | 1 | 11687 |
| RAS_PROTEIN_SIGNAL_TRANSDUCTION | 58 | 0.1 | 0.9 | 0.537 | 0.894 | 1 | 10865 |
| LYASE_ACTIVITY | 65 | 0.1 | 0.9 | 0.579 | 0.931 | 1 | 9672 |
| NEGATIVE_REGULATION_OF_NUCLEOBASENUCLEOSIDENUCLEOTIDE_AND_NUCLEIC_ACID_METABOLIC_PROCESS | 186 | 0.1 | 0.9 | 0.57 | 0.926 | 1 | 3709 |
| PROTEIN_HOMODIMERIZATION_ACTIVITY | 108 | 0.1 | 0.9 | 0.578 | 0.922 | 1 | 11217 |
| ORGAN_MORPHOGENESIS | 128 | 0.1 | 0.9 | 0.582 | 0.928 | 1 | 12177 |
| SOLUBLE_FRACTION | 148 | 0.1 | 0.9 | 0.579 | 0.929 | 1 | 6965 |
| INTERPHASE_OF_MITOTIC_CELL_CYCLE | 57 | 0.1 | 0.9 | 0.601 | 0.924 | 1 | 8280 |
| REGULATION_OF_CATALYTIC_ACTIVITY | 240 | 0 | 0.9 | 0.617 | 0.921 | 1 | 5348 |
| CELLULAR_CATABOLIC_PROCESS | 188 | 0.1 | 0.9 | 0.616 | 0.919 | 1 | 12351 |
| POSITIVE_REGULATION_OF_CELLULAR_PROTEIN_METABOLIC_PROCESS | 65 | 0.1 | 0.9 | 0.598 | 0.916 | 1 | 8687 |
| STRUCTURAL_MOLECULE_ACTIVITY | 192 | 0.1 | 0.9 | 0.613 | 0.91 | 1 | 12175 |
| REGULATION_OF_MULTICELLULAR_ORGANISMAL_PROCESS | 136 | 0.1 | 0.9 | 0.603 | 0.912 | 1 | 12283 |
| TRANSCRIPTION_COFACTOR_ACTIVITY | 196 | 0.1 | 0.9 | 0.597 | 0.927 | 1 | 12429 |
| LIPID_BINDING | 79 | 0.1 | 0.9 | 0.63 | 0.923 | 1 | 12751 |
| REGULATION_OF_MAP_KINASE_ACTIVITY | 54 | 0.1 | 0.9 | 0.614 | 0.921 | 1 | 3169 |
| POSITIVE_REGULATION_OF_I_KAPPAB_KINASE_NF_KAPPAB_CASCADE | 76 | 0.1 | 0.9 | 0.603 | 0.919 | 1 | 9729 |
| POSITIVE_REGULATION_OF_PROTEIN_METABOLIC_PROCESS | 67 | 0.1 | 0.9 | 0.623 | 0.927 | 1 | 8687 |
| PROTEIN_AMINO_ACID_PHOSPHORYLATION | 251 | 0 | 0.9 | 0.635 | 0.925 | 1 | 11887 |
| HYDROLASE_ACTIVITY_ACTING_ON_ESTER_BONDS | 244 | 0 | 0.8 | 0.645 | 0.923 | 1 | 13028 |

TABLE F-continued

Gene Set Enrichment Analysis output for negative selection of essential genes in HUES62 hES cells after 14 additional days in culture. For the analysis, the ALL Gene Ontology set was used from from the Moleular Signatures Database (MSigDB) with a minimum set size of 50 and max set size of 300.

| NAME | SIZE | ES | NES | NOMp | FDRq | FWERp | RANK AT MAX |
|---|---|---|---|---|---|---|---|
| CYTOPLASMIC_VESICLE | 105 | 0.1 | 0.8 | 0.637 | 0.919 | 1 | 13797 |
| REGULATION_OF_I_KAPPAB_KINASE_NF_KAPPAB_CASCADE | 81 | 0.1 | 0.8 | 0.635 | 0.927 | 1 | 9729 |
| SKELETAL_DEVELOPMENT | 96 | 0.1 | 0.8 | 0.639 | 0.935 | 1 | 11294 |
| SMALL_GTPASE_REGULATOR_ACTIVITY | 62 | 0.1 | 0.8 | 0.673 | 0.945 | 1 | 12082 |
| REGULATION_OF_BINDING | 52 | 0.1 | 0.8 | 0.701 | 0.939 | 1 | 12761 |
| ENDOMEMBRANE_SYSTEM | 190 | 0.1 | 0.8 | 0.687 | 0.946 | 1 | 11505 |
| CYTOPLASMIC_MEMBRANE_BOUND_VESICLE | 102 | 0.1 | 0.8 | 0.709 | 0.949 | 1 | 13797 |
| TRANSITION_METAL_ION_BINDING | 94 | 0.1 | 0.8 | 0.708 | 0.946 | 1 | 2628 |
| MUSCLE_DEVELOPMENT | 88 | 0.1 | 0.8 | 0.696 | 0.94 | 1 | 12772 |
| GAMETE_GENERATION | 96 | 0.1 | 0.8 | 0.695 | 0.94 | 1 | 12659 |
| RESPONSE_TO_DNA_DAMAGE_STIMULUS | 140 | 0.1 | 0.8 | 0.758 | 0.941 | 1 | 9799 |
| GTPASE_REGULATOR_ACTIVITY | 111 | 0.1 | 0.8 | 0.722 | 0.938 | 1 | 5348 |
| LIGASE_ACTIVITY | 86 | 0.1 | 0.8 | 0.739 | 0.947 | 1 | 5410 |
| NEGATIVE_REGULATION_OF_TRANSCRIPTION | 171 | 0.1 | 0.8 | 0.734 | 0.942 | 1 | 3709 |
| PROTEIN_KINASE_ACTIVITY | 256 | 0 | 0.8 | 0.765 | 0.944 | 1 | 7338 |
| STRUCTURAL_CONSTITUENT_OF_CYTOSKELETON | 50 | 0.1 | 0.8 | 0.743 | 0.944 | 1 | 2346 |
| VACUOLE | 62 | 0.1 | 0.8 | 0.727 | 0.945 | 1 | 6726 |
| NEGATIVE_REGULATION_OF_APOPTOSIS | 130 | 0.1 | 0.8 | 0.759 | 0.94 | 1 | 4654 |
| SECRETION | 158 | 0.1 | 0.8 | 0.756 | 0.936 | 1 | 11635 |
| REGULATION_OF_MOLECULAR_FUNCTION | 283 | 0 | 0.8 | 0.752 | 0.937 | 1 | 5603 |
| REGULATION_OF_TRANSPORT | 61 | 0.1 | 0.8 | 0.768 | 0.943 | 1 | 14839 |
| REGULATION_OF_TRANSLATION | 82 | 0.1 | 0.8 | 0.778 | 0.942 | 1 | 8502 |
| PROTEIN_IMPORT | 53 | 0.1 | 0.8 | 0.765 | 0.939 | 1 | 412 |
| ION_BINDING | 232 | 0 | 0.8 | 0.759 | 0.942 | 1 | 11557 |
| ORGANELLE_ENVELOPE | 147 | 0.1 | 0.8 | 0.782 | 0.937 | 1 | 3663 |
| GROWTH | 67 | 0.1 | 0.8 | 0.771 | 0.934 | 1 | 12240 |
| FATTY_ACID_METABOLIC_PROCESS | 56 | 0.1 | 0.8 | 0.787 | 0.934 | 1 | 12183 |
| NEGATIVE_REGULATION_OF_DEVELOPMENTAL_PROCESS | 173 | 0 | 0.7 | 0.794 | 0.94 | 1 | 4654 |
| I_KAPPAB_KINASE_NF_KAPPAB_CASCADE | 99 | 0.1 | 0.7 | 0.808 | 0.938 | 1 | 14020 |
| NEGATIVE_REGULATION_OF_PROGRAMMED_CELL_DEATH | 131 | 0.1 | 0.7 | 0.807 | 0.935 | 1 | 4654 |
| ENVELOPE | 147 | 0.1 | 0.7 | 0.788 | 0.929 | 1 | 3663 |
| PROTEIN_KINASE_CASCADE | 258 | 0 | 0.7 | 0.842 | 0.948 | 1 | 13666 |
| TRANSCRIPTION_COREPRESSOR_ACTIVITY | 78 | 0.1 | 0.7 | 0.826 | 0.945 | 1 | 3220 |
| REGULATION_OF_TRANSCRIPTION_FROM RNA_POLYMERASE_II_PROMOTER | 255 | 0 | 0.7 | 0.806 | 0.949 | 1 | 3002 |
| MEMBRANE_BOUND_VESICLE | 104 | 0.1 | 0.7 | 0.85 | 0.95 | 1 | 11308 |
| ENZYME_ACTIVATOR_ACTIVITY | 111 | 0.1 | 0.7 | 0.852 | 0.948 | 1 | 12334 |
| TRANSFERASE_ACTIVITY_TRANSFERRING_HEXOSYL_GROUPS | 75 | 0.1 | 0.7 | 0.84 | 0.955 | 1 | 12906 |
| TRANSCRIPTION_REPRESSOR_ACTIVITY | 131 | 0.1 | 0.7 | 0.853 | 0.958 | 1 | 3240 |
| EXTRACELLULAR_REGION_PART | 294 | 0 | 0.7 | 0.868 | 0.956 | 1 | 12644 |
| RECEPTOR_COMPLEX | 51 | 0.1 | 0.7 | 0.868 | 0.976 | 1 | 2182 |
| NEGATIVE_REGULATION_OF_CATALYTIC_ACTIVITY | 64 | 0.1 | 0.7 | 0.903 | 0.977 | 1 | 4937 |
| MITOCHONDRIAL_PART | 125 | 0 | 0.6 | 0.928 | 0.986 | 1 | 11489 |
| PROTEIN_COMPLEX_ASSEMBLY | 146 | 0 | 0.6 | 0.902 | 0.982 | 1 | 4562 |
| MICROTUBULE_BASED_PROCESS | 74 | 0.1 | 0.6 | 0.893 | 0.978 | 1 | 12093 |
| NUCLEAR_ENVELOPE_ENDOPLASMIC_RETICULUM_NETWORK | 82 | 0.1 | 0.6 | 0.91 | 0.994 | 1 | 3200 |
| ORGANELLE_INNER_MEMBRANE | 65 | 0.1 | 0.6 | 0.93 | 0.989 | 1 | 3663 |
| TRANSFERASE_ACTIVITY_TRANSFERRING_ACYL_GROUPS | 54 | 0.1 | 0.6 | 0.939 | 0.992 | 1 | 10232 |
| REGULATION_OF_GROWTH | 51 | 0.1 | 0.6 | 0.922 | 0.989 | 1 | 11803 |
| IMMUNE_SYSTEM_DEVELOPMENT | 75 | 0.1 | 0.6 | 0.957 | 0.984 | 1 | 14325 |
| ATPASE_ACTIVITY_COUPLED | 82 | 0.1 | 0.6 | 0.948 | 0.982 | 1 | 13690 |
| POSITIVE_REGULATION_OF_CATALYTIC_ACTIVITY | 142 | 0 | 0.6 | 0.935 | 0.978 | 1 | 5324 |
| ACTIN_FILAMENT_BASED_PROCESS | 99 | 0.1 | 0.6 | 0.959 | 0.984 | 1 | 8813 |
| POSITIVE_REGULATION_OF_TRANSCRIPTION_FROM_RNA_POLYMERASE_II_PROMOTER | 59 | 0.1 | 0.6 | 0.959 | 0.986 | 1 | 8009 |
| HEMOPOIETIC_OR_LYMPHOID_ORGAN_DEVELOPMENT | 71 | 0.1 | 0.6 | 0.968 | 0.982 | 1 | 14325 |
| HEMOPOIESIS | 69 | 0.1 | 0.6 | 0.976 | 0.987 | 1 | 6829 |
| INTERPHASE | 63 | 0.1 | 0.6 | 0.978 | 0.983 | 1 | 8280 |
| ACTIN_BINDING | 70 | 0.1 | 0.5 | 0.996 | 0.995 | 1 | 3563 |
| ENDOPLASMIC_RETICULUM | 253 | 0 | 0.5 | 0.986 | 0.992 | 1 | 15352 |

Figure 27A:
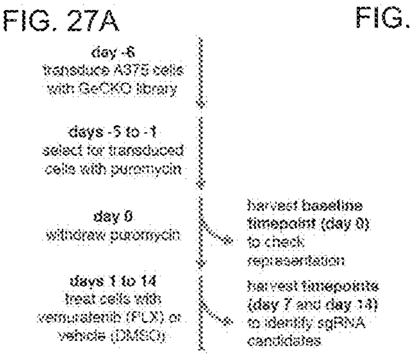
FIG. 27A-27F shows GeCKO screen in A375 melanoma cells reveals genes whose loss confers vemurafenib (PLX) resistance. (A) Timeline of PLX resistance screen in A375 melanoma cells. (B) Growth of A375 cells when treated with DMSO or PLX over 14 days. (C) Boxplot showing the distribution of sgRNA frequencies at different time points, with and without PLX treatment (vehicle=DMSO). The box extends from the first to the third quartile with the whiskers denoting 1.5 times the interquartile range. Enrichment of specific sgRNAs: 7 days of PLX treatment, 1 sgRNA greater than 10-fold enrichment; 14 days of PLX treatment, 379 and 49 sgRNAs greater than 10-fold and 100-fold enrichment respectively. (D) Rank correlation of normalized sgRNA read count between biological replicates and treatment conditions. (E) Scatterplot showing enrichment of specific sgRNAs after PLX treatment. (F) Identification of top candidate genes using the RNAi Gene Enrichment Ranking (RIGER) p value analysis.
Figure 27B:
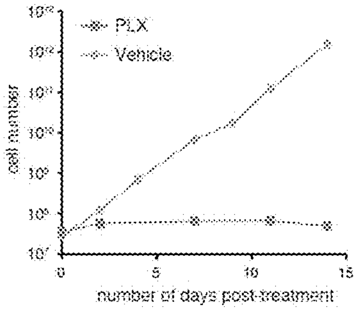
Figure 27C:
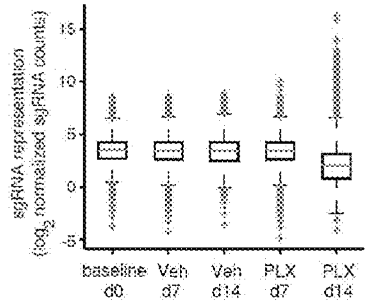
Figure 27D:
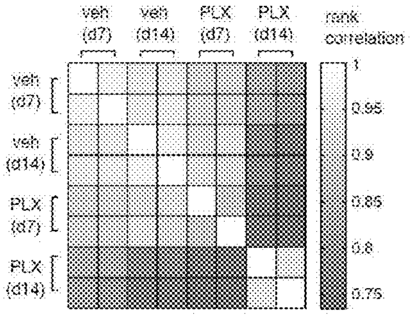
Figure 34:
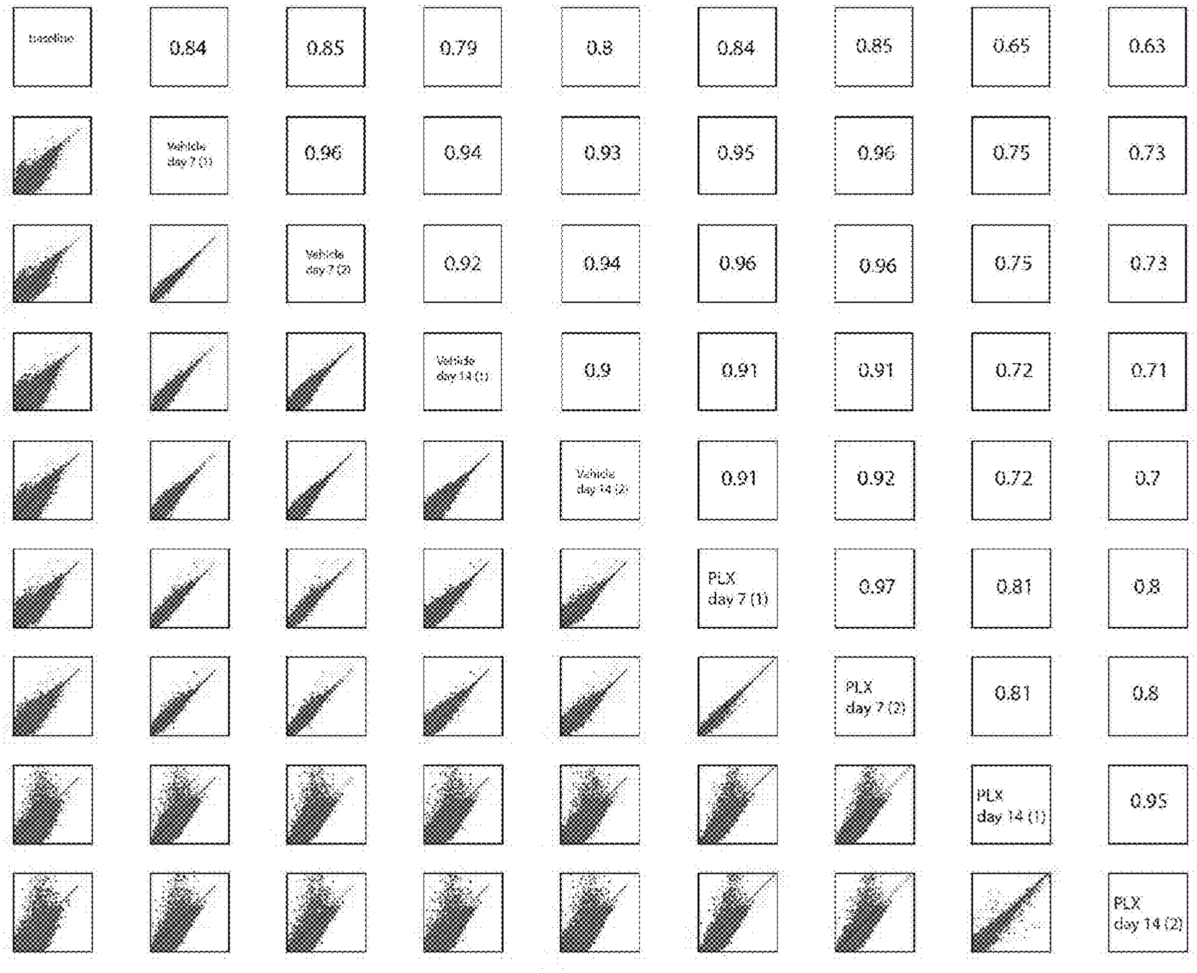
FIG. 34 shows Comparison of different treatment conditions and biological replicates in the first A375 PLX screen. Each square in the lower left half of the matrix compares the normalized sgRNA read count between two biological samples. Sample labels for each axis are indicated on the diagonal. For example, the box on the second row from the bottom and third column from the right compares PLX day 7 (2) on the x-axis with PLX day 14 (1) on the y-axis. The Pearson correlation coefficient for comparison (i,j) can be found in box (j,i); for the example described in the previous sentence, the correlation coefficient is 0.81.

To test the efficacy of GeCKO for positive selection, Applicants sought to identify gene knockouts that result in resistance to the BRAF protein kinase inhibitor vemurafenib (PLX) in melanoma (FIG. 27A). Exposure to PLX resulted in growth arrest of transduced A375 cells, which harbor the V600E gain-of-function BRAF mutation (FIG. 27B), therefore enabling the enrichment of a small group of cells that had been rendered drug-resistant by Cas9:sgRNA-mediated modification. After 14 days of PLX treatment, the sgRNA distribution was significantly different when compared with vehicle-treated cells (FIG. 27C; Wilcoxon rank-sum test, $p<10^{-10}$) and clustered separately from all other conditions (FIGS. 27D and 34).

Figure 27E:
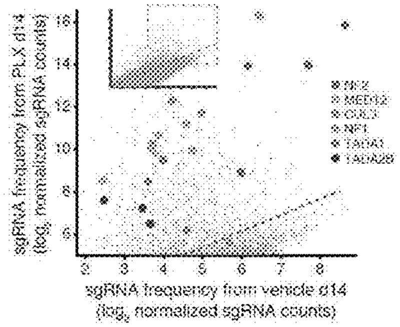
Figure 27F:
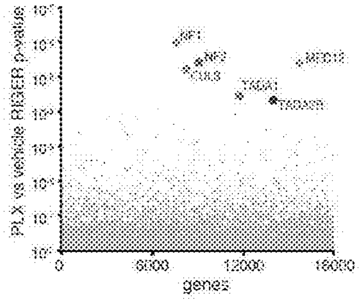
Figure 35A:
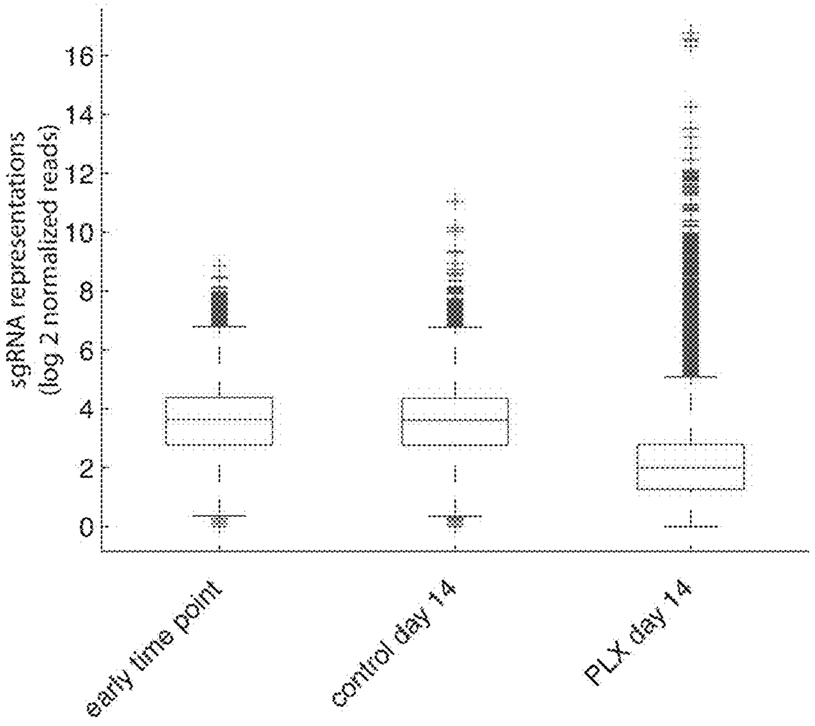
FIG. 35A-35B shows sgRNA and gene enrichment from the second A375 PLX screen. (A) Boxplot showing the distribution of reads from individual sgRNAs for the early timepoint, DMSO treated control, and PLX-4023 (PLX) treatment. The box extends from the first to the third quartile with the whiskers denoting 1.5 times the interquartile range. After 14 days of PLX treatment, while there is a decrease in the average number of reads per sgRNA, there is an increase in the number of reads for the most abundant sgRNAs. (B) Plot of the RIGER p value for genes enriched in PLX compared to vehicle control.
Figure 35B:
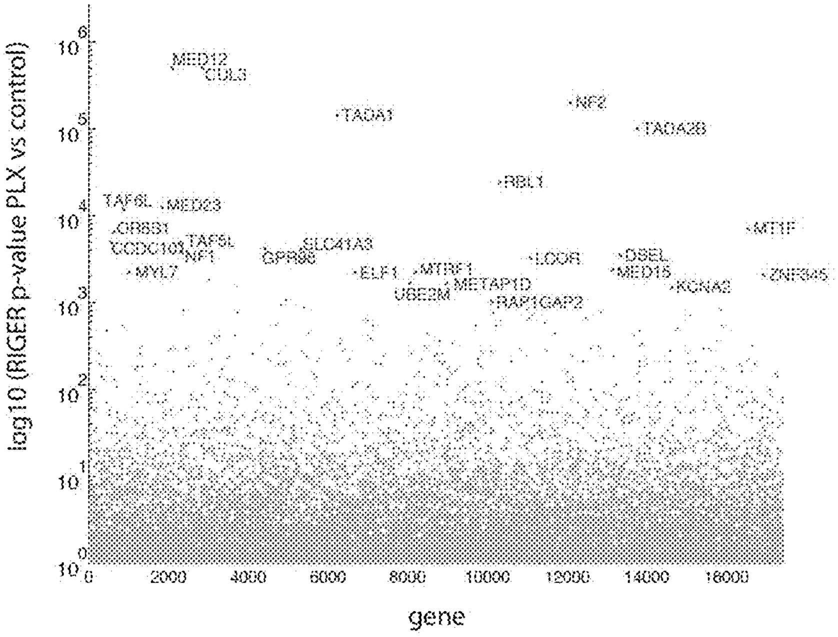
Figure 36:
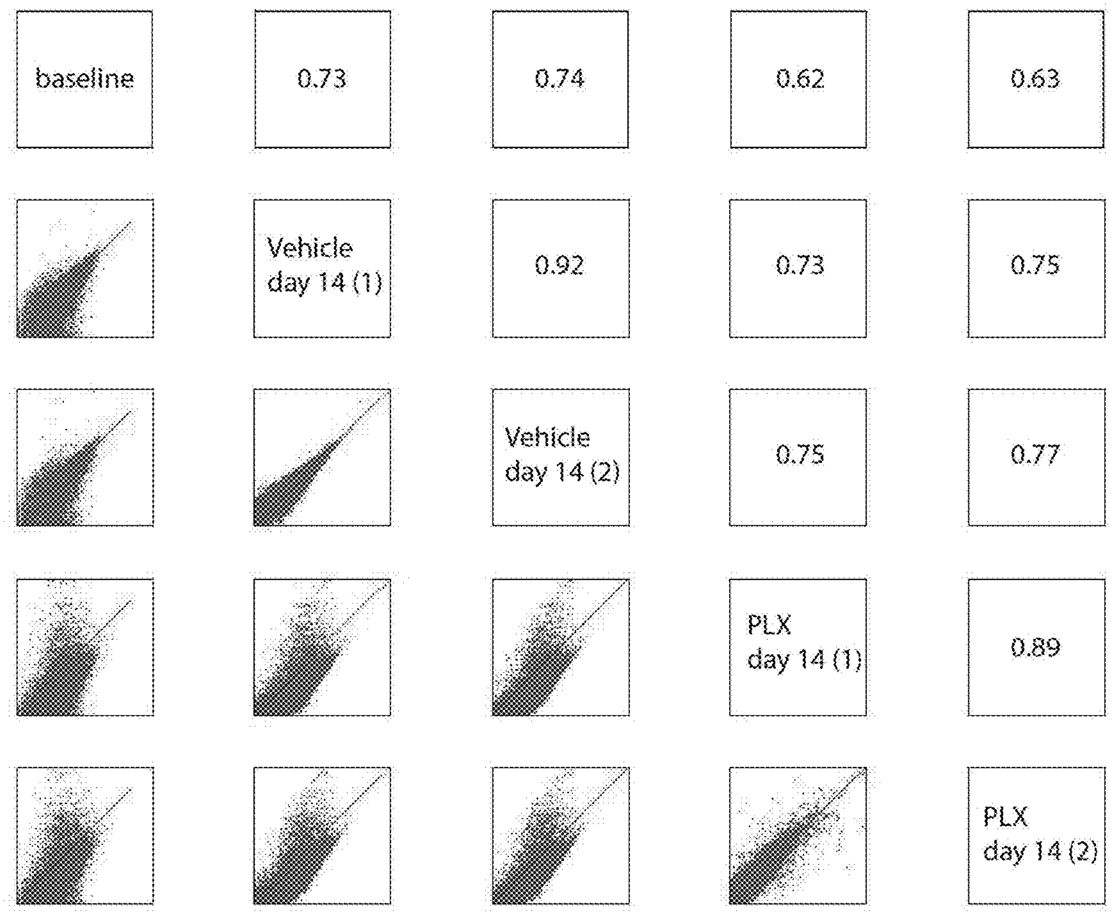
FIG. 36 shows Comparison of different treatment conditions and biological replicates in the infection replicate A375 screen. Each square in the lower left half of the matrix compares the normalized sgRNA read count between two biological samples. Sample labels for each axis are indicated on the diagonal. For example, the box on the second row from the bottom and third column from the right compares Vehicle day 14 (2) on the x-axis with PLX day 14 (1) on the y-axis. The Pearson correlation coefficient for comparison (i,j) can be found in box (j,i); for the example described in the previous sentence, the correlation coefficient is 0.75.

For a set of genes, Applicants found enrichment of multiple sgRNAs that target each gene after 14 days of PLX treatment (FIG. 27E), suggesting that loss of these particular genes contributes to PLX resistance. Applicants used the RNAi Gene Enrichment Ranking (RIGER) algorithm to rank screening hits by the consistent enrichment among multiple sgRNAs targeting the same gene (FIGS. 27F, 45). Applicants' highest ranking genes contained previously reported candidates NF1 and MED12 and also several previously unknown genes, including neurofibromin 2 (NF2), Cullin 3 E3 ligase (CUL3), and members of the STAGA histone acetyltransferase complex (TADA1 and TADA2B). These candidates yielded new testable hypotheses regarding PLX resistance mechanisms. For example, NF1 and NF2, although unrelated in sequence, are each mutated in similar but distinct forms of neurofibromatosis. In addition, epigenetic dysregulation resulting from mutations in the mechanistically related STAGA and Mediator complexes may have a role in acquired drug resistance. All of these hits were also identified through a second independent transduction (FIGS. 35 and 36, and Tables G and H).

TABLE G

Output of the RIGER algorithm for the initial A375 PLX screen comparing PLX (mean of the two replicates at day 14) to DMSO control (mean of the two replicates at day 14). The weighted sum method was used to convert sgRNAs to genes. Genes are sorted by RIGER rank.

| Gene | Hairpins | # Hairpins | Hairpin ranks | NES | Gene rank | p-value | p-value rank |
|---|---|---|---|---|---|---|---|
| NF2 | s_36796, s_36797, s_36798, s_36799 | 4 | 58, 415, 31, 22 | 8E−04 | 1 | 0.000004 | 2 |
| MED12 | s_33340, s_33341, s_33342, s_33343 | 4 | 53, 38, 45, 67 | 0.001 | 2 | 0.000004 | 3 |
| CUL3 | s_14311, s_14312, s_14313, s_14314, s_14315, s_14316 | 6 | 49523, 41, 17, 44, 6188, 18040 | 0.001 | 3 | 0.000006 | 5 |
| CLDN10 | s_12138, s_12139, s_12140, s_12141 | 4 | 23, 24918, 69, 4914 | 0.002 | 4 | 0.000005 | 4 |
| NF1 | s_36794, s_36795 | 2 | 130, 1 | 0.002 | 5 | 0.000001 | 1 |
| TADA1 | s_55204, s_55205, s_55206, s_55207 | 4 | 137, 93, 5672, 927 | 0.003 | 6 | 0.000035 | 6 |
| TADA2B | s_55211, s_55212, s_55213 | 3 | 127, 249, 429 | 0.005 | 7 | 0.000046 | 7 |
| SPECC1 | s_53443, s_53444, s_53445, s_53446, s_53447, s_53448, s_53449, s_53450, s_53451 | 9 | 145, 26652, 43674, 56582, 58227, 59830, 20, 22519, 21861 | 0.005 | 8 | 0.000146 | 11 |
| CCDC101 | s_9430, s_9431, s_9432 | 3 | 333, 492, 198 | 0.007 | 9 | 0.000082 | 8 |
| ALG3 | s_2023, s_2024, s_2025, s_2026 | 4 | 2441, 297, 138, 22771 | 0.007 | 10 | 0.000118 | 9 |
| P4HB | s_39947, s_39948, s_39949 | 3 | 59088, 30, 576 | 0.01 | 11 | 0.000189 | 12 |
| EED | s_17448, s_17449, s_17450, s_17451 | 4 | 2886, 293, 443, 16470 | 0.011 | 12 | 0.000313 | 15 |
| TAF6L | s_55283, s_55284, s_55285 | 3 | 1977, 330, 532 | 0.011 | 13 | 0.000234 | 13 |
| MED15 | s_33355, s_33356, s_33357, s_33358 | 4 | 285, 504, 3489, 542 | 0.012 | 14 | 0.000382 | 17 |

TABLE G-continued

Output of the RIGER algorithm for the initial A375 PLX screen comparing PLX (mean of the two replicates at day 14) to DMSO control (mean of the two replicates at day 14). The weighted sum method was used to convert sgRNAs to genes. Genes are sorted by RIGER rank.

| Gene | Hairpins | # Hairpins | Hairpin ranks | NES | Gene rank | p-value | p-value rank |
|---|---|---|---|---|---|---|---|
| NPPC | s_37703, s_37704, s_37705, s_37706, s_37707, s_37708 | 6 | 204, 6109, 39836, 60416, 10125, 403 | 0.012 | 15 | 0.000575 | 24 |
| TAF5L | s_55276, s_55277 | 2 | 199, 831 | 0.012 | 16 | 0.000141 | 10 |
| PGD | s_41483, s_41484, s_41485 | 3 | 624, 484, 1163 | 0.013 | 17 | 0.000349 | 16 |
| LGALS4 | s_30886, s_30887, s_30888, s_30889 | 4 | 33, 678, 16507, 14753 | 0.014 | 18 | 0.00051 | 22 |
| TAOK1 | s_55349, s_55350, s_55351 | 3 | 696, 505, 5374 | 0.014 | 19 | 0.000429 | 19 |
| CD320 | s_10386, s_10387, s_10388, s_10389, s_10390, s_10391 | 6 | 17447, 182, 35806, 50696, 49163, 488 | 0.014 | 20 | 0.000824 | 30 |
| CCNC | s_10026, s_10027, s_10028, s_10029, s_10030 | 5 | 52916, 817, 518, 51901, 385 | 0.015 | 21 | 0.000735 | 25 |
| SMARCB1 | s_52518, s_52519, s_52520 | 3 | 614, 733, 2280 | 0.016 | 22 | 0.000501 | 21 |
| ASIC1 | s_3947, s_3948, s_3949, s_3950, s_3951, s_3952 | 6 | 605, 53882, 17965, 48, 12823, 15216 | 0.016 | 23 | 0.001042 | 34 |
| MED19 | s_33371, s_33372, s_33373, s_33374 | 4 | 298, 3666, 7614, 748 | 0.017 | 24 | 0.000754 | 27 |
| GADD45GIP1 | s_22055, s_22056, s_22057, s_22058 | 4 | 832, 124, 9275, 1307 | 0.017 | 25 | 0.000795 | 29 |
| MED23 | s_33386, s_33387 | 2 | 430, 1171 | 0.018 | 26 | 0.000301 | 14 |
| ZDHHC15 | s_62858, s_62859, s_62860, s_62861 | 4 | 60, 48709, 953, 52940 | 0.019 | 27 | 0.000988 | 33 |
| TWF2 | s_59891, s_59892, s_59893, s_59894, s_59895, s_59896 | 6 | 25884, 211, 11866, 668, 55063, 18294 | 0.019 | 28 | 0.001489 | 41 |
| ADRA2B | s_1352, s_1353, s_1354 | 3 | 55393, 482, 1091 | 0.021 | 29 | 0.000873 | 31 |
| PDC | s_40830, s_40831, s_40832, s_40833, s_40834, s_40835 | 6 | 56956, 242, 720, 49078, 43057, 3523 | 0.021 | 30 | 0.001707 | 50 |
| KCTD10 | s_28876, s_28877, s_28878 | 3 | 1094, 3568, 534 | 0.021 | 31 | 0.000896 | 32 |

TABLE G-continued

Output of the RIGER algorithm for the initial A375 PLX screen comparing PLX (mean of the two replicates at day 14) to DMSO control (mean of the two replicates at day 14). The weighted sum method was used to convert sgRNAs to genes. Genes are sorted by RIGER rank.

| Gene | Hairpins | # Hairpins | Hairpin ranks | NES | Gene rank | p-value | p-value rank |
|---|---|---|---|---|---|---|---|
| MFSD9 | s_33784, s_33785 | 2 | 1176, 1027 | 0.021 | 32 | 0.000419 | 18 |
| TXNDC17 | s_59941, s_59942, s_59943, s_59944 | 4 | 25655, 509, 935, 6800 | 0.022 | 33 | 0.00128 | 38 |
| MED16 | s_33359, s_33360, s_33361, s_33362 | 4 | 912, 608, 20030, 4476 | 0.022 | 34 | 0.001299 | 40 |
| TADA3 | s_55214, s_55215 | 2 | 1504, 234 | 0.022 | 35 | 0.000455 | 20 |
| PDCD10 | s_40840, s_40841, s_40842, s_40843, s_40844 | 5 | 30804, 804, 1252, 20846, 561 | 0.023 | 36 | 0.001744 | 51 |
| TNFRSF17 | s_58081, s_58082, s_58083, s_58084 | 4 | 1184, 29, 50083, 12376 | 0.023 | 37 | 0.001491 | 42 |
| DARS | s_14981, s_14982, s_14983, s_14984, s_14985, s_14986 | 6 | 54968, 41173, 736, 52808, 20070, 493 | 0.023 | 38 | 0.002111 | 61 |
| ELMOD1 | s_18007, s_18008 | 2 | 221, 1617 | 0.024 | 39 | 0.000523 | 23 |
| ARID1A | s_3477, s_3478, s_3479, s_3480 | 4 | 53744, 167, 1145, 4655 | 0.024 | 40 | 0.001505 | 43 |
| GNB2L1 | s_23260, s_23261, s_23262, s_23263 | 4 | 12534, 598, 1022, 8784 | 0.024 | 41 | 0.001556 | 44 |
| SCPEP1 | s_49407, s_49408, s_49409, s_49410 | 4 | 949, 61876, 883, 50303 | 0.024 | 42 | 0.001613 | 45 |
| KEAP1 | s_29029, s_29030, s_29031, s_29032 | 4 | 4069, 1053, 43892, 601 | 0.025 | 43 | 0.001632 | 47 |
| NCOR2 | s_36330, s_36331, s_36332, s_36333 | 4 | 991, 11014, 20939, 822 | 0.025 | 44 | 0.00166 | 48 |
| OR2T33 | s_39119, s_39120, s_39121 | 3 | 1342, 9376, 500 | 0.025 | 45 | 0.001231 | 37 |
| BCL2L12 | s_5187, s_5188, s_5189, s_5190 | 4 | 1605, 711, 5895, 1061 | 0.025 | 46 | 0.001761 | 53 |
| SPOPL | s_53635, s_53636, s_53637 | 3 | 1325, 664, 56183 | 0.026 | 47 | 0.001289 | 39 |
| FGGY | s_21004, s_21005, s_21006, s_21007, s_21008, s_21009 | 6 | 852, 9579, 32124, 29464, 27460, 388 | 0.026 | 48 | 0.002495 | 68 |
| CA7 | s_8596, s_8597, s_8598, s_8599, s_8600, s_8601 | 6 | 273, 62443, 30916, 21259, 7063, 905 | 0.026 | 49 | 0.002567 | 69 |
| JMJD4 | s_28292, s_28293, | 6 | 975, 19283, 81, 29765, | 0.026 | 50 | 0.002601 | 70 |

TABLE G-continued

Output of the RIGER algorithm for the initial A375 PLX screen comparing PLX (mean of the two replicates at day 14) to DMSO control (mean of the two replicates at day 14). The weighted sum method was used to convert sgRNAs to genes. Genes are sorted by RIGER rank.

| Gene | Hairpins | # Hairpins | Hairpin ranks | NES | Gene rank | p-value | p-value rank |
|---|---|---|---|---|---|---|---|
| | s_28294, s_28295, s_28296, s_28297 | | 46303, 47416 | | | | |
| MYO9B | s_35776, s_35777, s_35778, s_35779 | 4 | 1257, 326, 21804, 23954 | 0.027 | 51 | 0.001952 | 57 |
| FAM19A4 | s_19778, s_19779, s_19780, s_19781, s_19782, s_19783 | 6 | 62838, 909, 383, 23595, 32237, 42288 | 0.027 | 52 | 0.002769 | 76 |
| EBF4 | s_17294, s_17295, s_17296, s_17297 | 4 | 64198, 1219, 506, 15439 | 0.027 | 53 | 0.002002 | 59 |
| TTC4 | s_59623, s_59624, s_59625, s_59626, s_59627 | 5 | 1161, 52043, 51855, 23126, 218 | 0.028 | 54 | 0.002705 | 74 |
| DPH2 | s_16717, s_16718, s_16719, s_16720, s_16721, s_16722 | 6 | 958, 363, 2412, 6120, 3930, 1644 | 0.028 | 55 | 0.00298 | 82 |
| DRAP1 | s_16840, s_16841, s_16842, s_16843 | 4 | 37730, 1221, 643, 31607 | 0.028 | 56 | 0.002136 | 62 |
| C1orf49 | s_7303, s_7304, s_7305, s_7306, s_7307, s_7308, s_7309 | 7 | 820, 63864, 34124, 47596, 60950, 413, 16428 | 0.028 | 57 | 0.003353 | 87 |
| ATXN2L | s_4596, s_4597 | 2 | 461, 1892 | 0.028 | 58 | 0.000746 | 26 |
| CCT8 | s_10201, s_10202 | 2 | 1836, 684 | 0.029 | 59 | 0.000757 | 28 |
| INA | s_27443, s_27444, s_27445, s_27446 | 4 | 2708, 1296, 502, 10303 | 0.029 | 60 | 0.00224 | 64 |
| SPRED1 | s_53662, s_53663, s_53664 | 3 | 1619, 50436, 448 | 0.029 | 61 | 0.001682 | 49 |
| FAM205A | s_19797, s_19798, s_19799 | 3 | 1158, 41145, 1417 | 0.03 | 62 | 0.001761 | 52 |
| ZNF679 | s_64444, s_64445, s_64446, s_64447 | 4 | 1393, 51433, 53714, 387 | 0.03 | 63 | 0.002404 | 66 |
| RARRES1 | s_46128, s_46129, s_46130, s_46131, s_46132 | 5 | 64493, 49693, 1031, 875, 32486 | 0.03 | 64 | 0.003121 | 86 |
| OXR1 | s_39853, s_39854, s_39855, s_39856, s_39857, s_39858, s_39859, s_39860, s_39861, s_39862, | 12 | 635, 13208, 3431, 40334, 44056, 34602, 40269, 15654, 27560, 14451, 43620, 75 | 0.031 | 65 | 0.004951 | 111 |

TABLE G-continued

Output of the RIGER algorithm for the initial A375 PLX screen comparing PLX (mean of the two replicates at day 14) to DMSO control (mean of the two replicates at day 14). The weighted sum method was used to convert sgRNAs to genes. Genes are sorted by RIGER rank.

| Gene | Hairpins | # Hairpins | Hairpin ranks | NES | Gene rank | p-value | p-value rank |
|---|---|---|---|---|---|---|---|
| | s_39863, s_39864 | | | | | | |
| ABCB5 | s_159, s_160, s_161, s_162, s_163, s_164, s_165, s_166, s_167 | 9 | 22148, 406, 716, 56705, 810, 24993, 32918, 2841, 8584 | 0.031 | 66 | 0.004499 | 103 |
| PCIF1 | s_40717, s_40718, s_40719 | 3 | 9090, 1441, 1264 | 0.031 | 67 | 0.00186 | 54 |
| TSPAN1 | s_59367, s_59368, s_59369, s_59370 | 4 | 2325, 13819, 864, 1297 | 0.031 | 68 | 0.002605 | 71 |
| GEN1 | s_22609, s_22610, s_22611, s_22612 | 4 | 11810, 887, 1299, 8422 | 0.031 | 69 | 0.002637 | 72 |
| EIF3D | s_17807, s_17808, s_17809, s_17810 | 4 | 973, 21108, 1274, 24555 | 0.031 | 70 | 0.00265 | 73 |
| CD4 | s_10420, s_10421, s_10422, s_10423 | 4 | 1354, 17639, 21819, 786 | 0.032 | 71 | 0.002719 | 75 |
| RASGEF1C | s_46195, s_46196, s_46197 | 3 | 1741, 57044, 527 | 0.032 | 72 | 0.001958 | 58 |
| RFX4 | s_46955, s_46956, s_46957, s_46958, s_46959, s_46960, s_46961, s_46962 | 8 | 41956, 37657, 844, 23401, 35269, 57099, 19421, 368 | 0.032 | 73 | 0.004515 | 104 |
| EP300 | s_18347, s_18348, s_18349, s_18350 | 4 | 56572, 687, 1414, 17568 | 0.032 | 74 | 0.002802 | 77 |
| MMS19 | s_34268, s_34269, s_34270, s_34271 | 4 | 48047, 59609, 1127, 1271 | 0.032 | 75 | 0.002818 | 78 |
| HEBP1 | s_24995, s_24996, s_24997, s_24998 | 4 | 923, 46506, 1368, 10469 | 0.033 | 76 | 0.002925 | 80 |
| DOK2 | s_16643, s_16644, s_16645 | 3 | 35762, 1884, 306 | 0.033 | 77 | 0.00211 | 60 |
| BRD9 | s_5732, s_5733, s_5734, s_5735, s_5736, s_5737, s_5738 | 7 | 827, 22740, 6866, 12005, 15293, 4165, 858 | 0.033 | 78 | 0.004695 | 109 |
| MAP1LC3A | s_32578, s_32579, s_32580 | 3 | 1401, 28791, 1572 | 0.034 | 79 | 0.002217 | 63 |
| GPR123 | s_23666, s_23667 | 2 | 89, 2438 | 0.034 | 80 | 0.001072 | 35 |

TABLE G-continued

Output of the RIGER algorithm for the initial A375 PLX screen comparing PLX (mean of the two replicates at day 14) to DMSO control (mean of the two replicates at day 14). The weighted sum method was used to convert sgRNAs to genes. Genes are sorted by RIGER rank.

| Gene | Hairpins | # Hairpins | Hairpin ranks | NES | Gene rank | p-value | p-value rank |
|---|---|---|---|---|---|---|---|
| FH | s_21023, s_21024, s_21025, s_21026, s_21027, s_21028 | 6 | 49396, 14069, 866, 14355, 1035, 36483 | 0.035 | 81 | 0.004382 | 102 |
| NUGGC | s_38328, s_38329, s_38330 | 3 | 49325, 1969, 470 | 0.035 | 82 | 0.002409 | 67 |
| OR52E2 | s_39294, s_39295 | 2 | 1537, 2022 | 0.035 | 83 | 0.001141 | 36 |
| CRNN | s_13692, s_13693, s_13694, s_13695, s_13696, s_13697 | 6 | 21178, 62333, 62987, 230, 62464, 1287 | 0.036 | 84 | 0.004655 | 107 |
| HDAC6 | s_24909, s_24910, s_24911, s_24912 | 4 | 1432, 1157, 37523, 5836 | 0.036 | 85 | 0.003451 | 88 |
| AHCYL2 | s_1615, s_1616, s_1617, s_1618, s_1619, s_1620 | 6 | 1275, 536, 15539, 41104, 16156, 7154 | 0.038 | 86 | 0.005333 | 117 |
| ZC3H18 | s_62742, s_62743, s_62744 | 3 | 885, 2013, 4091 | 0.038 | 87 | 0.002841 | 79 |
| RGS2 | s_47074, s_47075, s_47076, s_47077, s_47078 | 5 | 1366, 43591, 49134, 34175, 951 | 0.038 | 88 | 0.005052 | 113 |
| TMED3 | s_57021, s_57022, s_57023 | 3 | 2154, 20038, 590 | 0.039 | 89 | 0.00293 | 81 |
| TXNIP | s_59960, s_59961, s_59962, s_59963, s_59964 | 5 | 62111, 1181, 48123, 1335, 37778 | 0.039 | 90 | 0.005299 | 116 |
| MLN | s_34131, s_34132, s_34133 | 3 | 1893, 4200, 1493 | 0.04 | 91 | 0.003008 | 83 |
| CLEC2B | s_12245, s_12246, s_12247 | 3 | 52935, 1491, 1898 | 0.04 | 92 | 0.003019 | 84 |
| CASQ2 | s_9253, s_9254, s_9255 | 3 | 2052, 1075, 53344 | 0.04 | 93 | 0.003063 | 85 |
| GMDS | s_23142, s_23143, s_23144, s_23145, s_23146, s_23147 | 6 | 27864, 18095, 53905, 1284, 13005, 944 | 0.042 | 94 | 0.006445 | 141 |
| UBE2M | s_60195, s_60196 | 2 | 1767, 2418 | 0.042 | 95 | 0.001626 | 46 |
| RNF7 | s_47784, s_47785, s_47786, s_47787, s_47788 | 5 | 1179, 21752, 1461, 1846, 56079 | 0.042 | 96 | 0.006005 | 129 |
| CRYGN | s_13791, s_13792, s_13793 | 3 | 818, 2294, 7260 | 0.042 | 97 | 0.003478 | 89 |
| NDUFA8 | s_36466, s_36467, s_36468 | 3 | 8398, 636, 2393 | 0.043 | 98 | 0.003571 | 90 |
| NCL | s_36291, s_36292, | 5 | 13572, 1122, 9807, 8470, | 0.043 | 99 | 0.006281 | 133 |

TABLE G-continued

Output of the RIGER algorithm for the initial A375 PLX screen comparing PLX (mean of the two replicates at day 14) to DMSO control (mean of the two replicates at day 14). The weighted sum method was used to convert sgRNAs to genes. Genes are sorted by RIGER rank.

| Gene | Hairpins | # Hairpins | Hairpin ranks | NES | Gene rank | p-value | p-value rank |
|---|---|---|---|---|---|---|---|
| | s_36293, s_36294, s_36295 | | 1525 | | | | |
| PLK4 | s_42605, s_42606, s_42607, s_42608, s_42609 | 5 | 11718, 1841, 10567, 191, 16298 | 0.043 | 100 | 0.006321 | 134 |

TABLE H

Output of the RIGER algorithm for the transduction replicate A375 PLX screen comparing PLX (mean of the two replicates at day 14) to DMSO control (mean of the two replicates at day 14). The weighted sum method was used to convert sgRNAs to genes. Genes are sorted by RIGER rank.

| Gene | Hairpins | # Hairpins | Hairpin ranks | NES | Gene rank | p-value | p-value rank |
|---|---|---|---|---|---|---|---|
| MED12 | s_33340, s_33341, s_33342, s_33343 | 4 | 20, 18, 23, 36 | 0.00051 | 1 | 0.000002 | 1 |
| CUL3 | s_14311, s_14312, s_14313, s_14314, s_14315, s_14316 | 6 | 59797, 26, 17, 29, 18391, 13751 | 0.0008262 | 2 | 0.000002 | 2 |
| NF2 | s_36796, s_36797, s_36798, s_36799 | 4 | 71, 295, 67, 42 | 0.001589 | 3 | 0.000005 | 3 |
| TADA1 | s_55204, s_55205, s_55206, s_55207 | 4 | 28, 85, 2999, 379 | 0.00185 | 4 | 0.000007 | 4 |
| TADA2B | s_55211, s_55212, s_55213 | 3 | 101, 107, 83 | 0.00213 | 5 | 0.00001 | 5 |
| RBL1 | s_46360, s_46361, s_46362 | 3 | 386, 94, 245 | 0.004575 | 6 | 0.000041 | 6 |
| TAF6L | s_55283, s_55284, s_55285 | 3 | 2738, 129, 361 | 0.006689 | 7 | 0.000085 | 8 |
| OR8S1 | s_39543, s_39544, s_39545, s_39546 | 4 | 255, 21226, 25406, 325 | 0.008042 | 8 | 0.000157 | 10 |
| MED23 | s_33386, s_33387 | 2 | 376, 535 | 0.009179 | 9 | 0.000081 | 7 |
| SLC41A3 | s_51930, s_51931, s_51932, s_51933 | 4 | 134, 50489, 441, 60192 | 0.009526 | 10 | 0.000244 | 14 |
| CCDC101 | s_9430, s_9431, s_9432 | 3 | 742, 511, 283 | 0.01002 | 11 | 0.000201 | 11 |
| LCOR | s_30684, s_30685, s_30686, s_30687 | 4 | 362, 44569, 4583, 418 | 0.01057 | 12 | 0.00031 | 17 |
| GPR98 | s_23900, s_23901, s_23902 | 3 | 392, 518, 48952 | 0.01074 | 13 | 0.000239 | 13 |
| KCNA2 | s_28512, s_28513, s_28514, s_28515, | 8 | 29441, 30891, 63671, 3716, 48582, 37548, 297, 194 | 0.01187 | 14 | 0.000666 | 27 |

TABLE H-continued

Output of the RIGER algorithm for the transduction replicate A375 PLX screen comparing PLX (mean of the two replicates at day 14) to DMSO control (mean of the two replicates at day 14). The weighted sum method was used to convert sgRNAs to genes. Genes are sorted by RIGER rank.

| Gene | Hairpins | # Hairpins | Hairpin ranks | NES | Gene rank | p-value | p-value rank |
|---|---|---|---|---|---|---|---|
| | s_28516, s_28517, s_28518, s_28519 | | | | | | |
| MED15 | s_33355, s_33356, s_33357, s_33358 | 4 | 227, 552, 711, 647 | 0.01231 | 15 | 0.000416 | 18 |
| MT1F | s_35127, s_35128 | 2 | 842, 183 | 0.01255 | 16 | 0.000141 | 9 |
| MYL7 | s_35662, s_35663, s_35664, s_35665 | 4 | 135, 46125, 598, 37747 | 0.01261 | 17 | 0.000445 | 20 |
| SLC7A11 | s_52194, s_52195, s_52196, s_52197, s_52198 | 5 | 16607, 313, 460, 5262, 27650 | 0.01288 | 18 | 0.000554 | 23 |
| MTRF1 | s_35317, s_35318, s_35319 | 3 | 17905, 41, 862 | 0.0145 | 19 | 0.000445 | 19 |
| ELF1 | s_17940, s_17941, s_17942 | 3 | 35910, 873, 35 | 0.01465 | 20 | 0.000454 | 21 |
| METAP1D | s_33547, s_33548, s_33549, s_33550 | 4 | 411, 617, 35187, 34941 | 0.01479 | 21 | 0.000612 | 25 |
| FAM160A2 | s_19507, s_19508, s_19509, s_19510 | 4 | 48131, 49009, 459, 610 | 0.01497 | 22 | 0.000623 | 26 |
| TAF5L | s_55276, s_55277 | 2 | 57, 1089 | 0.0154 | 23 | 0.000207 | 12 |
| NF1 | s_36794, s_36795 | 2 | 1227, 12 | 0.01711 | 24 | 0.000261 | 15 |
| DSEL | s_16908, s_16909 | 2 | 642, 1068 | 0.01782 | 25 | 0.000287 | 16 |
| RAP1GAP2 | s_46063, s_46064, s_46065, s_46066 | 4 | 740, 58091, 49142, 709 | 0.01915 | 26 | 0.000992 | 29 |
| MPG | s_34467, s_34468, s_34469, s_34470, s_34471, s_34472 | 6 | 597, 474, 37985, 7657, 49238, 24732 | 0.0197 | 27 | 0.001548 | 41 |
| MED16 | s_33359, s_33360, s_33361, s_33362 | 4 | 619, 825, 25639, 27832 | 0.02023 | 28 | 0.001103 | 31 |
| XKR4 | s_62252, s_62253, s_62254, s_62255 | 4 | 29846, 897, 14605, 473 | 0.02069 | 29 | 0.001163 | 32 |
| ERP27 | s_18694, s_18695, s_18696, s_18697 | 4 | 57819, 843, 26738, 768 | 0.02156 | 30 | 0.001269 | 35 |
| MAB21L2 | s_32293, s_32294, s_32295 | 3 | 1088, 654, 49187 | 0.02162 | 31 | 0.000938 | 28 |
| ASIC5 | s_3967, s_3968, s_3969, s_3970, s_3971 | 5 | 84, 36168, 2836, 46662, 924 | 0.02172 | 32 | 0.001596 | 42 |
| MSMB | s_35048, s_35049, s_35050, | 5 | 63246, 51785, 916, 124, 60194 | 0.02184 | 33 | 0.001613 | 43 |

TABLE H-continued

Output of the RIGER algorithm for the transduction replicate A375 PLX screen comparing PLX (mean of the two replicates at day 14) to DMSO control (mean of the two replicates at day 14). The weighted sum method was used to convert sgRNAs to genes. Genes are sorted by RIGER rank.

| Gene | Hairpins | # Hairpins | Hairpin ranks | NES | Gene rank | p-value | p-value rank |
|---|---|---|---|---|---|---|---|
| | s_35051, s_35052 | | | | | | |
| ZNF182 | s_63394, s_63395, s_63396, s_63397 | 4 | 856, 814, 58286, 44944 | 0.02211 | 34 | 0.001328 | 37 |
| ZNF345 | s_63726, s_63727 | 2 | 1558, 196 | 0.02256 | 35 | 0.000479 | 22 |
| TNFSF18 | s_58159, s_58160, s_58161, s_58162 | 4 | 766, 19361, 905, 33444 | 0.02276 | 36 | 0.00141 | 39 |
| NDUFAF2 | s_36477, s_36478, s_36479 | 3 | 1232, 22725, 494 | 0.02312 | 37 | 0.001063 | 30 |
| PDCD10 | s_40840, s_40841, s_40842, s_40843, s_40844 | 5 | 43, 3962, 1002, 5014, 3313 | 0.02319 | 38 | 0.001844 | 49 |
| CCNC | s_10026, s_10027, s_10028, s_10029, s_10030 | 5 | 48614, 1596, 868, 1864, 584 | 0.02425 | 39 | 0.002022 | 52 |
| SPRED1 | s_53662, s_53663, s_53664 | 3 | 950, 24805, 1164 | 0.02451 | 40 | 0.001188 | 33 |
| GDPD2 | s_22566, s_22567, s_22568, s_22569, s_22570, s_22571 | 6 | 367, 60779, 819, 52875, 24938, 6538 | 0.02456 | 41 | 0.002293 | 57 |
| DYRK3 | s_17200, s_17201, s_17202, s_17203 | 4 | 9900, 22246, 1101, 455 | 0.02457 | 42 | 0.001629 | 44 |
| MBP | s_33068, s_33069, s_33070, s_33071, s_33072, s_33073, s_33074, s_33075, s_33076 | 9 | 15442, 25428, 529, 29634, 16368, 8819, 36773, 478, 52354 | 0.02489 | 43 | 0.002965 | 71 |
| PARP3 | s_40316, s_40317, s_40318 | 3 | 506, 1352, 59418 | 0.02518 | 44 | 0.001243 | 34 |
| UBE2M | s_60195, s_60196 | 2 | 491, 1665 | 0.02542 | 45 | 0.000595 | 24 |
| HDGF | s_24936, s_24937, s_24938 | 3 | 756, 1285, 5163 | 0.02545 | 46 | 0.00127 | 36 |
| KCNC2 | s_28558, s_28559, s_28560, s_28561, s_28562, s_28563, s_28564 | 7 | 42492, 6191, 648, 54771, 50213, 652, 22159 | 0.02554 | 47 | 0.002731 | 66 |
| GALNS | s_22109, s_22110, s_22111, s_22112 | 4 | 999, 8504, 52589, 986 | 0.02604 | 48 | 0.00184 | 47 |
| METTL21B | s_33609, s_33610, s_33611, s_33612 | 4 | 46303, 472, 1171, 29308 | 0.02605 | 49 | 0.001842 | 48 |

TABLE H-continued

Output of the RIGER algorithm for the transduction replicate A375 PLX screen comparing PLX (mean of the two replicates at day 14) to DMSO control (mean of the two replicates at day 14). The weighted sum method was used to convert sgRNAs to genes. Genes are sorted by RIGER rank.

| Gene | Hairpins | # Hairpins | Hairpin ranks | NES | Gene rank | p-value | p-value rank |
|---|---|---|---|---|---|---|---|
| BTBD17 | s_5890, s_5891, s_5892 | 3 | 1185, 64382, 1200 | 0.02641 | 50 | 0.001371 | 38 |
| HSD11B1 | s_26144, s_26145, s_26146, s_26147, s_26148 | 5 | 1048, 391, 7446, 21804, 42773 | 0.02689 | 51 | 0.002482 | 61 |
| LGR5 | s_30925, s_30926, s_30927, s_30928 | 4 | 1394, 241, 38237, 49566 | 0.02892 | 52 | 0.002269 | 56 |
| BUB1B | s_5999, s_6000, s_6001, s_6002 | 4 | 30283, 1179, 47822, 935 | 0.02924 | 53 | 0.0023 | 58 |
| MRFAP1L1 | s_34603, s_34604, s_34605 | 3 | 18516, 421, 1627 | 0.02926 | 54 | 0.00168 | 45 |
| CCDC83 | s_9835, s_9836, s_9837, s_9838 | 4 | 1148, 21192, 1041, 54459 | 0.02932 | 55 | 0.002316 | 59 |
| DRAP1 | s_16840, s_16841, s_16842, s_16843 | 4 | 33445, 508, 1328, 44015 | 0.02937 | 56 | 0.002321 | 60 |
| RELT | s_46777, s_46778, s_46779 | 3 | 187, 61852, 1740 | 0.02984 | 57 | 0.001756 | 46 |
| RANBP9 | s_46039, s_46040, s_46041 | 3 | 1837, 11418, 52 | 0.0307 | 58 | 0.001849 | 50 |
| HMMR | s_25651, s_25652, s_25653, s_25654 | 4 | 1502, 48474, 27570, 234 | 0.03099 | 59 | 0.002589 | 64 |
| MALSU1 | s_32462, s_32463, s_32464 | 3 | 1575, 5215, 920 | 0.03115 | 60 | 0.001886 | 51 |
| TACC1 | s_55171, s_55172, s_55173, s_55174, s_55175, s_55176 | 6 | 4921, 24086, 6177, 328, 10098, 1110 | 0.03181 | 61 | 0.003733 | 94 |
| HOXC13 | s_25901, s_25902, s_25903, s_25904 | 4 | 9058, 894, 1336, 22970 | 0.03205 | 62 | 0.00277 | 67 |
| EAPP | s_17273, s_17274, s_17275, s_17276 | 4 | 1388, 21167, 820, 26512 | 0.03259 | 63 | 0.002875 | 68 |
| C1QA | s_6997, s_6998, s_6999, s_7000, s_7001, s_7002 | 6 | 26254, 946, 914, 57738, 2934, 961 | 0.03263 | 64 | 0.003918 | 99 |
| SELRC1 | s_49728, s_49729, s_49730 | 3 | 1215, 6860, 1574 | 0.03276 | 65 | 0.00209 | 53 |
| B3GALNT2 | s_4738, s_4739, s_4740, s_4741, s_4742, s_4743 | 6 | 827, 29762, 38965, 31290, 23785, 981 | 0.03279 | 66 | 0.003962 | 101 |
| RBM15B | s_46395, s_46396, s_46397 | 3 | 893, 1695, 44505 | 0.03299 | 67 | 0.002127 | 54 |

TABLE H-continued

Output of the RIGER algorithm for the transduction replicate A375 PLX screen comparing PLX (mean of the two replicates at day 14) to DMSO control (mean of the two replicates at day 14). The weighted sum method was used to convert sgRNAs to genes. Genes are sorted by RIGER rank.

| Gene | Hairpins | # Hairpins | Hairpin ranks | NES | Gene rank | p-value | p-value rank |
|---|---|---|---|---|---|---|---|
| PDE12 | s_40901, s_40902, s_40903, s_40904, s_40905, s_40906 | 6 | 2381, 1262, 58589, 2108, 38, 10016 | 0.03326 | 68 | 0.004098 | 104 |
| PAFAH2 | s_40041, s_40042, s_40043, s_40044, s_40045, s_40046 | 6 | 5602, 61209, 1155, 63735, 375, 37029 | 0.03339 | 69 | 0.004132 | 106 |
| LAMA3 | s_30412, s_30413, s_30414, s_30415, s_30416, s_30417, s_30418, s_30419 | 8 | 9450, 1177, 17134, 27544, 874, 456, 38308, 45063 | 0.03369 | 70 | 0.005071 | 132 |
| TDRD5 | s_55980, s_55981, s_55982, s_55983, s_55984, s_55985 | 6 | 1131, 41843, 44717, 513, 54260, 50377 | 0.03397 | 71 | 0.004252 | 108 |
| MBNL2 | s_33046, s_33047, s_33048, s_33049 | 4 | 60513, 1365, 1158, 40330 | 0.03435 | 72 | 0.003193 | 76 |
| ADI1 | s_1254, s_1255, s_1256, s_1257, s_1258, s_1259 | 6 | 1267, 209, 12112, 3449, 25692, 52308 | 0.03487 | 73 | 0.004464 | 111 |
| MED19 | s_33371, s_33372, s_33373, s_33374 | 4 | 306, 12467, 2378, 1694 | 0.03523 | 74 | 0.003361 | 81 |
| PRKRA | s_44162, s_44163, s_44164, s_44165, s_44166 | 5 | 47085, 863, 19810, 1257, 23209 | 0.03524 | 75 | 0.004253 | 109 |
| ATP1B4 | s_4304, s_4305, s_4306, s_4307 | 4 | 1486, 31149, 944, 43483 | 0.03532 | 76 | 0.003379 | 83 |
| PRR7 | s_44424, s_44425, s_44426, s_44427 | 4 | 904, 38806, 59763, 1506 | 0.03545 | 77 | 0.003414 | 84 |
| GBP2 | s_22365, s_22366, s_22367, s_22368, s_22369, s_22370 | 6 | 1003, 60810, 58109, 1029, 43443, 48442 | 0.03557 | 78 | 0.004654 | 116 |
| KCTD15 | s_28890, s_28891, s_28892, s_28893 | 4 | 23114, 8725, 1747, 290 | 0.03616 | 79 | 0.003546 | 87 |
| MAPKAPK3 | s_32778, s_32779, s_32780, s_32781 | 4 | 1795, 169, 21907, 29592 | 0.03631 | 80 | 0.003576 | 89 |
| MRPS12 | s_34814, s_34815, s_34816 | 3 | 1726, 1417, 15155 | 0.0364 | 81 | 0.002585 | 63 |
| TNR | s_58261, s_58262, | 6 | 1368, 52097, 29987, 60673, | 0.03661 | 82 | 0.004941 | 127 |

TABLE H-continued

Output of the RIGER algorithm for the transduction replicate A375 PLX screen comparing PLX (mean of the two replicates at day 14) to DMSO control (mean of the two replicates at day 14). The weighted sum method was used to convert sgRNAs to genes. Genes are sorted by RIGER rank.

| Gene | Hairpins | # Hairpins | Hairpin ranks | NES | Gene rank | p-value | p-value rank |
|---|---|---|---|---|---|---|---|
| | s_58263, s_58264, s_58265, s_58266 | | 37039, 106 | | | | |
| PET117 | s_41313, s_41314, s_41315 | 3 | 1789, 1416, 1742 | 0.03666 | 83 | 0.002611 | 65 |
| SRM | s_53860, s_53861, s_53862, s_53863, s_53864 | 5 | 1466, 5441, 2247, 3169, 430 | 0.03672 | 84 | 0.004589 | 114 |
| INO80E | s_27530, s_27531, s_27532, s_27533 | 4 | 46304, 1464, 1278, 16053 | 0.03707 | 85 | 0.003727 | 93 |
| ZSWIM6 | s_64963, s_64964, s_64965, s_64966 | 4 | 25840, 1465, 19204, 1294 | 0.0372 | 86 | 0.003755 | 95 |
| SLC4A3 | s_52020, s_52021, s_52022, s_52023, s_52024, s_52025 | 6 | 29005, 52591, 64538, 39136, 1319, 334 | 0.03732 | 87 | 0.005147 | 134 |
| CDKL4 | s_10939, s_10940, s_10941, s_10942 | 4 | 63413, 1274, 36650, 1510 | 0.03795 | 88 | 0.003903 | 98 |
| EED | s_17448, s_17449, s_17450, s_17451 | 4 | 1999, 352, 1852, 22596 | 0.03863 | 89 | 0.004041 | 103 |
| MRPL17 | s_34661, s_34662, s_34663 | 3 | 2009, 1162, 1959 | 0.03885 | 90 | 0.002918 | 69 |
| ANGEL2 | s_2338, s_2339, s_2340, s_2341, s_2342 | 5 | 28245, 840, 1423, 56505, 62188 | 0.03886 | 91 | 0.005154 | 135 |
| PLK1 | s_42592, s_42593, s_42594, s_42595 | 4 | 18870, 1327, 15990, 1544 | 0.03896 | 92 | 0.00412 | 105 |
| CARS2 | s_9155, s_9156, s_9157 | 3 | 1198, 1989, 11196 | 0.03954 | 93 | 0.003005 | 72 |
| PODN | s_42919, s_42920, s_42921, s_42922, s_42923, s_42924 | 6 | 49093, 58125, 330, 36756, 41658, 1412 | 0.03971 | 94 | 0.005858 | 150 |
| AMPD2 | s_2260, s_2261, s_2262, s_2263, s_2264, s_2265 | 6 | 672, 1977, 27046, 41151, 34556, 1308 | 0.03997 | 95 | 0.005936 | 151 |
| TRIM67 | s_59007, s_59008 | 2 | 2416, 1455 | 0.04032 | 96 | 0.001521 | 40 |
| ACOX1 | s_673, s_674, s_675 | 3 | 618, 2238, 44076 | 0.04046 | 97 | 0.003153 | 74 |
| PRPF4B | s_44329, s_44330, s_44331 | 3 | 17853, 1143, 2063 | 0.04046 | 98 | 0.003153 | 75 |

TABLE H-continued

Output of the RIGER algorithm for the transduction replicate A375 PLX screen comparing PLX (mean of the two replicates at day 14) to DMSO control (mean of the two replicates at day 14). The weighted sum method was used to convert sgRNAs to genes. Genes are sorted by RIGER rank.

| Gene | Hairpins | # Hairpins | Hairpin ranks | NES | Gene rank | p-value | p-value rank |
|---|---|---|---|---|---|---|---|
| TCEB2 | s_55778, s_55779, s_55780, s_55781 | 4 | 3561, 1732, 1896, 1034 | 0.04073 | 99 | 0.004475 | 112 |
| VAX1 | s_61156, s_61157, s_61158, s_61159, s_61160 | 5 | 61659, 1770, 53, 22962, 60237 | 0.04079 | 100 | 0.005648 | 147 |

Figure 28A:
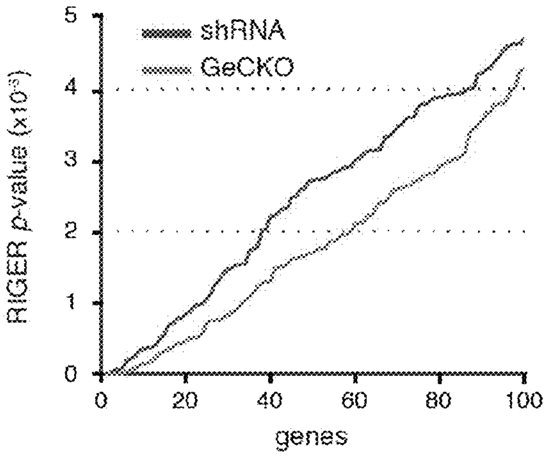
FIG. 28A-28E shows Comparison of GeCKO and shRNA screens and validation of neurofibromin 2 (NF2). (A) RIGER p values for the top 100 hits from GeCKO and shRNA screens for genes whose loss results in PLX resistance. Analysis using the Redundant siRNA Activity (RSA) algorithm shows a similar trend (fig. S9). (B) For the top 10 RIGER hits, the percent of unique sgRNAs (top) or shRNAs (bottom) targeting each gene that are in top 5% of all enriched sgRNAs or shRNAs. (C) Deep sequencing analysis of lentiCRISPR-mediated indel at the NF2 locus. (D) A375 cells transduced with NF2-targeting lentiCRISPR and shRNA vectors both show a decrease in NF2 protein levels. (E) Dose response curves for A375 cells transduced with individual NF2-targeting lentiCRISPR or shRNA vectors. Controls were EGFP-targeting lentiCRISPR or null hairpin shRNA vectors. Cells transduced with NF2-targeting lentiCRISPRs show a significant increase ($F_{1,8}$=30.3, p<0.001, n=4 replicates) in the half maximal effective concentration ($EC_{50}$) whereas cells transduced with NF2-targeting shRNA vectors do not ($F_{1,8}$=0.47, p=0.51, n=4 replicates).
Figure 28B:
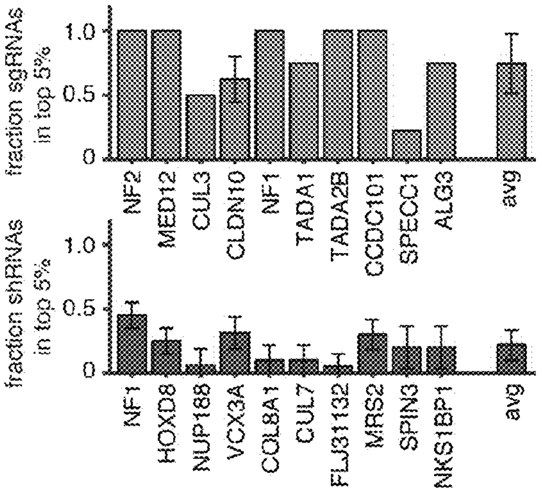
Figure 37:
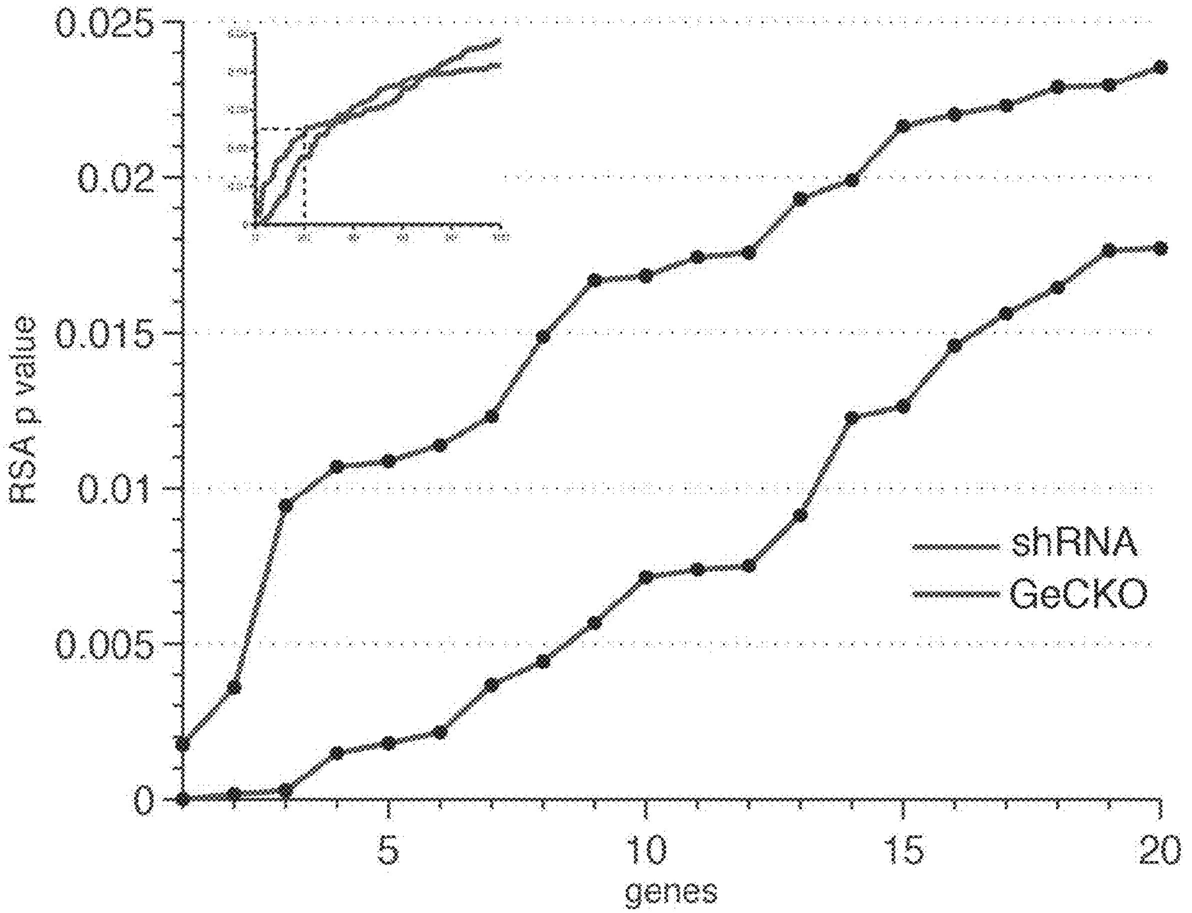
FIG. 37 shows Cumulative p value distribution for the top hits as determined by the Redundant siRNA Activity (RSA) algorithm. Lower p values signify a higher consistency of distinct reagents targeting the same genes. RSA calculates the significance of reagents concentrated near the top or bottom of an enrichment list through an iterative hypergeometric test
Figure 38A:
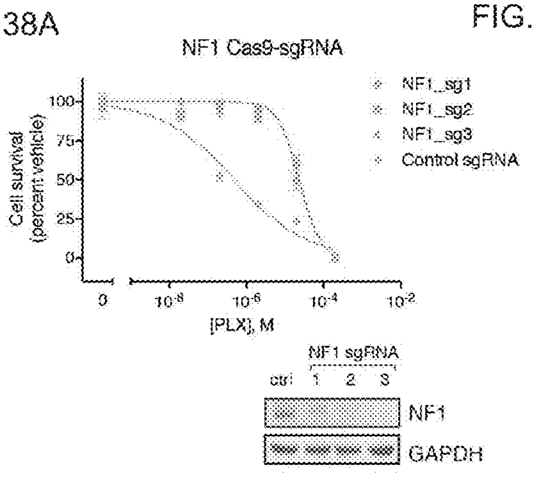
FIG. 38A-38F shows Array validation and comparison of the three highest-ranking genes using both CRISPR and shRNAs. Each panel shows cell survival data at different PLX doses as determined by CELLTITER-GLO® and protein quantification using western analysis. The gray line shows the mean of 2 control sgRNAs (targeting EGFP) or 2 control shRNAs (pLKO-nullT control vectors) and the colored line (blue for Cas9-sgRNAs, pink for shRNAs) shows the mean of all targeting reagents for the gene. n=4 replicates for dose response data. Shift in the dose response curve to the right of the control curve indicates greater resistance to PLX in the perturbed cell lines. (A), (B) Cas9-sgRNA and shRNA reagents respectively targeting NF1. (C), (D) Cas9-sgRNA and shRNA reagents respectively targeting MED12. (E), (F) Cas9-sgRNA and shRNA reagents respectively targeting TADA2B gene.
Figure 38B:
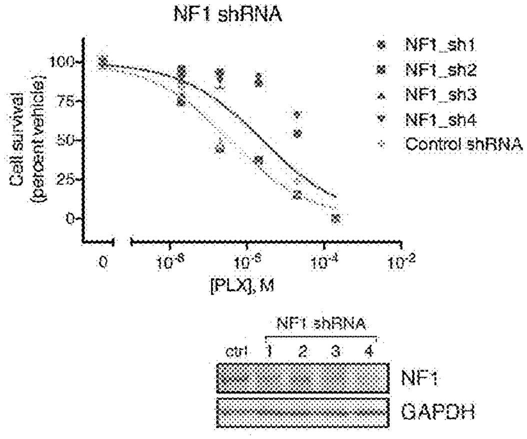
Figure 38C:
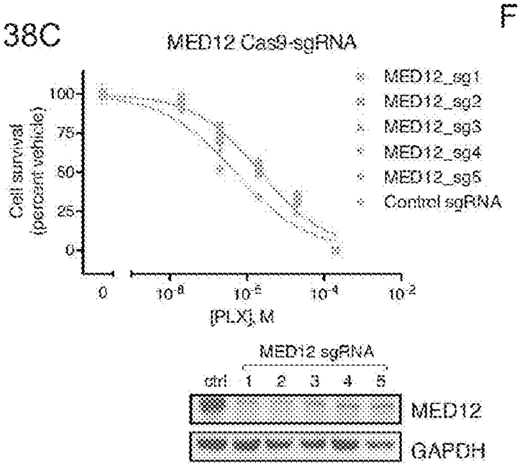
Figure 38D:
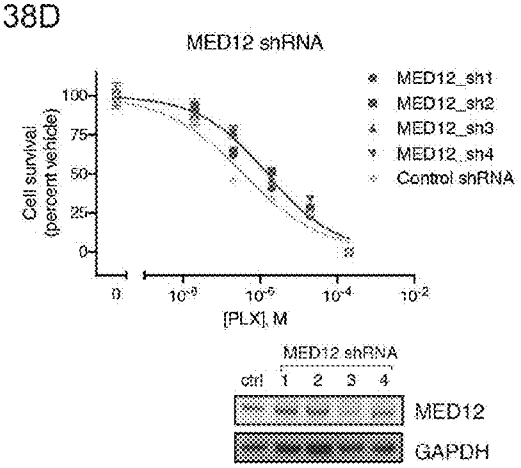
Figure 38E:
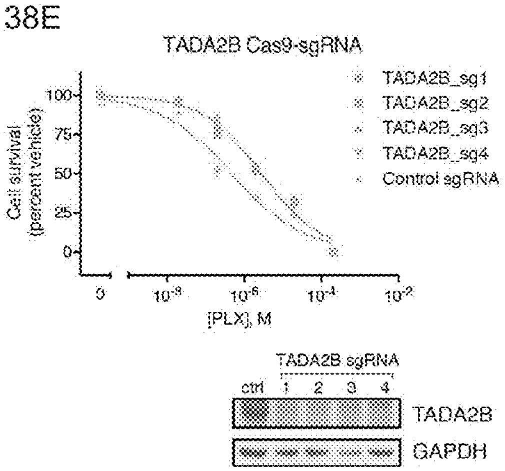
Figure 38F:
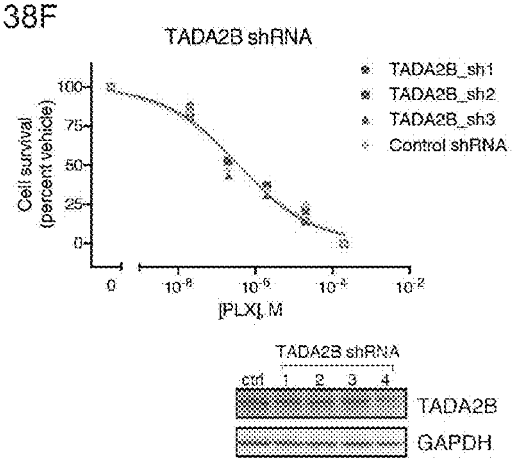

A similar screen to identify PLX drug resistance in A375 cells was previously conducted using a pooled library of 90,000 shRNAs. To compare the efficacy and reliability of genome-scale shRNA screen with GeCKO, Applicants used several methods to evaluate the degree of consistency among the multiple sgRNAs or shRNAs for the top candidate genes. First, Applicants calculated the aggregate p value distribution for the top 100 hits using either RIGER (FIG. 28A) or RSA (FIG. 37) scoring. Lower p values for the GeCKO versus shRNA screen indicate better scoring consistency among sgRNAs. Second, for the top 10 RIGER hits, 78±27% of the sgRNAs targeting each gene ranked among the top 5% of enriched sgRNAs, whereas 20±12% of shRNAs targeting each gene ranked among the top 5% of enriched shRNAs (FIG. 28B).

Figure 28C:
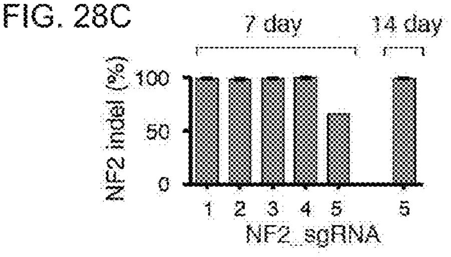
Figure 28D:
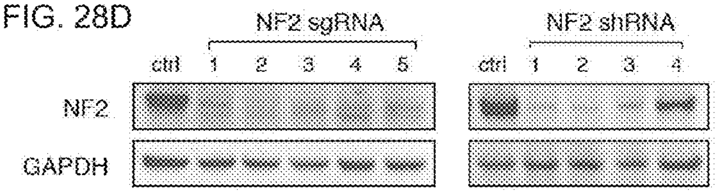
Figure 28E:
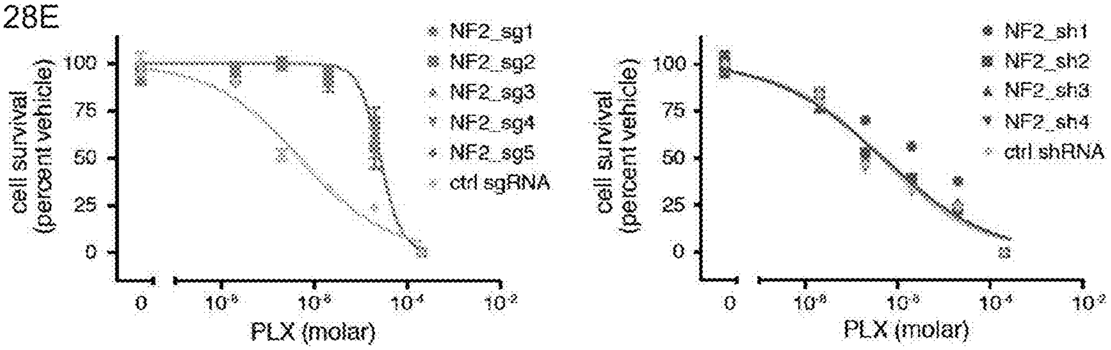
Figure 39A:
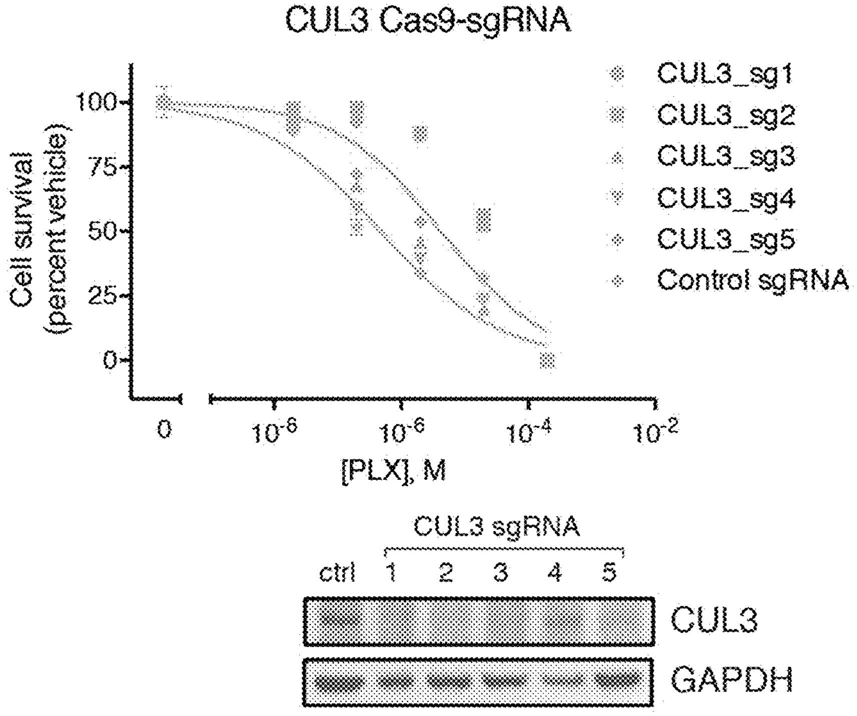
FIG. 39A-39B shows Array validation of the two additional high-ranking genes. Each panel shows cell survival data at different PLX doses as determined by CELLTITER-GLO® and protein quantification using western analysis. The gray line shows the mean of 2 control sgRNAs that target EGFP and the blue line shows the mean of Cas9-sgRNAs targeted to the gene. Shift in the dose response curve displays the reduced sensitivity to PLX in the perturbed cell lines. (A) Cas9-sgRNAs targeting CUL3. (B) Cas9-sgRNAs targeting TADA1. Western analysis was not performed for TADA1 since neither of the two antibodies attempted yielded a band of the correct molecular weight.
Figure 39B:
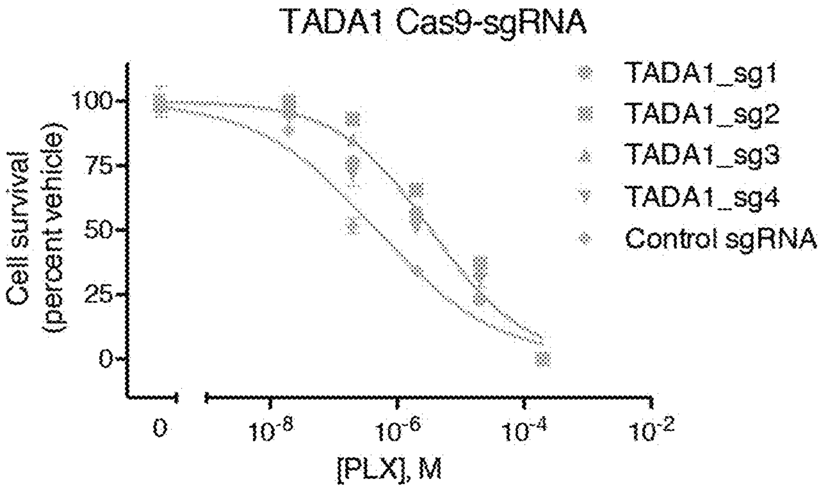
Figure 40:
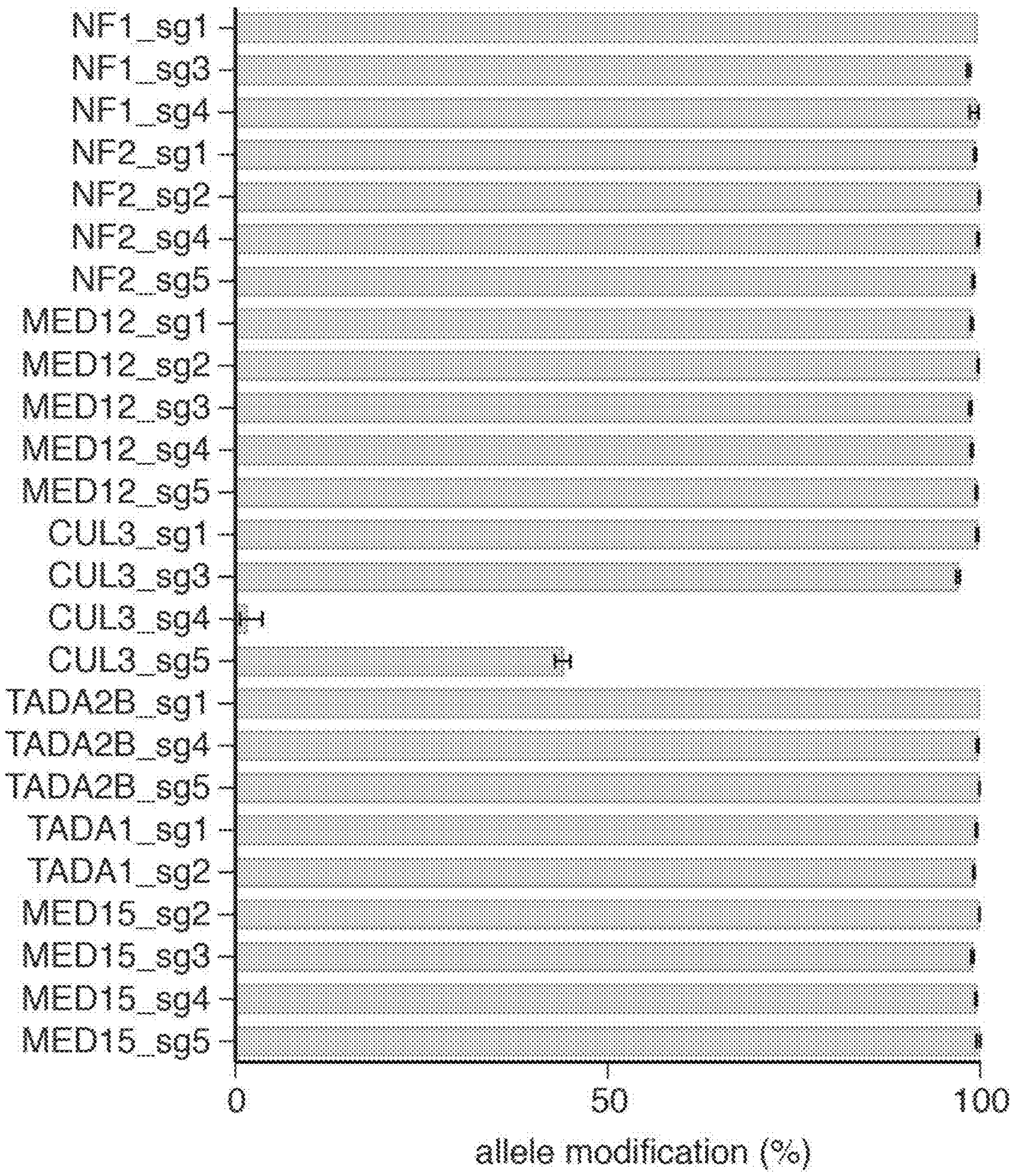
FIG. 40 shows Measurements of allele modification frequencies in 25 sgRNAs targeting the seven highest-ranking genes in the A375 GeCKO screen. Bar plot shows the percentage of modified alleles determined by PCR followed by deep sequencing. Error bars representing Wilson intervals.
Figure 41:
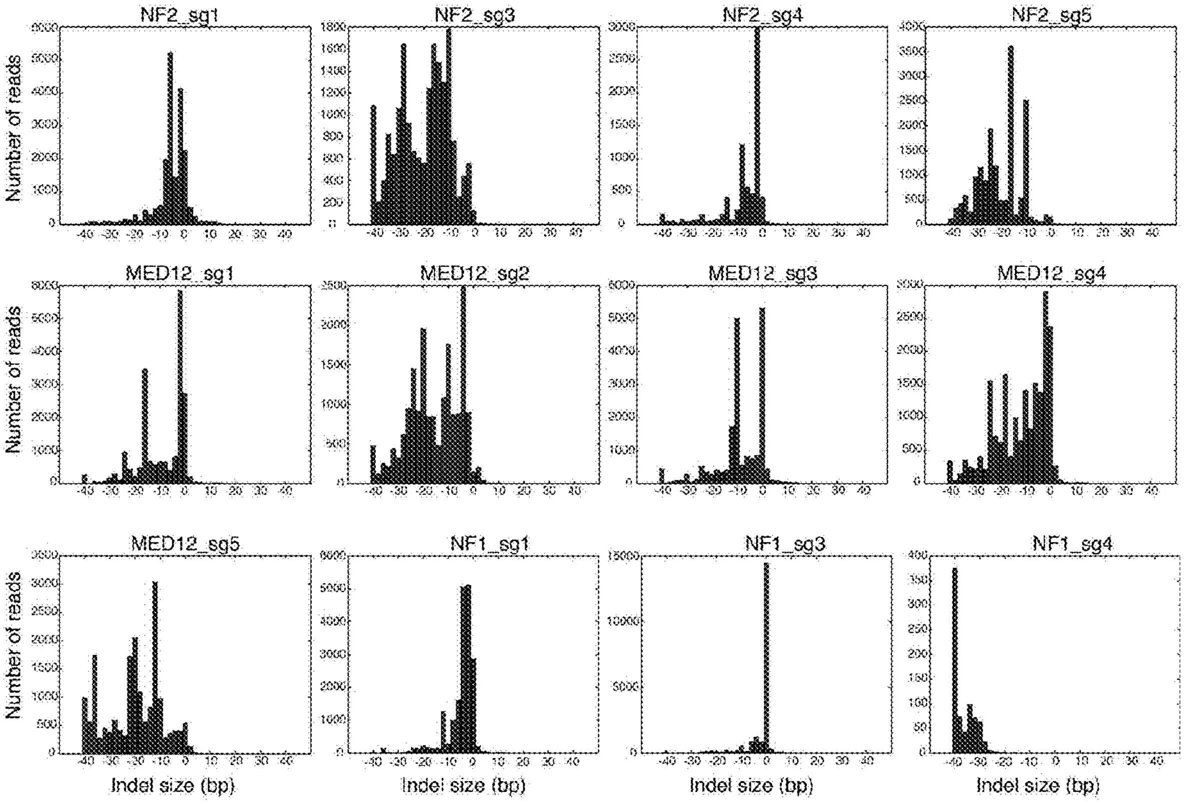
FIG. 41 shows Histograms of on-target indel sizes for NF2, MED12, and NF1. Each subpanel shows the distribution of indel sizes for a single sgRNA at its intended genomic target locus. Each locus is PCR amplified and deep sequenced. Negative values indicate deletions and positive values indicate insertions.
Figure 42:
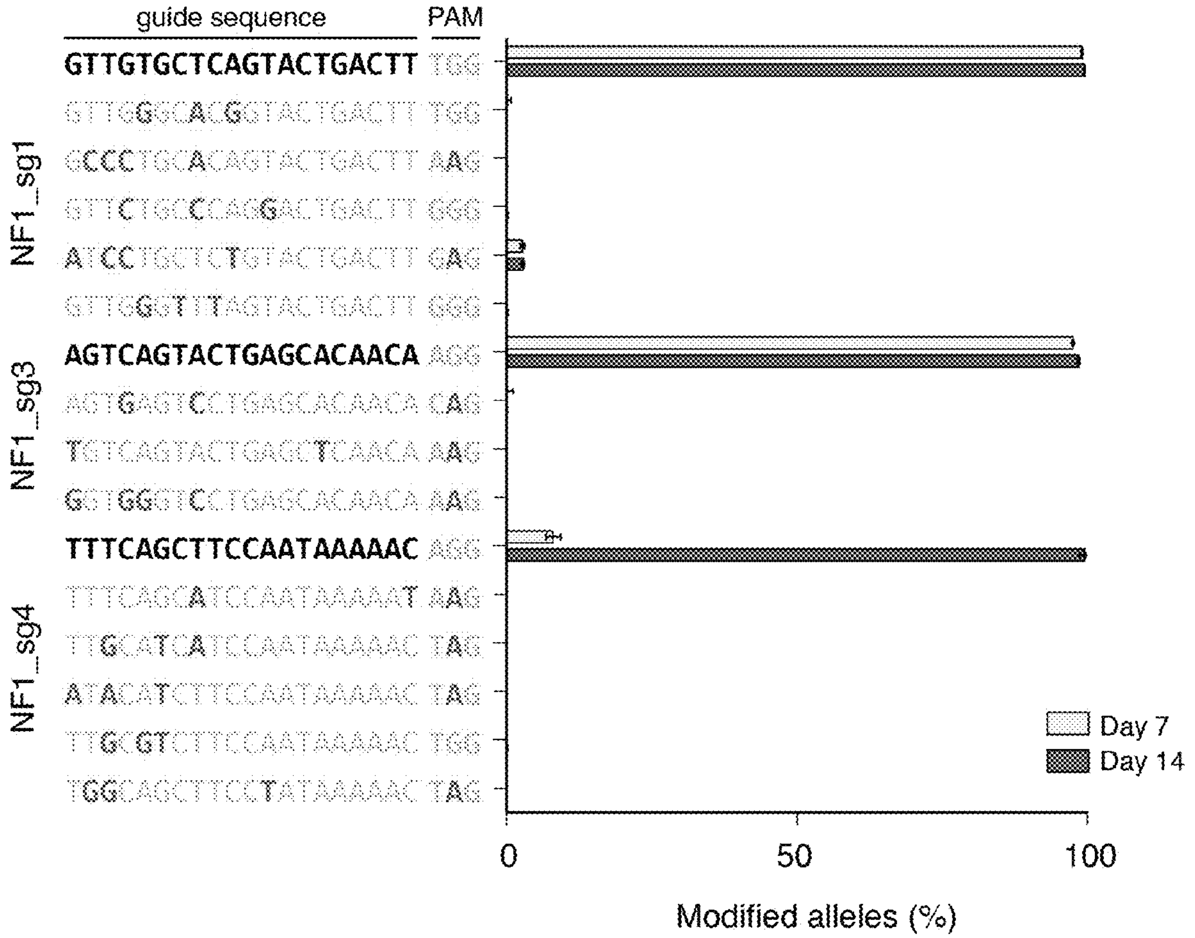
FIG. 42 shows Measurements of on and off target allele modification frequencies for three sgRNAs targeting NF1. Each row represents a genomic locus consisting of a 20 bp sgRNA site (in black or gray letters) followed by a 3 bp PAM sequence (in light blue letters). Sequences in bold black letters indicate the genomic sequences that the GeCKO library sgRNAs were designed to target. Below each bold line are 3 to 5 predicted potential off target genomic sequences identified using the CRISPR design tool (available at the website tools.genome-engineering.org). Red nucleotides highlight the differences in these off target sequences from the on target site. Each locus (on and off target) was PCR amplified and then deep sequenced. Bars show the percentage of modified alleles 7 and 14 days post transduction with error bars representing Wilson intervals.
Figure 43:
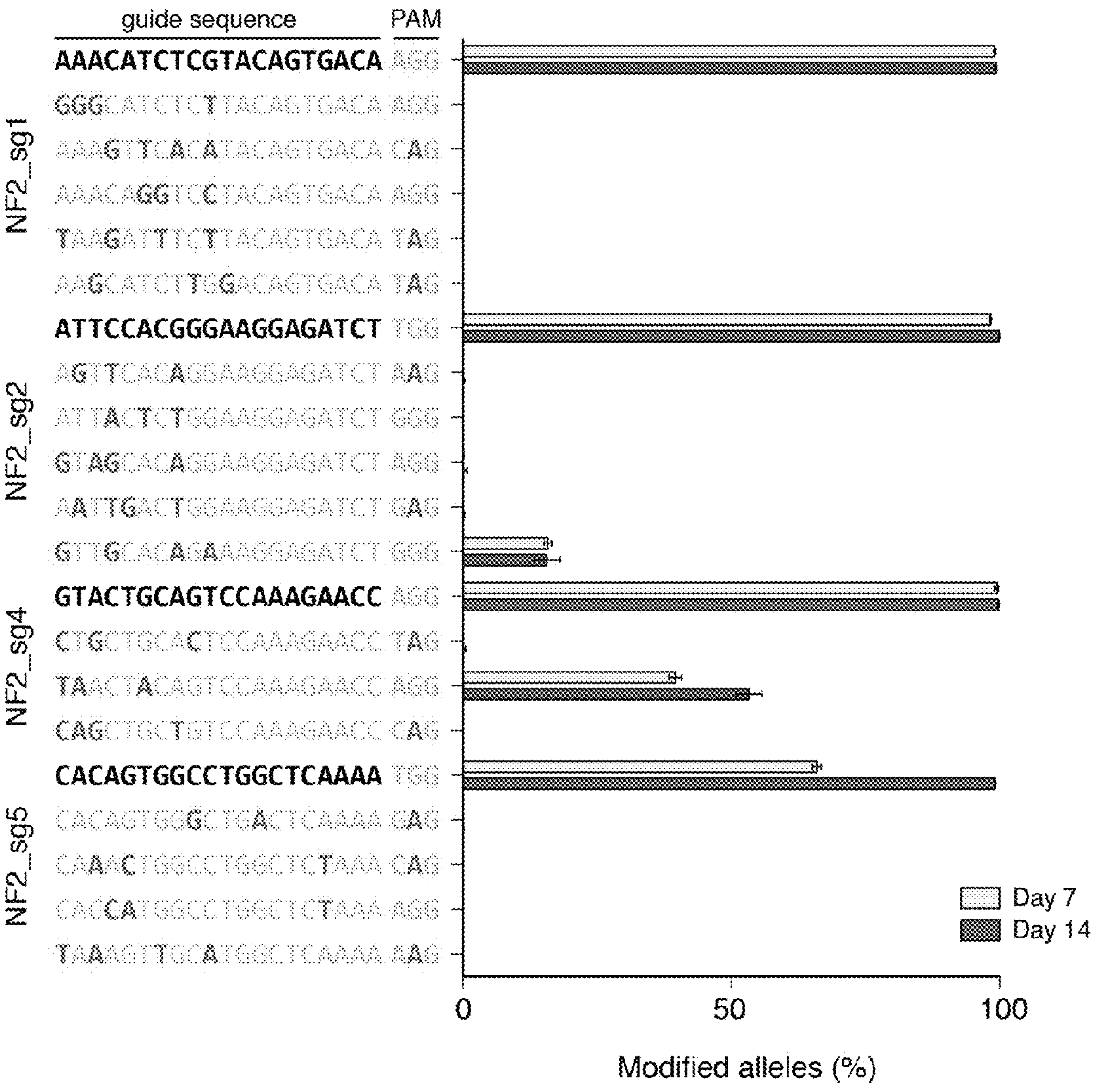
FIG. 43 shows Measurements of on and off target allele modification frequencies for three sgRNAs targeting NF2. Each row represents a genomic locus consisting of a 20 bp sgRNA site (in black or gray letters) followed by a 3 bp PAM sequence (in light blue letters). Sequences in bold black letters indicate the genomic sequences that the GeCKO library sgRNAs were designed to target. Below each bold line are 3 to 5 predicted potential off target genomic sequences identified using the CRISPR design tool (available at the website tools.genome-engineering.org). Red nucleotides highlight the differences in these off target sequences from the on target site. Each locus (on and off target) was PCR amplified and then deep sequenced. Bars show the percentage of modified alleles 7 and 14 days post transduction with error bars representing Wilson intervals.
Figure 44:
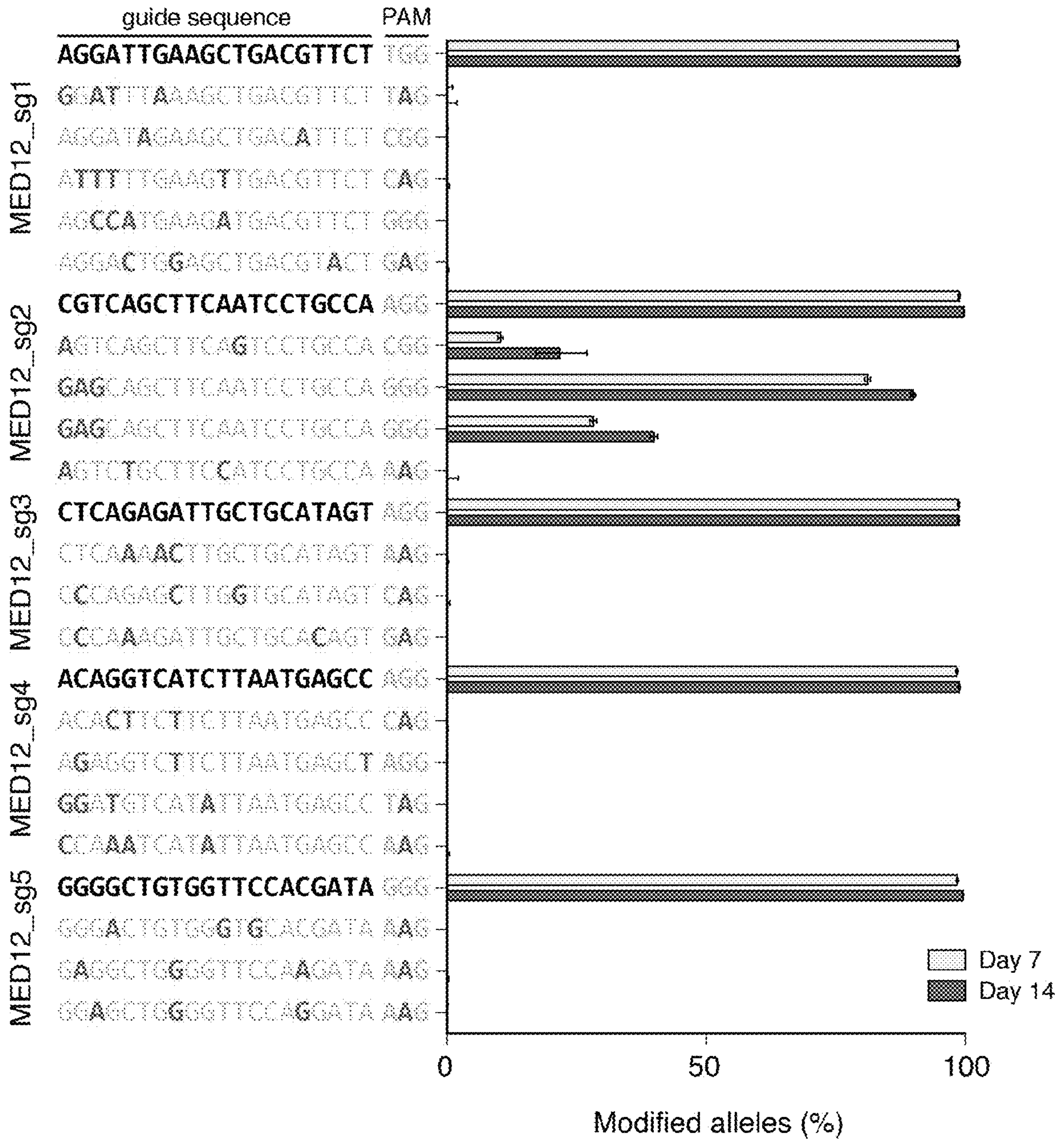
FIG. 44 shows Measurements of on and off target allele modification frequencies for three sgRNAs targeting MED12. Each row represents a genomic locus consisting of a 20 bp sgRNA site (in black or gray letters) followed by a 3 bp PAM sequence (in light blue letters). Sequences in bold black letters indicate the genomic sequences that the GeCKO library sgRNAs were designed to target. Below each bold line are 3 to 5 predicted potential off target genomic sequences identified using the CRISPR design tool (available at the website tools.genome-engineering.org). Red nucleotides highlight the differences in these off target sequences from the on target site. Each locus (on and off target) was PCR amplified and then deep sequenced. Bars show the percentage of modified alleles 7 and 14 days post transduction with error bars representing Wilson intervals.

Applicants validated top ranking genes from the GeCKO screen individually using 3-5 sgRNAs (FIGS. 28C-E, 38, 39). For NF2, Applicants found that 4/5 sgRNAs resulted in >98% allele modification 7 days post-transduction, and all 5 sgRNAs showed >99% allele modification 14 days post-transduction (FIG. 28C). Applicants compared sgRNA and shRNA-mediated protein depletion and PLX resistance using Western blot (FIG. 28D) and cell growth assays (FIG. 28E). Interestingly, while all five sgRNAs conferred resistance to PLX, only the best shRNA achieved sufficient knockdown to increase PLX resistance (FIG. 28E), suggesting that even low levels of NF2 are sufficient to retain sensitivity to PLX. Additionally, sgRNAs targeting NF1, MED12, CUL3, TADA1, and TADA2B led to a decrease in protein expression and increased resistance to PLX (FIGS. 38, 39). Deep sequencing confirmed a high rate of mutagenesis at targeted loci (FIGS. 40, 41), with a small subset of off-target sites exhibiting indels (FIGS. 42-44), which may be alleviated using an offset nicking approach that was shown to reduce off-target modifications.

GeCKO screening provides a complementary method to RNAi for systematic perturbation of gene function through generation of loss of function alleles. This can be useful in cases where incomplete knockdown retains gene function. The ability to achieve targeted genome modifications on a large scale using custom Cas9:sgRNA libraries presents unique opportunities to probe a broad range of coding and non-coding genomic elements.

GeCKO screening is carried out in three steps: Step 1—Library Design. Constitutive exons near the 5' end of transcripts are identified using Illumina Human BodyMap 2.0 and NCBI CCDS datasets. sgRNAs were ranked by an off-target score using a metric that includes the number of off-targets in the genome and the type of mutations (distance from protospacer-adjacent motif and clustering of mismatches) and those with lowest off-target scores were selected. This resulted in a library in which most genes have an average of 3 or 4 sgRNAs. Step 2—Viral vector generation. The sgRNA library was synthesized using array synthesis and cloned as a pool into the lentiCRISPR transfer plasmid for virus production. Viral vectors were produced in HEK293T cells and concentrated to increase viral titer. Cells of interest were infected at a low MOI (0.3) to ensure that most cells receive only 1 viral construct with high probability. Step 3—Readout. 24 hours after transduction, cells were selected with puromycin so that only cells transduced with a lentiCRISPR construct are preserved. At this point the cells can be used to carry out either positive or negative selection screens.

Screening timeline considerations: After infection, cells are selected with puromycin. For most cell types, 0.5-2 ug/ml puromycin works well, although the minimum dose that kills all cells without any viral transduction should be determined in advance and the minimum concentration should be used for selection. Usually, only 2-3 days of puromycin selection is needed to select for cells with viral integration and expression but a longer period of selection has the added benefit of allowing for enough time for genome modification by Cas9. As shown in the deep sequencing of the individual target (array) validations from the PLX resistance screen gene hits, genome modification increases over time. For most targets, genome modification was nearly complete after only 7 days. Some lentiCRISPRs had lower modification that increased by 14 days post-transduction (for example, NF1_sg4 in FIG. 42, NF2_sg5 in FIG. 43). As expected, for some sgRNAs, off-target modification also increases with time, albeit by a smaller amount (for example, NF2_sg4 in FIG. 42, MED12_sg2 in FIG. 43). In general, it is advisable to keep puromycin selection (and Cas9 expression since they are co-expressed) for at least 7 days post-transduction and possibly longer depending on the needs of the particular experiment.

Identification of gene candidates: Before any experiment, it is important to determine the distribution of sgRNAs before any selection pressure has been applied. This baseline sgRNA distribution will be used to infer either depletion or enrichment of specific sgRNA species. For both positive and negative selection screens, hits are identified by comparing the distribution of sgRNAs after selection with the baseline sgRNA distribution. Candidate genes are identified by searching for sgRNAs whose frequency has either significantly reduced or increased after selection for negative and positive screens respectively.

Using multiple sgRNAs to target the same gene, and transduction replicates are the main experimental features that enable discrimination between true and false positive hits. The reason is that each screen will have some background rate, meaning that with some probability an sgRNA can be enriched (or depleted) despite having no effect on the studied phenotype. The required number of unique sgRNAs for the same genes should be determined by the background rate of the screen and the overall efficacy of sgRNAs. As increasing sgRNA numbers per gene comes with a cost of increasing library complexity, additional infection replicates can compensate for it as long as there is a minimal number of sgRNAs that can effectively mediate gene targeting. Finally, ranking of the top hits requires the conversion of sgRNA scores into gene rankings. A simple method is to rank gene hits according to the mean or median of all sgRNAs for each respective gene. Applicants recommend combining this simple method with other analysis such as RIGER and RSA.

GeCKO versus shRNA screening: GeCKO screening operates through a fundamentally different mechanism than shRNA based screening. Whereas shRNAs reduce protein expression by targeting the mRNA, GeCKO achieves protein knockdown via frameshift mutations introduced into the genomic coding region. GeCKO-mediated frameshift mutations are achieved through targeted DNA double strand breaks (DSB) and subsequent mutagenic repair via the non-homologous end joining (NHEJ) pathway, which produces indels at the site of DSB. The indel being introduced into the DSB is random (FIG. 44), with some indels leading to frameshift mutations that cause premature termination of the transgene. Other indels with lengths that are multiples of three will not result in the frameshift of the candidate genes. In this scenario, the gene product might still be functional. In contrast, shRNA knockdown can generate a spectrum of expression levels of the target genes. Therefore GeCKO screening can provide potential advantages over shRNA, where the population of cells that has been homozygously knocked out can provide more screening sensitivity especially when probing gene products that can function normally even at significantly reduced concentrations.

Vemurafenib (PLX) resistance mechanisms: The protein kinase BRAF, a key regulator of the MAPK signaling cascade, is mutated in more than half of malignant melanomas and in several other types of cancer, such as thyroid, colorectal, lung, and hairy cell leukemia. The V600E mutant form of BRAF is a common gain of function mutation that allows BRAF to remain in a constitutively active state and phosphorylate MEK without forming a phosphorylated BRAF dimer. Vemurafenib (PLX) is a FDA-approved, ATP-competitive RAF inhibitor that displays higher binding affinity for V600E mutant BRAF over other RAF isoforms, including wild-type BRAF. Over 50% of melanoma patients with mutated BRAF treated with PLX display tumor reduction, but the effect is short-lived and resistance develops in a majority of cases. By applying the GeCKO library to A375 cells (which are homozygous for the BRAF V600E mutation), Applicants identified several genes whose loss resulted in resistance to PLX.

In the PLX screen, Applicants identified and validated NF2, NF1, MED12, CUL3, TADA1, and TADA2B as genes whose loss results in PLX resistance. Loss of NF1 and MED12 were previously identified resistance mechanisms from two separate, large-scale RNAi screens. MED12, a member of the Mediator transcription complex, is a negative regulator of TGF-βR and its loss results in activation of TGF-βR signaling and MEK/ERK. NF1 is a negative regulator of NRAS activity and its loss phenocopies activating NRAS mutations, an established PLX resistance mechanism.

Although they have similar names, NF1 and NF2 are tumor suppressors that function via distinct pathways. NF2 (or Merlin, Moesin-Ezrin-Radixin-Like Protein) is a tumor suppressor gene that encodes a cytoskeletal protein. Loss of NF2 leads to constitutive mTOR activation and cell proliferation by a MEK/ERK-independent mechanism and involves the Hippo signaling pathway. Mutation and copy number variation of the E3 ligase CUL3 has been described in lung squamous cell carcinomas and renal cell carcinomas. Quantitative proteomics in T24T bladder cancer cells found that silencing of CUL3 restored the expression of cytoskeleton proteins that are underexpressed in T24T, such as moesin and erzin. This suggests a possible interaction between CUL3 and NF2/merlin, a similar cytoskeletal protein to those ubiquitinated by CUL3.

TADA1 and TADA2B are chromatin-modifying enzymes involved in transcription and are members of the multiprotein STAGA (SPT3-TAF9-GCN5-acetylase) complex. The STAGA complex recruits Mediator complex proteins (such as MED12) to the oncoprotein c-Myc to activate proliferation. Applicants noted that CCDC101 had a high RIGER rank in both infection replicates (see Table I) and is also a subunit of the STAGA complex and thus may lead to PLX resistance through a similar mechanism as TADA1 and TADA2B. Since many of the gene hits from the PLX screen interact with each other and are involved in established cell proliferation pathways, therapeutics targeted to these pathways could be combined with BRAF inhibition to achieve better clinical outcomes in melanoma and other cancers.

Other applications of GeCKO screening: In addition to facilitating loss-of-function gene screening, GeCKO and similar Cas9-sgRNA libraries can be customized to carry out a variety of genome-scale perturbations to study the effect of non-coding elements, transcriptional changes, and epigenetic modulations. In this library, Applicants target the constitutive exons near the 5' end of genes for loss-of-function but sgRNAs can also be targeted to promoters, enhancers, intronic, and intergenic regions. Screens targeting non-coding regions or a mix of coding and non-coding regions can elucidate how these different elements contribute to gene expression and biological function. As Applicants have recently shown, Cas9 with mutated catalytic residues can be fused to a transcriptional activation domain such as VP16 or repressor domain such as SID4X or KRAB to create a Cas9 transcriptional modulator without any nuclease activity. By replacing the Cas9 in the lentiCRISPR plasmid with a null-nuclease version (e.g. with D10A and H840A mutations), libraries of sgRNAs for activation can be used to investigate how activation of different transcripts or different splice variants contribute to a screen phenotype. A null-nuclease Cas9 could also be fused with different effector domains capable of modifying the epigenetic state at a particular locus. Previous work from Applicants and others has demonstrated transcriptional changes using zinc-finger proteins and transcriptional activator like effectors (TALEs) fused to histone (de)acetylases, histone (de)methylases, DNA (de)methylases and other epigenetic modifiers. The easy programmability of Cas9 DNA binding using sgRNAs that can be array synthesized en masse opens up many new possibilities for genome-scale screens.

TABLE I

Comparison of the top 20 hits between the two A375 PLX infection replicate screens by RIGER rank. RNAi gene enrichment ranking (RIGER) uses a two-sample weighted likelihood ratio test to measure the support for a gene using the enrichment of the sgRNAs (or shRNAs) for each gene.

| 1st infection | | | 2nd infection | | |
|---|---|---|---|---|---|
| Gene symbol | RIGER rank | RIGER p-value | Gene symbol | RIGER rank | RIGER p-value |
| NF2 | 1 | 0.000004 | MED12 | 1 | 0.000002 |
| MED12 | 2 | 0.000004 | CUL3 | 2 | 0.000002 |
| CUL3 | 3 | 0.000006 | NF2 | 3 | 0.000005 |
| CLDN10 | 4 | 0.000005 | TADA1 | 4 | 0.000007 |
| **NF1** | 5 | 0.000001 | TADA2B | 5 | 0.00001 |
| TADA1 | 6 | 0.000035 | RBL1 | 6 | 0.000041 |
| TADA2B | 7 | 0.000046 | TAF6L | 7 | 0.000085 |
| SPECC1 | 8 | 0.000146 | OR8S1 | 8 | 0.000157 |
| CCDC101 | 9 | 0.000082 | **MED23** | 9 | 0.000081 |
| ALG3 | 10 | 0.000118 | SLC41A3 | 10 | 0.000244 |
| P4HB | 11 | 0.000189 | CCDC101 | 11 | 0.000201 |
| **EED** | 12 | 0.000313 | LCOR | 12 | 0.00031 |
| TAF6L | 13 | 0.000234 | GPR98 | 13 | 0.000239 |
| MED15 | 14 | 0.000382 | KCNA2 | 14 | 0.000666 |
| NPPC | 15 | 0.000575 | MED15 | 15 | 0.000416 |
| **TAF5L** | 16 | 0.000141 | MT1F | 16 | 0.000141 |
| PGD | 17 | 0.000349 | MYL7 | 17 | 0.000445 |
| LGALS4 | 18 | 0.00051 | SLC7A11 | 18 | 0.000554 |
| TAOK1 | 19 | 0.000429 | MTRF1 | 19 | 0.000445 |
| CD320 | 20 | 0.000824 | ELF1 | 20 | 0.000454 |

appear in the top 20 of the other replicate infection
appears in the top 100 of the other replicate infection (in bold)

TABLE J

Comparison of the top 20 hits between the two A375 PLX infection replicate screens by RSA rank. Redundant siRNA activity (RSA) uses an enrichment cutoff and hypergeometric test to measure the support for a gene using the enrichment of the sgRNAs (or shRNAs) for each gene.

| 1st infection | | | 2nd infection | | |
|---|---|---|---|---|---|
| Gene symbol | RSA rank | RSA log p value | Gene symbol | RSA rank | RSA log p value |
| MED12 | 1 | −12.467 | MED12 | 1 | −11.954 |
| NF2 | 2 | −9.147 | NF2 | 2 | −8.766 |
| CUL3 | 3 | −8.578 | CUL3 | 3 | −8.174 |
| MED15 | 4 | −7.684 | TADA2B | 4 | −6.512 |
| TADA2B | 5 | −7.418 | CCDC101 | 5 | −6.319 |
| RBL1 | 6 | −6.316 | DPH2 | 6 | −6.141 |
| TADA1 | 7 | −5.815 | MED15 | 7 | −5.609 |
| CCNC | 8 | −5.483 | **NF1** | 8 | −5.418 |
| CCDC101 | 9 | −5.313 | CLDN10 | 9 | −5.174 |
| PDCD10 | 10 | −5.278 | **PGD** | 10 | −4.944 |
| NOTCH2NL | 11 | −4.988 | TADA1 | 11 | −4.909 |
| PCLO | 12 | −4.971 | ZEB2 | 12 | −4.892 |
| PPP1R8 | 13 | −4.947 | CCNC | 13 | −4.697 |
| C1QA | 14 | −4.667 | **TAF6L** | 14 | −4.402 |
| DR1 | 15 | −4.311 | SMARCB1 | 15 | −4.371 |
| **KCTD10** | 16 | −4.284 | BCL2L12 | 16 | −4.228 |
| PDE12 | 17 | −4.236 | PDCD10 | 17 | −4.16 |
| SLC25A17 | 18 | −4.209 | GADD45GIP1 | 18 | −4.107 |
| **BRD9** | 19 | −4.206 | ZNF592 | 19 | −4.037 |
| PET117 | 20 | −4.168 | ACTA2 | 20 | −4.033 |

appear in the 20 top of other replicate infection
appears in the 100 top of other replicate infection (in bold)

TABLE K

Cas9-sgRNA array screening constructs used. Names and targeting sequence for all Cas9-sgRNA constructs used for validation in A375 screen. Cas9-sgRNAs (SEQ ID NOs: 24-51, respectively, in order of appearance) with names in italics are contained in the GeCKO library.

| Name | sg RNA 20 bp sequence |
|---|---|
| NF2_sg1 | AAACATCTCGTACAGTGACA |
| NF2_sg2 | ATTCCACGGGAAGGAGATCT |
| NF2_sg3 | CCTGGCTTCTTACGCCGTCC |
| NF2_sg4 | GTACTGCAGTCCAAAGAACC |
| NF2_sg5 | CACAGTGGCCTGGCTCAAAA |
| MED12_sg1 | AGGATTGAAGCTGACGTTCT |
| MED12_sg2 | CGTCAGCTTCAATCCTGCCA |
| MED12_sg3 | CTCAGAGATTGCTGCATAGT |
| MED12_sg4 | ACAGGTCATCTTAATGAGCC |
| MED12_sg5 | GGGGCTGTGGTTCCACGATA |
| NF1_sg1 | GTTGTGCTCAGTACTGACTT |
| NF1_sg2 | ACACTGGAAAAATGTCTTGC |
| NF1_sg3 | AGTCAGTACTGAGCACAACA |
| CUL3_sg1 | CTTACCTGGATATAGTCAAC |
| CUL3_sg2 | GAATCCTGTTGACTATATCC |
| CUL3_sg3 | GACCTAAAATCATTAACATC |
| CUL3_sg4 | TGCCAGATGTTAATGATTTT |
| CUL3_sg5 | TTATTTAGTCGTGTGCCAAA |
| TADA1_sg1 | ACTGGGCTAACCTAAAGCTG |
| TADA1_sg2 | TCTGCTTGAACCACAGCTTT |
| TADA1_sg3 | GGAGGAAATCATTGTGAGAA |
| TADA1_sg4 | TCTTTAGTGCAATCAGAATC |
| TADA2B_sg1 | ACGGCGGGCGCTTCACGCTC |
| TADA2B_sg2 | GCCATCGAGCAGTTCGGCTT |
| TADA2B_sg3 | GCACCTTCTCGCGATCTGAC |
| TADA2B_sg4 | GCTCCTGTCAGATCGCGAGA |
| Control_sg1 (EGFP_sg5) | GAAGTTCGAGGGCGACACCC |
| Control_sg2 (EGFP_sg6) | GGTGAACCGCATCGAGCTGA |

TABLE L shRNA array screening constructs (SEQ ID NOs: 52-66, respectively, in order of appearance) used. Names and The RNAi Consortium (TRC) identification numbers for all shRNA constructs used for validation in A375 screen.

| Name | TRC ID | Targeting Sequence |
|---|---|---|
| NF2_sh1 | TRCN0000010397 | GAAGCAACCCAAGACGTTCAC |
| NF2_sh2 | TRCN0000018338 | TAGTTCTCTGACCTGAGTCTT |
| NF2_sh3 | TRCN0000039974 | GCTCTGGATATTCTGCACAAT |
| NF2_sh4 | TRCN0000039975 | GCTTCGTGTTAATAAGCTGAT |
| MED12_sh1 | TRCN0000018574 | GCAGCATTATTGCAGAGAAAT |
| MED12_sh2 | TRCN0000018575 | GCTGTTCTCAAGGCTGTGTTT |
| MED12_sh3 | TRCN0000018576 | CGGGTACTTCATACTTTGGAA |
| MED12_sh4 | TRCN0000018578 | GCAGAGAAATTACGTTGTAAT |
| NF1_sh1 | TRCN0000039714 | GCCAACCTTAACCTTTCTAAT |
| NF1_sh2 | TRCN0000039715 | CCTCACAACAACCAACACTTT |
| NF1_sh3 | TRCN0000039716 | CCTGACACTTACAACAGTCAA |
| NF1_sh4 | TRCN0000039717 | GCTGGCAGTTTCAAACGTAAT |
| TADA2B_sh1 | TRCN0000237951 | CGTGACTGTGAAGACTATTAT |
| TADA2B_sh2 | TRCN0000237949 | ATGATTACGAGATCGAGTATG |
| TADA2B_sh3 | TRCN0000237950 | ACATCGCCCGTGACTACAATC |
| NullT_1 | TRCN0000208001 | n/a |
| NullT_2 | TRCN0000231782 | n/a |

GeCKO library design: A genome-scale sgRNA library was constructed as follows: First, early constitutive exons were identified for all coding genes. Then, sgRNAs to target these early constitutive exons were selected by choosing sgRNAs that were predicted to have minimal off-target activity.

To identify constitutive exons, RNA sequencing data from the Illumina Human Body Map 2.0 (GEO accession number: GSE30611) was mapped to the reference human genome (hg19) using TopHat v1.0.14 and transcripts were reconstructed with Cufflinks v1.0.2, as previously described in Merkin J. et al. Science 338, 1593 (Dec. 21, 2012). Exons expressed across all tissues in the Illumina dataset were chosen as constitutive exons for sgRNA targeting. In addition, for each gene, the first and last exons were excluded along with any exon that contained an alternative splicing site.

For the constitutive exons, genomic sequences were retrieved from the NCBI Consensus CoDing Sequence database (available at the website of ncbi.nlm.nih.gov/CCDS/). For each CCDS entry, the two earliest constitutive exons were chosen as candidate exons for library design. For genes without RNA sequencing data or where no exons qualified as constitutive, exons 2 and 3 were included as candidate exons for library design.

Next, for each candidate exon, all possible *S. pyogenes* Cas9 sgRNA sequences of the form $(N)_{20}$NGG were listed as candidate targets. Each 20mer candidate sgRNA was mapped to a precompiled index containing all 20mer sequences in the human genome followed by either NGG or NAG. This mapping was done using Bowtie short read aligner, allowing up to 3 base mismatches.

The following heuristic was used to rank sgRNAs for each exon based on the characterized sequence specificity of Cas9 nuclease. First, any sgRNAs with other targets in the genome that match exactly or differ by only 1 base are discarded. For the remaining sgRNAs, Applicants calculated the following off target score:

$$OS = \sum_{off\ targets} (\text{sum min location})\left(\frac{D(\min)}{D(\max)}\right)$$

sum mm location=sum of the mismatch locations from 3' to 5'. The PAM (NGG) proximal base is 1 and the PAM distal base is 20.

D(mm)=distance in bp between mismatch locations.

D(max)=maximal possible distance between 2 or 3 mismatches.

When mismatches are clustered more closely together, the cutting efficiency of Cas9 is significantly lower. Therefore, in the OS, the location of mismatches is weighted by their distances from each other. For each gene, the best (lowest OS) sgRNAs were chosen with the constraint that no sgRNAs have a OS5400. This resulted in a library of 64,751 unique sgRNAs targeting 18,080 coding genes with an average of 3-4 sgRNAs per gene. For all sgRNAs, an extra 5' G was added to improve U6 transcription.

Array oligo synthesis and pooled library cloning: DNA oligonucleotide library synthesis was performed on a programmable microarray using a B3 Synthesizer (CustomArray) and SAFC Proligo reagents (SIGMA®), as recommended by the manufacturer. The synthesis products were cleaved from the microarray and deprotected by overnight incubation in 28-30% ammonium hydroxide at 65° C., dried, resuspended in TE buffer and then purified using a QIAQUICK® spin column (QIAGEN®). Full-length oligonucleotides (74 nt) were amplified by PCR using PHUSION® HS Flex (NEB®) and size-selected using a 2% agarose E-GEL® EX (LIFE TECHNOLOGIES®, QIAGEN®).

```
ArrayF
                                        (SEQ ID NO: 67)
TAACTTGAAAGTATTTCGATTTCTTGGCTTTATATATCTTGTGGAAAGGAC
GAAACACCG

ArrayR
                                        (SEQ ID NO: 68)
ACTTTTTCAAGTTGATAACGGACTAGCCTTATTTTAACTTGCTATTTCT
AGCTCTAAAAC
```

The lentiCRISPR vector was digested with BsmBI (Fermentas) and treated with alkaline phosphatase (Fermentas) at 37° C. for 2 hours and gel-purified on a 1% E-GEL® EX (LIFE TECHNOLOGIES®, QIAGEN®). A 20 ul GIBSON® ligation reaction (NEB®) was performed using 10 ng of the gel-purified inserts and 25 ng of the vector. From the ligation, 0.5 ul of the reaction was transformed into 25 ul of electrocompetent cells (LUCIGEN®) according to the manufacturer's protocol using a GenePulser (BIORAD®). To ensure no loss of representation, 36 parallel transformations were performed using the same ligation reaction and plated onto 245 mm×245 mm plates (CORNING®) with carbenicillin selection (50 ug/ml), which yielded 166× library coverage. Colonies were scraped off plates and combined before plasmid DNA extraction using Endotoxin-Free Plasmid Maxiprep (QIAGEN®).

Lentivirus production and purification: To produce lentivirus, twelve T-225 flasks of HEK293T cells (Broad RNAi Platform) were seeded at ~40% confluence the day before transfection in D10 media (DMEM supplemented with 10% fetal bovine serum). One hour prior to transfection, media was removed and 13 mL of pre-warmed reduced serum OptiMEM™ media (LIFE TECHNOLOGIES®) was added to each flask. Transfection was performed using LIPOFECTAMINE® 2000 and Plus reagent (LIFE TECHNOLOGIES®). For each flask, 200 ul of Plus reagent was diluted in 4 ml OptiMEM™ (LIFE TECHNOLOGIES®) with 20 μg of lentiCRISPR plasmid library, 10 μg of pVSVg, and 15 μg of psPAX2 (Addgene). 100 ul of LIPOFECTAMINE® 2000 was diluted in 4 ml OptiMEM™ and, after 5 min, it was added to the mixture of DNA and Plus reagent. The complete mixture was incubated for 20 min before being added to cells. After 6 h, the media was changed to 30 ml D10 supplemented with 1% BSA (SIGMA®).

After 60 h, the media was removed and centrifuged at 3,000 rpm at 4° C. for 10 min to pellet cell debris. The supernatant was filtered through a 0.45 um low protein binding membrane (MILLIPORE STERIFLIP® HV/PVDF). To achieve 300× concentration of the GeCKO pooled library, the virus was ultracentrifuged (Sorvall) at 24,000 rpm for 2 h at 4° C. and then resuspended overnight at 4° C. in D10 supplemented with 1% BSA. Aliquots were stored at −80° C.

Cell transduction using the GeCKO library: Cells were transduced with the GeCKO library via spinfection. To find optimal virus volumes for achieving an MOI of 0.3-0.5, each new cell type and new virus lots were tested by spinfecting $3\times10^6$ cells with several different volumes of virus. Briefly, $3\times10^6$ cells per well were plated into a 12 well plate in the appropriate standard media for the cell type (see below) supplemented with 8 μg/ml polybrene (SIGMA®). For A375 cells (ATCC), standard media was R10: RPMI 1640 supplemented with 10% FBS. For HUES62 (Harvard Stem Cell Institute iPS Core Facility), standard media consists of mTeSR1 (STEMCELL Technologies) supplemented with 1× Normocin (INVIVOGEN®). Each well received a different titrated virus amount (usually between 5 and 50 ul) along with a no-transduction control. The 12-well plate was centrifuged at 2,000 rpm for 2 h at 37° C. After the spin, media was aspirated and fresh media (without polybrene) was added.

Cells were incubated overnight and then enzymatically detached using trypsin (CORNING®) for A375 and AccutaseACCUTASE® (STEMCELL®) for HUES62. Cells were counted and each well was split into duplicate wells. One replicate received 0.5 ug/mL puromycin (SIGMA®) for HUES62 cells or 1 μg/ml puromycin for A375 cells. After 3 days (or as soon as no surviving cells remained in the no-transduction control under puromycin selection), cells were counted to calculate a percent transduction. Percent transduction is calculated as cell count from the replicate with puromycin divided by cell count from the replicate without puromycin multiplied by 100. The virus volume yielding a MOI closest to 0.4 was chosen for large-scale screening.

Large-scale spinfection of $5\times10^7$ to $1\times10^8$ A375 or HUES62 cells was carried out in the same way as described above using 12-well plates with $3\times10^6$ cells per well. Wells were pooled together into larger flasks on the day after spinfection.

HUES62 depletion screen: $6\times10^7$ HUES62 human embryonic stem (hES) cells were transduced as described above. 30 μL of the concentrated GECKO library was applied to each well containing $3\times10^6$ cells, resulting in an transduction efficiency of 30% (approximately 270 cells per lentiCRISPR construct). Puromycin (0.5 ug/mL) was added to the cells 24 hours post transduction and maintained for 7 days. On day 7, cells were split into replicate flasks with a minimum of $2\times10^7$ cells per replicate and cultured for an additional 14 days before genomic DNA extraction and analysis. During the screen, hES cells were fed daily with mTeSR1.

A375 PLX-4032 resistance screen: $8\times10^7$ A375 cells were transduced as described above with $2\times10^6$ cells plated per transduction well. 10 μL of the concentrated GECKO library was applied to each well containing $2\times10^6$ cells, attaining a transduction efficiency of 30% (approximately 370 cells per lentiCRISPR construct or in aspects of the invention, this may be approximately 400 cells per lentiCRISPR construct). Puromycin (1 ug/mL) was added to the cells 24 hours post transduction and maintained for 7 days. On day 7, cells were split into drug conditions in duplicate with a minimum of $2.6\times10^7$ cells per replicate and an additional $3\times10^7$ cells were frozen down for genomic DNA analysis. Two replicates were cultured in R10 supplemented with 2 uM PLX4032 (Selleckchem) and two replicates were cultured in R10 supplemented with an equal volume DMSO (SIGMA® Aldrich). Replicates were either passaged or fresh media was added every 2-3 days. Cell pellets with a minimum of $3\times10^7$ cells were taken at 7 days after drug addition and 14 days after drug addition at which point the screen was terminated.

Genomic DNA sequencing: Frozen cell pellets were thawed and genomic DNA was extracted with a Blood & Cell Culture Midi kit (QIAGEN®). PCR was performed in two steps: For the first PCR, the amount of input genomic DNA (gDNA) for each sample was calculated in order to achieve 300× coverage over the GECKO library, which resulted in 130 ug DNA per sample (assuming 6.6 ug of gDNA for $10^6$ cells). For each sample, Applicants performed 13 separate 100 ul reactions with 10 ug genomic DNA in each reaction using Herculase II Fusion DNA Polymerase (AGILENT®) and then combined the resulting amplicons. Primers sequences (SEQ ID NOs: 69 and 70, respectively, in order of appearance) to amplify lentiCRISPR sgRNAs for the first PCR are:

```
F1
AATGGACTATCATATGCTTACCGTAACTTGAAAGTATTTCG

R1
CTTTAGTTTGTATGTCTGTTGCTATTATGTCTACTATTCTTTCC
```

A second PCR was performed to attach Illumina adaptors and to barcode samples. The second PCR was done in a 100 ul reaction volume using 5 ul of the product (preferably the pooled product) from the first PCR. Primers for the second PCR include both a variable length sequence to increase library complexity and an 8 bp barcode for multiplexing of different biological samples:

```
F2
                                        (SEQ ID NO: 71)
AATGATACGGCGACCACCGAGATCTACACTCTTTCCCTACACGACGCTCTT
CCGATCT (1-9 bp variable length sequence)(8 bp
barcode)tcttgtggaaaggacgaaacaccg

R2
                                        (SEQ ID NO: 72)
CAAGCAGAAGACGGCATACGAGATGTGACTGGAGTTCAGACGTGTGCTCTT
CCGATCT tctactattctttcccctgcactgt
```

Resulting amplicons from the second PCR were gel extracted, quantified, mixed and sequenced using a HiSeq 2500 (Illumina). Amplification was carried out with 18 cycles for the first PCR and 24 cycles for the second PCR.

Data processing and initial analysis: Raw FASTQ files were demultiplexed using the FASTX-Toolkit (available at the website of hannonlab.cshl.edu/fastx_toolkit/) and processed to contain only the unique sgRNA sequence. To align the processed reads to the library, the designed sgRNA sequences from the library were assembled into a Burrows-Wheeler index using the Bowtie build-index function. Reads were then aligned to the index using the Bowtie aligner. After alignment, the number of uniquely aligned reads for each library sequence was calculated.

The numbers of reads for each unique sgRNA for a given sample were normalized as follows:

$$\text{normalized reads per } sgRNA = \frac{\text{reads per } sgRNA}{\text{total reads for all } sgRNAs \text{ in sample}} \times 10^6$$

Array lentiCRISPR array screen: Individual lentiCRISPRs from the GECKO pool were produced as above except that viral supernatants were not concentrated by ultracentrifugation. For each lentiCRISPR, $5\times10^5$ A375 cells were infected via spinfection at 2,000 rpm for 2 h at 37° C. in R10 supplemented with 8 ug/ml polybrene. After 14 days of puromycin selection, infections were plated into separate dishes for Western blotting and the cell viability assay.

Western blotting: A375 cells were lysed in Cell Lysis Buffer (CELL SIGNALING® 9803) with protease inhibitors (SIGMA® P8340). Lysates were homogenized using a Bioruptor sonicator (Diagenode) for 5 minutes (30s on-30s off cycle, high power) and then centrifuged at 15,000 rpm for 20 min at 4° C. Supernatants were quantified using the BCA assay (THERMO/PIERCE®). 20 ug of protein was denatured at 70 C for 10 minutes before gel electrophoresis on a 4-12% Bis-Tris gel (LIFE TECHNOLOGIES®). Proteins were transferred to nitrocellulose membranes at 60V overnight at 4° C. Antibodies used: Anti-NF2 (1:1000, ABCAM® ab109244), Anti-NF1 (1:1000, ABCAM® ab17963), Anti-MED12 (1:1000, CELL SIGNALING® 4529S), Anti-CUL3 (1:1000, CELL SIGNALING® 2759S), Anti-TADA2B (1:1000, SIGMA® HPA035770), Anti-GAPDH (1:5000, CELL SIGNALING® 3683S). Membranes were developed by SuperSignal West Femto ECL (THERMO/PIERCE®) and imaged using BIORAD® CHEMIDOC® MP imaging system.

Cell viability assay: lentiCRISPR-infected A375 cells were plated in quadruplicate into 96-well plates at a density of $5\times10^3$ cells per well. Either PLX or vehicle (DMSO) was added 1 day after plating. PLX was added at the following concentrations: 20 nM, 200 nM, 2 uM, 20 uM, and 200 uM. Drug/vehicle was renewed every 2-3 days using a Janus liquid handler (PerkinElmer).

After 5 days of drug/vehicle treatment, cell viability was measured using CELLTITER GLO® (PROMEGA®). After allowing cells to reach room temperature, media was aspirated from the cells and CELLTITER GLO® (diluted 1:4 in phosphate-buffered saline) was added. Plates were placed on an orbital shaker for 2 min followed by a 10 min room temperature incubation. Luminescence was read out on an EnVision plate imager (PerkinElmer).

Flow cytometry analysis of GFP knockout or knockdown: lentiCRISPR with sgRNAs targeting EGFP (SEQ ID NOs: 73-76 and 50-51, respectively, in order of appearance) were cloned using the following sequences (annotated in FIG. 28):

```
EGFP sgRNA 1
GGGCGAGGAGCTGTTCACCG

EGFP sgRNA 2
GAGCTGGACGGCGACGTAAA

EGFP sgRNA 3
GGCCACAAGTTCAGCGTGTC

EGFP sgRNA 4
GGAGCGCACCATCTTCTTCA

EGFP sgRNA 5
GAAGTTCGAGGGCGACACCC

EGFP sgRNA 6
GGTGAACCGCATCGAGCTGA
```

Four shRNAs targeting EGFP in a pLKO (puromycin-selectable) vector were used (Broad RNAi Platform):

| | |
|---|---|
| EGFP shRNA 1 | TRCN0000072194 |
| EGFP shRNA 2 | TRCN0000072181 |
| EGFP shRNA 3 | TRCN0000072201 |
| EGFP shRNA 4 | TRCN0000072198 |

Control lentiCRISPR contained no spacer sequence and control shRNA was null hairpin TRCN0000208001.

For both lentiCRISPRs and shRNAs, virus was produced using a similar protocol as presented above but without ultracentrifuge purification. HEK293T cells with a single copy of EGFP (Broad RNAi Platform) were infected on Day 0 and then analyzed by flow cytometry on Day 5 and Day 11 post-infection. Flow cytometry was performed on a BD Accuri C6 cytometer in 96-well plates. Analysis was done in FlowJo (Treestar) by first gating for viable cells using forward and side scatter and then gating the fluorescence histogram.

Sequencing data analysis and indel detection: Off target loci in the human genome were identified for individual spacers using the CRISPR design tool (available at the website tools.genome-engineering.org). On-target and off-target loci were PCR amplified using Herculase II Fusion polymerase (Agilent), normalized, and pooled in equimolar proportions. Pooled libraries were denatured, diluted to a 14 pM concentration and sequenced using the MiSeq Personal Sequencer (Illumina). Sequencing data was demultiplexed using paired barcodes, aligned to reference amplicons, and analyzed for indels as described previously. Indel length analysis was performed by mapping the distance between multiple short reference sequences in individual reads.

Aspects of the invention also encompass a two vector, genome-wide KO system. Details are as follows:

1) Applicants utilize A375 (BRAF V600E mutation-containing) cells having Cas9 alone integrated into the genome. This may be done with lentivirus but may also be done with other methods of integration (integrase, recombinase, transposase, etc.) Typically the integration cassette will include Cas9 and a selectable marker to make sure that only cells with Cas9 active are kept. For e.g., the vector is EF1a-Cas9-2A-Blasticidin.
2) The A375 cells comprising Cas9 are exposed to a library of viruses. Each virus has U6 driving one sgRNA ("spacer" or "guide"). Thus in this case, the library delivers only the guide instead of Cas9 plus guide. The rationale for this approach is that it may be easier to produce a high titer virus with only having to deliver the guide. In aspects of the invention it may be practical for large scale screening and virus production to have only the variable part (the guide, which is one of 65,000 different guides) in the library virus and keep the constant part (Cas9) out of the library.
3) The rest of the screen proceeds from this point identically to the single vector system as described in this example which may include the following steps: Adding PLX (drug targeted to BRAF with V600E mutation); Killing most of the cells; Letting the cells that survive grow out; Extracting genomic DNA and Performing next generation (next gen) sequencing to find out which guides conferred the ability to survive PLX selection. Applicants have utilized the two vector system to knock out EGFP and hence this two vector system may be applied to a full-scale screen.

Example 10: Improved Lentiviral Vectors and Genome-Wide Libraries for CRISPR Screening in Human and Mouse Cells Initial genome-wide, targeted loss-of-function screens using the CRISPR (clustered regularly interspaced short palindrome repeats)-associated nuclease Cas9 in human and mouse cells have revealed new mechanisms of resistance to cancer therapeutics (including vemurafenib, etoposide, and 6-TG) and identified genes essential for cell survival. When compared to screens using genome-wide libraries of RNAi reagents, screens with Genome-scale CRISPR Knock-Out (GeCKO) libraries demonstrate higher consistency amongst unique reagents targeting the same gene and have a higher target validation rate among top screen candidates[1].

Figure 47A:
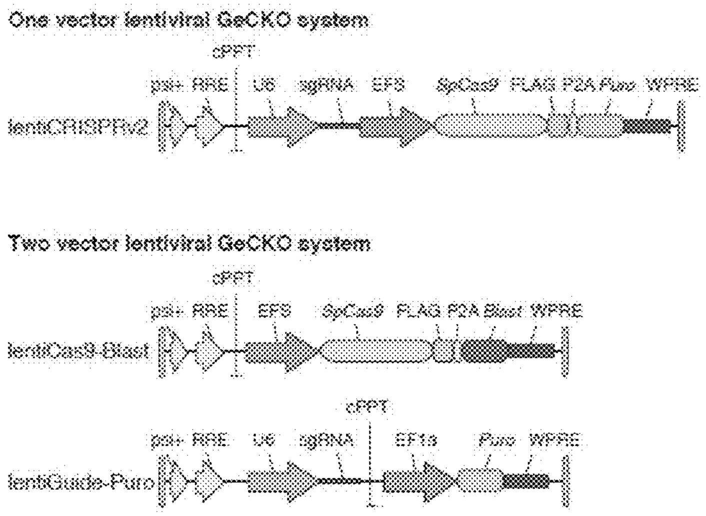
FIG. 47A-47B shows New lentiviral CRISPR designs produce viruses with higher functional titer. (A) Lentiviral expression vector for *Streptococcus pyogenes* Cas9 and sgRNA in the improved one vector system (lentiCRISPR v2) and the two vector system (lentiCas9-Blast, lentiGuide-Puro). Psi packaging signal (psi+), rev response element (RRE), central polypurine tract (cPPT), elongation factor-1$\alpha$ short promoter (EFS), FLAG octapeptide tag (FLAG), 2A self-cleaving peptide (P2A), puromycin selection marker (puro), posttranscriptional regulatory element (WPRE), blasticidin selection marker (blast), and elongation factor-1$\alpha$ promoter (EF1a). (B) Relative functional viral titer of viruses made from lentiCRISPR v1, lentiCRISPR v2, and lentiGuide-Puro vector with a EGFP-targeting sgRNA (n=3 transductions). HEK293FT cells were transduced with serial dilutions of virus and, after 24 hours, selected using puromycin (1 ug/ml). Puromycin-resistant cells were measured after 4 days from the start of selection using the CELLTITER-GLO® (PROMEGA®) luciferase assay. Relative titers were calculated using viral volumes that yielded less than 20% puromycin-resistant cells in order to minimize the number of cells with multiple infections. Numbers above each bar indicate the size of the packaged virus for each construct.
Figure 47B:
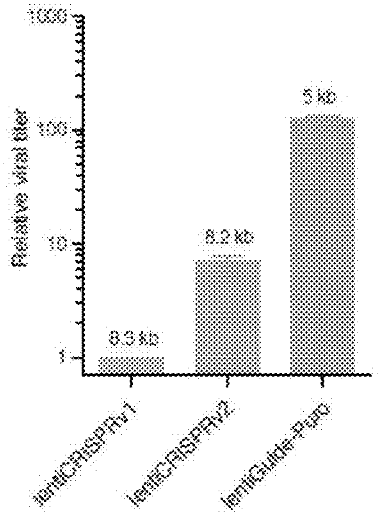

Applicants sought to improve both the lentiviral packaging and pooled library design of Applicant's original CRISPR screening system as described in Example 9. In the system described in Example 9, a pooled library of synthesized oligonucleotides was cloned into a lentiviral backbone containing both the Cas9 nuclease and the target-specific synthetic short guide RNA (sgRNA). This lentiviral vector (lentiCRISPR v1) had a low titer and required concentration of the virus using an ultracentrifuge or ultrafiltration membrane before performing a screen. To create a new vector capable of producing higher-titer virus, Applicants removed one of the nuclear localization signals (NLS), codon-optimized the remaining NLS and P2A bicistronic linker sequence, and changed the placement of the U6-driven sgRNA cassette (FIG. 47A). This optimized vector (lentiCRISPR v2) has a 7.1-fold increase in functional viral titer over lentiCRISPRv1 (FIG. 47B).

Figure 48A:
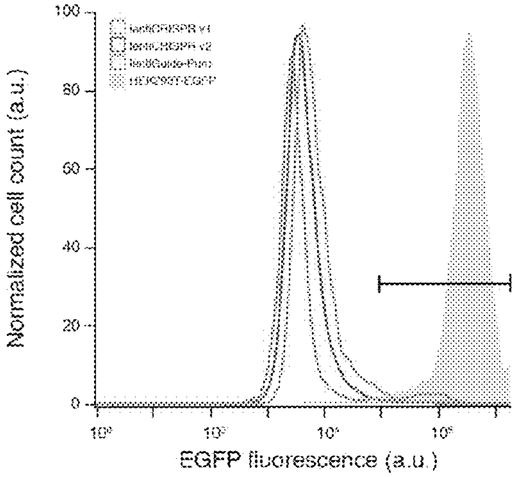
FIG. 48A-48B shows Flow cytometry of HEK293T-EGFP 7 days after lentiCRISPR transduction. (A) Representative histograms of EGFP fluorescence from single transductions of HEK293T-EGFP cells with lentiCRISPR v1, lentiCRISPR v2, lentiGuide-Puro or no virus. For lentiGuide-Puro, HEK293T-EGFP cells had previously been transduced with lentiCas9-Blast. Twenty-four hours after transduction, cells were selected in puromycin and then analyzed by flow cytometry at 7 days after infection. (B) Percentage of EGFP positive cells (as given by gate drawn in panel A) per viral construct (error bars indicate s.e.m, n=3 biological replicate transductions).
Figure 48B:
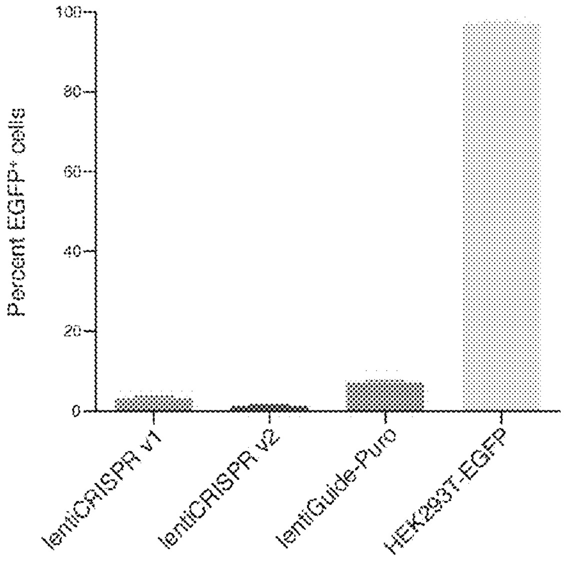

To further increase viral titer, Applicants also cloned a two vector system, in which the Cas9 nuclease and the sgRNA library are delivered in separate lentiviruses with separate antibiotic selection markers (FIG. 47A). The new lentiGuide-Puro virus has a 127-fold increase in functional viral titer over the original lentiCRISPR v1 (FIG. 47B). The increased viral titers of lentiCRISPR v2 and lentiGuide-Puro will greatly reduce reagent costs for GeCKO screens and enable infection without the need for concentration of viral supernatant. Cas9-mediated gene knock-out of a genomically-integrated copy of EGFP is efficient with both new lentiCRISPR systems (FIG. 48).

In addition to the vector improvements, Applicants designed and synthesized new human and mouse genome GeCKO libraries (See Tables 2A, 2B, 3, 4, 5, 6, 7, 8 and 9). These new libraries have a uniform coverage of 6 sgRNAs for each gene with higher gene and exon coverage (Table M).

TABLE M

Comparison of new GeCKO v2 human and mouse sgRNA libraries with existing CRISPR libraries.

| | Wang et al. (2014) library | Shalem et al. (2014) GeCKO v1 library | Yusa et al. (2014) library | GeCKO v2 human library | GeCKO v2 mouse library |
|---|---|---|---|---|---|
| Species | human | human | mouse | human | mouse |
| Number of genes targeted | 7,114 | 18,080 | 19,150 | 19,052 | 20,661 |

TABLE M-continued

Comparison of new GeCKO v2 human and mouse sgRNA libraries with existing CRISPR libraries.

| | Wang et al. (2014) library | Shalem et al. (2014) GeCKO v1 library | Yusa et al. (2014) library | GeCKO v2 human library | GeCKO v2 mouse library |
|---|---|---|---|---|---|
| Targeting constructs per gene | 10 per gene | variable (typically 3 to 4 per gene) | variable (typically 4 to 5 per gene) | 6 per gene (3 in Library A, 3 in Library B) | 6 per gene (3 in Library A, 3 in Library B) |
| Number of miRNA targeted | none | none | none | 1864 | 1175 |
| Targeting constructs per miRNA | n/a | n/a | n/a | 4 per miRNA | 4 per miRNA |
| Control (non-targeting) sgRNAs | 100 | none | none | 1000 | 1000 |
| Total sgRNA constructs | 73,151 | 64,751 | 87,897 | 122,417 (65,386 in Library A, 58,031 in Library B) | 130,209 (67,405 in Library A, 62,804 in Library B) |
| Viral plasmid vector | Dual vector: sgRNA only | Single vector: Cas9 and sgRNA (lentiCRISPR v1) | Dual vector: sgRNA only | Single and dual vector: lentiCRISPR v2 and lentiGuide-Puro | Single and dual vector: lentiCRISPR v2 and lentiGuide-Puro |

New GeCKO libraries target an increased number of genes with uniform coverage (6 sgRNAs per gene divided into sub-libraries with 3 sgRNAs per gene—see Tables 3, 4, 7 and 8). The GeCKO v2 libraries also contain sgRNAs that target microRNAs (Tables 5 and 9) and control sgRNAs (Tables 2A, 2B and 6) that do not target in the genome. The libraries have been cloned into lentiCRISPR v2 (which includes Cas9 in the same vector) and lentiGuide-Puro (sgRNA-only vector) and are available in either format.

Applicants also improved the calculation of off-target scores based on recent empirical data and added sgRNAs to target micro RNAs (miRNAs) by directing mutations to the mature hairpin structure. The GeCKOv2 human library described in the Example now covers 19,052 genes, which is almost 1,000 genes more than the original GeCKO library described in Example 9. The library is divided into 2 sub-libraries (A and B). Each sub-library contains 3 sgRNAs for all genes and 1000 control sgRNAs that do not target any sequence in the genome. Library A also contains 7288 sgRNAs to target 1864 miRNAs. Screens can be performed with the combined library (122,417 sgRNAs) with 6 sgRNAs per gene or with either sub-library. This flexibility allows use of a smaller sub-library in situations where cell numbers are limiting (e.g. primary cells, in vivo screens) or both sub-libraries together for better coverage. Similar to the human genome-wide library, Applicants also designed a GeCKOv2 mouse library with 2 sub-libraries containing 3 sgRNAs for each gene. The human and mouse libraries have been cloned into lentiCRISPR v2 and lentiGuide-Puro and deep sequenced.

Lentiviral cloning and production: For determination of lentiCRISPR v1, lentiCRISPR v2, and lentiGuide-Puro viral titers, the following sgRNA targeting EGFP (with no known targets in the human genome) was cloned into all 3 lentiviral transfer vectors:

```
EGFP sgRNA
                              (SEQ ID NO: 73)
GGGCGAGGAGCTGTTCACCG
```

To clone the sgRNA guide sequence, plasmids were cut and dephosporylated with FastDigest BsmBI and FastAP (Fermentas) at 37° C. for 2 hours. Oligonucleotides for the EGFP sgRNA guide sequence (Integrated DNA Technologies) were phosphorylated using polynucleotide kinase (Fermentas) at 37° C. for 30 minutes and then annealed by heating to 95° C. for 5 minutes and cooling to 25° C. at 1.5° C./minute. Using T7 ligase (Enzymatics), annealed oligos were ligated into gel purified vectors (QIAGEN®) at 25° C. for 5 minutes. Cloned transfer plasmids were amplified using a endotoxin-free midi-prep kit (QIAGEN®).

To make lentivirus, the transfer plasmids were co-transfected with packaging plasmids pMD2.G and psPAX2 (Addgene plasmids 12259 and 12260), as described previously in Shalem, O. et al. Genome-scale CRISPR-Cas9 knockout screening in human cells. Science 343, 84-87 (2014). Briefly, for each virus, a T-75 flask of 80% confluent HEK293T cells was transfected in OptiMEM™ (LIFE TECHNOLOGIES®) using 10 μg of the transfer plasmid, 5 ug pMD2.G, 7.5 ug psPAX2, 100 ul of Plus Reagent (LIFE TECHNOLOGIES®), and 50 ul of LIPOFECTAMINE® 2000 (LIFE TECHNOLOGIES®). After 6 hours, media was changed to D10 media, DMEM (LIFE TECHNOLOGIES®) with 10% fetal bovine serum (Hyclone), with 1% bovine serum albumin (SIGMA®) added to improve virus stability. After 60 hours, viral supernatants were harvested and centrifuged at 3,000 rpm at 4° C. for 10 min to pellet cell debris. The supernatant was filtered through a 0.45 um low protein binding membrane (Millipore) and used immediately.

Lentiviral functional titration: Lentiviruses were titered in a functional assay by measuring puromycin resistance after transduction. For each viral construct, $2.5\times10^4$ HEK293T-EGFP cells were transduced in suspension (i.e. during plating) with 10, 100, or 1000 ul of viral supernatant in wells of a 24-well plate. For lentiGuide-Puro transduction the HEK293T-EGFP cells also had a genomically-integrated copy of Cas9 from previous transduction with lentiCas9-Blast. Each transduction condition (construct and virus volume) was performed in triplicate. In each well, D10 culture media was added to make the final volume 1.5 ml. Cell without any virus added were also plated in six wells (3 wells for puromycin treatment, 3 wells as control).

At 24 hours post-transduction, media was changed to D10 with 1 μg/ml puromycin (SIGMA®) for all wells except the uninfected controls without puromycin. At 3 days post-transduction, cells in all wells were split 1:5 to prevent any well from reaching confluence. Except for the uninfected controls without puromycin, new D10 media was supplemented with 1 ug/ul puromycin. At 5 days post-transduction, all cells in the uninfected control wells treated with puromycin were floating/dead, which was verified using Trypan Blue exclusion (SIGMA®).

For the remaining wells, adherent cells were present and cell viability was measured using CELLTITER GLO® (PROMEGA®) following the manufacturer's protocol. After allowing cells to reach room temperature, media was aspirated from the cells and CELLTITER GLO® (diluted 1:1 in phosphate-buffered saline) was added. Plates were covered with foil, placed on an orbital shaker for 2 min, and then incubated for 10 minutes at room temperature. Luminescence was read out on an Synergy H4 plate imager (Biotek) using a 1 second integration time and auto-gain to utilize the full dynamic range of the detector. Positive controls (untranduced cells without puromycin) and negative controls (empty wells) were included in the assay.

Fold differences in titer between viral constructs were calculated using luminescence values. Specifically, comparisons were made between pairs of viruses for the same volume of supernatant. Only viral volumes for which cell survival was greater than 1% and less than 20% of control (untransduced) cells were directly compared. Assuming Poisson statistics, 20% cell survival impels that approximately 90% of cells surviving puromycin selection were infected by only a single virus.

Flow cytometry data was collected from the same set of infections using a BD Accuri C6 flow cytometer. Using FlowJo (TreeStar), cells were distinguished from debris and doublets by gating in forward vs. side scatter area plots. EGFP fluorescence was measured in the gated population from transduced and uninfected HEK293T-EGFP cells.

Design of new GeCKO libraries: Genome wide sgRNA libraries for the human and mouse genomes were designed using the following steps:

(1) Identification of conserved exons: For the human library, RNA sequencing data from the Illumina Human Body Map 2.0 (GEO accession number: GSE30611) was mapped to the reference human genome (hg19) using TopHat v1.0.14 and transcripts were reconstructed with Cufflinks v1.0.2. Exons expressed across all tissues in the Illumina dataset were chosen as constitutive exons for sgRNA targeting. In addition, for each gene, the first and last exons were excluded along with any exon that contained an alternative splicing site. For the mouse library, Applicants chose constitutive exons as exons that are shared by all RefGene (available at the website refgene.com/) transcripts for the same gene. Applicants then chose for each gene, 4 constitutive exons for targeting, in cases where there are not enough constitutive exons Applicants added exons starting from the second coding constitutive exon towards the end of the gene. In both mouse and human coding exons where identified using the CCDS database (available at the website ncbi.nlm.nih.gov/CCDS/CcdsBrowse.cgi).

(2) Choice of sgRNA sequences: For each candidate exon, all possible *S. pyogenes* Cas9 sgRNA sequences of the form $(N)_{20}NGG$ were listed as candidate targets. Each 20mer candidate sgRNA was mapped to a precompiled index containing all 20mer sequences in the human genome followed by either NGG or NAG. This mapping was done using Bowtie short read aligner, allowing up to 3 base mismatches.

Off target score was calculated as follows, as described in Hsu, P. D. et al. DNA targeting specificity of RNA-guided Cas9 nucleases. Nat Biotechnol 31, 827-832 (2013):

For a single off-target position:

$$\prod_{e\in M}(1-W[e])\times\frac{1}{\left(\frac{(19-d)}{19}\times 4+1\right)}\times\frac{1}{n_{mn}^2}$$

Then these are aggregated as follows:

$$S_{guide}=\frac{100}{100+\sum_{i=1}^{n_{mm}}S_{hit}(h_i)}$$

W: weight of the location of base mismatch (from Hsu, P. D. et al. DNA targeting specificity of RNA-guided Cas9 nucleases. Nat Biotechnol 31, 827-832 (2013)).

d: mean pairwise distance between mismatches.

$n_{mm}$: number of mutations $S_{hit}(h_i)$: the score for a single off-target

Applicants then chose for each gene 6 sgRNAs such that there were no more than 2 sgRNAs per exon.

(3) Targeting of mature miRNAs: For the design of miRNA targeting guides Applicants took the hairpin miRNA sequence coordinates from the mirBASE database (available at the website mirbase.org). Applicants then listed all the possible $(N)_{20}NGG$ sequences and chose 4 sgRNAs per miRNA preferentially choosing sgRNAs that target the stem region in the stem loop.

GeCKO library pooled synthesis and cloning: DNA oligonucleotide library synthesis was completed on a programmable microarray using a B3 Synthesizer (CustomArray) and SAFC Proligo reagents (SIGMA®), as recommended by the manufacturer. The synthesis products were cleaved from the microarray and deprotected by overnight incubation in 28-30% ammonium hydroxide at 65° C., dried, resuspended in 30 ul TE buffer and then purified using a QIAQUICK® spin column (QIAGEN®). Full-length oligonucleotides (74 nt) were amplified by PCR using PHUSION® HS Flex (NEB®). For the PCR reaction, the manufacturer's protocol was followed using 0.1 ul of synthesized oligonucleotide template, primers Array F and ArrayR (see below), an annealing temperature of 63° C., an extension time of 15 s, and 20 cycles. After PCR, the 140 bp amplicon was size-selected using a 2% agarose E-GEL® EX (LIFE TECHNOLOGIES®, QIAGEN®).

```
ArrayF
                                        (SEQ ID NO: 77)
TAACTTGAAAGTATTTCGATTTCTTGGCTTTATATATCTTGTGGAAAGGAC
GAAACACCG
```

-continued

ArrayR (SEQ ID NO: 78)

ACTTTTTCAAGTTGATAACGGACTAGCCTTATTTTAACTTGCTATTTCT
AGCTCTAAAAC

The vector backbone (lentiCRISPR v2 or lentiGuide-Puro) was digested with BsmBI (Fermentas) and treated with FastAP (Fermentas) at 37° C. for 2 hours and gel-purified on a 1% E-GEL® EX (LIFE TECHNOLOGIES®, QIAGEN®). A 20 ul GIBSON® ligation reaction (NEB®) was performed using 10 ng of the gel-purified inserts and 25 ng of the vector (for lentiCRISPR v2) and using 5 ng of the gel-purified inserts and 25 ng of the vector (for lentiGuide-Puro). From the ligation, 0.5 ul of the reaction was transformed into 25 ul of electrocompetent cells (LUCIGEN®) according to the manufacturer's protocol using a GenePulser (BIORAD®). To ensure no loss of representation, sufficient parallel transformations were performed using the same ligation reaction and plated onto 245 mm×245 mm plates (CORNING®) with carbenicillin selection (50 ug/ml), which yielded 30-200× library coverage. Colonies were scraped off plates and combined before plasmid DNA extraction using Endotoxin-Free Plasmid Maxiprep (QIAGEN®).

Library sequencing and validation: To check library representation, synthesis fidelity, and bias, libraries were amplified and then deep sequenced. First, libraries were PCR amplified for 16 cycles using PHUSION® Flash High-Fidelity (Thermo) with primers to add adaptors for Illumina sequencing. For all libraries, PCR reactions were performed in duplicate and barcoded to allow quantification of bias introduced by PCR. Samples were sequenced on a MiSeq following the manufacturer's protocol using a v3 150 cycle kit with 10% PhiX (Illumina).

PCR replicates were demultiplexed using FASTX-Toolkit (Hannon Lab, CSHL) and adaptors were trimmed using cutadapt to leave only the sgRNA guide sequence. Alignment of the guide sequence to the appropriate GeCKO library index was done using Bowtie with parameters to tolerate up to a single nucleotide mismatch. The Bowtie alignment was then read into Matlab for further analysis (Mathworks). For all libraries, greater than 90% of sgRNAs were represented with at least one sequencing read and the difference in representation between the $90^{th}$ and $10^{th}$ percentile sgRNAs was always less than 10-fold.

Vector maps and reagent distribution: All lentiCRISPR plasmids (FIGS. 49, 50 and 51) and GeCKO libraries are available on Addgene and vector maps are available at the website genome-engineering.org/gecko/.

Design specification on changes between lentiCRISPRv1 and lentiCRISPRv2 are indicated below. The lentiCRISPRv2 encompasses the following aspects:

- Novel hybrid LKO/FUGW design
  - 5' lenti elements and backbone are from FUGW,
  - 3' lenti elements are from LKO (Applicants took this approach because the 3' lenti elements in LKO have less wasted space after WPRE)
- Human codon-optimized FLAG tag was moved to C term of Cas9
- Removed N-terminal NLS
- Removed 2 residue linker between Cas9 and 2A
  - A convenient restriction site (BamHI) is now integrated at beginning of 2A sequence
- Unique human codon-optimized NLS
- Unique human codon-optimized P2A
- Moved U6 Pol3 cassette to after cPPT. Now directly upstream of EFS Pol2 cassette.
  - Enzyme sites for easy modular removal of Pol3 cassette, Pol2 promoter, Cas9 CDS LTR-LTR distance is now 8.2 kb: This is >100 bp shorter than the lentiCRISPRv1 vector.

Applicants have shown that these improved lentiCRISPR vectors and human and mouse libraries will make it easier to perform GeCKO screens with enhanced lentiviral delivery options and greater choice over library size for different screening applications.

Example 11: Generation of Gene Knockout Cell Library

This example demonstrates how to generate a library of cells where each cell has a single gene knocked out:

Applicants make a library of ES cells where each cell has a single gene knocked out, and the entire library of ES cells will have every single gene knocked out. This library is useful for the screening of gene function in cellular processes as well as diseases.

To make this cell library, Applicants integrate Cas9 driven by an inducible promoter (e.g. doxycycline inducible promoter) into the ES cell. In addition, Applicants integrate a single guide RNA targeting a specific gene in the ES cell. To make the ES cell library, Applicants simply mix ES cells with a library of genes encoding guide RNAs targeting each gene in the human genome. Applicants first introduce a single BxB1 attB site into the AAVS1 locus of the human ES cell. Then Applicants use the BxB1 integrase to facilitate the integration of individual guide RNA genes into the BxB1 attB site in AAVS1 locus. To facilitate integration, each guide RNA gene is contained on a plasmid that carries of a single attP site. This way BxB1 will recombine the attB site in the genome with the attP site on the guide RNA containing plasmid.

To generate the cell library, Applicants take the library of cells that have single guide RNAs integrated and induce Cas9 expression. After induction, Cas9 mediates double strand break at sites specified by the guide RNA. To verify the diversity of this cell library, Applicants carry out whole exome sequencing to ensure that Applicants are able to observe mutations in every single targeted gene. This cell library can be used for a variety of applications, including who library-based screens, or can be sorted into individual cell clones to facilitate rapid generation of clonal cell lines with individual human genes knocked out.

Example 12: Plasmid Genome-Wide Libraries Comprising a Plurality of Unique Guide Sequences The following plasmid libraries were deposited with ATCC on Jun. 10, 2014:

- GeCKO1—library of sgRNA plasmids each encoding selected guide sequences and cloned into vector (lentiCRISPRv2)—ATCC Deposit No. PTA121339;
- GeCKO2—half library A (human) sgRNA plasmids each encoding selected guide sequences and cloned into vector—ATCC Deposit No. PTA121340;
- GeCKO2—half library B (human) of sgRNA plasmids each encoding selected guide sequences and cloned into vector—ATCC Deposit No. PTA121341;
- GeCKO2—half library A (mouse) sgRNA plasmids each encoding selected guide sequences and cloned into vector—ATCC Deposit No. PTA121342; and
- GeCKO2—half library A (mouse) sgRNA plasmids each encoding selected guide sequences and cloned into vector—ATCC Deposit No. PTA121343.

The deposited libraries comprise pool of vectors each comprising sequence encoding a individual guide sequence of library useful according to the present invention, namely that may be used in the libraries, methods and/or kits of the present invention. The guide sequences are capable of targeting a plurality of target sequences in genomic loci, wherein the targeting results in a KO of gene function.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

REFERENCES (CONTENTS OF WHICH ARE INCORPORATED HEREIN IN THEIR ENTIRETY)

1. Urnov, F. D., Rebar, E. J., Holmes, M. C., Zhang, H. S. & Gregory, P. D. Genome editing with engineered zinc finger nucleases. *Nat. Rev. Genet.* 11, 636-646 (2010).
2. Bogdanove, A. J. & Voytas, D. F. TAL effectors: customizable proteins for DNA targeting. *Science* 333, 1843-1846 (2011).
3. Stoddard, B. L. Homing endonuclease structure and function. *Q. Rev. Biophys.* 38, 49-95 (2005).
4. Bae, T. & Schneewind, O. Allelic replacement in *Staphylococcus aureus* with inducible counter-selection. *Plasmid* 55, 58-63 (2006).
5. Sung, C. K., Li, H., Claverys, J. P. & Morrison, D. A. An rpsL cassette, janus, for gene replacement through negative selection in *Streptococcus pneumoniae. Appl. Environ. Microbiol.* 67, 5190-5196 (2001).
6. Sharan, S. K., Thomason, L. C., Kuznetsov, S. G. & Court, D. L. Recombineering: a homologous recombination-based method of genetic engineering. *Nat. Protoc.* 4, 206-223 (2009).
7. Jinek, M. et al. A programmable dual-RNA-guided DNA endonuclease in adaptive bacterial immunity. *Science* 337, 816-821 (2012).
8. Deveau, H., Garneau, J. E. & Moineau, S. CRISPR/Cas system and its role in phage-bacteria interactions. *Annu. Rev. Microbiol.* 64, 475-493 (2010).
9. Horvath, P. & Barrangou, R. CRISPR/Cas, the immune system of bacteria and archaea. *Science* 327, 167-170 (2010).
10. Terns, M. P. & Terns, R. M. CRISPR-based adaptive immune systems. *Curr. Opin. Microbiol.* 14, 321-327 (2011).
11. van der Oost, J., Jore, M. M., Westra, E. R., Lundgren, M. & Brouns, S. J. CRISPR-based adaptive and heritable immunity in prokaryotes. *Trends. Biochem. Sci.* 34, 401-407 (2009).
12. Brouns, S. J. et al. Small CRISPR RNAs guide antiviral defense in prokaryotes. *Science* 321, 960-964 (2008).
13. Carte, J., Wang, R., Li, H., Terns, R. M. & Terns, M. P. Cas6 is an endoribonuclease that generates guide RNAs for invader defense in prokaryotes. *Genes Dev.* 22, 3489-3496 (2008).
14. Deltcheva, E. et al. CRISPR RNA maturation by trans-encoded small RNA and host factor RNase III. *Nature* 471, 602-607 (2011).
15. Hatoum-Aslan, A., Maniv, I. & Marraffini, L. A. Mature clustered, regularly interspaced, short palindromic repeats RNA (crRNA) length is measured by a ruler mechanism anchored at the precursor processing site. *Proc. Natl. Acad. Sci. U.S.A.* 108, 21218-21222 (2011).
16. Haurwitz, R. E., Jinek, M., Wiedenheft, B., Zhou, K. & Doudna, J. A. Sequence- and structure-specific RNA processing by a CRISPR endonuclease. *Science* 329, 1355-1358 (2010).
17. Deveau, H. et al. Phage response to CRISPR-encoded resistance in *Streptococcus thermophilus. J. Bacteriol.* 190, 1390-1400 (2008).
18. Gasiunas, G., Barrangou, R., Horvath, P. & Siksnys, V. Cas9-crRNA ribonucleoprotein complex mediates specific DNA cleavage for adaptive immunity in bacteria. *Proc. Natl. Acad. Sci. U.S.A.* (2012).
19. Makarova, K. S., Aravind, L., Wolf, Y. I. & Koonin, E. V. Unification of Cas protein families and a simple scenario for the origin and evolution of CRISPR-Cas systems. *Biol. Direct.* 6, 38 (2011).
20. Barrangou, R. RNA-mediated programmable DNA cleavage. *Nat. Biotechnol.* 30, 836-838 (2012).
21. Brouns, S. J. Molecular biology. A Swiss army knife of immunity. *Science* 337, 808-809 (2012).
22. Carroll, D. A CRISPR Approach to Gene Targeting. *Mol. Ther.* 20, 1658-1660 (2012).
23. Bikard, D., Hatoum-Aslan, A., Mucida, D. & Marraffini, L. A. CRISPR interference can prevent natural transformation and virulence acquisition during in vivo bacterial infection. *Cell Host Microbe* 12, 177-186 (2012).
24. Sapranauskas, R. et al. The *Streptococcus thermophilus* CRISPR/Cas system provides immunity in *Escherichia coli. Nucleic Acids Res.* (2011).
25. Semenova, E. et al. Interference by clustered regularly interspaced short palindromic repeat (CRISPR) RNA is governed by a seed sequence. *Proc. Natl. Acad. Sci. U.S.A.* (2011).
26. Wiedenheft, B. et al. RNA-guided complex from a bacterial immune system enhances target recognition through seed sequence interactions. *Proc. Natl. Acad. Sci. U.S.A.* (2011).
27. Zahner, D. & Hakenbeck, R. The *Streptococcus pneumoniae* beta-galactosidase is a surface protein. *J. Bacteriol.* 182, 5919-5921 (2000).
28. Marraffini, L. A., Dedent, A. C. & Schneewind, O. Sortases and the art of anchoring proteins to the envelopes of gram-positive bacteria. *Microbiol. Mol. Biol. Rev.* 70, 192-221 (2006).
29. Motamedi, M. R., Szigety, S. K. & Rosenberg, S. M. Double-strand-break repair recombination in *Escherichia coli*: physical evidence for a DNA replication mechanism in vivo. *Genes Dev.* 13, 2889-2903 (1999).
30. Hosaka, T. et al. The novel mutation K87E in ribosomal protein S12 enhances protein synthesis activity during the late growth phase in *Escherichia coli. Mol. Genet. Genomics* 271, 317-324 (2004).
31. Costantino, N. & Court, D. L. Enhanced levels of lambda Red-mediated recombinants in mismatch repair mutants. *Proc. Natl. Acad. Sci. U.S.A.* 100, 15748-15753 (2003).
32. Edgar, R. & Qimron, U. The *Escherichia coli* CRISPR system protects from lambda lysogenization, lysogens, and prophage induction. *J. Bacteriol.* 192, 6291-6294 (2010).

33. Marraffini, L. A. & Sontheimer, E. J. Self versus non-self discrimination during CRISPR RNA-directed immunity. *Nature* 463, 568-571 (2010).
34. Fischer, S. et al. An archaeal immune system can detect multiple Protospacer Adjacent Motifs (PAMs) to target invader DNA. *J. Biol. Chem.* 287, 33351-33363 (2012).
35. Gudbergsdottir, S. et al. Dynamic properties of the *Sulfolobus* CRISPR/Cas and CRISPR/Cmr systems when challenged with vector-borne viral and plasmid genes and protospacers. *Mol. Microbiol.* 79, 35-49 (2011).
36. Wang, H. H. et al. Genome-scale promoter engineering by coselection MAGE. *Nat Methods* 9, 591-593 (2012).
37. Cong, L. et al. Multiplex Genome Engineering Using CRISPR/Cas Systems. *Science* 339, 819 (Feb. 15, 2013).
38. Mali, P. et al. RNA-Guided Human Genome Engineering via Cas9. *Science* 339, 823 (Feb. 15, 2013).
39. Hoskins, J. et al. Genome of the bacterium *Streptococcus pneumoniae* strain R6. *J. Bacteriol.* 183, 5709-5717 (2001).
40. Havarstein, L. S., Coomaraswamy, G. & Morrison, D. A. An unmodified heptadecapeptide pheromone induces competence for genetic transformation in *Streptococcus pneumoniae. Proc. Natl. Acad. Sci. U.S.A.* 92, 11140-11144 (1995).
41. Horinouchi, S. & Weisblum, B. Nucleotide sequence and functional map of pC194, a plasmid that specifies inducible chloramphenicol resistance. *J. Bacteriol.* 150, 815-825 (1982).
42. Horton, R. M. In Vitro Recombination and Mutagenesis of DNA: SOEing Together Tailor-Made Genes. *Methods Mol. Biol.* 15, 251-261 (1993).
43. Podbielski, A., Spellerberg, B., Woischnik, M., Pohl, B. & Lutticken, R. Novel series of plasmid vectors for gene inactivation and expression analysis in group A streptococci (GAS). *Gene* 177, 137-147 (1996).
44. Husmann, L. K., Scott, J. R., Lindahl, G. & Stenberg, L. Expression of the Arp protein, a member of the M protein family, is not sufficient to inhibit phagocytosis of *Streptococcus pyogenes. Infection and immunity* 63, 345-348 (1995).
45. GIBSON®, D. G. et al. Enzymatic assembly of DNA molecules up to several hundred kilobases. *Nat Methods* 6, 343-345 (2009).
46. Garneau J. E. et al. The CRISPR/Cas bacterial immune system cleaves bacteriophage and plasmid DNA. *Nature* 468, 67-71(4 Nov. 2010)
47. Barrangou R. et al. CRISPR provides acquired resistance against viruses in prokaryotes. *Science.* 2007 Mar. 23; 315(5819):1709-12.
48. Ishino Y. et al. Nucleotide sequence of the iap gene, responsible for alkaline phosphatase isozyme conversion in *Escherichia coli*, and identification of the gene product. J Bacteriol. 1987 December; 169(12):5429-33.
49. Mojica F. J. M et al. Biological significance of a family of regularly spaced repeats in the genomes of Archaea, Bacteria and mitochondria. Molecular Microbiology (2000) 36(1), 244-246.
50. Jansen R. et al. Identification of genes that are associated with DNA repeats in prokaryotes. Molecular Microbiology (2002) 43(6), 1565-1575.
51. Luo B et al., Highly parallel identification of essential genes in cancer cells. Proc Natl Acad Sci USA. 2008 Dec. 23; 105(51):20380-5
52. Paddison P J et al., A resource for large-scale RNA-interference-based screens in mammals. Nature. 2004 Mar. 25; 428(6981):427-31
53. Berns K et al., A large-scale RNAi screen in human cells identifies new components of the p53 pathway, Nature. 2004 Mar. 25; 428(6981):431-7
54. Moffat J et al., A lentiviral RNAi library for human and mouse genes applied to an arrayed viral high-content screen. Cell. 2006 Mar. 24; 124(6):1283-98.
55. Zeng Y et al., Both natural and designed micro RNAs can inhibit the expression of cognate mRNAs when expressed in human cells. Mol Cell. 2002 June; 9(6): 1327-33.
56. Hemann et al., An epi-allelic series of p53 hypomorphs created by stable RNAi produces distinct tumor phenotypes in vivo. Nat Genet. 2003 March; 33(3):396-400. Epub 2003 February 3.
57. Stewart S A et al., Lentivirus-delivered stable gene silencing by RNAi in primary cells. RNA. 2003 April; 9(4):493-501.
58. Brummelkamp T R et al., A system for stable expression of short interfering RNAs in mammalian cells. Science. 2002 Apr. 19; 296(5567):550-3. Epub 2002 Mar. 21.
59. E. S. Lander, Initial impact of the sequencing of the human genome. Nature 470, 187 (Feb. 10, 2011).
60. V. N. Ngo et al., A loss-of-function RNA interference screen for molecular targets in cancer. Nature 441, 106 (Apr. 29, 2006).
61. M. Boutros et al., Genome-wide RNAi analysis of growth and viability in Drosophila cells. *Science* 303, 832 (Feb. 6, 2004).
62. R. Rad et al., PiggyBac transposon mutagenesis: a tool for cancer gene discovery in mice. Science 330, 1104 (Nov. 19, 2010).
63. A. H. Tong et al., Global mapping of the yeast genetic interaction network. Science 303, 808 (Feb. 6, 2004).
64. J. E. Carette et al., Haploid genetic screens in human cells identify host factors used by pathogens. Science 326, 1231 (Nov. 27, 2009).
65. A. L. Jackson et al., Widespread siRNA “off-target” transcript silencing mediated by seed region sequence complementarity. Rna 12, 1179 (July, 2006).
66. W. G. Kaelin, Use and Abuse of RNAi to Study Mammalian Gene Function. Science 337, 421 (Jul. 26, 2012).
67. C. J. Echeverri et al., Minimizing the risk of reporting false positives in large-scale RNAi screens. Nature methods 3, 777 (October, 2006).
68. S. Konermann et al., Optical control of mammalian endogenous transcription and epigenetic states. Nature 500, 472 (Aug. 22, 2013).
69. L. A. Gilbert et al., CRISPR-Mediated Modular RNA-Guided Regulation of Transcription in Eukaryotes. Cell, (July, 2013).
70. P. Perez-Pinera et al., RNA-guided gene activation by CRISPR-Cas9-based transcription factors. Nature methods, (Jul. 25, 2013).
71. M. L. Maeder et al., CRISPR RNA-guided activation of endogenous human genes. Nature methods, (Jul. 25, 2013).
72. A. P. Blanchard, L. Hood, Sequence to array: probing the genome's secrets. Nat Biotechnol 14, 1649 (December, 1996).
73. P. D. Hsu et al., DNA targeting specificity of RNA-guided Cas9 nucleases. Nat Biotechnol 31, 827 (September, 2013).
74. A. Subramanian et al., Gene set enrichment analysis: a knowledge-based approach for interpreting genome-wide expression profiles. Proc Natl Acad Sci USA 102, 15545 (Oct. 25, 2005).

75. C. M. Johannessen et al., COT drives resistance to RAF inhibition through MAP kinase pathway reactivation. Nature 468, 968 (Dec. 16, 2010).
76. K. T. Flaherty et al., Inhibition of mutated, activated BRAF in metastatic melanoma. The New England journal of medicine 363, 809 (Aug. 26, 2010).
77. H. Davies et al., Mutations of the BRAF gene in human cancer. Nature 417, 949 (Jun. 27, 2002).
78. S. Huang et al., MED12 Controls the Response to Multiple Cancer Drugs through Regulation of TGF-β; Receptor Signaling. Cell 151, 937 (Nov. 21, 2012).
79. S. R. Whittaker et al., A Genome-Scale RNA Interference Screen Implicates NF1 Loss in Resistance to RAF Inhibition. Cancer Discovery 3, 350 (Apr. 7, 2013).
80. A. L. Lin, D. H. Gutmann, Advances in the treatment of neurofibromatosis-associated tumours. Nature reviews. Clinical oncology, (Aug. 13, 2013).
81. Y. Fu et al., High-frequency off-target mutagenesis induced by CRISPR-Cas nucleases in human cells. Nature Biotechnology, 1 (Jul. 23, 2013).
82. F. A. Ran et al., Double Nicking by RNA-Guided CRISPR Cas9 for Enhanced Genome Editing Specificity. Cell, 1 (Aug. 28, 2013).
83. C. Trapnell, L. Pachter, S. L. Salzberg, TopHat: discovering splice junctions with RNA-Seq. Bioinformatics 25, 1105 (May 1, 2009).
84. C. Trapnell et al., Differential gene and transcript expression analysis of RNA-seq experiments with TopHat and Cufflinks. Nature protocols 7, 562 (March, 2012).
85. J. Merkin, C. Russell, P. Chen, C. B. Burge, Evolutionary dynamics of gene and isoform regulation in Mammalian tissues. Science 338, 1593 (Dec. 21, 2012).
86. B. Langmead, C. Trapnell, M. Pop, S. L. Salzberg, Ultrafast and memory-efficient alignment of short DNA sequences to the human genome. Genome biology 10, R25 (2009).
87. P. Mali et al., CAS9 transcriptional activators for target specificity screening and paired nickases for cooperative genome engineering. Nat Biotechnol 31, 833 (September, 2013).
88. G. Giaever et al., Functional profiling of the Saccharomyces cerevisiae genome. *Nature* 418, 387 (2002).
89. M. Costanzo et al., The genetic landscape of a cell. *Science* 327, 425 (Jan. 22, 2010).
90. A. Fire et al., Potent and specific genetic interference by double-stranded RNA in *Caenorhabditis elegans. Nature.* 1998 Feb. 19; 391(6669):806-11.
91. H. W. Cheung et al., Systematic investigation of genetic vulnerabilities across cancer cell lines reveals lineage-specific dependencies in ovarian cancer. *Proceedings of the National Academy of Sciences* 108, 12372 (Jul. 26, 2011).
92. M. Booker et al., False negative rates in *Drosophila* cell-based RNAi screens: a case study, *BMC Genomics* 12, 50 (2011).
93. G. Guo, W. Wang, A. Bradley, Mismatch repair genes identified using genetic screens in Blm-deficient embryonic stem cells. *Nature* 429, 891 (2004).
94. K. Chylinski, A. Le Rhun, E. Charpentier, The tracrRNA and Cas9 families of type II CRISPR-Cas immunity systems. *RNA Biology* 10, 726 (2013).
95. W. Y. Hwang et al., Efficient genome editing in zebrafish using a CRISPR-Cas system. *Nat Biotech* 31, 227 (2013).
96. H. Wang et al., One-step generation of mice carrying mutations in multiple genes by CRISPR/Cas-mediated genome engineering. *Cell* 153, 910 (2013).
97. T. *Horii*, D. Tamura, S. Morita, M. Kimura, I. Hatada, Generation of an ICF Syndrome Model by Efficient Genome Editing of Human Induced Pluripotent Stem Cells Using the CRISPR System. *International Journal of Molecular Sciences* 14, 19774 (2013).
98. T. Yan, S. E. Berry, A. B. Desai, T. J. Kinsella, DNA mismatch repair (MMR) mediates 6-thioguanine genotoxicity by introducing single-strand breaks to signal a G2-M arrest in MMR-proficient RKO cells. *Clinical Cancer Research* 9, 2327 (Jun. 1, 2003, 2003).
99. R. D. Kolodner, G. T. Marsischky, Eukaryotic DNA mismatch repair. *Current Opinion in Genetics & Development* 9, 89 (1999).
100. D. J. Burgess et al., Topoisomerase levels determine chemotherapy response in vitro and in vivo. *Proceedings of the National Academy of Sciences* 105, 9053 (Jul. 1, 2008).
101. B. Scappini et al., Changes associated with the development of resistance to imatinib (STI571) in two leukemia cell lines expressing p210 Bcr/Abl protein. *Cancer* 100, 1459 (2004).
102. S. Xue, M. Barna, Specialized ribosomes: a new frontier in gene regulation and organismal biology. *Nat Rev Mol Cell Biol* 13, 355 (2012).
103. C. M. Johnston et al., Large-scale population study of human cell lines indicates that dosage compensation is virtually complete. *PLoS Genet* 4, e9 (2008).
104. Luke A. Gilbert et al., CRISPR-mediated modular RNA-guided regulation of transcription in eukaryotes. *Cell* 154, 442 (2013).
105. Lei S. Qi et al., Repurposing CRISPR as an RNA-guided platform for sequence-specific control of gene expression. *Cell* 152, 1173 (2013).
106. T. J. Cradick, E. J. Fine, C. J. Antico, G. Bao, CRISPR/Cas9 systems targeting β-globin and CCR5 genes have substantial off-target activity. *Nucleic Acids Research*, (Aug. 11, 2013).
107. J. M. Engreitz et al., The Xist lncRNA exploits three-dimensional genome architecture to spread across the X chromosome. *Science.* 2013 Aug. 16; 341(6147).
108. K. Yoshimoto et al., Complex DNA repair pathways as possible therapeutic targets to overcome temozolomide resistance in glioblastoma. *Front Oncol.* 2012 Dec. 5; 2:186.
109. X. Liu, M. Vorontchikhina, Y. L. Wang, F. Faiola, E. Martinez, STAGA recruits Mediator to the MYC oncoprotein to stimulate transcription and cell proliferation. Molecular and cellular biology 28, 108 (January, 2008).
110. B. Langmead, S. L. Salzberg, Fast gapped-read alignment with Bowtie 2. Nat Meth 9, 357-359 (2012).
111. S. S. Liu et al., Identification and characterization of a novel gene, c1orf109, encoding a CK2 substrate that is involved in cancer cell proliferation. *Journal of Biomedical Science* 19, 49 (2012).
112. R. Renella et al., Codanin-1 mutations in congenital dyserythropoietic anemia type 1 affect HP1a localization in erythroblasts. Blood 117, 6928-6938 (2011).
113. S. H. Chen et al., A Knockout Mouse Approach Reveals that TCTP Functions as an Essential Factor for Cell Proliferation and Survival in a Tissue- or Cell Type-specific Manner. Molecular Biology of the Cell 18, 2525-2532 (2007).
114. C. Cayrol et al., The THAP-zinc finger protein THAP1 regulates endothelial cell proliferation through modulation of pRB/E2F cell-cycle target genes. *Blood* 109, 584-594 (2007).

115. B. Sonnichsen et al., Full-genome RNAi profiling of early embryogenesis in *Caenorhabditis elegans. Nature* 434, 462-469 (2005).
116. J. F. Rual et al., Toward Improving *Caenorhabditis elegans* Phenome Mapping With an ORFeome-Based RNAi Library. *Genome Research* 14, 2162-2168 (2004).
117. J L. Mummery-Widmer et al., Genome-wide analysis of Notch signalling in *Drosophila* by transgenic RNAi. *Nature* 458, 987-992 (2009).
118. A. C. Spradling et al., The Berkeley *Drosophila* Genome Project Gene Disruption Project: Single P-Element Insertions Mutating 25% of Vital *Drosophila* Genes. Genetics 153, 135-177 (1999).
119. A. Amsterdam et al. Identification of 315 genes essential for early zebrafish development. Proc Natl Acad Sci USA. 2004 Aug. 31; 101(35):12792-7.
120. Shalem, O. et al. Genome-scale CRISPR-Cas9 knockout screening in human cells. Science 343, 84-87 (2014).
121. Martin, M. Cutadapt removes adapter sequences from high-throughput sequencing reads. EMBnet.journal 17, 10-12 (2011).
122. Wang, T., Wei, J. J., Sabatini, D. M. & Lander, E. S. Genetic screens in human cells using the CRISPR-Cas9 system. Science 343, 80-84 (2014).
123. Koike-Yusa, H., Li, Y., Tan, E.-P., Velasco-Herrera, M. D. C. & Yusa, K. Genome-wide recessive genetic screening in mammalian cells with a lentiviral CRISPR-guide RNA library. Nat Biotechnol (2013). doi:10.1038/nbt.2800

PARTIES TO A JOINT RESEARCH AGREEMENT

The claimed invention was made by or on behalf of one or more of the following parties to a joint research agreement: The Broad Institute, Inc., Massachusetts Institute of Technology, and Whitehead Institute for Biomedical Research. The joint research agreement was in effect on and before the effective filing date of the claimed invention, and the claimed invention was made as a result of activities undertaken within the scope of the joint research agreement.

What is claimed is:

1. A method for identifying one or more genomic loci associated with drug resistance, comprising:

contacting a population of cells with a composition comprising one or more vectors that encode (a) a Cas9 protein and (b) a plurality of CRISPR-Cas system guide RNAs targeting a plurality of different genomic loci, wherein the plurality of CRISPR-Cas system guide RNAs comprise guide RNAs encoded by plasmid library of ATCC Deposit No. PTA121339, guide RNAs encoded by plasmid library of ATCC Deposit No. 121340, guide RNAs encoded by plasmid library of ATCC Deposit No. 121341, guide RNAs encoded by plasmid library of ATCC Deposit No. 121342, guide RNAs encoded by plasmid library of ATCC Deposit No. 121343, or a combination thereof, selecting cells successfully transduced with the vectors, wherein the selected cells each comprises a CRISPR-Cas system comprising the Cas9 protein and one of the guide RNAs;

treating the selected cells with a drug to obtain cells having resistance to the drug; and profiling the depletion or enrichment of the guide RNAs in the cells having resistance to the drug by high-throughput sequencing to identify one or more genomic loci associated with the resistance to the drug.

2. The method of claim 1, wherein the cells are eukaryotic cells.

3. The method of claim 2, wherein the cells are mammalian cells or human cells.

4. The method of claim 3, wherein the cells are cancer cells or stem cells.

5. The method of claim 1, wherein the cells are transduced with a multiplicity of infection (MOI) of 0.3-0.75.

6. The method of claim 1, wherein the cells are transduced with a multiplicity of infection (MOI) of 0.3-0.4.

7. The method of claim 1, wherein the Cas9 is *Streptococcus pyogenes* Cas9.

8. The method of claim 1, wherein the Cas9 is *Staphylococcus aureus* Cas9.

9. The method of claim 1, wherein the Cas9 and the guide RNAs are encoded in the same vector.

10. The method of claim 1, wherein the Cas9 and the guide RNAs are encoded in different vectors.

11. The method of claim 1, wherein the vectors are lentivirus, adenovirus, or adeno-associated virus vectors.

12. The method of claim 1, wherein the composition comprises vectors encoding 100 or more different guide RNAs.

13. The method of claim 1, wherein the composition comprises vectors encoding 1,000 or more different guide RNAs.

14. The method of claim 1, wherein the composition comprises vectors encoding 20,000 or more different guide RNAs.

15. The method of claim 1, wherein the drug is a cancer drug.

16. A method for identifying one or more genomic loci associated with cell survival comprising:

contacting a population of cells with a composition comprising one or more vectors that encode (a) a Cas9 protein and (b) a plurality of CRISPR-Cas system guide RNAs targeting a plurality of different genomic loci, wherein the plurality of CRISPR-Cas system guide RNAs comprise guide RNAs encoded by plasmid library of ATCC Deposit No. PTA121339, guide RNAs encoded by plasmid library of ATCC Deposit No. 121340, guide RNAs encoded by plasmid library of ATCC Deposit No. 121341, guide RNAs encoded by plasmid library of ATCC Deposit No. 121342, guide RNAs encoded by plasmid library of ATCC Deposit No. 121343, or a combination thereof, selecting cells successfully transduced with the vectors, wherein the selected cells each comprises a CRISPR-Cas system comprising the Cas9 protein and one of the guide RNAs;

applying an selective pressure to the selected cells to obtain cells survived under the selective pressure; and profiling the depletion or enrichment of the guide RNAs in the cells survived under the selective pressure by high-throughput sequencing to identify one or more genomic loci associated with survival under the selective pressure.

17. A method for identifying one or more genomic loci associated with a phenotype comprising:

contacting a population of cells with a composition comprising one or more vectors that encode (a) a Cas9 protein and (b) a plurality of CRISPR-Cas system guide RNAs targeting a plurality of different genomic loci, wherein the plurality of CRISPR-Cas system guide RNAs comprise guide RNAs encoded by plasmid library of ATCC Deposit No. PTA121339, guide RNAs encoded by plasmid library of ATCC Deposit No. 121340, guide RNAs encoded by plasmid library of ATCC Deposit No. 121341, guide RNAs encoded by plasmid library of ATCC Deposit No. 121342, guide RNAs encoded by plasmid library of ATCC Deposit No. 121343, or a combination thereof, selecting cells successfully transduced with the vectors, wherein the selected cells each comprises a CRISPR-Cas system comprising the Cas9 protein and one of the guide RNAs;

applying an selective pressure to the selected cells to obtain cells having a phenotype; and profiling the depletion or enrichment of the guide RNAs in the cells having the phenotype by high-throughput sequencing to identify one or more genomic loci associated with the phenotype.

* * * * *

SEQUENCE LISTING

```
<160> NUMBER OF SEQ ID NOS: 310

<210> SEQ ID NO 1
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(22)
<223> OTHER INFORMATION: a, c, t, g, unknown or other

<400> SEQUENCE: 1

nnnnnnnnnn nnnnnnnnnn nnagaaw                                          27


<210> SEQ ID NO 2
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(12)
<223> OTHER INFORMATION: a, c, t or g
<220> FEATURE:
<221> NAME/KEY: modified_base
<222> LOCATION: (13)..(14)
<223> OTHER INFORMATION: a, c, t, g, unknown or other

<400> SEQUENCE: 2

nnnnnnnnnn nnnnagaaw                                                   19


<210> SEQ ID NO 3
<211> LENGTH: 27
<212> TYPE: DNA
<213> ORGANISM: Artificial Sequence
<220> FEATURE:
```

<221> NAME/KEY: source
<223> OTHER INFORMATION: /note="Description of Artificial Sequence:
Synthetic oligonucleotide"
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(22)
<223> OTHER INFORMATION: a, c, t, g, unknown or other

<400> SEQUENCE: 3
nnnnnnnnnn nnnnnnnnnn nnagaaw 27

<210> SEQ ID NO 4
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: modified_base
<222> LOCATION: (1)..(11)
<223> OTHER INFORMATION: a, c, t or g
<220> FEATURE:
<221> NAME/KEY: modified_base
<222> LOCATION: (12)..(13)
<223> OTHER INFORMATION: a, c, t, g, unknown or other

<400> SEQUENCE: 4
nnnnnnnnnn nnnagaaw 18

<210> SEQ ID NO 5
<211> LENGTH: 137
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 5
nnnnnnnnnn nnnnnnnnnn gtttttgtac tctcaagatt tagaaataaa tcttgcagaa 60
gctacaaaga taaggcttca tgccgaaatc aacaccctgt cattttatgg cagggtgttt 120
tcgttattta atttttt 137

<210> SEQ ID NO 6
<211> LENGTH: 123
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 6
nnnnnnnnnn nnnnnnnnnn gtttttgtac tctcagaaat gcagaagcta caaagataag 60
gcttcatgcc gaaatcaaca ccctgtcatt ttatggcagg gtgttttcgt tatttaattt 120

```
ttt                                                                  123


<210> SEQ ID NO 7
<211> LENGTH: 110
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 7

nnnnnnnnnn nnnnnnnnnn gtttttgtac tctcagaaat gcagaagcta caaagataag     60

gcttcatgcc gaaatcaaca ccctgtcatt ttatggcagg gtgttttttt               110


<210> SEQ ID NO 8
<211> LENGTH: 102
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 8

nnnnnnnnnn nnnnnnnnnn gttttagagc tagaaatagc aagttaaaat aaggctagtc     60

cgttatcaac ttgaaaaagt ggcaccgagt cggtgctttt tt                       102


<210> SEQ ID NO 9
<211> LENGTH: 88
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t, g, unknown or other

<400> SEQUENCE: 9

nnnnnnnnnn nnnnnnnnnn gttttagagc tagaaatagc aagttaaaat aaggctagtc     60

cgttatcaac ttgaaaaagt gttttttt                                        88


<210> SEQ ID NO 10
<211> LENGTH: 76
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t, g, unknown or other

<400> SEQUENCE: 10
```

```
nnnnnnnnnn nnnnnnnnnn gttttagagc tagaaatagc aagttaaaat aaggctagtc      60

cgttatcatt tttttt                                                     76


<210> SEQ ID NO 11
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 11

gttttagagc ta                                                         12


<210> SEQ ID NO 12
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12

tagcaagtta aaataaggct agtccgtttt t                                    31


<210> SEQ ID NO 13
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(22)
<223> OTHER INFORMATION: a, c, t, g, unknown or other

<400> SEQUENCE: 13

nnnnnnnnnn nnnnnnnnnn nnagaaw                                         27


<210> SEQ ID NO 14
<211> LENGTH: 12
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 14

guuuuagagc ua                                                         12


<210> SEQ ID NO 15
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 15

ggacatcgat gtcacctcca atgactaggg tgg                                  33
```

<210> SEQ ID NO 16
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 16
cattggaggt gacatcgatg tcctccccat tgg 33

<210> SEQ ID NO 17
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 17
ggaagggcct gagtccgagc agaagaagaa ggg 33

<210> SEQ ID NO 18
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 18
ggtggcgaga ggggccgaga ttgggtgttc agg 33

<210> SEQ ID NO 19
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 19
atgcaggagg gtggcgagag gggccgagat tgg 33

<210> SEQ ID NO 20
<211> LENGTH: 4677
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 20
tctttcttgc gctatgacac ttccagcaaa aggtagggcg ggctgcgaga cggcttcccg 60
gcgctgcatg caacaccgat gatgcttcga ccccccgaag ctccttcggg gctgcatggg 120
cgctccgatg ccgctccagg gcgagcgctg tttaaatagc caggcccccg attgcaaaga 180
cattatagcg agctaccaaa gccatattca aacacctaga tcactaccac ttctacacag 240
gccactcgag cttgtgatcg cactccgcta agggggcgcc tcttcctctt cgtttcagtc 300
acaacccgca aacatgtacc catacgatgt tccagattac gcttcgccga agaaaaagcg 360

-continued

```
caaggtcgaa gcgtccgaca agaagtacag catcggcctg gacatcggca ccaactctgt    420
gggctgggcc gtgatcaccg acgagtacaa ggtgcccagc aagaaattca aggtgctggg    480
caacaccgac cggcacagca tcaagaagaa cctgatcgga gccctgctgt tcgacagcgg    540
cgaaacagcc gaggccaccc ggctgaagag aaccgccaga agaagataca ccagacggaa    600
gaaccggatc tgctatctgc aagagatctt cagcaacgag atggccaagg tggacgacag    660
cttcttccac agactggaag agtccttcct ggtggaagag gataagaagc acgagcggca    720
ccccatcttc ggcaacatcg tggacgaggt ggcctaccac gagaagtacc ccaccatcta    780
ccacctgaga aagaaactgg tggacagcac cgacaaggcc gacctgcggc tgatctatct    840
ggccctggcc cacatgatca agttccgggg ccacttcctg atcgagggcg acctgaaccc    900
cgacaacagc gacgtggaca agctgttcat ccagctggtg cagacctaca accagctgtt    960
cgaggaaaac cccatcaacg ccagcggcgt ggacgccaag gccatcctgt ctgccagact   1020
gagcaagagc agacggctgg aaaatctgat cgcccagctg cccggcgaga agaagaatgg   1080
cctgttcggc aacctgattg ccctgagcct gggcctgacc cccaacttca agagcaactt   1140
cgacctggcc gaggatgcca aactgcagct gagcaaggac acctacgacg acgacctgga   1200
caacctgctg gcccagatcg gcgaccagta cgccgacctg tttctggccg ccaagaacct   1260
gtccgacgcc atcctgctga gcgacatcct gagagtgaac accgagatca ccaaggcccc   1320
cctgagcgcc tctatgatca agagatacga cgagcaccac caggacctga ccctgctgaa   1380
agctctcgtg cggcagcagc tgcctgagaa gtacaaagag attttcttcg accagagcaa   1440
gaacggctac gccggctaca ttgacggcgg agccagccag gaagagttct acaagttcat   1500
caagcccatc ctggaaaaga tggacggcac cgaggaactg ctcgtgaagc tgaacagaga   1560
ggacctgctg cggaagcagc ggaccttcga caacggcagc atccccccacc agatccacct   1620
gggagagctg cacgccattc tgcggcggca ggaagatttt tacccattcc tgaaggacaa   1680
ccgggaaaag atcgagaaga tcctgacctt ccgcatcccc tactacgtgg gccctctggc   1740
caggggaaac agcagattcg cctggatgac cagaaagagc gaggaaacca tcaccccctg   1800
gaacttcgag gaagtggtgg acaagggcgc ttccgcccag agcttcatcg agcggatgac   1860
caacttcgat aagaacctgc ccaacgagaa ggtgctgccc aagcacagcc tgctgtacga   1920
gtacttcacc gtgtataacg agctgaccaa agtgaaatac gtgaccgagg gaatgagaaa   1980
gcccgccttc ctgagcggcg agcagaaaaa ggccatcgtg gacctgctgt tcaagaccaa   2040
ccggaaagtg accgtgaagc agctgaaaga ggactacttc aagaaaatcg agtgcttcga   2100
ctccgtggaa atctccggcg tggaagatcg gttcaacgcc tccctgggca cataccacga   2160
tctgctgaaa attatcaagg acaaggactt cctggacaat gaggaaaacg aggacattct   2220
ggaagatatc gtgctgaccc tgacactgtt tgaggacaga gagatgatcg aggaacggct   2280
gaaaacctat gcccacctgt tcgacgacaa agtgatgaag cagctgaagc ggcggagata   2340
caccggctgg ggcaggctga gccggaagct gatcaacggc atccgggaca agcagtccgg   2400
caagacaatc ctggatttcc tgaagtccga cggcttcgcc aacagaaact tcatgcagct   2460
gatccacgac gacagcctga cctttaaaga ggacatccag aaagcccagg tgtccggcca   2520
gggcgatagc ctgcacgagc acattgccaa tctggccggc agccccgcca ttaagaaggg   2580
catcctgcag acagtgaagg tggtggacga gctcgtgaaa gtgatgggcc ggcacaagcc   2640
cgagaacatc gtgatcgaaa tggccagaga gaaccagacc acccagaagg gacagaagaa   2700
cagccgcgag agaatgaagc ggatcgaaga gggcatcaaa gagctgggca gccagatcct   2760
```

gaaagaacac cccgtggaaa acacccagct gcagaacgag aagctgtacc tgtactacct 2820
gcagaatggg cgggatatgt acgtggacca ggaactggac atcaaccggc tgtccgacta 2880
cgatgtggac catatcgtgc ctcagagctt tctgaaggac gactccatcg acaacaaggt 2940
gctgaccaga agcgacaaga accggggcaa gagcgacaac gtgccctccg aagaggtcgt 3000
gaagaagatg aagaactact ggcggcagct gctgaacgcc aagctgatta cccagagaaa 3060
gttcgacaat ctgaccaagg ccgagagagg cggcctgagc gaactggata aggccggctt 3120
catcaagaga cagctggtgg aaacccggca gatcacaaag cacgtggcac agatcctgga 3180
ctcccggatg aacactaagt acgacgagaa tgacaagctg atccgggaag tgaaagtgat 3240
caccctgaag tccaagctgg tgtccgattt ccggaaggat ttccagtttt acaaagtgcg 3300
cgagatcaac aactaccacc acgcccacga cgcctacctg aacgccgtcg tgggaaccgc 3360
cctgatcaaa aagtacccta agctggaaag cgagttcgtg tacggcgact acaaggtgta 3420
cgacgtgcgg aagatgatcg ccaagagcga gcaggaaatc ggcaaggcta ccgccaagta 3480
cttcttctac agcaacatca tgaacttttt caagaccgag attaccctgg ccaacggcga 3540
gatccggaag cggcctctga tcgagacaaa cggcgaaacc ggggagatcg tgtgggataa 3600
gggccgggat tttgccaccg tgcggaaagt gctgagcatg ccccaagtga atatcgtgaa 3660
aaagaccgag gtgcagacag gcggcttcag caaagagtct atcctgccca agaggaacag 3720
cgataagctg atcgccagaa agaaggactg ggaccctaag aagtacggcg gcttcgacag 3780
ccccaccgtg gcctattctg tgctggtggt ggccaaagtg gaaaagggca agtccaagaa 3840
actgaagagt gtgaaagagc tgctggggat caccatcatg gaaagaagca gcttcgagaa 3900
gaatcccatc gactttctgg aagccaaggg ctacaaagaa gtgaaaaagg acctgatcat 3960
caagctgcct aagtactccc tgttcgagct ggaaaacggc cggaagagaa tgctggcctc 4020
tgccggcgaa ctgcagaagg gaaacgaact ggccctgccc tccaaatatg tgaacttcct 4080
gtacctggcc agccactatg agaagctgaa gggctccccc gaggataatg agcagaaaca 4140
gctgtttgtg gaacagcaca agcactacct ggacgagatc atcgagcaga tcagcgagtt 4200
ctccaagaga gtgatcctgg ccgacgctaa tctggacaaa gtgctgtccg cctacaacaa 4260
gcaccgggat aagcccatca gagagcaggc cgagaatatc atccacctgt ttaccctgac 4320
caatctggga gcccctgccg ccttcaagta ctttgacacc accatcgacc ggaagaggta 4380
caccagcacc aaagaggtgc tggacgccac cctgatccac cagagcatca ccggcctgta 4440
cgagacacgg atcgacctgt ctcagctggg aggcgacagc cccaagaaga agagaaaggt 4500
ggaggccagc taaggatccg gcaagactgg ccccgcttgg caacgcaaca gtgagcccct 4560
ccctagtgtg tttggggatg tgactatgta ttcgtgtgtt ggccaacggg tcaacccgaa 4620
cagattgata cccgccttgg catttcctgt cagaatgtaa cgtcagttga tggtact 4677

<210> SEQ ID NO 21
<211> LENGTH: 3150
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 21
tctttcttgc gctatgacac ttccagcaaa aggtagggcg ggctgcgaga cggcttcccg 60

```
gcgctgcatg caacaccgat gatgcttcga ccccccgaag ctccttcggg gctgcatggg    120
cgctccgatg ccgctccagg gcgagcgctg tttaaatagc caggcccccg attgcaaaga    180
cattatagcg agctaccaaa gccatattca aacacctaga tcactaccac ttctacacag    240
gccactcgag cttgtgatcg cactccgcta agggggcgcc tcttcctctt cgtttcagtc    300
acaacccgca aacatgccta agaagaagag gaaggttaac acgattaaca tcgctaagaa    360
cgacttctct gacatcgaac tggctgctat cccgttcaac actctggctg accattacgg    420
tgagcgttta gctcgcgaac agttggccct tgagcatgag tcttacgaga tgggtgaagc    480
acgcttccgc aagatgtttg agcgtcaact taaagctggt gaggttgcgg ataacgctgc    540
cgccaagcct ctcatcacta ccctactccc taagatgatt gcacgcatca acgactggtt    600
tgaggaagtg aaagctaagc gcggcaagcg cccgacagcc ttccagttcc tgcaagaaat    660
caagccggaa gccgtagcgt acatcaccat taagaccact ctggcttgcc taaccagtgc    720
tgacaataca accgttcagg ctgtagcaag cgcaatcggt cgggccattg aggacgaggc    780
tcgcttcggt cgtatccgtg accttgaagc taagcacttc aagaaaaacg ttgaggaaca    840
actcaacaag cgcgtagggc acgtctacaa gaaagcattt atgcaagttg tcgaggctga    900
catgctctct aagggtctac tcggtggcga ggcgtggtct tcgtggcata aggaagactc    960
tattcatgta ggagtacgct gcatcgagat gctcattgag tcaaccggaa tggttagctt   1020
acaccgccaa aatgctggcg tagtaggtca agactctgag actatcgaac tcgcacctga   1080
atacgctgag gctatcgcaa cccgtgcagg tgcgctggct ggcatctctc cgatgttcca   1140
accttgcgta gttcctccta agccgtggac tggcattact ggtggtggct attgggctaa   1200
cggtcgtcgt cctctggcgc tggtgcgtac tcacagtaag aaagcactga tgcgctacga   1260
agacgtttac atgcctgagg tgtacaaagc gattaacatt gcgcaaaaca ccgcatggaa   1320
aatcaacaag aaagtcctag cggtcgccaa cgtaatcacc aagtggaagc attgtccggt   1380
cgaggacatc cctgcgattg agcgtgaaga actcccgatg aaaccggaag acatcgacat   1440
gaatcctgag gctctcaccg cgtggaaacg tgctgccgct gctgtgtacc gcaaggacaa   1500
ggctcgcaag tctcgccgta tcagccttga gttcatgctt gagcaagcca ataagtttgc   1560
taaccataag gccatctggt tcccttacaa catggactgg cgcggtcgtg tttacgctgt   1620
gtcaatgttc aacccgcaag gtaacgatat gaccaaagga ctgcttacgc tggcgaaagg   1680
taaaccaatc ggtaaggaag gttactactg gctgaaaatc cacggtgcaa actgtgcggg   1740
tgtcgacaag gttccgttcc ctgagcgcat caagttcatt gaggaaaacc acgagaacat   1800
catggcttgc gctaagtctc cactggagaa cacttggtgg gctgagcaag attctccgtt   1860
ctgcttcctt gcgttctgct ttgagtacgc tggggtacag caccacggcc tgagctataa   1920
ctgctccctt ccgctggcgt ttgacgggtc ttgctctggc atccagcact tctccgcgat   1980
gctccgagat gaggtaggtg gtcgcgcggt taacttgctt cctagtgaaa ccgttcagga   2040
catctacggg attgttgcta agaaagtcaa cgagattcta caagcagacg caatcaatgg   2100
gaccgataac gaagtagtta ccgtgaccga tgagaacact ggtgaaatct ctgagaaagt   2160
caagctgggc actaaggcac tggctggtca atggctggct tacggtgtta ctcgcagtgt   2220
gactaagcgt tcagtcatga cgctggctta cgggtccaaa gagttcggct tccgtcaaca   2280
agtgctggaa gataccattc agccagctat tgattccggc aagggtctga tgttcactca   2340
gccgaatcag gctgctggat acatggctaa gctgatttgg gaatctgtga gcgtgacggt   2400
ggtagctgcg gttgaagcaa tgaactggct taagtctgct gctaagctgc tggctgctga   2460
```

```
ggtcaaagat aagaagactg gagagattct tcgcaagcgt tgcgctgtgc attgggtaac   2520

tcctgatggt ttccctgtgt ggcaggaata caagaagcct attcagacgc gcttgaacct   2580

gatgttcctc ggtcagttcc gcttacagcc taccattaac accaacaaag atagcgagat   2640

tgatgcacac aaacaggagt ctggtatcgc tcctaacttt gtacacagcc aagacggtag   2700

ccaccttcgt aagactgtag tgtgggcaca cgagaagtac ggaatcgaat cttttgcact   2760

gattcacgac tccttcggta cgattccggc tgacgctgcg aacctgttca aagcagtgcg   2820

cgaaactatg gttgacacat atgagtcttg tgatgtactg gctgatttct acgaccagtt   2880

cgctgaccag ttgcacgagt ctcaattgga caaaatgcca gcacttccgg ctaaaggtaa   2940

cttgaacctc cgtgacatct tagagtcgga cttcgcgttc gcgtaaggat ccggcaagac   3000

tggccccgct tggcaacgca acagtgagcc cctccctagt gtgtttgggg atgtgactat   3060

gtattcgtgt gttggccaac gggtcaaccc gaacagattg atacccgcct tggcatttcc   3120

tgtcagaatg taacgtcagt tgatggtact                                    3150
```

<210> SEQ ID NO 22
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: modified_base
<222> LOCATION: (23)..(42)
<223> OTHER INFORMATION: a, c, t, g, unknown or other

<400> SEQUENCE: 22

```
gaaattaata cgactcacta tannnnnnnn nnnnnnnnnn nngttttaga gctagaaata     60

gcaagttaaa ataaggctag tccgttatca acttgaaaaa gtggcaccga gtcggtgctt    120

ttttt                                                                125
```

<210> SEQ ID NO 23
<211> LENGTH: 8452
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 23

```
tgcggtattt cacaccgcat caggtggcac ttttcgggga aatgtgcgcg gaacccctat     60

ttgtttattt ttctaaatac attcaaatat gtatccgctc atgagattat caaaaaggat    120

cttcacctag atccttttaa attaaaaatg aagttttaaa tcaatctaaa gtatatatga    180

gtaaacttgg tctgacagtt accaatgctt aatcagtgag gcacctatct cagcgatctg    240

tctatttcgt tcatccatag ttgcctgact ccccgtcgtg tagataacta cgatacggga    300

gggcttacca tctggcccca gtgctgcaat gataccgcga gacccacgct caccggctcc    360

agatttatca gcaataaacc agccagccgg aagggccgag cgcagaagtg gtcctgcaac    420

tttatccgcc tccatccagt ctattaattg ttgccgggaa gctagagtaa gtagttcgcc    480

agttaatagt ttgcgcaacg ttgttgccat tgctacaggc atcgtggtgt cacgctcgtc    540

gtttggtatg gcttcattca gctccggttc ccaacgatca aggcgagtta catgatcccc    600
```

-continued

```
catgttgtgc aaaaaagcgg ttagctcctt cggtcctccg atcgttgtca gaagtaagtt    660
ggccgcagtg ttatcactca tggttatggc agcactgcat aattctctta ctgtcatgcc    720
atccgtaaga tgcttttctg tgactggtga gtactcaacc aagtcattct gagaatagtg    780
tatgcggcga ccgagttgct cttgcccggc gtcaatacgg gataataccg cgccacatag    840
cagaacttta aaagtgctca tcattggaaa acgttcttcg gggcgaaaac tctcaaggat    900
cttaccgctg ttgagatcca gttcgatgta acccactcgt gcacccaact gatcttcagc    960
atcttttact ttcaccagcg tttctgggtg agcaaaaaca ggaaggcaaa atgccgcaaa   1020
aaagggaata agggcgacac ggaaatgttg aatactcata ctcttccttt ttcaatatta   1080
ttgaagcatt tatcagggtt attgtctcat gaccaaaatc ccttaacgtg agttttcgtt   1140
ccactgagcg tcagaccccg tagaaaagat caaaggatct tcttgagatc cttttttct   1200
gcgcgtaatc tgctgcttgc aaacaaaaaa accaccgcta ccagcggtgg tttgtttgcc   1260
ggatcaagag ctaccaactc tttttccgaa ggtaactggc ttcagcagag cgcagatacc   1320
aaatactgtt cttctagtgt agccgtagtt aggccaccac ttcaagaact ctgtagcacc   1380
gcctacatac ctcgctctgc taatcctgtt accagtggct gttgccagtg gcgataagtc   1440
gtgtcttacc gggttggact caagacgata gttaccggat aaggcgcagc ggtcgggctg   1500
aacggggggt tcgtgcacac agcccagctt ggagcgaacg acctacaccg aactgagata   1560
cctacagcgt gagctatgag aaagcgccac gcttcccgaa gggagaaagg cggacaggta   1620
tccggtaagc ggcagggtcg gaacaggaga gcgcacgagg gagcttccag ggggaaacgc   1680
ctggtatctt tatagtcctg tcgggtttcg ccacctctga cttgagcgtc gatttttgtg   1740
atgctcgtca ggggggcgga gcctatggaa aaacgccagc aacgcggcct ttttacggtt   1800
cctggccttt tgctggcctt ttgctcacat gttctttcct gcgttatccc ctgattctgt   1860
ggataaccgt attaccgcct ttgagtgagc tgataccgct cgccgcagcc gaacgaccga   1920
gcgcagcgag tcagtgagcg aggaagcggt cgctgaggct tgacatgatt ggtgcgtatg   1980
tttgtatgaa gctacaggac tgatttggcg ggctatgagg gcgggggaag ctctggaagg   2040
gccgcgatgg ggcgcgcggc gtccagaagg cgccatacgg cccgctggcg gcacccatcc   2100
ggtataaaag cccgcgaccc cgaacggtga cctccacttt cagcgacaaa cgagcactta   2160
tacatacgcg actattctgc cgctatacat aaccactcag ctagcttaag atcccatcaa   2220
gcttgcatgc cgggcgcgcc agaaggagcg cagccaaacc aggatgatgt ttgatggggt   2280
atttgagcac ttgcaaccct tatccggaag cccccctggcc cacaaaggct aggcgccaat   2340
gcaagcagtt cgcatgcagc ccctggagcg gtgccctcct gataaaccgg ccagggggcc   2400
tatgttcttt actttttac aagagaagtc actcaacatc ttaaaatggc caggtgagtc   2460
gacgagcaag cccggcggat caggcagcgt gcttgcagat ttgacttgca acgcccgcat   2520
tgtgtcgacg aaggcttttg gctcctctgt cgctgtctca agcagcatct aaccctgcgt   2580
cgccgtttcc atttgcagga gattcgaggt accatgtacc catacgatgt tccagattac   2640
gcttcgccga agaaaaagcg caaggtcgaa gcgtccgaca agaagtacag catcggcctg   2700
gacatcggca ccaactctgt gggctgggcc gtgatcaccg acgagtacaa ggtgcccagc   2760
aagaaattca aggtgctggg caacaccgac cggcacagca tcaagaagaa cctgatcgga   2820
gccctgctgt tcgacagcgg cgaaacagcc gaggccaccc ggctgaagag aaccgccaga   2880
agaagataca ccagacggaa gaaccggatc tgctatctgc aagagatctt cagcaacgag   2940
atggccaagg tggacgacag cttcttccac agactggaag agtccttcct ggtggaagag   3000
```

```
gataagaagc acgagcggca ccccatcttc ggcaacatcg tggacgaggt ggcctaccac   3060
gagaagtacc ccaccatcta ccacctgaga aagaaactgg tggacagcac cgacaaggcc   3120
gacctgcggc tgatctatct ggccctggcc cacatgatca agttccgggg ccacttcctg   3180
atcgagggcg acctgaaccc cgacaacagc gacgtggaca agctgttcat ccagctggtg   3240
cagacctaca accagctgtt cgaggaaaac cccatcaacg ccagcggcgt ggacgccaag   3300
gccatcctgt ctgccagact gagcaagagc agacggctgg aaaatctgat cgcccagctg   3360
cccggcgaga agaagaatgg cctgttcggc aacctgattg ccctgagcct gggcctgacc   3420
cccaacttca agagcaactt cgacctggcc gaggatgcca aactgcagct gagcaaggac   3480
acctacgacg acgacctgga caacctgctg gcccagatcg gcgaccagta cgccgacctg   3540
tttctggccg ccaagaacct gtccgacgcc atcctgctga gcgacatcct gagagtgaac   3600
accgagatca ccaaggcccc cctgagcgcc tctatgatca agagatacga cgagcaccac   3660
caggacctga ccctgctgaa agctctcgtg cggcagcagc tgcctgagaa gtacaaagag   3720
attttcttcg accagagcaa gaacggctac gccggctaca ttgacggcgg agccagccag   3780
gaagagttct acaagttcat caagcccatc ctggaaaaga tggacggcac cgaggaactg   3840
ctcgtgaagc tgaacagaga ggacctgctg cggaagcagc ggaccttcga caacggcagc   3900
atcccccacc agatccacct gggagagctg cacgccattc tgcggcggca ggaagatttt   3960
tacccattcc tgaaggacaa ccgggaaaag atcgagaaga tcctgacctt ccgcatcccc   4020
tactacgtgg gccctctggc caggggaaac agcagattcg cctggatgac cagaaagagc   4080
gaggaaacca tcacccccctg gaacttcgag gaagtggtgg acaagggcgc ttccgcccag   4140
agcttcatcg agcggatgac caacttcgat aagaacctgc ccaacgagaa ggtgctgccc   4200
aagcacagcc tgctgtacga gtacttcacc gtgtataacg agctgaccaa agtgaaatac   4260
gtgaccgagg gaatgagaaa gcccgccttc ctgagcggcg agcagaaaaa ggccatcgtg   4320
gacctgctgt tcaagaccaa ccggaaagtg accgtgaagc agctgaaaga ggactacttc   4380
aagaaaatcg agtgcttcga ctccgtggaa atctccggcg tggaagatcg gttcaacgcc   4440
tccctgggca cataccacga tctgctgaaa attatcaagg acaaggactt cctggacaat   4500
gaggaaaacg aggacattct ggaagatatc gtgctgaccc tgacactgtt tgaggacaga   4560
gagatgatcg aggaacggct gaaaacctat gcccacctgt tcgacgacaa agtgatgaag   4620
cagctgaagc ggcggagata caccggctgg ggcaggctga gccggaagct gatcaacggc   4680
atccgggaca agcagtccgg caagacaatc ctggatttcc tgaagtccga cggcttcgcc   4740
aacagaaact tcatgcagct gatccacgac gacagcctga cctttaaaga ggacatccag   4800
aaagcccagg tgtccggcca gggcgatagc ctgcacgagc acattgccaa tctggccggc   4860
agccccgcca ttaagaaggg catcctgcag acagtgaagg tggtggacga gctcgtgaaa   4920
gtgatgggcc ggcacaagcc cgagaacatc gtgatcgaaa tggccagaga gaaccagacc   4980
acccagaagg gacagaagaa cagccgcgag agaatgaagc ggatcgaaga gggcatcaaa   5040
gagctgggca gccagatcct gaaagaacac cccgtggaaa acacccagct gcagaacgag   5100
aagctgtacc tgtactacct gcagaatggg cgggatatgt acgtggacca ggaactggac   5160
atcaaccggc tgtccgacta cgatgtggac catatcgtgc ctcagagctt tctgaaggac   5220
gactccatcg acaacaaggt gctgaccaga agcgacaaga accggggcaa gagcgacaac   5280
gtgccctccg aagaggtcgt gaagaagatg aagaactact ggcggcagct gctgaacgcc   5340
```

```
aagctgatta cccagagaaa gttcgacaat ctgaccaagg ccgagagagg cggcctgagc   5400
gaactggata aggccggctt catcaagaga cagctggtgg aaacccggca gatcacaaag   5460
cacgtggcac agatcctgga ctcccggatg aacactaagt acgacgagaa tgacaagctg   5520
atccgggaag tgaaagtgat caccctgaag tccaagctgg tgtccgattt ccggaaggat   5580
ttccagtttt acaaagtgcg cgagatcaac aactaccacc acgcccacga cgcctacctg   5640
aacgccgtcg tgggaaccgc cctgatcaaa aagtacccta agctggaaag cgagttcgtg   5700
tacggcgact acaaggtgta cgacgtgcgg aagatgatcg ccaagagcga gcaggaaatc   5760
ggcaaggcta ccgccaagta cttcttctac agcaacatca tgaacttttt caagaccgag   5820
attaccctgg ccaacggcga gatccggaag cggcctctga tcgagacaaa cggcgaaacc   5880
ggggagatcg tgtgggataa gggccgggat tttgccaccg tgcggaaagt gctgagcatg   5940
ccccaagtga atatcgtgaa aaagaccgag gtgcagacag gcggcttcag caaagagtct   6000
atcctgccca agaggaacag cgataagctg atcgccagaa agaaggactg ggaccctaag   6060
aagtacggcg gcttcgacag ccccaccgtg gcctattctg tgctggtggt ggccaaagtg   6120
gaaaagggca agtccaagaa actgaagagt gtgaaagagc tgctggggat caccatcatg   6180
gaaagaagca gcttcgagaa gaatcccatc gactttctgg aagccaaggg ctacaaagaa   6240
gtgaaaaagg acctgatcat caagctgcct aagtactccc tgttcgagct ggaaaacggc   6300
cggaagagaa tgctggcctc tgccggcgaa ctgcagaagg gaaacgaact ggccctgccc   6360
tccaaatatg tgaacttcct gtacctggcc agccactatg agaagctgaa gggctccccc   6420
gaggataatg agcagaaaca gctgtttgtg gaacagcaca agcactacct ggacgagatc   6480
atcgagcaga tcagcgagtt ctccaagaga gtgatcctgg ccgacgctaa tctggacaaa   6540
gtgctgtccg cctacaacaa gcaccgggat aagcccatca gagagcaggc cgagaatatc   6600
atccacctgt ttaccctgac caatctggga gcccctgccg ccttcaagta ctttgacacc   6660
accatcgacc ggaagaggta caccagcacc aaagaggtgc tggacgccac cctgatccac   6720
cagagcatca ccggcctgta cgagacacgg atcgacctgt ctcagctggg aggcgacagc   6780
cccaagaaga agagaaaggt ggaggccagc taacatatga ttcgaatgtc tttcttgcgc   6840
tatgacactt ccagcaaaag gtagggcggg ctgcgagacg gcttcccggc gctgcatgca   6900
acaccgatga tgcttcgacc ccccgaagct ccttcggggc tgcatgggcg ctccgatgcc   6960
gctccagggc gagcgctgtt taaatagcca ggcccccgat tgcaaagaca ttatagcgag   7020
ctaccaaagc catattcaaa cacctagatc actaccactt ctacacaggc cactcgagct   7080
tgtgatcgca ctccgctaag ggggcgcctc ttcctcttcg tttcagtcac aacccgcaaa   7140
catgacacaa gaatccctgt tacttctcga ccgtattgat tcggatgatt cctacgcgag   7200
cctgcggaac gaccaggaat tctgggaggt gagtcgacga gcaagcccgg cggatcaggc   7260
agcgtgcttg cagatttgac ttgcaacgcc cgcattgtgt cgacgaaggc ttttggctcc   7320
tctgtcgctg tctcaagcag catctaaccc tgcgtcgccg tttccatttg cagccgctgg   7380
cccgccgagc cctggaggag ctcgggctgc cggtgccgcc ggtgctgcgg gtgcccggcg   7440
agagcaccaa ccccgtactg gtcggcgagc ccggcccggt gatcaagctg ttcggcgagc   7500
actggtgcgg tccggagagc ctcgcgtcgg agtcggaggc gtacgcggtc ctggcggacg   7560
ccccggtgcc ggtgccccgc ctcctcggcc gcggcgagct gcggcccggc accggagcct   7620
ggccgtggcc ctacctggtg atgagccgga tgaccggcac cacctggcgg tccgcgatgg   7680
acggcacgac cgaccggaac gcgctgctcg ccctggcccg cgaactcggc cgggtgctcg   7740
```

```
gccggctgca cagggtgccg ctgaccggga acaccgtgct caccccccat tccgaggtct   7800

tcccggaact gctgcgggaa cgccgcgcgg cgaccgtcga ggaccaccgc gggtggggct   7860

acctctcgcc ccggctgctg gaccgcctgg aggactggct gccggacgtg gacacgctgc   7920

tggccggccg cgaaccccgg ttcgtccacg gcgacctgca cgggaccaac atcttcgtgg   7980

acctggccgc gaccgaggtc accgggatcg tcgacttcac cgacgtctat gcgggagact   8040

cccgctacag cctggtgcaa ctgcatctca acgccttccg gggcgaccgc gagatcctgg   8100

ccgcgctgct cgacggggcg cagtggaagc ggaccgagga cttcgcccgc gaactgctcg   8160

ccttcacctt cctgcacgac ttcgaggtgt tcgaggagac cccgctggat ctctccggct   8220

tcaccgatcc ggaggaactg gcgcagttcc tctgggggcc gccggacacc gcccccggcg   8280

cctgataagg atccggcaag actggccccg cttggcaacg caacagtgag cccctcccta   8340

gtgtgtttgg ggatgtgact atgtattcgt gtgttggcca acgggtcaac ccgaacagat   8400

tgatacccgc cttggcattt cctgtcagaa tgtaacgtca gttgatggta ct          8452
```

```
<210> SEQ ID NO 24
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 24

aaacatctcg tacagtgaca                                                 20


<210> SEQ ID NO 25
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 25

attccacggg aaggagatct                                                 20


<210> SEQ ID NO 26
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 26

cctggcttct tacgccgtcc                                                 20


<210> SEQ ID NO 27
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 27
```

```
gtactgcagt ccaaagaacc                                              20


<210> SEQ ID NO 28
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 28

cacagtggcc tggctcaaaa                                              20


<210> SEQ ID NO 29
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 29

aggattgaag ctgacgttct                                              20


<210> SEQ ID NO 30
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 30

cgtcagcttc aatcctgcca                                              20


<210> SEQ ID NO 31
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 31

ctcagagatt gctgcatagt                                              20


<210> SEQ ID NO 32
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 32

acaggtcatc ttaatgagcc                                              20


<210> SEQ ID NO 33
<211> LENGTH: 20
<212> TYPE: DNA
<213> ORGANISM: Artificial Sequence
<220> FEATURE:
<221> NAME/KEY: source
```

<223> OTHER INFORMATION: /note="Description of Artificial Sequence:
Synthetic oligonucleotide"

<400> SEQUENCE: 33
ggggctgtgg ttccacgata 20

<210> SEQ ID NO 34
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 34
gttgtgctca gtactgactt 20

<210> SEQ ID NO 35
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 35
acactggaaa aatgtcttgc 20

<210> SEQ ID NO 36
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 36
agtcagtact gagcacaaca 20

<210> SEQ ID NO 37
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 37
cttacctgga tatagtcaac 20

<210> SEQ ID NO 38
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 38
gaatcctgtt gactatatcc 20

<210> SEQ ID NO 39

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 39

gacctaaaat cattaacatc                                                20


<210> SEQ ID NO 40
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 40

tgccagatgt taatgatttt                                                20


<210> SEQ ID NO 41
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 41

ttatttagtc gtgtgccaaa                                                20


<210> SEQ ID NO 42
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 42

actgggctaa cctaaagctg                                                20


<210> SEQ ID NO 43
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 43

tctgcttgaa ccacagcttt                                                20


<210> SEQ ID NO 44
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 44
```

ggaggaaatc attgtgagaa 20

<210> SEQ ID NO 45
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 45
tctttagtgc aatcagaatc 20

<210> SEQ ID NO 46
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 46
acggcgggcg cttcacgctc 20

<210> SEQ ID NO 47
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 47
gccatcgagc agttcggctt 20

<210> SEQ ID NO 48
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 48
gcaccttctc gcgatctgac 20

<210> SEQ ID NO 49
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 49
gctcctgtca gatcgcgaga 20

<210> SEQ ID NO 50
<211> LENGTH: 20
<212> TYPE: DNA
<213> ORGANISM: Artificial Sequence
<220> FEATURE:

<221> NAME/KEY: source
<223> OTHER INFORMATION: /note="Description of Artificial Sequence:
Synthetic oligonucleotide"

<400> SEQUENCE: 50
gaagttcgag ggcgacaccc 20

<210> SEQ ID NO 51
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 51
ggtgaaccgc atcgagctga 20

<210> SEQ ID NO 52
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 52
gaagcaaccc aagacgttca c 21

<210> SEQ ID NO 53
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 53
tagttctctg acctgagtct t 21

<210> SEQ ID NO 54
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 54
gctctggata ttctgcacaa t 21

<210> SEQ ID NO 55
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 55
gcttcgtgtt aataagctga t 21

<210> SEQ ID NO 56
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 56
gcagcattat tgcagagaaa t 21

<210> SEQ ID NO 57
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 57
gctgttctca aggctgtgtt t 21

<210> SEQ ID NO 58
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 58
cgggtacttc atactttgga a 21

<210> SEQ ID NO 59
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 59
gcagagaaat tacgttgtaa t 21

<210> SEQ ID NO 60
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 60
gccaacctta acctttctaa t 21

<210> SEQ ID NO 61
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 61
cctcacaaca accaacactt t 21

<210> SEQ ID NO 62
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 62
cctgacactt acaacagtca a 21

<210> SEQ ID NO 63
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 63
gctggcagtt tcaaacgtaa t 21

<210> SEQ ID NO 64
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 64
cgtgactgtg aagactatta t 21

<210> SEQ ID NO 65
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 65
atgattacga gatcgagtat g 21

<210> SEQ ID NO 66
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 66
acatcgcccg tgactacaat c 21

<210> SEQ ID NO 67
<211> LENGTH: 60
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 67

taacttgaaa gtatttcgat ttcttggctt tatatatctt gtggaaagga cgaaacaccg     60


<210> SEQ ID NO 68
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 68

actttttcaa gttgataacg gactagcctt attttaactt gctatttcta gctctaaaac     60


<210> SEQ ID NO 69
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 69

aatggactat catatgctta ccgtaacttg aaagtatttc g                         41


<210> SEQ ID NO 70
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 70

ctttagtttg tatgtctgtt gctattatgt ctactattct ttcc                      44


<210> SEQ ID NO 71
<211> LENGTH: 99
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (59)..(75)
<223> OTHER INFORMATION: a, c, t, g, unknown or other
<220> FEATURE:
<221> NAME/KEY: variation
<222> LOCATION: (60)..(67)
<223> OTHER INFORMATION: /replace=" "
<220> FEATURE:
<221> NAME/KEY: misc_feature
<222> LOCATION: (1)..(99)
<223> OTHER INFORMATION: /note="Variation nucleotides given in the
      sequence have no preference with respect to those in the
      annotations for the variation positions"

<400> SEQUENCE: 71

aatgatacgg cgaccaccga gatctacact ctttccctac acgacgctct tccgatctnn     60
```

nnnnnnnnnn nnnnntcttg tggaaaggac gaaacaccg 99

<210> SEQ ID NO 72
<211> LENGTH: 83
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 72
caagcagaag acggcatacg agatgtgact ggagttcaga cgtgtgctct tccgatcttc 60
tactattctt tcccctgcac tgt 83

<210> SEQ ID NO 73
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 73
gggcgaggag ctgttcaccg 20

<210> SEQ ID NO 74
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 74
gagctggacg gcgacgtaaa 20

<210> SEQ ID NO 75
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 75
ggccacaagt tcagcgtgtc 20

<210> SEQ ID NO 76
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 76
ggagcgcacc atcttcttca 20

<210> SEQ ID NO 77
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 77
taacttgaaa gtatttcgat ttcttggctt tatatatctt gtggaaagga cgaaacaccg 60

<210> SEQ ID NO 78
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 78
actttttcaa gttgataacg gactagcctt attttaactt gctatttcta gctctaaaac 60

<210> SEQ ID NO 79
<211> LENGTH: 102
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 79
gttttagagc tatgctgttt tgaatggtcc caaaacggaa gggcctgagt ccgagcagaa 60
gaagaagttt tagagctatg ctgttttgaa tggtcccaaa ac 102

<210> SEQ ID NO 80
<211> LENGTH: 100
<212> TYPE: DNA
<213> ORGANISM: Homo sapiens

<400> SEQUENCE: 80
cggaggacaa agtacaaacg gcagaagctg gaggaggaag ggcctgagtc cgagcagaag 60
aagaagggct cccatcacat caaccggtgg cgcattgcca 100

<210> SEQ ID NO 81
<211> LENGTH: 50
<212> TYPE: DNA
<213> ORGANISM: Homo sapiens

<400> SEQUENCE: 81
agctggagga ggaagggcct gagtccgagc agaagaagaa gggctcccac 50

<210> SEQ ID NO 82
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 82
gaguccgagc agaagaagaa guuuuagagc 30

<210> SEQ ID NO 83
<211> LENGTH: 49
<212> TYPE: DNA

<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 83
agctggagga ggaagggcct gagtccgagc agaagagaag ggctcccat 49

<210> SEQ ID NO 84
<211> LENGTH: 53
<212> TYPE: DNA
<213> ORGANISM: Homo sapiens

<400> SEQUENCE: 84
ctggaggagg aagggcctga gtccgagcag aagaagaagg gctcccatca cat 53

<210> SEQ ID NO 85
<211> LENGTH: 52
<212> TYPE: DNA
<213> ORGANISM: Homo sapiens

<400> SEQUENCE: 85
ctggaggagg aagggcctga gtccgagcag aagagaaggg ctcccatcac at 52

<210> SEQ ID NO 86
<211> LENGTH: 54
<212> TYPE: DNA
<213> ORGANISM: Homo sapiens

<400> SEQUENCE: 86
ctggaggagg aagggcctga gtccgagcag aagaaagaag ggctcccatc acat 54

<210> SEQ ID NO 87
<211> LENGTH: 50
<212> TYPE: DNA
<213> ORGANISM: Homo sapiens

<400> SEQUENCE: 87
ctggaggagg aagggcctga gtccgagcag aagaagggct cccatcacat 50

<210> SEQ ID NO 88
<211> LENGTH: 47
<212> TYPE: DNA
<213> ORGANISM: Homo sapiens

<400> SEQUENCE: 88
ctggaggagg aagggcctga gcccgagcag aagggctccc atcacat 47

<210> SEQ ID NO 89
<211> LENGTH: 48
<212> TYPE: DNA
<213> ORGANISM: Homo sapiens

<400> SEQUENCE: 89
ctggaggagg aagggcctga gtccgagcag aagaagaagg gctcccat 48

<210> SEQ ID NO 90
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 90
gaguccgagc agaagaagau 20

<210> SEQ ID NO 91
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 91
gaguccgagc agaagaagua 20

<210> SEQ ID NO 92
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 92
gaguccgagc agaagaacaa 20

<210> SEQ ID NO 93
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 93
gaguccgagc agaagaugaa 20

<210> SEQ ID NO 94
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 94
gaguccgagc agaaguagaa 20

<210> SEQ ID NO 95
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 95
gaguccgagc agaugaagaa 20

<210> SEQ ID NO 96
<211> LENGTH: 20
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 96

gaguccgagc acaagaagaa                                                20


<210> SEQ ID NO 97
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 97

gaguccgagg agaagaagaa                                                20


<210> SEQ ID NO 98
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 98

gaguccgugc agaagaagaa                                                20


<210> SEQ ID NO 99
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 99

gagucggagc agaagaagaa                                                20


<210> SEQ ID NO 100
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 100

gagaccgagc agaagaagaa                                                20


<210> SEQ ID NO 101
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 101

aatgacaagc ttgctagcgg tggg                                           24
```

<210> SEQ ID NO 102
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 102
aaaacggaag ggcctgagtc cgagcagaag aagaagttt 39

<210> SEQ ID NO 103
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 103
aaacaggggc cgagattggg tgttcagggc agaggtttt 39

<210> SEQ ID NO 104
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 104
aaaacggaag ggcctgagtc cgagcagaag aagaagtt 38

<210> SEQ ID NO 105
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 105
aacggaggga ggggcacaga tgagaaactc agggttttag 40

<210> SEQ ID NO 106
<211> LENGTH: 38
<212> TYPE: DNA
<213> ORGANISM: Homo sapiens

<400> SEQUENCE: 106
agcccttctt cttctgctcg gactcaggcc cttcctcc 38

<210> SEQ ID NO 107
<211> LENGTH: 40
<212> TYPE: DNA
<213> ORGANISM: Homo sapiens

<400> SEQUENCE: 107
cagggaggga ggggcacaga tgagaaactc aggaggcccc 40

<210> SEQ ID NO 108

<211> LENGTH: 80
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 108
ggcaatgcgc caccggttga tgtgatggga gcccttctag gaggcccccca gagcagccac 60 tggggcctca acactcaggc 80

<210> SEQ ID NO 109
<211> LENGTH: 33
<212> TYPE: DNA
<213> ORGANISM: Homo sapiens

<400> SEQUENCE: 109
catcgatgtc ctccccattg gcctgcttcg tgg 33

<210> SEQ ID NO 110
<211> LENGTH: 33
<212> TYPE: DNA
<213> ORGANISM: Homo sapiens

<400> SEQUENCE: 110
ttcgtggcaa tgcgccaccg gttgatgtga tgg 33

<210> SEQ ID NO 111
<211> LENGTH: 33
<212> TYPE: DNA
<213> ORGANISM: Homo sapiens

<400> SEQUENCE: 111
tcgtggcaat gcgccaccgg ttgatgtgat ggg 33

<210> SEQ ID NO 112
<211> LENGTH: 33
<212> TYPE: DNA
<213> ORGANISM: Homo sapiens

<400> SEQUENCE: 112
tccagcttct gccgtttgta ctttgtcctc cgg 33

<210> SEQ ID NO 113
<211> LENGTH: 33
<212> TYPE: DNA
<213> ORGANISM: Homo sapiens

<400> SEQUENCE: 113
ggagggaggg gcacagatga gaaactcagg agg 33

<210> SEQ ID NO 114
<211> LENGTH: 33
<212> TYPE: DNA
<213> ORGANISM: Homo sapiens

<400> SEQUENCE: 114
aggggccgag attgggtgtt cagggcagag agg 33

<210> SEQ ID NO 115
<211> LENGTH: 33
<212> TYPE: DNA
<213> ORGANISM: Mus musculus

<400> SEQUENCE: 115
caagcactga gtgccattag ctaaatgcat agg 33

<210> SEQ ID NO 116
<211> LENGTH: 33
<212> TYPE: DNA
<213> ORGANISM: Mus musculus

<400> SEQUENCE: 116
aatgcatagg gtaccaccca caggtgccag ggg 33

<210> SEQ ID NO 117
<211> LENGTH: 33
<212> TYPE: DNA
<213> ORGANISM: Mus musculus

<400> SEQUENCE: 117
acacacatgg gaaagcctct gggccaggaa agg 33

<210> SEQ ID NO 118
<211> LENGTH: 37
<212> TYPE: DNA
<213> ORGANISM: Homo sapiens

<400> SEQUENCE: 118
ggaggaggta gtatacagaa acacagagaa gtagaat 37

<210> SEQ ID NO 119
<211> LENGTH: 37
<212> TYPE: DNA
<213> ORGANISM: Homo sapiens

<400> SEQUENCE: 119
agaatgtaga ggagtcacag aaactcagca ctagaaa 37

<210> SEQ ID NO 120
<211> LENGTH: 98
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 120
ggacgaaaca ccggaaccat tcaaaacagc atagcaagtt aaaataaggc tagtccgtta 60
tcaacttgaa aaagtggcac cgagtcggtg cttttttt 98

<210> SEQ ID NO 121
<211> LENGTH: 186
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 121
ggacgaaaca ccggtagtat taagtattgt tttatggctg ataaatttct ttgaatttct 60
ccttgattat ttgttataaa agttataaaa taatcttgtt ggaaccattc aaaacagcat 120
agcaagttaa aataaggcta gtccgttatc aacttgaaaa agtggcaccg agtcggtgct 180

```
tttttt                                                                 186


<210> SEQ ID NO 122
<211> LENGTH: 95
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 122

gggttttaga gctatgctgt tttgaatggt cccaaaacgg gtcttcgaga agacgtttta      60

gagctatgct gttttgaatg gtcccaaaac ttttt                                 95


<210> SEQ ID NO 123
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (5)..(34)
<223> OTHER INFORMATION: a, c, t, g, unknown or other

<400> SEQUENCE: 123

aaacnnnnnn nnnnnnnnnn nnnnnnnnnn nnnngt                                36


<210> SEQ ID NO 124
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (7)..(36)
<223> OTHER INFORMATION: a, c, t, g, unknown or other

<400> SEQUENCE: 124

taaaacnnnn nnnnnnnnnn nnnnnnnnnn nnnnnn                                36


<210> SEQ ID NO 125
<211> LENGTH: 84
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 125

gtggaaagga cgaaacaccg ggtcttcgag aagacctgtt ttagagctag aaatagcaag      60

ttaaaataag gctagtccgt tttt                                             84


<210> SEQ ID NO 126
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<220> FEATURE:
<221> NAME/KEY: modified_base
<222> LOCATION: (6)..(24)
<223> OTHER INFORMATION: a, c, t, g, unknown or other

<400> SEQUENCE: 126
caccgnnnnn nnnnnnnnnn nnnn 24

<210> SEQ ID NO 127
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (5)..(23)
<223> OTHER INFORMATION: a, c, t, g, unknown or other

<400> SEQUENCE: 127
aaacnnnnnn nnnnnnnnnn nnnc 24

<210> SEQ ID NO 128
<211> LENGTH: 46
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (1)..(19)
<223> OTHER INFORMATION: a, c, u, g, unknown or other

<400> SEQUENCE: 128
nnnnnnnnnn nnnnnnnnng uuauuguacu cucaagauuu auuuuu 46

<210> SEQ ID NO 129
<211> LENGTH: 91
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 129
guuacuuaaa ucuugcagaa gcuacaaaga uaaggcuuca ugccgaaauc aacacccugu 60
cauuuuaugg cagggguguu ucguuauuua a 91

<210> SEQ ID NO 130
<211> LENGTH: 70
<212> TYPE: DNA
<213> ORGANISM: Homo sapiens

<400> SEQUENCE: 130
ttttctagtg ctgagtttct gtgactcctc tacattctac ttctctgtgt ttctgtatac 60
tacctcctcc 70

<210> SEQ ID NO 131
<211> LENGTH: 122
<212> TYPE: DNA
<213> ORGANISM: Homo sapiens

<400> SEQUENCE: 131
ggaggaaggg cctgagtccg agcagaagaa gaagggctcc catcacatca accggtggcg 60
cattgccacg aagcaggcca atggggagga catcgatgtc acctccaatg actagggtgg 120
gc 122

<210> SEQ ID NO 132
<211> LENGTH: 48
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (3)..(32)
<223> OTHER INFORMATION: a, c, u, g, unknown or other

<400> SEQUENCE: 132
acnnnnnnnn nnnnnnnnnn nnnnnnnnnn nnguuuuaga gcuaugcu 48

<210> SEQ ID NO 133
<211> LENGTH: 67
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 133
agcauagcaa guuaaaauaa ggctaguccg uuaucaacuu gaaaaagugg caccgagucg 60
gugcuuu 67

<210> SEQ ID NO 134
<211> LENGTH: 62
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (1)..(20)
<223> OTHER INFORMATION: a, c, u, g, unknown or other

<400> SEQUENCE: 134
nnnnnnnnnn nnnnnnnnnn guuuuagagc uagaaauagc aaguuaaaau aaggcuaguc 60
cg 62

<210> SEQ ID NO 135
<211> LENGTH: 73
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 135
tgaatggtcc caaaacggaa gggcctgagt ccgagcagaa gaagaagttt tagagctatg 60
ctgttttgaa tgg 73

<210> SEQ ID NO 136
<211> LENGTH: 69
<212> TYPE: DNA
<213> ORGANISM: Homo sapiens

<400> SEQUENCE: 136
ctggtcttcc acctctctgc cctgaacacc caatctcggc ccctctcgcc accctcctgc 60
atttctgtt 69

<210> SEQ ID NO 137
<211> LENGTH: 138
<212> TYPE: DNA
<213> ORGANISM: Mus musculus

<400> SEQUENCE: 137
acccaagcac tgagtgccat tagctaaatg catagggtac cacccacagg tgccaggggc 60
ctttcccaaa gttcccagcc ccttctccaa cctttcctgg cccagaggct ttcccatgtg 120
tgtggctgga ccctttga 138

<210> SEQ ID NO 138
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 138
aaaaccaccc ttctctctgg c 21

<210> SEQ ID NO 139
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 139
ggagattgga gacacggaga g 21

<210> SEQ ID NO 140
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 140
ctggaaagcc aatgcctgac 20

<210> SEQ ID NO 141
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic primer"

<400> SEQUENCE: 141
ggcagcaaac tccttgtcct 20

<210> SEQ ID NO 142
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 142
gtgctttgca gaggcctacc 20

<210> SEQ ID NO 143
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 143
cctggagcgc atgcagtagt 20

<210> SEQ ID NO 144
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 144
accttctgtg tttccaccat tc 22

<210> SEQ ID NO 145
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 145
ttggggagtg cacagacttc 20

<210> SEQ ID NO 146
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 146
ggctccctgg gttcaaagta 20

<210> SEQ ID NO 147
<211> LENGTH: 21

<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 147
agaggggtct ggatgtcgta a 21

<210> SEQ ID NO 148
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic probe"

<400> SEQUENCE: 148
tagctctaaa acttcttctt ctgctcggac 30

<210> SEQ ID NO 149
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic probe"

<400> SEQUENCE: 149
ctagccttat tttaacttgc tatgctgttt 30

<210> SEQ ID NO 150
<211> LENGTH: 99
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (1)..(20)
<223> OTHER INFORMATION: a, c, u, g, unknown or other

<400> SEQUENCE: 150
nnnnnnnnnn nnnnnnnnnn guuuuagagc uagaaauagc aaguuaaaau aaggcuaguc 60
cguuaucaac uugaaaaagu ggcaccgagu cggugcuuu 99

<210> SEQ ID NO 151
<211> LENGTH: 12
<212> TYPE: DNA
<213> ORGANISM: Homo sapiens

<400> SEQUENCE: 151
tagcgggtaa gc 12

<210> SEQ ID NO 152
<211> LENGTH: 12
<212> TYPE: DNA
<213> ORGANISM: Homo sapiens

<400> SEQUENCE: 152
tcggtgacat gt 12

<210> SEQ ID NO 153
<211> LENGTH: 12
<212> TYPE: DNA
<213> ORGANISM: Homo sapiens

<400> SEQUENCE: 153
actccccgta gg 12

<210> SEQ ID NO 154
<211> LENGTH: 12
<212> TYPE: DNA
<213> ORGANISM: Homo sapiens

<400> SEQUENCE: 154
actgcgtgtt aa 12

<210> SEQ ID NO 155
<211> LENGTH: 12
<212> TYPE: DNA
<213> ORGANISM: Homo sapiens

<400> SEQUENCE: 155
acgtcgcctg at 12

<210> SEQ ID NO 156
<211> LENGTH: 12
<212> TYPE: DNA
<213> ORGANISM: Homo sapiens

<400> SEQUENCE: 156
taggtcgacc ag 12

<210> SEQ ID NO 157
<211> LENGTH: 12
<212> TYPE: DNA
<213> ORGANISM: Homo sapiens

<400> SEQUENCE: 157
ggcgttaatg at 12

<210> SEQ ID NO 158
<211> LENGTH: 12
<212> TYPE: DNA
<213> ORGANISM: Homo sapiens

<400> SEQUENCE: 158
tgtcgcatgt ta 12

<210> SEQ ID NO 159
<211> LENGTH: 12
<212> TYPE: DNA
<213> ORGANISM: Homo sapiens

<400> SEQUENCE: 159
atggaaacgc at 12

<210> SEQ ID NO 160
<211> LENGTH: 12
<212> TYPE: DNA
<213> ORGANISM: Homo sapiens

<400> SEQUENCE: 160
gccgaattcc tc 12

<210> SEQ ID NO 161
<211> LENGTH: 12
<212> TYPE: DNA
<213> ORGANISM: Homo sapiens

<400> SEQUENCE: 161
gcatggtacg ga 12

<210> SEQ ID NO 162
<211> LENGTH: 12
<212> TYPE: DNA
<213> ORGANISM: Homo sapiens

<400> SEQUENCE: 162
cggtactctt ac 12

<210> SEQ ID NO 163
<211> LENGTH: 12
<212> TYPE: DNA
<213> ORGANISM: Homo sapiens

<400> SEQUENCE: 163
gcctgtgccg ta 12

<210> SEQ ID NO 164
<211> LENGTH: 12
<212> TYPE: DNA
<213> ORGANISM: Homo sapiens

<400> SEQUENCE: 164
tacggtaagt cg 12

<210> SEQ ID NO 165
<211> LENGTH: 12
<212> TYPE: DNA
<213> ORGANISM: Homo sapiens

<400> SEQUENCE: 165
cacgaaatta cc 12

<210> SEQ ID NO 166
<211> LENGTH: 12
<212> TYPE: DNA
<213> ORGANISM: Homo sapiens

<400> SEQUENCE: 166
aaccaagata cg 12

<210> SEQ ID NO 167
<211> LENGTH: 12
<212> TYPE: DNA
<213> ORGANISM: Homo sapiens

<400> SEQUENCE: 167
gagtcgatac gc 12

<210> SEQ ID NO 168
<211> LENGTH: 12
<212> TYPE: DNA
<213> ORGANISM: Homo sapiens

<400> SEQUENCE: 168
gtctcacgat cg 12

<210> SEQ ID NO 169
<211> LENGTH: 12
<212> TYPE: DNA
<213> ORGANISM: Homo sapiens

<400> SEQUENCE: 169
tcgtcgggtg ca 12

<210> SEQ ID NO 170
<211> LENGTH: 12
<212> TYPE: DNA
<213> ORGANISM: Homo sapiens

<400> SEQUENCE: 170
actccgtagt ga 12

<210> SEQ ID NO 171
<211> LENGTH: 12
<212> TYPE: DNA
<213> ORGANISM: Homo sapiens

<400> SEQUENCE: 171
caggacgtcc gt 12

<210> SEQ ID NO 172
<211> LENGTH: 12
<212> TYPE: DNA
<213> ORGANISM: Homo sapiens

<400> SEQUENCE: 172
tcgtatccct ac 12

<210> SEQ ID NO 173
<211> LENGTH: 12
<212> TYPE: DNA
<213> ORGANISM: Homo sapiens

<400> SEQUENCE: 173
tttcaaggcc gg 12

<210> SEQ ID NO 174
<211> LENGTH: 12
<212> TYPE: DNA
<213> ORGANISM: Homo sapiens

<400> SEQUENCE: 174
cgccggtgga at 12

<210> SEQ ID NO 175
<211> LENGTH: 12
<212> TYPE: DNA
<213> ORGANISM: Homo sapiens

<400> SEQUENCE: 175
gaacccgtcc ta 12

<210> SEQ ID NO 176
<211> LENGTH: 12
<212> TYPE: DNA
<213> ORGANISM: Homo sapiens

<400> SEQUENCE: 176
gattcatcag cg 12

<210> SEQ ID NO 177
<211> LENGTH: 12
<212> TYPE: DNA
<213> ORGANISM: Homo sapiens

<400> SEQUENCE: 177
acaccggtct tc 12

<210> SEQ ID NO 178
<211> LENGTH: 12
<212> TYPE: DNA
<213> ORGANISM: Homo sapiens

<400> SEQUENCE: 178
atcgtgccct aa 12

<210> SEQ ID NO 179
<211> LENGTH: 12
<212> TYPE: DNA
<213> ORGANISM: Homo sapiens

<400> SEQUENCE: 179
gcgtcaatgt tc 12

<210> SEQ ID NO 180
<211> LENGTH: 12
<212> TYPE: DNA
<213> ORGANISM: Homo sapiens

<400> SEQUENCE: 180
ctccgtatct cg 12

<210> SEQ ID NO 181
<211> LENGTH: 12
<212> TYPE: DNA
<213> ORGANISM: Homo sapiens

<400> SEQUENCE: 181
ccgattcctt cg 12

<210> SEQ ID NO 182
<211> LENGTH: 12
<212> TYPE: DNA
<213> ORGANISM: Homo sapiens

<400> SEQUENCE: 182
tgcgcctcca gt 12

<210> SEQ ID NO 183
<211> LENGTH: 12
<212> TYPE: DNA
<213> ORGANISM: Homo sapiens

<400> SEQUENCE: 183
taacgtcgga gc 12

<210> SEQ ID NO 184
<211> LENGTH: 12
<212> TYPE: DNA
<213> ORGANISM: Homo sapiens

<400> SEQUENCE: 184
aaggtcgccc at 12

<210> SEQ ID NO 185
<211> LENGTH: 12
<212> TYPE: DNA
<213> ORGANISM: Homo sapiens

<400> SEQUENCE: 185
gtcggggact at 12

<210> SEQ ID NO 186
<211> LENGTH: 12
<212> TYPE: DNA
<213> ORGANISM: Homo sapiens

<400> SEQUENCE: 186
ttcgagcgat tt 12

<210> SEQ ID NO 187
<211> LENGTH: 12
<212> TYPE: DNA
<213> ORGANISM: Homo sapiens

<400> SEQUENCE: 187
tgagtcgtcg ag 12

<210> SEQ ID NO 188
<211> LENGTH: 12
<212> TYPE: DNA
<213> ORGANISM: Homo sapiens

<400> SEQUENCE: 188
tttacgcaga gg 12

<210> SEQ ID NO 189
<211> LENGTH: 12
<212> TYPE: DNA
<213> ORGANISM: Homo sapiens

<400> SEQUENCE: 189
aggaagtatc gc 12

<210> SEQ ID NO 190
<211> LENGTH: 12
<212> TYPE: DNA
<213> ORGANISM: Homo sapiens

<400> SEQUENCE: 190
actcgatacc at 12

<210> SEQ ID NO 191
<211> LENGTH: 12
<212> TYPE: DNA
<213> ORGANISM: Homo sapiens

<400> SEQUENCE: 191
cgctacatag ca 12

<210> SEQ ID NO 192
<211> LENGTH: 12
<212> TYPE: DNA
<213> ORGANISM: Homo sapiens

<400> SEQUENCE: 192
ttcataaccg gc 12

<210> SEQ ID NO 193
<211> LENGTH: 12
<212> TYPE: DNA
<213> ORGANISM: Homo sapiens

<400> SEQUENCE: 193
ccaaacggtt aa 12

<210> SEQ ID NO 194
<211> LENGTH: 12
<212> TYPE: DNA
<213> ORGANISM: Homo sapiens

<400> SEQUENCE: 194
cgattccttc gt 12

<210> SEQ ID NO 195
<211> LENGTH: 12
<212> TYPE: DNA
<213> ORGANISM: Homo sapiens

<400> SEQUENCE: 195
cgtcatgaat aa 12

<210> SEQ ID NO 196
<211> LENGTH: 12
<212> TYPE: DNA
<213> ORGANISM: Homo sapiens

<400> SEQUENCE: 196
agtggcgatg ac 12

<210> SEQ ID NO 197
<211> LENGTH: 12
<212> TYPE: DNA
<213> ORGANISM: Homo sapiens

<400> SEQUENCE: 197
cccctacggc ac 12

<210> SEQ ID NO 198
<211> LENGTH: 12
<212> TYPE: DNA
<213> ORGANISM: Homo sapiens

<400> SEQUENCE: 198
gccaacccgc ac 12

<210> SEQ ID NO 199
<211> LENGTH: 12
<212> TYPE: DNA
<213> ORGANISM: Homo sapiens

<400> SEQUENCE: 199
tgggacaccg gt 12

<210> SEQ ID NO 200
<211> LENGTH: 12
<212> TYPE: DNA

<213> ORGANISM: Homo sapiens

<400> SEQUENCE: 200
ttgactgcgg cg 12

<210> SEQ ID NO 201
<211> LENGTH: 12
<212> TYPE: DNA
<213> ORGANISM: Homo sapiens

<400> SEQUENCE: 201
actatgcgta gg 12

<210> SEQ ID NO 202
<211> LENGTH: 12
<212> TYPE: DNA
<213> ORGANISM: Homo sapiens

<400> SEQUENCE: 202
tcacccaaag cg 12

<210> SEQ ID NO 203
<211> LENGTH: 12
<212> TYPE: DNA
<213> ORGANISM: Homo sapiens

<400> SEQUENCE: 203
gcaggacgtc cg 12

<210> SEQ ID NO 204
<211> LENGTH: 12
<212> TYPE: DNA
<213> ORGANISM: Homo sapiens

<400> SEQUENCE: 204
acaccgaaaa cg 12

<210> SEQ ID NO 205
<211> LENGTH: 12
<212> TYPE: DNA
<213> ORGANISM: Homo sapiens

<400> SEQUENCE: 205
cggtgtattg ag 12

<210> SEQ ID NO 206
<211> LENGTH: 12
<212> TYPE: DNA
<213> ORGANISM: Homo sapiens

<400> SEQUENCE: 206
cacgaggtat gc 12

<210> SEQ ID NO 207
<211> LENGTH: 12
<212> TYPE: DNA
<213> ORGANISM: Homo sapiens

<400> SEQUENCE: 207
taaagcgacc cg 12

<210> SEQ ID NO 208
<211> LENGTH: 12

<212> TYPE: DNA
<213> ORGANISM: Homo sapiens

<400> SEQUENCE: 208
cttagtcggc ca 12

<210> SEQ ID NO 209
<211> LENGTH: 12
<212> TYPE: DNA
<213> ORGANISM: Homo sapiens

<400> SEQUENCE: 209
cgaaaacgtg gc 12

<210> SEQ ID NO 210
<211> LENGTH: 12
<212> TYPE: DNA
<213> ORGANISM: Homo sapiens

<400> SEQUENCE: 210
cgtgccctga ac 12

<210> SEQ ID NO 211
<211> LENGTH: 12
<212> TYPE: DNA
<213> ORGANISM: Homo sapiens

<400> SEQUENCE: 211
tttaccatcg aa 12

<210> SEQ ID NO 212
<211> LENGTH: 12
<212> TYPE: DNA
<213> ORGANISM: Homo sapiens

<400> SEQUENCE: 212
cgtagccatg tt 12

<210> SEQ ID NO 213
<211> LENGTH: 12
<212> TYPE: DNA
<213> ORGANISM: Homo sapiens

<400> SEQUENCE: 213
cccaaacggt ta 12

<210> SEQ ID NO 214
<211> LENGTH: 12
<212> TYPE: DNA
<213> ORGANISM: Homo sapiens

<400> SEQUENCE: 214
gcgttatcag aa 12

<210> SEQ ID NO 215
<211> LENGTH: 12
<212> TYPE: DNA
<213> ORGANISM: Homo sapiens

<400> SEQUENCE: 215
tcgatggtaa ac 12

<210> SEQ ID NO 216

<211> LENGTH: 12
<212> TYPE: DNA
<213> ORGANISM: Homo sapiens

<400> SEQUENCE: 216
cgactttttg ca 12

<210> SEQ ID NO 217
<211> LENGTH: 12
<212> TYPE: DNA
<213> ORGANISM: Homo sapiens

<400> SEQUENCE: 217
tcgacgactc ac 12

<210> SEQ ID NO 218
<211> LENGTH: 12
<212> TYPE: DNA
<213> ORGANISM: Homo sapiens

<400> SEQUENCE: 218
acgcgtcaga ta 12

<210> SEQ ID NO 219
<211> LENGTH: 12
<212> TYPE: DNA
<213> ORGANISM: Homo sapiens

<400> SEQUENCE: 219
cgtacggcac ag 12

<210> SEQ ID NO 220
<211> LENGTH: 12
<212> TYPE: DNA
<213> ORGANISM: Homo sapiens

<400> SEQUENCE: 220
ctatgccgtg ca 12

<210> SEQ ID NO 221
<211> LENGTH: 12
<212> TYPE: DNA
<213> ORGANISM: Homo sapiens

<400> SEQUENCE: 221
cgcgtcagat at 12

<210> SEQ ID NO 222
<211> LENGTH: 12
<212> TYPE: DNA
<213> ORGANISM: Homo sapiens

<400> SEQUENCE: 222
aagatcggta gc 12

<210> SEQ ID NO 223
<211> LENGTH: 12
<212> TYPE: DNA
<213> ORGANISM: Homo sapiens

<400> SEQUENCE: 223
cttcgcaagg ag 12

<210> SEQ ID NO 224
<211> LENGTH: 12
<212> TYPE: DNA
<213> ORGANISM: Homo sapiens

<400> SEQUENCE: 224
gtcgtggact ac 12

<210> SEQ ID NO 225
<211> LENGTH: 12
<212> TYPE: DNA
<213> ORGANISM: Homo sapiens

<400> SEQUENCE: 225
ggtcgtcatc aa 12

<210> SEQ ID NO 226
<211> LENGTH: 12
<212> TYPE: DNA
<213> ORGANISM: Homo sapiens

<400> SEQUENCE: 226
gttaacagcg tg 12

<210> SEQ ID NO 227
<211> LENGTH: 12
<212> TYPE: DNA
<213> ORGANISM: Homo sapiens

<400> SEQUENCE: 227
tagctaaccg tt 12

<210> SEQ ID NO 228
<211> LENGTH: 12
<212> TYPE: DNA
<213> ORGANISM: Homo sapiens

<400> SEQUENCE: 228
agtaaaggcg ct 12

<210> SEQ ID NO 229
<211> LENGTH: 12
<212> TYPE: DNA
<213> ORGANISM: Homo sapiens

<400> SEQUENCE: 229
ggtaatttcg tg 12

<210> SEQ ID NO 230
<211> LENGTH: 15
<212> TYPE: DNA
<213> ORGANISM: Homo sapiens

<400> SEQUENCE: 230
cagaagaaga agggc 15

<210> SEQ ID NO 231
<211> LENGTH: 51
<212> TYPE: DNA
<213> ORGANISM: Homo sapiens

<400> SEQUENCE: 231
ccaatgggga ggacatcgat gtcacctcca atgactaggg tggtgggcaa c 51

<210> SEQ ID NO 232
<211> LENGTH: 15
<212> TYPE: DNA
<213> ORGANISM: Homo sapiens

<400> SEQUENCE: 232
ctctggccac tccct 15

<210> SEQ ID NO 233
<211> LENGTH: 52
<212> TYPE: DNA
<213> ORGANISM: Homo sapiens

<400> SEQUENCE: 233
acatcgatgt cacctccaat gacaagcttg ctagcggtgg gcaaccacaa ac 52

<210> SEQ ID NO 234
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: modified_base
<222> LOCATION: (6)..(25)
<223> OTHER INFORMATION: a, c, t, g, unknown or other

<400> SEQUENCE: 234
caccgnnnnn nnnnnnnnnn nnnnn 25

<210> SEQ ID NO 235
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: modified_base
<222> LOCATION: (5)..(24)
<223> OTHER INFORMATION: a, c, t, g, unknown or other

<400> SEQUENCE: 235
aaacnnnnnn nnnnnnnnnn nnnnc 25

<210> SEQ ID NO 236
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 236
aacaccgggt cttcgagaag acctgtttta gagctagaaa tagcaagtta aaat 54

<210> SEQ ID NO 237
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 237
caaaacgggt cttcgagaag acgttttaga gctatgctgt tttgaatggt ccca 54

<210> SEQ ID NO 238
<211> LENGTH: 720
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 238
atggtgagca agggcgagga gctgttcacc ggggtggtgc ccatcctggt cgagctggac 60
ggcgacgtaa acggccacaa gttcagcgtg tccggcgagg gcgagggcga tgccacctac 120
ggcaagctga ccctgaagtt catctgcacc accggcaagc tgcccgtgcc ctggcccacc 180
ctcgtgacca ccctgaccta cggcgtgcag tgcttcagcc gctaccccga ccacatgaag 240
cagcacgact tcttcaagtc cgccatgccc gaaggctacg tccaggagcg caccatcttc 300
ttcaaggacg acggcaacta caagacccgc gccgaggtga agttcgaggg cgacaccctg 360
gtgaaccgca tcgagctgaa gggcatcgac ttcaaggagg acggcaacat cctggggcac 420
aagctggagt acaactacaa cagccacaac gtctatatca tggccgacaa gcagaagaac 480
ggcatcaagg tgaacttcaa gatccgccac aacatcgagg acggcagcgt gcagctcgcc 540
gaccactacc agcagaacac ccccatcggc gacggccccg tgctgctgcc cgacaaccac 600
tacctgagca cccagtccgc cctgagcaaa gaccccaacg agaagcgcga tcacatggtc 660
ctgctggagt tcgtgaccgc cgccgggatc actctcggca tggacgagct gtacaagtaa 720

<210> SEQ ID NO 239
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 239
gttgtgctca gtactgactt tgg 23

<210> SEQ ID NO 240
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 240
gttgggcacg gtactgactt tgg 23

<210> SEQ ID NO 241
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 241
gccctgcaca gtactgactt aag 23

<210> SEQ ID NO 242
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 242
gttctgccca ggactgactt ggg 23

<210> SEQ ID NO 243
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 243
atcctgctct gtactgactt gag 23

<210> SEQ ID NO 244
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 244
gttgggttta gtactgactt ggg 23

<210> SEQ ID NO 245
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 245
agtcagtact gagcacaaca agg 23

<210> SEQ ID NO 246
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 246
agtgagtcct gagcacaaca cag 23

<210> SEQ ID NO 247
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 247
tgtcagtact gagctcaaca aag 23

<210> SEQ ID NO 248
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 248
ggtgggtcct gagcacaaca aag 23

<210> SEQ ID NO 249
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 249
tttcagcttc caataaaaac agg 23

<210> SEQ ID NO 250
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 250
tttcagcatc caataaaaat aag 23

<210> SEQ ID NO 251
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 251
ttgcatcatc caataaaaac tag 23

<210> SEQ ID NO 252
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 252
atacatcttc caataaaaac tag 23

<210> SEQ ID NO 253
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 253
ttgcgtcttc caataaaaac tgg 23

<210> SEQ ID NO 254
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 254
tggcagcttc ctataaaaac tag 23

<210> SEQ ID NO 255
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 255
aaacatctcg tacagtgaca agg 23

<210> SEQ ID NO 256
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 256
gggcatctct tacagtgaca agg 23

<210> SEQ ID NO 257
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 257
aaagttcaca tacagtgaca cag 23

<210> SEQ ID NO 258
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 258
aaacaggtcc tacagtgaca agg 23

<210> SEQ ID NO 259
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 259
taagatttct tacagtgaca tag 23

<210> SEQ ID NO 260
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 260
aagcatcttg gacagtgaca tag 23

<210> SEQ ID NO 261
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 261
attccacggg aaggagatct tgg 23

<210> SEQ ID NO 262
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 262
agttcacagg aaggagatct aag 23

<210> SEQ ID NO 263
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 263
attactctgg aaggagatct ggg 23

<210> SEQ ID NO 264
<211> LENGTH: 23
<212> TYPE: DNA

<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 264
gtagcacagg aaggagatct agg 23

<210> SEQ ID NO 265
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 265
aattgactgg aaggagatct gag 23

<210> SEQ ID NO 266
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 266
gttgcacaga aaggagatct ggg 23

<210> SEQ ID NO 267
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 267
gtactgcagt ccaaagaacc agg 23

<210> SEQ ID NO 268
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 268
ctgctgcact ccaaagaacc tag 23

<210> SEQ ID NO 269
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 269
taactacagt ccaaagaacc agg 23

<210> SEQ ID NO 270
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 270
cagctgctgt ccaaagaacc cag 23

<210> SEQ ID NO 271
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 271
cacagtggcc tggctcaaaa tgg 23

<210> SEQ ID NO 272
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 272
cacagtgggc tgactcaaaa gag 23

<210> SEQ ID NO 273
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 273
caaactggcc tggctctaaa cag 23

<210> SEQ ID NO 274
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 274
caccatggcc tggctctaaa agg 23

<210> SEQ ID NO 275
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 275
taaagttgca tggctcaaaa aag 23

<210> SEQ ID NO 276
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 276
aggattgaag ctgacgttct tgg 23

<210> SEQ ID NO 277
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 277
ggatttaaag ctgacgttct tag 23

<210> SEQ ID NO 278
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 278
aggatagaag ctgacattct cgg 23

<210> SEQ ID NO 279
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 279
atttttgaag ttgacgttct cag 23

<210> SEQ ID NO 280
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 280
agccatgaag atgacgttct ggg 23

<210> SEQ ID NO 281
<211> LENGTH: 23

<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 281
aggactggag ctgacgtact gag 23

<210> SEQ ID NO 282
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 282
cgtcagcttc aatcctgcca agg 23

<210> SEQ ID NO 283
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 283
agtcagcttc agtcctgcca cgg 23

<210> SEQ ID NO 284
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 284
gagcagcttc aatcctgcca ggg 23

<210> SEQ ID NO 285
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 285
agtctgcttc catcctgcca aag 23

<210> SEQ ID NO 286
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 286
ctcagagatt gctgcatagt agg 23

<210> SEQ ID NO 287
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 287
ctcaaaactt gctgcatagt aag 23

<210> SEQ ID NO 288
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 288
cccagagctt ggtgcatagt cag 23

<210> SEQ ID NO 289
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 289
cccaaagatt gctgcacagt gag 23

<210> SEQ ID NO 290
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 290
acaggtcatc ttaatgagcc agg 23

<210> SEQ ID NO 291
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 291
acacttcttc ttaatgagcc cag 23

<210> SEQ ID NO 292
<211> LENGTH: 23
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 292

agaggtcttc ttaatgagct agg                                              23


<210> SEQ ID NO 293
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 293

ggatgtcata ttaatgagcc tag                                              23


<210> SEQ ID NO 294
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 294

ccaaatcata ttaatgagcc aag                                              23


<210> SEQ ID NO 295
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 295

ggggctgtgg ttccacgata ggg                                              23


<210> SEQ ID NO 296
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 296

gggactgtgg gtgcacgata aag                                              23


<210> SEQ ID NO 297
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 297

gaggctgggg ttccaagata aag                                              23


<210> SEQ ID NO 298
```

<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 298
ggagctgggg ttccaggata aag 23

<210> SEQ ID NO 299
<211> LENGTH: 12743
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 299
ttaatgtagt cttatgcaat actcttgtag tcttgcaaca tggtaacgat gagttagcaa 60
catgccttac aaggagagaa aaagcaccgt gcatgccgat tggtggaagt aaggtggtac 120
gatcgtgcct tattaggaag gcaacagacg ggtctgacat ggattggacg aaccactgaa 180
ttgccgcatt gcagagatat tgtatttaag tgcctagctc gatacataaa cgggtctctc 240
tggttagacc agatctgagc ctgggagctc tctggctaac tagggaaccc actgcttaag 300
cctcaataaa gcttgccttg agtgcttcaa gtagtgtgtg cccgtctgtt gtgtgactct 360
ggtaactaga gatccctcag acccttttag tcagtgtgga aaatctctag cagtggcgcc 420
cgaacaggga cttgaaagcg aaagggaaac cagaggagct ctctcgacgc aggactcggc 480
ttgctgaagc gcgcacggca agaggcgagg ggcggcgact ggtgagtacg ccaaaaattt 540
tgactagcgg aggctagaag gagagagatg ggtgcgagag cgtcagtatt aagcggggga 600
gaattagatc gcgatgggaa aaaattcggt taaggccagg gggaaagaaa aaatataaat 660
taaaacatat agtatgggca agcagggagc tagaacgatt cgcagttaat cctggcctgt 720
tagaaacatc agaaggctgt agacaaatac tgggacagct acaaccatcc cttcagacag 780
gatcagaaga acttagatca ttatataata cagtagcaac cctctattgt gtgcatcaaa 840
ggatagagat aaaagacacc aaggaagctt tagacaagat agaggaagag caaaacaaaa 900
gtaagaccac cgcacagcaa gcggccgctg atcttcagac ctggaggagg agatatgagg 960
gacaattgga gaagtgaatt atataaatat aaagtagtaa aaattgaacc attaggagta 1020
gcacccacca aggcaaagag aagagtggtg cagagagaaa aaagagcagt gggaatagga 1080
gctttgttcc ttgggttctt gggagcagca ggaagcacta tgggcgcagc gtcaatgacg 1140
ctgacggtac aggccagaca attattgtct ggtatagtgc agcagcagaa caatttgctg 1200
agggctattg aggcgcaaca gcatctgttg caactcacag tctggggcat caagcagctc 1260
caggcaagaa tcctggctgt ggaaagatac ctaaaggatc aacagctcct ggggatttgg 1320
ggttgctctg gaaaactcat ttgcaccact gctgtgcctt ggaatgctag ttggagtaat 1380
aaatctctgg aacagatttg gaatcacacg acctggatgg agtgggacag agaaattaac 1440
aattacacaa gcttaataca ctccttaatt gaagaatcgc aaaaccagca agaaaagaat 1500
gaacaagaat tattggaatt agataaatgg gcaagtttgt ggaattggtt taacataaca 1560
aattggctgt ggtatataaa attattcata atgatagtag gaggcttggt aggtttaaga 1620
atagtttttg ctgtactttc tatagtgaat agagttaggc agggatattc accattatcg 1680

```
tttcagaccc acctcccaac cccgagggga cccagagagg gcctatttcc catgattcct   1740
tcatatttgc atatacgata caaggctgtt agagagataa ttagaattaa tttgactgta   1800
aacacaaaga tattagtaca aaatacgtga cgtagaaagt aataatttct tgggtagttt   1860
gcagttttaa aattatgttt taaaatggac tatcatatgc ttaccgtaac ttgaaagtat   1920
ttcgatttct tggctttata tatcttgtgg aaaggacgaa acaccggaga cggttgtaaa   1980
tgagcacaca aaatacacat gctaaaatat tatattctat gacctttata aaatcaacca   2040
aaatcttctt tttaataact ttagtatcaa taattagaat ttttatgttc ctttttgcaa   2100
acttttaata aaaatgagca aaataaaaaa acgctagttt tagtaactcg cgttgttttc   2160
ttcaccttta ataatagcta ctccaccact tgttcctaag cggtcagctc ctgcttcaat   2220
catttttga gcatcttcaa atgttctaac tccaccagct gctttaacta aagcattgtc   2280
tttaacaact gacttcatta gtttaacatc ttcaaatgtt gcacctgatt ttgaaaatcc   2340
tgttgatgtt ttaacaaatt ctaatccagc ttcaacagct atttcacaag ctttcatgat   2400
ttcttctttt gttaataaac aattttccat aatacattta acaacatgtg atccagctgc   2460
ttttttaca gctttcatgt cttctaaaac taattcataa tttttgtctt ttaatgcacc   2520
aatatttaat accatatcaa tttctgttgc accatcttta attgcttcag aaacttcgaa   2580
tgcttttgta gctgttgtgc atgcacctag aggaaaacct acaacatttg ttattcctac   2640
atttgtgcct tttaataatt ctttacaata gcttgttcaa tatgaattaa cacaaactgt   2700
tgcaaaatca aattcaattg cttcatcaca taattgttta atttcagctt tcgtagcatc   2760
ttgttttaat aatgtgtgat ctatatattt gtttagtttc attttttctc ctatatattc   2820
atttttaatt ttaattcttt aataatttcg tctactttaa ctttagcgtt ttgaacagat   2880
tcaccaacac ctataaaata aatttttagt ttaggttcag ttccacttgg gcgaacagca   2940
aatcatgact tatcttctaa ataaaatttt agtaagtctt gtcctggcat attatacatt   3000
ccatcgatgt agtcttcaac attaacaact ttaagtccag caatttgagt taagggtgtt   3060
gctctcaatg atttcattaa tggttcaatt tttaatttct tttcttctgg tttaaaattc   3120
aagtttaaag tgaaagtgta atatgcaccc atttctttaa ataaatcttc taaatagtct   3180
actaatgttt tattttgttt tttataaaat caagcagcct ctgctattaa tatagaagct   3240
tgtattccat ctttatctct agctgagtca tcaattacat atccataact ttcttcataa   3300
gcaaaaacaa aatttaatcc gttatcttct tctttagcaa tttctctacc cattcattta   3360
aatccagtta aagtttttac aatattaact ccatattttt catgagcgat tctatcaccc   3420
aaatcacttg ttacaaaact tgaatataga gccggatttt ttggaatgct atttaagcgt   3480
tttagatttg ataattttca atcaattaaa attggtcctg tttgatttcc atctaatctt   3540
acaaaatgac catcatgttt tattgccatt ccaaatctgt cagcatctgg gtcattcata   3600
ataataatat ctgcatcatg tttaatacca tattcaagcg gtatttttca tgcaggatca   3660
aattctggat ttggatttac aacattttta aatgtttcat cttcaaatgc atgctcttca   3720
acctcaataa cgttatatcc tgattcacgt aatatttttg gggtaaattt agttcctgtt   3780
ccattaactg cgctaaaaat aatttttaaa tctttttag cttcttgctc tttttgtac    3840
gtctctgttt tagagctaga aatagcaagt taaaataagg ctagtccgtt atcaacttga   3900
aaaagtggca ccgagtcggt gcttttttga attctagatc ttgagacaaa tggcagtatt   3960
catccacaat tttaaaagaa aaggggggat tggggggtac agtgcagggg aaagaatagt   4020
```

agacataata gcaacagaca tacaaactaa agaattacaa aaacaaatta caaaaattca 4080
aaattttcgg gtttattaca gggacagcag agatccactt tggcgccggc tcgagtggct 4140
ccggtgcccg tcagtgggca gagcgcacat cgcccacagt ccccgagaag ttggggggag 4200
gggtcggcaa ttgaaccggt gcctagagaa ggtggcgcgg ggtaaactgg gaaagtgatg 4260
tcgtgtactg gctccgcctt tttcccgagg gtgggggaga accgtatata agtgcagtag 4320
tcgccgtgaa cgttcttttt cgcaacgggt ttgccgccag aacacaggtg tcgtgacgcg 4380
ggatccgcca ccatggatta caaagacgat gacgataaga tggccccaaa gaagaagcgg 4440
aaggtcggta tccacggagt cccagcagcc gacaagaagt acagcatcgg cctggacatc 4500
ggcaccaact ctgtgggctg ggccgtgatc accgacgagt acaaggtgcc cagcaagaaa 4560
ttcaaggtgc tgggcaacac cgaccggcac agcatcaaga agaacctgat cggagccctg 4620
ctgttcgaca gcggcgaaac agccgaggcc acccggctga agagaaccgc cagaagaaga 4680
tacaccagac ggaagaaccg gatctgctat ctgcaagaga tcttcagcaa cgagatggcc 4740
aaggtggacg acagcttctt ccacagactg gaagagtcct tcctggtgga agaggataag 4800
aagcacgagc ggcaccccat cttcggcaac atcgtggacg aggtggccta ccacgagaag 4860
taccccacca tctaccacct gagaaagaaa ctggtggaca gcaccgacaa ggccgacctg 4920
cggctgatct atctggccct ggcccacatg atcaagttcc ggggccactt cctgatcgag 4980
ggcgacctga accccgacaa cagcgacgtg gacaagctgt tcatccagct ggtgcagacc 5040
tacaaccagc tgttcgagga aaaccccatc aacgccagcg gcgtggacgc caaggccatc 5100
ctgtctgcca gactgagcaa gagcagacgg ctggaaaatc tgatcgccca gctgcccggc 5160
gagaagaaga atggcctgtt cggcaacctg attgccctga gcctgggcct gacccccaac 5220
ttcaagagca acttcgacct ggccgaggat gccaaactgc agctgagcaa ggacacctac 5280
gacgacgacc tggacaacct gctggcccag atcggcgacc agtacgccga cctgtttctg 5340
gccgccaaga acctgtccga cgccatcctg ctgagcgaca tcctgagagt gaacaccgag 5400
atcaccaagg ccccccctgag cgcctctatg atcaagagat acgacgagca ccaccaggac 5460
ctgaccctgc tgaaagctct cgtgcggcag cagctgcctg agaagtacaa agagattttc 5520
ttcgaccaga gcaagaacgg ctacgccggc tacattgacg gcggagccag ccaggaagag 5580
ttctacaagt tcatcaagcc catcctggaa aagatggacg gcaccgagga actgctcgtg 5640
aagctgaaca gagaggacct gctgcggaag cagcggacct tcgacaacgg cagcatcccc 5700
caccagatcc acctgggaga gctgcacgcc attctgcggc ggcaggaaga tttttaccca 5760
ttcctgaagg acaaccggga aaagatcgag aagatcctga ccttccgcat cccctactac 5820
gtgggccctc tggccagggg aaacagcaga ttcgcctgga tgaccagaaa gagcgaggaa 5880
accatcaccc cctggaactt cgaggaagtg gtggacaagg gcgcttccgc ccagagcttc 5940
atcgagcgga tgaccaactt cgataagaac ctgcccaacg agaaggtgct gcccaagcac 6000
agcctgctgt acgagtactt caccgtgtat aacgagctga ccaaagtgaa atacgtgacc 6060
gagggaatga gaaagcccgc cttcctgagc ggcgagcaga aaaaggccat cgtggacctg 6120
ctgttcaaga ccaaccggaa agtgaccgtg aagcagctga aagaggacta cttcaagaaa 6180
atcgagtgct tcgactccgt ggaaatctcc ggcgtggaag atcggttcaa cgcctccctg 6240
ggcacatacc acgatctgct gaaaattatc aaggacaagg acttcctgga caatgaggaa 6300
aacgaggaca ttctggaaga tatcgtgctg accctgacac tgtttgagga cagagagatg 6360
atcgaggaac ggctgaaaac ctatgcccac ctgttcgacg acaaagtgat gaagcagctg 6420

```
aagcggcgga gatacaccgg ctggggcagg ctgagccgga agctgatcaa cggcatccgg   6480
gacaagcagt ccggcaagac aatcctggat ttcctgaagt ccgacggctt cgccaacaga   6540
aacttcatgc agctgatcca cgacgacagc ctgaccttta aagaggacat ccagaaagcc   6600
caggtgtccg gccagggcga tagcctgcac gagcacattg ccaatctggc cggcagcccc   6660
gccattaaga agggcatcct gcagacagtg aaggtggtgg acgagctcgt gaaagtgatg   6720
ggccggcaca agcccgagaa catcgtgatc gaaatggcca gagagaacca gaccacccag   6780
aagggacaga agaacagccg cgagagaatg aagcggatcg aagagggcat caaagagctg   6840
ggcagccaga tcctgaaaga acaccccgtg gaaaacaccc agctgcagaa cgagaagctg   6900
tacctgtact acctgcagaa tgggcgggat atgtacgtgg accaggaact ggacatcaac   6960
cggctgtccg actacgatgt ggaccatatc gtgcctcaga gctttctgaa ggacgactcc   7020
atcgacaaca aggtgctgac cagaagcgac aagaaccggg gcaagagcga caacgtgccc   7080
tccgaagagg tcgtgaagaa gatgaagaac tactggcggc agctgctgaa cgccaagctg   7140
attacccaga gaaagttcga caatctgacc aaggccgaga gaggcggcct gagcgaactg   7200
gataaggccg gcttcatcaa gagacagctg gtggaaaccc ggcagatcac aaagcacgtg   7260
gcacagatcc tggactcccg gatgaacact aagtacgacg agaatgacaa gctgatccgg   7320
gaagtgaaag tgatcaccct gaagtccaag ctggtgtccg atttccggaa ggatttccag   7380
ttttacaaag tgcgcgagat caacaactac caccacgccc acgacgccta cctgaacgcc   7440
gtcgtgggaa ccgccctgat caaaaagtac cctaagctgg aaagcgagtt cgtgtacggc   7500
gactacaagg tgtacgacgt gcggaagatg atcgccaaga gcgagcagga aatcggcaag   7560
gctaccgcca agtacttctt ctacagcaac atcatgaact tttcaagac cgagattacc    7620
ctggccaacg gcgagatccg gaagcggcct ctgatcgaga caaacggcga aaccggggag   7680
atcgtgtggg ataagggccg ggattttgcc accgtgcgga aagtgctgag catgccccaa   7740
gtgaatatcg tgaaaaagac cgaggtgcag acaggcggct tcagcaaaga gtctatcctg   7800
cccaagagga acagcgataa gctgatcgcc agaaagaagg actgggaccc taagaagtac   7860
ggcggcttcg acagccccac cgtggcctat tctgtgctgg tggtggccaa agtggaaaag   7920
ggcaagtcca agaaactgaa gagtgtgaaa gagctgctgg ggatcaccat catggaaaga   7980
agcagcttcg agaagaatcc catcgacttt ctggaagcca agggctacaa agaagtgaaa   8040
aaggacctga tcatcaagct gcctaagtac tccctgttcg agctggaaaa cggccggaag   8100
agaatgctgg cctctgccgg cgaactgcag aagggaaacg aactggccct gccctccaaa   8160
tatgtgaact tcctgtacct ggccagccac tatgagaagc tgaagggctc cccgaggat    8220
aatgagcaga aacagctgtt tgtggaacag cacaagcact acctggacga gatcatcgag   8280
cagatcagcg agttctccaa gagagtgatc ctggccgacg ctaatctgga caaagtgctg   8340
tccgcctaca acaagcaccg ggataagccc atcagagagc aggccgagaa tatcatccac   8400
ctgtttaccc tgaccaatct gggagcccct gccgccttca agtactttga caccaccatc   8460
gaccggaaga ggtacaccag caccaaagag gtgctggacg ccaccctgat ccaccagagc   8520
atcaccggcc tgtacgagac acggatcgac ctgtctcagc tgggaggcga caagcgtcct   8580
gctgctacta agaaagctgg tcaagctaag aaaaagaaag ctagcggcag cggcgccacc   8640
aacttcagcc tgctgaagca ggccggcgac gtggaggaga accccggccc catgaccgag   8700
tacaagccca cggtgcgcct cgccacccgc gacgacgtcc ccagggccgt acgcaccctc   8760
```

gccgccgcgt tcgccgacta ccccgccacg cgccacaccg tcgatccgga ccgccacatc 8820
gagcgggtca ccgagctgca agaactcttc ctcacgcgcg tcgggctcga catcggcaag 8880
gtgtgggtcg cggacgacgg cgcggccgtg gcggtctgga ccacgccgga gagcgtcgaa 8940
gcgggggcgg tgttcgccga gatcggcccg cgcatggccg agttgagcgg ttcccggctg 9000
gccgcgcagc aacagatgga aggcctcctg gcgccgcacc ggcccaagga gcccgcgtgg 9060
ttcctggcca ccgtcggagt ctcgcccgac caccagggca agggtctggg cagcgccgtc 9120
gtgctccccg gagtggaggc ggccgagcgc gccggggtgc ccgccttcct ggagacctcc 9180
gcgccccgca acctcccctt ctacgagcgg ctcggcttca ccgtcaccgc cgacgtcgag 9240
gtgcccgaag gaccgcgcac ctggtgcatg acccgcaagc ccggtgcctg aacgcgttaa 9300
gtcgacaatc aacctctgga ttacaaaatt tgtgaaagat tgactggtat tcttaactat 9360
gttgctcctt ttacgctatg tggatacgct gctttaatgc ctttgtatca tgctattgct 9420
tcccgtatgg ctttcatttt ctcctccttg tataaatcct ggttgctgtc tctttatgag 9480
gagttgtggc ccgttgtcag gcaacgtggc gtggtgtgca ctgtgtttgc tgacgcaacc 9540
cccactggtt ggggcattgc caccacctgt cagctccttt ccgggacttt cgctttcccc 9600
ctccctattg ccacggcgga actcatcgcc gcctgccttg cccgctgctg gacaggggct 9660
cggctgttgg gcactgacaa ttccgtggtg ttgtcgggga aatcatcgtc ctttccttgg 9720
ctgctcgcct gtgttgccac ctggattctg cgcgggacgt ccttctgcta cgtcccttcg 9780
gccctcaatc cagcggacct tccttcccgc ggcctgctgc cggctctgcg gcctcttccg 9840
cgtcttcgcc ttcgccctca gacgagtcgg atctcccttt gggccgcctc cccgcgtcga 9900
ctttaagacc aatgacttac aaggcagctg tagatcttag ccacttttta aaagaaaagg 9960
ggggactgga agggctaatt cactcccaac gaagacaaga tctgcttttt gcttgtactg 10020
ggtctctctg gttagaccag atctgagcct gggagctctc tggctaacta gggaacccac 10080
tgcttaagcc tcaataaagc ttgccttgag tgcttcaagt agtgtgtgcc cgtctgttgt 10140
gtgactctgg taactagaga tccctcagac ccttttagtc agtgtggaaa atctctagca 10200
gtacgtatag tagttcatgt catcttatta ttcagtattt ataacttgca aagaaatgaa 10260
tatcagagag tgagaggaac ttgtttattg cagcttataa tggttacaaa taaagcaata 10320
gcatcacaaa tttcacaaat aaagcatttt tttcactgca ttctagttgt ggtttgtcca 10380
aactcatcaa tgtatcttat catgtctggc tctagctatc ccgcccctaa ctccgcccat 10440
cccgccccta actccgccca gttccgccca ttctccgccc catggctgac taattttttt 10500
tatttatgca gaggccgagg ccgcctcggc ctctgagcta ttccagaagt agtgaggagg 10560 ctttttttgga ggcctaggga cgtacccaat tcgccctata gtgagtcgta ttacgcgcgc 10620
tcactggccg tcgttttaca acgtcgtgac tgggaaaacc ctggcgttac ccaacttaat 10680
cgccttgcag cacatccccc tttcgccagc tggcgtaata gcgaagaggc ccgcaccgat 10740
cgcccttccc aacagttgcg cagcctgaat ggcgaatggg acgcgccctg tagcggcgca 10800
ttaagcgcgg cgggtgtggt ggttacgcgc agcgtgaccg ctacacttgc cagcgcccta 10860
gcgcccgctc ctttcgcttt cttcccttcc tttctcgcca cgttcgccgg ctttccccgt 10920
caagctctaa atcgggggct ccctttaggg ttccgattta gtgctttacg gcacctcgac 10980
cccaaaaaac ttgattaggg tgatggttca cgtagtgggc catcgccctg atagacggtt 11040
tttcgccctt tgacgttgga gtccacgttc tttaatagtg gactcttgtt ccaaactgga 11100
acaacactca accctatctc ggtctattct tttgatttat aagggatttt gccgatttcg 11160

```
gcctattggt taaaaaatga gctgatttaa caaaaattta acgcgaattt taacaaaata  11220

ttaacgctta caatttaggt ggcacttttc ggggaaatgt gcgcggaacc cctatttgtt  11280

tatttttcta aatacattca aatatgtatc cgctcatgag acaataaccc tgataaatgc  11340

ttcaataata ttgaaaaagg aagagtatga gtattcaaca tttccgtgtc gcccttattc  11400

cctttttgc ggcattttgc cttcctgttt ttgctcaccc agaaacgctg gtgaaagtaa  11460

aagatgctga agatcagttg ggtgcacgag tgggttacat cgaactggat ctcaacagcg  11520

gtaagatcct tgagagtttt cgccccgaag aacgttttcc aatgatgagc acttttaaag  11580

ttctgctatg tggcgcggta ttatcccgta ttgacgccgg gcaagagcaa ctcggtcgcc  11640

gcatacacta ttctcagaat gacttggttg agtactcacc agtcacagaa aagcatctta  11700

cggatggcat gacagtaaga gaattatgca gtgctgccat aaccatgagt gataacactg  11760

cggccaactt acttctgaca acgatcggag gaccgaagga gctaaccgct tttttgcaca  11820

acatgggga tcatgtaact cgccttgatc gttgggaacc ggagctgaat gaagccatac  11880

caaacgacga gcgtgacacc acgatgcctg tagcaatggc aacaacgttg cgcaaactat  11940

taactggcga actacttact ctagcttccc ggcaacaatt aatagactgg atggaggcgg  12000

ataaagttgc aggaccactt ctgcgctcgg cccttccggc tggctggttt attgctgata  12060

aatctggagc cggtgagcgt gggtctcgcg gtatcattgc agcactgggg ccagatggta  12120

agccctcccg tatcgtagtt atctacacga cggggagtca ggcaactatg gatgaacgaa  12180

atagacagat cgctgagata ggtgcctcac tgattaagca ttggtaactg tcagaccaag  12240

tttactcata tatactttag attgatttaa aacttcattt ttaatttaaa aggatctagg  12300

tgaagatcct ttttgataat ctcatgacca aaatccctta acgtgagttt tcgttccact  12360

gagcgtcaga ccccgtagaa aagatcaaag gatcttcttg agatcctttt tttctgcgcg  12420

taatctgctg cttgcaaaca aaaaaaccac cgctaccagc ggtggtttgt ttgccggatc  12480

aagagctacc aactcttttt ccgaaggtaa ctggcttcag cagagcgcag ataccaaata  12540

ctgttcttct agtgtagccg tagttaggcc accacttcaa gaactctgta gcaccgccta  12600

catacctcgc tctgctaatc ctgttaccag tggctgctgc cagtggcgat aagtcgtgtc  12660

ttaccgggtt ggactcaaga cgatagttac cggataaggc gcagcggtcg ggctgaacgg  12720

ggggttcgtg cacacagccc agc                                          12743
```

<210> SEQ ID NO 300
<211> LENGTH: 14873
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 300

```
gtcgacggat cgggagatct cccgatcccc tatggtgcac tctcagtaca atctgctctg     60

atgccgcata gttaagccag tatctgctcc ctgcttgtgt gttggaggtc gctgagtagt    120

gcgcgagcaa aatttaagct acaacaaggc aaggcttgac cgacaattgc atgaagaatc    180

tgcttagggt taggcgtttt gcgctgcttc gcgatgtacg ggccagatat acgcgttgac    240

attgattatt gactagttat taatagtaat caattacggg gtcattagtt catagcccat    300

atatggagtt ccgcgttaca taacttacgg taaatggccc gcctggctga ccgcccaacg    360
```

-continued

```
acccccgccc attgacgtca ataatgacgt atgttcccat agtaacgcca atagggactt    420
tccattgacg tcaatgggtg gagtatttac ggtaaactgc ccacttggca gtacatcaag    480
tgtatcatat gccaagtacg ccccctattg acgtcaatga cggtaaatgg cccgcctggc    540
attatgccca gtacatgacc ttatgggact ttcctacttg gcagtacatc tacgtattag    600
tcatcgctat taccatggtg atgcggtttt ggcagtacat caatgggcgt ggatagcggt    660
ttgactcacg gggatttcca agtctccacc ccattgacgt caatgggagt ttgttttggc    720
accaaaatca acgggacttt ccaaaatgtc gtaacaactc cgccccattg acgcaaatgg    780
gcggtaggcg tgtacggtgg gaggtctata taagcagcgc gttttgcctg tactgggtct    840
ctctggttag accagatctg agcctgggag ctctctggct aactagggaa cccactgctt    900
aagcctcaat aaagcttgcc ttgagtgctt caagtagtgt gtgcccgtct gttgtgtgac    960
tctggtaact agagatccct cagacccttt tagtcagtgt ggaaaatctc tagcagtggc   1020
gcccgaacag ggacttgaaa gcgaaaggga aaccagagga gctctctcga cgcaggactc   1080
ggcttgctga agcgcgcacg gcaagaggcg aggggcggcg actggtgagt acgccaaaaa   1140
ttttgactag cggaggctag aaggagagag atgggtgcga gagcgtcagt attaagcggg   1200
ggagaattag atcgcgatgg gaaaaaattc ggttaaggcc agggggaaag aaaaaatata   1260
aattaaaaca tatagtatgg gcaagcaggg agctagaacg attcgcagtt aatcctggcc   1320
tgttagaaac atcagaaggc tgtagacaaa tactgggaca gctacaacca tcccttcaga   1380
caggatcaga agaacttaga tcattatata atacagtagc aaccctctat tgtgtgcatc   1440
aaaggataga gataaaagac accaaggaag ctttagacaa gatagaggaa gagcaaaaca   1500
aaagtaagac caccgcacag caagcggccg ctgatcttca gacctggagg aggagatatg   1560
agggacaatt ggagaagtga attatataaa tataaagtag taaaaattga accattagga   1620
gtagcaccca ccaaggcaaa gagaagagtg gtgcagagag aaaaaagagc agtgggaata   1680
ggagctttgt tccttgggtt cttgggagca gcaggaagca ctatgggcgc agcgtcaatg   1740
acgctgacgg tacaggccag acaattattg tctggtatag tgcagcagca gaacaatttg   1800
ctgagggcta ttgaggcgca acagcatctg ttgcaactca cagtctgggg catcaagcag   1860
ctccaggcaa gaatcctggc tgtggaaaga tacctaaagg atcaacagct cctggggatt   1920
tggggttgct ctggaaaact catttgcacc actgctgtgc cttggaatgc tagttggagt   1980
aataaatctc tggaacagat ttggaatcac acgacctgga tggagtggga cagagaaatt   2040
aacaattaca caagcttaat acactcctta attgaagaat cgcaaaacca gcaagaaaag   2100
aatgaacaag aattattgga attagataaa tgggcaagtt tgtggaattg gtttaacata   2160
acaaattggc tgtggtatat aaaattattc ataatgatag taggaggctt ggtaggttta   2220
agaatagttt ttgctgtact ttctatagtg aatagagtta ggcagggata ttcaccatta   2280
tcgtttcaga cccacctccc aaccccgagg ggacccgaca ggcccgaagg aatagaagaa   2340
gaaggtggag agagagacag agacagatcc attcgattag tgaacggatc ggcactgcgt   2400
gcgccaattc tgcagacaaa tggcagtatt catccacaat tttaaaagaa aaggggggat   2460
tggggggtac agtgcagggg aaagaatagt agacataata gcaacagaca tacaaactaa   2520
agaattacaa aaacaaatta caaaaattca aaattttcgg gtttattaca gggacagcag   2580
agatccagtt tggttaatta aggtaccgag ggcctatttc ccatgattcc ttcatatttg   2640
catatacgat acaaggctgt tagagagata attagaatta atttgactgt aaacacaaag   2700
atattagtac aaaatacgtg acgtagaaag taataatttc ttgggtagtt tgcagtttta   2760
```

```
aaattatgtt ttaaaatgga ctatcatatg cttaccgtaa cttgaaagta tttcgatttc   2820
ttggctttat atatcttgtg gaaaggacga aacaccggag acggttgtaa atgagcacac   2880
aaaatacaca tgctaaaata ttatattcta tgacctttat aaaatcaacc aaaatcttct   2940
ttttaataac tttagtatca ataattagaa tttttatgtt cctttttgca aacttttaat   3000
aaaaatgagc aaaataaaaa aacgctagtt ttagtaactc gcgttgtttt cttcaccttt   3060
aataatagct actccaccac ttgttcctaa gcggtcagct cctgcttcaa tcattttttg   3120
agcatcttca aatgttctaa ctccaccagc tgctttaact aaagcattgt ctttaacaac   3180
tgacttcatt agtttaacat cttcaaatgt tgcacctgat tttgaaaatc ctgttgatgt   3240
tttaacaaat tctaatccag cttcaacagc tatttcacaa gctttcatga tttcttcttt   3300
tgttaataaa caattttcca taatacattt aacaacatgt gatccagctg cttttttttac   3360
agctttcatg tcttctaaaa ctaattcata atttttgtct tttaatgcac caatatttaa   3420
taccatatca atttctgttg caccatcttt aattgcttca gaaacttcga atgcttttgt   3480
agctgttgtg catgcaccta gaggaaaacc tacaacattt gttattccta catttgtgcc   3540
ttttaataat tctttacaat agcttgttca atatgaatta acacaaactg ttgcaaaatc   3600
aaattcaatt gcttcatcac ataattgttt aatttcagct ttcgtagcat cttgttttaa   3660
taatgtgtga tctatatatt tgtttagttt catttttttct cctatatatt catttttaat   3720
tttaattctt taataatttc gtctacttta actttagcgt tttgaacaga ttcaccaaca   3780
cctataaaat aaatttttag tttaggttca gttccacttg ggcgaacagc aaatcatgac   3840
ttatcttcta aataaaattt tagtaagtct tgtcctggca tattatacat tccatcgatg   3900
tagtcttcaa cattaacaac tttaagtcca gcaatttgag ttaagggtgt tgctctcaat   3960
gatttcatta atggttcaat ttttaatttc ttttcttctg gtttaaaatt caagtttaaa   4020
gtgaaagtgt aatatgcacc catttcttta aataaatctt ctaaatagtc tactaatgtt   4080
ttattttgtt ttttataaaa tcaagcagcc tctgctatta atatagaagc ttgtattcca   4140
tctttatctc tagctgagtc atcaattaca tatccataac tttcttcata agcaaaaaca   4200
aaatttaatc cgttatcttc ttctttagca atttctctac ccattcattt aaatccagtt   4260
aaagttttta caatattaac tccatatttt tcatgagcga ttctatcacc caaatcactt   4320
gttacaaaac ttgaatatag agccggattt tttggaatgc tatttaagcg ttttagattt   4380
gataattttc aatcaattaa aattggtcct gtttgatttc catctaatct tacaaaatga   4440
ccatcatgtt ttattgccat tccaaatctg tcagcatctg ggtcattcat aataataata   4500
tctgcatcat gtttaatacc atattcaagc ggtatttttc atgcaggatc aaattctgga   4560
tttggattta caacattttt aaatgtttca tcttcaaatg catgctcttc aacctcaata   4620
acgttatatc ctgattcacg taatattttt ggggtaaatt tagttcctgt tccattaact   4680
gcgctaaaaa taatttttaa atctttttta gcttcttgct ctttttgta cgtctctgtt   4740
ttagagctag aaatagcaag ttaaaataag gctagtccgt tatcaacttg aaaaagtggc   4800
accgagtcgg tgcttttttg aattcgctag ctaggtcttg aaaggagtgg gaattggctc   4860
cggtgcccgt cagtgggcag agcgcacatc gcccacagtc cccgagaagt tggggggagg   4920
ggtcggcaat tgatccggtg cctagagaag gtggcgcggg gtaaactggg aaagtgatgt   4980
cgtgtactgg ctccgccttt ttcccgaggg tgggggagaa ccgtatataa gtgcagtagt   5040
cgccgtgaac gttctttttc gcaacgggtt tgccgccaga acacaggacc ggttctagag   5100
```

```
cgctgccacc atggacaaga agtacagcat cggcctggac atcggcacca actctgtggg   5160
ctgggccgtg atcaccgacg agtacaaggt gcccagcaag aaattcaagg tgctgggcaa   5220
caccgaccgg cacagcatca agaagaacct gatcggagcc ctgctgttcg acagcggcga   5280
aacagccgag gccacccggc tgaagagaac cgccagaaga agatacacca gacggaagaa   5340
ccggatctgc tatctgcaag agatcttcag caacgagatg gccaaggtgg acgacagctt   5400
cttccacaga ctggaagagt ccttcctggt ggaagaggat aagaagcacg agcggcaccc   5460
catcttcggc aacatcgtgg acgaggtggc ctaccacgag aagtacccca ccatctacca   5520
cctgagaaag aaactggtgg acagcaccga caaggccgac ctgcggctga tctatctggc   5580
cctggcccac atgatcaagt tccggggcca cttcctgatc gagggcgacc tgaaccccga   5640
caacagcgac gtggacaagc tgttcatcca gctggtgcag acctacaacc agctgttcga   5700
ggaaaacccc atcaacgcca gcggcgtgga cgccaaggcc atcctgtctg ccagactgag   5760
caagagcaga cggctggaaa atctgatcgc ccagctgccc ggcgagaaga agaatggcct   5820
gttcggaaac ctgattgccc tgagcctggg cctgaccccc aacttcaaga gcaacttcga   5880
cctggccgag gatgccaaac tgcagctgag caaggacacc tacgacgacg acctggacaa   5940
cctgctggcc cagatcggcg accagtacgc cgacctgttt ctggccgcca agaacctgtc   6000
cgacgccatc ctgctgagcg acatcctgag agtgaacacc gagatcacca aggcccccct   6060
gagcgcctct atgatcaaga gatacgacga gcaccaccag gacctgaccc tgctgaaagc   6120
tctcgtgcgg cagcagctgc ctgagaagta caaagagatt ttcttcgacc agagcaagaa   6180
cggctacgcc ggctacattg acggcggagc cagccaggaa gagttctaca agttcatcaa   6240
gcccatcctg gaaaagatgg acggcaccga ggaactgctc gtgaagctga acagagagga   6300
cctgctgcgg aagcagcgga ccttcgacaa cggcagcatc ccccaccaga tccacctggg   6360
agagctgcac gccattctgc ggcggcagga agatttttac ccattcctga aggacaaccg   6420
ggaaaagatc gagaagatcc tgaccttccg catcccctac tacgtgggcc ctctggccag   6480
gggaaacagc agattcgcct ggatgaccag aaagagcgag gaaaccatca ccccctggaa   6540
cttcgaggaa gtggtggaca agggcgcttc cgcccagagc ttcatcgagc ggatgaccaa   6600
cttcgataag aacctgccca acgagaaggt gctgcccaag cacagcctgc tgtacgagta   6660
cttcaccgtg tataacgagc tgaccaaagt gaaatacgtg accgagggaa tgagaaagcc   6720
cgccttcctg agcggcgagc agaaaaaggc catcgtggac ctgctgttca agaccaaccg   6780
gaaagtgacc gtgaagcagc tgaaagagga ctacttcaag aaaatcgagt gcttcgactc   6840
cgtggaaatc tccggcgtgg aagatcggtt caacgcctcc ctgggcacat accacgatct   6900
gctgaaaatt atcaaggaca aggacttcct ggacaatgag gaaaacgagg acattctgga   6960
agatatcgtg ctgaccctga cactgtttga ggacagagag atgatcgagg aacggctgaa   7020
aacctatgcc cacctgttcg acgacaaagt gatgaagcag ctgaagcggc ggagatacac   7080
cggctggggc aggctgagcc ggaagctgat caacggcatc cgggacaagc agtccggcaa   7140
gacaatcctg gatttcctga agtccgacgg cttcgccaac agaaacttca tgcagctgat   7200
ccacgacgac agcctgacct ttaaagagga catccagaaa gcccaggtgt ccggccaggg   7260
cgatagcctg cacgagcaca ttgccaatct ggccggcagc cccgccatta agaagggcat   7320
cctgcagaca gtgaaggtgg tggacgagct cgtgaaagtg atgggccggc acaagcccga   7380
gaacatcgtg atcgaaatgg ccagagagaa ccagaccacc cagaagggac agaagaacag   7440
ccgcgagaga atgaagcgga tcgaagaggg catcaaagag ctgggcagcc agatcctgaa   7500
```

agaacacccc gtggaaaaca cccagctgca gaacgagaag ctgtacctgt actacctgca 7560
gaatgggcgg gatatgtacg tggaccagga actggacatc aaccggctgt ccgactacga 7620
tgtggaccat atcgtgcctc agagctttct gaaggacgac tccatcgaca acaaggtgct 7680
gaccagaagc gacaagaacc ggggcaagag cgacaacgtg ccctccgaag aggtcgtgaa 7740
gaagatgaag aactactggc ggcagctgct gaacgccaag ctgattaccc agagaaagtt 7800
cgacaatctg accaaggccg agagaggcgg cctgagcgaa ctggataagg ccggcttcat 7860
caagagacag ctggtggaaa cccggcagat cacaaagcac gtggcacaga tcctggactc 7920
ccggatgaac actaagtacg acgagaatga caagctgatc cgggaagtga aagtgatcac 7980
cctgaagtcc aagctggtgt ccgatttccg gaaggatttc cagttttaca aagtgcgcga 8040
gatcaacaac taccaccacg cccacgacgc ctacctgaac gccgtcgtgg gaaccgccct 8100
gatcaaaaag taccctaagc tggaaagcga gttcgtgtac ggcgactaca aggtgtacga 8160
cgtgcggaag atgatcgcca agagcgagca ggaaatcggc aaggctaccg ccaagtactt 8220
cttctacagc aacatcatga actttttcaa gaccgagatt accctggcca acggcgagat 8280
ccggaagcgg cctctgatcg agacaaacgg cgaaaccggg gagatcgtgt gggataaggg 8340
ccgggatttt gccaccgtgc ggaaagtgct gagcatgccc caagtgaata tcgtgaaaaa 8400
gaccgaggtg cagacaggcg gcttcagcaa agagtctatc ctgcccaaga ggaacagcga 8460
taagctgatc gccagaaaga aggactggga ccctaagaag tacggcggct tcgacagccc 8520
caccgtggcc tattctgtgc tggtggtggc caaagtggaa aagggcaagt ccaagaaact 8580
gaagagtgtg aaagagctgc tggggatcac catcatggaa agaagcagct tcgagaagaa 8640
tcccatcgac tttctggaag ccaagggcta caaagaagtg aaaaaggacc tgatcatcaa 8700
gctgcctaag tactccctgt tcgagctgga aaacggccgg aagagaatgc tggcctctgc 8760
cggcgaactg cagaagggaa acgaactggc cctgccctcc aaatatgtga acttcctgta 8820
cctggccagc cactatgaga agctgaaggg ctcccccgag gataatgagc agaaacagct 8880
gtttgtggaa cagcacaagc actacctgga cgagatcatc gagcagatca gcgagttctc 8940
caagagagtg atcctggccg acgctaatct ggacaaagtg ctgtccgcct acaacaagca 9000
ccgggataag cccatcagag agcaggccga gaatatcatc cacctgttta ccctgaccaa 9060
tctgggagcc cctgccgcct tcaagtactt tgacaccacc atcgaccgga agaggtacac 9120
cagcaccaaa gaggtgctgg acgccaccct gatccaccag agcatcaccg gcctgtacga 9180
gacacggatc gacctgtctc agctgggagg cgacaagcga cctgccgcca caaagaaggc 9240
tggacaggct aagaagaaga aagattacaa agacgatgac gataagggat ccggcgcaac 9300
aaacttctct ctgctgaaac aagccggaga tgtcgaagag aatcctggac cgaccgagta 9360
caagcccacg gtgcgcctcg ccacccgcga cgacgtcccc agggccgtac gcaccctcgc 9420
cgccgcgttc gccgactacc ccgccacgcg ccacaccgtc gatccggacc gccacatcga 9480
gcgggtcacc gagctgcaag aactcttcct cacgcgcgtc gggctcgaca tcggcaaggt 9540
gtgggtcgcg gacgacggcg ccgcggtggc ggtctggacc acgccggaga gcgtcgaagc 9600
gggggcggtg ttcgccgaga tcggcccgcg catggccgag ttgagcggtt cccggctggc 9660
cgcgcagcaa cagatggaag gcctcctggc gccgcaccgg cccaaggagc ccgcgtggtt 9720
cctggccacc gtcggagtct cgcccgacca ccagggcaag ggtctgggca gcgccgtcgt 9780
gctccccgga gtggaggcgg ccgagcgcgc cggggtgccc gccttcctgg agacctccgc 9840

```
gccccgcaac ctccccttct acgagcggct cggcttcacc gtcaccgccg acgtcgaggt   9900
gcccgaagga ccgcgcacct ggtgcatgac ccgcaagccc ggtgcctgaa cgcgttaagt   9960
cgacaatcaa cctctggatt acaaaatttg tgaaagattg actggtattc ttaactatgt  10020
tgctcctttt acgctatgtg gatacgctgc tttaatgcct ttgtatcatg ctattgcttc  10080
ccgtatggct ttcattttct cctccttgta taaatcctgg ttgctgtctc tttatgagga  10140
gttgtggccc gttgtcaggc aacgtggcgt ggtgtgcact gtgtttgctg acgcaacccc  10200
cactggttgg ggcattgcca ccacctgtca gctcctttcc gggactttcg ctttccccct  10260
ccctattgcc acggcggaac tcatcgccgc ctgccttgcc cgctgctgga caggggctcg  10320
gctgttgggc actgacaatt ccgtggtgtt gtcggggaaa tcatcgtcct ttccttggct  10380
gctcgcctgt gttgccacct ggattctgcg cgggacgtcc ttctgctacg tcccttcggc  10440
cctcaatcca gcggaccttc cttcccgcgg cctgctgccg gctctgcggc ctcttccgcg  10500
tcttcgcctt cgccctcaga cgagtcggat ctccctttgg gccgcctccc cgcgtcgact  10560
ttaagaccaa tgacttacaa ggcagctgta gatcttagcc actttttaaa agaaaagggg  10620
ggactggaag ggctaattca ctcccaacga agacaagatc tgctttttgc ttgtactggg  10680
tctctctggt tagaccagat ctgagcctgg gagctctctg gctaactagg gaacccactg  10740
cttaagcctc aataaagctt gccttgagtg cttcaagtag tgtgtgcccg tctgttgtgt  10800
gactctggta actagagatc cctcagaccc ttttagtcag tgtggaaaat ctctagcagg  10860
gcccgtttaa acccgctgat cagcctcgac tgtgccttct agttgccagc catctgttgt  10920
ttgcccctcc cccgtgcctt ccttgaccct ggaaggtgcc actcccactg tcctttccta  10980
ataaaatgag gaaattgcat cgcattgtct gagtaggtgt cattctattc tggggggtgg  11040
ggtggggcag gacagcaagg gggaggattg ggaagacaat agcaggcatg ctggggatgc  11100
ggtgggctct atggcttctg aggcggaaag aaccagctgg ggctctaggg ggtatcccca  11160
cgcgccctgt agcggcgcat taagcgcggc gggtgtggtg gttacgcgca gcgtgaccgc  11220
tacacttgcc agcgccctag cgcccgctcc tttcgctttc ttcccttcct ttctcgccac  11280
gttcgccggc tttccccgtc aagctctaaa tcgggggctc cctttagggt tccgatttag  11340
tgctttacgg cacctcgacc ccaaaaaact tgattagggt gatggttcac gtagtgggcc  11400
atcgccctga tagacggttt ttcgcccttt gacgttggag tccacgttct ttaatagtgg  11460
actcttgttc caaactggaa caacactcaa ccctatctcg gtctattctt ttgatttata  11520
agggattttg ccgatttcgg cctattggtt aaaaaatgag ctgatttaac aaaaatttaa  11580
cgcgaattaa ttctgtggaa tgtgtgtcag ttagggtgtg gaaagtcccc aggctcccca  11640
gcaggcagaa gtatgcaaag catgcatctc aattagtcag caaccaggtg tggaaagtcc  11700
ccaggctccc cagcaggcag aagtatgcaa agcatgcatc tcaattagtc agcaaccata  11760
gtcccgcccc taactccgcc catcccgccc ctaactccgc ccagttccgc ccattctccg  11820
ccccatggct gactaatttt ttttatttat gcagaggccg aggccgcctc tgcctctgag  11880
ctattccaga agtagtgagg aggctttttt ggaggcctag gcttttgcaa aaagctcccg  11940
ggagcttgta tatccatttt cggatctgat cagcacgtgt tgacaattaa tcatcggcat  12000
agtatatcgg catagtataa tacgacaagg tgaggaacta aaccatggcc aagttgacca  12060
gtgccgttcc ggtgctcacc gcgcgcgacg tcgccggagc ggtcgagttc tggaccgacc  12120
ggctcgggtt ctcccgggac ttcgtggagg acgacttcgc cggtgtggtc cgggacgacg  12180
tgaccctgtt catcagcgcg gtccaggacc aggtggtgcc ggacaacacc ctggcctggg  12240
```

tgtgggtgcg cggcctggac gagctgtacg ccgagtggtc ggaggtcgtg tccacgaact 12300
tccgggacgc ctccgggccg gccatgaccg agatcggcga gcagccgtgg gggcgggagt 12360
tcgccctgcg cgacccggcc ggcaactgcg tgcacttcgt ggccgaggag caggactgac 12420
acgtgctacg agatttcgat tccaccgccg ccttctatga aaggttgggc ttcggaatcg 12480
ttttccggga cgccggctgg atgatcctcc agcgcgggga tctcatgctg gagttcttcg 12540
cccaccccaa cttgtttatt gcagcttata atggttacaa ataaagcaat agcatcacaa 12600
atttcacaaa taaagcattt ttttcactgc attctagttg tggtttgtcc aaactcatca 12660
atgtatctta tcatgtctgt ataccgtcga cctctagcta gagcttggcg taatcatggt 12720
catagctgtt tcctgtgtga aattgttatc cgctcacaat tccacacaac atacgagccg 12780
gaagcataaa gtgtaaagcc tggggtgcct aatgagtgag ctaactcaca ttaattgcgt 12840
tgcgctcact gcccgctttc cagtcgggaa acctgtcgtg ccagctgcat taatgaatcg 12900
gccaacgcgc ggggagaggc ggtttgcgta ttgggcgctc ttccgcttcc tcgctcactg 12960
actcgctgcg ctcggtcgtt cggctgcggc gagcggtatc agctcactca aaggcggtaa 13020
tacggttatc cacagaatca ggggataacg caggaaagaa catgtgagca aaaggccagc 13080
aaaaggccag gaaccgtaaa aaggccgcgt tgctggcgtt tttccatagg ctccgccccc 13140
ctgacgagca tcacaaaaat cgacgctcaa gtcagaggtg gcgaaacccg acaggactat 13200
aaagatacca ggcgtttccc cctggaagct ccctcgtgcg ctctcctgtt ccgaccctgc 13260
cgcttaccgg atacctgtcc gcctttctcc cttcgggaag cgtggcgctt tctcatagct 13320
cacgctgtag gtatctcagt tcggtgtagg tcgttcgctc caagctgggc tgtgtgcacg 13380
aaccccccgt tcagcccgac cgctgcgcct tatccggtaa ctatcgtctt gagtccaacc 13440
cggtaagaca cgacttatcg ccactggcag cagccactgg taacaggatt agcagagcga 13500
ggtatgtagg cggtgctaca gagttcttga agtggtggcc taactacggc tacactagaa 13560
gaacagtatt tggtatctgc gctctgctga agccagttac cttcggaaaa agagttggta 13620
gctcttgatc cggcaaacaa accaccgctg gtagcggtgg tttttttgtt tgcaagcagc 13680
agattacgcg cagaaaaaaa ggatctcaag aagatccttt gatcttttct acggggtctg 13740
acgctcagtg gaacgaaaac tcacgttaag ggattttggt catgagatta tcaaaaagga 13800
tcttcaccta gatcctttta aattaaaaat gaagttttaa atcaatctaa agtatatatg 13860
agtaaacttg gtctgacagt taccaatgct taatcagtga ggcacctatc tcagcgatct 13920
gtctatttcg ttcatccata gttgcctgac tccccgtcgt gtagataact acgatacggg 13980
agggcttacc atctggcccc agtgctgcaa tgataccgcg agacccacgc tcaccggctc 14040
cagatttatc agcaataaac cagccagccg gaagggccga gcgcagaagt ggtcctgcaa 14100
ctttatccgc ctccatccag tctattaatt gttgccggga agctagagta agtagttcgc 14160
cagttaatag tttgcgcaac gttgttgcca ttgctacagg catcgtggtg tcacgctcgt 14220
cgtttggtat ggcttcattc agctccggtt cccaacgatc aaggcgagtt acatgatccc 14280
ccatgttgtg caaaaaagcg gttagctcct tcggtcctcc gatcgttgtc agaagtaagt 14340
tggccgcagt gttatcactc atggttatgg cagcactgca taattctctt actgtcatgc 14400
catccgtaag atgcttttct gtgactggtg agtactcaac caagtcattc tgagaatagt 14460
gtatgcggcg accgagttgc tcttgcccgg cgtcaatacg ggataatacc gcgccacata 14520
gcagaacttt aaaagtgctc atcattggaa aacgttcttc ggggcgaaaa ctctcaagga 14580
tcttaccgct gttgagatcc agttcgatgt aacccactcg tgcacccaac tgatcttcag 14640
catcttttac tttcaccagc gtttctgggt gagcaaaaac aggaaggcaa aatgccgcaa 14700
aaaagggaat aagggcgaca cggaaatgtt gaatactcat actcttcctt tttcaatatt 14760
attgaagcat ttatcagggt tattgtctca tgagcggata catatttgaa tgtatttaga 14820
aaaataaaca aataggggtt ccgcgcacat ttccccgaaa agtgccacct gac 14873

<210> SEQ ID NO 301
<211> LENGTH: 12860
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 301
gtcgacggat cgggagatct cccgatcccc tatggtgcac tctcagtaca atctgctctg 60
atgccgcata gttaagccag tatctgctcc ctgcttgtgt gttggaggtc gctgagtagt 120
gcgcgagcaa aatttaagct acaacaaggc aaggcttgac cgacaattgc atgaagaatc 180
tgcttagggt taggcgtttt gcgctgcttc gcgatgtacg ggccagatat acgcgttgac 240
attgattatt gactagttat taatagtaat caattacggg gtcattagtt catagcccat 300
atatggagtt ccgcgttaca taacttacgg taaatggccc gcctggctga ccgcccaacg 360
acccccgccc attgacgtca ataatgacgt atgttcccat agtaacgcca atagggactt 420
tccattgacg tcaatgggtg gagtatttac ggtaaactgc ccacttggca gtacatcaag 480
tgtatcatat gccaagtacg ccccctattg acgtcaatga cggtaaatgg cccgcctggc 540
attatgccca gtacatgacc ttatgggact ttcctacttg gcagtacatc tacgtattag 600
tcatcgctat taccatggtg atgcggtttt ggcagtacat caatgggcgt ggatagcggt 660
ttgactcacg gggatttcca agtctccacc ccattgacgt caatgggagt ttgttttggc 720
accaaaatca acgggacttt ccaaaatgtc gtaacaactc cgccccattg acgcaaatgg 780
gcggtaggcg tgtacggtgg gaggtctata taagcagcgc gttttgcctg tactgggtct 840
ctctggttag accagatctg agcctgggag ctctctggct aactagggaa cccactgctt 900
aagcctcaat aaagcttgcc ttgagtgctt caagtagtgt gtgcccgtct gttgtgtgac 960
tctggtaact agagatccct cagacccttt tagtcagtgt ggaaaatctc tagcagtggc 1020
gcccgaacag ggacttgaaa gcgaaaggga aaccagagga gctctctcga cgcaggactc 1080
ggcttgctga agcgcgcacg gcaagaggcg aggggcggcg actggtgagt acgccaaaaa 1140
ttttgactag cggaggctag aaggagagag atgggtgcga gagcgtcagt attaagcggg 1200
ggagaattag atcgcgatgg gaaaaaattc ggttaaggcc agggggaaag aaaaaatata 1260
aattaaaaca tatagtatgg gcaagcaggg agctagaacg attcgcagtt aatcctggcc 1320
tgttagaaac atcagaaggc tgtagacaaa tactgggaca gctacaacca tcccttcaga 1380
caggatcaga agaacttaga tcattatata atacagtagc aaccctctat tgtgtgcatc 1440
aaaggataga gataaaagac accaaggaag ctttagacaa gatagaggaa gagcaaaaca 1500
aaagtaagac caccgcacag caagcggccg ctgatcttca gacctggagg aggagatatg 1560
agggacaatt ggagaagtga attatataaa tataaagtag taaaaattga accattagga 1620
gtagcaccca ccaaggcaaa gagaagagtg gtgcagagag aaaaaagagc agtgggaata 1680
ggagctttgt tccttgggtt cttgggagca gcaggaagca ctatgggcgc agcgtcaatg 1740
acgctgacgg tacaggccag acaattattg tctggtatag tgcagcagca gaacaatttg 1800
ctgagggcta ttgaggcgca acagcatctg ttgcaactca cagtctgggg catcaagcag 1860
ctccaggcaa gaatcctggc tgtggaaaga tacctaaagg atcaacagct cctggggatt 1920
tggggttgct ctggaaaact catttgcacc actgctgtgc cttggaatgc tagttggagt 1980
aataaatctc tggaacagat ttggaatcac acgacctgga tggagtggga cagagaaatt 2040
aacaattaca caagcttaat acactcctta attgaagaat cgcaaaacca gcaagaaaag 2100
aatgaacaag aattattgga attagataaa tgggcaagtt tgtggaattg gtttaacata 2160
acaaattggc tgtggtatat aaaattattc ataatgatag taggaggctt ggtaggttta 2220
agaatagttt ttgctgtact ttctatagtg aatagagtta ggcagggata ttcaccatta 2280
tcgtttcaga cccacctccc aaccccgagg ggacccgaca ggcccgaagg aatagaagaa 2340
gaaggtggag agagagacag agacagatcc attcgattag tgaacggatc ggcactgcgt 2400
gcgccaattc tgcagacaaa tggcagtatt catccacaat tttaaaagaa aaggggggat 2460
tggggggtac agtgcagggg aaagaatagt agacataata gcaacagaca tacaaactaa 2520
agaattacaa aaacaaatta caaaaattca aaattttcgg gtttattaca gggacagcag 2580
agatccagtt tggttaatta agctagctag gtcttgaaag gagtgggaat tggctccggt 2640
gcccgtcagt gggcagagcg cacatcgccc acagtccccg agaagttggg gggagggggtc 2700 ggcaattgat ccggtgccta gagaaggtgg cgcggggtaa actgggaaag tgatgtcgtg 2760
tactggctcc gcctttttcc cgagggtggg ggagaaccgt atataagtgc agtagtcgcc 2820
gtgaacgttc tttttcgcaa cgggtttgcc gccagaacac aggaccggtt ctagagcgct 2880
gccaccatgg acaagaagta cagcatcggc ctggacatcg gcaccaactc tgtgggctgg 2940
gccgtgatca ccgacgagta caaggtgccc agcaagaaat tcaaggtgct gggcaacacc 3000
gaccggcaca gcatcaagaa gaacctgatc ggagccctgc tgttcgacag cggcgaaaca 3060
gccgaggcca cccggctgaa gagaaccgcc agaagaagat acaccagacg gaagaaccgg 3120
atctgctatc tgcaagagat cttcagcaac gagatggcca aggtggacga cagcttcttc 3180
cacagactgg aagagtcctt cctggtggaa gaggataaga agcacgagcg gcaccccatc 3240
ttcggcaaca tcgtggacga ggtggcctac cacgagaagt accccaccat ctaccacctg 3300
agaaagaaac tggtggacag caccgacaag gccgacctgc ggctgatcta tctggccctg 3360
gcccacatga tcaagttccg gggccacttc ctgatcgagg gcgacctgaa ccccgacaac 3420
agcgacgtgg acaagctgtt catccagctg gtgcagacct acaaccagct gttcgaggaa 3480
aaccccatca acgccagcgg cgtggacgcc aaggccatcc tgtctgccag actgagcaag 3540
agcagacggc tggaaaatct gatcgcccag ctgcccggcg agaagaagaa tggcctgttc 3600
ggaaacctga ttgccctgag cctgggcctg acccccaact tcaagagcaa cttcgacctg 3660
gccgaggatg ccaaactgca gctgagcaag gacacctacg acgacgacct ggacaacctg 3720
ctggcccaga tcggcgacca gtacgccgac ctgtttctgg ccgccaagaa cctgtccgac 3780
gccatcctgc tgagcgacat cctgagagtg aacaccgaga tcaccaaggc ccccctgagc 3840
gcctctatga tcaagagata cgacgagcac caccaggacc tgaccctgct gaaagctctc 3900
gtgcggcagc agctgcctga gaagtacaaa gagattttct tcgaccagag caagaacggc 3960
tacgccggct acattgacgg cggagccagc caggaagagt tctacaagtt catcaagccc 4020
atcctggaaa agatggacgg caccgaggaa ctgctcgtga agctgaacag agaggacctg 4080

-continued ctgcggaagc agcggacctt cgacaacggc agcatccccc accagatcca cctgggagag 4140
ctgcacgcca ttctgcggcg gcaggaagat tttaccccat tcctgaagga caaccgggaa 4200
aagatcgaga agatcctgac cttccgcatc ccctactacg tgggccctct ggccagggga 4260
aacagcagat tcgcctggat gaccagaaag agcgaggaaa ccatcacccc ctggaacttc 4320
gaggaagtgg tggacaaggg cgcttccgcc cagagcttca tcgagcggat gaccaacttc 4380
gataagaacc tgcccaacga gaaggtgctg cccaagcaca gcctgctgta cgagtacttc 4440
accgtgtata acgagctgac caaagtgaaa tacgtgaccg agggaatgag aaagcccgcc 4500
ttcctgagcg gcgagcagaa aaaggccatc gtggacctgc tgttcaagac caaccggaaa 4560
gtgaccgtga agcagctgaa agaggactac ttcaagaaaa tcgagtgctt cgactccgtg 4620
gaaatctccg gcgtggaaga tcggttcaac gcctccctgg gcacatacca cgatctgctg 4680
aaaattatca aggacaagga cttcctggac aatgaggaaa acgaggacat tctggaagat 4740
atcgtgctga ccctgacact gtttgaggac agagagatga tcgaggaacg gctgaaaacc 4800
tatgcccacc tgttcgacga caaagtgatg aagcagctga agcggcggag atacaccggc 4860
tggggcaggc tgagccggaa gctgatcaac ggcatccggg acaagcagtc cggcaagaca 4920
atcctggatt tcctgaagtc cgacggcttc gccaacagaa acttcatgca gctgatccac 4980
gacgacagcc tgacctttaa agaggacatc cagaaagccc aggtgtccgg ccagggcgat 5040
agcctgcacg agcacattgc caatctggcc ggcagccccg ccattaagaa gggcatcctg 5100
cagacagtga aggtggtgga cgagctcgtg aaagtgatgg gccggcacaa gcccgagaac 5160
atcgtgatcg aaatggccag agagaaccag accacccaga agggacagaa gaacagccgc 5220
gagagaatga agcggatcga agagggcatc aaagagctgg gcagccagat cctgaaagaa 5280
caccccgtgg aaaacaccca gctgcagaac gagaagctgt acctgtacta cctgcagaat 5340
gggcgggata tgtacgtgga ccaggaactg gacatcaacc ggctgtccga ctacgatgtg 5400
gaccatatcg tgcctcagag ctttctgaag gacgactcca tcgacaacaa ggtgctgacc 5460
agaagcgaca agaaccgggg caagagcgac aacgtgccct ccgaagaggt cgtgaagaag 5520
atgaagaact actggcggca gctgctgaac gccaagctga ttacccagag aaagttcgac 5580
aatctgacca aggccgagag aggcggcctg agcgaactgg ataaggccgg cttcatcaag 5640
agacagctgg tggaaacccg gcagatcaca aagcacgtgg cacagatcct ggactcccgg 5700
atgaacacta agtacgacga gaatgacaag ctgatccggg aagtgaaagt gatcaccctg 5760
aagtccaagc tggtgtccga tttccggaag gatttccagt tttacaaagt gcgcgagatc 5820
aacaactacc accacgccca cgacgcctac ctgaacgccg tcgtgggaac cgccctgatc 5880
aaaaagtacc ctaagctgga aagcgagttc gtgtacggcg actacaaggt gtacgacgtg 5940
cggaagatga tcgccaagag cgagcaggaa atcggcaagg ctaccgccaa gtacttcttc 6000
tacagcaaca tcatgaactt tttcaagacc gagattaccc tggccaacgg cgagatccgg 6060
aagcggcctc tgatcgagac aaacggcgaa accggggaga tcgtgtggga taagggccgg 6120
gattttgcca ccgtgcggaa agtgctgagc atgccccaag tgaatatcgt gaaaaagacc 6180
gaggtgcaga caggcggctt cagcaaagag tctatcctgc ccaagaggaa cagcgataag 6240
ctgatcgcca gaaagaagga ctgggaccct aagaagtacg gcggcttcga cagccccacc 6300
gtggcctatt ctgtgctggt ggtggccaaa gtggaaaagg gcaagtccaa gaaactgaag 6360
agtgtgaaag agctgctggg gatcaccatc atggaaagaa gcagcttcga gaagaatccc 6420
atcgactttc tggaagccaa gggctacaaa gaagtgaaaa aggacctgat catcaagctg 6480
cctaagtact ccctgttcga gctggaaaac ggccggaaga gaatgctggc ctctgccggc 6540
gaactgcaga agggaaacga actggccctg ccctccaaat atgtgaactt cctgtacctg 6600
gccagccact atgagaagct gaagggctcc cccgaggata atgagcagaa acagctgttt 6660
gtggaacagc acaagcacta cctggacgag atcatcgagc agatcagcga gttctccaag 6720
agagtgatcc tggccgacgc taatctggac aaagtgctgt ccgcctacaa caagcaccgg 6780
gataagccca tcagagagca ggccgagaat atcatccacc tgtttaccct gaccaatctg 6840
ggagcccctg ccgccttcaa gtactttgac accaccatcg accggaagag gtacaccagc 6900
accaaagagg tgctggacgc caccctgatc caccagagca tcaccggcct gtacgagaca 6960
cggatcgacc tgtctcagct gggaggcgac aagcgacctg ccgccacaaa gaaggctgga 7020
caggctaaga agaagaaaga ttacaaagac gatgacgata agggatccgg cgcaacaaac 7080
ttctctctgc tgaaacaagc cggagatgtc gaagagaatc ctggaccgat ggccaagcct 7140
ttgtctcaag aagaatccac cctcattgaa agagcaacgg ctacaatcaa cagcatcccc 7200
atctctgaag actacagcgt cgccagcgca gctctctcta gcgacggccg catcttcact 7260
ggtgtcaatg tatatcattt tactggggga ccttgtgcag aactcgtggt gctgggcact 7320
gctgctgctg cggcagctgg caacctgact tgtatcgtcg cgatcggaaa tgagaacagg 7380
ggcatcttga gcccctgcgg acggtgccga caggtgcttc tcgatctgca tcctgggatc 7440
aaagccatag tgaaggacag tgatggacag ccgacggcag ttgggattcg tgaattgctg 7500
ccctctggtt atgtgtggga gggctaagaa ttcgatatca agcttatcga taatcaacct 7560
ctggattaca aaatttgtga aagattgact ggtattctta actatgttgc tccttttacg 7620
ctatgtggat acgctgcttt aatgcctttg tatcatgcta ttgcttcccg tatggctttc 7680
attttctcct ccttgtataa atcctggttg ctgtctcttt atgaggagtt gtggcccgtt 7740
gtcaggcaac gtggcgtggt gtgcactgtg tttgctgacg caacccccac tggttggggc 7800
attgccacca cctgtcagct cctttccggg actttcgctt tccccctccc tattgccacg 7860
gcggaactca tcgccgcctg ccttgcccgc tgctggacag gggctcggct gttgggcact 7920
gacaattccg tggtgttgtc ggggaaatca tcgtcctttc cttggctgct cgcctgtgtt 7980
gccacctgga ttctgcgcgg gacgtccttc tgctacgtcc cttcggccct caatccagcg 8040
gaccttcctt cccgcggcct gctgccggct ctgcggcctc ttccgcgtct tcgccttcgc 8100
cctcagacga gtcggatctc cctttgggcc gcctccccgc atcgataccg tcgacctcga 8160
gacctagaaa aacatggagc aatcacaagt agcaatacag cagctaccaa tgctgattgt 8220
gcctggctag aagcacaaga ggaggaggag gtgggttttc cagtcacacc tcaggtacct 8280
ttaagaccaa tgacttacaa ggcagctgta gatcttagcc actttttaaa agaaaagggg 8340
ggactggaag ggctaattca ctcccaacga agacaagata tccttgatct gtggatctac 8400
cacacacaag gctacttccc tgattggcag aactacacac cagggccagg gatcagatat 8460
ccactgacct ttggatggtg ctacaagcta gtaccagttg agcaagagaa ggtagaagaa 8520
gccaatgaag gagagaacac ccgcttgtta caccctgtga gcctgcatgg gatggatgac 8580
ccggagagag aagtattaga gtggaggttt gacagccgcc tagcatttca tcacatggcc 8640
cgagagctgc atccggactg tactgggtct ctctggttag accagatctg agcctgggag 8700
ctctctggct aactagggaa cccactgctt aagcctcaat aaagcttgcc ttgagtgctt 8760
caagtagtgt gtgcccgtct gttgtgtgac tctggtaact agagatccct cagacccttt 8820

```
tagtcagtgt ggaaaatctc tagcagggcc cgtttaaacc cgctgatcag cctcgactgt   8880
gccttctagt tgccagccat ctgttgtttg cccctccccc gtgccttcct tgaccctgga   8940
aggtgccact cccactgtcc tttcctaata aaatgaggaa attgcatcgc attgtctgag   9000
taggtgtcat tctattctgg ggggtggggt ggggcaggac agcaaggggg aggattggga   9060
agacaatagc aggcatgctg gggatgcggt gggctctatg gcttctgagg cggaaagaac   9120
cagctggggc tctagggggt atccccacgc gccctgtagc ggcgcattaa gcgcggcggg   9180
tgtggtggtt acgcgcagcg tgaccgctac acttgccagc gccctagcgc ccgctccttt   9240
cgctttcttc ccttcctttc tcgccacgtt cgccggcttt ccccgtcaag ctctaaatcg   9300
ggggctccct ttagggttcc gatttagtgc tttacggcac ctcgacccca aaaaacttga   9360
ttagggtgat ggttcacgta gtgggccatc gccctgatag acggtttttc gccctttgac   9420
gttggagtcc acgttcttta atagtggact cttgttccaa actggaacaa cactcaaccc   9480
tatctcggtc tattcttttg atttataagg gattttgccg atttcggcct attggttaaa   9540
aaatgagctg atttaacaaa aatttaacgc gaattaattc tgtggaatgt gtgtcagtta   9600
gggtgtggaa agtccccagg ctccccagca ggcagaagta tgcaaagcat gcatctcaat   9660
tagtcagcaa ccaggtgtgg aaagtcccca ggctccccag caggcagaag tatgcaaagc   9720
atgcatctca attagtcagc aaccatagtc ccgcccctaa ctccgcccat cccgccccta   9780
actccgccca gttccgccca ttctccgccc catggctgac taattttttt tatttatgca   9840
gaggccgagg ccgcctctgc ctctgagcta ttccagaagt agtgaggagg cttttttgga   9900
ggcctaggct tttgcaaaaa gctcccggga gcttgtatat ccattttcgg atctgatcag   9960
cacgtgttga caattaatca tcggcatagt atatcggcat agtataatac gacaaggtga  10020
ggaactaaac catggccaag ttgaccagtg ccgttccggt gctcaccgcg cgcgacgtcg  10080
ccggagcggt cgagttctgg accgaccggc tcgggttctc ccgggacttc gtggaggacg  10140
acttcgccgg tgtggtccgg gacgacgtga ccctgttcat cagcgcggtc caggaccagg  10200
tggtgccgga caacaccctg gcctgggtgt gggtgcgcgg cctggacgag ctgtacgccg  10260
agtggtcgga ggtcgtgtcc acgaacttcc gggacgcctc cgggccggcc atgaccgaga  10320
tcggcgagca gccgtggggg cgggagttcg ccctgcgcga cccggccggc aactgcgtgc  10380
acttcgtggc cgaggagcag gactgacacg tgctacgaga tttcgattcc accgccgcct  10440
tctatgaaag gttgggcttc ggaatcgttt tccgggacgc cggctggatg atcctccagc  10500
gcggggatct catgctggag ttcttcgccc accccaactt gtttattgca gcttataatg  10560
gttacaaata aagcaatagc atcacaaatt tcacaaataa agcatttttt tcactgcatt  10620
ctagttgtgg tttgtccaaa ctcatcaatg tatcttatca tgtctgtata ccgtcgacct  10680
ctagctagag cttggcgtaa tcatggtcat agctgtttcc tgtgtgaaat tgttatccgc  10740
tcacaattcc acacaacata cgagccggaa gcataaagtg taaagcctgg ggtgcctaat  10800
gagtgagcta actcacatta attgcgttgc gctcactgcc cgctttccag tcgggaaacc  10860
tgtcgtgcca gctgcattaa tgaatcggcc aacgcgcggg gagaggcggt ttgcgtattg  10920
ggcgctcttc cgcttcctcg ctcactgact cgctgcgctc ggtcgttcgg ctgcggcgag  10980
cggtatcagc tcactcaaag gcggtaatac ggttatccac agaatcaggg gataacgcag  11040
gaaagaacat gtgagcaaaa ggccagcaaa aggccaggaa ccgtaaaaag gccgcgttgc  11100
tggcgttttt ccataggctc cgcccccctg acgagcatca caaaaatcga cgctcaagtc  11160
agaggtggcg aaacccgaca ggactataaa gataccaggc gtttccccct ggaagctccc  11220
```

```
tcgtgcgctc tcctgttccg accctgccgc ttaccggata cctgtccgcc tttctccctt  11280
cgggaagcgt ggcgctttct catagctcac gctgtaggta tctcagttcg gtgtaggtcg  11340
ttcgctccaa gctgggctgt gtgcacgaac cccccgttca gcccgaccgc tgcgccttat  11400
ccggtaacta tcgtcttgag tccaacccgg taagacacga cttatcgcca ctggcagcag  11460
ccactggtaa caggattagc agagcgaggt atgtaggcgg tgctacagag ttcttgaagt  11520
ggtggcctaa ctacggctac actagaagaa cagtatttgg tatctgcgct ctgctgaagc  11580
cagttacctt cggaaaaaga gttggtagct cttgatccgg caaacaaacc accgctggta  11640
gcggtggttt ttttgtttgc aagcagcaga ttacgcgcag aaaaaaagga tctcaagaag  11700
atcctttgat cttttctacg gggtctgacg ctcagtggaa cgaaaactca cgttaaggga  11760
ttttggtcat gagattatca aaaaggatct tcacctagat ccttttaaat taaaaatgaa  11820
gttttaaatc aatctaaagt atatatgagt aaacttggtc tgacagttac caatgcttaa  11880
tcagtgaggc acctatctca gcgatctgtc tatttcgttc atccatagtt gcctgactcc  11940
ccgtcgtgta gataactacg atacgggagg gcttaccatc tggccccagt gctgcaatga  12000
taccgcgaga cccacgctca ccggctccag atttatcagc aataaaccag ccagccggaa  12060
gggccgagcg cagaagtggt cctgcaactt tatccgcctc catccagtct attaattgtt  12120
gccgggaagc tagagtaagt agttcgccag ttaatagttt gcgcaacgtt gttgccattg  12180
ctacaggcat cgtggtgtca cgctcgtcgt ttggtatggc ttcattcagc tccggttccc  12240
aacgatcaag gcgagttaca tgatccccca tgttgtgcaa aaaagcggtt agctccttcg  12300
gtcctccgat cgttgtcaga agtaagttgg ccgcagtgtt atcactcatg gttatggcag  12360
cactgcataa ttctcttact gtcatgccat ccgtaagatg cttttctgtg actggtgagt  12420
actcaaccaa gtcattctga gaatagtgta tgcggcgacc gagttgctct tgcccggcgt  12480
caatacggga taataccgcg ccacatagca gaactttaaa agtgctcatc attggaaaac  12540
gttcttcggg gcgaaaactc tcaaggatct taccgctgtt gagatccagt tcgatgtaac  12600
ccactcgtgc acccaactga tcttcagcat cttttacttt caccagcgtt tctgggtgag  12660
caaaaacagg aaggcaaaat gccgcaaaaa agggaataag ggcgacacgg aaatgttgaa  12720
tactcatact cttccttttt caatattatt gaagcattta tcagggttat tgtctcatga  12780
gcggatacat atttgaatgt atttagaaaa ataaacaaat aggggttccg cgcacatttc  12840
cccgaaaagt gccacctgac                                             12860
```

```
<210> SEQ ID NO 302
<211> LENGTH: 10182
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 302

cccgggtgca aagatggata aagttttaaa cagagaggaa tctttgcagc taatggacct     60
tctaggtctt gaaaggagtg ggaattggct ccggtgcccg tcagtgggca gagcgcacat    120
cgcccacagt ccccgagaag ttggggggag gggtcggcaa ttgatccggt gcctagagaa    180
ggtggcgcgg ggtaaactgg gaaagtgatg tcgtgtactg gctccgcctt tttcccgagg    240
gtgggggaga accgtatata agtgcagtag tcgccgtgaa cgttcttttt cgcaacgggt    300
```

```
ttgccgccag aacacaggta agtgccgtgt gtggttcccg cgggcctggc ctctttacgg    360
gttatggccc ttgcgtgcct tgaattactt ccactggctg cagtacgtga ttcttgatcc    420
cgagcttcgg gttggaagtg ggtgggagag ttcgaggcct tgcgcttaag gagccccttc    480
gcctcgtgct tgagttgagg cctggcctgg gcgctggggc cgccgcgtgc gaatctggtg    540
gcaccttcgc gcctgtctcg ctgctttcga taagtctcta gccatttaaa atttttgatg    600
acctgctgcg acgctttttt tctggcaaga tagtcttgta aatgcgggcc aagatctgca    660
cactggtatt tcggtttttg gggccgcggg cggcgacggg gcccgtgcgt cccagcgcac    720
atgttcggcg aggcggggcc tgcgagcgcg gccaccgaga atcggacggg ggtagtctca    780
agctggccgg cctgctctgg tgcctggcct cgcgccgccg tgtatcgccc cgccctgggc    840
ggcaaggctg gcccggtcgg caccagttgc gtgagcggaa agatggccgc ttcccggccc    900
tgctgcaggg agctcaaaat ggaggacgcg gcgctcggga gagcgggcgg gtgagtcacc    960
cacacaaagg aaaagggcct ttccgtcctc agccgtcgct tcatgtgact ccacggagta   1020
ccgggcgccg tccaggcacc tcgattagtt ctcgagcttt tggagtacgt cgtctttagg   1080
ttggggggag gggttttatg cgatggagtt tccccacact gagtgggtgg agactgaagt   1140
taggccagct tggcacttga tgtaattctc cttggaattt gccctttttg agtttggatc   1200
ttggttcatt ctcaagcctc agacagtggt tcaaagtttt tttcttccat ttcaggtgtc   1260
gtgacgtacg gccaccatga ccgagtacaa gcccacggtg cgcctcgcca cccgcgacga   1320
cgtccccagg gccgtacgca ccctcgccgc cgcgttcgcc gactaccccg ccacgcgcca   1380
caccgtcgat ccggaccgcc acatcgagcg ggtcaccgag ctgcaagaac tcttcctcac   1440
gcgcgtcggg ctcgacatcg gcaaggtgtg ggtcgcggac gacggcgccg ccgtggcggt   1500
ctggaccacg ccggagagcg tcgaagcggg ggcggtgttc gccgagatcg gcccgcgcat   1560
ggccgagttg agcggttccc ggctggccgc gcagcaacag atggaaggcc tcctggcgcc   1620
gcaccggccc aaggagcccg cgtggttcct ggccaccgtc ggagtctcgc ccgaccacca   1680
gggcaagggt ctgggcagcg ccgtcgtgct ccccggagtg gaggcggccg agcgcgccgg   1740
ggtgcccgcc ttcctggaga cctccgcgcc ccgcaacctc cccttctacg agcggctcgg   1800
cttcaccgtc accgccgacg tcgaggtgcc cgaaggaccg cgcacctggt gcatgacccg   1860
caagcccggt gcctgaacgc gttaagtcga caatcaacct ctggattaca aaatttgtga   1920
aagattgact ggtattctta actatgttgc tccttttacg ctatgtggat acgctgcttt   1980
aatgcctttg tatcatgcta ttgcttcccg tatggctttc attttctcct ccttgtataa   2040
atcctggttg ctgtctcttt atgaggagtt gtggcccgtt gtcaggcaac gtggcgtggt   2100
gtgcactgtg tttgctgacg caacccccac tggttggggc attgccacca cctgtcagct   2160
cctttccggg actttcgctt tccccctccc tattgccacg gcggaactca tcgccgcctg   2220
ccttgcccgc tgctggacag gggctcggct gttgggcact gacaattccg tggtgttgtc   2280
ggggaaatca tcgtcctttc cttggctgct cgcctgtgtt gccacctgga ttctgcgcgg   2340
gacgtccttc tgctacgtcc cttcggccct caatccagcg gaccttcctt cccgcggcct   2400
gctgccggct ctgcggcctc ttccgcgtct tcgccttcgc cctcagacga gtcggatctc   2460
cctttgggcc gcctccccgc gtcgacttta agaccaatga cttacaaggc agctgtagat   2520
cttagccact ttttaaaaga aaagggggga ctggaagggc taattcactc ccaacgaaga   2580
caagatctgc tttttgcttg tactgggtct ctctggttag accagatctg agcctgggag   2640
ctctctggct aactagggaa cccactgctt aagcctcaat aaagcttgcc ttgagtgctt   2700
```

caagtagtgt gtgcccgtct gttgtgtgac tctggtaact agagatccct cagacccttt 2760
tagtcagtgt ggaaaatctc tagcagtacg tatagtagtt catgtcatct tattattcag 2820
tatttataac ttgcaaagaa atgaatatca gagagtgaga ggaacttgtt tattgcagct 2880
tataatggtt acaaataaag caatagcatc acaaatttca caaataaagc atttttttca 2940
ctgcattcta gttgtggttt gtccaaactc atcaatgtat cttatcatgt ctggctctag 3000
ctatcccgcc cctaactccg cccatcccgc ccctaactcc gcccagttcc gcccattctc 3060
cgccccatgg ctgactaatt ttttttattt atgcagaggc cgaggccgcc tcggcctctg 3120
agctattcca gaagtagtga ggaggctttt ttggaggcct agggacgtac ccaattcgcc 3180
ctatagtgag tcgtattacg cgcgctcact ggccgtcgtt ttacaacgtc gtgactggga 3240
aaaccctggc gttacccaac ttaatcgcct tgcagcacat ccccctttcg ccagctggcg 3300
taatagcgaa gaggcccgca ccgatcgccc ttcccaacag ttgcgcagcc tgaatggcga 3360
atgggacgcg ccctgtagcg gcgcattaag cgcggcgggt gtggtggtta cgcgcagcgt 3420
gaccgctaca cttgccagcg ccctagcgcc cgctcctttc gctttcttcc cttcctttct 3480
cgccacgttc gccggctttc cccgtcaagc tctaaatcgg gggctccctt tagggttccg 3540
atttagtgct ttacggcacc tcgaccccaa aaaacttgat tagggtgatg gttcacgtag 3600
tgggccatcg ccctgataga cggtttttcg ccctttgacg ttggagtcca cgttctttaa 3660
tagtggactc ttgttccaaa ctggaacaac actcaaccct atctcggtct attcttttga 3720
tttataaggg attttgccga tttcggccta ttggttaaaa aatgagctga tttaacaaaa 3780
atttaacgcg aattttaaca aaatattaac gcttacaatt taggtggcac ttttcgggga 3840
aatgtgcgcg gaacccctat ttgtttattt ttctaaatac attcaaatat gtatccgctc 3900
atgagacaat aaccctgata aatgcttcaa taatattgaa aaaggaagag tatgagtatt 3960
caacatttcc gtgtcgccct tattcccttt tttgcggcat tttgccttcc tgtttttgct 4020
cacccagaaa cgctggtgaa agtaaaagat gctgaagatc agttgggtgc acgagtgggt 4080
tacatcgaac tggatctcaa cagcggtaag atccttgaga gttttcgccc cgaagaacgt 4140
tttccaatga tgagcacttt taaagttctg ctatgtggcg cggtattatc ccgtattgac 4200
gccgggcaag agcaactcgg tcgccgcata cactattctc agaatgactt ggttgagtac 4260
tcaccagtca cagaaaagca tcttacggat ggcatgacag taagagaatt atgcagtgct 4320
gccataacca tgagtgataa cactgcggcc aacttacttc tgacaacgat cggaggaccg 4380
aaggagctaa ccgctttttt gcacaacatg ggggatcatg taactcgcct tgatcgttgg 4440
gaaccggagc tgaatgaagc cataccaaac gacgagcgtg acaccacgat gcctgtagca 4500
atggcaacaa cgttgcgcaa actattaact ggcgaactac ttactctagc ttcccggcaa 4560
caattaatag actggatgga ggcggataaa gttgcaggac cacttctgcg ctcggccctt 4620
ccggctggct ggtttattgc tgataaatct ggagccggtg agcgtgggtc tcgcggtatc 4680
attgcagcac tggggccaga tggtaagccc tcccgtatcg tagttatcta cacgacgggg 4740
agtcaggcaa ctatggatga acgaaataga cagatcgctg agataggtgc ctcactgatt 4800
aagcattggt aactgtcaga ccaagtttac tcatatatac tttagattga tttaaaactt 4860
catttttaat ttaaaaggat ctaggtgaag atcctttttg ataatctcat gaccaaaatc 4920
ccttaacgtg agttttcgtt ccactgagcg tcagaccccg tagaaaagat caaaggatct 4980
tcttgagatc cttttttttct gcgcgtaatc tgctgcttgc aaacaaaaaa accaccgcta 5040

```
ccagcggtgg tttgtttgcc ggatcaagag ctaccaactc tttttccgaa ggtaactggc   5100
ttcagcagag cgcagatacc aaatactgtt cttctagtgt agccgtagtt aggccaccac   5160
ttcaagaact ctgtagcacc gcctacatac ctcgctctgc taatcctgtt accagtggct   5220
gctgccagtg gcgataagtc gtgtcttacc gggttggact caagacgata gttaccggat   5280
aaggcgcagc ggtcgggctg aacggggggt tcgtgcacac agcccagctt ggagcgaacg   5340
acctacaccg aactgagata cctacagcgt gagctatgag aaagcgccac gcttcccgaa   5400
gggagaaagg cggacaggta tccggtaagc ggcagggtcg gaacaggaga gcgcacgagg   5460
gagcttccag ggggaaacgc ctggtatctt tatagtcctg tcgggtttcg ccacctctga   5520
cttgagcgtc gatttttgtg atgctcgtca ggggggcgga gcctatggaa aaacgccagc   5580
aacgcggcct ttttacggtt cctggccttt tgctggcctt ttgctcacat gttctttcct   5640
gcgttatccc ctgattctgt ggataaccgt attaccgcct ttgagtgagc tgataccgct   5700
cgccgcagcc gaacgaccga gcgcagcgag tcagtgagcg aggaagcgga agagcgccca   5760
atacgcaaac cgcctctccc cgcgcgttgg ccgattcatt aatgcagctg gcacgacagg   5820
tttcccgact ggaaagcggg cagtgagcgc aacgcaatta atgtgagtta gctcactcat   5880
taggcacccc aggctttaca ctttatgctt ccggctcgta tgttgtgtgg aattgtgagc   5940
ggataacaat ttcacacagg aaacagctat gaccatgatt acgccaagcg cgcaattaac   6000
cctcactaaa gggaacaaaa gctggagctg caagcttaat gtagtcttat gcaatactct   6060
tgtagtcttg caacatggta acgatgagtt agcaacatgc cttacaagga gagaaaaagc   6120
accgtgcatg ccgattggtg gaagtaaggt ggtacgatcg tgccttatta ggaaggcaac   6180
agacgggtct gacatggatt ggacgaacca ctgaattgcc gcattgcaga gatattgtat   6240
ttaagtgcct agctcgatac ataaacgggt ctctctggtt agaccagatc tgagcctggg   6300
agctctctgg ctaactaggg aacccactgc ttaagcctca ataaagcttg ccttgagtgc   6360
ttcaagtagt gtgtgcccgt ctgttgtgtg actctggtaa ctagagatcc ctcagaccct   6420
tttagtcagt gtggaaaatc tctagcagtg gcgcccgaac agggacttga aagcgaaagg   6480
gaaaccagag gagctctctc gacgcaggac tcggcttgct gaagcgcgca cggcaagagg   6540
cgaggggcgg cgactggtga gtacgccaaa aattttgact agcggaggct agaaggagag   6600
agatgggtgc gagagcgtca gtattaagcg ggggagaatt agatcgcgat gggaaaaaat   6660
tcggttaagg ccagggggaa agaaaaaata taaattaaaa catatagtat gggcaagcag   6720
ggagctagaa cgattcgcag ttaatcctgg cctgttagaa acatcagaag gctgtagaca   6780
aatactggga cagctacaac catcccttca gacaggatca gaagaactta gatcattata   6840
taatacagta gcaaccctct attgtgtgca tcaaaggata gagataaaag acaccaagga   6900
agctttagac aagatagagg aagagcaaaa caaaagtaag accaccgcac agcaagcggc   6960
cgctgatctt cagacctgga ggaggagata tgagggacaa ttggagaagt gaattatata   7020
aatataaagt agtaaaaatt gaaccattag gagtagcacc caccaaggca aagagaagag   7080
tggtgcagag agaaaaaaga gcagtgggaa taggagcttt gttccttggg ttcttgggag   7140
cagcaggaag cactatgggc gcagcgtcaa tgacgctgac ggtacaggcc agacaattat   7200
tgtctggtat agtgcagcag cagaacaatt tgctgagggc tattgaggcg caacagcatc   7260
tgttgcaact cacagtctgg ggcatcaagc agctccaggc aagaatcctg gctgtggaaa   7320
gatacctaaa ggatcaacag ctcctgggga tttggggttg ctctggaaaa ctcatttgca   7380
ccactgctgt gccttggaat gctagttgga gtaataaatc tctggaacag atttggaatc   7440
```

```
acacgacctg gatggagtgg gacagagaaa ttaacaatta cacaagctta atacactcct   7500
taattgaaga atcgcaaaac cagcaagaaa agaatgaaca agaattattg gaattagata   7560
aatgggcaag tttgtggaat tggtttaaca taacaaattg gctgtggtat ataaaattat   7620
tcataatgat agtaggaggc ttggtaggtt taagaatagt tttgctgta ctttctatag   7680
tgaatagagt taggcaggga tattcaccat tatcgtttca gacccacctc ccaaccccga   7740
ggggacccag agagggccta tttcccatga ttccttcata tttgcatata cgatacaagg   7800
ctgttagaga gataattaga attaatttga ctgtaaacac aaagatatta gtacaaaata   7860
cgtgacgtag aaagtaataa tttcttgggt agtttgcagt tttaaaatta tgttttaaaa   7920
tggactatca tatgcttacc gtaacttgaa agtatttcga tttcttggct ttatatatct   7980
tgtggaaagg acgaaacacc ggagacggtt gtaaatgagc acacaaaata cacatgctaa   8040
aatattatat tctatgacct ttataaaatc aaccaaaatc ttctttttaa taactttagt   8100
atcaataatt agaattttta tgttcctttt tgcaaacttt taataaaaat gagcaaaata   8160
aaaaaacgct agttttagta actcgcgttg ttttcttcac ctttaataat agctactcca   8220
ccacttgttc ctaagcggtc agctcctgct tcaatcattt tttgagcatc ttcaaatgtt   8280
ctaactccac cagctgcttt aactaaagca ttgtctttaa caactgactt cattagttta   8340
acatcttcaa atgttgcacc tgattttgaa aatcctgttg atgttttaac aaattctaat   8400
ccagcttcaa cagctatttc acaagctttc atgatttctt cttttgttaa taaacaattt   8460
tccataatac atttaacaac atgtgatcca gctgcttttt ttacagcttt catgtcttct   8520
aaaactaatt cataattttt gtcttttaat gcaccaatat ttaataccat atcaatttct   8580
gttgcaccat ctttaattgc ttcagaaact tcgaatgctt ttgtagctgt tgtgcatgca   8640
cctagaggaa aacctacaac atttgttatt cctacatttg tgccttttaa taattcttta   8700
caatagcttg ttcaatatga attaacacaa actgttgcaa aatcaaattc aattgcttca   8760
tcacataatt gtttaatttc agctttcgta gcatcttgtt ttaataatgt gtgatctata   8820
tatttgttta gtttcatttt ttctcctata tattcatttt taattttaat tctttaataa   8880
tttcgtctac tttaacttta gcgttttgaa cagattcacc aacacctata aaataaattt   8940
ttagtttagg ttcagttcca cttgggcgaa cagcaaatca tgacttatct tctaaataaa   9000
attttagtaa gtcttgtcct ggcatattat acattccatc gatgtagtct tcaacattaa   9060
caactttaag tccagcaatt tgagttaagg gtgttgctct caatgatttc attaatggtt   9120
caatttttaa tttcttttct tctggtttaa aattcaagtt taaagtgaaa gtgtaatatg   9180
cacccatttc tttaaataaa tcttctaaat agtctactaa tgttttattt tgttttttat   9240
aaaatcaagc agcctctgct attaatatag aagcttgtat tccatcttta tctctagctg   9300
agtcatcaat tacatatcca taactttctt cataagcaaa aacaaaattt aatccgttat   9360
cttcttcttt agcaatttct ctacccattc atttaaatcc agttaaagtt tttacaatat   9420
taactccata tttttcatga gcgattctat cacccaaatc acttgttaca aaacttgaat   9480
atagagccgg attttttgga atgctattta agcgttttag atttgataat tttcaatcaa   9540
ttaaaattgg tcctgtttga tttccatcta atcttacaaa atgaccatca tgttttattg   9600
ccattccaaa tctgtcagca tctgggtcat tcataataat aatatctgca tcatgtttaa   9660
taccatattc aagcggtatt tttcatgcag gatcaaattc tggatttgga tttacaacat   9720
ttttaaatgt ttcatcttca aatgcatgct cttcaacctc aataacgtta tatcctgatt   9780
```

```
cacgtaatat ttttggggta aatttagttc ctgttccatt aactgcgcta aaaataattt   9840

ttaaatcttt tttagcttct tgctcttttt tgtacgtctc tgttttagag ctagaaatag   9900

caagttaaaa taaggctagt ccgttatcaa cttgaaaaag tggcaccgag tcggtgcttt   9960

tttaagcttg gcgtaactag atcttgagac aaatggcagt attcatccac aattttaaaa  10020

gaaaaggggg gattgggggg tacagtgcag gggaaagaat agtagacata atagcaacag  10080

acatacaaac taaagaatta caaaaacaaa ttacaaaaat tcaaaatttt cgggtttatt  10140

acagggacag cagagatcca ctttggcgcc ggctcgaggg gg                     10182
```

```
<210> SEQ ID NO 303
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(21)
<223> OTHER INFORMATION: a, c, t, g, unknown or other

<400> SEQUENCE: 303

nnnnnnnnnn nnnnnnnnnn ngg                                             23
```

```
<210> SEQ ID NO 304
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(12)
<223> OTHER INFORMATION: a, c, t or g
<220> FEATURE:
<221> NAME/KEY: modified_base
<222> LOCATION: (13)..(13)
<223> OTHER INFORMATION: a, c, t, g, unknown or other

<400> SEQUENCE: 304

nnnnnnnnnn nnngg                                                      15
```

```
<210> SEQ ID NO 305
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(21)
<223> OTHER INFORMATION: a, c, t, g, unknown or other

<400> SEQUENCE: 305

nnnnnnnnnn nnnnnnnnnn ngg                                             23
```

```
<210> SEQ ID NO 306
```

<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(11)
<223> OTHER INFORMATION: a, c, t or g
<220> FEATURE:
<221> NAME/KEY: modified_base
<222> LOCATION: (12)..(12)
<223> OTHER INFORMATION: a, c, t, g, unknown or other

<400> SEQUENCE: 306
nnnnnnnnnn nngg 14

<210> SEQ ID NO 307
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(21)
<223> OTHER INFORMATION: a, c, t, g, unknown or other
<220> FEATURE:
<221> NAME/KEY: modified_base
<222> LOCATION: (24)..(24)
<223> OTHER INFORMATION: a, c, t, g, unknown or other

<400> SEQUENCE: 307
nnnnnnnnnn nnnnnnnnnn nggng 25

<210> SEQ ID NO 308
<211> LENGTH: 17
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(12)
<223> OTHER INFORMATION: a, c, t or g
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: modified_base
<222> LOCATION: (16)..(16)
<223> OTHER INFORMATION: a, c, t, g, unknown or other

<400> SEQUENCE: 308
nnnnnnnnnn nnnggng 17

<210> SEQ ID NO 309
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base

```
<222> LOCATION: (1)..(20)
<223> OTHER INFORMATION: a, c, t or g
<220> FEATURE:
<221> NAME/KEY: modified_base
<222> LOCATION: (21)..(21)
<223> OTHER INFORMATION: a, c, t, g, unknown or other
<220> FEATURE:
<221> NAME/KEY: modified_base
<222> LOCATION: (24)..(24)
<223> OTHER INFORMATION: a, c, t, g, unknown or other

<400> SEQUENCE: 309

nnnnnnnnnn nnnnnnnnnn nggng                                      25


<210> SEQ ID NO 310
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(11)
<223> OTHER INFORMATION: a, c, t or g
<220> FEATURE:
<221> NAME/KEY: modified_base
<222> LOCATION: (12)..(12)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other

<400> SEQUENCE: 310

nnnnnnnnnn nnggng                                                16
```